US012583932B2

(12) United States Patent
Liu et al.

(10) Patent No.: US 12,583,932 B2
(45) Date of Patent: Mar. 24, 2026

(54) CD38 AND ICAM1 ANTIBODIES AND USES THEREOF

(71) Applicants: Virtuoso BINco, Inc., San Mateo, CA (US); The Regents of the University of California, Oakland, CA (US)

(72) Inventors: Bin Liu, San Francisco, CA (US); Xiaocheng Chen, San Mateo, CA (US); Scott Bidlingmaier, San Francisco, CA (US); Leonard Post, San Mateo, CA (US); Yang Su, South San Francisco, CA (US); Namkyung Lee, Iksan-si (KR)

(73) Assignees: Virtuoso BINco, Inc., San Mateo, CA (US); The Regents of the University of California, Oakland, CA (US)

( * ) Notice: Subject to any disclaimer, the term of this patent is extended or adjusted under 35 U.S.C. 154(b) by 1111 days.

(21) Appl. No.: 17/293,258

(22) PCT Filed: Nov. 15, 2019

(86) PCT No.: PCT/US2019/061884
§ 371 (c)(1),
(2) Date: May 12, 2021

(87) PCT Pub. No.: WO2020/102777
PCT Pub. Date: May 22, 2020

(65) Prior Publication Data
US 2022/0002432 A1      Jan. 6, 2022
Related U.S. Application Data

(60) Provisional application No. 62/768,566, filed on Nov. 16, 2018.

(51) Int. Cl.
*C07K 16/28*          (2006.01)
*A61K 45/06*          (2006.01)

(52) U.S. Cl.
CPC .......... *C07K 16/2896* (2013.01); *A61K 45/06* (2013.01); *C07K 2317/31* (2013.01)

(58) Field of Classification Search
None
See application file for complete search history.

(56) References Cited

U.S. PATENT DOCUMENTS 4,474,814 A      10/1984  Fujita et al.
4,694,778 A       9/1987  Learn et al.
(Continued)

FOREIGN PATENT DOCUMENTS

EP          0610046 B1      12/2005
WO      WO-9627011 A1       9/1996
(Continued)

OTHER PUBLICATIONS

Rouet et al. Fully Human VH Single Domains That Rival the Stability and Cleft Recognition of Camelid Antibodies, 2015 the Journal of Biological Chemistry vol. 290, No. 19, pp. 11905-11917 (Year: 2015).*
(Continued)

*Primary Examiner* — Amy E Juedes
*Assistant Examiner* — Hilary Ann Petrash
(74) *Attorney, Agent, or Firm* — Mintz Levin Cohn Ferris Glovsky and Popeo, P.C.

(57) ABSTRACT

Disclosed herein are anti-CD38 antibodies, anti-ICAM1 antibodies, pharmaceutical compositions comprising anti-CD38 antibodies and/or anti-ICAM1 antibodies, and methods of use for the treatment of a proliferative disease. In certain embodiments, also disclosed herein are multi-specific antibodies (e.g., bispecific antibodies) comprising a first targeting moiety that specifically binds to CD38 and a second targeting moiety that specifically binds to ICAM1, pharmaceutical compositions comprising the multi-specific
(Continued)

antibodies, and methods of use for the treatment of a proliferative disease.

23 Claims, 38 Drawing Sheets

Specification includes a Sequence Listing.

(56)                    References Cited

U.S. PATENT DOCUMENTS

| | | | |
|---|---|---|---|
| 4,866,132 | A | 9/1989 | Obligin et al. |
| 4,921,963 | A | 5/1990 | Skov et al. |
| 5,064,849 | A | 11/1991 | Suzuki et al. |
| 5,208,020 | A | 5/1993 | Chari et al. |
| 5,256,334 | A | 10/1993 | Smid et al. |
| 5,346,981 | A | 9/1994 | Sarpeshkar et al. |
| 5,416,064 | A | 5/1995 | Chari et al. |
| 5,700,825 | A | 12/1997 | Hofer et al. |
| 5,849,738 | A | 12/1998 | Lee et al. |
| 5,872,107 | A | 2/1999 | Schinazi et al. |
| 5,939,045 | A | 8/1999 | Suzuki et al. |
| 5,945,439 | A | 8/1999 | Richter et al. |
| 6,562,806 | B1 | 5/2003 | Thurston et al. |
| 6,608,192 | B1 | 8/2003 | Thurston et al. |
| 6,716,821 | B2 | 4/2004 | Zhao et al. |
| 6,821,783 | B1 | 11/2004 | Comely et al. |
| 6,884,869 | B2 | 4/2005 | Senter et al. |
| 7,049,311 | B1 | 5/2006 | Thurston et al. |
| 7,067,511 | B2 | 6/2006 | Thurston et al. |
| 7,244,724 | B2 | 7/2007 | Liu et al. |
| 7,276,497 | B2 | 10/2007 | Chari et al. |
| 7,335,744 | B2 * | 2/2008 | Liu .......................... A61P 35/00 |
| | | | 530/387.3 |
| 7,498,298 | B2 | 3/2009 | Doronina et al. |
| 7,528,126 | B2 | 5/2009 | Howard et al. |
| 7,612,062 | B2 | 11/2009 | Gregson et al. |
| 7,659,241 | B2 | 2/2010 | Senter et al. |
| 7,704,924 | B2 | 4/2010 | Thurston et al. |
| 7,709,226 | B2 | 5/2010 | Foote |
| 7,750,116 | B1 | 7/2010 | Doronina et al. |
| 7,964,566 | B2 | 6/2011 | Doronina et al. |
| 8,093,359 | B2 | 1/2012 | Lazar et al. |
| 8,163,736 | B2 | 4/2012 | Gauzy et al. |
| 8,288,352 | B2 | 10/2012 | Doronina et al. |
| 8,404,678 | B2 | 3/2013 | Bouchard et al. |
| 8,426,402 | B2 | 4/2013 | Li et al. |
| 8,501,934 | B2 | 8/2013 | Howard et al. |
| 8,580,820 | B2 | 11/2013 | Zanda et al. |
| 8,633,185 | B2 | 1/2014 | Howard et al. |
| 8,697,688 | B2 | 4/2014 | Howard et al. |
| 8,703,714 | B2 | 4/2014 | Doronina et al. |
| 8,802,667 | B2 | 8/2014 | Li et al. |
| 8,809,320 | B2 | 8/2014 | Li et al. |
| 8,871,720 | B2 | 10/2014 | Doronina et al. |
| 8,936,910 | B2 | 1/2015 | Mitsch et al. |
| 8,980,833 | B2 | 3/2015 | Richter |
| 9,089,614 | B2 | 7/2015 | Lin et al. |
| 9,242,013 | B2 | 1/2016 | Howard et al. |
| 2003/0219876 | A1 | 11/2003 | Ledbetter et al. |
| 2009/0076249 | A1 * | 3/2009 | De Weers .......... C07K 16/2896 |
| | | | 530/387.3 |
| 2013/0029900 | A1 | 1/2013 | Widdison |
| 2013/0217638 | A1 | 8/2013 | Wessjohann |
| 2013/0224228 | A1 | 8/2013 | Jackson et al. |
| 2013/0323268 | A1 | 12/2013 | Chari et al. |
| 2014/0242075 | A1 | 8/2014 | Parren et al. |
| 2014/0286970 | A1 | 9/2014 | Jeffrey et al. |
| 2014/0294868 | A1 | 10/2014 | Howard et al. |
| 2014/0363454 | A1 | 12/2014 | Jackson et al. |
| 2015/0105539 | A1 | 4/2015 | Miao et al. |
| 2015/0105540 | A1 | 4/2015 | Miao et al. |
| 2017/0022291 | A1 | 1/2017 | Baruah et al. |
| 2018/0215834 | A1 * | 8/2018 | Desjarlais ............ C07K 16/468 |

FOREIGN PATENT DOCUMENTS

| | | |
|---|---|---|
| WO | WO-2007146968 A2 | 12/2007 |
| WO | WO-2013/004842 A2 | 1/2013 |
| WO | WO-2014140317 A2 | 9/2014 |
| WO | WO-2015038426 A1 | 3/2015 |
| WO | WO-2017/136562 A2 | 8/2017 |
| WO | WO-2020102777 A1 | 5/2020 |

OTHER PUBLICATIONS

Holt et al. 2003 Domain antibodies: proteins for therapy, Trends in Biotechnology vol. 21 No. 11, pp. 484-490 (Year: 2003).*

Kapingidza et al. 2020 Antigen-Antibody Complexes. Vertebrate and Invertebrate Respiratory Proteins, Lipoproteins and other Body Fluid, CH 19, pp. 465-484 (Year: 2020).*

Culang et al. The structural basis of antibody-antigen recognition. Front. In Immun. 2013. Vol. 4, Article 302 (Year: 2013).*

Clark et al. Influence of canonical structure determining residues on antibody affinity and stability. Journal of Structural Biology 185 (2014) 223-227 (Year: 2014).*

Brown et al. Tolerance to Single, but Not Multiple, Amino Acid Replacements in Antibody VH, CDR2. J Immunol (1996) 156 (9): 3285-3291 (Year: 1996).*

Neils et al. CD38 antibodies in multiple myeloma: back to the future. 2018. The American Society of Hematology. vol. 131, No. 1, pp. 13-29 (Year: 2018).*

Klausz et al. A novel Fc-engineered human ICAM-1/CD54 antibody with potent anti-myeloma activity developed by cellular panning of phage display libraries. Oncotarget, 2017, vol. 8, (No. 44), pp. 77552-77566 (Year: 2017).*

Smalley et al. 2012 Current challenges in personalized cancer medicine. Chapter 6, Emerging strategies for targeting cell adhesion in multiple myeloma, pp. 143-189 (Year: 2012).*

Weidle et al. Tumor-Antigen-Binding Bispecific Antibodies for Cancer Treatment. Seminars in Oncology, vol. 41, No. 5, Oct. 2014, pp. 653-660 (Year: 2014).*

Adriouch et al. Extracellular NAD+: a danger signal hindering regulatory T cells. Microbes Infect 14:1284-92 (2012).

Agarwal et al. A Pictet-Spengler ligation for protein chemical modification. PNAS 110(1):46-51 (2013).

Alegre et al. Effect of a Single Amino Acid Mutation on the Activating and Immunosuppressive Properties of a "Humanized" OKT3 Monoclonal Antibody. J Immunol 148:3461-3468 (1992).

Al-Lazikani et al. Standard conformations for the canonical structures of immunoglobulins. J. Mol Biology 273(4):927-948 (1997).

Axup et al. Synthesis of site-specific antibody-drug conjugates using unnatural amino acids. PNAS 109(40):16101-16106 (2012).

Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).

Bird et al. Single-chain antigen-binding proteins. Science 242:423-442 (1988).

Blaney et al. Traceless solid-phase organic synthesis. Chem. Rev. 102:2607-2024 (2002.

Boerner et al. Production of antigen-specific human monoclonal antibodies from in vitro-primed human splenocytes. J Immunol. 147(1):86-95 (Jul. 1, 1991).

Borchardt et al. Targeted actinium-225 in Vivo Generators for Therapy of Ovarian Cancer Cancer Res. 63:5084-50 (2003).

Brinkmann et al. The making of bispecific antibodies. MABS 9(2):182-212 (2017).

Bruggemann et al. Designer mice: the production of human antibody repertoires in transgenic animals. Year Immunol. 7:33-40 (1993).

Carter. Bispecific human IgG by design. J Immunol Methods 248:7-15 (2001).

Casi et al. Site-specific traceless coupling of potent cytotoxic drugs to recombinant antibodies for pharmacodelivery. J Am Chem Soc 134(13):5887-5892 (2012).

Chiarugi et al. The NAD metabolome—a key determinant of cancer cell biology. Nat Rev 12:741-52 (2012).

(56)         References Cited

OTHER PUBLICATIONS

Chotha et al. Structural repertoire of the human VH segments. J. Mol. Biol. 227:799-817 (1992).

Chothia et al. Canonical structures for the hypervariable regions of immunoglobulins. J Mol Biol. 196(4):901-917 (1987).

Clackson et al. Making antibody fragments using phage display libraries. Nature 352(6336):624-628 (1991).

Colberre-Garapin et al. A new dominant hybrid selective marker for higher eukaryotic cells. J Mol Biol 150:1-14 (1981).

Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).

Crouse et al. Expression and amplification of engineered mouse dihydrofolate reductase minigenes. Mol Cell Biol 3(2):257-266 (1983).

Dawson et al. Modulation of Reactivity in Native Chemical Ligation through the Use of Thiol Additives. J. Am. Chem. Soc. 119:4325-4329 (1997).

Dawson et al. Synthesis of proteins by native chemical ligation. Science 266(5186):776-779 (1994).

Funaro et al. Involvement of the multilineage CD38 molecule in a unique pathway of cell activation and proliferation. J Immunol 145:2390-6 (1990).

Gazzano-Santoro et al. A non-radioactive complement-dependent cytotoxicity assay for anti-CD20 monoclonal antibody. J Immunol Methods 202(2):163-171 (Mar. 28, 1997).

Goldspiel et al. Human gene therapy. Clin Pharm 12:488-505 (1993).

Guse et al. Regulation of calcium signalling in T lymphocytes by the second messenger cyclic ADP-ribose. Nature 398:70-73 (1999).

Hackeng et al. Protein synthesis by native chemical ligation: Expanded scope by using straightforward methodology. PNAS USA 96:10068-10073 (1999).

Hanes et al. In vitro selection and evolution of functional proteins by using ribosome display. PNAS USA 94:4937-4942 (1997).

Hejesen et al. A traceless aryl-triazene linker for DNA-directed chemistry. Org Biomol Chem 11(15):2493-2497 (2013).

Hoogenboom, et al. By-passing immunisation. Human antibodies from synthetic repertoires of germline VH gene segments rear-ranged in vitro. J Mol Biol. Sep. 20, 1992;227(2):381-8.

Huse et al. Generation of a large combinatorial library of the immunoglobulin repertoire in phage lambda. Science 246(4935):1275-1281 (1989).

Huston et al. Protein engineering of antibody binding sites: recovery of specific activity in an anti-digoxin single-chain Fv analogue produced in *Escherichia coli*. PNAS USA 85(16):5879-5883 (1988).

Idusogie al., Engineered Antibodies with Increased Activity to Recruit Complement. J Immunol. 166(4):2571-5 (2001).

Jakobovits et al. Analysis of homozygous mutant chimeric mice: deletion of the immunoglobulin heavy-chain joining region blocks B-cell development and antibody production. PNAS 90:2551-2555 (1993).

Jakobovits et al. Germ-line transmission and expression of a human-derived yeast artificial chromosome. Nature 362(6417):255-8 (1993).

Kabat et al. Attempts to Locate Complementarity-Determining Residues in the Variable Positions of Light and Heavy Chains. Ann. NY Acad. Sci. 190:382-391 (1971).

Kabat et al. Sequences of proteins of immunological interest. NIH Publ. No. 91-3242 1:647-669 (1991).

Kaneko et al. Optimizing Therapeutic Antibody Function: Progress With Fc Domain Engineering. Biodrugs 25(1):1-11 (2011).

Kohler et al. Continuous cultures of fused cells secreting antibody of predefined specificity. Nature 256:495-497 (1975).

Kozbor et al. The production of monoclonal antibodies from human lymphocytes. Immunology Today 4:72-79 (1983).

Kutmeier et al. Assembly of humanized antibody genes from synthetic oligonucleotides using a single-round PCR. BioTechniques 17:242 (1994).

Lazar et al. Engineered antibody Fc variants with enhanced effector function. PNAS USA 103(11):4005-10 (2006).

Lefranc et al. IMGT, the International ImMunoGeneTics Database. Nucleic Acids Res. 27:209-212 (1999).

Lefranc. The IMGT Unique Numbering for Immunoglobulins, T-Cell Receptors, and Ig-Like Domains. The Immunologist 7:132-136 (1999).

Lowy et al., Isolation of transforming DNA: Cloning the hamster aprt gene. Cell 22:817-823 (1980).

Maccallum et al. Antibody-antigen interactions: contact analysis and binding site topography. J Mol Biol. 262(5):732-745 (1996).

Marks et al. By-passing immunization: Human antibodies from v-gene libraries displayed on phage. J. Mol. Biol. 222:581-597 (1991).

Martin. Chapter 31. Protein Sequence and Structure Analysis of Antibody Variable Domains. in Antibody Engineering, Kontermann and Diibel, eds., pp. 422-439, Springer-Verlag, Berlin (2001).

McDevitt et al. Tumor Therapy With Targeted Atomic Nanogenera-tors. Science 294:1537-1540 (2001).

Merchant et al. An efficient route to human bispecific IgG. Nature Biotechnology 16(7):677-81 (1998).

Moore et al. Engineered Fc variant antibodies with enhanced ability to recruit complement and mediate effector functions. mAbs 2(2):181-189 (2010).

Morgan et al. Human gene therapy. Ann Rev Biochem 62:191-217 (1993).

Morrison et al. Chimeric human antibody molecules: mouse antigen-binding domains with human constant region domains. PNAS USA 81(21):6851-6855 (1984).

Mulligan et al. Selection for animal cells that express the *Escherichia coli* gene coding for xanthine-guanine phosphoribosyltransferase. PNAS USA 78(4):2072-2076 (1981).

Mulligan. The basic science of gene therapy. Science 260(5110):926-932 (1993).

Natsume et al. Engineered Antibodies of IgG1/IgG3 Mixed Isotype With Enhanced Cytotoxic Activities. Cancer Res 68(10):3863-72 (2008).

NCBI, GenBank accession No. AAO17823.1 (Jun. 26, 2003) sequence.

NCBI, GenBank accession No. AFR78283.2 (Feb. 3, 2014) sequence.

NCBI, GenBank accession No. APZ76731.1 (Jul. 18, 2017)sequence.

Neuberger et al. Recombinant antibodies possessing novel effector functions. Nature 312(5995):604-608 (1984).

O'Hare et al. Transformation of mouse fibroblasts to methotrexate resistance by a recombinant plasmid expressing a prokaryotic dihydrofolate reductase. PNAS USA 78:1527-1531 (1981).

PCT/US2019/061884 International Search Report and Written Opin-ion dated Mar. 17, 2020.

Ravetch et al. Fc receptors. Annu Rev Immunol. 9:457-92 (1991).

Ridgway et al.: 'Knobs-into-holes' engineering of antibody CH3 domains for heavy chain heterodimerization. Protein Engineering. 9(7):617-621 (1996).

Santerre et al. Expression of prokaryotic genes for hygromycin B and G418 resistance as dominant-selection markers in mouse L cells. Gene 30(1-3):147-156 (1984).

Shields et al. High Resolution Mapping of the Binding Site on Human IgG1 for FcγRI, FcγRII, FcγRIII, and FcRn and Design of IgG1 Variants with Improved Binding to the FcγR. J Biol Chem 276(9):6591-6604 (2001).

Skerra et al. Assembly of a functional Immunoglobulin Fv fragment in *Escherichia coli*. Science 240(4855):1038-1041 (1988).

Stavenhagen et al. Enhancing the potency of therapeutic monoclo-nal antibodies via Fc optimization. Adv Enzyme Regul. 48:152-64 (2008).

Stavenhagen et al. Fc optimization of therapeutic antibodies enhances their ability to kill tumor cells in vitro and controls tumor expansion in vivo via low-affinity activating Fcgamma receptors. Cancer Res. 67(18):8882-90 (2007).

Strop et al. Location matters: site of conjugation modulates stability and pharmacokinetics of antibody drug conjugates. Chem Biol 20(2):161-167 (2013).

Szybalska et al. Genetics of human cell line. IV. DNA-mediated heritable transformation of a biochemical trait. PNAS USA 48:2026-2034 (1962).

(56)                References Cited

OTHER PUBLICATIONS

Takeda et al. Construction of chimaeric processed immunoglobulin genes containing mouse variable and human constant region sequences. Nature 314(6010):452-454 (1985).

Tolstoshev. Gene Therapy, Concepts, Current Trials and Future Directions. Ann. Rev. Pharmacol. Toxicol. 32:573-596 (1993).

Tramontano et al. Framework Residue 71 Is a Major Determinant of the Position and Conformation of the Second Hypervariable Region in the VH Domains of Immunoglobulins. J. Mol. Biol. 215(1):175-82 (1990).

Van Dijk et al. Human antibodies as next generation therapeutics. Curr Opin Chem Biol. 5(4):368-74 (Aug. 2001).

Ward et al. Binding activities of a repertoire of single immuno-globulin variable domains secreted from *Escherichia coli*. Nature 341(6242):544-546 (1989).

Wigler et al. Transfer of purified herpes virus thymidine kinase gene to cultured mouse cells. Cell 11:223-232 (1977).

Wigler et al. Transformation of mammalian cells with an amplifi-able dominant-acting gene. PNAS USA 77:3567-3570 (1980).

Wu et al. Building complex glycopeptides: Development of a cysteine-free native chemical ligation protocol. Angew. Chem. Int. Ed. 45:4116-4125 (2006).

Wu et al. Delivery systems for gene therapy. Biotherapy 3:87-95 (1991).

Yu et al. Beyond Antibodies as Binding Partners: The Role of Antibody Mimetics in Bioanalysis. Annu Rev Anal Chem (Palo Alto Calif). 10(1):293-320 (Jun. 12, 2017).

Zapata et al. Engineering linear F(ab')2 fragments for efficient production in *Escherichia coli* and enhanced antiproliferative activity. Protein Eng. 8(10):1057-1062 (1995).

Chen, X. et al. (Jan. 1, 2022). "Multiple Modes of Action of the CD38 x ICAM-1 Bispecific Antibody," Virtuoso Therapeutics, AACR Poster 5385, 1 page.

Choi, H.-J. et al. (Dec. 2013, e-published Oct. 16, 2013). "A heterodimeric Fc-based bispecific antibody simultaneously target-ing VEGFR-2 and Met exhibits potent antitumor activity," *Molecu-lar Cancer Therapeutics* 12(12):2748-2759.

Extended European Search Report mailed on Mar. 16, 2023, for EP Patent Application No. 19885142.0, 22 pages.

Katja, K. et al. (Dec. 2, 2016). "The Novel ADCC-Optimized Human CD54 (ICAM-1) Antibody MSH-TP15e Has Potent Anti-Myeloma Activity," *Blood* 128(22):4471.

Krejcik, J. et al. (Dec. 15, 2017). "Monocytes and Granulocytes Reduce CD38 Expression Levels on Myeloma Cells in Patients Treated with Daratumumab," *Clinical Cancer Research* 23(24):7498-7511.

Leo, R. et al. (Mar. 1992). "Multiparameter analyses of normal and malignant human plasma cells: CD38++, CD56+, CD54+, clg+ is the common phenotype of myeloma cells," *Ann Hematol* 64(3):132-139.

Lu, D. et al. (Sep. 15, 2002). "Fab-scFv fusion protein: an efficient approach to production of bispecific antibody fragments," *J Immun Methods* 267(2):213-226.

Niels W.C.J van de Donk et al. (Sep. 2018). "CD38 Antibodies in Multiple Myeloma: Mechanisms of Action and Modes of Resis-tance," *Frontiers in Immunology* vol. 9, Article 2134.

Zahavi, D. et al. (Jun. 24, 2018). "Enhancing antibody-dependent cell-mediated cytotoxicity: a strategy for improving antibody-based immunotherapy," *Antibody Therapeutics* 1(1):7-12.

Zucchetto, A. et al. (Jul. 2005). "Signature of B-CLL with different prognosis by Shrunken centroids of surface antigen expression profiling," *Journal of Cellular Physiology* 204(1):113-123.

* cited by examiner

CH1/CL
fuscion proteins

⑰ scFv₂-CH1-hinge/CL modified IgGs

⑱ DAF
(two-in-one-IgG)   DutaMab   mAb² non-immunoglobulin
fusions

⑲ DNL-Fab₄-IgG

- Ctrl.huIgG1
- anti-ICAM1 G12
- 3D8
- 6G8
- 6B10
- 2E3
- 15D10
- 8H1
- 11G7
- 14H1
- 4H5
- 11F2
- 16E4
- 8B12
- 5B12
- 10B8
- 14B3
- 8E5

17E9
17F7
1E2
20B5
18E4
21H9
21G2
22H6
23B3
anti-CD38 BMK
Ctrl.huIgG1
23D1
25C3
25E4
25F12
26D4
27F6

- Ctrl.huIgG1
- anti-ICAM1 G12
- 3D8
- 6G8
- 6B10
- 2E3
- 15D10
- 8H1
- 11G7
- 14H1
- 4H5
- 11F2
- 16E4
- 8B12
- 5B12
- 10B8
- 14B3
- 8E5

- Three Chain KIH (18E4X11F2)
- afuco_three Chain KIH (18E4X11F2)
- Control_huIgG1

- Three Chain KIH (18E4X11F2)
- afuco_three Chain KIH (18E4X11F2)
- Control_huIgG1

SEQUENCE LISTING

<160> NUMBER OF SEQ ID NOS: 430

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Pro Phe Asp Val Tyr Ala Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ile Ser Gly Ser Gly Gly Ser Thr Phe Tyr Ala Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Lys Arg Gly Thr Tyr Ala Tyr Ser Phe Pro Thr Gly Phe Asp Tyr
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gly Phe Pro Phe Asp Ala Tyr Ala Met Ser
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ile Ser Gly Ser Gly Gly Ser Thr Tyr Tyr Ala Asp Ser Val Lys
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Pro Phe Gly Val Tyr Ala Met Ser
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Lys Arg Gly Thr Tyr Ala Tyr Ser Tyr Pro Thr Gly Phe Asp Tyr
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Pro Phe Asp Thr Tyr Ala Met Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Pro Phe Gly Thr Tyr Ala Met Ser
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Lys Arg Gly Thr Tyr Gly Tyr Ser Phe Pro Thr Gly Phe Asp Tyr
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Ser Leu Ser Arg Tyr Tyr Val Thr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ile Ile Tyr Ile Ser Gly Thr Thr Tyr Tyr Ala Thr Trp Ala Lys
1               5                   10                  15

Gly

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Ala Trp Pro Val Gly Thr Tyr Val Leu Pro Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Phe Ser Leu Ser Ser Tyr Tyr Met Ser
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic -continued

```
        peptide

<400> SEQUENCE: 15

Gly Phe Ile Ser Lys Thr Ala Ile Thr Tyr Tyr Ala Ser Trp Ala Arg
1               5                   10                  15

Gly

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 16

Ala Arg Val Asp Ala Tyr Ser Ala Gly Asp Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 17

Gly Phe Ser Phe Asn Asn Tyr Trp Ile Cys
1               5                   10

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 18

Ala Cys Ile Tyr Ser Pro Ser Gly Asp Ile Lys Tyr Tyr Ala Asn Trp
1               5                   10                  15

Ala Lys Gly

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 19

Ala Arg Glu Leu Ser Gly Ser Ser Tyr Glu Gly Tyr Phe Glu Ser
1               5                   10                  15

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 20

Gly Ile Asp Leu Asn Ser Tyr Ala Met Gly
```

-continued

```
1               5                    10

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ile Met Thr Ser Gly Gly Asn Ile Tyr Tyr Ala Asn Trp Ala Lys
1               5                    10                  15

Gly

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Arg Glu Arg Glu Phe Tyr Gly Gly Gly Thr Ser Gly Ser Arg Leu
1               5                    10                  15

Asp Leu

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Phe Ser Phe Ser Ser Arg Tyr Trp Ile Cys
1               5                    10

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Cys Ile Val Ala Gly Thr Thr Asn Thr Tyr Tyr Ala Ser Trp Ala
1               5                    10                  15

Lys Gly

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Gly Asp Pro Arg Thr Gly Ser Asn Val Gly Tyr Phe Asn Leu
1               5                    10                  15
```

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Ser Leu Ser Asn Tyr Gly Val Ser
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Tyr Ile Leu Thr Ser Gly Gly Thr Tyr Tyr Ala Asn Trp Ala Gln
1               5                   10                  15

Gly

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Arg Pro Lys Asp Ser Asp Ser Ser Ala Phe Val Ser Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Ser Ala Thr Thr Tyr Tyr Tyr Tyr Met Cys
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Cys Thr Tyr Thr Gly Asp Gly Ala Thr Tyr Tyr Ala Thr Trp Ala
1               5                   10                  15

Lys Gly

<210> SEQ ID NO 31
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 31

Ala Arg Ser Ala Asp Asn Ser Ile Tyr Tyr Gly Tyr Phe Asn Leu
1               5                   10                  15

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Phe Ser Leu Ser Asn Asn Ala Ile Ser
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ser Ile Tyr Gly Ser Gly Asn Thr Tyr Tyr Ala Thr Trp Ala Lys
1               5                   10                  15

Gly

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Arg Glu Gly Ala Gly Ser Ser Trp Gly Phe Asn Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Ser Leu Asn Asn Asn Ala Ile Ser
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Ile Tyr Gly Thr Gly Asn Thr Tyr Tyr Ala Thr Trp Ala Lys
1               5                   10                  15

-continued

Gly

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Thr Glu Gly Ala Gly Ser Ile Trp Gly Phe Asn Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ser Leu Ser Asn Tyr Asp Met Thr
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Val Ile Ser Ser Gly Asp Asn Thr Asn Tyr Ala Arg Trp Ala Lys
1               5                   10                  15

Gly

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Ile Leu Tyr Asn Lys Gly Arg Tyr Tyr Phe Thr Phe
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Phe Ser Leu Ser Asn Ile Tyr Val Met Cys
1               5                   10

<210> SEQ ID NO 42
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 42

Ala Cys Ile Gly Thr Gly Ser Gly Asp Thr Asp Tyr Ala Thr Trp Ala
1               5                   10                  15

Lys Gly

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Arg Asp Pro Gly Ala Gly Thr Trp Asn Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Phe Ser Phe Ser Ser Ala Tyr Asp Met Cys
1               5                   10

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Cys Leu Tyr Thr Val Ser Ser Asp Ser Ile Tyr Tyr Ala Ser Trp
1               5                   10                  15

Ala Lys Gly

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Asp Gly Asp Tyr Phe Ala Leu
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Gly Ile Asp Leu Ser Ile Tyr Thr Met Ala
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ile Ile Ser Gly Tyr Gly Thr Thr Tyr Tyr Ala Thr Trp Ala Lys
1               5                   10                  15

Gly

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Arg Thr Thr Val Gln Ser Thr Asp Leu
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Ser Leu Ser Ser Tyr Asp Met Ser
1               5                   10

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Tyr Ile Thr Tyr Gly Gly Asn Ile Tyr Tyr Ala Thr Trp Ala Lys
1               5                   10                  15

Gly

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Arg Thr Leu Tyr Thr Gly Gly Arg Tyr Tyr Phe Ser Leu
1               5                   10
```

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gly Phe Ser Phe Ser Asn Asp Ala Ile Cys
1               5                   10

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Cys Ile Tyr Ala Gly Ser Gly Asn Thr Tyr Tyr Ala Ser Trp Ala
1               5                   10                  15

Lys Gly

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Ser Ala Asp Thr Ile Asp Tyr Phe Asn Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Phe Ser Phe Ser Ser Gly Cys Asp Met Cys
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Cys Ile Tyr Thr Gly Ser Gly Ser Thr Tyr Tyr Ala Asn Trp Ala
1               5                   10                  15

Lys Gly

<210> SEQ ID NO 58
<211> LENGTH: 9
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 58

Ala Gly Asp Ser Asp Tyr Leu Gly Leu
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Phe Thr Phe Ser Thr Tyr Ala Met Ser
1               5                   10

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ile Ser Gly Ser Gly Gly Ser Thr Tyr Tyr Ala Asp Ser Val Lys
1               5                   10                  15

Gly

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Lys Arg Gly Thr Tyr Gly Tyr Ser Phe Pro Thr Gly Phe Asp Tyr
1               5                   10                  15

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ala Ser Gln Asp Val Asn Thr Ala Val Ala
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ala Ser Phe Leu Tyr Ser
```

-continued

```
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln His Tyr Thr Thr Pro Pro Thr
1               5

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ser Ser Gln Ser Val Val Asn Ala Asn Asn Leu Ser
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Ala Ser Thr Leu Ala Ser
1               5

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Gly Val Tyr Asp Asp Asp Gly Asp Asn Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Ala Ser Gln Ser Val Tyr Ser Asp Asn Arg Leu Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 69

Ser Thr Ser Ser Leu Ala Ser
1               5

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gly Glu Phe Ile Cys Thr Ser Ala Asp Cys Phe Val
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Cys Ser Gln Ser Val Tyr Gly His Asn Trp Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ala Ser Asn Leu Ala Ser
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gly Tyr Tyr Asn Gly Gly Ser Tyr Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ala Ser Gln Ser Ile Tyr Asn Phe Leu Asn
1               5                   10

<210> SEQ ID NO 75

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Ala Ser Thr Leu Ala Phe
1               5

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Gly Trp Asn Ser Gly Ile Leu Asp Asn Ser
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ala Ser Gln Ser Val Tyr Asn Asn Asn Tyr Leu Ala
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Ala Ser Thr Leu Ala Ser
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Ala Tyr Tyr Ser Gly Gly Ile Tyr Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80
```

```
Gln Ala Ser Glu Ser Ile Tyr Ser Asn Leu Ala
1               5                   10
```

```
<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Ala Ser Thr Leu Ala Ser
1               5
```

```
<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ala Asn His Met Ile Val Ile Tyr Gly Asn Gly
1               5                   10
```

```
<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Ala Ser Glu Asn Ile Tyr Ser Ser Leu Ala
1               5                   10
```

```
<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Thr Leu Ala Ser
1               5
```

```
<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Thr Tyr Tyr Gly Ser Thr Ser Thr Gly Phe Thr
1               5                   10
```

```
<210> SEQ ID NO 86
<211> LENGTH: 13
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 86

Gln Ser Ser Glu Ser Val Tyr Lys Asn Asn Tyr Leu Ser
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Gly Gly Tyr Ser Gly Asn Ile Asn Gly
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Gly Gly Tyr Thr Gly Asn Ile Asn Gly
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ser Ser Gln Ser Ile Ala Asn Ser Asp Glu Leu Ala
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Ala Ser Thr Leu Ala Pro
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gly Thr Val Tyr Asp Ser Gly Trp Tyr Ala Ala
1               5                   10

-continued

```
<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ala Ser Gln Thr Ile Gly Ser Arg Leu Ala
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Ser Tyr Tyr Tyr Thr Ser Thr Ser Tyr Pro Asn Ala
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Ala Ser Gln Asn Ile Gly Gly Tyr Leu Ser
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Thr Tyr Tyr Tyr Ser Gly Ser Ser Arg Tyr Trp Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Ala Ser Gln Asn Ile Tyr Ser Asn Leu Ala
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97
```

```
Gln Ser Tyr Tyr Gly Ala Thr Ser Ser Ser Phe Gly Tyr Gly
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Ser Ser Gln Ser Ile Ala Asn Ser Asn Glu Val Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Ala Ser Thr Leu Ala Ser
1               5

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gly Thr Val Tyr Asp Asn Val Trp Tyr Ala Ala
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Ala Tyr Tyr Arg Asp Pro Thr Thr Ala
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Ala Ser Gln Asn Ile Gly Asn Tyr Leu Ala
1               5                   10

<210> SEQ ID NO 103
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 103

Gln Ser Tyr Tyr Tyr Thr Thr Asp Asp Asn Tyr Arg Ser Trp Ala
1               5                   10                  15

<210> SEQ ID NO 104
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Val Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
            100                 105                 110

Trp Gly Gln Gly Thr Leu Val Thr Val Ser Ser
            115                 120

<210> SEQ ID NO 105
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Ala Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
            100                 105                 110

Trp Gly Gln Gly Thr Leu Val Thr Val Ser Ser
            115                 120
```

-continued

```
<210> SEQ ID NO 106
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Gly Val Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Tyr Pro Thr Gly Phe Asp Tyr
            100                 105                 110

Trp Gly Gln Gly Thr Leu Val Thr Val Ser Ser
        115                 120

<210> SEQ ID NO 107
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Val Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Tyr Pro Thr Gly Phe Asp Tyr
            100                 105                 110

Trp Gly Gln Gly Thr Leu Val Thr Val Ser Ser
        115                 120

<210> SEQ ID NO 108
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Ala Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Tyr Pro Thr Gly Phe Asp Tyr
            100                 105                 110

Trp Gly Gln Gly Thr Leu Val Thr Val Ser Ser
        115                 120

<210> SEQ ID NO 109
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Ala Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Tyr Pro Thr Gly Phe Asp Tyr
            100                 105                 110

Trp Gly Gln Gly Thr Leu Val Thr Val Ser Ser
        115                 120

<210> SEQ ID NO 110
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Gly Val Tyr
            20                  25                  30

Ala Met Ser Trp Val Arg Gln Ala Pro Gly Lys Gly Leu Glu Trp Val
```

-continued

```
                35                  40                  45
Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
                100                 105                 110

Trp Gly Gln Gly Thr Leu Val Thr Val Ser Ser
        115                 120
```

<210> SEQ ID NO 111
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Pro Phe Asp Thr Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
                100                 105                 110

Trp Gly Gln Gly Thr Leu Val Thr Val Ser Ser
        115                 120
```

<210> SEQ ID NO 112
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Pro Phe Gly Thr Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                    85               90              95

Ala Lys Arg Gly Thr Tyr Gly Tyr Ser Phe Pro Thr Gly Phe Asp Tyr
            100             105             110

Trp Gly Gln Gly Thr Leu Val Thr Val Ser Ser
        115             120

<210> SEQ ID NO 113
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Ser Val Glu Glu Ser Gly Gly Arg Leu Val Thr Pro Gly Thr Pro
1               5                   10              15

Leu Thr Leu Thr Cys Thr Ala Ser Gly Phe Ser Leu Ser Arg Tyr Tyr
            20              25              30

Val Thr Trp Val Arg Gln Ala Pro Gly Lys Gly Leu Glu Trp Ile Gly
        35              40              45

Ile Ile Tyr Ile Ser Gly Thr Thr Tyr Tyr Ala Thr Trp Ala Lys Gly
    50              55              60

Arg Phe Thr Ile Ser Lys Ser Ala Thr Thr Val Asp Leu Arg Ile Ala
65              70              75              80

Ser Pro Thr Thr Glu Asp Thr Ala Thr Tyr Phe Cys Ala Ala Ala Trp
            85              90              95

Pro Val Gly Thr Tyr Val Leu Pro Leu Trp Gly Pro Gly Thr Leu Val
            100             105             110

Thr Val Ser Ser
        115

<210> SEQ ID NO 114
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Ser Val Glu Glu Ser Gly Gly Arg Leu Val Thr Pro Gly Thr Pro
1               5                   10              15

Leu Thr Leu Thr Cys Thr Ala Ser Gly Phe Ser Leu Ser Ser Tyr Tyr
            20              25              30

Met Ser Trp Val Arg Gln Ala Pro Gly Lys Gly Leu Glu Trp Ile Gly
        35              40              45

Phe Ile Ser Lys Thr Ala Ile Thr Tyr Tyr Ala Ser Trp Ala Arg Gly
    50              55              60

Arg Phe Thr Ile Ser Lys Thr Ser Thr Ala Val Asp Leu Lys Ile Thr
65              70              75              80

Ser Pro Thr Thr Glu Asp Thr Ala Thr Tyr Phe Cys Ala Arg Val Asp
            85              90              95

Ala Tyr Ser Ala Gly Asp Leu Trp Gly Pro Gly Thr Leu Val Thr Val
            100             105             110

Ser Ser

<210> SEQ ID NO 115
```

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Asn Asn Tyr Trp
            20                  25                  30

Ile Cys Trp Ile Arg Gln Ala Pro Gly Lys Gly Leu Glu Trp Val Ala
        35                  40                  45

Cys Ile Tyr Ser Pro Ser Gly Asp Ile Lys Tyr Tyr Ala Asn Trp Ala
    50                  55                  60

Lys Gly Arg Phe Thr Val Ser Lys Thr Ser Thr Thr Val Thr Leu
65                  70                  75                  80

Gln Met Thr Ser Leu Thr Gly Ala Asp Thr Ala Thr Tyr Phe Cys Ala
                85                  90                  95

Arg Glu Leu Ser Gly Ser Ser Tyr Glu Gly Tyr Phe Glu Ser Trp Gly
            100                 105                 110

Pro Gly Thr Leu Val Thr Val Ser Ser
        115                 120

<210> SEQ ID NO 116
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser Tyr Ala
            20                  25                  30

Met Gly Trp Val Arg Gln Ala Pro Gly Lys Gly Leu Lys Tyr Ile Gly
        35                  40                  45

Ile Met Thr Ser Gly Gly Asn Ile Tyr Tyr Ala Asn Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Arg Glu Arg
                85                  90                  95

Glu Phe Tyr Gly Gly Gly Thr Ser Gly Ser Arg Leu Asp Leu Trp Gly
            100                 105                 110

Gln Gly Thr Leu Val Thr Val Ser Ser
        115                 120

<210> SEQ ID NO 117
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117
```

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Arg Tyr
            20                  25                  30

Trp Ile Cys Trp Val Arg Gln Ala Pro Gly Lys Gly Leu Glu Trp Ile
        35                  40                  45

Ala Cys Ile Val Ala Gly Thr Thr Asn Thr Tyr Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Gly Asp Pro Arg Thr Gly Ser Asn Val Gly Tyr Phe Asn Leu Trp Gly
            100                 105                 110

Pro Gly Thr Leu Val Thr Val Ser Ser
            115                 120

<210> SEQ ID NO 118
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Gly
            20                  25                  30

Val Ser Trp Val Arg Gln Ala Pro Gly Lys Gly Leu Glu Trp Ile Gly
        35                  40                  45

Tyr Ile Leu Thr Ser Gly Gly Thr Tyr Tyr Ala Asn Trp Ala Gln Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Gly Arg Pro Lys
                85                  90                  95

Asp Ser Asp Ser Ser Ala Phe Val Ser Leu Trp Gly Pro Gly Thr Leu
            100                 105                 110

Val Thr Val Ser Ser
        115

<210> SEQ ID NO 119
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Ala Thr Thr Tyr Tyr
            20                  25                  30

Tyr Tyr Met Cys Trp Val Arg Gln Ala Pro Gly Lys Gly Leu Glu Trp
            35                  40                  45
```

-continued

```
Ile Ala Cys Thr Tyr Thr Gly Asp Gly Ala Thr Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Ala Asp Asn Ser Ile Tyr Tyr Gly Tyr Phe Asn Leu Trp
                100                 105                 110

Gly Pro Gly Thr Leu Val Thr Val Ser Ser
        115                 120
```

```
<210> SEQ ID NO 120
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Asn Ala
                20                  25                  30

Ile Ser Trp Val Arg Gln Ala Pro Gly Lys Gly Leu Gln Trp Ile Gly
            35                  40                  45

Ser Ile Tyr Gly Ser Gly Asn Thr Tyr Tyr Ala Thr Trp Ala Lys Gly
        50                  55                  60

Arg Phe Thr Val Ser Lys Thr Ser Thr Thr Val Asp Leu Lys Ile Asn
65                  70                  75                  80

Ser Pro Thr Thr Glu Asp Thr Ala Thr Tyr Phe Cys Ala Arg Glu Gly
                85                  90                  95

Ala Gly Ser Ser Trp Gly Phe Asn Leu Trp Gly Pro Gly Thr Leu Val
                100                 105                 110

Thr Val Ser Ser
        115
```

```
<210> SEQ ID NO 121
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Asn Ala
                20                  25                  30

Ile Ser Trp Val Arg Gln Ala Pro Gly Lys Gly Leu Gln Trp Ile Gly
            35                  40                  45

Ser Ile Tyr Gly Thr Gly Asn Thr Tyr Tyr Ala Thr Trp Ala Lys Gly
        50                  55                  60

Arg Phe Ser Val Ser Lys Thr Ser Thr Thr Val Asp Leu Lys Ile Asn
65                  70                  75                  80

Ser Pro Thr Thr Glu Asp Thr Ala Thr Tyr Phe Cys Ala Thr Glu Gly
                85                  90                  95
```

-continued

Ala Gly Ser Ile Trp Gly Phe Asn Leu Trp Gly Pro Gly Thr Leu Val
            100                 105                 110

Thr Val Ser Ser
        115

<210> SEQ ID NO 122
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asp
            20                  25                  30

Met Thr Trp Val Arg Gln Ala Pro Gly Arg Gly Leu Glu Trp Ile Gly
        35                  40                  45

Val Ile Ser Ser Gly Asp Asn Thr Asn Tyr Ala Arg Trp Ala Lys Gly
    50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Ile
                85                  90                  95

Leu Tyr Asn Lys Gly Arg Tyr Tyr Phe Thr Phe Trp Gly Pro Gly Thr
            100                 105                 110

Leu Val Thr Val Ser Ser
        115

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Glu Leu Val Glu Ser Gly Gly Gly Leu Phe Gln Pro Gly Gly Ser
1               5                   10                  15

Leu Ala Leu Thr Cys Lys Ala Ser Gly Phe Ser Leu Ser Asn Ile Tyr
            20                  25                  30

Val Met Cys Trp Val Arg Gln Ala Pro Gly Lys Gly Leu Glu Trp Ile
        35                  40                  45

Ala Cys Ile Gly Thr Gly Ser Gly Asp Thr Asp Tyr Ala Thr Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Pro Gly Ala Gly Thr Trp Asn Leu Trp Gly Pro Gly Thr Leu
            100                 105                 110

Val Thr Val Ser Ser
        115

<210> SEQ ID NO 124
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Glu Gln Leu Glu Glu Ser Gly Gly Asp Leu Val Lys Pro Gly Ala
1               5                   10                  15

Ser Leu Thr Leu Thr Cys Lys Ala Ser Gly Phe Ser Phe Ser Ser Ala
            20                  25                  30

Tyr Asp Met Cys Trp Val Arg Gln Ala Pro Gly Lys Gly Leu Glu Trp
        35                  40                  45

Val Ala Cys Leu Tyr Thr Val Ser Ser Asp Ser Ile Tyr Tyr Ala Ser
    50                  55                  60

Trp Ala Lys Gly Arg Phe Thr Ile Ser Arg Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Gly Asp Tyr Phe Ala Leu Trp Gly Pro Gly Thr Leu
            100                 105                 110

Val Thr Val Ser Ser
        115

<210> SEQ ID NO 125
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ile Tyr Thr
            20                  25                  30

Met Ala Trp Val Arg Gln Ala Pro Gly Lys Gly Leu Glu Tyr Ile Gly
            35                  40                  45

Ile Ile Ser Gly Tyr Gly Thr Thr Tyr Tyr Ala Thr Trp Ala Lys Gly
    50                  55                  60

Arg Phe Ile Val Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Thr Thr
                85                  90                  95

Val Gln Ser Thr Asp Leu Trp Gly Pro Gly Thr Leu Val Thr Val Ser
            100                 105                 110

Ser

<210> SEQ ID NO 126
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Arg Ser Leu Glu Glu Ser Gly Gly Arg Leu Val Thr Pro Gly Thr Pro
1               5                   10                  15
```

```
Leu Thr Leu Thr Cys Thr Thr Ser Gly Phe Ser Leu Ser Ser Tyr Asp
            20                  25                  30

Met Ser Trp Val Arg Gln Ala Pro Gly Lys Gly Leu Glu Trp Ile Gly
        35                  40                  45

Tyr Ile Thr Tyr Gly Gly Asn Ile Tyr Tyr Ala Thr Trp Ala Lys Gly
    50                  55                  60

Arg Phe Thr Thr Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Thr Leu
                85                  90                  95

Tyr Thr Gly Gly Arg Tyr Tyr Phe Ser Leu Trp Gly Pro Gly Thr Leu
                100                 105                 110

Val Thr Val Ser Ser
            115
```

```
<210> SEQ ID NO 127
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Asn Asp
            20                  25                  30

Ala Ile Cys Trp Val Arg Gln Ala Pro Gly Lys Gly Leu Glu Trp Ile
        35                  40                  45

Ala Cys Ile Tyr Ala Gly Ser Gly Asn Thr Tyr Tyr Ala Ser Trp Ala
    50                  55                  60

Lys Gly Arg Phe Ser Ile Ser Lys Thr Ser Ser Thr Thr Val Thr Leu
65                  70                  75                  80

Gln Met Thr Ser Leu Thr Val Ala Asp Thr Ala Thr Tyr Phe Cys Ala
                85                  90                  95

Ser Ala Asp Thr Ile Asp Tyr Phe Asn Leu Trp Gly Pro Gly Thr Leu
                100                 105                 110

Val Thr Val Ser Ser
            115
```

```
<210> SEQ ID NO 128
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Ser Leu Glu Glu Ser Gly Gly Gly Leu Val Lys Pro Gly Ala Ser
1               5                   10                  15

Leu Thr Leu Thr Cys Lys Ala Ser Gly Phe Ser Phe Ser Ser Gly Cys
            20                  25                  30

Asp Met Cys Trp Val Arg Gln Ala Pro Gly Lys Gly Leu Glu Trp Ile
        35                  40                  45

Ser Cys Ile Tyr Thr Gly Ser Gly Ser Thr Tyr Tyr Ala Asn Trp Ala
    50                  55                  60
```

```
Lys Gly Arg Phe Thr Ile Ser Arg Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Gly Asp Ser Asp Tyr Leu Gly Leu Trp Gly Pro Gly Thr Leu Val Thr
            100                 105                 110

Val Ser Ser
        115

<210> SEQ ID NO 129
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Gly Tyr Ser Phe Pro Thr Gly Phe Asp Tyr
            100                 105                 110

Trp Gly Gln Gly Thr Leu Val Thr Val Ser Ser
        115                 120

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

-continued

```
<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys
            100                 105

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105
```

<210> SEQ ID NO 139
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Val Asn Ala
                20                  25                  30

Asn Asn Leu Ser Trp Tyr Gln Gln Lys Pro Gly Gln Pro Pro Lys Leu
            35                  40                  45

Leu Ile Tyr Leu Ala Ser Thr Leu Ala Ser Gly Val Pro Ser Arg Phe
    50                  55                  60

Ser Gly Ser Gly Ser Gly Thr Gln Phe Thr Leu Thr Ile Ser Ser Val
65                  70                  75                  80

Gln Ser Asp Asp Ala Ala Thr Tyr Tyr Cys Leu Gly Val Tyr Asp Asp
                85                  90                  95

Asp Gly Asp Asn Ala Phe Gly Gly Gly Thr Glu Val Val Val Lys
            100                 105                 110
```

<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Ser Asp
                20                  25                  30

Asn Arg Leu Ser Trp Phe Gln Gln Lys Ser Gly Gln Pro Pro Lys Leu
            35                  40                  45

Leu Ile Tyr Ser Thr Ser Ser Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Ser Asp Asp Ala Ala Ser Tyr Tyr Cys Gln Gly Glu Phe Ile Cys
```

-continued

```
                        85                  90                  95

Thr Ser Ala Asp Cys Phe Val Phe Gly Gly Gly Thr Glu Val Val Val
                100                 105                 110

Lys

<210> SEQ ID NO 141
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Gln Val Leu Thr Gln Thr Pro Ser Ser Val Ser Ala Ala Val Gly
1               5                   10                  15

Gly Thr Val Thr Ile Asn Cys Gln Cys Ser Gln Ser Val Tyr Gly His
                20                  25                  30

Asn Trp Leu Ala Trp Tyr Gln His Lys Pro Gly Gln Pro Pro Lys Leu
            35                  40                  45

Leu Met Tyr Arg Ala Ser Asn Leu Ala Ser Gly Val Pro Ser Arg Phe
        50                  55                  60

Lys Gly Ser Gly Ser Gly Ser Gln Phe Thr Leu Thr Ile Gly Glu Val
65                  70                  75                  80

Gln Ser Asp Asp Ala Ala Thr Tyr Tyr Cys Gln Gly Tyr Tyr Asn Gly
                85                  90                  95

Gly Ser Tyr Ala Phe Gly Gly Gly Thr Glu Val Val Val Arg
                100                 105                 110

<210> SEQ ID NO 142
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Tyr Asp Met Thr Gln Thr Pro Ala Ser Val Glu Ala Ala Val Gly
1               5                   10                  15

Gly Thr Val Thr Ile Lys Cys Gln Ala Ser Gln Ser Ile Tyr Asn Phe
                20                  25                  30

Leu Asn Trp Tyr Gln Gln Lys Pro Gly Gln Pro Pro Lys Leu Leu Ile
            35                  40                  45

Tyr Tyr Ala Ser Thr Leu Ala Phe Gly Val Pro Ser Arg Phe Lys Gly
        50                  55                  60

Ser Gly Ser Gly Thr Glu Tyr Thr Leu Thr Ile Ser Gly Val Glu Ser
65                  70                  75                  80

Ala Asp Ala Ala Thr Tyr Tyr Cys Gln Gln Gly Trp Asn Ser Gly Ile
                85                  90                  95

Leu Asp Asn Ser Phe Gly Gly Gly Thr Glu Val Val Val Lys
                100                 105                 110

<210> SEQ ID NO 143
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 143

```
Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Asn Asn
            20                  25                  30

Asn Tyr Leu Ala Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Glu Val
65                  70                  75                  80

Gln Ser Asp Asp Ala Ala Thr Tyr Tyr Cys Gln Ala Tyr Tyr Ser Gly
                85                  90                  95

Gly Ile Tyr Ala Phe Gly Gly Gly Thr Glu Val Val Val Lys
                100                 105                 110
```

<210> SEQ ID NO 144
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Ala Asp Val Val Met Thr Gln Thr Pro Ala Ser Val Ser Glu Pro Val
1               5                   10                  15

Gly Gly Thr Val Thr Ile Asn Cys Gln Ala Ser Glu Ser Ile Tyr Ser
            20                  25                  30

Asn Leu Ala Trp Tyr Gln Gln Lys Pro Gly Gln Pro Pro Lys Leu Leu
        35                  40                  45

Ile Tyr Lys Ala Ser Thr Leu Ala Ser Gly Val Ser Ser Arg Phe Lys
    50                  55                  60

Gly Ser Gly Ser Gly Thr Glu Phe Thr Leu Thr Ile Ser Asp Leu Glu
65                  70                  75                  80

Ser Ala Asp Ala Ala Thr Tyr Tyr Cys Gln Ala Asn His Met Ile Val
                85                  90                  95

Ile Tyr Gly Asn Gly Phe Gly Gly Gly Thr Glu Val Val Val Lys
                100                 105                 110
```

<210> SEQ ID NO 145
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Ala Phe Glu Leu Thr Gln Thr Pro Phe Ser Val Ser Glu Pro Val Gly
1               5                   10                  15

Gly Thr Val Thr Ile Asn Cys Gln Ala Ser Glu Asn Ile Tyr Ser Ser
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60
```

-continued

```
Ser Gly Ser Gly Thr Glu Phe Thr Leu Thr Ile Ser Gly Val Gln Ser
65                  70                  75                  80

Asp Asp Ala Ala Thr Tyr Tyr Cys Gln Thr Tyr Tyr Gly Ser Thr Ser
                85                  90                  95

Thr Gly Phe Thr Phe Gly Gly Gly Thr Glu Val Val Val Lys
            100                 105                 110
```

```
<210> SEQ ID NO 146
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146
```

```
Ala Gln Val Leu Thr Gln Thr Ala Ser Ser Val Ser Ala Ala Val Gly
1               5                   10                  15

Gly Thr Val Thr Ile Ser Cys Gln Ser Ser Glu Ser Val Tyr Lys Asn
                20                  25                  30

Asn Tyr Leu Ser Trp Tyr Gln Gln Lys Pro Gly Gln Pro Leu Lys Cys
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Ser Asp Asp Ala Ala Thr Tyr Tyr Cys Ala Gly Gly Tyr Ser Gly
                85                  90                  95

Asn Ile Asn Gly Phe Gly Gly Gly Thr Glu Val Val Val Lys
            100                 105                 110
```

```
<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147
```

```
Ala Gln Val Leu Thr Gln Thr Ala Ser Ser Val Ser Ala Ala Val Gly
1               5                   10                  15

Gly Thr Val Thr Ile Ser Cys Gln Ser Ser Glu Ser Val Tyr Lys Asn
                20                  25                  30

Asn Tyr Leu Ser Trp Tyr Gln Gln Lys Pro Gly Gln Pro Pro Lys Gly
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Ser Asp Asp Ala Ala Thr Tyr Tyr Cys Ala Gly Gly Tyr Thr Gly
                85                  90                  95

Asn Ile Asn Gly Phe Gly Gly Gly Thr Glu Val Val Val Lys
            100                 105                 110
```

```
<210> SEQ ID NO 148
<211> LENGTH: 112
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 148

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Ile Ala Asn Ser
                20                  25                  30

Asp Glu Leu Ala Trp Tyr Gln Gln Lys Pro Gly Gln Pro Pro Lys Leu
            35                  40                  45

Leu Ile Tyr Asp Ala Ser Thr Leu Ala Pro Gly Val Pro Ser Arg Phe
        50                  55                  60

Ser Gly Ser Gly Ser Gly Thr Gln Phe Thr Leu Thr Ile Ser Gly Val
65                  70                  75                  80

Gln Ser Asp Asp Ala Ala Thr Tyr Tyr Cys Gln Gly Thr Val Tyr Asp
                85                  90                  95

Ser Gly Trp Tyr Ala Ala Phe Gly Gly Gly Thr Glu Val Val Val Lys
            100                 105                 110
```

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 149

```
Ala Asp Ile Val Met Thr Gln Thr Pro Ser Ser Val Glu Ala Ala Val
1               5                   10                  15

Gly Gly Thr Val Thr Ile Lys Cys Gln Ala Ser Gln Thr Ile Gly Ser
                20                  25                  30

Arg Leu Ala Trp Tyr Gln Gln Lys Pro Gly Gln Pro Pro Lys Leu Leu
            35                  40                  45

Ile Tyr Ser Ala Ser Thr Leu Ala Ser Gly Val Ser Ser Arg Phe Lys
        50                  55                  60

Gly Ser Gly Ser Gly Thr Gln Phe Thr Leu Thr Ile Ser Asp Leu Asp
65                  70                  75                  80

Ser Ala Asp Ala Ala Thr Tyr Tyr Cys Gln Ser Tyr Tyr Tyr Thr Ser
                85                  90                  95

Thr Ser Tyr Pro Asn Ala Phe Gly Gly Gly Thr Glu Val Val Val Lys
            100                 105                 110
```

<210> SEQ ID NO 150
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 150

```
Ala Asp Ile Val Met Thr His Thr Pro Ala Ser Val Glu Ala Ala Val
1               5                   10                  15

Gly Gly Thr Val Thr Ile Lys Cys Gln Ala Ser Gln Asn Ile Gly Gly
                20                  25                  30

Tyr Leu Ser Trp Tyr Gln Gln Lys Pro Gly Gln Arg Pro Lys Leu Leu
            35                  40                  45

Ile Tyr Arg Ala Ser Thr Leu Ala Ser Gly Val Pro Ser Arg Phe Lys
```

-continued

```
            50                 55                 60

Gly Ser Gly Ser Gly Thr Gln Phe Thr Leu Thr Ile Ser Asp Leu Glu
65                  70                  75                  80

Ser Ala Asp Ala Ala Thr Tyr Tyr Cys Gln Thr Tyr Tyr Ser Gly
                85                  90                  95

Ser Ser Arg Tyr Trp Ala Phe Gly Gly Gly Thr Glu Val Val Val Lys
                100                 105                 110

<210> SEQ ID NO 151
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ala Asp Ile Val Met Thr Gln Thr Pro Ala Ser Val Glu Ala Ala Val
1               5                   10                  15

Gly Gly Thr Val Thr Ile Asn Cys Gln Ala Ser Gln Asn Ile Tyr Ser
                20                  25                  30

Asn Leu Ala Trp Tyr Gln Gln Lys Pro Gly Gln Arg Pro Lys Leu Leu
        35                  40                  45

Ile Tyr Lys Ala Ser Thr Leu Ala Ser Gly Val Ser Ser Arg Phe Lys
        50                  55                  60

Gly Ser Gly Ser Gly Thr Glu Phe Thr Leu Thr Ile Ser Asp Leu Ala
65                  70                  75                  80

Ser Ala Asp Ala Ala Thr Tyr Tyr Cys Gln Ser Tyr Tyr Gly Ala Thr
                85                  90                  95

Ser Ser Ser Phe Gly Tyr Gly Phe Gly Gly Gly Thr Glu Val Val Val
                100                 105                 110

Lys

<210> SEQ ID NO 152
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ala Gln Val Leu Thr Gln Thr Pro Ser Ser Val Ser Ala Val Val Gly
1               5                   10                  15

Gly Thr Val Thr Ile Asn Cys Gln Ser Ser Gln Ser Ile Ala Asn Ser
                20                  25                  30

Asn Glu Val Ala Trp Tyr Gln Gln Lys Leu Gly Gln Pro Pro Lys Leu
        35                  40                  45

Leu Ile Tyr Asp Ala Ser Thr Leu Ala Ser Gly Val Pro Ser Arg Phe
        50                  55                  60

Ser Gly Ser Gly Ser Gly Thr Gln Phe Thr Leu Ile Ile Ser Gly Val
65                  70                  75                  80

Gln Ser Asp Asp Ala Ala Thr Tyr Tyr Cys Gln Gly Thr Val Tyr Asp
                85                  90                  95

Asn Val Trp Tyr Ala Ala Phe Gly Gly Gly Thr Glu Val Val Val Lys
                100                 105                 110

<210> SEQ ID NO 153
```

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Asn Asn
            20                  25                  30

Asn Tyr Leu Ala Trp Tyr Gln Gln Lys Pro Gly Gln Pro Pro Lys Leu
        35                  40                  45

Leu Ile Tyr Arg Ala Ser Asn Leu Ala Ser Gly Val Pro Ser Arg Phe
    50                  55                  60

Ser Ala Ser Gly Ser Gly Thr Gln Phe Thr Leu Thr Ile Ser Glu Val
65                  70                  75                  80

Gln Ser Asp Asp Ala Ala Thr Tyr Tyr Cys Gln Ala Tyr Tyr Arg Asp
                85                  90                  95

Pro Thr Thr Ala Phe Gly Gly Gly Thr Glu Val Val Val Lys
            100                 105                 110

<210> SEQ ID NO 154
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ala Asp Ile Val Met Thr Gln Thr Pro Ser Ser Val Glu Ala Ala Val
1               5                   10                  15

Gly Gly Thr Val Thr Ile Lys Cys Gln Ala Ser Gln Asn Ile Gly Asn
            20                  25                  30

Tyr Leu Ala Trp Tyr Gln Gln Lys Pro Gly Gln Pro Pro Lys Val Leu
        35                  40                  45

Ile Tyr Arg Ala Ser Thr Leu Ala Ser Gly Val Pro Ser Arg Phe Lys
    50                  55                  60

Gly Ser Gly Ser Gly Thr His Phe Thr Leu Thr Ile Ser Asp Leu Glu
65                  70                  75                  80

Ser Ala Asp Ala Ala Thr Tyr Tyr Cys Gln Ser Tyr Tyr Tyr Thr Thr
                85                  90                  95

Asp Asp Asn Tyr Arg Ser Trp Ala Phe Gly Gly Gly Thr Glu Val Val
            100                 105                 110

Val Lys

<210> SEQ ID NO 155
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
```

-continued

```
                20              25              30

Val Ala Trp Tyr Gln Gln Lys Pro Gly Lys Ala Pro Lys Leu Leu Ile
        35              40              45

Tyr Ser Ala Ser Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln His Tyr Thr Thr Pro Pro
                85              90              95

Thr Phe Gly Gln Gly Thr Lys Val Glu Ile Lys
            100             105

<210> SEQ ID NO 156
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Thr Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Arg Gly Thr Tyr Gly Tyr Ser Phe Pro Thr Gly Phe Asp Tyr
            100             105             110

Trp Gly Gln Gly Thr Leu Val Thr Val Ser Ser Ala Ser Thr Lys Gly
        115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270
```

```
Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 157
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Val Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
                245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
                325             330             335

Pro Ile Glu Lys Thr Ile Ser Lys Ala Lys Gly Gln Pro Arg Glu Pro
                340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
                405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450

<210> SEQ ID NO 158
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Pro Phe Asp Ala Tyr
            20              25              30

Ala Met Ser Trp Val Arg Gln Ala Pro Gly Lys Gly Leu Glu Trp Val
            35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
```

```
65              70              75              80

Leu Gln Met Asn Ser Leu Arg Ala Glu Asp Thr Ala Val Tyr Tyr Cys
            85              90              95

Ala Lys Arg Gly Thr Tyr Ala Tyr Ser Phe Pro Thr Gly Phe Asp Tyr
            100             105             110

Trp Gly Gln Gly Thr Leu Val Thr Val Ser Ser Ala Ser Thr Lys Gly
            115             120             125

Pro Ser Val Phe Pro Leu Ala Pro Ser Ser Lys Ser Thr Ser Gly Gly
            130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Gln Ser Ser Gly Leu Tyr Ser Leu Ser Ser Val Val
                180             185             190

Thr Val Pro Ser Ser Ser Leu Gly Thr Gln Thr Tyr Ile Cys Asn Val
                195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
                245             250             255

Leu Met Ile Ser Arg Thr Pro Glu Val Thr Cys Val Val Val Asp Val
                260             265             270

Ser His Glu Asp Pro Glu Val Lys Phe Asn Trp Tyr Val Asp Gly Val
                275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
                325             330             335

Pro Ile Glu Lys Thr Ile Ser Lys Ala Lys Gly Gln Pro Arg Glu Pro
                340             345             350

Gln Val Tyr Thr Leu Pro Pro Ser Arg Asp Glu Leu Thr Lys Asn Gln
                355             360             365

Val Ser Leu Thr Cys Leu Val Lys Gly Phe Tyr Pro Ser Asp Ile Ala
                370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
                405             410             415

Thr Val Asp Lys Ser Arg Trp Gln Gln Gly Asn Val Phe Ser Cys Ser
                420             425             430

Val Met His Glu Ala Leu His Asn His Tyr Thr Gln Lys Ser Leu Ser
            435             440             445

Leu Ser Pro Gly Lys
        450

<210> SEQ ID NO 159
<211> LENGTH: 453
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Gly Val Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Tyr Pro Thr Gly Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

-continued

```
385                390                395                400

Pro Pro Val Leu Asp Ser Asp Gly Ser Phe Phe Leu Tyr Ser Lys Leu
            405                410                415

Thr Val Asp Lys Ser Arg Trp Gln Gln Gly Asn Val Phe Ser Cys Ser
            420                425                430

Val Met His Glu Ala Leu His Asn His Tyr Thr Gln Lys Ser Leu Ser
            435                440                445

Leu Ser Pro Gly Lys
        450

<210> SEQ ID NO 160
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Pro Phe Asp Val Tyr
            20                 25                 30

Ala Met Ser Trp Val Arg Gln Ala Pro Gly Lys Gly Leu Glu Trp Val
            35                 40                 45

Ser Ala Ile Ser Gly Ser Gly Gly Ser Thr Phe Tyr Ala Asp Ser Val
        50                 55                 60

Lys Gly Arg Phe Thr Ile Ser Arg Asp Asn Ser Lys Asn Thr Leu Tyr
65                 70                 75                 80

Leu Gln Met Asn Ser Leu Arg Ala Glu Asp Thr Ala Val Tyr Tyr Cys
                85                 90                 95

Ala Lys Arg Gly Thr Tyr Ala Tyr Ser Tyr Pro Thr Gly Phe Asp Tyr
            100                105                110

Trp Gly Gln Gly Thr Leu Val Thr Val Ser Ser Ala Ser Thr Lys Gly
            115                120                125

Pro Ser Val Phe Pro Leu Ala Pro Ser Ser Lys Ser Thr Ser Gly Gly
        130                135                140

Thr Ala Ala Leu Gly Cys Leu Val Lys Asp Tyr Phe Pro Glu Pro Val
145                150                155                160

Thr Val Ser Trp Asn Ser Gly Ala Leu Thr Ser Gly Val His Thr Phe
                165                170                175

Pro Ala Val Leu Gln Ser Ser Gly Leu Tyr Ser Leu Ser Ser Val Val
            180                185                190

Thr Val Pro Ser Ser Ser Leu Gly Thr Gln Thr Tyr Ile Cys Asn Val
            195                200                205

Asn His Lys Pro Ser Asn Thr Lys Val Asp Lys Lys Val Glu Pro Lys
        210                215                220

Ser Cys Asp Lys Thr His Thr Cys Pro Pro Cys Pro Ala Pro Glu Leu
225                230                235                240

Leu Gly Gly Pro Ser Val Phe Leu Phe Pro Pro Lys Pro Lys Asp Thr
                245                250                255

Leu Met Ile Ser Arg Thr Pro Glu Val Thr Cys Val Val Val Asp Val
            260                265                270

Ser His Glu Asp Pro Glu Val Lys Phe Asn Trp Tyr Val Asp Gly Val
        275                280                285
```

```
Glu Val His Asn Ala Lys Thr Lys Pro Arg Glu Glu Gln Tyr Asn Ser
    290                 295             300

Thr Tyr Arg Val Val Ser Val Leu Thr Val Leu His Gln Asp Trp Leu
305                 310             315                 320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395                 400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
        435             440             445

Leu Ser Pro Gly Lys
    450
```

```
<210> SEQ ID NO 161
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161
```

```
Glu Val Gln Leu Leu Glu Ser Gly Gly Gly Leu Val Gln Pro Gly Gly
1               5               10              15

Ser Leu Arg Leu Ser Cys Ala Ala Ser Gly Phe Pro Phe Asp Ala Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Lys Arg Gly Thr Tyr Ala Tyr Ser Tyr Pro Thr Gly Phe Asp Tyr
            100             105             110

Trp Gly Gln Gly Thr Leu Val Thr Val Ser Ser Ala Ser Thr Lys Gly
        115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
        180             185             190
```

-continued

```
Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450
```

```
<210> SEQ ID NO 162
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Asp Ala Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                      85                  90                  95
Ala Lys Arg Gly Thr Tyr Ala Tyr Ser Tyr Pro Thr Gly Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450
```

<210> SEQ ID NO 163
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 163

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Gly Val Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
```

-continued

```
                    405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 164
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Pro Phe Asp Thr Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Arg Gly Thr Tyr Ala Tyr Ser Phe Pro Thr Gly Phe Asp Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Lys Val Glu Pro Lys
        210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450
```

```
<210> SEQ ID NO 165
<211> LENGTH: 453
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 165
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Gly Thr Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Gly Tyr Ser Phe Pro Thr Gly Phe Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205
```

```
Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
        275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
        355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
        435             440             445

Leu Ser Pro Gly Lys
    450
```

```
<210> SEQ ID NO 166
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166
```

```
Gln Ser Val Glu Glu Ser Gly Gly Arg Leu Val Thr Pro Gly Thr Pro
1               5               10              15

Leu Thr Leu Thr Cys Thr Ala Ser Gly Phe Ser Leu Ser Arg Tyr Tyr
            20              25              30

Val Thr Trp Val Arg Gln Ala Pro Gly Lys Gly Leu Glu Trp Ile Gly
        35              40              45

Ile Ile Tyr Ile Ser Gly Thr Thr Tyr Ala Thr Trp Ala Lys Gly
    50              55              60

Arg Phe Thr Ile Ser Lys Ser Ala Thr Thr Val Asp Leu Arg Ile Ala
65              70              75              80

Ser Pro Thr Thr Glu Asp Thr Ala Thr Tyr Phe Cys Ala Ala Ala Trp
            85              90              95

Pro Val Gly Thr Tyr Val Leu Pro Leu Trp Gly Pro Gly Thr Leu Val
```

-continued

```
              100                 105                 110
Thr Val Ser Ser Ala Ser Thr Lys Gly Pro Ser Val Phe Pro Leu Ala
          115                 120                 125

Pro Ser Ser Lys Ser Thr Ser Gly Gly Thr Ala Ala Leu Gly Cys Leu
      130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
              165                 170                 175

Gly Leu Tyr Ser Leu Ser Ser Val Val Thr Val Pro Ser Ser Ser Leu
          180                 185                 190

Gly Thr Gln Thr Tyr Ile Cys Asn Val Asn His Lys Pro Ser Asn Thr
          195                 200                 205

Lys Val Asp Lys Lys Val Glu Pro Lys Ser Cys Asp Lys Thr His Thr
      210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
              245                 250                 255

Glu Val Thr Cys Val Val Val Asp Val Ser His Glu Asp Pro Glu Val
              260                 265                 270

Lys Phe Asn Trp Tyr Val Asp Gly Val Glu Val His Asn Ala Lys Thr
              275                 280                 285

Lys Pro Arg Glu Glu Gln Tyr Asn Ser Thr Tyr Arg Val Val Ser Val
      290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
              325                 330                 335

Lys Ala Lys Gly Gln Pro Arg Glu Pro Gln Val Tyr Thr Leu Pro Pro
          340                 345                 350

Ser Arg Asp Glu Leu Thr Lys Asn Gln Val Ser Leu Thr Cys Leu Val
          355                 360                 365

Lys Gly Phe Tyr Pro Ser Asp Ile Ala Val Glu Trp Glu Ser Asn Gly
      370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
              405                 410                 415

Gln Gln Gly Asn Val Phe Ser Cys Ser Val Met His Glu Ala Leu His
          420                 425                 430

Asn His Tyr Thr Gln Lys Ser Leu Ser Leu Ser Pro Gly Lys
          435                 440                 445

<210> SEQ ID NO 167
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Ser Val Glu Glu Ser Gly Gly Arg Leu Val Thr Pro Gly Thr Pro
1               5                   10                  15
```

```
Leu Thr Leu Thr Cys Thr Ala Ser Gly Phe Ser Leu Ser Ser Tyr Tyr
        20                  25                  30

Met Ser Trp Val Arg Gln Ala Pro Gly Lys Gly Leu Glu Trp Ile Gly
        35                  40                  45

Phe Ile Ser Lys Thr Ala Ile Thr Tyr Tyr Ala Ser Trp Ala Arg Gly
        50                  55                  60

Arg Phe Thr Ile Ser Lys Thr Ser Thr Ala Val Asp Leu Lys Ile Thr
65                  70                  75                  80

Ser Pro Thr Thr Glu Asp Thr Ala Thr Tyr Phe Cys Ala Arg Val Asp
                85                  90                  95

Ala Tyr Ser Ala Gly Asp Leu Trp Gly Pro Gly Thr Leu Val Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
        210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
```

-continued

```
                435                    440

<210> SEQ ID NO 168
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Asn Asn Tyr Trp
            20                  25                  30

Ile Cys Trp Ile Arg Gln Ala Pro Gly Lys Gly Leu Glu Trp Val Ala
        35                  40                  45

Cys Ile Tyr Ser Pro Ser Gly Asp Ile Lys Tyr Tyr Ala Asn Trp Ala
    50                  55                  60

Lys Gly Arg Phe Thr Val Ser Lys Thr Ser Thr Thr Val Thr Leu
65                  70                  75                  80

Gln Met Thr Ser Leu Thr Gly Ala Asp Thr Ala Thr Tyr Phe Cys Ala
                85                  90                  95

Arg Glu Leu Ser Gly Ser Ser Tyr Glu Gly Tyr Phe Glu Ser Trp Gly
            100                 105                 110

Pro Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Asp Glu Leu Thr Lys Asn Gln Val Ser
        355             360         365

Leu Thr Cys Leu Val Lys Gly Phe Tyr Pro Ser Asp Ile Ala Val Glu
        370             375         380

Trp Glu Ser Asn Gly Gln Pro Glu Asn Asn Tyr Lys Thr Thr Pro Pro
385             390         395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425         430

His Glu Ala Leu His Asn His Tyr Thr Gln Lys Ser Leu Ser Leu Ser
        435             440         445

Pro Gly Lys
    450

<210> SEQ ID NO 169
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Ser Val Glu Glu Ser Gly Gly Arg Leu Val Thr Pro Gly Thr Pro
1           5               10              15

Leu Thr Leu Thr Cys Thr Val Ser Gly Ile Asp Leu Asn Ser Tyr Ala
        20              25              30

Met Gly Trp Val Arg Gln Ala Pro Gly Lys Gly Leu Lys Tyr Ile Gly
        35              40              45

Ile Met Thr Ser Gly Gly Asn Ile Tyr Tyr Ala Asn Trp Ala Lys Gly
    50              55              60

Arg Phe Thr Ile Ser Lys Thr Ser Thr Thr Val Asp Leu Arg Ile Thr
65              70              75              80

Ser Pro Thr Thr Glu Asp Thr Ala Thr Tyr Phe Cys Ala Arg Glu Arg
            85              90              95

Glu Phe Tyr Gly Gly Gly Thr Ser Gly Ser Arg Leu Asp Leu Trp Gly
            100             105             110

Gln Gly Thr Leu Val Thr Val Ser Ser Ala Ser Thr Lys Gly Pro Ser
        115             120             125

Val Phe Pro Leu Ala Pro Ser Ser Lys Ser Thr Ser Gly Gly Thr Ala
    130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
        180             185             190

Pro Ser Ser Ser Leu Gly Thr Gln Thr Tyr Ile Cys Asn Val Asn His
        195             200             205

Lys Pro Ser Asn Thr Lys Val Asp Lys Lys Val Glu Pro Lys Ser Cys
    210             215             220

Asp Lys Thr His Thr Cys Pro Pro Cys Pro Ala Pro Glu Leu Leu Gly
225             230             235             240

Gly Pro Ser Val Phe Leu Phe Pro Pro Lys Pro Lys Asp Thr Leu Met
            245             250             255
```

```
Ile Ser Arg Thr Pro Glu Val Thr Cys Val Val Val Asp Val Ser His
            260                 265             270

Glu Asp Pro Glu Val Lys Phe Asn Trp Tyr Val Asp Gly Val Glu Val
            275                 280             285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

```
<210> SEQ ID NO 170
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Arg Tyr
            20                  25                  30

Trp Ile Cys Trp Val Arg Gln Ala Pro Gly Lys Gly Leu Glu Trp Ile
            35                  40                  45

Ala Cys Ile Val Ala Gly Thr Thr Asn Thr Tyr Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Gly Asp Pro Arg Thr Gly Ser Asn Val Gly Tyr Phe Asn Leu Trp Gly
            100                 105                 110

Pro Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
```

-continued

```
145              150              155              160

Ser Trp Asn Ser Gly Ala Leu Thr Ser Gly Val His Thr Phe Pro Ala
            165              170              175

Val Leu Gln Ser Ser Gly Leu Tyr Ser Leu Ser Ser Val Val Thr Val
            180              185              190

Pro Ser Ser Ser Leu Gly Thr Gln Thr Tyr Ile Cys Asn Val Asn His
            195              200              205

Lys Pro Ser Asn Thr Lys Val Asp Lys Lys Val Glu Pro Lys Ser Cys
    210              215              220

Asp Lys Thr His Thr Cys Pro Pro Cys Pro Ala Pro Glu Leu Leu Gly
225              230              235              240

Gly Pro Ser Val Phe Leu Phe Pro Pro Lys Pro Lys Asp Thr Leu Met
            245              250              255

Ile Ser Arg Thr Pro Glu Val Thr Cys Val Val Val Asp Val Ser His
            260              265              270

Glu Asp Pro Glu Val Lys Phe Asn Trp Tyr Val Asp Gly Val Glu Val
            275              280              285

His Asn Ala Lys Thr Lys Pro Arg Glu Glu Gln Tyr Asn Ser Thr Tyr
    290              295              300

Arg Val Val Ser Val Leu Thr Val Leu His Gln Asp Trp Leu Asn Gly
305              310              315              320

Lys Glu Tyr Lys Cys Lys Val Ser Asn Lys Ala Leu Pro Ala Pro Ile
            325              330              335

Glu Lys Thr Ile Ser Lys Ala Lys Gly Gln Pro Arg Glu Pro Gln Val
            340              345              350

Tyr Thr Leu Pro Pro Ser Arg Asp Glu Leu Thr Lys Asn Gln Val Ser
            355              360              365

Leu Thr Cys Leu Val Lys Gly Phe Tyr Pro Ser Asp Ile Ala Val Glu
            370              375              380

Trp Glu Ser Asn Gly Gln Pro Glu Asn Asn Tyr Lys Thr Thr Pro Pro
385              390              395              400

Val Leu Asp Ser Asp Gly Ser Phe Phe Leu Tyr Ser Lys Leu Thr Val
            405              410              415

Asp Lys Ser Arg Trp Gln Gln Gly Asn Val Phe Ser Cys Ser Val Met
            420              425              430

His Glu Ala Leu His Asn His Tyr Thr Gln Lys Ser Leu Ser Leu Ser
            435              440              445

Pro Gly Lys
    450

<210> SEQ ID NO 171
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Ser Val Glu Glu Ser Gly Gly Arg Leu Val Thr Pro Gly Thr Pro
1               5               10              15

Leu Thr Leu Thr Cys Thr Val Ser Gly Phe Ser Leu Ser Asn Tyr Gly
            20              25              30

Val Ser Trp Val Arg Gln Ala Pro Gly Lys Gly Leu Glu Trp Ile Gly
        35              40              45
```

-continued

```
Tyr Ile Leu Thr Ser Gly Gly Thr Tyr Tyr Ala Asn Trp Ala Gln Gly
    50              55                  60

Arg Phe Thr Ile Ser Lys Thr Ser Thr Thr Val Asp Leu Lys Ile Thr
65              70                  75                  80

Ser Pro Thr Thr Glu Asp Thr Ala Thr Tyr Phe Cys Gly Arg Pro Lys
                85                  90                  95

Asp Ser Asp Ser Ser Ala Phe Val Ser Leu Trp Gly Pro Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445
```

<210> SEQ ID NO 172
<211> LENGTH: 452
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 172

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Ala Thr Thr Tyr Tyr
            20                  25                  30

Tyr Tyr Met Cys Trp Val Arg Gln Ala Pro Gly Lys Gly Leu Glu Trp
        35                  40                  45

Ile Ala Cys Thr Tyr Thr Gly Asp Gly Ala Thr Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Ala Asp Asn Ser Ile Tyr Tyr Gly Tyr Phe Asn Leu Trp
            100                 105                 110

Gly Pro Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

-continued

_____

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 173
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Asn Ala
                20                  25                  30

Ile Ser Trp Val Arg Gln Ala Pro Gly Lys Gly Leu Gln Trp Ile Gly
            35                  40                  45

Ser Ile Tyr Gly Ser Gly Asn Thr Tyr Tyr Ala Thr Trp Ala Lys Gly
        50                  55                  60

Arg Phe Thr Val Ser Lys Thr Ser Thr Thr Val Asp Leu Lys Ile Asn
65                  70                  75                  80

Ser Pro Thr Thr Glu Asp Thr Ala Thr Tyr Phe Cys Ala Arg Glu Gly
                85                  90                  95

Ala Gly Ser Ser Trp Gly Phe Asn Leu Trp Gly Pro Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

-continued

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 174
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Asn Ala
                20                  25                  30

Ile Ser Trp Val Arg Gln Ala Pro Gly Lys Gly Leu Gln Trp Ile Gly
        35                  40                  45

Ser Ile Tyr Gly Thr Gly Asn Thr Tyr Tyr Ala Thr Trp Ala Lys Gly
    50                  55                  60

Arg Phe Ser Val Ser Lys Thr Ser Thr Thr Val Asp Leu Lys Ile Asn
65                  70                  75                  80

Ser Pro Thr Thr Glu Asp Thr Ala Thr Tyr Phe Cys Ala Thr Glu Gly
                85                  90                  95

Ala Gly Ser Ile Trp Gly Phe Asn Leu Trp Gly Pro Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
```

-continued

```
                195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

```
<210> SEQ ID NO 175
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asp
                20                  25                  30

Met Thr Trp Val Arg Gln Ala Pro Gly Arg Gly Leu Glu Trp Ile Gly
            35                  40                  45

Val Ile Ser Ser Gly Asp Asn Thr Asn Tyr Ala Arg Trp Ala Lys Gly
    50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Ile
                85                  90                  95

Leu Tyr Asn Lys Gly Arg Tyr Tyr Phe Thr Phe Trp Gly Pro Gly Thr
                100                 105                 110
```

```
Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 176
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Gln Glu Leu Val Glu Ser Gly Gly Gly Leu Phe Gln Pro Gly Gly Ser
1               5                   10                  15

Leu Ala Leu Thr Cys Lys Ala Ser Gly Phe Ser Leu Ser Asn Ile Tyr
            20                  25                  30
```

```
Val Met Cys Trp Val Arg Gln Ala Pro Gly Lys Gly Leu Glu Trp Ile
        35              40              45
Ala Cys Ile Gly Thr Gly Ser Gly Asp Thr Asp Tyr Ala Thr Trp Ala
        50              55              60
Lys Gly Arg Phe Thr Ile Ser Lys Thr Ser Ser Thr Thr Val Thr Leu
65              70              75              80
Gln Met Thr Ser Leu Thr Ala Ala Asp Thr Ala Thr Tyr Phe Cys Ala
            85              90              95
Arg Asp Pro Gly Ala Gly Thr Trp Asn Leu Trp Gly Pro Gly Thr Leu
            100             105             110
Val Thr Val Ser Ser Ala Ser Thr Lys Gly Pro Ser Val Phe Pro Leu
            115             120             125
Ala Pro Ser Ser Lys Ser Thr Ser Gly Gly Thr Ala Ala Leu Gly Cys
        130             135             140
Leu Val Lys Asp Tyr Phe Pro Glu Pro Val Thr Val Ser Trp Asn Ser
145             150             155             160
Gly Ala Leu Thr Ser Gly Val His Thr Phe Pro Ala Val Leu Gln Ser
            165             170             175
Ser Gly Leu Tyr Ser Leu Ser Ser Val Val Thr Val Pro Ser Ser Ser
            180             185             190
Leu Gly Thr Gln Thr Tyr Ile Cys Asn Val Asn His Lys Pro Ser Asn
            195             200             205
Thr Lys Val Asp Lys Lys Val Glu Pro Lys Ser Cys Asp Lys Thr His
        210             215             220
Thr Cys Pro Pro Cys Pro Ala Pro Glu Leu Leu Gly Gly Pro Ser Val
225             230             235             240
Phe Leu Phe Pro Pro Lys Pro Lys Asp Thr Leu Met Ile Ser Arg Thr
            245             250             255
Pro Glu Val Thr Cys Val Val Val Asp Val Ser His Glu Asp Pro Glu
            260             265             270
Val Lys Phe Asn Trp Tyr Val Asp Gly Val Glu Val His Asn Ala Lys
            275             280             285
Thr Lys Pro Arg Glu Glu Gln Tyr Asn Ser Thr Tyr Arg Val Val Ser
        290             295             300
Val Leu Thr Val Leu His Gln Asp Trp Leu Asn Gly Lys Glu Tyr Lys
305             310             315             320
Cys Lys Val Ser Asn Lys Ala Leu Pro Ala Pro Ile Glu Lys Thr Ile
            325             330             335
Ser Lys Ala Lys Gly Gln Pro Arg Glu Pro Gln Val Tyr Thr Leu Pro
            340             345             350
Pro Ser Arg Asp Glu Leu Thr Lys Asn Gln Val Ser Leu Thr Cys Leu
            355             360             365
Val Lys Gly Phe Tyr Pro Ser Asp Ile Ala Val Glu Trp Glu Ser Asn
            370             375             380
Gly Gln Pro Glu Asn Asn Tyr Lys Thr Thr Pro Pro Val Leu Asp Ser
385             390             395             400
Asp Gly Ser Phe Phe Leu Tyr Ser Lys Leu Thr Val Asp Lys Ser Arg
            405             410             415
Trp Gln Gln Gly Asn Val Phe Ser Cys Ser Val Met His Glu Ala Leu
            420             425             430
His Asn His Tyr Thr Gln Lys Ser Leu Ser Leu Ser Pro Gly Lys
            435             440             445
```

<210> SEQ ID NO 177
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Glu Gln Leu Glu Glu Ser Gly Gly Asp Leu Val Lys Pro Gly Ala
1               5                   10                  15

Ser Leu Thr Leu Thr Cys Lys Ala Ser Gly Phe Ser Phe Ser Ser Ala
            20                  25                  30

Tyr Asp Met Cys Trp Val Arg Gln Ala Pro Gly Lys Gly Leu Glu Trp
            35                  40                  45

Val Ala Cys Leu Tyr Thr Val Ser Ser Asp Ser Ile Tyr Tyr Ala Ser
        50                  55                  60

Trp Ala Lys Gly Arg Phe Thr Ile Ser Arg Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Gly Asp Tyr Phe Ala Leu Trp Gly Pro Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

-continued

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 178
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ile Tyr Thr
                20                  25                  30

Met Ala Trp Val Arg Gln Ala Pro Gly Lys Gly Leu Glu Tyr Ile Gly
            35                  40                  45

Ile Ile Ser Gly Tyr Gly Thr Thr Tyr Tyr Ala Thr Trp Ala Lys Gly
    50                  55                  60

Arg Phe Ile Val Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Thr Thr
                85                  90                  95

Val Gln Ser Thr Asp Leu Trp Gly Pro Gly Thr Leu Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
```

-continued

```
                275                 280                 285
Glu Glu Gln Tyr Asn Ser Thr Tyr Arg Val Val Ser Val Leu Thr Val
        290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
                340                 345                 350
Glu Leu Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
                370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
                435                 440

<210> SEQ ID NO 179
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Arg Ser Leu Glu Glu Ser Gly Gly Arg Leu Val Thr Pro Gly Thr Pro
1               5                   10                  15
Leu Thr Leu Thr Cys Thr Thr Ser Gly Phe Ser Leu Ser Ser Tyr Asp
                20                  25                  30
Met Ser Trp Val Arg Gln Ala Pro Gly Lys Gly Leu Glu Trp Ile Gly
            35                  40                  45
Tyr Ile Thr Tyr Gly Gly Asn Ile Tyr Tyr Ala Thr Trp Ala Lys Gly
        50                  55                  60
Arg Phe Thr Thr Ser Lys Thr Ser Thr Thr Val Asp Leu Lys Ile Thr
65                  70                  75                  80
Ser Pro Thr Thr Glu Asp Thr Ala Thr Tyr Phe Cys Ala Arg Thr Leu
                85                  90                  95
Tyr Thr Gly Gly Arg Tyr Tyr Phe Ser Leu Trp Gly Pro Gly Thr Leu
                100                 105                 110
Val Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
```

-continued

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 180
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Asn Asp
        20                  25                  30

Ala Ile Cys Trp Val Arg Gln Ala Pro Gly Lys Gly Leu Glu Trp Ile
        35                  40                  45

Ala Cys Ile Tyr Ala Gly Ser Gly Asn Thr Tyr Tyr Ala Ser Trp Ala
    50                  55                  60

Lys Gly Arg Phe Ser Ile Ser Lys Thr Ser Ser Thr Thr Val Thr Leu
65                  70                  75                  80

Gln Met Thr Ser Leu Thr Val Ala Asp Thr Ala Thr Tyr Phe Cys Ala
                85                  90                  95

Ser Ala Asp Thr Ile Asp Tyr Phe Asn Leu Trp Gly Pro Gly Thr Leu
            100                 105                 110
```

-continued

```
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 181
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Ser Leu Glu Glu Ser Gly Gly Gly Leu Val Lys Pro Gly Ala Ser
1               5                   10                  15

Leu Thr Leu Thr Cys Lys Ala Ser Gly Phe Ser Phe Ser Ser Gly Cys
```

-continued

```
             20                25                30
Asp Met Cys Trp Val Arg Gln Ala Pro Gly Lys Gly Leu Glu Trp Ile
        35                40                45

Ser Cys Ile Tyr Thr Gly Ser Gly Ser Thr Tyr Tyr Ala Asn Trp Ala
    50                55                60

Lys Gly Arg Phe Thr Ile Ser Arg Thr Ser Ser Thr Thr Val Thr Leu
65                70                75                80

Gln Met Thr Ser Leu Thr Ala Ala Asp Thr Ala Thr Tyr Phe Cys Ala
            85                90                95

Gly Asp Ser Asp Tyr Leu Gly Leu Trp Gly Pro Gly Thr Leu Val Thr
            100               105               110

Val Ser Ser Ala Ser Thr Lys Gly Pro Ser Val Phe Pro Leu Ala Pro
        115               120               125

Ser Ser Lys Ser Thr Ser Gly Gly Thr Ala Ala Leu Gly Cys Leu Val
    130               135               140

Lys Asp Tyr Phe Pro Glu Pro Val Thr Val Ser Trp Asn Ser Gly Ala
145               150               155               160

Leu Thr Ser Gly Val His Thr Phe Pro Ala Val Leu Gln Ser Ser Gly
            165               170               175

Leu Tyr Ser Leu Ser Ser Val Val Thr Val Pro Ser Ser Ser Leu Gly
        180               185               190

Thr Gln Thr Tyr Ile Cys Asn Val Asn His Lys Pro Ser Asn Thr Lys
        195               200               205

Val Asp Lys Lys Val Glu Pro Lys Ser Cys Asp Lys Thr His Thr Cys
    210               215               220

Pro Pro Cys Pro Ala Pro Glu Leu Leu Gly Gly Pro Ser Val Phe Leu
225               230               235               240

Phe Pro Pro Lys Pro Lys Asp Thr Leu Met Ile Ser Arg Thr Pro Glu
            245               250               255

Val Thr Cys Val Val Val Asp Val Ser His Glu Asp Pro Glu Val Lys
            260               265               270

Phe Asn Trp Tyr Val Asp Gly Val Glu Val His Asn Ala Lys Thr Lys
        275               280               285

Pro Arg Glu Glu Gln Tyr Asn Ser Thr Tyr Arg Val Val Ser Val Leu
    290               295               300

Thr Val Leu His Gln Asp Trp Leu Asn Gly Lys Glu Tyr Lys Cys Lys
305               310               315               320

Val Ser Asn Lys Ala Leu Pro Ala Pro Ile Glu Lys Thr Ile Ser Lys
            325               330               335

Ala Lys Gly Gln Pro Arg Glu Pro Gln Val Tyr Thr Leu Pro Pro Ser
            340               345               350

Arg Asp Glu Leu Thr Lys Asn Gln Val Ser Leu Thr Cys Leu Val Lys
            355               360               365

Gly Phe Tyr Pro Ser Asp Ile Ala Val Glu Trp Glu Ser Asn Gly Gln
        370               375               380

Pro Glu Asn Asn Tyr Lys Thr Thr Pro Pro Val Leu Asp Ser Asp Gly
385               390               395               400

Ser Phe Phe Leu Tyr Ser Lys Leu Thr Val Asp Lys Ser Arg Trp Gln
            405               410               415

Gln Gly Asn Val Phe Ser Cys Ser Val Met His Glu Ala Leu His Asn
            420               425               430

His Tyr Thr Gln Lys Ser Leu Ser Leu Ser Pro Gly Lys
        435               440               445
```

```
<210> SEQ ID NO 182
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 183
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 184
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
```

-continued

```
<210> SEQ ID NO 185
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 186
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
65                    70                    75                    80

Glu Asp Phe Ala Thr Tyr Tyr Cys Gln Gln His Tyr Thr Thr Pro Pro
                85                    90                    95

Thr Phe Gly Gln Gly Thr Lys Val Glu Ile Lys Arg Thr Val Ala Ala
            100                   105                   110

Pro Ser Val Phe Ile Phe Pro Pro Ser Asp Glu Gln Leu Lys Ser Gly
            115                   120                   125

Thr Ala Ser Val Val Cys Leu Leu Asn Asn Phe Tyr Pro Arg Glu Ala
        130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                165                   170                   175

Ser Thr Leu Thr Leu Ser Lys Ala Asp Tyr Glu Lys His Lys Val Tyr
            180                   185                   190

Ala Cys Glu Val Thr His Gln Gly Leu Ser Ser Pro Val Thr Lys Ser
            195                   200                   205

Phe Asn Arg Gly Glu Cys
    210

<210> SEQ ID NO 187
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

-continued

Phe Asn Arg Gly Glu Cys
    210

<210> SEQ ID NO 188
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 189
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

-continued

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 190
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205
```

-continued

Phe Asn Arg Gly Glu Cys
    210

<210> SEQ ID NO 191
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 192
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Val Asn Ala
            20                  25                  30

Asn Asn Leu Ser Trp Tyr Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

-continued

```
Ser Gly Ser Gly Ser Gly Thr Gln Phe Thr Leu Thr Ile Ser Ser Val
65                  70                  75                  80

Gln Ser Asp Asp Ala Ala Thr Tyr Tyr Cys Leu Gly Val Tyr Asp Asp
                85                  90                  95

Asp Gly Asp Asn Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

```
<210> SEQ ID NO 193
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193
```

```
Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Ser Asp
                20                  25                  30

Asn Arg Leu Ser Trp Phe Gln Gln Lys Ser Gly Gln Pro Pro Lys Leu
            35                  40                  45

Leu Ile Tyr Ser Thr Ser Ser Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Ser Asp Asp Ala Ala Ser Tyr Tyr Cys Gln Gly Glu Phe Ile Cys
                85                  90                  95

Thr Ser Ala Asp Cys Phe Val Phe Gly Gly Gly Thr Glu Val Val Val
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

-continued

```
          195              200              205

Ser Pro Val Thr Lys Ser Phe Asn Arg Gly Glu Cys
    210              215              220

<210> SEQ ID NO 194
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ala Gln Val Leu Thr Gln Thr Pro Ser Ser Val Ser Ala Ala Val Gly
1               5                   10                  15

Gly Thr Val Thr Ile Asn Cys Gln Cys Ser Gln Ser Val Tyr Gly His
            20                  25                  30

Asn Trp Leu Ala Trp Tyr Gln His Lys Pro Gly Gln Pro Pro Lys Leu
        35                  40                  45

Leu Met Tyr Arg Ala Ser Asn Leu Ala Ser Gly Val Pro Ser Arg Phe
    50                  55                  60

Lys Gly Ser Gly Ser Gly Ser Gln Phe Thr Leu Thr Ile Gly Glu Val
65                  70                  75                  80

Gln Ser Asp Asp Ala Ala Thr Tyr Tyr Cys Gln Gly Tyr Tyr Asn Gly
                85                  90                  95

Gly Ser Tyr Ala Phe Gly Gly Gly Thr Glu Val Val Val Arg Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 195
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Ala Tyr Asp Met Thr Gln Thr Pro Ala Ser Val Glu Ala Ala Val Gly
1               5                   10                  15

Gly Thr Val Thr Ile Lys Cys Gln Ala Ser Gln Ser Ile Tyr Asn Phe
            20                  25                  30

Leu Asn Trp Tyr Gln Gln Lys Pro Gly Gln Pro Pro Lys Leu Leu Ile
        35                  40                  45

Tyr Tyr Ala Ser Thr Leu Ala Phe Gly Val Pro Ser Arg Phe Lys Gly
```

-continued

```
          50                  55                  60

Ser Gly Ser Gly Thr Glu Tyr Thr Leu Thr Ile Ser Gly Val Glu Ser
65                  70                  75                  80

Ala Asp Ala Ala Thr Tyr Tyr Cys Gln Gln Gly Trp Asn Ser Gly Ile
                85                  90                  95

Leu Asp Asn Ser Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
        210                 215
```

<210> SEQ ID NO 196
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Asn Asn
                20                  25                  30

Asn Tyr Leu Ala Trp Phe Gln Gln Lys Pro Gly Gln Pro Pro Lys Leu
            35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Glu Val
65                  70                  75                  80

Gln Ser Asp Asp Ala Ala Thr Tyr Tyr Cys Gln Ala Tyr Tyr Ser Gly
                85                  90                  95

Gly Ile Tyr Ala Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190
```

-continued

```
Lys Val Tyr Ala Cys Glu Val Thr His Gln Gly Leu Ser Ser Pro Val
        195             200             205

Thr Lys Ser Phe Asn Arg Gly Glu Cys
    210             215

<210> SEQ ID NO 197
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ala Asp Val Val Met Thr Gln Thr Pro Ala Ser Val Ser Glu Pro Val
1               5                   10                  15

Gly Gly Thr Val Thr Ile Asn Cys Gln Ala Ser Glu Ser Ile Tyr Ser
            20                  25                  30

Asn Leu Ala Trp Tyr Gln Gln Lys Pro Gly Gln Pro Pro Lys Leu Leu
        35                  40                  45

Ile Tyr Lys Ala Ser Thr Leu Ala Ser Gly Val Ser Ser Arg Phe Lys
    50                  55                  60

Gly Ser Gly Ser Gly Thr Glu Phe Thr Leu Thr Ile Ser Asp Leu Glu
65                  70                  75                  80

Ser Ala Asp Ala Ala Thr Tyr Tyr Cys Gln Ala Asn His Met Ile Val
                85                  90                  95

Ile Tyr Gly Asn Gly Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 198
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Ala Phe Glu Leu Thr Gln Thr Pro Phe Ser Val Ser Glu Pro Val Gly
1               5                   10                  15

Gly Thr Val Thr Ile Asn Cys Gln Ala Ser Glu Asn Ile Tyr Ser Ser
            20                  25                  30

Leu Ala Trp Tyr Gln Gln Lys Pro Gly Gln Pro Pro Lys Leu Leu Ile
        35                  40                  45
```

-continued

```
Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Gln Thr Tyr Tyr Gly Ser Thr Ser
                85                  90                  95

Thr Gly Phe Thr Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

```
<210> SEQ ID NO 199
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199
```

```
Ala Gln Val Leu Thr Gln Thr Ala Ser Ser Val Ser Ala Ala Val Gly
1               5                   10                  15

Gly Thr Val Thr Ile Ser Cys Gln Ser Ser Glu Ser Val Tyr Lys Asn
                20                  25                  30

Asn Tyr Leu Ser Trp Tyr Gln Gln Lys Pro Gly Gln Pro Leu Lys Cys
            35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Ser Asp Asp Ala Ala Thr Tyr Tyr Cys Ala Gly Gly Tyr Ser Gly
                85                  90                  95

Asn Ile Asn Gly Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190
```

-continued

```
Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 200
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Ala Gln Val Leu Thr Gln Thr Ala Ser Ser Val Ser Ala Ala Val Gly
1               5                   10                  15

Gly Thr Val Thr Ile Ser Cys Gln Ser Ser Glu Ser Val Tyr Lys Asn
            20                  25                  30

Asn Tyr Leu Ser Trp Tyr Gln Gln Lys Pro Gly Gln Pro Pro Lys Gly
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Ser Asp Asp Ala Ala Thr Tyr Tyr Cys Ala Gly Gly Tyr Thr Gly
                85                  90                  95

Asn Ile Asn Gly Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 201
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Ile Ala Asn Ser
            20                  25                  30

Asp Glu Leu Ala Trp Tyr Gln Gln Lys Pro Gly Gln Pro Pro Lys Leu
        35                  40                  45
```

```
Leu Ile Tyr Asp Ala Ser Thr Leu Ala Pro Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Ser Asp Asp Ala Ala Thr Tyr Tyr Cys Gln Gly Thr Val Tyr Asp
                85                  90                  95

Ser Gly Trp Tyr Ala Ala Phe Gly Gly Gly Thr Glu Val Val Val Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 202
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Ala Asp Ile Val Met Thr Gln Thr Pro Ser Ser Val Glu Ala Ala Val
1               5                   10                  15

Gly Gly Thr Val Thr Ile Lys Cys Gln Ala Ser Gln Thr Ile Gly Ser
            20                  25                  30

Arg Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Leu Asp
65                  70                  75                  80

Ser Ala Asp Ala Ala Thr Tyr Tyr Cys Gln Ser Tyr Tyr Tyr Thr Ser
                85                  90                  95

Thr Ser Tyr Pro Asn Ala Phe Gly Gly Gly Thr Glu Val Val Val Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

-continued

```
                180              185              190

Lys His Lys Val Tyr Ala Cys Glu Val Thr His Gln Gly Leu Ser Ser
        195              200              205

Pro Val Thr Lys Ser Phe Asn Arg Gly Glu Cys
        210              215

<210> SEQ ID NO 203
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Ala Asp Ile Val Met Thr His Thr Pro Ala Ser Val Glu Ala Ala Val
1               5                10               15

Gly Gly Thr Val Thr Ile Lys Cys Gln Ala Ser Gln Asn Ile Gly Gly
            20               25               30

Tyr Leu Ser Trp Tyr Gln Gln Lys Pro Gly Gln Arg Pro Lys Leu Leu
        35               40               45

Ile Tyr Arg Ala Ser Thr Leu Ala Ser Gly Val Pro Ser Arg Phe Lys
    50               55               60

Gly Ser Gly Ser Gly Thr Gln Phe Thr Leu Thr Ile Ser Asp Leu Glu
65               70               75               80

Ser Ala Asp Ala Ala Thr Tyr Tyr Cys Gln Thr Tyr Tyr Tyr Ser Gly
            85               90               95

Ser Ser Arg Tyr Trp Ala Phe Gly Gly Gly Thr Glu Val Val Val Lys
            100              105              110

Arg Thr Val Ala Ala Pro Ser Val Phe Ile Phe Pro Pro Ser Asp Glu
        115              120              125

Gln Leu Lys Ser Gly Thr Ala Ser Val Val Cys Leu Leu Asn Asn Phe
    130              135              140

Tyr Pro Arg Glu Ala Lys Val Gln Trp Lys Val Asp Asn Ala Leu Gln
145              150              155              160

Ser Gly Asn Ser Gln Glu Ser Val Thr Glu Gln Asp Ser Lys Asp Ser
            165              170              175

Thr Tyr Ser Leu Ser Ser Thr Leu Thr Leu Ser Lys Ala Asp Tyr Glu
            180              185              190

Lys His Lys Val Tyr Ala Cys Glu Val Thr His Gln Gly Leu Ser Ser
        195              200              205

Pro Val Thr Lys Ser Phe Asn Arg Gly Glu Cys
        210              215

<210> SEQ ID NO 204
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Ala Asp Ile Val Met Thr Gln Thr Pro Ala Ser Val Glu Ala Ala Val
1               5                10               15

Gly Gly Thr Val Thr Ile Asn Cys Gln Ala Ser Gln Asn Ile Tyr Ser
            20               25               30

Asn Leu Ala Trp Tyr Gln Gln Lys Pro Gly Gln Arg Pro Lys Leu Leu
```

-continued

```
            35                    40                    45
Ile Tyr Lys Ala Ser Thr Leu Ala Ser Gly Val Ser Ser Arg Phe Lys
        50                    55                    60

Gly Ser Gly Ser Gly Thr Glu Phe Thr Leu Thr Ile Ser Asp Leu Ala
65                    70                    75                    80

Ser Ala Asp Ala Ala Thr Tyr Tyr Cys Gln Ser Tyr Tyr Gly Ala Thr
                    85                    90                    95

Ser Ser Ser Phe Gly Tyr Gly Phe Gly Gly Gly Thr Glu Val Val Val
                100                   105                   110

Lys Arg Thr Val Ala Ala Pro Ser Val Phe Ile Phe Pro Pro Ser Asp
                115                   120                   125

Glu Gln Leu Lys Ser Gly Thr Ala Ser Val Val Cys Leu Leu Asn Asn
        130                   135                   140

Phe Tyr Pro Arg Glu Ala Lys Val Gln Trp Lys Val Asp Asn Ala Leu
145                   150                   155                   160

Gln Ser Gly Asn Ser Gln Glu Ser Val Thr Glu Gln Asp Ser Lys Asp
                165                   170                   175

Ser Thr Tyr Ser Leu Ser Ser Thr Leu Thr Leu Ser Lys Ala Asp Tyr
                180                   185                   190

Glu Lys His Lys Val Tyr Ala Cys Glu Val Thr His Gln Gly Leu Ser
        195                   200                   205

Ser Pro Val Thr Lys Ser Phe Asn Arg Gly Glu Cys
    210                   215                   220

<210> SEQ ID NO 205
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Ala Gln Val Leu Thr Gln Thr Pro Ser Ser Val Ser Ala Val Val Gly
1               5                   10                   15

Gly Thr Val Thr Ile Asn Cys Gln Ser Ser Gln Ser Ile Ala Asn Ser
                20                   25                   30

Asn Glu Val Ala Trp Tyr Gln Gln Lys Leu Gly Gln Pro Pro Lys Leu
        35                   40                   45

Leu Ile Tyr Asp Ala Ser Thr Leu Ala Ser Gly Val Pro Ser Arg Phe
        50                   55                   60

Ser Gly Ser Gly Ser Gly Thr Gln Phe Thr Leu Ile Ile Ser Gly Val
65                   70                   75                   80

Gln Ser Asp Asp Ala Ala Thr Tyr Tyr Cys Gln Gly Thr Val Tyr Asp
                    85                   90                   95

Asn Val Trp Tyr Ala Ala Phe Gly Gly Gly Thr Glu Val Val Val Lys
                100                   105                   110

Arg Thr Val Ala Ala Pro Ser Val Phe Ile Phe Pro Pro Ser Asp Glu
            115                   120                   125

Gln Leu Lys Ser Gly Thr Ala Ser Val Val Cys Leu Leu Asn Asn Phe
        130                   135                   140

Tyr Pro Arg Glu Ala Lys Val Gln Trp Lys Val Asp Asn Ala Leu Gln
145                   150                   155                   160

Ser Gly Asn Ser Gln Glu Ser Val Thr Glu Gln Asp Ser Lys Asp Ser
                165                   170                   175
```

-continued

```
Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215
```

<210> SEQ ID NO 206
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Ala Gln Val Leu Thr Gln Thr Pro Ser Pro Val Ser Ala Ala Val Gly
1               5               10              15

Gly Thr Val Thr Ile Asn Cys Gln Ala Ser Gln Ser Val Tyr Asn Asn
            20              25              30

Asn Tyr Leu Ala Trp Tyr Gln Gln Lys Pro Gly Gln Pro Pro Lys Leu
        35              40              45

Leu Ile Tyr Arg Ala Ser Asn Leu Ala Ser Gly Val Pro Ser Arg Phe
    50              55              60

Ser Ala Ser Gly Ser Gly Thr Gln Phe Thr Leu Thr Ile Ser Glu Val
65              70              75              80

Gln Ser Asp Asp Ala Ala Thr Tyr Tyr Cys Gln Ala Tyr Tyr Arg Asp
                85              90              95

Pro Thr Thr Ala Phe Gly Gly Gly Thr Glu Val Val Val Lys Arg Thr
            100             105             110

Val Ala Ala Pro Ser Val Phe Ile Phe Pro Pro Ser Asp Glu Gln Leu
        115             120             125

Lys Ser Gly Thr Ala Ser Val Val Cys Leu Leu Asn Asn Phe Tyr Pro
    130             135             140

Arg Glu Ala Lys Val Gln Trp Lys Val Asp Asn Ala Leu Gln Ser Gly
145             150             155             160

Asn Ser Gln Glu Ser Val Thr Glu Gln Asp Ser Lys Asp Ser Thr Tyr
                165             170             175

Ser Leu Ser Ser Thr Leu Thr Leu Ser Lys Ala Asp Tyr Glu Lys His
            180             185             190

Lys Val Tyr Ala Cys Glu Val Thr His Gln Gly Leu Ser Ser Pro Val
        195             200             205

Thr Lys Ser Phe Asn Arg Gly Glu Cys
    210             215
```

<210> SEQ ID NO 207
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Ala Asp Ile Val Met Thr Gln Thr Pro Ser Ser Val Glu Ala Ala Val
1               5               10              15

Gly Gly Thr Val Thr Ile Lys Cys Gln Ala Ser Gln Asn Ile Gly Asn
            20              25              30
```

```
Tyr Leu Ala Trp Tyr Gln Gln Lys Pro Gly Gln Pro Pro Lys Val Leu
        35                  40                  45

Ile Tyr Arg Ala Ser Thr Leu Ala Ser Gly Val Pro Ser Arg Phe Lys
    50                  55                  60

Gly Ser Gly Ser Gly Thr His Phe Thr Leu Thr Ile Ser Asp Leu Glu
65                  70                  75                  80

Ser Ala Asp Ala Ala Thr Tyr Tyr Cys Gln Ser Tyr Tyr Tyr Thr Thr
                85                  90                  95

Asp Asp Asn Tyr Arg Ser Trp Ala Phe Gly Gly Gly Thr Glu Val Val
            100                 105                 110

Val Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Phe Ser Leu Ser Ser Tyr Gly Met Ser
1               5                   10

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Trp Ile Ser Phe Ser Gly Ser Thr Tyr Tyr Ala Ser Trp Ala Lys
1               5                   10                  15

Gly

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Arg Gly Gly Asp Tyr Gly Gly Ser Thr Tyr Ile Leu Asn Leu
1               5                   10                  15
```

-continued

```
<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Phe Ser Phe Ser Ser Ser Tyr Trp Met Cys
1               5                   10

<210> SEQ ID NO 212
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Cys Ile Asp Gly Gly Ser Ala Gly Tyr Asn Tyr Tyr Ala Thr Trp
1               5                   10                  15

Ala Lys Gly

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Arg Gly Pro Gly Ser Ser Tyr Asn Leu
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Phe Ser Leu Ser Ser Tyr Ala Met Gly
1               5                   10

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Ile Ile Gly Ser Ser Gly Ser Thr Tyr Tyr Ala Thr Trp Ala Lys
1               5                   10                  15

Gly

<210> SEQ ID NO 216
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 216

Val Arg Asp Pro Tyr Asp Ser Tyr Asp Ala Ala Tyr Arg Leu
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Phe Ser Leu Asn Asn Tyr Tyr Met Ser
1               5                   10

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Ile Ile Ser Asp Ser Asp Asn Thr Tyr Tyr Ala Ser Trp Ala Lys
1               5                   10                  15

Gly

<210> SEQ ID NO 219
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Arg Asp Trp Ser Leu Asp Ser Ser Ser Gly Tyr Tyr Tyr Tyr Asp
1               5                   10                  15

Met Asp Leu

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Ile Ile Gly Ser Ser Gly Ser Thr Tyr Tyr Ala Ser Trp Ala Lys
1               5                   10                  15

Gly

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 221

Val Arg Asp Pro Tyr Asp Ser Phe Gly Asp Gly Tyr Arg Leu
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Phe Ser Leu Ser Asn Tyr Tyr Met Ser
1               5                   10

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Ile Ile Ser Asp Ser Gly Ser Thr Tyr Tyr Ala Ser Trp Ala Lys
1               5                   10                  15

Gly

<210> SEQ ID NO 224
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Arg Asp Trp Ser Tyr Asp Ser Ser Ser Gly Tyr Tyr Tyr Tyr Asp
1               5                   10                  15

Met Asp Leu

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Phe Ser Leu Ser Asp Tyr Tyr Met Ser
1               5                   10

<210> SEQ ID NO 226
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Arg Asp Trp Ser Tyr Asp Ser Thr Ser Gly Tyr Tyr Tyr Tyr Asp

-continued

```
1               5               10              15

Met Asp Leu

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Ile Ile Ser Asp Ser Gly Thr Thr Tyr Tyr Ala Ser Trp Ala Lys
1               5               10              15

Gly

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Phe Ser Leu Ser Ser His Ala Met Gly
1               5               10

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Ile Ile Gly Ser Ser Asp Arg Thr Tyr Tyr Ala Ser Trp Ala Lys
1               5               10              15

Gly

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Val Arg Asp Pro Tyr Asp Ser Tyr Asp Gly Tyr Arg Leu
1               5               10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Val Arg Asp Pro Tyr Asp Ser Phe Gly Asp Ala Tyr Arg Leu
1               5               10
```

```
<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Phe Ser Leu Ser Thr His Ala Met Gly
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Val Arg Asp Pro Tyr Asp Ser Phe Asp Asp Gly Tyr Arg Leu
1               5                   10

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Trp Ile Ser Phe Ser Gly Ser Ala Tyr Tyr Ala Asn Trp Ala Lys
1               5                   10                  15

Gly

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Phe Ser Ser Ser Ser Gly Tyr Tyr Ile Cys
1               5                   10

<210> SEQ ID NO 236
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Cys Ile Gly Ala Gly Ser Gly Ala Ala Tyr Tyr Ala Ser Trp Ala
1               5                   10                  15

Lys Gly

<210> SEQ ID NO 237
<211> LENGTH: 18
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 237

Ala Arg Gly Gly Phe Val Val Gly Gly Gly Tyr Gly Gly Tyr Cys Phe
1               5                   10                  15

Asn Leu

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Phe Ser Leu Ser Asn Tyr Ala Met Asn
1               5                   10

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Tyr Ile Ser Thr Arg Gly Ser Ala Tyr Tyr Ala Ser Trp Ala Lys
1               5                   10                  15

Gly

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Arg Gly Asp Leu Val Gly Gly Gly Tyr Ile Arg Gly Ser Phe Asp
1               5                   10                  15

Pro

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Phe Thr Phe Ser Asn Tyr Gly Met Ser
1               5                   10

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 242

Thr Ile Ser Thr Gly Gly Gly Tyr Thr His Tyr Pro Asp Ser Val Lys
1               5                   10                  15

Gly

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Arg Pro Asp Tyr Tyr Gly Ser Ser Tyr Gly Pro Ala Trp Phe Ala
1               5                   10                  15

Tyr

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Thr Ile Ser Thr Gly Gly Gly Tyr Thr Tyr Tyr Pro Asp Ser Val Lys
1               5                   10                  15

Gly

<210> SEQ ID NO 245
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ala Arg Pro Asp Tyr Tyr Gly Ser Ser Tyr Gly Pro Ala Trp Leu Ala
1               5                   10                  15

Tyr

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Ile Ser Thr Gly Gly Ser Tyr Thr Tyr Tyr Pro Asp Ser Val Lys
1               5                   10                  15

Gly

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 247

Glu Phe Thr Phe Ser Asp Tyr Phe Met Ser
1               5                   10

<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Tyr Ile Ser Ser Gly Arg Ser Pro Tyr Thr Asn Tyr Ala Asp Ser Val
1               5                   10                  15

Lys Gly

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Arg Val Arg Gly Pro Gly Asp Val Phe Asp Ile
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Tyr Ser Phe Ser Ser His Trp Ile Ser
1               5                   10

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ile Ile Tyr Pro Gly Asp Ser Asp Thr Ser Tyr Ser Pro Ser Phe Gln
1               5                   10                  15

Gly

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Ile Ala Asn Trp Gly Glu Gly Ala Phe Asp Val
1               5                   10

```
<210> SEQ ID NO 253
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gln Ala Ser Glu Ser Val Tyr Asn Asn Lys Trp Leu Ser
1               5                   10

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Leu Ala Ser Thr Leu Ala Ser
1               5

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Gly Tyr Lys Asn Arg Gly Thr Asp Gly Leu Ala
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gln Ala Ser Gln Ser Ile Ser Ser Tyr Leu Ser
1               5                   10

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ser Thr Leu Ala Ser
1               5

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 258

Gln Ser Tyr Val Phe Gly Ser Ser Arg Ser Tyr Asp Asn Ala
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Ala Ser Gln Ser Ile Tyr Ser Tyr Leu Ser
1               5                   10

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Asp Ala Ser Lys Leu Ala Ser
1               5

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Gln Ala Tyr Ser Ser Ser Asn Val Asp Asn Val
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gln Ala Ser Gln Asn Ile His Ser Trp Leu Ala
1               5                   10

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Ala Ser Thr Leu Ala Ser
1               5

<210> SEQ ID NO 264
<211> LENGTH: 12
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Gln Gly Tyr Ser Arg Ser Asp Gly Glu His Val
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gln Ala Ser Glu Asn Ile Tyr Arg Tyr Leu Leu
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gln Gln Ala Tyr Ser Ser Ser Asn Val Asp Asn Ala
1               5                   10

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gln Ala Ser Gln Ser Ile Asn Ser Trp Leu Ala
1               5                   10

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gln Ala Ser Gln Ser Ile Asn Ser Trp Leu Ser
1               5                   10

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Ala Ser Gln Ser Ile Asn Ser Trp Leu Val
```

-continued

```
1               5                  10

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Ala Ser Gln Ser Ile Tyr Arg Tyr Leu Ser
1               5                  10

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gln Gln Ala Tyr Ser Ser Gly Ser Ile Asp Asn Ala
1               5                  10

<210> SEQ ID NO 272
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gln Ala Ser Gln Ser Ile Tyr Ser Tyr Cys Ser
1               5                  10

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asp Ala Ser Lys Val Ala Ser
1               5

<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Ala Ser Glu Ser Ile Asp Ser Tyr Leu Ser
1               5                  10

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
           peptide

<400> SEQUENCE: 275

Ala Ala Ser Thr Leu Ala Ser
1               5

<210> SEQ ID NO 276
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gln Ser Tyr Ser Gly Thr Ile Thr Thr Ser Gly Gly Ala
1               5                   10

<210> SEQ ID NO 277
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gln Ala Ser Glu Ser Ile Asn Ser Tyr Leu Ser
1               5                   10

<210> SEQ ID NO 278
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gln Ser Tyr Ser Gly Thr Ile Ser Thr Ser Gly Gly Ala
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Ser Ser Glu Ser Val Asp Val Asn Asn Leu Ala
1               5                   10

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ser Ala Ser Thr Leu Ala Ser
1               5

<210> SEQ ID NO 281
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Gly Gly Tyr Ser Gly Asn Ile Phe Ala
1               5                   10

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Ser Ser Gln Ser Val Val Ser Asp Lys Leu Leu Ser
1               5                   10

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gly Ala Ser Thr Leu Ala Ser
1               5

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Gly Ala Tyr Ser Thr Asp Ser Asp Ile Arg Ala
1               5                   10

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288
<211> LENGTH: 119
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 288

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser
        115
```

<210> SEQ ID NO 289
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

```
Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Ser Tyr Gly
            20                  25                  30

Met Ser Trp Val Arg Gln Ala Pro Gly Lys Gly Leu Glu Tyr Ile Gly
        35                  40                  45

Trp Ile Ser Phe Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Tyr Gly Gly Ser Thr Tyr Ile Leu Asn Leu Trp Gly Pro Gly Thr
            100                 105                 110

Leu Val Thr Val Ser Ser
        115
```

<210> SEQ ID NO 290
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

```
Gln Ser Leu Glu Glu Ser Gly Gly Asp Leu Val Lys Pro Gly Ala Ser
1               5                   10                  15
```

```
Leu Thr Leu Thr Cys Thr Ala Ser Gly Phe Ser Phe Ser Ser Ser Tyr
            20                  25                  30

Trp Met Cys Trp Val Arg Gln Ala Pro Gly Lys Gly Leu Glu Trp Ile
            35                  40                  45

Ala Cys Ile Asp Gly Gly Ser Ala Gly Tyr Asn Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Arg Ala Thr Tyr Phe Cys
                85                  90                  95

Ala Arg Gly Pro Gly Ser Ser Tyr Asn Leu Trp Gly Pro Gly Thr Leu
            100                 105                 110

Val Thr Val Ser Ser
        115

<210> SEQ ID NO 291
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Ser Tyr Ala
            20                  25                  30

Met Gly Trp Val Arg Gln Ala Pro Gly Lys Gly Leu Glu Tyr Ile Gly
        35                  40                  45

Ile Ile Gly Ser Ser Gly Ser Thr Tyr Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Asp Pro
                85                  90                  95

Tyr Asp Ser Tyr Asp Ala Ala Tyr Arg Leu Trp Gly Pro Gly Thr Leu
            100                 105                 110

Val Thr Val Ser Ser
        115

<210> SEQ ID NO 292
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Asn Asn Tyr Tyr
            20                  25                  30

Met Ser Trp Val Arg Gln Ala Pro Gly Lys Gly Leu Glu Trp Ile Gly
        35                  40                  45

Ile Ile Ser Asp Ser Asp Asn Thr Tyr Tyr Ala Ser Trp Ala Lys Gly
    50                  55                  60
```

```
Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Trp
                85                  90                  95

Ser Leu Asp Ser Ser Ser Gly Tyr Tyr Tyr Tyr Asp Met Asp Leu Trp
            100                 105                 110

Gly Pro Gly Thr Leu Val Thr Val Ser Ala
        115                 120

<210> SEQ ID NO 293
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Ser Tyr Ala
            20                  25                  30

Met Gly Trp Val Arg Gln Ala Pro Gly Lys Gly Leu Glu Tyr Ile Gly
        35                  40                  45

Ile Ile Gly Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Asp Pro
                85                  90                  95

Tyr Asp Ser Phe Gly Asp Gly Tyr Arg Leu Trp Gly Pro Gly Thr Leu
            100                 105                 110

Val Thr Val Ser Ser
        115

<210> SEQ ID NO 294
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Ser Trp Val Arg Gln Ala Pro Gly Lys Gly Leu Glu Trp Ile Gly
        35                  40                  45

Ile Ile Ser Asp Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Trp
                85                  90                  95

Ser Tyr Asp Ser Ser Ser Gly Tyr Tyr Tyr Tyr Asp Met Asp Leu Trp
            100                 105                 110
```

-continued

```
Gly Pro Gly Thr Leu Val Thr Val Ser Ala
        115                 120
```

```
<210> SEQ ID NO 295
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Tyr Tyr
            20                  25                  30

Met Ser Trp Val Arg Gln Ala Pro Gly Lys Gly Leu Glu Trp Ile Gly
            35                  40                  45

Ile Ile Ser Asp Ser Gly Ser Thr Tyr Tyr Ala Ser Trp Ala Lys Gly
        50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Asp
                85                  90                  95

Trp Ser Tyr Asp Ser Ser Ser Gly Tyr Tyr Tyr Tyr Asp Met Asp Leu
            100                 105                 110

Trp Gly Pro Gly Thr Leu Val Thr Val Ser Ala
        115                 120
```

```
<210> SEQ ID NO 296
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Tyr
            20                  25                  30

Met Ser Trp Val Arg Gln Ala Pro Gly Lys Gly Leu Glu Trp Ile Gly
            35                  40                  45

Ile Ile Ser Asp Ser Gly Ser Thr Tyr Tyr Ala Ser Trp Ala Lys Gly
        50                  55                  60

Arg Phe Thr Ile Ser Lys Thr Ser Thr Thr Val Asp Leu Ser Ile Thr
65                  70                  75                  80

Ser Pro Thr Thr Glu Asp Thr Ala Thr Tyr Phe Cys Ala Arg Asp Trp
                85                  90                  95

Ser Tyr Asp Ser Thr Ser Gly Tyr Tyr Tyr Tyr Asp Met Asp Leu Trp
            100                 105                 110

Gly Pro Gly Thr Leu Val Thr Val Ser Ala
        115                 120
```

```
<210> SEQ ID NO 297
<211> LENGTH: 122
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 297

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Ser Trp Val Arg Gln Ala Pro Gly Lys Gly Leu Glu Trp Ile Gly
        35                  40                  45

Ile Ile Ser Asp Ser Gly Thr Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Trp
                85                  90                  95

Ser Tyr Asp Ser Ser Ser Gly Tyr Tyr Tyr Tyr Asp Met Asp Leu Trp
            100                 105                 110

Gly Pro Gly Thr Leu Val Thr Val Ser Ala
        115                 120

<210> SEQ ID NO 298
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Ser His Ala
            20                  25                  30

Met Gly Trp Val Arg Gln Ala Pro Gly Lys Gly Leu Glu Tyr Ile Gly
        35                  40                  45

Ile Ile Gly Ser Ser Asp Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Asp Pro
                85                  90                  95

Tyr Asp Ser Tyr Asp Asp Gly Tyr Arg Leu Trp Gly Pro Gly Thr Leu
            100                 105                 110

Val Thr Val Ser Ser
        115

<210> SEQ ID NO 299
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Gln Ser Val Glu Glu Ser Gly Gly Arg Leu Val Thr Pro Gly Thr Pro
1               5                   10                  15
```

-continued

```
Leu Thr Leu Thr Cys Thr Val Ser Gly Phe Ser Leu Ser Ser His Ala
            20                  25                  30

Met Gly Trp Val Arg Gln Ala Pro Gly Lys Gly Leu Gln Tyr Ile Gly
        35                  40                  45

Ile Ile Gly Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Arg Leu Thr
65                  70                  75                  80

Ser Pro Thr Thr Glu Asp Thr Ala Thr Tyr Phe Cys Val Arg Asp Pro
                85                  90                  95

Tyr Asp Ser Phe Gly Asp Ala Tyr Arg Leu Trp Gly Pro Gly Thr Leu
                100                 105                 110

Val Thr Val Ser Ser
        115

<210> SEQ ID NO 300
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Thr His Ala
            20                  25                  30

Met Gly Trp Val Arg Gln Ala Pro Gly Lys Gly Leu Glu Tyr Ile Gly
        35                  40                  45

Ile Ile Gly Ser Ser Asp Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Asp Pro
                85                  90                  95

Tyr Asp Ser Phe Asp Asp Gly Tyr Arg Leu Trp Gly Pro Gly Thr Leu
                100                 105                 110

Val Thr Val Ser Ser
        115

<210> SEQ ID NO 301
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Gly
            20                  25                  30

Met Ser Trp Val Arg Gln Ala Pro Gly Lys Gly Leu Glu Tyr Ile Gly
        35                  40                  45

Trp Ile Ser Phe Ser Gly Ser Ala Tyr Tyr Ala Asn Trp Ala Lys Gly
    50                  55                  60
```

```
Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Tyr Gly Gly Ser Thr Tyr Ile Leu Asn Leu Trp Gly Pro Gly Thr
                100                 105                 110

Leu Val Thr Val Ser Ser
        115

<210> SEQ ID NO 302
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Ser Tyr Gly
                20                  25                  30

Met Ser Trp Val Arg Gln Ala Pro Gly Lys Gly Leu Glu Tyr Ile Gly
        35                  40                  45

Trp Ile Ser Phe Ser Gly Ser Ala Tyr Tyr Ala Asn Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Tyr Gly Gly Ser Thr Tyr Ile Leu Asn Leu Trp Gly Pro Gly Thr
                100                 105                 110

Leu Val Thr Val Ser Ser
        115

<210> SEQ ID NO 303
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Ser Ser Ser Gly Tyr
                20                  25                  30

Tyr Ile Cys Trp Val Arg Gln Ala Pro Gly Lys Gly Leu Glu Trp Ile
        35                  40                  45

Ala Cys Ile Gly Ala Gly Ser Gly Ala Ala Tyr Tyr Ala Ser Trp Ala
        50                  55                  60

Lys Gly Arg Phe Thr Met Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Gly Phe Val Val Gly Gly Gly Tyr Gly Gly Tyr Cys Phe Asn
                100                 105                 110
```

```
Leu Trp Gly Pro Gly Thr Leu Val Thr Val Ser Ser
        115                 120
```

<210> SEQ ID NO 304
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Asn Trp Val Arg Gln Ala Pro Gly Lys Gly Leu Glu Trp Ile Gly
            35                  40                  45

Tyr Ile Ser Thr Arg Gly Ser Ala Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Gly Asp
                85                  90                  95

Leu Val Gly Gly Gly Tyr Ile Arg Gly Ser Phe Asp Pro Trp Gly Pro
            100                 105                 110

Gly Thr Leu Val Thr Val Ser Ser
        115                 120
```

<210> SEQ ID NO 305
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

```
Glu Val Lys Leu Met Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
            35                  40                  45

Ala Thr Ile Ser Thr Gly Gly Gly Tyr Thr His Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Pro Asp Tyr Tyr Gly Ser Ser Tyr Gly Pro Ala Trp Phe Ala
            100                 105                 110

Tyr Trp Gly Gln Gly Thr Leu Val Thr Val Ser Ala
        115                 120
```

<210> SEQ ID NO 306
<211> LENGTH: 124
<212> TYPE: PRT
<213> ORGANISM: Artificial Sequence
<220> FEATURE:

-continued

```
<223> OTHER INFORMATION: Description of Artificial Sequence: Synthetic
      polypeptide

<400> SEQUENCE: 306

Glu Val Gln Leu Met Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Thr Gly Gly Gly Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Pro Asp Tyr Tyr Gly Ser Ser Tyr Gly Pro Ala Trp Leu Ala
            100                 105                 110

Tyr Trp Gly Gln Gly Thr Leu Val Thr Val Ser Ala
        115                 120

<210> SEQ ID NO 307
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Gln Val
        35                  40                  45

Ala Thr Ile Ser Thr Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Pro Asp Tyr Tyr Gly Ser Ser Tyr Gly Pro Ala Trp Leu Ala
            100                 105                 110

Tyr Trp Gly Gln Gly Thr Leu Val Thr Val Ser Ala
        115                 120

<210> SEQ ID NO 308
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Glu Val Gln Leu Val Glu Ser Gly Gly Gly Leu Val Lys Pro Gly Gly
1               5                   10                  15

Ser Leu Arg Leu Ser Cys Ala Ala Ser Glu Phe Thr Phe Ser Asp Tyr
```

-continued

```
            20              25              30

Phe Met Ser Trp Ile Arg Gln Ala Pro Gly Lys Gly Leu Glu Trp Val
        35              40              45

Ser Tyr Ile Ser Ser Gly Arg Ser Pro Tyr Thr Asn Tyr Ala Asp Ser
    50              55              60

Val Lys Gly Arg Phe Thr Ile Ser Arg Asp Asn Ala Lys Asn Ser Leu
65              70              75              80

Tyr Leu Gln Met Asn Ser Leu Arg Val Glu Asp Thr Ala Val Tyr Phe
            85              90              95

Cys Ala Arg Val Arg Gly Pro Gly Asp Val Phe Asp Ile Trp Gly Gln
            100             105             110

Gly Thr Leu Val Thr Val Ser Ser
        115             120
```

<210> SEQ ID NO 309
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

```
Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Ser Ser His
            20              25              30

Trp Ile Ser Trp Val Arg Gln Met Pro Gly Lys Gly Leu Glu Trp Met
        35              40              45

Gly Ile Ile Tyr Pro Gly Asp Ser Asp Thr Ser Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Ala Ile Ala Asn Trp Gly Glu Gly Ala Phe Asp Val Trp Gly Gln Gly
            100             105             110

Thr Leu Val Thr Val Ser Ser
        115
```

<210> SEQ ID NO 310
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

```
Ala Ser Glu Leu Thr Gln Asp Pro Ala Val Ser Val Ala Leu Gly Gln
1               5               10              15

Thr Val Lys Ile Thr Cys Gln Gly Asp Ser Leu Arg Thr Tyr Tyr Ala
            20              25              30

Ser Trp Tyr Gln Gln Arg Pro Gly Gln Ala Pro Val Leu Val Ile Tyr
        35              40              45

Gly Glu Asn Ser Arg Pro Ser Gly Ile Pro Asp Arg Phe Ser Gly Ser
    50              55              60

Ser Ser Gly Asn Thr Ala Ser Leu Thr Ile Thr Gly Ala Gln Ala Glu
```

-continued

```
65                 70                 75                 80
```

```
Asp Glu Ala Asp Tyr Tyr Cys Asn Ser Arg Asp Ser Ser Gly Asn His
                85                  90                  95

Leu Arg Val Phe Gly Gly Gly Thr Lys Leu Thr Val Leu
                100                 105
```

```
<210> SEQ ID NO 311
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Ala Ile Val Met Thr Gln Thr Pro Ser Ser Lys Ser Val Pro Val Gly
1               5                   10                  15

Asp Thr Val Thr Ile Asn Cys Gln Ala Ser Glu Ser Val Tyr Asn Asn
                20                  25                  30

Lys Trp Leu Ser Trp Tyr Gln Gln Lys Pro Gly Gln Pro Pro Lys Leu
            35                  40                  45

Leu Ile Tyr Leu Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Val
65                  70                  75                  80

Val Ser Asp Asp Ala Ala Thr Tyr Tyr Cys Ala Gly Tyr Lys Asn Arg
                85                  90                  95

Gly Thr Asp Gly Leu Ala Phe Gly Gly Gly Thr Glu Val Val Val Glu
                100                 105                 110
```

```
<210> SEQ ID NO 312
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Ala Asp Ile Val Met Thr Gln Thr Pro Ala Ser Val Glu Ala Ala Val
1               5                   10                  15

Gly Gly Thr Val Thr Ile Lys Cys Gln Ala Ser Gln Ser Ile Ser Ser
                20                  25                  30

Tyr Leu Ser Trp Tyr Gln Gln Lys Pro Gly Gln Pro Pro Lys Leu Leu
            35                  40                  45

Ile Tyr Arg Ala Ser Thr Leu Ala Ser Gly Val Pro Ser Arg Phe Lys
        50                  55                  60

Gly Ser Gly Ser Gly Thr Glu Phe Thr Leu Thr Ile Ser Asp Leu Glu
65                  70                  75                  80

Ser Ala Asp Ala Ala Thr Tyr Tyr Cys Gln Ser Tyr Val Phe Gly Ser
                85                  90                  95

Ser Arg Ser Tyr Asp Asn Ala Phe Gly Gly Gly Thr Glu Val Val Val
                100                 105                 110

Lys
```

```
<210> SEQ ID NO 313
<211> LENGTH: 110
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 313

Ala Tyr Asp Met Ser Gln Thr Pro Ala Ser Val Glu Val Ala Val Gly
1               5                   10                  15

Gly Thr Val Thr Ile Lys Cys Gln Ala Ser Gln Ser Ile Tyr Ser Tyr
                20                  25                  30

Leu Ser Trp Tyr Gln Gln Lys Pro Gly Gln Arg Pro Lys Leu Leu Ile
            35                  40                  45

Tyr Asp Ala Ser Lys Leu Ala Ser Gly Val Pro Ser Arg Phe Thr Gly
        50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Gln Gln Ala Tyr Ser Ser Ser Asn
                85                  90                  95

Val Asp Asn Val Phe Gly Gly Gly Thr Glu Val Val Val Lys
            100                 105                 110

<210> SEQ ID NO 314
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Ala Tyr Asp Met Thr Gln Thr Pro Ala Ser Met Glu Val Ala Val Gly
1               5                   10                  15

Gly Thr Val Thr Ile Lys Cys Gln Ala Ser Gln Asn Ile His Ser Trp
                20                  25                  30

Leu Ala Trp Phe Gln Gln Lys Pro Gly Gln Pro Pro Lys Arg Leu Ile
            35                  40                  45

Tyr Lys Ala Ser Thr Leu Ala Ser Gly Val Pro Ser Arg Phe Lys Gly
        50                  55                  60

Ser Gly Ser Gly Thr Gln Phe Thr Leu Thr Ile Ser Gly Val Gln Ser
65                  70                  75                  80

Asp Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys
            100                 105                 110

<210> SEQ ID NO 315
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Asn Ile Tyr Arg Tyr
                20                  25                  30

Leu Leu Trp Tyr Gln Gln Lys Leu Gly Gln Arg Pro Ser Leu Leu Ile
            35                  40                  45
```

-continued

```
Tyr Asp Ala Ser Lys Leu Ala Ser Gly Val Pro Ser Arg Phe Lys Gly
    50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Gln Gln Ala Tyr Ser Ser Ser Asn
                85                  90                  95

Val Asp Asn Ala Phe Gly Gly Gly Thr Glu Val Val Val Lys
                100                 105                 110

<210> SEQ ID NO 316
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Gly Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
                20                  25                  30

Leu Ala Trp Phe Gln His Lys Pro Gly Gln Pro Pro Lys Arg Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys
                100                 105                 110

<210> SEQ ID NO 317
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
                20                  25                  30

Leu Ser Trp Phe His Gln Lys Pro Gly Gln Pro Pro Lys Arg Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys
                100                 105                 110

<210> SEQ ID NO 318
<211> LENGTH: 110
```

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
            20                  25                  30

Leu Ser Trp Phe His Gln Lys Pro Gly Gln Pro Pro Lys Arg Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys
            100                 105                 110

<210> SEQ ID NO 319
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Gly Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
            20                  25                  30

Leu Val Trp Phe Gln His Lys Pro Gly Gln Pro Pro Lys Arg Leu Ile
        35                  40                  45

Tyr Lys Ala Ser Thr Leu Ala Ser Gly Val Ser Ser Arg Phe Lys Gly
    50                  55                  60

Ser Gly Ser Gly Thr His Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys
            100                 105                 110

<210> SEQ ID NO 320
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Arg Tyr
            20                  25                  30

Leu Ser Trp Tyr Gln Lys Lys Pro Gly Gln Arg Pro Lys Phe Leu Ile
```

-continued

```
                 35                    40                    45

Tyr Asp Ala Ser Lys Leu Ala Ser Gly Val Pro Ser Arg Phe Glu Gly
    50                    55                    60

Ser Gly Ser Gly Thr Glu Phe Thr Leu Thr Ile Ser Gly Ala Gln Ser
65                    70                    75                    80

Asp Asp Ala Ala Thr Tyr Tyr Cys Gln Gln Ala Tyr Ser Ser Gly Ser
                 85                    90                    95

Ile Asp Asn Ala Phe Gly Gly Gly Thr Glu Val Val Val Lys
                100                   105                   110
```

```
<210> SEQ ID NO 321
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Ala Tyr Asp Met Thr Gln Thr Pro Ala Ser Val Glu Val Ala Val Gly
1                 5                    10                    15

Gly Thr Val Thr Ile Lys Cys Gln Ala Ser Gln Ser Ile Tyr Ser Tyr
                 20                    25                    30

Cys Ser Trp Tyr Gln Gln Lys Pro Gly Gln Arg Pro Lys Phe Leu Ile
            35                    40                    45

Tyr Asp Ala Ser Lys Leu Ala Ser Gly Val Pro Ser Arg Phe Lys Gly
    50                    55                    60

Ser Gly Ser Gly Thr Glu Phe Thr Leu Thr Ile Ser Gly Met Gln Ser
65                    70                    75                    80

Asp Asp Ala Ala Thr Tyr Tyr Cys Gln Gln Ala Tyr Ser Ser Ser Asn
                 85                    90                    95

Val Asp Asn Ala Phe Gly Gly Gly Thr Glu Val Val Val Lys
                100                   105                   110
```

```
<210> SEQ ID NO 322
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Ala Tyr Asp Met Thr Gln Thr Pro Ala Ser Val Glu Val Ala Val Gly
1                 5                    10                    15

Gly Thr Val Thr Ile Lys Cys Gln Ala Ser Gln Ser Ile Tyr Ser Tyr
                 20                    25                    30

Leu Ser Trp Tyr Gln Gln Lys Pro Gly Gln Arg Pro Lys Phe Leu Ile
            35                    40                    45

Tyr Asp Ala Ser Lys Val Ala Ser Gly Val Pro Ser Arg Phe Lys Gly
    50                    55                    60

Ser Gly Ser Gly Thr Glu Phe Thr Leu Thr Ile Ser Ala Val Gln Ser
65                    70                    75                    80

Asp Asp Ala Ala Thr Tyr Tyr Cys Gln Gln Ala Tyr Ser Ser Ser Asn
                 85                    90                    95

Val Asp Asn Ala Phe Gly Gly Gly Thr Glu Val Met Val Lys
                100                   105                   110
```

-continued

```
<210> SEQ ID NO 323
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Ala Phe Glu Leu Thr Gln Thr Pro Ser Ser Val Glu Ala Ala Val Gly
1               5                   10                  15

Gly Thr Val Thr Ile Lys Cys Gln Ala Ser Glu Ser Ile Asp Ser Tyr
            20                  25                  30

Leu Ser Trp Tyr Gln Gln Lys Pro Gly Gln Pro Pro Lys Leu Leu Ile
        35                  40                  45

Tyr Ala Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Ser Tyr Ser Gly Thr Ile Thr
                85                  90                  95

Thr Ser Gly Gly Ala Phe Gly Gly Gly Thr Glu Val Val Val Lys
            100                 105                 110

<210> SEQ ID NO 324
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Ala Phe Glu Leu Thr Gln Thr Pro Ser Ser Val Glu Ala Ala Val Gly
1               5                   10                  15

Gly Thr Val Thr Ile Lys Cys Gln Ala Ser Glu Ser Ile Asn Ser Tyr
            20                  25                  30

Leu Ser Trp Tyr Gln Gln Lys Pro Gly Gln Pro Pro Lys Leu Leu Ile
        35                  40                  45

Tyr Ala Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Ser Tyr Ser Gly Thr Ile Ser
                85                  90                  95

Thr Ser Gly Gly Ala Phe Gly Gly Gly Thr Glu Val Val Val Lys
            100                 105                 110

<210> SEQ ID NO 325
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Ala Gln Val Leu Thr Gln Thr Ala Ser Ser Val Ser Ala Thr Val Gly
1               5                   10                  15

Gly Thr Val Thr Ile Ser Cys Gln Ser Ser Glu Ser Val Asp Val Asn
            20                  25                  30
```

```
Asn Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Gln Phe Thr Leu Thr Val Ser Asp Leu Glu
65                  70                  75                  80

Ser Ala Asp Ala Ala Thr Tyr Tyr Cys Ala Gly Gly Tyr Ser Gly Asn
                85                  90                  95

Ile Phe Ala Phe Gly Gly Gly Thr Ala Val Val Val Lys
            100                 105
```

```
<210> SEQ ID NO 326
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326
```

```
Ala Gln Val Leu Thr Gln Thr Pro Ser Pro Val Ser Ala Ala Val Gly
1               5                   10                  15

Gly Thr Val Thr Ile Asn Cys Gln Ser Ser Gln Ser Val Val Ser Asp
                20                  25                  30

Lys Leu Leu Ser Trp Phe Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Ser Asp Asp Ala Ala Thr Tyr Tyr Cys Ala Gly Ala Tyr Ser Thr
                85                  90                  95

Asp Ser Asp Ile Arg Ala Phe Gly Gly Gly Thr Glu Val Val Val Lys
            100                 105                 110
```

```
<210> SEQ ID NO 327

<400> SEQUENCE: 327

000
```

```
<210> SEQ ID NO 328
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328
```

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
65                70                75                80

Leu Gln Met Ser Ser Leu Arg Ala Glu Asp Thr Ala Phe Tyr Tyr Cys
            85                90                95

Ala Asn Ser Ala Tyr Thr Gly Gly Trp Tyr Asp Tyr Trp Gly His Gly
            100               105               110

Thr Leu Val Thr Val Ser Ser Ala Ser Thr Lys Gly Pro Ser Val Phe
            115               120               125

Pro Leu Ala Pro Ser Ser Lys Ser Thr Ser Gly Gly Thr Ala Ala Leu
    130               135               140

Gly Cys Leu Val Lys Asp Tyr Phe Pro Glu Pro Val Thr Val Ser Trp
145               150               155               160

Asn Ser Gly Ala Leu Thr Ser Gly Val His Thr Phe Pro Ala Val Leu
            165               170               175

Gln Ser Ser Gly Leu Tyr Ser Leu Ser Ser Val Val Thr Val Pro Ser
            180               185               190

Ser Ser Leu Gly Thr Gln Thr Tyr Ile Cys Asn Val Asn His Lys Pro
            195               200               205

Ser Asn Thr Lys Val Asp Lys Arg Val Glu Pro Lys Ser Cys Asp Lys
    210               215               220

Thr His Thr Cys Pro Pro Cys Pro Ala Pro Glu Leu Leu Gly Gly Pro
225               230               235               240

Ser Val Phe Leu Phe Pro Pro Lys Pro Lys Asp Thr Leu Met Ile Ser
            245               250               255

Arg Thr Pro Glu Val Thr Cys Val Val Val Asp Val Ser His Glu Asp
            260               265               270

Pro Glu Val Lys Phe Asn Trp Tyr Val Asp Gly Val Glu Val His Asn
            275               280               285

Ala Lys Thr Lys Pro Arg Glu Glu Gln Tyr Asn Ser Thr Tyr Arg Val
    290               295               300

Val Ser Val Leu Thr Val Leu His Gln Asp Trp Leu Asn Gly Lys Glu
305               310               315               320

Tyr Lys Cys Lys Val Ser Asn Lys Ala Leu Pro Ala Pro Ile Glu Lys
            325               330               335

Thr Ile Ser Lys Ala Lys Gly Gln Pro Arg Glu Pro Gln Val Tyr Thr
            340               345               350

Leu Pro Pro Ser Arg Glu Glu Met Thr Lys Asn Gln Val Ser Leu Thr
            355               360               365

Cys Leu Val Lys Gly Phe Tyr Pro Ser Asp Ile Ala Val Glu Trp Glu
    370               375               380

Ser Asn Gly Gln Pro Glu Asn Asn Tyr Lys Thr Thr Pro Pro Val Leu
385               390               395               400

Asp Ser Asp Gly Ser Phe Phe Leu Tyr Ser Lys Leu Thr Val Asp Lys
            405               410               415

Ser Arg Trp Gln Gln Gly Asn Val Phe Ser Cys Ser Val Met His Glu
            420               425               430

Ala Leu His Asn His Tyr Thr Gln Lys Ser Leu Ser Leu Ser Pro Gly
            435               440               445

Lys
```

<210> SEQ ID NO 329
<211> LENGTH: 448
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 329

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Ser Tyr Gly
            20                  25                  30

Met Ser Trp Val Arg Gln Ala Pro Gly Lys Gly Leu Glu Tyr Ile Gly
        35                  40                  45

Trp Ile Ser Phe Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Tyr Gly Gly Ser Thr Tyr Ile Leu Asn Leu Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                410                415

Arg Trp Gln Gln Gly Asn Val Phe Ser Cys Ser Val Met His Glu Ala
            420                425                430

Leu His Asn His Tyr Thr Gln Lys Ser Leu Ser Leu Ser Pro Gly Lys
        435                440                445

<210> SEQ ID NO 330
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gln Ser Leu Glu Glu Ser Gly Gly Asp Leu Val Lys Pro Gly Ala Ser
1                5                10                15

Leu Thr Leu Thr Cys Thr Ala Ser Gly Phe Ser Phe Ser Ser Ser Tyr
            20                25                30

Trp Met Cys Trp Val Arg Gln Ala Pro Gly Lys Gly Leu Glu Trp Ile
        35                40                45

Ala Cys Ile Asp Gly Gly Ser Ala Gly Tyr Asn Tyr Tyr Ala Thr Trp
    50                55                60

Ala Lys Gly Arg Phe Thr Ile Ser Lys Thr Ser Ser Thr Thr Val Thr
65                70                75                80

Leu Gln Met Thr Ser Leu Thr Ala Ala Asp Arg Ala Thr Tyr Phe Cys
            85                90                95

Ala Arg Gly Pro Gly Ser Ser Tyr Asn Leu Trp Gly Pro Gly Thr Leu
            100                105                110

Val Thr Val Ser Ser Ala Ser Thr Lys Gly Pro Ser Val Phe Pro Leu
            115                120                125

Ala Pro Ser Ser Lys Ser Thr Ser Gly Gly Thr Ala Ala Leu Gly Cys
        130                135                140

Leu Val Lys Asp Tyr Phe Pro Glu Pro Val Thr Val Ser Trp Asn Ser
145                150                155                160

Gly Ala Leu Thr Ser Gly Val His Thr Phe Pro Ala Val Leu Gln Ser
            165                170                175

Ser Gly Leu Tyr Ser Leu Ser Ser Val Val Thr Val Pro Ser Ser Ser
            180                185                190

Leu Gly Thr Gln Thr Tyr Ile Cys Asn Val Asn His Lys Pro Ser Asn
        195                200                205

Thr Lys Val Asp Lys Lys Val Glu Pro Lys Ser Cys Asp Lys Thr His
    210                215                220

Thr Cys Pro Pro Cys Pro Ala Pro Glu Leu Leu Gly Gly Pro Ser Val
225                230                235                240

Phe Leu Phe Pro Pro Lys Pro Lys Asp Thr Leu Met Ile Ser Arg Thr
            245                250                255

Pro Glu Val Thr Cys Val Val Val Asp Val Ser His Glu Asp Pro Glu
            260                265                270

Val Lys Phe Asn Trp Tyr Val Asp Gly Val Glu Val His Asn Ala Lys
            275                280                285

Thr Lys Pro Arg Glu Glu Gln Tyr Asn Ser Thr Tyr Arg Val Val Ser
    290                295                300

Val Leu Thr Val Leu His Gln Asp Trp Leu Asn Gly Lys Glu Tyr Lys

```
305              310              315              320
Cys Lys Val Ser Asn Lys Ala Leu Pro Ala Pro Ile Glu Lys Thr Ile
                325              330              335

Ser Lys Ala Lys Gly Gln Pro Arg Glu Pro Gln Val Tyr Thr Leu Pro
            340              345              350

Pro Ser Arg Asp Glu Leu Thr Lys Asn Gln Val Ser Leu Thr Cys Leu
            355              360              365

Val Lys Gly Phe Tyr Pro Ser Asp Ile Ala Val Glu Trp Glu Ser Asn
        370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
                405              410              415

Trp Gln Gln Gly Asn Val Phe Ser Cys Ser Val Met His Glu Ala Leu
            420              425              430

His Asn His Tyr Thr Gln Lys Ser Leu Ser Leu Ser Pro Gly Lys
            435              440              445

<210> SEQ ID NO 331
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gln Ser Val Glu Glu Ser Gly Gly Gly Leu Val Lys Pro Gly Gly Thr
1               5               10              15

Leu Thr Leu Thr Cys Thr Val Ser Gly Phe Ser Leu Ser Ser Tyr Ala
            20              25              30

Met Gly Trp Val Arg Gln Ala Pro Gly Lys Gly Leu Glu Tyr Ile Gly
        35              40              45

Ile Ile Gly Ser Ser Gly Ser Thr Tyr Tyr Ala Thr Trp Ala Lys Gly
    50              55              60

Arg Phe Thr Ile Ser Lys Thr Ser Thr Thr Val Asp Leu Lys Ile Thr
65              70              75              80

Ser Pro Thr Thr Glu Asp Thr Ala Thr Tyr Phe Cys Val Arg Asp Pro
                85              90              95

Tyr Asp Ser Tyr Asp Ala Ala Tyr Arg Leu Trp Gly Pro Gly Thr Leu
            100             105             110

Val Thr Val Ser Ser Ala Ser Thr Lys Gly Pro Ser Val Phe Pro Leu
            115             120             125

Ala Pro Ser Ser Lys Ser Thr Ser Gly Gly Thr Ala Ala Leu Gly Cys
        130             135             140

Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
            165             170             175

Ser Gly Leu Tyr Ser Leu Ser Ser Val Val Thr Val Pro Ser Ser Ser
            180             185             190

Leu Gly Thr Gln Thr Tyr Ile Cys Asn Val Asn His Lys Pro Ser Asn
            195             200             205

Thr Lys Val Asp Lys Lys Val Glu Pro Lys Ser Cys Asp Lys Thr His
        210             215             220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

```
<210> SEQ ID NO 332
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332
```

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Asn Asn Tyr Tyr
            20                  25                  30

Met Ser Trp Val Arg Gln Ala Pro Gly Lys Gly Leu Glu Trp Ile Gly
        35                  40                  45

Ile Ile Ser Asp Ser Asp Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Trp
                85                  90                  95

Ser Leu Asp Ser Ser Ser Gly Tyr Tyr Tyr Tyr Asp Met Asp Leu Trp
            100                 105                 110

Gly Pro Gly Thr Leu Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140
```

-continued

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450
```

```
<210> SEQ ID NO 333
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Ser Tyr Ala
                20                  25                  30

Met Gly Trp Val Arg Gln Ala Pro Gly Lys Gly Leu Glu Tyr Ile Gly
```

-continued

```
            35                  40                  45
Ile Ile Gly Ser Ser Gly Ser Thr Tyr Tyr Ala Ser Trp Ala Lys Gly
    50                  55                  60
Arg Phe Thr Ile Ser Lys Thr Ser Thr Thr Val Asp Leu Lys Ile Thr
65                  70                  75                  80
Ser Pro Thr Thr Glu Asp Thr Ala Thr Tyr Phe Cys Val Arg Asp Pro
                85                  90                  95
Tyr Asp Ser Phe Gly Asp Gly Tyr Arg Leu Trp Gly Pro Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445
```

<210> SEQ ID NO 334

```
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Ser Trp Val Arg Gln Ala Pro Gly Lys Gly Leu Glu Trp Ile Gly
        35                  40                  45

Ile Ile Ser Asp Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Trp
                85                  90                  95

Ser Tyr Asp Ser Ser Ser Gly Tyr Tyr Tyr Tyr Asp Met Asp Leu Trp
            100                 105                 110

Gly Pro Gly Thr Leu Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
```

-continued

```
              370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
        435                 440                 445

Ser Pro Gly Lys
        450

<210> SEQ ID NO 335
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Tyr Tyr
                20                  25                  30

Met Ser Trp Val Arg Gln Ala Pro Gly Lys Gly Leu Glu Trp Ile Gly
        35                  40                  45

Ile Ile Ser Asp Ser Gly Ser Thr Tyr Tyr Ala Ser Trp Ala Lys Gly
    50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Asp
                85                  90                  95

Trp Ser Tyr Asp Ser Ser Ser Gly Tyr Tyr Tyr Asp Met Asp Leu
                100                 105                 110

Trp Gly Pro Gly Thr Leu Val Thr Val Ser Ala Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270
```

-continued

```
Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 336
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Tyr
                20                  25                  30

Met Ser Trp Val Arg Gln Ala Pro Gly Lys Gly Leu Glu Trp Ile Gly
            35                  40                  45

Ile Ile Ser Asp Ser Gly Ser Thr Tyr Tyr Ala Ser Trp Ala Lys Gly
    50                  55                  60

Arg Phe Thr Ile Ser Lys Thr Ser Thr Val Asp Leu Ser Ile Thr
65                  70                  75                  80

Ser Pro Thr Thr Glu Asp Thr Ala Thr Tyr Phe Cys Ala Arg Asp Trp
                85                  90                  95

Ser Tyr Asp Ser Thr Ser Gly Tyr Tyr Tyr Asp Met Asp Leu Trp
                100                 105                 110

Gly Pro Gly Thr Leu Val Thr Val Ser Ala Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

-continued

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 337
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Ser Trp Val Arg Gln Ala Pro Gly Lys Gly Leu Glu Trp Ile Gly
            35                  40                  45

Ile Ile Ser Asp Ser Gly Thr Thr Tyr Tyr Ala Ser Trp Ala Lys Gly
    50                  55                  60

Arg Phe Thr Ile Ser Lys Thr Ser Thr Thr Val Asp Leu Lys Ile Thr
```

-continued

```
65                   70                   75                   80

Ser Pro Thr Thr Glu Asp Thr Ala Thr Tyr Phe Cys Ala Arg Asp Trp
                85                   90                   95

Ser Tyr Asp Ser Ser Ser Gly Tyr Tyr Tyr Asp Met Asp Leu Trp
                100              105              110

Gly Pro Gly Thr Leu Val Thr Val Ser Ala Ala Ser Thr Lys Gly Pro
        115              120              125

Ser Val Phe Pro Leu Ala Pro Ser Ser Lys Ser Thr Ser Gly Gly Thr
    130              135              140

Ala Ala Leu Gly Cys Leu Val Lys Asp Tyr Phe Pro Glu Pro Val Thr
145              150              155              160

Val Ser Trp Asn Ser Gly Ala Leu Thr Ser Gly Val His Thr Phe Pro
                165              170              175

Ala Val Leu Gln Ser Ser Gly Leu Tyr Ser Leu Ser Ser Val Val Thr
            180              185              190

Val Pro Ser Ser Ser Leu Gly Thr Gln Thr Tyr Ile Cys Asn Val Asn
        195              200              205

His Lys Pro Ser Asn Thr Lys Val Asp Lys Lys Val Glu Pro Lys Ser
    210              215              220

Cys Asp Lys Thr His Thr Cys Pro Pro Cys Pro Ala Pro Glu Leu Leu
225              230              235              240

Gly Gly Pro Ser Val Phe Leu Phe Pro Pro Lys Pro Lys Asp Thr Leu
            245              250              255

Met Ile Ser Arg Thr Pro Glu Val Thr Cys Val Val Val Asp Val Ser
            260              265              270

His Glu Asp Pro Glu Val Lys Phe Asn Trp Tyr Val Asp Gly Val Glu
        275              280              285

Val His Asn Ala Lys Thr Lys Pro Arg Glu Glu Gln Tyr Asn Ser Thr
    290              295              300

Tyr Arg Val Val Ser Val Leu Thr Val Leu His Gln Asp Trp Leu Asn
305              310              315              320

Gly Lys Glu Tyr Lys Cys Lys Val Ser Asn Lys Ala Leu Pro Ala Pro
            325              330              335

Ile Glu Lys Thr Ile Ser Lys Ala Lys Gly Gln Pro Arg Glu Pro Gln
            340              345              350

Val Tyr Thr Leu Pro Pro Ser Arg Asp Glu Leu Thr Lys Asn Gln Val
        355              360              365

Ser Leu Thr Cys Leu Val Lys Gly Phe Tyr Pro Ser Asp Ile Ala Val
    370              375              380

Glu Trp Glu Ser Asn Gly Gln Pro Glu Asn Asn Tyr Lys Thr Thr Pro
385              390              395              400

Pro Val Leu Asp Ser Asp Gly Ser Phe Phe Leu Tyr Ser Lys Leu Thr
            405              410              415

Val Asp Lys Ser Arg Trp Gln Gln Gly Asn Val Phe Ser Cys Ser Val
        420              425              430

Met His Glu Ala Leu His Asn His Tyr Thr Gln Lys Ser Leu Ser Leu
        435              440              445

Ser Pro Gly Lys
    450
```

<210> SEQ ID NO 338
<211> LENGTH: 447
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 338

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Ser His Ala
                20                  25                  30

Met Gly Trp Val Arg Gln Ala Pro Gly Lys Gly Leu Glu Tyr Ile Gly
            35                  40                  45

Ile Ile Gly Ser Ser Asp Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Asp Pro
                85                  90                  95

Tyr Asp Ser Tyr Asp Asp Gly Tyr Arg Leu Trp Gly Pro Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

-continued

```
385                   390                   395                   400

Asp Gly Ser Phe Phe Leu Tyr Ser Lys Leu Thr Val Asp Lys Ser Arg
                405                   410                   415

Trp Gln Gln Gly Asn Val Phe Ser Cys Ser Val Met His Glu Ala Leu
                420                   425                   430

His Asn His Tyr Thr Gln Lys Ser Leu Ser Leu Ser Pro Gly Lys
            435                   440                   445

<210> SEQ ID NO 339
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser His Ala
                20                  25                  30

Met Gly Trp Val Arg Gln Ala Pro Gly Lys Gly Leu Gln Tyr Ile Gly
            35                  40                  45

Ile Ile Gly Ser Ser Gly Ser Thr Tyr Tyr Ala Ser Trp Ala Lys Gly
        50                  55                  60

Arg Phe Thr Ile Ser Lys Thr Ser Thr Thr Val Asp Leu Arg Leu Thr
65                  70                  75                  80

Ser Pro Thr Thr Glu Asp Thr Ala Thr Tyr Phe Cys Val Arg Asp Pro
                85                  90                  95

Tyr Asp Ser Phe Gly Asp Ala Tyr Arg Leu Trp Gly Pro Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300
```

-continued

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 340
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Leu Ser Thr His Ala
            20                  25                  30

Met Gly Trp Val Arg Gln Ala Pro Gly Lys Gly Leu Glu Tyr Ile Gly
        35                  40                  45

Ile Ile Gly Ser Ser Asp Arg Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Asp Pro
                85                  90                  95

Tyr Asp Ser Phe Asp Asp Gly Tyr Arg Leu Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

-continued

```
Thr Cys Pro Pro Cys Pro Ala Pro Glu Leu Leu Gly Gly Pro Ser Val
225                 230             235             240

Phe Leu Phe Pro Pro Lys Pro Lys Asp Thr Leu Met Ile Ser Arg Thr
                245             250             255

Pro Glu Val Thr Cys Val Val Val Asp Val Ser His Glu Asp Pro Glu
            260             265             270

Val Lys Phe Asn Trp Tyr Val Asp Gly Val Glu Val His Asn Ala Lys
        275             280             285

Thr Lys Pro Arg Glu Glu Gln Tyr Asn Ser Thr Tyr Arg Val Val Ser
        290             295             300

Val Leu Thr Val Leu His Gln Asp Trp Leu Asn Gly Lys Glu Tyr Lys
305             310             315             320

Cys Lys Val Ser Asn Lys Ala Leu Pro Ala Pro Ile Glu Lys Thr Ile
            325             330             335

Ser Lys Ala Lys Gly Gln Pro Arg Glu Pro Gln Val Tyr Thr Leu Pro
            340             345             350

Pro Ser Arg Asp Glu Leu Thr Lys Asn Gln Val Ser Leu Thr Cys Leu
            355             360             365

Val Lys Gly Phe Tyr Pro Ser Asp Ile Ala Val Glu Trp Glu Ser Asn
        370             375             380

Gly Gln Pro Glu Asn Asn Tyr Lys Thr Thr Pro Pro Val Leu Asp Ser
385             390             395             400

Asp Gly Ser Phe Phe Leu Tyr Ser Lys Leu Thr Val Asp Lys Ser Arg
                405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys
            435             440             445
```

```
<210> SEQ ID NO 341
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341
```

```
Gln Ser Leu Glu Glu Ser Gly Gly Arg Leu Val Thr Pro Gly Thr Pro
1               5               10              15

Leu Thr Leu Thr Cys Thr Val Ser Gly Phe Ser Leu Ser Ser Tyr Gly
            20              25              30

Met Ser Trp Val Arg Gln Ala Pro Gly Lys Gly Leu Glu Tyr Ile Gly
        35              40              45

Trp Ile Ser Phe Ser Gly Ser Ala Tyr Tyr Ala Asn Trp Ala Lys Gly
    50              55              60

Arg Phe Thr Ile Ser Lys Thr Ser Thr Thr Val Asp Leu Lys Ile Thr
65              70              75              80

Ser Pro Thr Thr Glu Asp Thr Ala Thr Tyr Phe Cys Ala Arg Gly Gly
                85              90              95

Asp Tyr Gly Gly Ser Thr Tyr Ile Leu Asn Leu Trp Gly Pro Gly Thr
            100             105             110

Leu Val Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
```

-continued

```
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 342
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Ser Tyr Gly
                20                  25                  30

Met Ser Trp Val Arg Gln Ala Pro Gly Lys Gly Leu Glu Tyr Ile Gly
        35                  40                  45
```

```
Trp Ile Ser Phe Ser Gly Ser Ala Tyr Tyr Ala Asn Trp Ala Lys Gly
    50              55                  60

Arg Phe Thr Ile Ser Lys Thr Ser Thr Thr Val Asp Leu Lys Ile Thr
65              70                  75                  80

Ser Pro Thr Thr Glu Asp Thr Ala Thr Tyr Phe Cys Ala Arg Gly Gly
                85                  90                  95

Asp Tyr Gly Gly Ser Thr Tyr Ile Leu Asn Leu Trp Gly Pro Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 343
<211> LENGTH: 454
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 343

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Ser Ser Ser Gly Tyr
            20                  25                  30

Tyr Ile Cys Trp Val Arg Gln Ala Pro Gly Lys Gly Leu Glu Trp Ile
        35                  40                  45

Ala Cys Ile Gly Ala Gly Ser Gly Ala Ala Tyr Tyr Ala Ser Trp Ala
    50                  55                  60

Lys Gly Arg Phe Thr Met Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Gly Phe Val Val Gly Gly Gly Tyr Gly Gly Tyr Cys Phe Asn
                100                 105                 110

Leu Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 344
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
                20                  25                  30

Met Asn Trp Val Arg Gln Ala Pro Gly Lys Gly Leu Glu Trp Ile Gly
            35                  40                  45

Tyr Ile Ser Thr Arg Gly Ser Ala Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Gly Asp
                85                  90                  95

Leu Val Gly Gly Gly Tyr Ile Arg Gly Ser Phe Asp Pro Trp Gly Pro
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285
```

-continued

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 345
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Glu Val Lys Leu Met Glu Ser Gly Gly Asp Leu Val Lys Pro Gly Gly
1                   5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Thr Gly Gly Gly Tyr Thr His Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Pro Asp Tyr Tyr Gly Ser Ser Tyr Gly Pro Ala Trp Phe Ala
                100                 105                 110

Tyr Trp Gly Gln Gly Thr Leu Val Thr Val Ser Ala Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
```

-continued

```
              180              185                 190
Val Thr Val Pro Ser Ser Ser Leu Gly Thr Gln Thr Tyr Ile Cys Asn
         195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
             245                 250                 255

Thr Leu Met Ile Ser Arg Thr Pro Glu Val Thr Cys Val Val Val Asp
             260                 265                 270

Val Ser His Glu Asp Pro Glu Val Lys Phe Asn Trp Tyr Val Asp Gly
         275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
             325                 330                 335

Ala Pro Ile Glu Lys Thr Ile Ser Lys Ala Lys Gly Gln Pro Arg Glu
             340                 345                 350

Pro Gln Val Tyr Thr Leu Pro Pro Ser Arg Asp Glu Leu Thr Lys Asn
         355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
             405                 410                 415

Leu Thr Val Asp Lys Ser Arg Trp Gln Gln Gly Asn Val Phe Ser Cys
             420                 425                 430

Ser Val Met His Glu Ala Leu His Asn His Tyr Thr Gln Lys Ser Leu
         435                 440                 445

Ser Leu Ser Pro Gly Lys
    450
```

<210> SEQ ID NO 346
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

```
Glu Val Gln Leu Met Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
             20                  25                  30

Gly Met Ser Trp Val Arg Gln Thr Pro Asp Lys Arg Leu Glu Trp Val
         35                  40                  45

Ala Thr Ile Ser Thr Gly Gly Gly Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80
```

-continued

```
Leu Gln Met Ser Ser Leu Lys Ser Glu Asp Thr Ala Met Tyr Tyr Cys
            85                  90                  95

Ala Arg Pro Asp Tyr Tyr Gly Ser Ser Tyr Gly Pro Ala Trp Leu Ala
            100                 105                 110

Tyr Trp Gly Gln Gly Thr Leu Val Thr Val Ser Ala Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450
```

<210> SEQ ID NO 347
<211> LENGTH: 454
<212> TYPE: PRT
<213> ORGANISM: Artificial Sequence
<220> FEATURE:
<223> OTHER INFORMATION: Description of Artificial Sequence: Synthetic -continued

```
    polypeptide

<400> SEQUENCE: 347

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
                20                  25                  30

Gly Met Ser Trp Val Arg Gln Thr Pro Asp Lys Arg Leu Glu Gln Val
            35                  40                  45

Ala Thr Ile Ser Thr Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Pro Asp Tyr Tyr Gly Ser Ser Tyr Gly Pro Ala Trp Leu Ala
            100                 105                 110

Tyr Trp Gly Gln Gly Thr Leu Val Thr Val Ser Ala Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

-continued

```
Thr Pro Pro Val Leu Asp Ser Asp Gly Ser Phe Phe Leu Tyr Ser Lys
              405             410             415

Leu Thr Val Asp Lys Ser Arg Trp Gln Gln Gly Asn Val Phe Ser Cys
              420             425             430

Ser Val Met His Glu Ala Leu His Asn His Tyr Thr Gln Lys Ser Leu
          435             440             445

Ser Leu Ser Pro Gly Lys
      450

<210> SEQ ID NO 348
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Glu Val Gln Leu Val Glu Ser Gly Gly Gly Leu Val Lys Pro Gly Gly
1               5               10              15

Ser Leu Arg Leu Ser Cys Ala Ala Ser Glu Phe Thr Phe Ser Asp Tyr
              20              25              30

Phe Met Ser Trp Ile Arg Gln Ala Pro Gly Lys Gly Leu Glu Trp Val
          35              40              45

Ser Tyr Ile Ser Ser Gly Arg Ser Pro Tyr Thr Asn Tyr Ala Asp Ser
      50              55              60

Val Lys Gly Arg Phe Thr Ile Ser Arg Asp Asn Ala Lys Asn Ser Leu
65              70              75              80

Tyr Leu Gln Met Asn Ser Leu Arg Val Glu Asp Thr Ala Val Tyr Phe
              85              90              95

Cys Ala Arg Val Arg Gly Pro Gly Asp Val Phe Asp Ile Trp Gly Gln
          100             105             110

Gly Thr Leu Val Thr Val Ser Ser Ala Ser Thr Lys Gly Pro Ser Val
          115             120             125

Phe Pro Leu Ala Pro Ser Ser Lys Ser Thr Ser Gly Gly Thr Ala Ala
      130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
              165             170             175

Leu Gln Ser Ser Gly Leu Tyr Ser Leu Ser Ser Val Val Thr Val Pro
          180             185             190

Ser Ser Ser Leu Gly Thr Gln Thr Tyr Ile Cys Asn Val Asn His Lys
          195             200             205

Pro Ser Asn Thr Lys Val Asp Lys Lys Val Glu Pro Lys Ser Cys Asp
      210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
              245             250             255

Ser Arg Thr Pro Glu Val Thr Cys Val Val Val Asp Val Ser His Glu
              260             265             270

Asp Pro Glu Val Lys Phe Asn Trp Tyr Val Asp Gly Val Glu Val His
      275             280             285

Asn Ala Lys Thr Lys Pro Arg Glu Glu Gln Tyr Asn Ser Thr Tyr Arg
      290             295             300
```

-continued

Val Val Ser Val Leu Thr Val Leu His Gln Asp Trp Leu Asn Gly Lys
305              310              315              320

Glu Tyr Lys Cys Lys Val Ser Asn Lys Ala Leu Pro Ala Pro Ile Glu
             325              330              335

Lys Thr Ile Ser Lys Ala Lys Gly Gln Pro Arg Glu Pro Gln Val Tyr
             340              345              350

Thr Leu Pro Pro Ser Arg Asp Glu Leu Thr Lys Asn Gln Val Ser Leu
             355              360              365

Thr Cys Leu Val Lys Gly Phe Tyr Pro Ser Asp Ile Ala Val Glu Trp
             370              375              380

Glu Ser Asn Gly Gln Pro Glu Asn Asn Tyr Lys Thr Thr Pro Pro Val
385              390              395              400

Leu Asp Ser Asp Gly Ser Phe Phe Leu Tyr Ser Lys Leu Thr Val Asp
             405              410              415

Lys Ser Arg Trp Gln Gln Gly Asn Val Phe Ser Cys Ser Val Met His
             420              425              430

Glu Ala Leu His Asn His Tyr Thr Gln Lys Ser Leu Ser Leu Ser Pro
             435              440              445

Gly Lys
    450

<210> SEQ ID NO 349
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Glu Val Gln Leu Val Gln Ser Gly Ala Glu Val Lys Lys Pro Gly Glu
1              5              10              15

Ser Leu Lys Ile Ser Cys Lys Gly Ser Gly Tyr Ser Phe Ser Ser His
             20              25              30

Trp Ile Ser Trp Val Arg Gln Met Pro Gly Lys Gly Leu Glu Trp Met
             35              40              45

Gly Ile Ile Tyr Pro Gly Asp Ser Asp Thr Ser Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
             85              90              95

Ala Ile Ala Asn Trp Gly Glu Gly Ala Phe Asp Val Trp Gly Gln Gly
             100             105             110

Thr Leu Val Thr Val Ser Ser Ala Ser Thr Lys Gly Pro Ser Val Phe
             115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
             165             170             175

Gln Ser Ser Gly Leu Tyr Ser Leu Ser Ser Val Val Thr Val Pro Ser
             180             185             190

Ser Ser Leu Gly Thr Gln Thr Tyr Ile Cys Asn Val Asn His Lys Pro

-continued

```
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
    435                 440                 445

Lys
```

<210> SEQ ID NO 350
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

```
Ala Ser Glu Leu Thr Gln Asp Pro Ala Val Ser Val Ala Leu Gly Gln
1               5                   10                  15

Thr Val Lys Ile Thr Cys Gln Gly Asp Ser Leu Arg Thr Tyr Tyr Ala
                20                  25                  30

Ser Trp Tyr Gln Gln Arg Pro Gly Gln Ala Pro Val Leu Val Ile Tyr
                35                  40                  45

Gly Glu Asn Ser Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Arg Val Phe Gly Gly Gly Thr Lys Leu Thr Val Leu Gly Gln Pro
```

-continued

```
              100              105              110
Lys Ala Ala Pro Ser Val Thr Leu Phe Pro Pro Ser Ser Glu Glu Leu
        115              120              125

Gln Ala Asn Lys Ala Thr Leu Val Cys Leu Ile Ser Asp Phe Tyr Pro
    130              135              140

Gly Ala Val Thr Val Ala Trp Lys Ala Asp Ser Ser Pro Val Lys Ala
145              150              155              160

Gly Val Glu Thr Thr Thr Pro Ser Lys Gln Ser Asn Asn Lys Tyr Ala
                165              170              175

Ala Ser Ser Tyr Leu Ser Leu Thr Pro Glu Gln Trp Lys Ser His Arg
                180              185              190

Ser Tyr Ser Cys Gln Val Thr His Glu Gly Ser Thr Val Glu Lys Thr
            195              200              205

Val Ala Pro Thr Glu Cys Ser
    210              215
```

```
<210> SEQ ID NO 351
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351
```

```
Ala Ile Val Met Thr Gln Thr Pro Ser Ser Lys Ser Val Pro Val Gly
1               5               10              15

Asp Thr Val Thr Ile Asn Cys Gln Ala Ser Glu Ser Val Tyr Asn Asn
            20              25              30

Lys Trp Leu Ser Trp Tyr Gln Gln Lys Pro Gly Gln Pro Pro Lys Leu
        35              40              45

Leu Ile Tyr Leu Ala Ser Thr Leu Ala Ser Gly Val Pro Ser Arg Phe
    50              55              60

Lys Gly Ser Gly Ser Gly Thr Gln Phe Thr Leu Thr Ile Ser Asp Val
65              70              75              80

Val Ser Asp Asp Ala Ala Thr Tyr Tyr Cys Ala Gly Tyr Lys Asn Arg
                85              90              95

Gly Thr Asp Gly Leu Ala Phe Gly Gly Gly Thr Glu Val Val Val Glu
            100              105              110

Arg Thr Val Ala Ala Pro Ser Val Phe Ile Phe Pro Pro Ser Asp Glu
        115              120              125

Gln Leu Lys Ser Gly Thr Ala Ser Val Val Cys Leu Leu Asn Asn Phe
    130              135              140

Tyr Pro Arg Glu Ala Lys Val Gln Trp Lys Val Asp Asn Ala Leu Gln
145              150              155              160

Ser Gly Asn Ser Gln Glu Ser Val Thr Glu Gln Asp Ser Lys Asp Ser
                165              170              175

Thr Tyr Ser Leu Ser Ser Thr Leu Thr Leu Ser Lys Ala Asp Tyr Glu
                180              185              190

Lys His Lys Val Tyr Ala Cys Glu Val Thr His Gln Gly Leu Ser Ser
        195              200              205

Pro Val Thr Lys Ser Phe Asn Arg Gly Glu Cys
    210              215
```

```
<210> SEQ ID NO 352
<211> LENGTH: 220
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Ala Asp Ile Val Met Thr Gln Thr Pro Ala Ser Val Glu Ala Ala Val
1               5                   10                  15

Gly Gly Thr Val Thr Ile Lys Cys Gln Ala Ser Gln Ser Ile Ser Ser
            20                  25                  30

Tyr Leu Ser Trp Tyr Gln Gln Lys Pro Gly Gln Pro Pro Lys Leu Leu
        35                  40                  45

Ile Tyr Arg Ala Ser Thr Leu Ala Ser Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Ser Ala Asp Ala Ala Thr Tyr Tyr Cys Gln Ser Tyr Val Phe Gly Ser
                85                  90                  95

Ser Arg Ser Tyr Asp Asn Ala Phe Gly Gly Gly Thr Glu Val Val Val
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 353
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Ala Tyr Asp Met Ser Gln Thr Pro Ala Ser Val Glu Val Ala Val Gly
1               5                   10                  15

Gly Thr Val Thr Ile Lys Cys Gln Ala Ser Gln Ser Ile Tyr Ser Tyr
            20                  25                  30

Leu Ser Trp Tyr Gln Gln Lys Pro Gly Gln Arg Pro Lys Leu Leu Ile
        35                  40                  45

Tyr Asp Ala Ser Lys Leu Ala Ser Gly Val Pro Ser Arg Phe Thr Gly
    50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Gln Gln Ala Tyr Ser Ser Ser Asn
                85                  90                  95

-continued

```
Val Asp Asn Val Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

```
<210> SEQ ID NO 354
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354
```

```
Ala Tyr Asp Met Thr Gln Thr Pro Ala Ser Met Glu Val Ala Val Gly
1               5                   10                  15

Gly Thr Val Thr Ile Lys Cys Gln Ala Ser Gln Asn Ile His Ser Trp
            20                  25                  30

Leu Ala Trp Phe Gln Gln Lys Pro Gly Gln Pro Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Gln Ser
65                  70                  75                  80

Asp Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

```
<210> SEQ ID NO 355
```

```
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Asn Ile Tyr Arg Tyr
                20                  25                  30

Leu Leu Trp Tyr Gln Gln Lys Leu Gly Gln Arg Pro Ser Leu Leu Ile
            35                  40                  45

Tyr Asp Ala Ser Lys Leu Ala Ser Gly Val Pro Ser Arg Phe Lys Gly
        50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Gln Gln Ala Tyr Ser Ser Ser Asn
                85                  90                  95

Val Asp Asn Ala Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 356
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Gly Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
                20                  25                  30

Leu Ala Trp Phe Gln His Lys Pro Gly Gln Pro Pro Lys Arg Leu Ile
            35                  40                  45

Tyr Lys Ala Ser Thr Leu Ala Ser Gly Val Ser Ser Arg Phe Lys Gly
        50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                85                  90                  95
```

-continued

```
Gly Glu His Val Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
        210                 215
```

<210> SEQ ID NO 357
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
                20                  25                  30

Leu Ser Trp Phe His Gln Lys Pro Gly Gln Pro Pro Lys Arg Leu Ile
            35                  40                  45

Tyr Lys Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                85                  90                  95

Gly Glu His Val Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
        210                 215
```

-continued

```
<210> SEQ ID NO 358
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
                20                  25                  30

Leu Ser Trp Phe His Gln Lys Pro Gly Gln Pro Pro Lys Arg Leu Ile
            35                  40                  45

Tyr Lys Ala Ser Thr Leu Ala Ser Gly Val Ser Ser Arg Phe Lys Gly
        50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
                    85                  90                  95

Gly Glu His Val Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 359
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Gly Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asn Ser Trp
                20                  25                  30

Leu Val Trp Phe Gln His Lys Pro Gly Gln Pro Pro Lys Arg Leu Ile
            35                  40                  45

Tyr Lys Ala Ser Thr Leu Ala Ser Gly Val Ser Ser Arg Phe Lys Gly
        50                  55                  60

Ser Gly Ser Gly Thr His Phe Thr Leu Thr Ile Ser Gly Val Glu Ser
65                  70                  75                  80

Ala Asp Ala Ala Thr Tyr Tyr Cys Gln Gln Gly Tyr Ser Arg Ser Asp
```

-continued

```
                85                    90                    95
Gly Glu His Val Phe Gly Gly Gly Thr Glu Val Val Val Lys Arg Thr
            100                   105                   110
Val Ala Ala Pro Ser Val Phe Ile Phe Pro Pro Ser Asp Glu Gln Leu
            115                   120                   125
Lys Ser Gly Thr Ala Ser Val Val Cys Leu Leu Asn Asn Phe Tyr Pro
            130                   135                   140
Arg Glu Ala Lys Val Gln Trp Lys Val Asp Asn Ala Leu Gln Ser Gly
145                   150                   155                   160
Asn Ser Gln Glu Ser Val Thr Glu Gln Asp Ser Lys Asp Ser Thr Tyr
                165                   170                   175
Ser Leu Ser Ser Thr Leu Thr Leu Ser Lys Ala Asp Tyr Glu Lys His
                180                   185                   190
Lys Val Tyr Ala Cys Glu Val Thr His Gln Gly Leu Ser Ser Pro Val
                195                   200                   205
Thr Lys Ser Phe Asn Arg Gly Glu Cys
            210                   215

<210> SEQ ID NO 360
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Ala Tyr Asp Met Thr Gln Thr Pro Ala Ser Val Glu Val Ala Val Gly
1               5                   10                  15
Gly Thr Val Thr Ile Lys Cys Gln Ala Ser Gln Ser Ile Tyr Arg Tyr
            20                  25                  30
Leu Ser Trp Tyr Gln Lys Lys Pro Gly Gln Arg Pro Lys Phe Leu Ile
            35                  40                  45
Tyr Asp Ala Ser Lys Leu Ala Ser Gly Val Pro Ser Arg Phe Glu Gly
        50                  55                  60
Ser Gly Ser Gly Thr Glu Phe Thr Leu Thr Ile Ser Gly Ala Gln Ser
65                  70                  75                  80
Asp Asp Ala Ala Thr Tyr Tyr Cys Gln Gln Ala Tyr Ser Ser Gly Ser
                85                  90                  95
Ile Asp Asn Ala Phe Gly Gly Gly Thr Glu Val Val Val Lys Arg Thr
            100                 105                 110
Val Ala Ala Pro Ser Val Phe Ile Phe Pro Pro Ser Asp Glu Gln Leu
            115                 120                 125
Lys Ser Gly Thr Ala Ser Val Val Cys Leu Leu Asn Asn Phe Tyr Pro
            130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
                180                 185                 190
Lys Val Tyr Ala Cys Glu Val Thr His Gln Gly Leu Ser Ser Pro Val
                195                 200                 205
Thr Lys Ser Phe Asn Arg Gly Glu Cys
            210                 215
```

-continued

<210> SEQ ID NO 361
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Tyr
                20                  25                  30

Cys Ser Trp Tyr Gln Gln Lys Pro Gly Gln Arg Pro Lys Phe Leu Ile
            35                  40                  45

Tyr Asp Ala Ser Lys Leu Ala Ser Gly Val Pro Ser Arg Phe Lys Gly
    50                  55                  60

Ser Gly Ser Gly Thr Glu Phe Thr Leu Thr Ile Ser Gly Met Gln Ser
65                  70                  75                  80

Asp Asp Ala Ala Thr Tyr Tyr Cys Gln Gln Ala Tyr Ser Ser Ser Asn
                85                  90                  95

Val Asp Asn Ala Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

<210> SEQ ID NO 362
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Tyr
                20                  25                  30

Leu Ser Trp Tyr Gln Gln Lys Pro Gly Gln Arg Pro Lys Phe Leu Ile
            35                  40                  45

Tyr Asp Ala Ser Lys Val Ala Ser Gly Val Pro Ser Arg Phe Lys Gly
    50                  55                  60

Ser Gly Ser Gly Thr Glu Phe Thr Leu Thr Ile Ser Ala Val Gln Ser
65                  70                  75                  80
```

-continued

```
Asp Asp Ala Ala Thr Tyr Tyr Cys Gln Gln Ala Tyr Ser Ser Ser Asn
            85              90              95

Val Asp Asn Ala Phe Gly Gly Gly Thr Glu Val Met Val Lys Arg Thr
            100             105             110

Val Ala Ala Pro Ser Val Phe Ile Phe Pro Pro Ser Asp Glu Gln Leu
            115             120             125

Lys Ser Gly Thr Ala Ser Val Val Cys Leu Leu Asn Asn Phe Tyr Pro
    130             135             140

Arg Glu Ala Lys Val Gln Trp Lys Val Asp Asn Ala Leu Gln Ser Gly
145             150             155             160

Asn Ser Gln Glu Ser Val Thr Glu Gln Asp Ser Lys Asp Ser Thr Tyr
            165             170             175

Ser Leu Ser Ser Thr Leu Thr Leu Ser Lys Ala Asp Tyr Glu Lys His
            180             185             190

Lys Val Tyr Ala Cys Glu Val Thr His Gln Gly Leu Ser Ser Pro Val
            195             200             205

Thr Lys Ser Phe Asn Arg Gly Glu Cys
    210             215

<210> SEQ ID NO 363
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Ala Phe Glu Leu Thr Gln Thr Pro Ser Ser Val Glu Ala Ala Val Gly
1               5               10              15

Gly Thr Val Thr Ile Lys Cys Gln Ala Ser Glu Ser Ile Asp Ser Tyr
            20              25              30

Leu Ser Trp Tyr Gln Gln Lys Pro Gly Gln Pro Pro Lys Leu Leu Ile
            35              40              45

Tyr Ala Ala Ser Thr Leu Ala Ser Gly Val Ser Ser Arg Phe Lys Gly
    50              55              60

Ser Gly Ser Gly Thr Glu Phe Thr Leu Thr Ile Ser Asp Leu Glu Ser
65              70              75              80

Ala Asp Ala Ala Thr Tyr Tyr Cys Gln Ser Tyr Ser Gly Thr Ile Thr
            85              90              95

Thr Ser Gly Gly Ala Phe Gly Gly Gly Thr Glu Val Val Val Lys Arg
            100             105             110

Thr Val Ala Ala Pro Ser Val Phe Ile Phe Pro Pro Ser Asp Glu Gln
            115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
            195             200             205

Val Thr Lys Ser Phe Asn Arg Gly Glu Cys
    210             215
```

<210> SEQ ID NO 364
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Ala Phe Glu Leu Thr Gln Thr Pro Ser Ser Val Glu Ala Ala Val Gly
1               5                   10                  15

Gly Thr Val Thr Ile Lys Cys Gln Ala Ser Glu Ser Ile Asn Ser Tyr
                20                  25                  30

Leu Ser Trp Tyr Gln Gln Lys Pro Gly Gln Pro Pro Lys Leu Leu Ile
            35                  40                  45

Tyr Ala Ala Ser Thr Leu Ala Ser Gly Val Ser Ser Arg Phe Lys Gly
        50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Ser Tyr Ser Gly Thr Ile Ser
                85                  90                  95

Thr Ser Gly Gly Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 365
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Ala Gln Val Leu Thr Gln Thr Ala Ser Ser Val Ser Ala Thr Val Gly
1               5                   10                  15

Gly Thr Val Thr Ile Ser Cys Gln Ser Ser Glu Ser Val Asp Val Asn
                20                  25                  30

Asn Leu Ala Trp Tyr Gln Gln Lys Pro Gly Gln Pro Pro Lys Leu Leu
            35                  40                  45

Ile Tyr Ser Ala Ser Thr Leu Ala Ser Gly Val Pro Ser Arg Phe Lys
        50                  55                  60

Gly Ser Gly Ser Gly Thr Gln Phe Thr Leu Thr Val Ser Asp Leu Glu
65                  70                  75                  80

-continued

```
Ser Ala Asp Ala Ala Thr Tyr Tyr Cys Ala Gly Gly Tyr Ser Gly Asn
            85                  90                  95

Ile Phe Ala Phe Gly Gly Gly Thr Ala Val Val Val Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 366
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Ala Gln Val Leu Thr Gln Thr Pro Ser Pro Val Ser Ala Ala Val Gly
1               5                   10                  15

Gly Thr Val Thr Ile Asn Cys Gln Ser Ser Gln Ser Val Val Ser Asp
            20                  25                  30

Lys Leu Leu Ser Trp Phe Gln Gln Lys Pro Gly Gln Pro Pro Lys Leu
            35                  40                  45

Leu Ile Tyr Gly Ala Ser Thr Leu Ala Ser Gly Val Pro Ser Arg Phe
            50                  55                  60

Lys Gly Ser Gly Ser Gly Thr Gln Phe Thr Leu Thr Ile Ser Asp Val
65                  70                  75                  80

Gln Ser Asp Asp Ala Ala Thr Tyr Tyr Cys Ala Gly Ala Tyr Ser Thr
            85                  90                  95

Asp Ser Asp Ile Arg Ala Phe Gly Gly Gly Thr Glu Val Val Val Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
```

```
      210               215
```

<210> SEQ ID NO 367
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Ala Arg Thr Gly Gly Gly Ser Gly Gly Gly Ser Val
225                 230                 235                 240

Pro Arg Trp Arg Gln Gln Trp Ser Gly Pro Gly Thr Thr Lys Arg Phe
                245                 250                 255

Pro Glu Thr Val Leu Ala Arg Cys Val Lys Tyr Thr Glu Ile His Pro
            260                 265                 270

Glu Met Arg His Val Asp Cys Gln Ser Val Trp Asp Ala Phe Lys Gly
            275                 280                 285

Ala Phe Ile Ser Lys His Pro Cys Asn Ile Thr Glu Glu Asp Tyr Gln
    290                 295                 300

Pro Leu Met Lys Leu Gly Thr Gln Thr Val Pro Cys Asn Lys Ile Leu
305                 310                 315                 320

Leu Trp Ser Arg Ile Lys Asp Leu Ala His Gln Phe Thr Gln Val Gln
                325                 330                 335

Arg Asp Met Phe Thr Leu Glu Asp Thr Leu Leu Gly Tyr Leu Ala Asp
            340                 345                 350
```

```
Asp Leu Thr Trp Cys Gly Glu Phe Asn Thr Ser Lys Ile Asn Tyr Gln
        355                 360                 365

Ser Cys Pro Asp Trp Arg Lys Asp Cys Ser Asn Asn Pro Val Ser Val
        370                 375                 380

Phe Trp Lys Thr Val Ser Arg Arg Phe Ala Glu Ala Ala Cys Asp Val
385                 390                 395                 400

Val His Val Met Leu Asn Gly Ser Arg Ser Lys Ile Phe Asp Lys Asn
                405                 410                 415

Ser Thr Phe Gly Ser Val Glu Val His Asn Leu Gln Pro Glu Lys Val
                420                 425                 430

Gln Thr Leu Glu Ala Trp Val Ile His Gly Gly Arg Glu Asp Ser Arg
            435                 440                 445

Asp Leu Cys Gln Asp Pro Thr Ile Lys Glu Leu Glu Ser Ile Ile Ser
        450                 455                 460

Lys Arg Asn Ile Gln Phe Ser Cys Lys Asn Ile Tyr Arg Pro Asp Lys
465                 470                 475                 480

Phe Leu Gln Cys Val Lys Asn Pro Glu Asp Ser Ser Cys Thr Ser Glu
                485                 490                 495

Ile

<210> SEQ ID NO 368
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Ser Gly Leu Asn Asp Ile Phe Glu Ala Gln Lys Ile Glu Trp His Glu
1               5                   10                  15

Val Pro Arg Trp Arg Gln Gln Trp Ser Gly Pro Gly Thr Thr Lys Arg
            20                  25                  30

Phe Pro Glu Thr Val Leu Ala Arg Cys Val Lys Tyr Thr Glu Ile His
            35                  40                  45

Pro Glu Met Arg His Val Asp Cys Gln Ser Val Trp Asp Ala Phe Lys
        50                  55                  60

Gly Ala Phe Ile Ser Lys His Pro Cys Asn Ile Thr Glu Glu Asp Tyr
65                  70                  75                  80

Gln Pro Leu Met Lys Leu Gly Thr Gln Thr Val Pro Cys Asn Lys Ile
                85                  90                  95

Leu Leu Trp Ser Arg Ile Lys Asp Leu Ala His Gln Phe Thr Gln Val
                100                 105                 110

Gln Arg Asp Met Phe Thr Leu Glu Asp Thr Leu Leu Gly Tyr Leu Ala
            115                 120                 125

Asp Asp Leu Thr Trp Cys Gly Glu Phe Asn Thr Ser Lys Ile Asn Tyr
        130                 135                 140

Gln Ser Cys Pro Asp Trp Arg Lys Asp Cys Ser Asn Asn Pro Val Ser
145                 150                 155                 160

Val Phe Trp Lys Thr Val Ser Arg Arg Phe Ala Glu Ala Ala Cys Asp
                165                 170                 175

Val Val His Val Met Leu Asn Gly Ser Arg Ser Lys Ile Phe Asp Lys
                180                 185                 190

Asn Ser Thr Phe Gly Ser Val Glu Val His Asn Leu Gln Pro Glu Lys
            195                 200                 205
```

-continued

```
Val Gln Thr Leu Glu Ala Trp Val Ile His Gly Gly Arg Glu Asp Ser
    210             215             220

Arg Asp Leu Cys Gln Asp Pro Thr Ile Lys Glu Leu Glu Ser Ile Ile
225             230             235             240

Ser Lys Arg Asn Ile Gln Phe Ser Cys Lys Asn Ile Tyr Arg Pro Asp
            245             250             255

Lys Phe Leu Gln Cys Val Lys Asn Pro Glu Asp Ser Ser Cys Thr Ser
            260             265             270

Glu Ile

<210> SEQ ID NO 369
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Ser Gly Leu Asn Asp Ile Phe Glu Ala Gln Lys Ile Glu Trp His Glu
1               5               10              15

Leu Pro Arg Trp Arg Gln Gln Trp Ser Gly Ser Gly Thr Thr Ser Arg
            20              25              30

Phe Pro Glu Thr Val Leu Ala Arg Cys Val Lys Tyr Thr Glu Val His
            35              40              45

Pro Glu Met Arg His Val Asp Cys Gln Ser Val Trp Asp Ala Phe Lys
            50              55              60

Gly Ala Phe Ile Ser Lys Tyr Pro Cys Asn Ile Thr Glu Glu Asp Tyr
65              70              75              80

Gln Pro Leu Val Lys Leu Gly Thr Gln Thr Val Pro Cys Asn Lys Thr
            85              90              95

Leu Leu Trp Ser Arg Ile Lys Asp Leu Ala His Gln Phe Thr Gln Val
            100             105             110

Gln Arg Asp Met Phe Thr Leu Glu Asp Met Leu Leu Gly Tyr Leu Ala
            115             120             125

Asp Asp Leu Thr Trp Cys Gly Glu Phe Asn Thr Phe Glu Ile Asn Tyr
            130             135             140

Gln Ser Cys Pro Asp Trp Arg Lys Asp Cys Ser Asn Asn Pro Val Ser
145             150             155             160

Val Phe Trp Lys Thr Val Ser Arg Arg Phe Ala Glu Thr Ala Cys Gly
            165             170             175

Val Val His Val Met Leu Asn Gly Ser Arg Ser Lys Ile Phe Asp Lys
            180             185             190

Asn Ser Thr Phe Gly Ser Val Glu Val His Asn Leu Gln Pro Glu Lys
            195             200             205

Val Gln Ala Leu Glu Ala Trp Val Ile His Gly Gly Arg Glu Asp Ser
    210             215             220

Arg Asp Leu Cys Gln Asp Pro Thr Ile Lys Glu Leu Glu Ser Ile Ile
225             230             235             240

Ser Lys Arg Asn Ile Arg Phe Phe Cys Lys Asn Ile Tyr Arg Pro Asp
            245             250             255

Lys Phe Leu Gln Cys Val Lys Asn Pro Glu Asp Ser Ser Cys Leu Ser
            260             265             270

Gly Ile
```

```
<210> SEQ ID NO 370
<211> LENGTH: 691
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Gln Thr Ser Val Ser Pro Ser Lys Val Ile Leu Pro Arg Gly Gly Ser
1               5                   10                  15

Val Leu Val Thr Cys Ser Thr Ser Cys Asp Gln Pro Lys Leu Leu Gly
                20                  25                  30

Ile Glu Thr Pro Leu Pro Lys Lys Glu Leu Leu Leu Pro Gly Asn Asn
            35                  40                  45

Arg Lys Val Tyr Glu Leu Ser Asn Val Gln Glu Asp Ser Gln Pro Met
        50                  55                  60

Cys Tyr Ser Asn Cys Pro Asp Gly Gln Ser Thr Ala Lys Thr Phe Leu
65                  70                  75                  80

Thr Val Tyr Trp Thr Pro Glu Arg Val Glu Leu Ala Pro Leu Pro Ser
                85                  90                  95

Trp Gln Pro Val Gly Lys Asn Leu Thr Leu Arg Cys Gln Val Glu Gly
            100                 105                 110

Gly Ala Pro Arg Ala Asn Leu Thr Val Val Leu Leu Arg Gly Glu Lys
            115                 120                 125

Glu Leu Lys Arg Glu Pro Ala Val Gly Glu Pro Ala Glu Val Thr Thr
        130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
            195                 200                 205

Val Cys Ser Leu Asp Gly Leu Phe Pro Val Ser Glu Ala Gln Val His
        210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
            275                 280                 285

Ile Leu Thr Lys Pro Glu Val Ser Glu Gly Thr Glu Val Thr Val Lys
        290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Leu Lys Ala Thr Pro Glu
                325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
            355                 360                 365
```

-continued

```
Pro Arg Leu Asp Glu Arg Asp Cys Pro Gly Asn Trp Thr Trp Pro Glu
    370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
            405                 410                 415

Ser Val Thr Val Thr Arg Asp Leu Glu Gly Thr Tyr Leu Cys Arg Ala
            420                 425                 430

Arg Ser Thr Gln Gly Glu Val Thr Arg Lys Val Thr Val Asn Val Leu
            435                 440                 445

Ser Pro Arg Tyr Glu Gly Gly Gly Gly Gly Ser Gly Gly Gly Gly Ser
    450                 455                 460

Asp Lys Thr His Thr Cys Pro Pro Cys Pro Ala Pro Glu Leu Leu Gly
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510

Glu Asp Pro Glu Val Lys Phe Asn Trp Tyr Val Asp Gly Val Glu Val
            515                 520                 525

His Asn Ala Lys Thr Lys Pro Arg Glu Glu Gln Tyr Asn Ser Thr Tyr
    530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
            565                 570                 575

Glu Lys Thr Ile Ser Lys Ala Lys Gly Gln Pro Arg Glu Pro Gln Val
            580                 585                 590

Tyr Thr Leu Pro Pro Ser Arg Glu Glu Met Thr Lys Asn Gln Val Ser
    595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
            645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
            675                 680                 685

Pro Gly Lys
    690
```

```
<210> SEQ ID NO 371
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Tyr Trp Thr Pro Glu Arg Val Glu Leu Ala Pro Leu Pro Ser Trp Gln
1               5                   10                  15

Pro Val Gly Lys Asn Leu Thr Leu Arg Cys Gln Val Glu Gly Gly Ala
            20                  25                  30
```

```
Pro Arg Ala Asn Leu Thr Val Val Leu Leu Arg Gly Glu Lys Glu Leu
        35                  40                  45

Lys Arg Glu Pro Ala Val Gly Glu Pro Ala Glu Val Thr Thr Thr Val
    50                  55                  60

Leu Val Arg Arg Asp His His Gly Ala Asn Phe Ser Cys Arg Thr Glu
65                  70                  75                  80

Leu Asp Leu Arg Pro Gln Gly Leu Glu Leu Phe Glu Asn Thr Ser Ala
                85                  90                  95

Pro Tyr Gln Leu Gln Thr Phe Val Leu Pro Ala Thr Pro Pro Gln Leu
                100                 105                 110

Val Ser Pro Arg Val Leu Glu Val Asp Thr Gln Gly Thr Val Val Cys
            115                 120                 125

Ser Leu Asp Gly Leu Phe Pro Val Ser Glu Ala Gln Val His Leu Ala
        130                 135                 140

Leu Gly Asp Gln Arg Leu Asn Pro Thr Val Thr Tyr Gly Asn Asp Ser
145                 150                 155                 160

Phe Ser Ala Lys Ala Ser Val Ser Val Thr Ala Glu Asp Glu Gly Thr
                165                 170                 175

Gln Arg Leu Thr Cys Ala Val Ile Leu Gly Asn Gln Ser Gln Glu Thr
                180                 185                 190

Leu Gln Thr Val Thr Ile Tyr Ser Phe Pro Ala Pro Asn Val Ile Leu
            195                 200                 205

Thr Lys Pro Glu Val Ser Glu Gly Thr Glu Val Thr Val Lys Cys Glu
    210                 215                 220

Ala His Pro Arg Ala Lys Val Thr Leu Asn Gly Val Pro Ala Gln Pro
225                 230                 235                 240

Leu Gly Pro Arg Ala Gln Leu Leu Leu Lys Ala Thr Pro Glu Asp Asn
                245                 250                 255

Gly Arg Ser Phe Ser Cys Ser Ala Thr Leu Glu Val Ala Gly Gln Leu
                260                 265                 270

Ile His Lys Asn Gln Thr Arg Glu Leu Arg Val Leu Tyr Gly Pro Arg
            275                 280                 285

Leu Asp Glu Arg Asp Cys Pro Gly Asn Trp Thr Trp Pro Glu Asn Ser
        290                 295                 300

Gln Gln Thr Pro Met Cys Gln Ala Trp Gly Asn Pro Leu Pro Glu Leu
305                 310                 315                 320

Lys Cys Leu Lys Asp Gly Thr Phe Pro Leu Pro Ile Gly Glu Ser Val
            325                 330                 335

Thr Val Thr Arg Asp Leu Glu Gly Thr Tyr Leu Cys Arg Ala Arg Ser
            340                 345                 350

Thr Gln Gly Glu Val Thr Arg Lys Val Thr Val Asn Val Leu Ser Pro
            355                 360                 365

Arg Tyr Glu Gly Gly Gly Gly Ser Gly Gly Gly Gly Ser Asp Lys
    370                 375                 380

Thr His Thr Cys Pro Pro Cys Pro Ala Pro Glu Leu Leu Gly Gly Pro
385                 390                 395                 400

Ser Val Phe Leu Phe Pro Pro Lys Pro Lys Asp Thr Leu Met Ile Ser
                405                 410                 415

Arg Thr Pro Glu Val Thr Cys Val Val Val Asp Val Ser His Glu Asp
            420                 425                 430

Pro Glu Val Lys Phe Asn Trp Tyr Val Asp Gly Val Glu Val His Asn
        435                 440                 445
```

-continued

```
Ala Lys Thr Lys Pro Arg Glu Glu Gln Tyr Asn Ser Thr Tyr Arg Val
    450             455                 460

Val Ser Val Leu Thr Val Leu His Gln Asp Trp Leu Asn Gly Lys Glu
465             470                 475                 480

Tyr Lys Cys Lys Val Ser Asn Lys Ala Leu Pro Ala Pro Ile Glu Lys
            485                 490                 495

Thr Ile Ser Lys Ala Lys Gly Gln Pro Arg Glu Pro Gln Val Tyr Thr
            500                 505                 510

Leu Pro Pro Ser Arg Glu Glu Met Thr Lys Asn Gln Val Ser Leu Thr
            515                 520                 525

Cys Leu Val Lys Gly Phe Tyr Pro Ser Asp Ile Ala Val Glu Trp Glu
    530                 535                 540

Ser Asn Gly Gln Pro Glu Asn Asn Tyr Lys Thr Thr Pro Pro Val Leu
545                 550                 555                 560

Asp Ser Asp Gly Ser Phe Phe Leu Tyr Ser Lys Leu Thr Val Asp Lys
                565                 570                 575

Ser Arg Trp Gln Gln Gly Asn Val Phe Ser Cys Ser Val Met His Glu
            580                 585                 590

Ala Leu His Asn His Tyr Thr Gln Lys Ser Leu Ser Leu Ser Pro Gly
        595                 600                 605

Lys
```

```
<210> SEQ ID NO 372
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372
```

```
Phe Pro Ala Pro Asn Val Ile Leu Thr Lys Pro Glu Val Ser Glu Gly
1               5                   10                  15

Thr Glu Val Thr Val Lys Cys Glu Ala His Pro Arg Ala Lys Val Thr
                20                  25                  30

Leu Asn Gly Val Pro Ala Gln Pro Leu Gly Pro Arg Ala Gln Leu Leu
        35                  40                  45

Leu Lys Ala Thr Pro Glu Asp Asn Gly Arg Ser Phe Ser Cys Ser Ala
    50                  55                  60

Thr Leu Glu Val Ala Gly Gln Leu Ile His Lys Asn Gln Thr Arg Glu
65                  70                  75                  80

Leu Arg Val Leu Tyr Gly Pro Arg Leu Asp Glu Arg Asp Cys Pro Gly
                85                  90                  95

Asn Trp Thr Trp Pro Glu Asn Ser Gln Gln Thr Pro Met Cys Gln Ala
            100                 105                 110

Trp Gly Asn Pro Leu Pro Glu Leu Lys Cys Leu Lys Asp Gly Thr Phe
            115                 120                 125

Pro Leu Pro Ile Gly Glu Ser Val Thr Val Thr Arg Asp Leu Glu Gly
    130                 135                 140

Thr Tyr Leu Cys Arg Ala Arg Ser Thr Gln Gly Glu Val Thr Arg Lys
145                 150                 155                 160

Val Thr Val Asn Val Leu Ser Pro Arg Tyr Glu Gly Gly Gly Gly Gly
                165                 170                 175

Ser Gly Gly Gly Gly Ser Asp Lys Thr His Thr Cys Pro Pro Cys Pro
            180                 185                 190
```

```
Ala Pro Glu Leu Leu Gly Gly Pro Ser Val Phe Leu Phe Pro Pro Lys
        195                 200                 205

Pro Lys Asp Thr Leu Met Ile Ser Arg Thr Pro Glu Val Thr Cys Val
        210                 215                 220

Val Val Asp Val Ser His Glu Asp Pro Glu Val Lys Phe Asn Trp Tyr
225                 230                 235                 240

Val Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu His
                260                 265                 270

Gln Asp Trp Leu Asn Gly Lys Glu Tyr Lys Cys Lys Val Ser Asn Lys
        275                 280                 285

Ala Leu Pro Ala Pro Ile Glu Lys Thr Ile Ser Lys Ala Lys Gly Gln
        290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
                340                 345                 350

Tyr Lys Thr Thr Pro Pro Val Leu Asp Ser Asp Gly Ser Phe Phe Leu
                355                 360                 365

Tyr Ser Lys Leu Thr Val Asp Lys Ser Arg Trp Gln Gln Gly Asn Val
        370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                405
```

```
<210> SEQ ID NO 373
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Gln Thr Ser Val Ser Pro Ser Lys Val Ile Leu Pro Arg Gly Gly Ser
1                   5                   10                  15

Val Leu Val Thr Cys Ser Thr Ser Cys Asp Gln Pro Lys Leu Leu Gly
                20                  25                  30

Ile Glu Thr Pro Leu Pro Lys Lys Glu Leu Leu Leu Pro Gly Asn Asn
        35                  40                  45

Arg Lys Val Tyr Glu Leu Ser Asn Val Gln Glu Asp Ser Gln Pro Met
        50                  55                  60

Cys Tyr Ser Asn Cys Pro Asp Gly Gln Ser Thr Ala Lys Thr Phe Leu
65                  70                  75                  80

Thr Val Tyr Trp Thr Pro Glu Arg Val Glu Leu Ala Pro Leu Pro Ser
                85                  90                  95

Trp Gln Pro Val Gly Lys Asn Leu Thr Leu Arg Cys Gln Val Glu Gly
                100                 105                 110

Gly Ala Pro Arg Ala Asn Leu Thr Val Val Leu Leu Arg Gly Glu Lys
        115                 120                 125

Glu Leu Lys Arg Glu Pro Ala Val Gly Glu Pro Ala Glu Val Thr Thr
        130                 135                 140
```

-continued

```
Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
            165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
            245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
        290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Leu Lys Ala Thr Pro Glu
            325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
        355                 360                 365

Pro Arg Leu Asp Glu Arg Asp Cys Pro Gly Asn Trp Thr Trp Pro Glu
    370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
            405                 410                 415

Ser Val Thr Val Thr Arg Asp Leu Glu Gly Thr Tyr Leu Cys Arg Ala
            420                 425                 430

Arg Ser Thr Gln Gly Glu Val Thr Arg Lys Val Thr Val Asn Val Leu
        435                 440                 445

Ser Pro Arg Tyr Glu Gly Gly Ser Gly Gly Ser Gly Leu Asn Asp Ile
    450                 455                 460

Phe Glu Ala Gln Lys Ile Glu Trp His Glu Glu Asn Leu Tyr Phe Gln
465                 470                 475                 480
```

```
<210> SEQ ID NO 374
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Gln Thr Ser Val Phe Pro Pro Glu Val Ile Leu Pro Arg Gly Gly Ser
1               5                   10                  15

Val Lys Val Asn Cys Ser Ala Ser Cys Asp Gln Pro Ile Ser Leu Gly
```

-continued

```
            20                  25                  30
Met Glu Thr Pro Leu Pro Lys Lys Glu Ile Leu Pro Gly Gly Asn Asn
            35                  40                  45
Trp Lys Met Tyr Glu Leu Ser Asn Val Gln Glu Asp Ser Gln Pro Met
        50                  55                  60
Cys Tyr Ser Asn Cys Pro Asp Gly Gln Ser Ser Ala Lys Thr Leu Leu
65                  70                  75                  80
Thr Val Tyr Trp Thr Pro Glu Arg Val Glu Leu Ala Pro Leu Pro Pro
                    85                  90                  95
Trp Gln Pro Val Gly Lys Asn Leu Thr Leu Arg Cys Gln Val Glu Gly
                100                 105                 110
Gly Ala Pro Arg Ala Asn Leu Thr Val Met Leu Leu Arg Gly Glu Lys
                115                 120                 125
Glu Leu Ser Arg Gln Ser Ala Val Gly Glu Pro Ala Glu Val Thr Thr
        130                 135                 140
Thr Val Pro Val Gly Arg Asp Asp His Gly Ala Asn Phe Ser Cys Arg
145                 150                 155                 160
Thr Glu Leu Asp Leu Arg Pro Tyr Val Leu Lys Leu Phe Glu Asn Thr
                165                 170                 175
Ser Ala Pro His Gln Leu Gln Thr Phe Asp Leu Pro Ala Thr Pro Pro
                180                 185                 190
Gln Leu Val Ser Pro Gln Val Leu Glu Val Asp Thr Gln Gly Thr Val
                195                 200                 205
Val Cys Ser Leu Asp Gly Leu Phe Pro Val Ser Glu Ala Gln Val Ser
        210                 215                 220
Leu Ala Leu Gly Asp Gln Lys Leu Asn Pro Thr Ile Thr Tyr Gly Asn
225                 230                 235                 240
Asn Ser Leu Ser Ala Lys Ala Ser Val Lys Val Thr Ala Glu Glu Glu
                245                 250                 255
Gly Thr Gln Gln Leu Leu Cys Gly Val Met Leu Gly Asn Gln Thr Gln
                260                 265                 270
Glu Thr Arg Gln Thr Val Thr Ile Tyr Ser Phe Pro Ala Pro Asn Val
        275                 280                 285
Asn Leu Thr Lys Pro Glu Val Ser Glu Gly Thr Glu Val Ile Val Glu
        290                 295                 300
Cys Glu Ala His Pro Arg Ala Lys Val Met Leu Asn Gly Val Pro Ala
305                 310                 315                 320
Gln Pro Pro Gly Pro Arg Ala Gln Phe Leu Leu Lys Ala Thr Pro Glu
                325                 330                 335
Asp Asn Gly Arg Ser Phe Ser Cys Ser Ala Thr Leu Glu Val Ala Gly
                340                 345                 350
Gln Leu Val His Lys Asn Gln Thr Arg Glu Leu Arg Val Leu Tyr Gly
                355                 360                 365
Pro Arg Leu Asp Glu Lys Asp Cys Pro Gly Asn Trp Thr Trp Pro Glu
        370                 375                 380
Asn Ser Gln Gln Thr Pro Met Cys Gln Ala Trp Gly Asn Pro Leu Pro
385                 390                 395                 400
Gln Leu Lys Cys Leu Lys Asp Gly Thr Phe Pro Leu Pro Ile Gly Gln
                405                 410                 415
Ser Val Thr Val Thr Arg Asp Leu Glu Gly Thr Tyr Leu Cys Gln Ala
                420                 425                 430
Arg Ser Thr Arg Gly Glu Val Thr Arg Glu Val Thr Val Asn Val Leu
                435                 440                 445
```

```
Ser Pro Arg Tyr Glu Gly Gly Ser Gly Gly Ser Gly Leu Asn Asp Ile
    450             455             460

Phe Glu Ala Gln Lys Ile Glu Trp His Glu Glu Asn Leu Tyr Phe Gln
465             470             475             480

<210> SEQ ID NO 375
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Tyr Trp Thr Pro Glu Arg Val Glu Leu Ala Pro Leu Pro Pro Trp Gln
1               5               10              15

Pro Val Gly Lys Asn Leu Thr Leu Arg Cys Gln Val Glu Gly Gly Ala
                20              25              30

Pro Arg Ala Asn Leu Thr Val Met Leu Leu Arg Gly Glu Lys Glu Leu
        35              40              45

Ser Arg Gln Ser Ala Val Gly Glu Pro Ala Glu Val Thr Thr Thr Val
    50              55              60

Pro Val Gly Arg Asp Asp His Gly Ala Asn Phe Ser Cys Arg Thr Glu
65              70              75              80

Leu Asp Leu Arg Pro Tyr Val Leu Lys Leu Phe Glu Asn Thr Ser Ala
                85              90              95

Pro His Gln Leu Gln Thr Phe Asp Leu Pro Ala Thr Pro Pro Gln Leu
        100             105             110

Val Ser Pro Gln Val Leu Glu Val Asp Thr Gln Gly Thr Val Val Cys
        115             120             125

Ser Leu Asp Gly Leu Phe Pro Val Ser Glu Ala Gln Val Ser Leu Ala
    130             135             140

Leu Gly Asp Gln Lys Leu Asn Pro Thr Ile Thr Tyr Gly Asn Asn Ser
145             150             155             160

Leu Ser Ala Lys Ala Ser Val Lys Val Thr Ala Glu Glu Glu Gly Thr
                165             170             175

Gln Gln Leu Leu Cys Gly Val Met Leu Gly Asn Gln Thr Gln Glu Thr
        180             185             190

Arg Gln Thr Val Thr Ile Tyr Ser Phe Pro Ala Pro Asn Val Asn Leu
        195             200             205

Thr Lys Pro Glu Val Ser Glu Gly Thr Glu Val Ile Val Glu Cys Glu
    210             215             220

Ala His Pro Arg Ala Lys Val Met Leu Asn Gly Val Pro Ala Gln Pro
225             230             235             240

Pro Gly Pro Arg Ala Gln Phe Leu Leu Lys Ala Thr Pro Glu Asp Asn
        245             250             255

Gly Arg Ser Phe Ser Cys Ser Ala Thr Leu Glu Val Ala Gly Gln Leu
        260             265             270

Val His Lys Asn Gln Thr Arg Glu Leu Arg Val Leu Tyr Gly Pro Arg
        275             280             285

Leu Asp Glu Lys Asp Cys Pro Gly Asn Trp Thr Trp Pro Glu Asn Ser
    290             295             300

Gln Gln Thr Pro Met Cys Gln Ala Trp Gly Asn Pro Leu Pro Gln Leu
305             310             315             320

Lys Cys Leu Lys Asp Gly Thr Phe Pro Leu Pro Ile Gly Gln Ser Val
```

-continued

```
                325                 330                 335

Thr Val Thr Arg Asp Leu Glu Gly Thr Tyr Leu Cys Gln Ala Arg Ser
        340                 345                 350

Thr Arg Gly Glu Val Thr Arg Glu Val Thr Val Asn Val Leu Ser Pro
            355                 360                 365

Arg Tyr Glu Gly Gly Gly Gly Ser Gly Gly Gly Gly Ser Asp Lys
        370                 375                 380

Thr His Thr Cys Pro Pro Cys Pro Ala Pro Glu Leu Leu Gly Gly Pro
385                 390                 395                 400

Ser Val Phe Leu Phe Pro Pro Lys Pro Lys Asp Thr Leu Met Ile Ser
                405                 410                 415

Arg Thr Pro Glu Val Thr Cys Val Val Val Asp Val Ser His Glu Asp
            420                 425                 430

Pro Glu Val Lys Phe Asn Trp Tyr Val Asp Gly Val Glu Val His Asn
            435                 440                 445

Ala Lys Thr Lys Pro Arg Glu Glu Gln Tyr Asn Ser Thr Tyr Arg Val
    450                 455                 460

Val Ser Val Leu Thr Val Leu His Gln Asp Trp Leu Asn Gly Lys Glu
465                 470                 475                 480

Tyr Lys Cys Lys Val Ser Asn Lys Ala Leu Pro Ala Pro Ile Glu Lys
                485                 490                 495

Thr Ile Ser Lys Ala Lys Gly Gln Pro Arg Glu Pro Gln Val Tyr Thr
                500                 505                 510

Leu Pro Pro Ser Arg Glu Glu Met Thr Lys Asn Gln Val Ser Leu Thr
            515                 520                 525

Cys Leu Val Lys Gly Phe Tyr Pro Ser Asp Ile Ala Val Glu Trp Glu
    530                 535                 540

Ser Asn Gly Gln Pro Glu Asn Asn Tyr Lys Thr Thr Pro Pro Val Leu
545                 550                 555                 560

Asp Ser Asp Gly Ser Phe Phe Leu Tyr Ser Lys Leu Thr Val Asp Lys
                565                 570                 575

Ser Arg Trp Gln Gln Gly Asn Val Phe Ser Cys Ser Val Met His Glu
            580                 585                 590

Ala Leu His Asn His Tyr Thr Gln Lys Ser Leu Ser Leu Ser Pro Gly
        595                 600                 605

Lys
```

```
<210> SEQ ID NO 376
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
```

-continued

```
65              70              75              80

Leu Gln Met Asn Ser Leu Arg Ala Glu Asp Thr Ala Val Tyr Phe Cys
                85              90              95

Ala Lys Asp Lys Ile Leu Trp Phe Gly Glu Pro Val Phe Asp Tyr Trp
            100             105             110

Gly Gln Gly Thr Leu Val Thr Val Ser Ser Ala Ser Thr Lys Gly Pro
            115             120             125

Ser Val Phe Pro Leu Ala Pro Ser Ser Lys Ser Thr Ser Gly Gly Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
                165             170             175

Ala Val Leu Gln Ser Ser Gly Leu Tyr Ser Leu Ser Ser Val Val Thr
            180             185             190

Val Pro Ser Ser Ser Leu Gly Thr Gln Thr Tyr Ile Cys Asn Val Asn
            195             200             205

His Lys Pro Ser Asn Thr Lys Val Asp Lys Arg Val Glu Pro Lys Ser
    210             215             220

Cys Asp Lys Thr His Thr Cys Pro Pro Cys Pro Ala Pro Glu Leu Leu
225             230             235             240

Gly Gly Pro Ser Val Phe Leu Phe Pro Pro Lys Pro Lys Asp Thr Leu
            245             250             255

Met Ile Ser Arg Thr Pro Glu Val Thr Cys Val Val Val Asp Val Ser
            260             265             270

His Glu Asp Pro Glu Val Lys Phe Asn Trp Tyr Val Asp Gly Val Glu
            275             280             285

Val His Asn Ala Lys Thr Lys Pro Arg Glu Glu Gln Tyr Asn Ser Thr
    290             295             300

Tyr Arg Val Val Ser Val Leu Thr Val Leu His Gln Asp Trp Leu Asn
305             310             315             320

Gly Lys Glu Tyr Lys Cys Lys Val Ser Asn Lys Ala Leu Pro Ala Pro
            325             330             335

Ile Glu Lys Thr Ile Ser Lys Ala Lys Gly Gln Pro Arg Glu Pro Gln
            340             345             350

Val Tyr Thr Leu Pro Pro Ser Arg Glu Glu Met Thr Lys Asn Gln Val
            355             360             365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
            405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
            435             440             445

Ser Pro Gly Lys
    450
```

```
<210> SEQ ID NO 377
<211> LENGTH: 710
<212> TYPE: PRT
<213> ORGANISM: Artificial Sequence
```

-continued

<220> FEATURE:
<223> OTHER INFORMATION: Description of Artificial Sequence: Synthetic
      polypeptide

<400> SEQUENCE: 377

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Gly Gly Gly Ser Gly Gly Gly Ser Gly Gly Gly
    450                 455                 460

Gly Ser Ala Ser Gln Val Gln Leu Val Glu Ser Gly Gly Gly Leu Val
465                 470                 475                 480

Gln Pro Gly Gly Ser Leu Arg Leu Ser Cys Ala Ala Ser Gly Phe Thr
                485                 490                 495

Phe Ser Ser Tyr Ala Met Ser Trp Val Arg Gln Ala Pro Gly Lys Gly
                500                 505                 510

Leu Glu Trp Val Ser Ala Ile Ser Gly Ser Gly Gly Ser Thr Tyr Tyr
                515                 520                 525

Ala Asp Ser Val Lys Gly Arg Phe Thr Ile Ser Arg Asp Asn Ser Lys
    530                 535                 540

Asn Thr Leu Tyr Leu Gln Met Ser Ser Leu Arg Ala Glu Asp Thr Ala
545                 550                 555                 560

Phe Tyr Tyr Cys Ala Asn Ser Ala Tyr Thr Gly Gly Trp Tyr Asp Tyr
                565                 570                 575

Trp Gly His Gly Thr Leu Val Thr Val Ser Ser Gly Gly Gly Gly Ser
                580                 585                 590

Gly Gly Gly Gly Ser Gly Gly Gly Gly Ser Ser Glu Leu Thr Gln Asp
                595                 600                 605

Pro Ala Val Ser Val Ala Leu Gly Gln Thr Val Lys Ile Thr Cys Gln
    610                 615                 620

Gly Asp Ser Leu Arg Thr Tyr Tyr Ala Ser Trp Tyr Gln Gln Arg Pro
625                 630                 635                 640

Gly Gln Ala Pro Val Leu Val Ile Tyr Gly Glu Asn Ser Arg Pro Ser
                645                 650                 655

Gly Ile Pro Asp Arg Phe Ser Gly Ser Ser Ser Gly Asn Thr Ala Ser
                660                 665                 670

Leu Thr Ile Thr Gly Ala Gln Ala Glu Asp Glu Ala Asp Tyr Tyr Cys
                675                 680                 685

Asn Ser Arg Asp Ser Ser Gly Asn His Leu Arg Val Phe Gly Gly Gly
    690                 695                 700

Thr Lys Val Thr Val Leu
705                 710

<210> SEQ ID NO 378
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
                20                  25                  30
```

```
Ala Met Ser Trp Val Arg Gln Ala Pro Gly Lys Gly Leu Glu Trp Val
    35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Ala Ser Thr Lys Gly Pro Ser Val Phe
        115                 120                 125

Pro Leu Ala Pro Glu Val Gln Leu Leu Glu Ser Gly Gly Gly Leu Val
    130                 135                 140

Gln Pro Gly Gly Ser Leu Arg Leu Ser Cys Ala Val Ser Gly Phe Thr
145                 150                 155                 160

Phe Asn Ser Phe Ala Met Ser Trp Val Arg Gln Ala Pro Gly Lys Gly
                165                 170                 175

Leu Glu Trp Val Ser Ala Ile Ser Gly Ser Gly Gly Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Phe Cys Ala Lys Asp Lys Ile Leu Trp Phe Gly Glu Pro Val
225                 230                 235                 240

Phe Asp Tyr Trp Gly Gln Gly Thr Leu Val Thr Val Ser Ser Ala Ser
                245                 250                 255

Thr Lys Gly Pro Ser Val Phe Pro Leu Ala Pro Ser Ser Lys Ser Thr
                260                 265                 270

Ser Gly Gly Thr Ala Ala Leu Gly Cys Leu Val Lys Asp Tyr Phe Pro
            275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Gln Thr Tyr Ile
                325                 330                 335

Cys Asn Val Asn His Lys Pro Ser Asn Thr Lys Val Asp Lys Lys Val
            340                 345                 350

Glu Pro Lys Ser Cys Asp Lys Thr His Thr Cys Pro Pro Cys Pro Ala
        355                 360                 365

Pro Glu Leu Leu Gly Gly Pro Ser Val Phe Leu Phe Pro Pro Lys Pro
    370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
                405                 410                 415

Asp Gly Val Glu Val His Asn Ala Lys Thr Lys Pro Arg Glu Glu Gln
            420                 425                 430

Tyr Asn Ser Thr Tyr Arg Val Val Ser Val Leu Thr Val Leu His Gln
        435                 440                 445

Asp Trp Leu Asn Gly Lys Glu Tyr Lys Cys Lys Val Ser Asn Lys Ala
```

```
         450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Asp Glu Leu Thr
                485                 490                 495

Lys Asn Gln Val Ser Leu Thr Cys Leu Val Lys Gly Phe Tyr Pro Ser
                500                 505                 510

Asp Ile Ala Val Glu Trp Glu Ser Asn Gly Gln Pro Glu Asn Asn Tyr
            515                 520                 525

Lys Thr Thr Pro Pro Val Leu Asp Ser Asp Gly Ser Phe Phe Leu Tyr
        530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly Lys
                580
```

```
<210> SEQ ID NO 379
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379
```

```
Gln Val Gln Leu Gln Glu Ser Gly Gly Gly Leu Val Gln Leu Gly Gly
1                   5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Ala Ser Thr Lys Gly Pro Arg Gly Ser
        115                 120                 125

Thr Ser Gly Gly Gly Ser Gly Gly Gly Ser Gly Gly Gly Gly Ser Ser
        130                 135                 140

Ser Ser Glu Leu Thr Gln Asp Pro Ala Val Ser Val Ala Leu Gly Gln
145                 150                 155                 160

Thr Val Lys Ile Thr Cys Gln Gly Asp Ser Leu Arg Thr Tyr Tyr Ala
                165                 170                 175

Ser Trp Tyr Gln Gln Arg Pro Gly Gln Ala Pro Val Leu Val Ile Tyr
                180                 185                 190

Gly Glu Asn Ser Arg Pro Ser Gly Ile Pro Asp Arg Phe Ser Gly Ser
            195                 200                 205

Ser Ser Gly Asn Thr Ala Ser Leu Thr Ile Thr Gly Ala Gln Ala Glu
        210                 215                 220
```

-continued

```
Asp Glu Ala Asp Tyr Tyr Cys Asn Ser Arg Asp Ser Ser Gly Asn His
225             230             235             240

Leu Arg Val Phe Gly Gly Gly Thr Lys Leu Thr Val Leu Gly Gly Gly
            245             250             255

Ser Gly Gly Gly Ser Gly Gly Gly Ser Glu Val Gln Leu Leu Glu Ser
            260             265             270

Gly Gly Gly Leu Val Gln Pro Gly Gly Ser Leu Arg Leu Ser Cys Ala
            275             280             285

Val Ser Gly Phe Thr Phe Asn Ser Phe Ala Met Ser Trp Val Arg Gln
    290             295             300

Ala Pro Gly Lys Gly Leu Glu Trp Val Ser Ala Ile Ser Gly Ser Gly
305             310             315             320

Gly Gly Thr Tyr Tyr Ala Asp Ser Val Lys Gly Arg Phe Thr Ile Ser
            325             330             335

Arg Asp Asn Ser Lys Asn Thr Leu Tyr Leu Gln Met Asn Ser Leu Arg
            340             345             350

Ala Glu Asp Thr Ala Val Tyr Phe Cys Ala Lys Asp Lys Ile Leu Trp
            355             360             365

Phe Gly Glu Pro Val Phe Asp Tyr Trp Gly Gln Gly Thr Leu Val Thr
    370             375             380

Val Ser Ser Ala Ser Thr Lys Gly Pro Ser Val Phe Pro Leu Ala Pro
385             390             395             400

Ser Ser Lys Ser Thr Ser Gly Gly Thr Ala Ala Leu Gly Cys Leu Val
            405             410             415

Lys Asp Tyr Phe Pro Glu Pro Val Thr Val Ser Trp Asn Ser Gly Ala
            420             425             430

Leu Thr Ser Gly Val His Thr Phe Pro Ala Val Leu Gln Ser Ser Gly
            435             440             445

Leu Tyr Ser Leu Ser Ser Val Val Thr Val Pro Ser Ser Ser Leu Gly
    450             455             460

Thr Gln Thr Tyr Ile Cys Asn Val Asn His Lys Pro Ser Asn Thr Lys
465             470             475             480

Val Asp Lys Arg Val Glu Pro Lys Ser Cys Asp Lys Thr His Thr Cys
            485             490             495

Pro Pro Cys Pro Ala Pro Glu Leu Leu Gly Gly Pro Ser Val Phe Leu
            500             505             510

Phe Pro Pro Lys Pro Lys Asp Thr Leu Met Ile Ser Arg Thr Pro Glu
            515             520             525

Val Thr Cys Val Val Val Asp Val Ser His Glu Asp Pro Glu Val Lys
    530             535             540

Phe Asn Trp Tyr Val Asp Gly Val Glu Val His Asn Ala Lys Thr Lys
545             550             555             560

Pro Arg Glu Glu Gln Tyr Asn Ser Thr Tyr Arg Val Val Ser Val Leu
            565             570             575

Thr Val Leu His Gln Asp Trp Leu Asn Gly Lys Glu Tyr Lys Cys Lys
            580             585             590

Val Ser Asn Lys Ala Leu Pro Ala Pro Ile Glu Lys Thr Ile Ser Lys
            595             600             605

Ala Lys Gly Gln Pro Arg Glu Pro Gln Val Tyr Thr Leu Pro Pro Ser
    610             615             620

Arg Glu Glu Met Thr Lys Asn Gln Val Ser Leu Thr Cys Leu Val Lys
625             630             635             640

Gly Phe Tyr Pro Ser Asp Ile Ala Val Glu Trp Glu Ser Asn Gly Gln
```

-continued

```
                    645              650              655
Pro Glu Asn Asn Tyr Lys Thr Thr Pro Pro Val Leu Asp Ser Asp Gly
            660              665              670

Ser Phe Phe Leu Tyr Ser Lys Leu Thr Val Asp Lys Ser Arg Trp Gln
        675              680              685

Gln Gly Asn Val Phe Ser Cys Ser Val Met His Glu Ala Leu His Asn
    690              695              700

His Tyr Thr Gln Lys Ser Leu Ser Leu Ser Pro Gly Lys
705              710              715

<210> SEQ ID NO 380
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Met Gly Trp Ser Cys Ile Ile Leu Phe Leu Val Ala Thr Ala Thr Gly
1               5               10              15

Val His Ser Glu Ile Val Leu Thr Gln Ser Pro Ala Thr Leu Ser Leu
            20              25              30

Ser Pro Gly Glu Arg Ala Thr Leu Ser Cys Arg Ala Ser Gln Ser Val
        35              40              45

Ser Ser Tyr Leu Ala Trp Tyr Gln Gln Lys Pro Gly Gln Ala Pro Arg
    50              55              60

Leu Leu Ile Tyr Asp Ala Ser Asn Arg Ala Thr Gly Ile Pro Ala Arg
65              70              75              80

Phe Ser Gly Ser Gly Ser Gly Thr Asp Phe Thr Leu Thr Ile Ser Ser
            85              90              95

Leu Glu Pro Glu Asp Phe Ala Val Tyr Tyr Cys Gln Gln Arg Ser Asn
        100             105             110

Trp Pro Pro Thr Phe Gly Gln Gly Thr Lys Val Glu Ile Lys Arg Thr
    115             120             125

Val Ala Ala Pro Ser Val Phe Ile Phe Pro Pro Ser Asp Glu Gln Leu
    130             135             140

Lys Ser Gly Thr Ala Ser Val Val Cys Leu Leu Asn Asn Phe Tyr Pro
145             150             155             160

Arg Glu Ala Lys Val Gln Trp Lys Val Asp Asn Ala Leu Gln Ser Gly
            165             170             175

Asn Ser Gln Glu Ser Val Thr Glu Gln Asp Ser Lys Asp Ser Thr Tyr
        180             185             190

Ser Leu Ser Ser Thr Leu Thr Leu Ser Lys Ala Asp Tyr Glu Lys His
        195             200             205

Lys Val Tyr Ala Cys Glu Val Thr His Gln Gly Leu Ser Ser Pro Val
    210             215             220

Thr Lys Ser Phe Asn Arg Gly Glu Cys Gly Gly Gly Ser Gly Gly
225             230             235             240

Gly Gly Ser Gly Gly Gly Gly Ser Arg Ser Gln Val Gln Leu Val Glu
            245             250             255

Ser Gly Gly Gly Leu Val Gln Pro Gly Gly Ser Leu Arg Leu Ser Cys
        260             265             270

Ala Ala Ser Gly Phe Thr Phe Ser Ser Tyr Ala Met Ser Trp Val Arg
        275             280             285
```

-continued

```
Gln Ala Pro Gly Lys Gly Leu Glu Trp Val Ser Ala Ile Ser Gly Ser
    290                 295                 300

Gly Gly Ser Thr His Cys Ala Asp Ser Val Lys Gly Arg Phe Thr Ile
305                 310                 315                 320

Ser Arg Asp Asn Ser Lys Asn Thr Leu Tyr Leu Gln Met Ser Ser Leu
                325                 330                 335

Arg Ala Glu Asp Thr Ala Phe Tyr Tyr Cys Ala Asn Ser Ala Tyr Thr
                340                 345                 350

Gly Gly Trp Tyr Asp Tyr Trp Gly His Gly Thr Leu Val Thr Val Ser
                355                 360                 365

Ser Gly Gly Gly Gly Ser Gly Gly Gly Ser Gly Gly Gly Gly Ser
    370                 375                 380

Ser Glu Leu Thr Gln Asp Pro Ala Val Ser Val Ala Leu Gly Gln Thr
385                 390                 395                 400

Val Lys Ile Thr Cys Gln Gly Asp Ser Leu Arg Thr Tyr Tyr Ala Ser
                405                 410                 415

Trp Tyr Gln Gln Arg Pro Gly Gln Ala Pro Val Leu Val Ile Tyr Gly
                420                 425                 430

Glu Asn Ser Arg Pro Ser Gly Ile Pro Asp Arg Phe Ser Gly Ser Ser
                435                 440                 445

Ser Gly Asn Thr Ala Ser Leu Thr Ile Thr Gly Ala Gln Ala Glu Asp
    450                 455                 460

Glu Ala Asp Tyr Tyr Cys Asn Ser Arg Asp Ser Ser Gly Asn His Leu
465                 470                 475                 480

Arg Val Phe Gly Gly Gly Thr Lys Leu Thr Val Leu Gly
                485                 490

<210> SEQ ID NO 381
<211> LENGTH: 214
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 381

Glu Ile Val Leu Thr Gln Ser Pro Ala Thr Leu Ser Leu Ser Pro Gly
1                 5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 382
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Ser Ser Glu Leu Thr Gln Asp Pro Ala Val Ser Val Ala Leu Gly Gln
1               5                   10                  15

Thr Val Lys Ile Thr Cys Gln Gly Asp Ser Leu Arg Thr Tyr Tyr Ala
                20                  25                  30

Ser Trp Tyr Gln Gln Arg Pro Gly Gln Ala Pro Val Leu Val Ile Tyr
            35                  40                  45

Gly Glu Asn Ser Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Arg Val Phe Gly Gly Gly Thr Lys Leu Thr Val Leu Arg Thr Val
                100                 105                 110

Ala Ala Pro Ser Val Phe Ile Phe Pro Glu Ile Val Leu Thr Gln Ser
            115                 120                 125

Pro Ala Thr Leu Ser Leu Ser Pro Gly Glu Arg Ala Thr Leu Ser Cys
        130                 135                 140

Arg Ala Ser Gln Ser Val Ser Ser Tyr Leu Ala Trp Tyr Gln Gln Lys
145                 150                 155                 160

Pro Gly Gln Ala Pro Arg Leu Leu Ile Tyr Asp Ala Ser Asn Arg Ala
                165                 170                 175

Thr Gly Ile Pro Ala Arg Phe Ser Gly Ser Gly Ser Gly Thr Asp Phe
            180                 185                 190

Thr Leu Thr Ile Ser Ser Leu Glu Pro Glu Asp Phe Ala Val Tyr Tyr
            195                 200                 205

Cys Gln Gln Arg Ser Asn Trp Pro Pro Thr Phe Gly Gln Gly Thr Lys
    210                 215                 220

Val Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
                260                 265                 270

Asn Ala Leu Gln Ser Gly Asn Ser Gln Glu Ser Val Thr Glu Gln Asp
            275                 280                 285

Ser Lys Asp Ser Thr Tyr Ser Leu Ser Ser Thr Leu Thr Leu Ser Lys
```

-continued

```
          290                 295                 300
Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335

<210> SEQ ID NO 383
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Ala Ser Thr Lys Gly Pro Arg Gly Ser
            115                 120                 125

Thr Ser Gly Gly Gly Ser Gly Gly Gly Ser Gly Gly Gly Gly Ser Ser
        130                 135                 140

Ser Ser Glu Leu Thr Gln Asp Pro Ala Val Ser Val Ala Leu Gly Gln
145                 150                 155                 160

Thr Val Lys Ile Thr Cys Gln Gly Asp Ser Leu Arg Thr Tyr Tyr Ala
                165                 170                 175

Ser Trp Tyr Gln Gln Arg Pro Gly Gln Ala Pro Val Leu Val Ile Tyr
            180                 185                 190

Gly Glu Asn Ser Arg Pro Ser Gly Ile Pro Asp Arg Phe Ser Gly Ser
            195                 200                 205

Ser Ser Gly Asn Thr Ala Ser Leu Thr Ile Thr Gly Ala Gln Ala Glu
        210                 215                 220

Asp Glu Ala Asp Tyr Tyr Cys Asn Ser Arg Asp Ser Ser Gly Asn His
225                 230                 235                 240

Leu Arg Val Phe Gly Gly Gly Thr Lys Leu Thr Val Leu Gly Gly Ser
                245                 250                 255

Gly Gly Ser Gly Gly Ala Ser Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
        290                 295                 300

Val Val Asp Val Ser His Glu Asp Pro Glu Val Lys Phe Asn Trp Tyr
305                 310                 315                 320
```

-continued

```
Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Asp Glu Leu
385                 390                 395                 400

Thr Lys Asn Gln Val Ser Leu Ser Cys Ala Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
            435                 440                 445

Val Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485
```

```
<210> SEQ ID NO 384
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Gly Tyr Ser Phe Pro Thr Gly Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

-continued

```
Thr Val Pro Ser Ser Ser Leu Gly Thr Gln Thr Tyr Ile Cys Asn Val
        195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
        275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
        355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
        435             440             445

Leu Ser Pro Gly Lys Gly Gly Gly Gly Ser Gly Gly Gly Gly Ser Gly
    450             455             460

Gly Gly Gly Ser Arg Ser Gln Val Gln Leu Val Glu Ser Gly Gly Gly
465             470             475             480

Leu Val Gln Pro Gly Gly Ser Leu Arg Leu Ser Cys Ala Ala Ser Gly
            485             490             495

Phe Thr Phe Ser Ser Tyr Ala Met Ser Trp Val Arg Gln Ala Pro Gly
            500             505             510

Lys Gly Leu Glu Trp Val Ser Ala Ile Ser Gly Ser Gly Gly Ser Thr
        515             520             525

His Cys Ala Asp Ser Val Lys Gly Arg Phe Thr Ile Ser Arg Asp Asn
    530             535             540

Ser Lys Asn Thr Leu Tyr Leu Gln Met Ser Ser Leu Arg Ala Glu Asp
545             550             555             560

Thr Ala Phe Tyr Tyr Cys Ala Asn Ser Ala Tyr Thr Gly Gly Trp Tyr
            565             570             575

Asp Tyr Trp Gly His Gly Thr Leu Val Thr Val Ser Ser Gly Gly Gly
            580             585             590

Gly Ser Gly Gly Gly Gly Ser Gly Gly Gly Gly Ser Ser Glu Leu Thr
            595             600             605
```

-continued

```
Gln Asp Pro Ala Val Ser Val Ala Leu Gly Gln Thr Val Lys Ile Thr
    610                 615                 620

Cys Gln Gly Asp Ser Leu Arg Thr Tyr Tyr Ala Ser Trp Tyr Gln Gln
625                 630                 635                 640

Arg Pro Gly Gln Ala Pro Val Leu Val Ile Tyr Gly Glu Asn Ser Arg
                645                 650                 655

Pro Ser Gly Ile Pro Asp Arg Phe Ser Gly Ser Ser Ser Gly Asn Thr
                660                 665                 670

Ala Ser Leu Thr Ile Thr Gly Ala Gln Ala Glu Asp Glu Ala Asp Tyr
                675                 680                 685

Tyr Cys Asn Ser Arg Asp Ser Ser Gly Asn His Leu Arg Val Phe Gly
    690                 695                 700

Gly Gly Thr Lys Leu Thr Val Leu Gly
705                 710
```

```
<210> SEQ ID NO 385
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385
```

```
Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Ala Ser Thr Lys Gly Pro Arg Gly Ser
        115                 120                 125

Thr Ser Gly Gly Gly Ser Gly Gly Ser Gly Gly Gly Gly Ser Ser
    130                 135                 140

Ser Ser Glu Leu Thr Gln Asp Pro Ala Val Ser Val Ala Leu Gly Gln
145                 150                 155                 160

Thr Val Lys Ile Thr Cys Gln Gly Asp Ser Leu Arg Thr Tyr Tyr Ala
                165                 170                 175

Ser Trp Tyr Gln Gln Arg Pro Gly Gln Ala Pro Val Leu Val Ile Tyr
            180                 185                 190

Gly Glu Asn Ser Arg Pro Ser Gly Ile Pro Asp Arg Phe Ser Gly Ser
        195                 200                 205

Ser Ser Gly Asn Thr Ala Ser Leu Thr Ile Thr Gly Ala Gln Ala Glu
    210                 215                 220

Asp Glu Ala Asp Tyr Tyr Cys Asn Ser Arg Asp Ser Ser Gly Asn His
225                 230                 235                 240

Leu Arg Val Phe Gly Gly Gly Thr Lys Leu Thr Val Leu Gly Gly Gly
                245                 250                 255
```

-continued

```
Ser Gly Gly Gly Ser Gly Gly Ser Glu Val Gln Leu Leu Glu Ser
        260                 265                 270

Gly Gly Gly Leu Val Gln Pro Gly Gly Ser Leu Arg Leu Ser Cys Ala
        275                 280                 285

Ala Ser Gly Phe Thr Phe Ser Thr Tyr Ala Met Ser Trp Val Arg Gln
    290                 295                 300

Ala Pro Gly Lys Gly Leu Glu Trp Val Ser Ala Ile Ser Gly Ser Gly
305                 310                 315                 320

Gly Ser Thr Tyr Tyr Ala Asp Ser Val Lys Gly Arg Phe Thr Ile Ser
                325                 330                 335

Arg Asp Asn Ser Lys Asn Thr Leu Tyr Leu Gln Met Asn Ser Leu Arg
            340                 345                 350

Ala Glu Asp Thr Ala Val Tyr Tyr Cys Ala Lys Arg Gly Thr Tyr Gly
            355                 360                 365

Tyr Ser Phe Pro Thr Gly Phe Asp Tyr Trp Gly Gln Gly Thr Leu Val
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
            435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495

Cys Pro Pro Cys Pro Ala Pro Glu Leu Leu Gly Gly Pro Ser Val Phe
                500                 505                 510

Leu Phe Pro Pro Lys Pro Lys Asp Thr Leu Met Ile Ser Arg Thr Pro
            515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
            595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
        660                 665                 670
```

```
Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
        690                 695                 700

Asn His Tyr Thr Gln Lys Ser Leu Ser Leu Ser Pro Gly Lys
705                 710                 715
```

```
<210> SEQ ID NO 386
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Gln Val Gln Leu Gln Glu Ser Gly Gly Gly Leu Val Gln Leu Gly Gly
1                   5                   10                  15

Ser Leu Arg Leu Ser Cys Ala Ala Ser Gly Phe Thr Phe Ser Ser Tyr
        20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
                100                 105                 110

Thr Leu Val Thr Val Ser Ser Ala Ser Thr Lys Gly Pro Ser Val Phe
                115                 120                 125

Pro Leu Ala Pro Glu Val Gln Leu Leu Glu Ser Gly Gly Gly Leu Val
        130                 135                 140

Gln Pro Gly Gly Ser Leu Arg Leu Ser Cys Ala Ala Ser Gly Phe Thr
145                 150                 155                 160

Phe Ser Thr Tyr Ala Met Ser Trp Val Arg Gln Ala Pro Gly Lys Gly
                165                 170                 175

Leu Glu Trp Val Ser Ala Ile Ser Gly Ser Gly Gly Ser Thr Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
        210                 215                 220

Val Tyr Tyr Cys Ala Lys Arg Gly Thr Tyr Gly Tyr Ser Phe Pro Thr
225                 230                 235                 240

Gly Phe Asp Tyr Trp Gly Gln Gly Thr Leu Val Thr Val Ser Ser Ala
                245                 250                 255

Ser Thr Lys Gly Pro Ser Val Phe Pro Leu Ala Pro Ser Ser Lys Ser
                260                 265                 270

Thr Ser Gly Gly Thr Ala Ala Leu Gly Cys Leu Val Lys Asp Tyr Phe
                275                 280                 285

Pro Glu Pro Val Thr Val Ser Trp Asn Ser Gly Ala Leu Thr Ser Gly
        290                 295                 300

Val His Thr Phe Pro Ala Val Leu Gln Ser Ser Gly Leu Tyr Ser Leu
305                 310                 315                 320
```

-continued

```
Ser Ser Val Val Thr Val Pro Ser Ser Ser Leu Gly Thr Gln Thr Tyr
            325             330                 335

Ile Cys Asn Val Asn His Lys Pro Ser Asn Thr Lys Val Asp Lys Lys
            340             345                 350

Val Glu Pro Lys Ser Cys Asp Lys Thr His Thr Cys Pro Pro Cys Pro
        355             360                 365

Ala Pro Glu Leu Leu Gly Gly Pro Ser Val Phe Leu Phe Pro Pro Lys
    370             375                 380

Pro Lys Asp Thr Leu Met Ile Ser Arg Thr Pro Glu Val Thr Cys Val
385             390                 395                 400

Val Val Asp Val Ser His Glu Asp Pro Glu Val Lys Phe Asn Trp Tyr
            405             410                 415

Val Asp Gly Val Glu Val His Asn Ala Lys Thr Lys Pro Arg Glu Glu
            420             425                 430

Gln Tyr Asn Ser Thr Tyr Arg Val Val Ser Val Leu Thr Val Leu His
        435             440                 445

Gln Asp Trp Leu Asn Gly Lys Glu Tyr Lys Cys Lys Val Ser Asn Lys
    450             455                 460

Ala Leu Pro Ala Pro Ile Glu Lys Thr Ile Ser Lys Ala Lys Gly Gln
465             470                 475                 480

Pro Arg Glu Pro Gln Val Tyr Thr Leu Pro Pro Ser Arg Asp Glu Leu
            485             490                 495

Thr Lys Asn Gln Val Ser Leu Thr Cys Leu Val Lys Gly Phe Tyr Pro
            500             505                 510

Ser Asp Ile Ala Val Glu Trp Glu Ser Asn Gly Gln Pro Glu Asn Asn
            515             520                 525

Tyr Lys Thr Thr Pro Pro Val Leu Asp Ser Asp Gly Ser Phe Phe Leu
            530             535                 540

Tyr Ser Lys Leu Thr Val Asp Lys Ser Arg Trp Gln Gln Gly Asn Val
545             550                 555                 560

Phe Ser Cys Ser Val Met His Glu Ala Leu His Asn His Tyr Thr Gln
            565                 570                 575

Lys Ser Leu Ser Leu Ser Pro Gly Lys
            580             585

<210> SEQ ID NO 387
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
```

-continued

```
                85                90                95

Ala Asn Ser Ala Tyr Thr Gly Gly Trp Tyr Asp Tyr Trp Gly His Gly
            100                105                110

Thr Leu Val Thr Val Ser Ser Ala Ser Thr Lys Gly Pro Arg Gly Ser
            115                120                125

Thr Ser Gly Gly Gly Ser Gly Gly Gly Ser Gly Gly Gly Ser Ser
            130                135                140

Ser Ser Glu Leu Thr Gln Asp Pro Ala Val Ser Val Ala Leu Gly Gln
145                150                155                160

Thr Val Lys Ile Thr Cys Gln Gly Asp Ser Leu Arg Thr Tyr Tyr Ala
                165                170                175

Ser Trp Tyr Gln Gln Arg Pro Gly Gln Ala Pro Val Leu Val Ile Tyr
                180                185                190

Gly Glu Asn Ser Arg Pro Ser Gly Ile Pro Asp Arg Phe Ser Gly Ser
                195                200                205

Ser Ser Gly Asn Thr Ala Ser Leu Thr Ile Thr Gly Ala Gln Ala Glu
                210                215                220

Asp Glu Ala Asp Tyr Tyr Cys Asn Ser Arg Asp Ser Ser Gly Asn His
225                230                235                240

Leu Arg Val Phe Gly Gly Gly Thr Lys Leu Thr Val Leu Gly Gly Gly
                245                250                255

Ser Gly Gly Gly Ser Gly Gly Gly Ser Glu Val Gln Leu Leu Glu Ser
                260                265                270

Gly Gly Gly Leu Val Gln Pro Gly Gly Ser Leu Arg Leu Ser Cys Ala
                275                280                285

Ala Ser Gly Phe Pro Phe Gly Val Tyr Ala Met Ser Trp Val Arg Gln
                290                295                300

Ala Pro Gly Lys Gly Leu Glu Trp Val Ser Ala Ile Ser Gly Ser Gly
305                310                315                320

Gly Ser Thr Phe Tyr Ala Asp Ser Val Lys Gly Arg Phe Thr Ile Ser
                325                330                335

Arg Asp Asn Ser Lys Asn Thr Leu Tyr Leu Gln Met Asn Ser Leu Arg
                340                345                350

Ala Glu Asp Thr Ala Val Tyr Tyr Cys Ala Lys Arg Gly Thr Tyr Ala
                355                360                365

Tyr Ser Phe Pro Thr Gly Phe Asp Tyr Trp Gly Gln Gly Thr Leu Val
                370                375                380

Thr Val Ser Ser Ala Ser Thr Lys Gly Pro Ser Val Phe Pro Leu Ala
385                390                395                400

Pro Ser Ser Lys Ser Thr Ser Gly Gly Thr Ala Ala Leu Gly Cys Leu
                405                410                415

Val Lys Asp Tyr Phe Pro Glu Pro Val Thr Val Ser Trp Asn Ser Gly
                420                425                430

Ala Leu Thr Ser Gly Val His Thr Phe Pro Ala Val Leu Gln Ser Ser
                435                440                445

Gly Leu Tyr Ser Leu Ser Ser Val Val Thr Val Pro Ser Ser Ser Leu
                450                455                460

Gly Thr Gln Thr Tyr Ile Cys Asn Val Asn His Lys Pro Ser Asn Thr
465                470                475                480

Lys Val Asp Lys Lys Val Glu Pro Lys Ser Cys Asp Lys Thr His Thr
                485                490                495

Cys Pro Pro Cys Pro Ala Pro Glu Leu Leu Gly Gly Pro Ser Val Phe
                500                505                510
```

-continued

```
Leu Phe Pro Pro Lys Pro Lys Asp Thr Leu Met Ile Ser Arg Thr Pro
        515         520             525

Glu Val Thr Cys Val Val Val Asp Val Ser His Glu Asp Pro Glu Val
    530             535             540

Lys Phe Asn Trp Tyr Val Asp Gly Val Glu Val His Asn Ala Lys Thr
545             550             555             560

Lys Pro Arg Glu Glu Gln Tyr Asn Ser Thr Tyr Arg Val Val Ser Val
            565             570             575

Leu Thr Val Leu His Gln Asp Trp Leu Asn Gly Lys Glu Tyr Lys Cys
        580             585             590

Lys Val Ser Asn Lys Ala Leu Pro Ala Pro Ile Glu Lys Thr Ile Ser
        595             600             605

Lys Ala Lys Gly Gln Pro Arg Glu Pro Gln Val Tyr Thr Leu Pro Pro
    610             615             620

Ser Arg Asp Glu Leu Thr Lys Asn Gln Val Ser Leu Thr Cys Leu Val
625             630             635             640

Lys Gly Phe Tyr Pro Ser Asp Ile Ala Val Glu Trp Glu Ser Asn Gly
            645             650             655

Gln Pro Glu Asn Asn Tyr Lys Thr Thr Pro Pro Val Leu Asp Ser Asp
            660             665             670

Gly Ser Phe Phe Leu Tyr Ser Lys Leu Thr Val Asp Lys Ser Arg Trp
            675             680             685

Gln Gln Gly Asn Val Phe Ser Cys Ser Val Met His Glu Ala Leu His
        690             695             700

Asn His Tyr Thr Gln Lys Ser Leu Ser Leu Ser Pro Gly Lys
705             710             715
```

```
<210> SEQ ID NO 388
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388
```

```
Gln Val Gln Leu Gln Glu Ser Gly Gly Gly Leu Val Gln Leu Gly Gly
1               5               10              15

Ser Leu Arg Leu Ser Cys Ala Ala Ser Gly Phe Thr Phe Ser Ser Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Ser Ser Leu Arg Ala Glu Asp Thr Ala Phe Tyr Tyr Cys
            85              90              95

Ala Asn Ser Ala Tyr Thr Gly Gly Trp Tyr Asp Tyr Trp Gly His Gly
            100             105             110

Thr Leu Val Thr Val Ser Ser Ala Ser Thr Lys Gly Pro Arg Gly Ser
        115             120             125

Thr Ser Gly Gly Gly Ser Gly Gly Gly Ser Gly Gly Gly Gly Ser Ser
    130             135             140

Ser Ser Glu Leu Thr Gln Asp Pro Ala Val Ser Val Ala Leu Gly Gln
```

-continued

```
145              150              155              160

Thr Val Lys Ile Thr Cys Gln Gly Asp Ser Leu Arg Thr Tyr Tyr Ala
                165              170              175

Ser Trp Tyr Gln Gln Arg Pro Gly Gln Ala Pro Val Leu Val Ile Tyr
                180              185              190

Gly Glu Asn Ser Arg Pro Ser Gly Ile Pro Asp Arg Phe Ser Gly Ser
            195              200              205

Ser Ser Gly Asn Thr Ala Ser Leu Thr Ile Thr Gly Ala Gln Ala Glu
        210              215              220

Asp Glu Ala Asp Tyr Tyr Cys Asn Ser Arg Asp Ser Ser Gly Asn His
225              230              235              240

Leu Arg Val Phe Gly Gly Thr Lys Leu Thr Val Leu Gly Gly Gly
                245              250              255

Ser Gly Gly Gly Ser Gly Gly Gly Ser Glu Val Gln Leu Leu Glu Ser
            260              265              270

Gly Gly Gly Leu Val Gln Pro Gly Gly Ser Leu Arg Leu Ser Cys Ala
        275              280              285

Ala Ser Gly Phe Pro Phe Asp Thr Tyr Ala Met Ser Trp Val Arg Gln
    290              295              300

Ala Pro Gly Lys Gly Leu Glu Trp Val Ser Ala Ile Ser Gly Ser Gly
305              310              315              320

Gly Ser Thr Tyr Tyr Ala Asp Ser Val Lys Gly Arg Phe Thr Ile Ser
                325              330              335

Arg Asp Asn Ser Lys Asn Thr Leu Tyr Leu Gln Met Asn Ser Leu Arg
            340              345              350

Ala Glu Asp Thr Ala Val Tyr Tyr Cys Ala Lys Arg Gly Thr Tyr Ala
        355              360              365

Tyr Ser Phe Pro Thr Gly Phe Asp Tyr Trp Gly Gln Gly Thr Leu Val
    370              375              380

Thr Val Ser Ser Ala Ser Thr Lys Gly Pro Ser Val Phe Pro Leu Ala
385              390              395              400

Pro Ser Ser Lys Ser Thr Ser Gly Gly Thr Ala Ala Leu Gly Cys Leu
            405              410              415

Val Lys Asp Tyr Phe Pro Glu Pro Val Thr Val Ser Trp Asn Ser Gly
            420              425              430

Ala Leu Thr Ser Gly Val His Thr Phe Pro Ala Val Leu Gln Ser Ser
        435              440              445

Gly Leu Tyr Ser Leu Ser Ser Val Val Thr Val Pro Ser Ser Ser Leu
    450              455              460

Gly Thr Gln Thr Tyr Ile Cys Asn Val Asn His Lys Pro Ser Asn Thr
465              470              475              480

Lys Val Asp Lys Lys Val Glu Pro Lys Ser Cys Asp Lys Thr His Thr
            485              490              495

Cys Pro Pro Cys Pro Ala Pro Glu Leu Leu Gly Gly Pro Ser Val Phe
            500              505              510

Leu Phe Pro Pro Lys Pro Lys Asp Thr Leu Met Ile Ser Arg Thr Pro
        515              520              525

Glu Val Thr Cys Val Val Val Asp Val Ser His Glu Asp Pro Glu Val
    530              535              540

Lys Phe Asn Trp Tyr Val Asp Gly Val Glu Val His Asn Ala Lys Thr
545              550              555              560

Lys Pro Arg Glu Glu Gln Tyr Asn Ser Thr Tyr Arg Val Val Ser Val
            565              570              575
```

-continued

```
Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
            595                 600                 605

Lys Ala Lys Gly Gln Pro Arg Glu Pro Gln Val Tyr Thr Leu Pro Pro
        610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
            675                 680                 685

Gln Gln Gly Asn Val Phe Ser Cys Ser Val Met His Glu Ala Leu His
        690                 695                 700

Asn His Tyr Thr Gln Lys Ser Leu Ser Leu Ser Pro Gly Lys
705                 710                 715
```

```
<210> SEQ ID NO 389
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389
```

```
Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Ala Ser Thr Lys Gly Pro Arg Gly Ser
            115                 120                 125

Thr Ser Gly Gly Gly Ser Gly Gly Ser Gly Gly Gly Gly Ser Ser
            130                 135                 140

Ser Ser Glu Leu Thr Gln Asp Pro Ala Val Ser Val Ala Leu Gly Gln
145                 150                 155                 160

Thr Val Lys Ile Thr Cys Gln Gly Asp Ser Leu Arg Thr Tyr Tyr Ala
                165                 170                 175

Ser Trp Tyr Gln Gln Arg Pro Gly Gln Ala Pro Val Leu Val Ile Tyr
            180                 185                 190

Gly Glu Asn Ser Arg Pro Ser Gly Ile Pro Asp Arg Phe Ser Gly Ser
            195                 200                 205

Ser Ser Gly Asn Thr Ala Ser Leu Thr Ile Thr Gly Ala Gln Ala Glu
```

-continued

```
            210                 215                 220

Asp Glu Ala Asp Tyr Tyr Cys Asn Ser Arg Asp Ser Ser Gly Asn His
225                 230                 235                 240

Leu Arg Val Phe Gly Gly Gly Thr Lys Leu Thr Val Leu Gly Gly Gly
                245                 250                 255

Ser Gly Gly Gly Ser Gly Gly Gly Ser Glu Val Gln Leu Leu Glu Ser
                260                 265                 270

Gly Gly Gly Leu Val Gln Pro Gly Gly Ser Leu Arg Leu Ser Cys Ala
            275                 280                 285

Ala Ser Gly Phe Pro Phe Asp Val Tyr Ala Met Ser Trp Val Arg Gln
        290                 295                 300

Ala Pro Gly Lys Gly Leu Glu Trp Val Ser Ala Ile Ser Gly Ser Gly
305                 310                 315                 320

Gly Ser Thr Phe Tyr Ala Asp Ser Val Lys Gly Arg Phe Thr Ile Ser
                325                 330                 335

Arg Asp Asn Ser Lys Asn Thr Leu Tyr Leu Gln Met Asn Ser Leu Arg
                340                 345                 350

Ala Glu Asp Thr Ala Val Tyr Tyr Cys Ala Lys Arg Gly Thr Tyr Ala
            355                 360                 365

Tyr Ser Tyr Pro Thr Gly Phe Asp Tyr Trp Gly Gln Gly Thr Leu Val
        370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
                420                 425                 430

Ala Leu Thr Ser Gly Val His Thr Phe Pro Ala Val Leu Gln Ser Ser
            435                 440                 445

Gly Leu Tyr Ser Leu Ser Ser Val Val Thr Val Pro Ser Ser Ser Leu
        450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
            515                 520                 525

Glu Val Thr Cys Val Val Val Asp Val Ser His Glu Asp Pro Glu Val
        530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
            565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
            595                 600                 605

Lys Ala Lys Gly Gln Pro Arg Glu Pro Gln Val Tyr Thr Leu Pro Pro
        610                 615                 620

Ser Arg Asp Glu Leu Thr Lys Asn Gln Val Ser Leu Thr Cys Leu Val
625                 630                 635                 640
```

-continued

```
Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
                660                 665                 670

Gly Ser Phe Phe Leu Tyr Ser Lys Leu Thr Val Asp Lys Ser Arg Trp
            675                 680                 685

Gln Gln Gly Asn Val Phe Ser Cys Ser Val Met His Glu Ala Leu His
        690                 695                 700

Asn His Tyr Thr Gln Lys Ser Leu Ser Leu Ser Pro Gly Lys
705                 710                 715

<210> SEQ ID NO 390
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Gly Val Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

-continued

```
         275               280               285
Glu Val His Asn Ala Lys Thr Lys Pro Arg Glu Glu Gln Tyr Asn Ser
    290               295               300

Thr Tyr Arg Val Val Ser Val Leu Thr Val Leu His Gln Asp Trp Leu
305               310               315               320

Asn Gly Lys Glu Tyr Lys Cys Lys Val Ser Asn Lys Ala Leu Pro Ala
                325               330               335

Pro Ile Glu Lys Thr Ile Ser Lys Ala Lys Gly Gln Pro Arg Glu Pro
            340               345               350

Gln Val Tyr Thr Leu Pro Pro Ser Arg Asp Glu Leu Thr Lys Asn Gln
            355               360               365

Val Ser Leu Trp Cys Leu Val Lys Gly Phe Tyr Pro Ser Asp Ile Ala
    370               375               380

Val Glu Trp Glu Ser Asn Gly Gln Pro Glu Asn Asn Tyr Lys Thr Thr
385               390               395               400

Pro Pro Val Leu Asp Ser Asp Gly Ser Phe Phe Leu Tyr Ser Lys Leu
            405               410               415

Thr Val Asp Lys Ser Arg Trp Gln Gln Gly Asn Val Phe Ser Cys Ser
            420               425               430

Val Met His Glu Ala Leu His Asn His Tyr Thr Gln Lys Ser Leu Ser
            435               440               445

Leu Ser Pro Gly Lys
    450
```

```
<210> SEQ ID NO 391
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Pro Phe Asp Val Tyr
            20              25              30

Ala Met Ser Trp Val Arg Gln Ala Pro Gly Lys Gly Leu Glu Trp Val
            35              40              45

Ser Ala Ile Ser Gly Ser Gly Gly Ser Thr Phe Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Lys Arg Gly Thr Tyr Ala Tyr Ser Tyr Pro Thr Gly Phe Asp Tyr
            100             105             110

Trp Gly Gln Gly Thr Leu Val Thr Val Ser Ser Ala Ser Thr Lys Gly
            115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175
```

```
Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Trp Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450
```

```
<210> SEQ ID NO 392
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Pro Phe Asp Thr Tyr
            20              25              30

Ala Met Ser Trp Val Arg Gln Ala Pro Gly Lys Gly Leu Glu Trp Val
            35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80
```

-continued

Leu Gln Met Asn Ser Leu Arg Ala Glu Asp Thr Ala Val Tyr Tyr Cys
                85                  90                  95

Ala Lys Arg Gly Thr Tyr Ala Tyr Ser Phe Pro Thr Gly Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Trp Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 393
<211> LENGTH: 474
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 393

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Gly Ser Gly Gly Gly Gly Ser
    210                 215                 220

Gly Gly Gly Gly Ser Arg Ser Gln Val Gln Leu Val Glu Ser Gly Gly
225                 230                 235                 240

Gly Leu Val Gln Pro Gly Gly Ser Leu Arg Leu Ser Cys Ala Ala Ser
            245                 250                 255

Gly Phe Thr Phe Ser Ser Tyr Ala Met Ser Trp Val Arg Gln Ala Pro
            260                 265                 270

Gly Lys Gly Leu Glu Trp Val Ser Ala Ile Ser Gly Ser Gly Gly Ser
        275                 280                 285

Thr His Cys Ala Asp Ser Val Lys Gly Arg Phe Thr Ile Ser Arg Asp
    290                 295                 300

Asn Ser Lys Asn Thr Leu Tyr Leu Gln Met Ser Ser Leu Arg Ala Glu
305                 310                 315                 320

Asp Thr Ala Phe Tyr Tyr Cys Ala Asn Ser Ala Tyr Thr Gly Gly Trp
                325                 330                 335

Tyr Asp Tyr Trp Gly His Gly Thr Leu Val Thr Val Ser Ser Gly Gly
            340                 345                 350

Gly Gly Ser Gly Gly Gly Gly Ser Gly Gly Gly Gly Ser Ser Glu Leu
        355                 360                 365

Thr Gln Asp Pro Ala Val Ser Val Ala Leu Gly Gln Thr Val Lys Ile
    370                 375                 380

Thr Cys Gln Gly Asp Ser Leu Arg Thr Tyr Tyr Ala Ser Trp Tyr Gln
385                 390                 395                 400
```

-continued

```
Gln Arg Pro Gly Gln Ala Pro Val Leu Val Ile Tyr Gly Glu Asn Ser
            405                 410                 415

Arg Pro Ser Gly Ile Pro Asp Arg Phe Ser Gly Ser Ser Ser Gly Asn
            420                 425                 430

Thr Ala Ser Leu Thr Ile Thr Gly Ala Gln Ala Glu Asp Glu Ala Asp
            435                 440                 445

Tyr Tyr Cys Asn Ser Arg Asp Ser Ser Gly Asn His Leu Arg Val Phe
    450                 455                 460

Gly Gly Gly Thr Lys Leu Thr Val Leu Gly
465                 470

<210> SEQ ID NO 394
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Ser Ser Glu Leu Thr Gln Asp Pro Ala Val Ser Val Ala Leu Gly Gln
1               5                   10                  15

Thr Val Lys Ile Thr Cys Gln Gly Asp Ser Leu Arg Thr Tyr Tyr Ala
            20                  25                  30

Ser Trp Tyr Gln Gln Arg Pro Gly Gln Ala Pro Val Leu Val Ile Tyr
            35                  40                  45

Gly Glu Asn Ser Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Arg Val Phe Gly Gly Gly Thr Lys Leu Thr Val Leu Arg Thr Val
            100                 105                 110

Ala Ala Pro Ser Val Phe Ile Phe Pro Asp Ile Gln Met Thr Gln Ser
            115                 120                 125

Pro Ser Ser Leu Ser Ala Ser Val Gly Asp Arg Val Thr Ile Thr Cys
            130                 135                 140

Arg Ala Ser Gln Asp Val Asn Thr Ala Val Ala Trp Tyr Gln Gln Lys
145                 150                 155                 160

Pro Gly Lys Ala Pro Lys Leu Leu Ile Tyr Ser Ala Ser Phe Leu Tyr
                165                 170                 175

Ser Gly Val Pro Ser Arg Phe Ser Gly Ser Arg Ser Gly Thr Asp Phe
            180                 185                 190

Thr Leu Thr Ile Ser Ser Leu Gln Pro Glu Asp Phe Ala Thr Tyr Tyr
            195                 200                 205

Cys Gln Gln His Tyr Thr Thr Pro Pro Thr Phe Gly Gln Gly Thr Lys
    210                 215                 220

Val Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
            260                 265                 270

Asn Ala Leu Gln Ser Gly Asn Ser Gln Glu Ser Val Thr Glu Gln Asp
```

-continued

```
          275              280              285

Ser Lys Asp Ser Thr Tyr Ser Leu Ser Ser Thr Leu Thr Leu Ser Lys
    290              295              300

Ala Asp Tyr Glu Lys His Lys Val Tyr Ala Cys Glu Val Thr His Gln
305              310              315              320

Gly Leu Ser Ser Pro Val Thr Lys Ser Phe Asn Arg Gly Glu Cys
                325              330              335

<210> SEQ ID NO 395
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Asp Ile Gln Met Thr Gln Ser Pro Ser Ser Leu Ser Ala Ser Val Gly
1                5               10               15

Asp Arg Val Thr Ile Thr Cys Arg Ala Ser Gln Asp Val Asn Thr Ala
                20               25               30

Val Ala Trp Tyr Gln Gln Lys Pro Gly Lys Ala Pro Lys Leu Leu Ile
            35               40               45

Tyr Ser Ala Ser Phe Leu Tyr Ser Gly Val Pro Ser Arg Phe Ser Gly
    50               55               60

Ser Arg Ser Gly Thr Asp Phe Thr Leu Thr Ile Ser Ser Leu Gln Pro
65               70               75               80

Glu Asp Phe Ala Thr Tyr Tyr Cys Gln Gln His Tyr Thr Thr Pro Pro
                85               90               95

Thr Phe Gly Gln Gly Thr Lys Val Glu Ile Lys Arg Thr Val Ala Ala
            100              105              110

Pro Ser Val Phe Ile Phe Pro Pro Ser Asp Glu Gln Leu Lys Ser Gly
            115              120              125

Thr Ala Ser Val Val Cys Leu Leu Asn Asn Phe Tyr Pro Arg Glu Ala
    130              135              140

Lys Val Gln Trp Lys Val Asp Asn Ala Leu Gln Ser Gly Asn Ser Gln
145              150              155              160

Glu Ser Val Thr Glu Gln Asp Ser Lys Asp Ser Thr Tyr Ser Leu Ser
            165              170              175

Ser Thr Leu Thr Leu Ser Lys Ala Asp Tyr Glu Lys His Lys Val Tyr
            180              185              190

Ala Cys Glu Val Thr His Gln Gly Leu Ser Ser Pro Val Thr Lys Ser
            195              200              205

Phe Asn Arg Gly Glu Cys Gly Gly Gly Ser Gly Gly Gly Gly Ser
    210              215              220

Gly Gly Gly Gly Ser Arg Ser Gln Val Gln Leu Val Glu Ser Gly Gly
225              230              235              240

Gly Leu Val Gln Pro Gly Gly Ser Leu Arg Leu Ser Cys Ala Ala Ser
            245              250              255

Gly Phe Thr Phe Ser Ser Tyr Ala Met Ser Trp Val Arg Gln Ala Pro
            260              265              270

Gly Lys Gly Leu Glu Trp Val Ser Ala Ile Ser Gly Ser Gly Gly Ser
            275              280              285

Thr His Cys Ala Asp Ser Val Lys Gly Arg Phe Thr Ile Ser Arg Asp
    290              295              300
```

```
Asn Ser Lys Asn Thr Leu Tyr Leu Gln Met Ser Ser Leu Arg Ala Glu
305             310             315             320

Asp Thr Ala Phe Tyr Tyr Cys Ala Asn Ser Ala Tyr Thr Gly Gly Trp
                325             330             335

Tyr Asp Tyr Trp Gly His Gly Thr Leu Val Thr Val Ser Ser Gly Gly
            340             345             350

Gly Gly Ser Gly Gly Gly Gly Ser Gly Gly Gly Gly Ser Ser Glu Leu
            355             360             365

Thr Gln Asp Pro Ala Val Ser Val Ala Leu Gly Gln Thr Val Lys Ile
    370             375             380

Thr Cys Gln Gly Asp Ser Leu Arg Thr Tyr Tyr Ala Ser Trp Tyr Gln
385             390             395             400

Gln Arg Pro Gly Gln Ala Pro Val Leu Val Ile Tyr Gly Glu Asn Ser
            405             410             415

Arg Pro Ser Gly Ile Pro Asp Arg Phe Ser Gly Ser Ser Ser Gly Asn
            420             425             430

Thr Ala Ser Leu Thr Ile Thr Gly Ala Gln Ala Glu Asp Glu Ala Asp
            435             440             445

Tyr Tyr Cys Asn Ser Arg Asp Ser Ser Gly Asn His Leu Arg Val Phe
    450             455             460

Gly Gly Gly Thr Lys Leu Thr Val Leu Gly
465             470

<210> SEQ ID NO 396
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Asp Ile Gln Met Thr Gln Ser Pro Ser Ser Leu Ser Ala Ser Val Gly
1               5               10              15

Asp Arg Val Thr Ile Thr Cys Arg Ala Ser Gln Asp Val Asn Thr Ala
            20              25              30

Val Ala Trp Tyr Gln Gln Lys Pro Gly Lys Ala Pro Lys Leu Leu Ile
        35              40              45

Tyr Ser Ala Ser Phe Leu Tyr Ser Gly Val Pro Ser Arg Phe Ser Gly
    50              55              60

Ser Arg Ser Gly Thr Asp Phe Thr Leu Thr Ile Ser Ser Leu Gln Pro
65              70              75              80

Glu Asp Phe Ala Thr Tyr Tyr Cys Gln Gln His Tyr Thr Thr Pro Pro
            85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
            130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190
```

-continued

```
Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Arg Ser Gln Val Gln Leu Val Glu Ser Gly Gly
225                 230                 235                 240

Gly Leu Val Gln Pro Gly Gly Ser Leu Arg Leu Ser Cys Ala Ala Ser
                245                 250                 255

Gly Phe Thr Phe Ser Ser Tyr Ala Met Ser Trp Val Arg Gln Ala Pro
                260                 265                 270

Gly Lys Gly Leu Glu Trp Val Ser Ala Ile Ser Gly Ser Gly Gly Ser
                275                 280                 285

Thr His Cys Ala Asp Ser Val Lys Gly Arg Phe Thr Ile Ser Arg Asp
        290                 295                 300

Asn Ser Lys Asn Thr Leu Tyr Leu Gln Met Ser Ser Leu Arg Ala Glu
305                 310                 315                 320

Asp Thr Ala Phe Tyr Tyr Cys Ala Asn Ser Ala Tyr Thr Gly Gly Trp
                325                 330                 335

Tyr Asp Tyr Trp Gly His Gly Thr Leu Val Thr Val Ser Ser Gly Gly
                340                 345                 350

Gly Gly Ser Gly Gly Gly Gly Ser Gly Gly Gly Gly Ser Ser Glu Leu
                355                 360                 365

Thr Gln Asp Pro Ala Val Ser Val Ala Leu Gly Gln Thr Val Lys Ile
        370                 375                 380

Thr Cys Gln Gly Asp Ser Leu Arg Thr Tyr Tyr Ala Ser Trp Tyr Gln
385                 390                 395                 400

Gln Arg Pro Gly Gln Ala Pro Val Leu Val Ile Tyr Gly Glu Asn Ser
                405                 410                 415

Arg Pro Ser Gly Ile Pro Asp Arg Phe Ser Gly Ser Ser Ser Gly Asn
                420                 425                 430

Thr Ala Ser Leu Thr Ile Thr Gly Ala Gln Ala Glu Asp Glu Ala Asp
        435                 440                 445

Tyr Tyr Cys Asn Ser Arg Asp Ser Ser Gly Asn His Leu Arg Val Phe
    450                 455                 460

Gly Gly Gly Thr Lys Leu Thr Val Leu Gly
465                 470
```

<210> SEQ ID NO 397
<211> LENGTH: 474
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 397

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

-continued

```
65                    70                    75                    80
Glu Asp Phe Ala Thr Tyr Tyr Cys Gln Gln His Tyr Thr Thr Pro Pro
                85                    90                    95

Thr Phe Gly Gln Gly Thr Lys Val Glu Ile Lys Arg Thr Val Ala Ala
            100               105               110

Pro Ser Val Phe Ile Phe Pro Pro Ser Asp Glu Gln Leu Lys Ser Gly
            115               120               125

Thr Ala Ser Val Val Cys Leu Leu Asn Asn Phe Tyr Pro Arg Glu Ala
    130               135               140

Lys Val Gln Trp Lys Val Asp Asn Ala Leu Gln Ser Gly Asn Ser Gln
145               150               155               160

Glu Ser Val Thr Glu Gln Asp Ser Lys Asp Ser Thr Tyr Ser Leu Ser
                165               170               175

Ser Thr Leu Thr Leu Ser Lys Ala Asp Tyr Glu Lys His Lys Val Tyr
            180               185               190

Ala Cys Glu Val Thr His Gln Gly Leu Ser Ser Pro Val Thr Lys Ser
            195               200               205

Phe Asn Arg Gly Glu Cys Gly Gly Gly Ser Gly Gly Gly Ser
    210               215               220

Gly Gly Gly Gly Ser Arg Ser Gln Val Gln Leu Val Glu Ser Gly Gly
225               230               235               240

Gly Leu Val Gln Pro Gly Gly Ser Leu Arg Leu Ser Cys Ala Ala Ser
                245               250               255

Gly Phe Thr Phe Ser Ser Tyr Ala Met Ser Trp Val Arg Gln Ala Pro
            260               265               270

Gly Lys Gly Leu Glu Trp Val Ser Ala Ile Ser Gly Ser Gly Gly Ser
            275               280               285

Thr His Cys Ala Asp Ser Val Lys Gly Arg Phe Thr Ile Ser Arg Asp
    290               295               300

Asn Ser Lys Asn Thr Leu Tyr Leu Gln Met Ser Ser Leu Arg Ala Glu
305               310               315               320

Asp Thr Ala Phe Tyr Tyr Cys Ala Asn Ser Ala Tyr Thr Gly Gly Trp
            325               330               335

Tyr Asp Tyr Trp Gly His Gly Thr Leu Val Thr Val Ser Ser Gly Gly
            340               345               350

Gly Gly Ser Gly Gly Gly Gly Ser Gly Gly Gly Gly Ser Ser Glu Leu
            355               360               365

Thr Gln Asp Pro Ala Val Ser Val Ala Leu Gly Gln Thr Val Lys Ile
    370               375               380

Thr Cys Gln Gly Asp Ser Leu Arg Thr Tyr Tyr Ala Ser Trp Tyr Gln
385               390               395               400

Gln Arg Pro Gly Gln Ala Pro Val Leu Val Ile Tyr Gly Glu Asn Ser
            405               410               415

Arg Pro Ser Gly Ile Pro Asp Arg Phe Ser Gly Ser Ser Ser Gly Asn
            420               425               430

Thr Ala Ser Leu Thr Ile Thr Gly Ala Gln Ala Glu Asp Glu Ala Asp
            435               440               445

Tyr Tyr Cys Asn Ser Arg Asp Ser Ser Gly Asn His Leu Arg Val Phe
    450               455               460

Gly Gly Gly Thr Lys Leu Thr Val Leu Gly
465               470
```

<210> SEQ ID NO 398

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Phe Thr Phe Asn Ser Phe Ala Met Ser
1               5                   10

<210> SEQ ID NO 399
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ile Ser Gly Ser Gly Gly Gly Thr Tyr Tyr Ala Asp Ser Val Lys
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ala Lys Asp Lys Ile Leu Trp Phe Gly Glu Pro Val Phe Asp Tyr
1               5                   10                  15

<210> SEQ ID NO 401
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Arg Ala Ser Gln Ser Val Ser Ser Tyr Leu Ala
1               5                   10

<210> SEQ ID NO 402
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Asp Ala Ser Asn Arg Ala Thr
1               5

<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403
```

```
Gln Gln Arg Ser Asn Trp Pro Pro Thr
1               5

<210> SEQ ID NO 404
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Phe Thr Phe Ser Ser Tyr Ala Met Ser
1               5                   10

<210> SEQ ID NO 405
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ala Ile Ser Gly Ser Gly Gly Ser Thr Tyr Tyr Ala Asp Ser Val Lys
1               5                   10                  15

Gly

<210> SEQ ID NO 406
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ala Asn Ser Ala Tyr Thr Gly Gly Trp Tyr Asp Tyr
1               5                   10

<210> SEQ ID NO 407
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gln Gly Asp Ser Leu Arg Thr Tyr Tyr Ala Ser
1               5                   10

<210> SEQ ID NO 408
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gly Glu Asn Ser Arg Pro Ser
1               5

<210> SEQ ID NO 409
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 409

Asn Ser Arg Asp Ser Ser Gly Asn His Leu Arg Val
1               5                   10

<210> SEQ ID NO 410
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Gly or Arg
<220> FEATURE:
<221> NAME/KEY: MOD_RES
<222> LOCATION: (12)..(12)
<223> OTHER INFORMATION: Lys or Thr
<220> FEATURE:
<221> NAME/KEY: MOD_RES
<222> LOCATION: (15)..(15)
<223> OTHER INFORMATION: Gly or Thr
<220> FEATURE:
<221> NAME/KEY: MOD_RES
<222> LOCATION: (16)..(16)
<223> OTHER INFORMATION: Thr or Pro
<220> FEATURE:
<221> NAME/KEY: MOD_RES
<222> LOCATION: (30)..(30)
<223> OTHER INFORMATION: Ser or Thr
<220> FEATURE:
<221> NAME/KEY: MOD_RES
<222> LOCATION: (31)..(31)
<223> OTHER INFORMATION: His or Tyr
<220> FEATURE:
<221> NAME/KEY: MOD_RES
<222> LOCATION: (45)..(45)
<223> OTHER INFORMATION: Gln or Glu
<220> FEATURE:
<221> NAME/KEY: MOD_RES
<222> LOCATION: (54)..(54)
<223> OTHER INFORMATION: Asp or Gly
<220> FEATURE:
<221> NAME/KEY: MOD_RES
<222> LOCATION: (55)..(55)
<223> OTHER INFORMATION: Arg or Ser
<220> FEATURE:
<221> NAME/KEY: MOD_RES
<222> LOCATION: (60)..(60)
<223> OTHER INFORMATION: Ser or Thr
<220> FEATURE:
<221> NAME/KEY: MOD_RES
<222> LOCATION: (78)..(78)
<223> OTHER INFORMATION: Lys or Arg
<220> FEATURE:
<221> NAME/KEY: MOD_RES
<222> LOCATION: (79)..(79)
<223> OTHER INFORMATION: Ile or Leu
<220> FEATURE:
<221> NAME/KEY: MOD_RES
<222> LOCATION: (100)..(100)
<223> OTHER INFORMATION: Phe or Tyr
<220> FEATURE:
<221> NAME/KEY: MOD_RES
<222> LOCATION: (101)..(101)
<223> OTHER INFORMATION: Asp or Gly
<220> FEATURE:
<221> NAME/KEY: MOD_RES
<222> LOCATION: (102)..(102)
<223> OTHER INFORMATION: Asp or Ala
<220> FEATURE:
```

-continued

```
<221> NAME/KEY: MOD_RES
<222> LOCATION: (103)..(103)
<223> OTHER INFORMATION: Gly or Ala

<400> SEQUENCE: 410

Gln Ser Val Glu Glu Ser Gly Gly Xaa Leu Val Xaa Pro Gly Xaa Xaa
1               5                   10                  15

Leu Thr Leu Thr Cys Thr Val Ser Gly Phe Ser Leu Ser Xaa Xaa Ala
                20                  25                  30

Met Gly Trp Val Arg Gln Ala Pro Gly Lys Gly Leu Xaa Tyr Ile Gly
            35                  40                  45

Ile Ile Gly Ser Ser Xaa Xaa Thr Tyr Tyr Ala Xaa Trp Ala Lys Gly
    50                  55                  60

Arg Phe Thr Ile Ser Lys Thr Ser Thr Thr Val Asp Leu Xaa Xaa Thr
65                  70                  75                  80

Ser Pro Thr Thr Glu Asp Thr Ala Thr Tyr Phe Cys Val Arg Asp Pro
                85                  90                  95

Tyr Asp Ser Xaa Xaa Xaa Xaa Tyr Arg Leu Trp Gly Pro Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

-continued

```
385             390             395             400

Asp Gly Ser Phe Phe Leu Tyr Ser Lys Leu Thr Val Asp Lys Ser Arg
            405             410             415

Trp Gln Gln Gly Asn Val Phe Ser Cys Ser Val Met His Glu Ala Leu
        420             425             430

His Asn His Tyr Thr Gln Lys Ser Leu Ser Leu Ser Pro Gly Lys
        435             440             445

<210> SEQ ID NO 411
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (27)..(27)
<223> OTHER INFORMATION: Gln or Glu
<220> FEATURE:
<221> NAME/KEY: MOD_RES
<222> LOCATION: (28)..(28)
<223> OTHER INFORMATION: Ser or Asn
<220> FEATURE:
<221> NAME/KEY: MOD_RES
<222> LOCATION: (31)..(31)
<223> OTHER INFORMATION: Ser or Arg
<220> FEATURE:
<221> NAME/KEY: MOD_RES
<222> LOCATION: (33)..(33)
<223> OTHER INFORMATION: Cys or Leu
<220> FEATURE:
<221> NAME/KEY: MOD_RES
<222> LOCATION: (34)..(34)
<223> OTHER INFORMATION: Ser or Leu
<220> FEATURE:
<221> NAME/KEY: MOD_RES
<222> LOCATION: (38)..(38)
<223> OTHER INFORMATION: Lys or Gln
<220> FEATURE:
<221> NAME/KEY: MOD_RES
<222> LOCATION: (40)..(40)
<223> OTHER INFORMATION: Leu or Pro
<220> FEATURE:
<221> NAME/KEY: MOD_RES
<222> LOCATION: (45)..(45)
<223> OTHER INFORMATION: Lys or Ser
<220> FEATURE:
<221> NAME/KEY: MOD_RES
<222> LOCATION: (46)..(46)
<223> OTHER INFORMATION: Leu or Phe
<220> FEATURE:
<221> NAME/KEY: MOD_RES
<222> LOCATION: (54)..(54)
<223> OTHER INFORMATION: Val or Leu
<220> FEATURE:
<221> NAME/KEY: MOD_RES
<222> LOCATION: (63)..(63)
<223> OTHER INFORMATION: Lys, Glu or Thr
<220> FEATURE:
<221> NAME/KEY: MOD_RES
<222> LOCATION: (77)..(77)
<223> OTHER INFORMATION: Ala or Gly
<220> FEATURE:
<221> NAME/KEY: MOD_RES
<222> LOCATION: (78)..(78)
<223> OTHER INFORMATION: Val, Met or Ala
<220> FEATURE:
<221> NAME/KEY: MOD_RES
<222> LOCATION: (95)..(95)
<223> OTHER INFORMATION: Ser or Gly
```

```
<220> FEATURE:
<221> NAME/KEY: MOD_RES
<222> LOCATION: (96)..(96)
<223> OTHER INFORMATION: Ser or Asn
<220> FEATURE:
<221> NAME/KEY: MOD_RES
<222> LOCATION: (97)..(97)
<223> OTHER INFORMATION: Val or Ile
<220> FEATURE:
<221> NAME/KEY: MOD_RES
<222> LOCATION: (100)..(100)
<223> OTHER INFORMATION: Val or Ala
<220> FEATURE:
<221> NAME/KEY: MOD_RES
<222> LOCATION: (108)..(108)
<223> OTHER INFORMATION: Val or Met

<400> SEQUENCE: 411

Ala Tyr Asp Met Xaa Gln Thr Pro Ala Ser Val Glu Val Ala Val Gly
1               5                   10                  15

Gly Thr Val Thr Ile Lys Cys Gln Ala Ser Xaa Xaa Ile Tyr Xaa Tyr
                20                  25                  30

Xaa Xaa Trp Tyr Gln Xaa Lys Xaa Gly Gln Arg Pro Xaa Xaa Leu Ile
            35                  40                  45

Tyr Asp Ala Ser Lys Xaa Ala Ser Gly Val Pro Ser Arg Phe Xaa Gly
    50                  55                  60

Ser Gly Ser Gly Thr Glu Phe Thr Leu Thr Ile Ser Xaa Xaa Gln Ser
65                  70                  75                  80

Asp Asp Ala Ala Thr Tyr Tyr Cys Gln Gln Ala Tyr Ser Ser Xaa Xaa
                85                  90                  95

Xaa Asp Asn Xaa Phe Gly Gly Gly Thr Glu Val Xaa Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (7)..(7)
<223> OTHER INFORMATION: His or Tyr

<400> SEQUENCE: 412
```

```
Gly Phe Ser Leu Ser Xaa Xaa Ala Met Gly
1               5               10

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Asp or Gly
<220> FEATURE:
<221> NAME/KEY: MOD_RES
<222> LOCATION: (8)..(8)
<223> OTHER INFORMATION: Arg or Ser
<220> FEATURE:
<221> NAME/KEY: MOD_RES
<222> LOCATION: (13)..(13)
<223> OTHER INFORMATION: Ser or Thr

<400> SEQUENCE: 413

Gly Ile Ile Gly Ser Ser Xaa Xaa Thr Tyr Tyr Ala Xaa Trp Ala Lys
1               5               10              15

Gly

<210> SEQ ID NO 414
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phe or Tyr
<220> FEATURE:
<221> NAME/KEY: MOD_RES
<222> LOCATION: (9)..(9)
<223> OTHER INFORMATION: Asp or Gly
<220> FEATURE:
<221> NAME/KEY: MOD_RES
<222> LOCATION: (10)..(10)
<223> OTHER INFORMATION: Asp or Ala
<220> FEATURE:
<221> NAME/KEY: MOD_RES
<222> LOCATION: (11)..(11)
<223> OTHER INFORMATION: Gly or Ala

<400> SEQUENCE: 414

Val Arg Asp Pro Tyr Asp Ser Xaa Xaa Xaa Xaa Tyr Arg Leu
1               5               10

<210> SEQ ID NO 415
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (5)..(5)
<223> OTHER INFORMATION: Ser or Asn
<220> FEATURE:
```

<221> NAME/KEY: MOD_RES
<222> LOCATION: (8)..(8)
<223> OTHER INFORMATION: Ser or Arg
<220> FEATURE:
<221> NAME/KEY: MOD_RES
<222> LOCATION: (10)..(10)
<223> OTHER INFORMATION: Cys or Leu
<220> FEATURE:
<221> NAME/KEY: MOD_RES
<222> LOCATION: (11)..(11)
<223> OTHER INFORMATION: Ser or Leu

<400> SEQUENCE: 415

Gln Ala Ser Xaa Xaa Ile Tyr Xaa Tyr Xaa Xaa
1               5                   10

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Val or Leu

<400> SEQUENCE: 416

Asp Ala Ser Lys Xaa Ala Ser
1               5

<210> SEQ ID NO 417
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Ser or Asn
<220> FEATURE:
<221> NAME/KEY: MOD_RES
<222> LOCATION: (9)..(9)
<223> OTHER INFORMATION: Val or Ile
<220> FEATURE:
<221> NAME/KEY: MOD_RES
<222> LOCATION: (12)..(12)
<223> OTHER INFORMATION: Val or Ala

<400> SEQUENCE: 417

Gln Gln Ala Tyr Ser Ser Xaa Xaa Xaa Asp Asn Xaa
1               5                   10

<210> SEQ ID NO 418
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe or Tyr

<400> SEQUENCE: 418

-continued

```
Ala Ile Ser Gly Ser Gly Gly Ser Thr Xaa Tyr Ala Asp Ser Val Lys
1               5                   10                  15

Gly

<210> SEQ ID NO 419
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Ala
<220> FEATURE:
<221> NAME/KEY: MOD_RES
<222> LOCATION: (5)..(6)
<223> OTHER INFORMATION: Ser, Thr or Asn
<220> FEATURE:
<221> NAME/KEY: MOD_RES
<222> LOCATION: (7)..(7)
<223> OTHER INFORMATION: Tyr, Arg, Ala or Gly
<220> FEATURE:
<221> NAME/KEY: MOD_RES
<222> LOCATION: (8)..(8)
<223> OTHER INFORMATION: Trp, Tyr or Cys
<220> FEATURE:
<221> NAME/KEY: MOD_RES
<222> LOCATION: (9)..(9)
<223> OTHER INFORMATION: Ile, Trp, Tyr or Asp
<220> FEATURE:
<221> NAME/KEY: MOD_RES
<222> LOCATION: (10)..(10)
<223> OTHER INFORMATION: Cys, Ile, Tyr or Met
<220> FEATURE:
<221> NAME/KEY: MOD_RES
<222> LOCATION: (11)..(11)
<223> OTHER INFORMATION: Cys, Met or absent
<220> FEATURE:
<221> NAME/KEY: MISC_FEATURE
<222> LOCATION: (12)..(12)
<223> OTHER INFORMATION: May or may not be present

<400> SEQUENCE: 419

Gly Phe Ser Xaa Xaa Xaa Xaa Xaa Xaa Xaa Xaa Cys
1               5                   10

<210> SEQ ID NO 420
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Trp, Ile or Tyr
<220> FEATURE:
<221> NAME/KEY: MOD_RES
<222> LOCATION: (4)..(4)
<223> OTHER INFORMATION: Ser or Gly
<220> FEATURE:
<221> NAME/KEY: MOD_RES
<222> LOCATION: (5)..(5)
<223> OTHER INFORMATION: Phe, Ser, Asp or Thr
<220> FEATURE:
<221> NAME/KEY: MOD_RES
<222> LOCATION: (6)..(6)
<223> OTHER INFORMATION: Ser or Arg
<220> FEATURE:
<221> NAME/KEY: MOD_RES
<222> LOCATION: (7)..(7)
```

-continued

```
<223> OTHER INFORMATION: Gly or Asp
<220> FEATURE:
<221> NAME/KEY: MOD_RES
<222> LOCATION: (8)..(8)
<223> OTHER INFORMATION: Ser, Arg, Thr or Asn
<220> FEATURE:
<221> NAME/KEY: MOD_RES
<222> LOCATION: (9)..(9)
<223> OTHER INFORMATION: Thr or Ala
<220> FEATURE:
<221> NAME/KEY: MOD_RES
<222> LOCATION: (13)..(13)
<223> OTHER INFORMATION: Ser, Thr or Asn

<400> SEQUENCE: 420

Gly Xaa Ile Xaa Xaa Xaa Xaa Xaa Xaa Tyr Tyr Ala Xaa Trp Ala Lys
1               5                   10                  15

Gly

<210> SEQ ID NO 421
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ala or Gly
<220> FEATURE:
<221> NAME/KEY: MOD_RES
<222> LOCATION: (10)..(10)
<223> OTHER INFORMATION: Phe or Tyr

<400> SEQUENCE: 421

Ala Lys Arg Gly Thr Tyr Xaa Tyr Ser Xaa Pro Thr Gly Phe Asp Tyr
1               5                   10                  15

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Gly
<220> FEATURE:
<221> NAME/KEY: MOD_RES
<222> LOCATION: (3)..(3)
<223> OTHER INFORMATION: Glu, Asp or Ser
<220> FEATURE:
<221> NAME/KEY: MOD_RES
<222> LOCATION: (4)..(4)
<223> OTHER INFORMATION: Gly, Leu, Pro, Ser or Ala
<220> FEATURE:
<221> NAME/KEY: MOD_RES
<222> LOCATION: (5)..(5)
<223> OTHER INFORMATION: Asp, Ser or Arg
<220> FEATURE:
<221> NAME/KEY: MOD_RES
<222> LOCATION: (6)..(6)
<223> OTHER INFORMATION: Tyr, Thr, Asn or Gly
<220> FEATURE:
<221> NAME/KEY: MOD_RES
<222> LOCATION: (7)..(7)
<223> OTHER INFORMATION: Gly, Ser, Phe or Leu
<220> FEATURE:
<221> NAME/KEY: MOD_RES
<222> LOCATION: (8)..(8)
<223> OTHER INFORMATION: Ala, Gly, Ser or Ile
```

```
<220> FEATURE:
<221> NAME/KEY: MOD_RES
<222> LOCATION: (9)..(9)
<223> OTHER INFORMATION: Tyr, Asn or Leu
<220> FEATURE:
<221> NAME/KEY: MOD_RES
<222> LOCATION: (10)..(10)
<223> OTHER INFORMATION: Val, Tyr, Glu or absent
<220> FEATURE:
<221> NAME/KEY: MISC_FEATURE
<222> LOCATION: (11)..(13)
<223> OTHER INFORMATION: May or may not be present
<220> FEATURE:
<221> NAME/KEY: MOD_RES
<222> LOCATION: (14)..(14)
<223> OTHER INFORMATION: Glu, Asn or absent
<220> FEATURE:
<221> NAME/KEY: MOD_RES
<222> LOCATION: (15)..(15)
<223> OTHER INFORMATION: Ser, Leu or absent

<400> SEQUENCE: 422

Ala Xaa Xaa Xaa Xaa Xaa Xaa Xaa Xaa Xaa Gly Tyr Phe Xaa Xaa
1               5                   10                  15

<210> SEQ ID NO 423
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Gly
<220> FEATURE:
<221> NAME/KEY: MOD_RES
<222> LOCATION: (6)..(6)
<223> OTHER INFORMATION: Val, Ala or Thr

<400> SEQUENCE: 423

Gly Phe Pro Phe Xaa Xaa Tyr Ala Met Ser
1               5                   10

<210> SEQ ID NO 424
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Val
<220> FEATURE:
<221> NAME/KEY: MOD_RES
<222> LOCATION: (3)..(3)
<223> OTHER INFORMATION: Gly or Asp
<220> FEATURE:
<221> NAME/KEY: MOD_RES
<222> LOCATION: (4)..(4)
<223> OTHER INFORMATION: Gly, Pro, Trp or Asp
<220> FEATURE:
<221> NAME/KEY: MOD_RES
<222> LOCATION: (5)..(5)
<223> OTHER INFORMATION: Asp, Tyr, Ser or Leu
<220> FEATURE:
<221> NAME/KEY: MOD_RES
<222> LOCATION: (6)..(6)
<223> OTHER INFORMATION: Tyr, Asp, Val or Leu
<220> FEATURE:
<221> NAME/KEY: MOD_RES
<222> LOCATION: (7)..(7)
```

```
<223> OTHER INFORMATION: Gly, Ser or Asp
<220> FEATURE:
<221> NAME/KEY: MOD_RES
<222> LOCATION: (8)..(8)
<223> OTHER INFORMATION: Gly, Tyr, Phe or Ser
<220> FEATURE:
<221> NAME/KEY: MOD_RES
<222> LOCATION: (9)..(9)
<223> OTHER INFORMATION: Ser, Asp, Gly or Thr
<220> FEATURE:
<221> NAME/KEY: MOD_RES
<222> LOCATION: (10)..(10)
<223> OTHER INFORMATION: Thr, Ala, Asp, Ser or Tyr
<220> FEATURE:
<221> NAME/KEY: MOD_RES
<222> LOCATION: (11)..(11)
<223> OTHER INFORMATION: Tyr, Ala, Gly or Ile
<220> FEATURE:
<221> NAME/KEY: MOD_RES
<222> LOCATION: (12)..(12)
<223> OTHER INFORMATION: Ile, Tyr or Arg
<220> FEATURE:
<221> NAME/KEY: MOD_RES
<222> LOCATION: (13)..(13)
<223> OTHER INFORMATION: Leu, Arg, Tyr or Gly
<220> FEATURE:
<221> NAME/KEY: MOD_RES
<222> LOCATION: (14)..(14)
<223> OTHER INFORMATION: Asn, Leu, Tyr or Ser
<220> FEATURE:
<221> NAME/KEY: MOD_RES
<222> LOCATION: (15)..(15)
<223> OTHER INFORMATION: Leu, Tyr, Phe or absent
<220> FEATURE:
<221> NAME/KEY: MISC_FEATURE
<222> LOCATION: (16)..(16)
<223> OTHER INFORMATION: May or may not be present
<220> FEATURE:
<221> NAME/KEY: MOD_RES
<222> LOCATION: (17)..(17)
<223> OTHER INFORMATION: Met, Pro or absent
<220> FEATURE:
<221> NAME/KEY: MISC_FEATURE
<222> LOCATION: (18)..(19)
<223> OTHER INFORMATION: May or may not be present

<400> SEQUENCE: 424

Xaa Arg Xaa Xaa Xaa Xaa Xaa Xaa Xaa Xaa Xaa Xaa Xaa Xaa Xaa Asp
1               5                   10                  15

Xaa Asp Leu

<210> SEQ ID NO 425
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Ser, Asn, Thr or Asp
<220> FEATURE:
<221> NAME/KEY: MOD_RES
<222> LOCATION: (7)..(7)
<223> OTHER INFORMATION: Tyr or His
<220> FEATURE:
<221> NAME/KEY: MOD_RES
<222> LOCATION: (8)..(8)
<223> OTHER INFORMATION: Gly, Ala or Tyr
<220> FEATURE:
<221> NAME/KEY: MOD_RES
```

```
<222> LOCATION: (10)..(10)
<223> OTHER INFORMATION: Ser, Gly or Asn

<400> SEQUENCE: 425

Gly Phe Ser Leu Xaa Xaa Xaa Xaa Met Xaa
1               5                   10

<210> SEQ ID NO 426
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Arg, Ser or Asn
<220> FEATURE:
<221> NAME/KEY: MOD_RES
<222> LOCATION: (7)..(7)
<223> OTHER INFORMATION: Tyr, Ile or Asn
<220> FEATURE:
<221> NAME/KEY: MOD_RES
<222> LOCATION: (8)..(8)
<223> OTHER INFORMATION: Tyr, Asp, Gly or Ala
<220> FEATURE:
<221> NAME/KEY: MOD_RES
<222> LOCATION: (9)..(9)
<223> OTHER INFORMATION: Val, Met or Ile
<220> FEATURE:
<221> NAME/KEY: MOD_RES
<222> LOCATION: (10)..(10)
<223> OTHER INFORMATION: Thr, Ser or Met
<220> FEATURE:
<221> NAME/KEY: MISC_FEATURE
<222> LOCATION: (11)..(11)
<223> OTHER INFORMATION: May or may not be present

<400> SEQUENCE: 426

Gly Phe Ser Leu Xaa Xaa Xaa Xaa Xaa Xaa Cys
1               5                   10

<210> SEQ ID NO 427
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Gly Phe Leu Gly
1

<210> SEQ ID NO 428
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ala Leu Ala Leu
1
```

-continued

```
<210> SEQ ID NO 429
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gly Gly Phe Gly
1

<210> SEQ ID NO 430
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gln Gln Ala Tyr Ser Ser Gly Ser Ile Asp Asn Ala
1               5                   10
```

CD38 AND ICAM1 ANTIBODIES AND USES THEREOF

CROSS-REFERENCE

This application is a § 371 U.S. National Stage Entry of International Application No. PCT/US2019/061884, filed Nov. 15, 2019, which claims the benefit of U.S. Provisional Application No. 62/768,566, filed Nov. 16, 2018, which are incorporated by reference herein in their entirety.

SEQUENCE LISTING

The instant application contains a Sequence Listing which has been submitted electronically in ASCII format and is hereby incorporated by reference in its entirety. Said ASCII copy, created on Nov. 14, 2019, is named 55429-701_601_SL.txt and is 590,037 bytes in size.

BACKGROUND

Antibodies that bind to CD38 are useful for the treatment of cancers that express CD38. Anti-CD38 antibodies are thought to kill cancer cells by various mechanisms including antibody-dependent cell-mediated cytotoxicity and complement dependent cytotoxicity. One such antibody, daratumumab, is approved for the treatment of adults with multiple myeloma. Reduced CD38 expression can limit the efficacy of anti-CD38 antibodies. Proposals to overcome this limitation include treatment with an antibody having higher affinity for CD38, treatment with an antibody that binds to a different epitope on CD38, treatment with an antibody that more effectively inhibits CD38 enzymatic activity, treatment with a tetravalent anti-CD38 antibody, and concurrent treatment with all-trans retinoic acid to increase CD38 expression.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY OF THE DISCLOSURE

One embodiment provides a multispecific protein comprising a first component that specifically binds to CD38 and a second component that specifically binds to ICAM1. In some embodiments, the multispecific protein is bivalent, trivalent, or tetravalent. In some embodiments, the first component comprises an antibody or an antigen binding fragment thereof that specifically binds to CD38. In some embodiments, the second component comprises an antibody or an antigen binding fragment thereof that specifically binds to ICAM1. In some embodiments, the antibody or an antigen binding fragment thereof that specifically binds to CD38 comprises a variable domain of an IgG heavy chain and a variable domain of an IgG light chain. In some embodiments, the antibody or an antigen binding fragment thereof that specifically binds to ICAM1 comprises a variable domain of an IgG heavy chain and a variable domain of an IgG light chain. In some embodiments, the multispecific protein further comprises an Fc region. In some embodiments, the Fc region comprises a heterodimeric Fc region. In some embodiments, the Fc region comprises one or more mutations that increases the half-life of the multispecific protein. In some embodiments, the Fc region comprises one or more stabilizing mutations. In some embodiments, the Fc region comprises one or more mutations that modulate its interaction with an Fc receptor.

In some embodiments, the multispecific protein of claim 11, wherein the Fc region comprises one or more mutations that increase binding of the Fc region to an Fc receptor. In some embodiments, the Fc region comprises one or more mutations that decrease glycosylation of the Fc region. In some embodiments, the one or more mutations that decrease glycosylation of the Fc region comprises a mutation at a position corresponding to position N297 of human IgG1, wherein the numbering is according to the EU index of Kabat et al. In some embodiments, the Fc region is afucosylated. In some embodiments, the Fc region comprises one or more mutations that increases ADCC or CDC activity. In some embodiments, the Fc region comprises the one or more mutations that increase ADCC, wherein the mutations that increase ADCC are at positions corresponding to positions 239, 332, and 330 of human IgG1, wherein the mutations are S239D, I332E, and A330L, and wherein the amino acid numbering is according to the EU index in Kabat et al. In some embodiments, the heterodimeric Fc region, wherein the heterodimeric Fc region comprises a knob chain and a hole chain, forming a knob-in-hole (KIH) structure. In some embodiments, the knob chain comprises the mutation T366W and the hole chain comprises the mutations T366S, L368A, and Y407V, wherein amino acid position numbering is according to the EU index of Kabat et al. In some embodiments, the antibody or antigen binding fragment thereof that specifically binds to CD38 comprises an anti-CD38 IgG, and the antibody or an antigen binding fragment thereof that specifically binds to ICAM1 comprises an anti-ICAM1 single chain variable fragment (anti-ICAM1 scFv). In some embodiments, the anti-CD38 IgG comprises two light chains and each light chain is fused to a single anti-ICAM1 scFv. In some embodiments, the C-terminus of each light chain of the anti-CD38 IgG is fused to a single anti-ICAM1 scFv. In some embodiments, the N-terminus of each heavy chain of the anti-CD38 IgG is fused to a single anti-ICAM1 scFv. In some embodiments, the anti-CD38 IgG comprises two heavy chains and the C-terminus of each heavy chain is conjugated to a single anti-ICAM1 scFv.

In some embodiments, the first component comprises an anti-CD38 IgG and the second component comprises two anti-ICAM1 variable heavy domains and two anti-ICAM-1 variable light domains, and wherein each variable heavy domain of the anti-CD38 IgG is fused to one of the anti-ICAM1 variable heavy domains and each variable light domains of the anti-CD38 IgG is fused to one of the anti-ICAM1 variable light domains. In some embodiments, the antibody or antigen binding fragment thereof that specifically binds to CD38 is a monovalent anti-CD38 antibody or antigen binding fragment thereof. In some embodiments, the antibody or antigen binding fragment thereof that specifically binds to ICAM1 is a monovalent anti-ICAM1 antibody or antigen binding fragment thereof. In some embodiments, the monovalent anti-CD38 antibody or antigen binding fragment thereof comprises an anti-CD38 Fab. In some embodiments, the monovalent anti-ICAM1 antibody or antigen binding fragment thereof comprises an anti-ICAM1 scFv. In some embodiments, the multispecific protein comprises the anti-CD38 Fab, the anti-ICAM1 scFv, and the Fe region. In some embodiments, the Fc region is the heterodimeric Fc region comprising a KIH structure. In some embodiments, the monovalent anti-CD38 antibody or antigen binding fragment thereof comprises one variable heavy domain (VH) and a variable light domain (VL), and wherein the monovalent anti-ICAM1 antibody or antigen binding fragment thereof comprises one variable heavy domain (VH).

In some embodiments, the multispecific protein further comprises the Fe region. In some embodiments, the Fe region is the heterodimeric Fe region comprising a KIH structure, and wherein the multispecific protein is of the common light chain bispecific format. In some embodiments, the first component that specifically binds to CD38 comprises a heavy chain comprising complementarity determining regions CDR1, CDR2, and CDR3, wherein the CDR1, the CDR2, and the CDR3 of the heavy chain comprise a set of sequences selected from the group consisting of the following set of sequences:

CDR1: CDR2: CDR3 (SEQ ID No. 1: SEQ ID No: 2: SEQ ID No. 3);
CDR1: CDR2: CDR3 (SEQ ID No. 4: SEQ ID No. 5: SEQ ID No. 3);
CDR1: CDR2: CDR3 (SEQ ID No. 6: SEQ ID No. 2: SEQ ID No. 7);
CDR1: CDR2: CDR3 (SEQ ID No. 1: SEQ ID No. 2: SEQ ID No. 7);
CDR1: CDR2: CDR3 (SEQ ID No. 4: SEQ ID No. 5: SEQ ID No. 7);
CDR1: CDR2: CDR3 (SEQ ID No. 4: SEQ ID No. 2: SEQ ID No. 7);
CDR1: CDR2: CDR3 (SEQ ID No. 6: SEQ ID No. 2: SEQ ID No. 3);
CDR1: CDR2: CDR3 (SEQ ID No. 8: SEQ ID No. 5: SEQ ID No. 3);
CDR1: CDR2: CDR3 (SEQ ID No. 9: SEQ ID No. 2: SEQ ID No. 10);
CDR1: CDR2: CDR3 (SEQ ID No. 11: SEQ ID No. 12: SEQ ID No. 13);
CDR1: CDR2: CDR3 (SEQ ID No. 14: SEQ ID No. 15: SEQ ID No. 16);
CDR1: CDR2: CDR3 (SEQ ID No. 17: SEQ ID No. 18: SEQ ID No. 19);
CDR1: CDR2: CDR3 (SEQ ID No. 20: SEQ ID No. 21: SEQ ID No. 22);
CDR1: CDR2: CDR3 (SEQ ID No. 23: SEQ ID No. 24: SEQ ID No. 25);
CDR1: CDR2: CDR3 (SEQ ID No. 26: SEQ ID No. 27: SEQ ID No. 28);
CDR1: CDR2: CDR3 (SEQ ID No. 29: SEQ ID No. 30: SEQ ID No. 31);
CDR1: CDR2: CDR3 (SEQ ID No. 32: SEQ ID No. 33: SEQ ID No. 34);
CDR1: CDR2: CDR3 (SEQ ID No. 35: SEQ ID No. 36: SEQ ID No. 37);
CDR1: CDR2: CDR3 (SEQ ID No. 38: SEQ ID No. 39: SEQ ID No. 40);
CDR1: CDR2: CDR3 (SEQ ID No. 41: SEQ ID No. 42: SEQ ID No. 43);
CDR1: CDR2: CDR3 (SEQ ID No. 44: SEQ ID No. 45: SEQ ID No. 46);
CDR1: CDR2: CDR3 (SEQ ID No. 47: SEQ ID No. 48: SEQ ID No. 49);
CDR1: CDR2: CDR3 (SEQ ID No. 50: SEQ ID No. 51: SEQ ID No. 52);
CDR1: CDR2: CDR3 (SEQ ID No. 53: SEQ ID No. 54: SEQ ID No. 55);

CDR1: CDR2: CDR3 (SEQ ID No. 56: SEQ ID No. 57: SEQ ID No. 58); and
CDR1: CDR2: CDR3 (SEQ ID No. 59: SEQ ID No. 60: SEQ ID No. 61).

In some embodiments, the CDR1, the CDR2, and the CDR3 of the heavy chain of the first component comprise the following set of sequences: CDR1: CDR2: CDR3 (SEQ ID No. 14: SEQ ID No. 15: SEQ ID No. 16). In some embodiments, the CDR1, the CDR2, and the CDR3 of the heavy chain of the first component comprise the following set of sequences: CDR1: CDR2: CDR3 (SEQ ID No. 17: SEQ ID No. 18: SEQ ID No. 19). In some embodiments, the CDR1, the CDR2, and the CDR3 of the heavy chain of the first component comprise the following sequences: CDR1: CDR2: CDR3 (SEQ ID No. 1: SEQ ID No. 2: SEQ ID No. 7). In some embodiments, the first component that specifically binds to CD38 comprises a light chain comprising complementarity determining regions CDR1, CDR2, and CDR3, wherein the CDR1, the CDR2, and the CDR3 of the light chain comprise sequences selected from the group consisting of the following set of sequences:

CDR1: CDR2: CDR3 (SEQ ID No. 62: SEQ ID No: 63: SEQ ID No. 64);
CDR1: CDR2: CDR3 (SEQ ID No. 65: SEQ ID No. 66: SEQ ID No. 67);
CDR1: CDR2: CDR3 (SEQ ID No. 68: SEQ ID No. 69: SEQ ID No. 70);
CDR1: CDR2: CDR3 (SEQ ID No. 71: SEQ ID No. 72: SEQ ID No. 73);
CDR1: CDR2: CDR3 (SEQ ID No. 74: SEQ ID No. 75: SEQ ID No. 76);
CDR1: CDR2: CDR3 (SEQ ID No. 77: SEQ ID No. 78: SEQ ID No. 79);
CDR1: CDR2: CDR3 (SEQ ID No. 80: SEQ ID No. 81: SEQ ID No. 82);
CDR1: CDR2: CDR3 (SEQ ID No. 83: SEQ ID No. 84: SEQ ID No. 85);
CDR1: CDR2: CDR3 (SEQ ID No. 86: SEQ ID No. 78: SEQ ID No. 87);
CDR1: CDR2: CDR3 (SEQ ID No. 86: SEQ ID No. 78: SEQ ID No. 88);
CDR1: CDR2: CDR3 (SEQ ID No. 89: SEQ ID No. 90: SEQ ID No. 91);
CDR1: CDR2: CDR3 (SEQ ID No. 92: SEQ ID No. 78: SEQ ID No. 93);
CDR1: CDR2: CDR3 (SEQ ID No. 94: SEQ ID No. 84: SEQ ID No. 95);
CDR1: CDR2: CDR3 (SEQ ID No. 96: SEQ ID No. 81: SEQ ID No. 97);
CDR1: CDR2: CDR3 (SEQ ID No. 98: SEQ ID No. 99: SEQ ID No. 100);
CDR1: CDR2: CDR3 (SEQ ID No. 77: SEQ ID No. 72: SEQ ID No. 101); and
CDR1: CDR2: CDR3 (SEQ ID No. 102: SEQ ID No. 84: SEQ ID No. 103).

In some embodiments, the CDR1, the CDR2, and the CDR3 of the light chain of the first component comprise the following set of sequences: CDR1: CDR2:CDR3 (SEQ ID No. 68: SEQ ID No. 69: SEQ ID No. 70). In some embodiments, the CDR1, the CDR2, and the CDR3 of the light chain of the first component comprise the following set of sequences: CDR1: CDR2:CDR3 (SEQ ID No. 71: SEQ ID No. 72: SEQ ID No. 73). In some embodiments, the CDR1, the CDR2, and the CDR3 of the light chain of the first component comprise the following set of sequences: CDR1: CDR2:CDR3 (SEQ ID No. 62: SEQ ID No. 63: SEQ ID No. 64).

In some embodiments, the first component comprises six CDRs comprising sequences as set forth in any one of the following sets of sequences:

HC (CDR1: CDR2: CDR3)-LC (CDR1: CDR2: CDR3) (SEQ ID No. 1: SEQ ID No: 2: SEQ ID No. 3)-(SEQ ID No. 62: SEQ ID No: 63: SEQ ID No. 64);

HC (CDR1: CDR2: CDR3)-LC (CDR1:CDR2: CDR3) (SEQ ID No. 4: SEQ ID No: 5: SEQ ID No. 3)-(SEQ ID No. 62: SEQ ID No: 63: SEQ ID No. 64);

HC (CDR1: CDR2: CDR3)-LC (CDR1:CDR2: CDR3) (SEQ ID No. 6: SEQ ID No: 2: SEQ ID No. 7)-(SEQ ID No. 62: SEQ ID No: 63: SEQ ID No. 64);

HC (CDR1: CDR2: CDR3)-LC (CDR1:CDR2: CDR3) (SEQ ID No. 1: SEQ ID No: 2: SEQ ID No. 7)-(SEQ ID No. 62: SEQ ID No: 63: SEQ ID No. 64);

HC (CDR1: CDR2: CDR3)-LC (CDR1:CDR2: CDR3) (SEQ ID No. 4: SEQ ID No: 5: SEQ ID No. 7)-(SEQ ID No. 62: SEQ ID No: 63: SEQ ID No. 64);

HC (CDR1: CDR2: CDR3)-LC (CDR1:CDR2: CDR3) (SEQ ID No. 4: SEQ ID No: 2: SEQ ID No. 7)-(SEQ ID No. 62: SEQ ID No: 63: SEQ ID No. 64);

HC (CDR1: CDR2: CDR3)-LC (CDR1:CDR2: CDR3) (SEQ ID No. 6: SEQ ID No: 2: SEQ ID No. 3)-(SEQ ID No. 62: SEQ ID No: 63: SEQ ID No. 64);

HC (CDR1: CDR2: CDR3)-LC (CDR1:CDR2: CDR3) (SEQ ID No. 8: SEQ ID No: 5: SEQ ID No. 3)-(SEQ ID No. 62: SEQ ID No: 63: SEQ ID No. 64);

HC (CDR1: CDR2: CDR3)-LC (CDR1:CDR2: CDR3) (SEQ ID No. 9: SEQ ID No: 2: SEQ ID No. 10)-(SEQ ID No. 62: SEQ ID No: 63: SEQ ID No. 64);

HC (CDR1: CDR2: CDR3)-LC (CDR1:CDR2: CDR3) (SEQ ID No. 59: SEQ ID No: 60: SEQ ID No. 61)-(SEQ ID No. 62: SEQ ID No: 63: SEQ ID No. 64);

HC (CDR1: CDR2: CDR3)-LC (CDR1:CDR2: CDR3) (SEQ ID No. 11: SEQ ID No: 12: SEQ ID No. 13)-(SEQ ID No. 65: SEQ ID No: 66: SEQ ID No. 67);

HC (CDR1: CDR2: CDR3)-LC (CDR1:CDR2: CDR3) (SEQ ID No. 14: SEQ ID No: 15: SEQ ID No. 16)-(SEQ ID No. 68: SEQ ID No: 69: SEQ ID No. 70);

HC (CDR1: CDR2: CDR3)-LC (CDR1:CDR2: CDR3) (SEQ ID No. 17: SEQ ID No: 18: SEQ ID No. 19)-(SEQ ID No. 71: SEQ ID No: 72: SEQ ID No. 73);

HC (CDR1: CDR2: CDR3)-LC (CDR1:CDR2: CDR3) (SEQ ID No. 20: SEQ ID No: 21: SEQ ID No. 22)-(SEQ ID No. 74: SEQ ID No: 75: SEQ ID No. 76);

HC (CDR1: CDR2: CDR3)-LC (CDR1:CDR2: CDR3) (SEQ ID No. 23: SEQ ID No: 24: SEQ ID No. 25)-(SEQ ID No. 77: SEQ ID No: 78: SEQ ID No. 79);

HC (CDR1: CDR2: CDR3)-LC (CDR1:CDR2: CDR3) (SEQ ID No. 26: SEQ ID No: 27: SEQ ID No. 28)-(SEQ ID No. 80: SEQ ID No: 81: SEQ ID No. 82);

HC (CDR1: CDR2: CDR3)-LC (CDR1:CDR2: CDR3) (SEQ ID No. 29: SEQ ID No: 30: SEQ ID No. 31)-(SEQ ID No. 83: SEQ ID No: 84: SEQ ID No. 85);

HC (CDR1: CDR2: CDR3)-LC (CDR1:CDR2: CDR3) (SEQ ID No. 32: SEQ ID No: 33: SEQ ID No. 34)-(SEQ ID No. 86: SEQ ID No: 78: SEQ ID No. 87);

HC (CDR1: CDR2: CDR3)-LC (CDR1:CDR2: CDR3) (SEQ ID No. 35: SEQ ID No: 36: SEQ ID No. 37)-(SEQ ID No. 86: SEQ ID No: 78: SEQ ID No. 88);

HC (CDR1: CDR2: CDR3)-LC (CDR1:CDR2: CDR3) (SEQ ID No. 38: SEQ ID No: 39: SEQ ID No. 40)-(SEQ ID No. 89: SEQ ID No: 90: SEQ ID No. 91);

HC (CDR1: CDR2: CDR3)-LC (CDR1:CDR2: CDR3) (SEQ ID No. 41: SEQ ID No: 42: SEQ ID No. 43)-(SEQ ID No. 92: SEQ ID No: 78: SEQ ID No. 93);

HC (CDR1: CDR2: CDR3)-LC (CDR1:CDR2: CDR3) (SEQ ID No. 44: SEQ ID No: 45: SEQ ID No. 46)-(SEQ ID No. 94: SEQ ID No: 84: SEQ ID No. 95);

HC (CDR1: CDR2: CDR3)-LC (CDR1:CDR2: CDR3) (SEQ ID No. 47: SEQ ID No: 48: SEQ ID No. 49)-(SEQ ID No. 96: SEQ ID No: 81: SEQ ID No. 97);

HC (CDR1: CDR2: CDR3)-LC (CDR1:CDR2: CDR3) (SEQ ID No. 50: SEQ ID No: 51: SEQ ID No. 52)-(SEQ ID No. 98: SEQ ID No: 99: SEQ ID No. 100);

HC (CDR1: CDR2: CDR3)-LC (CDR1:CDR2: CDR3) (SEQ ID No. 53: SEQ ID No: 54: SEQ ID No. 55)-(SEQ ID No. 77: SEQ ID No: 72: SEQ ID No. 101); and HC (CDR1: CDR2: CDR3)-LC (CDR1:CDR2: CDR3) (SEQ ID No. 56: SEQ ID No: 57: SEQ ID No. 58)-(SEQ ID No. 102: SEQ ID No: 84: SEQ ID No. 103).

In some embodiments, the first component comprises six CDRs comprising the following set of sequences: HC (CDR1: CDR2: CDR3)-LC (CDR1: CDR2: CDR3) (SEQ ID No. 14: SEQ ID No: 15: SEQ ID No. 16)-(SEQ ID No. 68: SEQ ID No: 69: SEQ ID No. 70). In some embodiments, the first component comprises six CDRs the following sequence: HC (CDR1: CDR2: CDR3)-LC (CDR1: CDR2: CDR3) (SEQ ID No. 17: SEQ ID No: 18: SEQ ID No. 19)-(SEQ ID No. 71: SEQ ID No: 72: SEQ ID No. 73). In some embodiments, the first component comprises six CDRs comprising one of the following set of sequences: HC (CDR1: CDR2: CDR3)-LC (CDR1: CDR2: CDR3) (SEQ ID No. 1: SEQ ID No: 2: SEQ ID No. 7)-(SEQ ID No. 62: SEQ ID No: 63: SEQ ID No. 64).

In some embodiments, the second component that specifically binds to ICAM1 comprises a heavy chain comprising complementarity determining regions CDR1, CDR2, and CDR3, wherein the CDR1, the CDR2, and the CDR3 of the heavy chain comprise sequences selected from the group consisting of the following set of sequences:

CDR1: CDR2: CDR3 (SEQ ID No. 208: SEQ ID No. 209: SEQ ID No. 210);

CDR1: CDR2: CDR3 (SEQ ID No. 211: SEQ ID No. 212: SEQ ID No. 213);

CDR1: CDR2: CDR3 (SEQ ID No. 214: SEQ ID No. 215: SEQ ID No. 216);

CDR1: CDR2: CDR3 (SEQ ID No. 217: SEQ ID No. 218: SEQ ID No. 219);

CDR1: CDR2: CDR3 (SEQ ID No. 214: SEQ ID No. 220: SEQ ID No. 221);

CDR1: CDR2: CDR3 (SEQ ID No. 222: SEQ ID No. 223: SEQ ID No. 224);

CDR1: CDR2: CDR3 (SEQ ID No. 225: SEQ ID No. 223: SEQ ID No. 224);

CDR1: CDR2: CDR3 (SEQ ID No. 222: SEQ ID No. 223: SEQ ID No. 226);

CDR1: CDR2: CDR3 (SEQ ID No. 222: SEQ ID No. 227: SEQ ID No. 224);

CDR1: CDR2: CDR3 (SEQ ID No. 228: SEQ ID No. 229 SEQ ID No. 230);

CDR1: CDR2: CDR3 (SEQ ID No. 228: SEQ ID No. 220: SEQ ID No. 231);

CDR1: CDR2: CDR3 (SEQ ID No. 232: SEQ ID No. 229: SEQ ID No. 233);

CDR1: CDR2: CDR3 (SEQ ID No. 208: SEQ ID No. 234: SEQ ID No. 210);

CDR1: CDR2: CDR3 (SEQ ID No. 235: SEQ ID No. 236: SEQ ID No. 237);

CDR1: CDR2: CDR3 (SEQ ID No. 238: SEQ ID No. 239 SEQ ID No. 240);

CDR1: CDR2: CDR3 (SEQ ID No. 241: SEQ ID No. 242: SEQ ID No. 243);

CDR1: CDR2: CDR3 (SEQ ID No. 241: SEQ ID No. 244: SEQ ID No. 245);

CDR1: CDR2: CDR3 (SEQ ID No. 241: SEQ ID No. 246: SEQ ID No. 245);

CDR1: CDR2: CDR3 (SEQ ID No. 247: SEQ ID No. 248: SEQ ID No. 249);

CDR1: CDR2: CDR3 (SEQ ID No. 250: SEQ ID No. 251: SEQ ID No. 252); and

CDR1: CDR2: CDR3 (SEQ ID No. 404: SEQ ID No. 405: SEQ ID No. 406).

In some embodiments, the CDR1, the CDR2, and the CDR3 of the heavy chain of the second component comprises the following sequence: (CDR1: CDR2: CDR3 (SEQ ID No. 228: SEQ ID No. 229: SEQ ID No. 230). In some embodiments, the CDR1, the CDR2, and the CDR3 of the heavy chain of the second component comprise the following sequences: CDR1: CDR2: CDR3 (SEQ ID No. 222: SEQ ID No. 223: SEQ ID No. 224). In some embodiments, the CDR1, the CDR2, and the CDR3 of the heavy chain of the second component comprise the following set of sequences: CDR1: CDR2: CDR3 (SEQ ID No. 232: SEQ ID No. 229: SEQ ID No. 233). In some embodiments, the CDR1, the CDR2, and the CDR3 of the heavy chain of the second component comprise the following set of sequences: CDR1: CDR2: CDR3 (SEQ ID No. 404: SEQ ID No. 405: SEQ ID No. 406).

In some embodiments, the second component that specifically binds to ICAM1 comprises a light chain comprising complementarity determining regions CDR1, CDR2, and CDR3, wherein the CDR1, the CDR2, and the CDR3 of the light chain comprise a set of sequences selected from the group consisting of the following set of sequences:

CDR1: CDR2: CDR3 (SEQ ID No. 253: SEQ ID No. 254: SEQ ID No. 255);

CDR1: CDR2: CDR3 (SEQ ID No. 256: SEQ ID No. 257: SEQ ID No. 258);

CDR1: CDR2: CDR3 (SEQ ID No. 259: SEQ ID No. 260: SEQ ID No. 261);

CDR1: CDR2: CDR3 (SEQ ID No. 262: SEQ ID No. 263: SEQ ID No. 264);

CDR1: CDR2: CDR3 (SEQ ID No. 265: SEQ ID No. 260: SEQ ID No. 266);

CDR1: CDR2: CDR3 (SEQ ID No. 267: SEQ ID No. 263: SEQ ID No. 264);

CDR1: CDR2: CDR3 (SEQ ID No. 268: SEQ ID No. 263: SEQ ID No. 264);

CDR1: CDR2: CDR3 (SEQ ID No. 269: SEQ ID No. 263: SEQ ID No. 264);

CDR1: CDR2: CDR3 (SEQ ID No. 270: SEQ ID No. 260: SEQ ID No. 271);

CDR1: CDR2: CDR3 (SEQ ID No. 272: SEQ ID No. 260: SEQ ID No. 266);

CDR1: CDR2: CDR3 (SEQ ID No. 259: SEQ ID No. 273: SEQ ID No. 266);

CDR1: CDR2: CDR3 (SEQ ID No. 274: SEQ ID No. 275: SEQ ID No. 276);

CDR1: CDR2: CDR3 (SEQ ID No. 277: SEQ ID No. 275: SEQ ID No. 278);

CDR1: CDR2: CDR3 (SEQ ID No. 279: SEQ ID No. 280: SEQ ID No. 281);

CDR1: CDR2: CDR3 (SEQ ID No. 282: SEQ ID No. 283: SEQ ID No. 284);

CDR1: CDR2: CDR3 (SEQ ID No. 62: SEQ ID No. 63: SEQ ID No. 64); and

CDR1: CDR2: CDR3 (SEQ ID No. 407: SEQ ID No. 408: SEQ ID No. 409).

In some embodiments, the CDR1, the CDR2, and the CDR3 of the light chain of the second component comprise the following set of sequences: CDR1: CDR2: CDR3 (SEQ ID No. 270: SEQ ID No. 260: SEQ ID No. 271). In some embodiments, the CDR1, the CDR2, and the CDR3 of the light chain of the second component comprise the following set of sequences: CDR1: CDR2: CDR3 (SEQ ID No. 267: SEQ ID No. 263: SEQ ID No. 264). In some embodiments, the CDR1, the CDR2, and the CDR3 of the light chain of the second component comprise the following set of sequences: CDR1: CDR2: CDR3 (SEQ ID No. 259: SEQ ID No. 273: SEQ ID No. 266). In some embodiment, the CDR1, the CDR2, and the CDR3 of the light chain of the second component comprise the following set of sequences: (i) CDR1: CDR2: CDR3 (SEQ ID No. 407: SEQ ID No. 408: SEQ ID No. 409). In some embodiments, the second component comprises six CDRs comprising a set of sequences selected from the group consisting of the following sets of sequences:

HC (CDR1: CDR2: CDR3)-LC (CDR1:CDR2: CDR3) (SEQ ID No. 208: SEQ ID No: 209: SEQ ID No. 210)-(SEQ ID No. 253: SEQ ID No: 254: SEQ ID No. 255);

HC (CDR1: CDR2: CDR3)-LC (CDR1:CDR2: CDR3) (SEQ ID No. 211: SEQ ID No: 212: SEQ ID No. 213)-(SEQ ID No. 256: SEQ ID No: 257: SEQ ID No. 258);

HC (CDR1: CDR2: CDR3)-LC (CDR1:CDR2: CDR3) (SEQ ID No. 214: SEQ ID No: 215: SEQ ID No. 216)-(SEQ ID No. 259: SEQ ID No: 260: SEQ ID No. 261);

HC (CDR1: CDR2: CDR3)-LC (CDR1:CDR2: CDR3) (SEQ ID No. 217: SEQ ID No: 218: SEQ ID No. 219)-(SEQ ID No. 262: SEQ ID No: 263: SEQ ID No. 264);

HC (CDR1: CDR2: CDR3)-LC (CDR1:CDR2: CDR3) (SEQ ID No. 214: SEQ ID No: 220: SEQ ID No. 221)-(SEQ ID No. 265: SEQ ID No: 260: SEQ ID No. 266);

HC (CDR1: CDR2: CDR3)-LC (CDR1:CDR2: CDR3) (SEQ ID No. 222: SEQ ID No: 223: SEQ ID No. 224)-(SEQ ID No. 267: SEQ ID No: 263: SEQ ID No. 264);

HC (CDR1: CDR2: CDR3)-LC (CDR1:CDR2: CDR3) (SEQ ID No. 225: SEQ ID No: 223: SEQ ID No. 224)-(SEQ ID No. 268: SEQ ID No: 263: SEQ ID No. 264);

HC (CDR1: CDR2: CDR3)-LC (CDR1:CDR2: CDR3) (SEQ ID No. 222: SEQ ID No: 223: SEQ ID No. 226)-(SEQ ID No. 268: SEQ ID No: 263: SEQ ID No. 264);

HC (CDR1: CDR2: CDR3)-LC (CDR1:CDR2: CDR3) (SEQ ID No. 222: SEQ ID No: 227: SEQ ID No. 224)-(SEQ ID No. 269: SEQ ID No: 263: SEQ ID No. 264);

HC (CDR1: CDR2: CDR3)-LC (CDR1:CDR2: CDR3) (SEQ ID No. 228: SEQ ID No: 229: SEQ ID No. 230)-(SEQ ID No. 270: SEQ ID No: 260: SEQ ID No. 271);

HC (CDR1: CDR2: CDR3)-LC (CDR1:CDR2: CDR3) (SEQ ID No. 228: SEQ ID No: 220: SEQ ID No. 231)-(SEQ ID No. 272: SEQ ID No: 260: SEQ ID No. 266);

HC (CDR1: CDR2: CDR3)-LC (CDR1:CDR2: CDR3) (SEQ ID No. 232: SEQ ID No: 229: SEQ ID No. 233)-(SEQ ID No. 259: SEQ ID No: 273: SEQ ID No. 266);

HC (CDR1: CDR2: CDR3)-LC (CDR1:CDR2: CDR3) (SEQ ID No. 208: SEQ ID No: 234: SEQ ID No. 210)-(SEQ ID No. 274: SEQ ID No: 275: SEQ ID No. 276);

HC (CDR1: CDR2: CDR3)-LC (CDR1:CDR2: CDR3) (SEQ ID No. 208: SEQ ID No: 234: SEQ ID No. 210)-(SEQ ID No. 277: SEQ ID No: 275: SEQ ID No. 278);

HC (CDR1: CDR2: CDR3)-LC (CDR1:CDR2: CDR3) (SEQ ID No. 235: SEQ ID No: 236: SEQ ID No. 237)-(SEQ ID No. 279: SEQ ID No: 280: SEQ ID No. 281);

HC (CDR1: CDR2: CDR3)-LC (CDR1:CDR2: CDR3) (SEQ ID No. 238: SEQ ID No: 239: SEQ ID No. 240)-(SEQ ID No. 282: SEQ ID No: 283: SEQ ID No. 284);

HC (CDR1: CDR2: CDR3)-LC (CDR1:CDR2: CDR3) (SEQ ID No. 241: SEQ ID No: 244: SEQ ID No. 245)-(SEQ ID No. 62: SEQ ID No: 63: SEQ ID No. 64);

HC (CDR1: CDR2: CDR3)-LC (CDR1:CDR2: CDR3) (SEQ ID No. 241: SEQ ID No: 246: SEQ ID No. 245)-(SEQ ID No. 62: SEQ ID No: 63: SEQ ID No. 64);

HC (CDR1: CDR2: CDR3)-LC (CDR1:CDR2: CDR3) (SEQ ID No. 247: SEQ ID No: 248: SEQ ID No. 249)-(SEQ ID No. 62: SEQ ID No: 63: SEQ ID No. 64);

HC (CDR1: CDR2: CDR3)-LC (CDR1:CDR2: CDR3) (SEQ ID No. 250: SEQ ID No: 251: SEQ ID No. 252)-(SEQ ID No. 62: SEQ ID No: 63: SEQ ID No. 64); and HC (CDR1: CDR2: CDR3)-LC (CDR1:CDR2: CDR3) (SEQ ID No. 404: SEQ ID No. 405: SEQ ID No. 406)-(SEQ ID No. 407: SEQ ID No: 408: SEQ ID No. 409).

In some embodiment, the second component comprises six CDRs comprising the following sequences: HC (CDR1: CDR2: CDR3)-LC (CDR1:CDR2: CDR3) (SEQ ID No. 228: SEQ ID No. 229: SEQ ID No. 230)-(SEQ ID No. 270: SEQ ID No. 260: SEQ ID No. 271). In some embodiment, the second component comprises six CDRs comprising the following sequences: HC (CDR1: CDR2: CDR3)-LC (CDR1:CDR2: CDR3) (SEQ ID No. 222: SEQ ID No: 223: SEQ ID No. 224)-(SEQ ID No. 267: SEQ ID No: 263: SEQ ID No. 264). In some embodiment, the second component comprises six CDRs comprising the following sequences: HC (CDR1: CDR2: CDR3)-LC (CDR1:CDR2: CDR3) (SEQ ID No. 232: SEQ ID No: 229: SEQ ID No. 233)-(SEQ ID No. 259: SEQ ID No: 273: SEQ ID No. 266). In some embodiment, the second component comprises six CDRs comprising the following set of sequences: HC (CDR1: CDR2: CDR3)-LC (CDR1:CDR2: CDR3) (SEQ ID No. 404: SEQ ID No. 405: SEQ ID No. 406)-(SEQ ID No. 407: SEQ ID No. 408: SEQ ID No. 409. In some embodiment, the first component comprises a variable heavy domain and wherein the variable heavy domain comprises a sequence that is at least about 90% identical to a sequence selected from the group consisting of SEQ ID Nos. 104-129. In some embodiment, the first component comprises the variable light domain and wherein the variable light domain comprises a sequence that is at least about 90% identical to a sequence selected from the group consisting of SEQ ID Nos.

130-155. In some embodiment, the second component comprises a variable heavy domain and wherein the variable heavy domain comprises a sequence that is at least about 90% identical to a sequence selected from the group consisting of SEQ ID Nos. 288-309. In some embodiments, the second component comprises a variable light domain wherein the variable light domain comprises a sequence that is at least about 90% identical to a sequence selected from the group consisting of SEQ ID Nos. 310-326. In some embodiments, the first component that specifically binds to CD38 comprises a full-length antibody comprising a light chain and a heavy chain, wherein the heavy chain comprises a sequence that is at least about 90% identical to a sequence selected from the group consisting of SEQ ID Nos. 156-181. In some embodiments, the light chain comprises a sequence that is at least about 90% identical to a sequence selected from the group consisting of SEQ ID Nos. 182-207. In some embodiments, the second component that specifically binds to ICAM1 comprises a full-length antibody comprising a light chain and a heavy chain, wherein the heavy chain comprises a sequence that is at least about 90% identical to a sequence selected from the group consisting of SEQ ID Nos. 328-349. In some embodiments, the light chain comprises a sequence that is at least about 90% identical to a sequence selected from the group consisting of SEQ ID Nos. 183 and 350-366.

One embodiment provides a multispecific protein comprising a heavy chain polypeptide (HC) comprising the VH and a light chain polypeptide (LC) comprising the VL, wherein the heavy chain polypeptide and the light chain polypeptide comprise sequences that are at least about 90% identical to sequences selected from the following set of sequences:

HC: LC (SEQ ID No. 160: SEQ ID No. 397);
HC: LC (SEQ ID No. 389: SEQ ID No. 186);
HC: LC (SEQ ID No. 163: SEQ ID No. 395);
HC: LC (SEQ ID No. 387: SEQ ID No. 189);
HC: LC (SEQ ID No. 164: SEQ ID No. 396);
HC: LC (SEQ ID No. 388: SEQ ID No. 190);
HC: LC (SEQ ID No. 156: SEQ ID No. 393);
HC: LC (SEQ ID No. 384: SEQ ID No. 182);
HC: LC (SEQ ID No. 385: SEQ ID No. 182); and
HC: LC (SEQ ID No. 386: SEQ ID No. 394).

One embodiment provides a multispecific protein comprising a first heavy chain polypeptide (HC1), a light chain polypeptide (LC), and a second heavy chain polypeptide (HC2), wherein the HC1, the LC, and the HC2 comprise sequences that are at least about 90% identical to sequences selected from the group consisting of the following set of sequences:

HC1: LC: HC2 (SEQ ID No. 391: SEQ ID No. 186: SEQ ID No. 383);
HC1: LC: HC2 (SEQ ID No. 392: SEQ ID No. 190: SEQ ID No. 383); and
HC1: LC: HC2 (SEQ ID No. 156: SEQ ID No. 182: SEQ ID No. 383).

One embodiment provides a multispecific protein comprising a first heavy chain polypeptide (HC1), a first light chain polypeptide (LC1), a second heavy chain polypeptide (HC2), and a second heavy chain polypeptide (LC2), and wherein the HC1, LC1, HC2 and the LC2 comprise sequences that are at least about 90% identical to sequences selected from the group consisting of the following set of sequences:

HC1: LC1: HC2: HC3 (SEQ ID No. 390: SEQ I No. 189: SEQ ID No. 348: SEQ ID No. 189);

HC1: LC1: HC2: HC3 (SEQ ID No. 390: SEQ ID No. 189: SEQ ID No. 349: SEQ ID No. 189);

HC1: LC1: HC2: HC3 (SEQ ID No. 391: SEQ ID No. 186: SEQ ID No. 348: SEQ ID No. 186); and HC1: LC1: HC2: HC3 (SEQ ID No. 391: SEQ ID No. 186: SEQ ID No. 349: SEQ ID No. 186).

One embodiment provides a multispecific protein comprising a heavy chain sequence that is at least about 95% identical to the sequence set forth in SEQ ID No. 410 and a light chain sequence that is at least about 95% identical to the sequence as set forth in SEQ ID No. 411.

In some embodiments, the heavy chain comprises CDR1, CDR2, and CDR3, wherein CDR1 has a sequence of SEQ ID No. 412 (GFSLSZ$_1$Z$_2$AMG), CDR2 has a sequence of SEQ ID No. 413 (GIIGSSZ$_3$Z$_4$TYYAZ$_5$WAKG), and CDR3 has a sequence of SEQ ID No. 414 (VRDPYDSZ$_6$Z$_7$Z$_8$Z$_9$YRL).

In some embodiments, the light chain comprises CDR1, CDR2, and CDR3, wherein CDR1 has a sequence of SEQ ID No. 415 (QASZ$_{10}$Z$_{11}$IYZ$_{12}$YZ$_{13}$Z$_{14}$), CDR2 has a sequence of SEQ ID No. 416 (DASKZ$_{15}$AS), and CDR3 has a sequence of SEQ ID No. 417 (QQAYSSZ$_{16}$Z$_{17}$Z$_{18}$DNZ$_{19}$). In some embodiments, Z$_1$ is serine or threonine; Z$_2$ is histidine or tyrosine; Z$_3$ is aspartic acid or glycine; Z$_4$ is arginine or serine; Z$_5$ is serine or threonine; Z$_6$ is phenylalanine or tyrosine; Z$_7$ is aspartic acid or glycine; Z$_8$ is aspartic acid or alanine; Z$_9$ is glycine or alanine; Z$_{10}$ is glutamine or glutamic acid; Z$_{11}$ is serine or asparagine; Z$_{12}$ is serine or arginine; Z$_{13}$ is cysteine or leucine; Z$_{14}$ is serine of leucine; Z$_{15}$ is valine or leucine; Z$_{16}$ is serine or glycine; Z$_{17}$ is serine or asparagine; Z$_{18}$ is valine or isoleucine; and Z$_{19}$ is valine or alanine.

In some embodiments, the multispecific protein induces an enhanced antigen-dependent cellular cytotoxicity (ADCC) effect on a target cell, compared to an ADCC effect induced on the target cell by a an otherwise identical multispecific protein that does not comprise an Fc region that is afucosylated.

In some embodiments, the multispecific protein induces an enhanced ADCC effect on a target cell, compared to an ADCC effect induced on the target cell by an otherwise identical multispecific protein that does not comprises an Fc region comprising the mutations at positions corresponding to positions 239, 332, and 330 of human IgG1, wherein the mutations are S239D, I332E, and A330L, and wherein the amino acid numbering is according to the EU index in Kabat et al.

In some embodiments, an amount of the multispecific protein that binds to a cell expressing CD38 and ICAM1 is higher than an amount that binds to the cell of a monospecific protein comprising the first component that binds to CD38, wherein binding to the cell is measured by flow cytometry. In some embodiments, the multispecific protein induces an enhanced ADCC effect on a target cell compared to an ADCC effect induced on the target cell by a monospecific protein that comprises the first component that specifically binds to CD38 or the second component that specifically binds to ICAM1. In some embodiments, the multispecific protein induces an enhanced CDC effect on a target cell, compared to a CDC effect induced on the target cell by a monospecific protein that comprises the first component that specifically binds to CD38 or the second component that specifically binds to ICAM1. In some embodiments, the multispecific protein binds to a target cell that expresses CD38 and ICAM1 with an enhanced affinity compared to that of a monospecific protein that comprises the first component that specifically binds to CD38 or the second component that specifically binds to ICAM1. In some embodiments, the ratio of ICAM1 to CD38 on the surface of the cell is at least about 1, 1.5, 2.0, 2.5, 5, 10, 15, 20, 50, 100, or 200. In some embodiments, the ratio of ICAM1 to CD38 on the surface of the cell is greater than or equal to the ratio of ICAM1 to CD38 on the surface of a Raji cell. In some embodiments, the multispecific protein induces an enhanced ADCC effect on a target cell that expresses ICAM1 to CD38 compared to an ADCC effect induced on the target cell by a monospecific protein that comprises the first component that specifically binds to CD38 or the second component that specifically binds to ICAM1. In some embodiments, the cell expresses at least 5000, 10000, 150000, 20000, 30000, 50000, 100000, 150000, 200000, 250000, 300000, 400000, or 500000 ICAM1 proteins on its surface. In some embodiments, the cell expresses at least 50,000 ICAM1 proteins on its surface. In some embodiments, the cell expresses at least 100, 200, 300, 400, 500, 1000, 2000, 3000, 4000, or 5000 CD38 proteins on its surface. In some embodiments, the cell expresses at least 300 CD38 proteins on its surface. In some embodiments, the cell expresses less than about 350000, 300000, 250000, 200000, 150000, 100000, 50000, 30000, 20000, 15000, 10000, or 5000 CD38 proteins on its surface. In some embodiments, the cell expresses less than about 350,000 CD38 proteins on its surface. In some embodiments, the ratio of ICAM1 to CD38 on the surface of the cell is at least about 1, 1.5, 2.0, 2.5, 5, 10, 15, 20, 50, 100, or 200. In some embodiments, the ratio of ICAM1 to CD38 on the surface of the cell is at least about 1. In some embodiments, the ratio of ICAM1 to CD38 on the surface of the cell is at least about 10. In some embodiments, the cell expresses at least as much ICAM1 on its surface as an NCI-H2291 cell. In some embodiments, the cell expresses at least as much CD38 on its surface as an NCI-H2342 cell. In some embodiments, the cell expresses less CD38 on its surface than a Daudi cell. In some embodiments, the ratio of ICAM1 to CD38 on the surface of the cell is greater than or equal to the ratio of ICAM1 to CD38 on the surface of a Raji cell. In some embodiments, the multispecific protein induces an enhanced complement dependent cytotoxicity (CDC) effect on a target cell that expresses CD38 and ICAM1 compared to a CDC effect induced on the target cell by a monospecific protein that comprises the first component that specifically binds to CD38 or the second component that specifically binds to ICAM1. In some embodiments, the ratio of ICAM1 to CD38 on the surface of the cell is at least about 1, 1.5, 2.0, 2.5, 5, 10, 15, 20, 50, 100 or 200. In some embodiments, the ratio of ICAM1 to CD38 on the surface of the cell is greater than or equal to the ratio of ICAM1 to CD38 on the surface of a Raji cell. In some embodiments, the multispecific protein induces an enhanced apoptotic effect on a target cell that expresses CD38 and ICAM1 compared to an apoptotic effect induced on the target cell by a monospecific protein that comprises the first component that specifically binds to CD38 or the second component that specifically binds to ICAM1. In some embodiments, the ratio of ICAM1 to CD38 on the surface of the cell is at least about 1, 1.5, 2.0, 2.5, 5, 10, 15, 20, 50, 100, or 200. In some embodiments, the ratio of ICAM to CD38 on the surface of the cell is greater than or equal to the ratio of ICAM1 to CD38 on the surface of a Raji cell. In some embodiments, the multispecific protein has a reduced ability to kill NK (natural killer) cells in a population of fresh peripheral blood mononuclear cells compared to a monospecific protein that comprises the first component that specifically binds to CD38 or the second component that specifically binds to ICAM1. In some embodiments, the first component binds to human CD38 with a $K_D$ of from about 0.15 nM to about 64 nM, as determined by surface plasmon resonance. In some embodiments, the first component binds to human CD38 with a $K_D$ of from about 0.42 nM to about 13.14 nM, as determined by surface plasmon resonance. In some embodiments, the first component binds to human CD38 with a $K_D$ of from about 0.15 nM to about 0.45 nM, as determined by surface plasmon resonance. In some embodiments, the second component binds to human ICAM1 with a $K_D$ of from about 0.2 nM to about 24.4 nM, as determined by surface plasmon resonance. In some embodiments, the second component binds to human ICAM1 with a $K_D$ of from about 0.2 nM to about 0.6 nM, as determined by surface plasmon resonance.

One embodiment provides a pharmaceutical composition comprising the multispecific protein of this disclosure. In some embodiments, the pharmaceutical composition further comprises a pharmaceutically acceptable carrier, an excipient, or any combinations thereof.

One embodiment provides a method of killing a cell in a subject comprising administering to the subject the multispecific protein of this disclosure or the pharmaceutical composition of this disclosure, wherein the cell expresses CD38 and ICAM1. In some embodiments, the cell is lysed. In some embodiments, the cell is a tumor cell. One embodiment provides a method of treating a cancer in a subject comprising administering to the subject the multispecific protein of this disclosure or the pharmaceutical composition of this disclosure, wherein the cancer comprises a cell that expresses CD38 and ICAM1. In some embodiments, the cancer comprises a solid tumor or a hematological malignancy. In some embodiments, the cancer comprises the hematological malignancy. In some embodiments, the hematological malignancy is a multiple myeloma, a leukemia, a non-Hodgkin lymphoma, or a Hodgkin lymphoma. In some embodiments, the cancer is a lung cancer or a prostate cancer. In some embodiments, the cell expresses at least as much ICAM1 on its surface as an NCI-H2291 cell. In some embodiments, the cell expresses at least as much CD38 on its surface as an NCI-H2342 cell. In some embodiments, the cell expresses less CD38 on its surface than a Daudi cell. In some embodiments, the amount of CD38 on the surface of the cell is less than or equal to the amount of CD38 on the surface of a Raji cell. In some embodiments, the ratio of ICAM1 to CD38 on the surface of the cell is greater than the ratio of ICAM1 to CD38 on the surface of a Daudi cell.

In some embodiments, the ratio of ICAM1 to CD38 on the surface of the cell is greater than or equal to the ratio of ICAM1 to CD38 on the surface of a Raji cell. In some embodiments, the cell expresses at least 5000, 10000, 150000, 20000, 30000, 50000, 100000, 150000, 200000, 250000, 300000, 400000, or 500000 ICAM1 proteins on its surface. In some embodiments, the cell expresses at least 50,000 ICAM1 proteins on its surface. In some embodiments, the cell expresses at least 100, 200, 300, 400, 500, 1000, 2000, 3000, 4000, or 5000 CD38 proteins on its surface. In some embodiments, the cell expresses at least 300 CD38 proteins on its surface. In some embodiments, the cell expresses less than about 350000, 300000, 250000, 200000, 150000, 100000, 50000, 30000, 20000, 15000, 10000, or 5000 CD38 proteins on its surface. In some embodiments, the cell expresses less than about 350,000 CD38 proteins on its surface. In some embodiments, the ratio of ICAM1 to CD38 on the surface of the cell is at least about 1, 1.5, 2.0, 2.5, 5, 10, 15, 20, 50, 100, or 200. In some embodiments, the ratio of ICAM1 to CD38 on the surface of the cell is at least about 1. In some embodiments, the ratio of ICAM1 to CD38 on the surface of the cell is at least about 10. In some embodiments, the method further comprises administering an additional therapeutic agent. In some embodiments, the additional therapeutic agent comprises a chemotherapeutic agent, an immunotherapeutic agent, a targeted therapeutic agent, a hormone-based therapeutic agent, a stem-cell based therapeutic agent, or radiation. In some embodiments, the additional therapeutic agent comprises at least one of lenalidomide, dexamethasone, bortezomib, or any combinations thereof. In some embodiments, the additional therapeutic agent and the multispecific protein are administered simultaneously. In some embodiments, the additional therapeutic agent and the multispecific protein are administered sequentially. In some embodiments, the subject has received a prior therapy. In some embodiments, the prior therapy comprises a proteasome inhibitor (PI) therapy and an immunomodulatory agent. In some embodiments, the subject is double refractory to a therapy comprising a proteasome inhibitor (PI) therapy and an immunomodulatory agent. In some embodiments, the subject is a human. One embodiment provides a kit comprising a multispecific protein according to this disclosure or a pharmaceutical composition comprising the same.

Disclosed herein, in certain embodiments, are anti-CD38 antibodies, anti-ICAM1 antibodies, pharmaceutical compositions comprising anti-CD38 antibodies and/or anti-ICAM1 antibodies, and methods of use for treatment of a proliferative disease. In certain embodiments, also disclosed herein are multi-specific antibodies (e.g., bispecific antibodies) which comprise a first targeting moiety that specifically binds to CD38 and a second targeting moiety that specifically binds to ICAM1, pharmaceutical compositions comprising the multi-specific antibodies, and methods of use for treatment of a proliferative disease.

Disclosed herein, in certain embodiments, is a bispecific antibody comprising a first targeting moiety that specifically binds to CD38 or ICAM1 and comprising an enhanced complement dependent cytotoxicity (CDC) effect compared to a CDC effect by reference antibody daratumumab. Also described herein, in certain embodiments, is a bispecific antibody comprising a first targeting moiety that specifically binds to CD38 or ICAM1 and comprising an enhanced antibody-dependent cell-mediated cytotoxicity (ADCC) effect compared to an ADCC effect by reference antibody daratumumab. Additionally described herein, in certain embodiments, is a bispecific antibody comprising a first targeting moiety that specifically binds to CD38 or ICAM1 and comprising a reduced immune cell kill effect compared to an immune cell kill effect of reference antibody daratumumab. In some embodiments, the bispecific antibody further comprises a second targeting moiety that specifically binds to CD38 or ICAM1. In some embodiments, the enhanced CDC is at least 2-fold, 3-fold, 4-fold, or higher than the CDC effect of reference antibody daratumumab. In some embodiments, the enhanced CDC is at least 30%, 40%, 50%, 60%, 70%, 80%, 90%, or higher than the CDC effect of reference antibody daratumumab. In some embodiments, the enhanced ADCC is at least 2-fold, 3-fold, 4-fold, 5-fold, or higher than the ADCC effect of reference antibody daratumumab. In some embodiments, the enhanced ADCC is at least 30%, 40%, 50%, 60%, 70%, 80%, 90%, or higher than the ADCC effect of reference antibody daratumumab. In some embodiments, the immune cell is a Natural Killer cell. In some embodiments, the immune cell viability is improved by about 10%, 20%, 30%, 40%, 50%, 60%, 70%, 80%, 90%, or higher compared to the immune cell viability in the presence of reference antibody daratumumab. In some embodiments, the bispecific antibody is a bivalent antibody or binding fragments thereof. In some embodiments, the bivalent antibody or binding fragments thereof comprises an IgG-scFv(LC)C-terminal fusion format, an IgG-HC-scFv C-terminal fusion format, a scFv-HC-IgG N-terminal fusion format, or a DVD-Ig format. In some embodiments, the bispecific antibody is a monovalent antibody or binding fragments thereof. In some embodiments, the monovalent antibody or binding fragments thereof comprises a Fab-scFv-Fc(KIH) format or a Biclonics common LC format. In some embodiments, the scFv portion of the bispecific antibody specifically binds to ICAM1. In some embodiments, the first targeting moiety specifically binds to CD38 and the second targeting moiety specifically binds to ICAM1. In some embodiments, the first targeting moiety comprises a $K_D$ of from about 1 nM to about 100 nM. In some embodiments, the first targeting moiety comprises a $K_D$ of at least 1 nM, 2 nM, 3 nM, 3.15 nM, 3.2 nM, 3.39 nM, 3.5 nM, 4 nM, 4.5 nM, 5 nM, 5.32 nM, 5.5 nM, 6 nM, 6.5 nM, 7 nM, 7.5 nM, 8 nM, 8.5 nM, 9 nM, 9.5 nM, 10 nM, 15 nM, 18 nM, 20 nM, 25 nM, 30 nM, 35 nM, 40 nM, 45 nM, 50 nM, 60 nM, 70 nM, 80 nM, 90 nM, or 100 nM. In some embodiments, the second targeting moiety comprises a $K_D$ of from about 0.1 to about 20 nM. In some embodiments, the second targeting moiety comprises a $K_D$ of about 0.15 nM, 0.2 nM, 0.24 nM, 0.25 nM, 0.29 nM, 0.3 nM, 0.4 nM, 0.5 nM, 0.6 nM, 0.7 nM, 0.8 nM, 0.9 nM, 1 nM, 1.5 nM, 1.72 nM, 2 nM, 2.28 nM, 2.5 nM, 3 nM, 3.5 nM, 4 nM, 4.5 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, or 20 nM. In some embodiments, the bispecific antibody induces an apoptosis that is similar to an apoptosis induced by reference antibody daratumumab. In some embodiments, the first targeting moiety comprises a variable heavy chain (VH) region and a variable light chain (VL) region, wherein the VH region comprises: CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from P, S, or D; $X_4$ is selected from F, L, or A; $X_5$ is selected from D, G, S, N, or T; $X_6$ is selected from V, A, T, R, S, I, or N; $X_7$ is selected from Y, I, N, R, A, G, or D; $X_8$ is selected from A, Y, D, G, W, C, or T; $X_9$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence $X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}$; wherein $X_{13}$ is selected from A, G, or S; $X_{14}$ is selected from I, F, Y, V, S, or C; $X_{15}$ is selected from S, I, L, T, or M; $X_{16}$ is selected from G, Y, S, T, L, or V; $X_{17}$ is selected from S, I, K, Y, T, G, or A; $X_{18}$ is selected from G, S, T, P, V, or Y; $X_{19}$ selected from G, A, D, S, or T; $X_{20}$ is selected from S, T, I, N, or G; $X_{21}$ is selected from T, I, D, N, S, or A; $X_{22}$ is selected from F, Y, N, T, I, or S; $X_{23}$ is selected from Y, D, K, or I; $X_{24}$ is selected from A or Y; $X_{25}$ is selected from D, T, S, N, R, A, or Y; $X_{26}$ is selected from S, W, T, A, or N; $X_{27}$ is selected from V, A, W, N, or S; $X_{28}$ is selected from K, R, Q, A, or W; $X_{29}$ is selected from G, K, or A; $X_{30}$ is present or absent, if present, is selected from G or K; $X_{31}$ is present or absent, if present, is G; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; and wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L. In some embodiments, the VH region comprises CDR1 sequence GFPFX$_5$X$_6$YAMS, wherein $X_5$ is selected from D or G; and $X_6$ is selected from V, A, or T. In some embodiments, the VH region comprises CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from S or D; $X_4$ is selected from L, F, or A; $X_5$ is selected from S, N, or T; $X_6$ is selected from R, S, N, I, or T; $X_7$ is selected from Y, I, N, R, A, D, or G; $X_8$ is selected from Y, D, G, A, W, T, or C; $X_9$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C. In some embodiments, the VH region comprises CDR1 sequence GFSLX$_5$X$_6$X$_7$X$_8$X$_9$X$_{10}$X$_{11}$; wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; and $X_{11}$ is present or absent, if present, is C. In some embodiments, the VH region comprises CDR1 sequence GFSX$_4$X$_5$X$_6$X$_7$X$_8$X$_9$X$_{10}$X$_{11}$X$_{12}$; wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; and $X_{12}$ is present or absent, if present, is C. In some embodiments, the VH region comprises CDR2 sequence AISGSGGSTX$_{22}$YADSVKG, wherein $X_{22}$ is selected from F or Y. In some embodiments, the VH region comprises CDR2 sequence $X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}$; wherein $X_{13}$ is selected from A, G, or S; $X_{14}$ is selected from I, F, Y, V, S, or C; $X_{15}$ is selected from I, L, M, or T; $X_{16}$ is selected from G, Y, S, T, L, or V; $X_{17}$ is selected from S, I, K, Y, T, G, or A; $X_{18}$ is selected from G, S, T, P, or V; $X_{19}$ is selected from G, A, D, S, or T; $X_{20}$ is selected from S, T, I, N, or G; $X_{21}$ is selected from T, I, D, N, S, or A; $X_{22}$ is selected from Y, N, T, I, or S; $X_{23}$ is selected from Y, D, K, or I; $X_{24}$ is selected from A or Y; $X_{25}$ is selected from T, S, N, R, A, or Y; $X_{26}$ is selected from S, W, T, A, or N; $X_{27}$ is selected from A, W, N, or S; $X_{28}$ is selected from K, R, Q, A, or W; $X_{29}$ is selected from G, K, or A; $X_{30}$ is present or absent, if present, is selected from G or K; and $X_{31}$ is present or absent, if present, is G. In some embodiments, the VH region comprises CDR2 sequence $X_{13}X_{14}IX_{16}X_{17}X_{18}X_{19}X_{20}X_{21}X_{22}X_{23}X_{24}X_{25}X_{26}X_{27}X_{28}X_{29}X_{30}$; wherein $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; and $X_{30}$ is present or absent, if present, is G. In some embodiments, the VH region comprises CDR2 sequence $X_{13}CX_{15}X_{16}X_{17}X_{18}X_{19}X_{20}X_{21}X_{22}X_{23}YX_{25}X_{26}X_{27}X_{28}X_{29}X_{30}X_{31}$; wherein $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; and $X_{31}$ is present or absent, if present, is G. In some embodiments, the VH region comprises CDR3 sequence AKRGTYX$_{38}$YSX$_{41}$PTGFDY, wherein $X_{38}$ is selected from A or G; and $X_{41}$ is selected from F or Y. In some embodiments, the VH region comprises CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, or F; $X_{45}$ is present or absent, if present, is selected from L, F, E, S, or N; and $X_{46}$ is present or absent, if present, is selected from S, L, or R; $X_{47}$ is present or absent, if present, is L; $X_{48}$ is present or absent, if present, is D; and $X_{49}$ is present or absent, if present, is L. In some embodiments, the VH region comprises CDR3 sequence $X_{32}X_{33}X_{34}X_{35}X_{36}X_{37}X_{38}X_{39}X_{40}X_{41}X_{42}X_{43}X_{44}X_{45}$; wherein $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F. In some embodiments, the VH region comprises CDR3 sequence AX$_{33}X_{34}X_{35}X_{36}X_{37}X_{38}X_{39}X_{40}X_{41}X_{42}X_{43}X_{44}X_{45}X_{46}$; wherein $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L. In some embodiments, the VH region comprises CDR1 sequence GFPFX$_5$X$_6$YAMS, CDR2 sequence AISGSGGSTX$_{22}$YADSVKG, and CDR3 sequence AKRGTYX$_{38}$YSX$_{41}$PTGFDY; wherein $X_5$ is selected from D or G; $X_6$ is selected from V, A, or T; $X_{22}$ is selected from F or Y; $X_{38}$ is selected from A or G; and $X_{41}$ is selected from F or Y. In some embodiments, the VH region comprises CDR1 sequence GFSLX$_5$X$_6$X$_7$X$_8$X$_9$X$_{10}$X$_{11}$, CDR2 sequence $X_{13}X_{14}IX_{16}X_{17}X_{18}X_{19}X_{20}X_{21}X_{22}X_{23}X_{24}X_{25}X_{26}X_{27}X_{28}X_{29}X_{30}$, and CDR3 sequence $X_{32}X_{33}X_{34}X_{35}X_{36}X_{37}X_{38}X_{39}X_{40}X_{41}X_{42}X_{43}X_{44}X_{45}$; wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; $X_{11}$ is present or absent, if present, is C; $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; $X_{30}$ is present or absent, if present, is G; $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F. In some embodiments, the VH region comprises CDR1 sequence GFSX$_4$X$_5$X$_6$X$_7$X$_8$X$_9$X$_{10}$X$_{11}$X$_{12}$, CDR2 sequence $X_{13}CX_{15}X_{16}X_{17}X_{18}X_{19}X_{20}X_{21}X_{22}X_{23}YX_{25}X_{26}X_{27}X_{28}X_{29}X_{30}X_{31}$, and CDR3 sequence AX$_{33}X_{34}X_{35}X_{36}X_{37}X_{38}X_{39}X_{40}X_{41}X_{42}X_{43}X_{44}X_{45}X_{46}$; wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; $X_{12}$ is present or absent, if present, is C; $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; $X_{31}$ is present or absent, if present, is G; $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L. In some embodiments, the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L. In some embodiments, the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58. In some embodiments, the VH region comprises CDR1 sequence selected from SEQ ID NOs: 1, 4, 6, 8, and 9; CDR2 sequence selected from SEQ ID NOs: 2 and 5; and CDR3 sequence selected from SEQ ID NOs: 3, 7, and 10. In some embodiments, the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58. In some embodiments, the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52. In some embodiments, the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence selected from SEQ ID NOs: 19, 25, 31, 46, and 58. In some embodiments, the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103. In some embodiments, the VL region comprises CDR1 sequence selected from SEQ ID NOs: 65, 68, 80, 86, 89, 92, and 98; CDR2 sequence selected from SEQ ID NOs: 66, 69, 81, 78, 90, and 99; and CDR3 sequence selected from SEQ ID NOs: 67, 70, 82, 87, 88, 91, 93, and 100. In some embodiments, the VL region comprises CDR1 sequence selected from SEQ ID NOs: 71, 77, 83, 94, and 102; CDR2 sequence selected from SEQ ID NOs: 72, 78, and 84; and CDR3 sequence selected from SEQ ID NOs: 73, 79, 85, 95, and 103. In some embodiments, the first targeting moiety comprises a VH sequence selected from SEQ ID NOs: 104-128 and a VL sequence selected from SEQ ID NOs: 130-154. In some embodiments, the second targeting moiety comprises a variable heavy chain (VH) region and a variable light chain (VL) region, wherein the VH region comprises: CDR1 sequence $X^1X^2X^3X^4X^5X^6X^7X^8X^9X^{10}X^{11}$; wherein $X^1$ is selected from G or E; $X^2$ is selected from F or Y; $X^3$ is selected from S or T; $X^4$ is selected from L, F, or S; $X^5$ is selected from S or N; $X^6$ is selected from S, N, T, or D; $X^7$ is selected from Y, H, or G; $X^8$ is selected from G, A, Y, W, or F; $X^9$ is selected from M, W, Y, or I; $X^{10}$ is selected from S, G, N, M, or I; and $X^{11}$ is present or absent, if present, is C; CDR2 sequence $X^{12}X^{13}X^{14}X^{15}X^{16}X^{17}X^{18}X^{19}$ $X^{20}X^{21}X^{22}X^{23}X^{24}X^{25}X^{26}X^{27}X^{28}X^{29}X^{30}$; wherein $X^{12}$ is selected from G, T, A, I, or Y; $X^{13}$ is selected from W, I, Y, or C; $X^{14}$ is selected from I, S or Y; $X^{15}$ is selected from S, G, T, D, or P; $X^{16}$ is selected from F, S, D, T, or A; $X^{17}$ is selected from S, R, G, or D; $X^{18}$ is selected from G, D, or S; $X^{19}$ is selected from S, R, T, N, Y, A, D, or P; $X^{20}$ is selected from T, A, G, or Y; $X^{21}$ is selected from Y, H, A, S, or T; $X^{22}$ is selected from Y or N; $X^{23}$ is selected from A, P, Y, or S; $X^{24}$ is selected from S, T, N, D, Y, A, or P; $X^{25}$ is selected from W, S, A, or D; $X^{26}$ is selected from A, V, T, W, F, or S; $X^{27}$ is selected from K, W, A, Q, or V; $X^{28}$ is selected from G, A, or K; $X^{29}$ is present or absent, if present, is selected from K or G; and $X^{30}$ is present or absent, if present, is G; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}$ $X^{47}X^{48}X^{49}$; wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{41}$ is present or absent, if present, is selected from D or L; and $X^{49}$ is present or absent, if present, is L. In some embodiments, the VH region comprises CDR1 sequence GFSLX$^5$X$^6$X$^7$X$^8$MX$^{10}$, wherein X$^5$ is selected from S or N; X$^6$ is selected from S, N, T, or D; X$^7$ is selected from Y or H; X$^8$ is selected from G, A, or Y; and X$^{10}$ is selected from S, G, or N. In some embodiments, the VH region comprises CDR2 sequence GX$^{13}$IX$^{15}$X$^{16}$X$^{17}$X$^{18}$X$^{19}$X$^{20}$YYAX$^{24}$WAKG, wherein X$^{13}$ is selected from W, I, or Y; X$^{15}$ is selected from S or G; X$^{16}$ is selected from F, S, D, or T; X$^{17}$ is selected from S or R; X$^{18}$ is selected from G or D; X$^{19}$ is selected from S, R, T, or N; X$^{20}$ is selected from T or A; and X$^{24}$ is selected from S, T, or N. In some embodiments, the VH region comprises CDR3 sequence X$^{31}$RX$^{33}$X$^{34}$X$^{35}$X$^{36}$X$^{37}$X$^{38}$X$^{39}$X$^{40}$X$^{41}$ X$^{42}$X$^{43}$X$^{44}$X$^{45}$X$^{46}$X$^{47}$X$^{48}$X$^{49}$, wherein X$^{31}$ is selected from A or V; X$^{33}$ is selected from G or D; X$^{34}$ is selected from G, P, W, or D; X$^{35}$ is selected from D, Y, S, or L; X$^{36}$ is selected from Y, D, V, or L; X$^{37}$ is selected from G, S, or D; X$^{38}$ is selected from G, Y, F, or S; X$^{39}$ is selected from S, D, G, or T; X$^{40}$ is selected from T, A, D, S, or Y; X$^{41}$ is selected from Y, A, G, or I; X$^{42}$ is selected from I, Y, or R; X$^{43}$ is selected from L, R, Y, or G; X$^{44}$ is selected from N, L, Y, or S; X$^{45}$ is present or absent, if present, is selected from L, Y, or F; X$^{46}$ is present or absent, if present, is D; X$^{47}$ is present or absent, if present, is selected from M or P; X$^{48}$ is present or absent, if present, is D; and X$^{49}$ is present or absent, if present, is L. In some embodiments, the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252. In some embodiments, the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240. In some embodiments, the VH region comprises CDR1 sequence selected from SEQ ID NOs: 241, 247 and 250; CDR2 sequence selected from SEQ ID NOs: 242, 244, 246, 248, and 251; and CDR3 sequence selected from SEQ ID NOs: 243, 245, 249, and 252. In some embodiments, the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284. In some embodiments, the second targeting moiety comprises a VH sequence selected from SEQ ID NOs: 289-309 and a VL sequence selected from SEQ ID NOs: 311-326 and 155. In some embodiments, the bispecific antibody comprises a humanized antibody or binding fragment thereof or a chimeric antibody or binding fragment thereof. In some embodiments, the bispecific antibody comprises a IgG-scFv, nanobody, BiTE, diabody, DART, TandAb, scDiabody, scDiabody-CH3, triple body, mini-antibody, minibody, TriBi minibody, scFv-CH3 KIH, Fab-scFv-Fc KIH, Fab-scFv, scFv-CH-CL-scFv, F(ab')2, F(ab')2-scFv2. scFv-KIH, Fab-scFv-Fc, tetravalent HCAb, scDiabody-Fc, diabody-Fc, tandem scFv-Fc, or intrabody. In some embodiments, the bispecific antibody comprises an IgG1 framework sequence. In some embodiments, the bispecific antibody comprises an IgG2 framework sequence. In some embodiments, the bispecific antibody comprises an IgG4 framework sequence. In some embodiments, the bispecific antibody further comprises a payload. In some embodiments, the payload comprises a small molecule, a peptide, or a protein.

Disclosed herein, in certain embodiments, is an anti-CD38 antibody comprising a variable heavy chain (VH) region and a variable light chain (VL) region, wherein the VH region comprises: CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from P, S, or D; $X_4$ is selected from F, L, or A; $X_5$ is selected from D, G, S, N, or T; $X_6$ is selected from V, A, T, R, S, I, or N; $X_7$ is selected from Y, I, N, R, A, G, or D; $X_8$ is selected from A, Y, D, G, W, C, or T; $X_9$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence $X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}$; wherein $X_{13}$ is selected from A, G, or S; $X_{14}$ is selected from I, F, Y, V, S, or C; $X_{15}$ is selected from S, I, L, T, or M; $X_{16}$ is selected from G, Y, S, T, L, or V; $X_{17}$ is selected from S, I, K, Y, T, G, or A; $X_{18}$ is selected from G, S, T, P, V, or Y; $X_{19}$ is selected from G, A, D, S, or T; $X_{20}$ is selected from S, T, I, N, or G; $X_{21}$ is selected from T, I, D, N, S, or A; $X_{22}$ is selected from F, Y, N, T, I, or S; $X_{23}$ is selected from Y, D, K, or I; $X_{24}$ is selected from A or Y; $X_{25}$ is selected from D, T, S, N, R, A, or Y; $X_{26}$ is selected from S, W, T, A, or N; $X_{27}$ is selected from V, A, W, N, or S; $X_{28}$ is selected from K, R, Q, A, or W; $X_{29}$ is selected from G, K, or A; $X_{30}$ is present or absent, if present, is selected from G or K; $X_{31}$ is present or absent, if present, is G; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L. In some embodiments, the VH region comprises CDR1 sequence $GFPFX_5X_6YAMS$, wherein $X_5$ is selected from D or G; and $X_6$ is selected from V, A, or T. In some embodiments, the VH region comprises CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from S or D; $X_4$ is selected from L, F, or A; $X_5$ is selected from S, N, or T; $X_6$ is selected from R, S, N, I, or T; $X_7$ is selected from Y, I, N, R, A, D, or G; $X_8$ is selected from Y, D, G, A, W, T, or C; $X_9$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C. In some embodiments, the VH region comprises CDR1 sequence $GFSLX_5X_6X_7X_8X_9X_{10}X_{11}$; wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; and $X_{11}$ is present or absent, if present, is C. In some embodiments, the VH region comprises CDR1 sequence $GFSX_4X_5X_6X_7X_8X_9X_{10}X_{11}X_{12}$; wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; and $X_{12}$ is present or absent, if present, is C. In some embodiments, the VH region comprises CDR2 sequence $AISGSGGSTX_{22}YADSVKG$, wherein $X_{22}$ is selected from F or Y. In some embodiments, the VH region comprises CDR2 sequence $X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}$; wherein $X_{13}$ is selected from A, G, or S; $X_{14}$ is selected from I, F, Y, V, S, or C; $X_{15}$ is selected from I, L, M, or T; $X_{16}$ is selected from G, Y, S, T, L, or V; $X_{17}$ is selected from S, I, K, Y, T, G, or A; $X_{18}$ is selected from G, S, T, P, or V; $X_{19}$ is selected from G, A, D, S, or T; $X_{20}$ is selected from S, T, I, N, or G; $X_{21}$ is selected from T, I, D, N, S, or A; $X_{22}$ is selected from Y, N, T, I, or S; $X_{23}$ is selected from Y, D, K, or I; $X_{24}$ is selected from A or Y; $X_{25}$ is selected from T, S, N, R, A, or Y; $X_{26}$ is selected from S, W, T, A, or N; $X_{27}$ is selected from A, W, N, or S; $X_{28}$ is selected from K, R, Q, A, or W; $X_{29}$ is selected from G, K, or A; $X_{30}$ is present or absent, if present, is selected from G or K; and $X_{31}$ is present or absent, if present, is G. In some embodiments, the VH region comprises CDR2 sequence $X_{13}X_{14}IX_{16}X_{17}X_{18}X_{19}X_{20}X_{21}X_{22}X_{23}X_{24}X_{25}X_{26}X_{27}X_{28}X_{29}X_{30}$; wherein $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, S, or S; $X_{20}$ is selected from T, I, N, or G; $X_{21}$ is selected from T, I, or D; $X_{22}$ is selected from Y, N, or T; $X_{23}$ is selected from Y or D;

$X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; and $X_{30}$ is present or absent, if present, is G. In some embodiments, the VH region comprises CDR2 sequence $X_{13}CX_{15}X_{16}X_{17}X_{18}X_{19}X_{20}X_{21}X_{22}X_{23}YX_{25}X_{26}X_{27}X_{28}X_{29}X_{30}X_{31}$; wherein $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; and $X_{31}$ is present or absent, if present, is G. In some embodiments, the VH region comprises CDR3 sequence AKRGTYX$_{38}$YSX$_{41}$PTGFDY, wherein $X_{38}$ is selected from A or G; and $X_{41}$ is selected from F or Y. In some embodiments, the VH region comprises CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, F; $X_{45}$ is present or absent, if present, is selected from L, F, E, S, or N; $X_{46}$ is present or absent, if present, is selected from S, L, or R; $X_{47}$ is present or absent, if present, is L; $X_{48}$ is present or absent, if present, is D; and $X_{49}$ is present or absent, if present, is L. In some embodiments, the VH region comprises CDR3 sequence $X_{32}X_{33}X_{34}X_{35}X_{36}X_{37}X_{38}X_{39}X_{40}X_{41}X_{42}X_{43}X_{44}X_{45}$; wherein $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F. In some embodiments, the VH region comprises CDR3 sequence AX$_{33}X_{34}X_{35}X_{36}X_{37}X_{38}X_{39}X_{40}X_{41}X_{42}X_{43}X_{44}X_{45}X_{46}$; wherein $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L. In some embodiments, the VH region comprises CDR1 sequence GFPFX$_5$X$_6$YAMS, CDR2 sequence AISGSGGSTX$_{22}$YADSVKG, and CDR3 sequence AKRGTYX$_{38}$YSX$_{41}$PTGFDY; wherein $X_5$ is selected from D or G; $X_6$ is selected from V, A, or T; $X_{22}$ is selected from F or Y; $X_{38}$ is selected from A or G; and $X_{41}$ is selected from F or Y. In some embodiments, the VH region comprises CDR1 sequence GFSLX$_5$X$_6$X$_7$X$_8$X$_9$X$_{10}$X$_{11}$, CDR2 sequence $X_{13}X_{14}IX_{16}X_{17}X_{18}X_{19}X_{20}X_{21}X_{22}X_{23}X_{24}X_{25}X_{26}X_{27}X_{28}X_{29}X_{30}$, and CDR3 sequence $X_{32}X_{33}X_{34}X_{35}X_{36}X_{37}X_{38}X_{39}X_{40}X_{41}X_{42}X_{43}X_{44}X_{45}$; wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; $X_{11}$ is present or absent, if present, is C; $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; $X_{30}$ is present or absent, if present, is G; $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F. In some embodiments, the VH region comprises CDR1 sequence GFSX$_4$X$_5$X$_6$X$_7$X$_8$X$_9$X$_{10}$X$_{11}$X$_{12}$, CDR2 sequence $X_{13}CX_{15}X_{16}X_{17}X_{18}X_{19}X_{20}X_{21}X_{22}X_{23}YX_{25}X_{26}X_{27}X_{28}X_{29}X_{30}X_{31}$, and CDR3 sequence AX$_{33}X_{34}X_{35}X_{36}X_{37}X_{38}X_{39}X_{40}X_{41}X_{42}X_{43}X_{44}X_{45}X_{46}$; wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; $X_{12}$ is present or absent, if present, is C; $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; $X_{31}$ is present or absent, if present, is G; $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L. In some embodiments, the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}$ $X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L. In some embodiments, the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58. In some embodiments, the VH region comprises CDR1 sequence selected from SEQ ID NOs: 1, 4, 6, 8, and 9; CDR2 sequence selected from SEQ ID NOs: 2 and 5; and CDR3 sequence selected from SEQ ID NOs: 3, 7, and 10. In some embodiments, the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58. In some embodiments, the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52. In some embodiments, the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence selected from SEQ ID NOs: 19, 25, 31, 46, and 58. In some embodiments, the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103. In some embodiments, the VL region comprises CDR1 sequence selected from SEQ ID NOs: 65, 68, 80, 86, 89, 92, and 98; CDR2 sequence selected from SEQ ID NOs: 66, 69, 81, 78, 90, and 99; and CDR3 sequence selected from SEQ ID NOs: 67, 70, 82, 87, 88, 91, 93, and 100. In some embodiments, the VL region comprises CDR1 sequence selected from SEQ ID NOs: 71, 77, 83, 94, and 102; CDR2 sequence selected from SEQ ID NOs: 72, 78, and 84; and CDR3 sequence selected from SEQ ID NOs: 73, 79, 85, 95, and 103. In some embodiments, the anti-CD38 antibody comprises a VH sequence selected from SEQ ID NOs: 104-128 and a VL sequence selected from SEQ ID NOs: 130-154. In some embodiments, the anti-CD38 antibody is a multi-specific antibody comprising a second targeting moiety. In some embodiments, the second targeting moiety specifically binds to ICAM1. In some embodiments, the second targeting moiety comprises a variable heavy chain (VH) region and a variable light chain (VL) region, wherein the VH region comprises: CDR1 sequence $X^1X^2X^3X^4X^5X^6X^7X^8X^9X^{10}X^{11}$; wherein $X^1$ is selected from G or E; $X^2$ is selected from F or Y; $X^3$ is selected from S or T; $X^4$ is selected from L, F, or S; $X^5$ is selected from S or N; $X^6$ is selected from S, N, T, or D; $X^7$ is selected from Y, H, or G; $X^8$ is selected from G, A, Y, W, or F; $X^9$ is selected from M, W, Y, or I; $X^{10}$ is selected from S, G, N, M, or I; and $X^{11}$ is present or absent, if present, is C; CDR2 sequence $X^{12}X^{13}X^{14}X^{15}X^{16}X^{17}X^{18}X^{19}X^{20}X^{21}X^{22}X^{23}$ $X^{24}X^{25}X^{26}X^{27}X^{28}X^{29}X^{30}$; wherein $X^{12}$ is selected from G, T, A, I, or Y; $X^{13}$ is selected from W, I, Y, or C; $X^{14}$ is selected from I, S or Y; $X^{15}$ is selected from S, G, T, D, or P; $X^{16}$ is selected from F, S, D, T, or A; $X^{17}$ is selected from S, R, G, or D; $X^{18}$ is selected from G, D, or S; $X^{19}$ is selected from S, R, T, N, Y, A, D, or P; $X^{20}$ is selected from T, A, G, or Y; $X^{21}$ is selected from Y, H, A, S, or T; $X^{22}$ is selected from Y or N; $X^{23}$ is selected from A, P, Y, or S; $X^{24}$ is selected from S, T, N, D, Y, A, or P; $X^{25}$ is selected from W, S, A, or D; $X^{26}$ is selected from A, V, T, W, F, or S; $X^{27}$ is selected from K, W, A, Q, or V; $X^{28}$ is selected from G, A, or K; $X^{29}$ is present or absent, if present, is selected from K or G; and $X^{30}$ is present or absent, if present, is G; and CDR3 sequence $X^{31}X^{32}X^{33}X^{34}X^{35}X^{36}X^{37}X^{38}X^{39}X^{40}X^{41}X^{42}$ $X^{43}X^{44}X^{45}X^{46}X^{47}X^{48}X^{49}$; wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{41}$ is present or absent, if present, is selected from D or L; and $X^{49}$ is present or absent, if present, is L. In some embodiments, the VH region comprises CDR1 sequence GFSLX$^5$X$^6$X$^7$X$^8$MX$^{10}$, wherein $X^5$ is selected from S or N; $X^6$ is selected from S, N, T, or D; $X^7$ is selected from Y or H; $X^8$ is selected from G, A, or Y; and $X^{10}$ is selected from S, G, or N. In some embodiments, the VH region comprises CDR2 sequence GX$^{13}$IX$^{15}$X$^{16}$X$^{17}$X$^{18}$X$^{19}$X$^{20}$YYAX$^{24}$WAKG, wherein $X^{13}$ is selected from W, I, or Y; $X^{15}$ is selected from S or G; $X^{16}$ is selected from F, S, D, or T; $X^{17}$ is selected from S or R; $X^{18}$ is selected from G or D; $X^{19}$ is selected from S, R, T, or N; $X^{20}$ is selected from T or A; and $X^{24}$ is selected from S, T, or N. In some embodiments, the VH region comprises CDR3 sequence X$^{31}$RX$^{33}$X$^{34}$X$^{35}$X$^{36}$X$^{37}$X$^{38}$X$^{39}$X$^{40}$X$^{41}$ X$^{42}$X$^{43}$X$^{44}$X$^{45}$X$^{46}$X$^{47}$X$^{48}$X$^{49}$, wherein $X^{31}$ is selected from A or V; $X^{33}$ is selected from G or D; $X^{34}$ is selected from G, P, W, or D; $X^{35}$ is selected from D, Y, S, or L; $X^{36}$ is selected from Y, D, V, or L; $X^{37}$ is selected from G, S, or D; $X^{38}$ is selected from G, Y, F, or S; $X^{39}$ is selected from S, D, G, or T; $X^{40}$ is selected from T, A, D, S, or Y; $X_{41}$ is selected from Y, A, G, or I; $X^{42}$ is selected from I, Y, or R; $X^{43}$ is selected from L, R, Y, or G; $X^{44}$ is selected from N, L, Y, or S; $X^{45}$ is present or absent, if present, is selected from L, Y, or F; $X^{46}$ is present or absent, if present, is D; $X^{47}$ is present or absent, if present, is selected from M or P; $X^{48}$ is present or absent, if present, is D; and $X^{49}$ is present or absent, if present, is L. In some embodiments, the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252. In some embodiments, the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240. In some embodiments, the VH region comprises CDR1 sequence selected from SEQ ID NOs: 241, 247 and 250; CDR2 sequence selected from SEQ ID NOs: 242, 244, 246, 248, and 251; and CDR3 sequence selected from SEQ ID NOs: 243, 245, 249, and 252. In some embodiments, the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284. In some embodiments, the second targeting moiety comprises a VH sequence selected from SEQ ID NOs: 289-309 and a VL sequence selected from SEQ ID NOs: 311-326 and 155. In some embodiments, the anti-CD38 antibody comprises a humanized antibody or binding fragment thereof or a chimeric antibody or binding fragment thereof. In some embodiments, the anti-CD38 antibody comprises a bispecific antibody or binding fragment thereof. In some embodiments, the bispecific antibody or binding fragment thereof comprises a IgG-scFv, nanobody, BiTE, diabody, DART, TandAb, scDiabody, scDiabody-CH3, triple body, mini-antibody, minibody, TriBi minibody, scFv-CH3 KIH, Fab-scFv-Fc KIH, Fab-scFv, scFv-CH-CL-scFv, F(ab')2, F(ab')2-scFv2. scFv-KIH, Fab-scFv-Fc, tetravalent HCAb, scDiabody-Fc, diabody-Fc, tandem scFv-Fc, or intrabody. In some embodiments, the anti-CD38 antibody comprises an IgG1 framework sequence. In some embodiments, the anti-CD38 antibody comprises an IgG2 framework sequence. In some embodiments, the anti-CD38 antibody comprises an IgG4 framework sequence. In some embodiments, the anti-CD38 antibody comprises a HC sequence selected from SEQ ID NOs: 157-181 and a LC sequence selected from SEQ ID NOs: 183-207. In some embodiments, the anti-CD38 antibody further comprises a payload. In some embodiments, the payload comprises a small molecule, a peptide, or a protein.

Disclosed herein, in certain embodiments, is an anti-ICAM1 antibody comprising a variable heavy chain (VH) region and a variable light chain (VL) region, wherein the VH region comprises: CDR1 sequence $X^1X^2X^3X^4X^5X^6X^7X^8X^9X^{10}X^{11}$; wherein $X^1$ is selected from G or E; $X^2$ is selected from F or Y; $X^3$ is selected from S or T; $X^4$ is selected from L, F, or S; $X^5$ is selected from S or N; $X^6$ is selected from S, N, T, or D; $X^7$ is selected from Y, H, or G; $X^8$ is selected from G, A, Y, W, or F; $X^9$ is selected from M, W, Y, or I; $X^{10}$ is selected from S, G, N, M, or I; and $X^{11}$ is present or absent, if present, is C; CDR2 sequence $X^{12}X^{13}X^{14}X^{15}X^{16}X^{17}X^{18}X^{19}X^{20}X^{21}X^{22}X^{23}X^{24}X^{25}X^{26}X^{27}X^{28}X^{29}X^{30}$; wherein $X^{12}$ is selected from G, T, A, I, or Y; $X^{13}$ is selected from W, I, Y, or C; $X^{14}$ is selected from I, S or Y; $X^{15}$ is selected from S, G, T, D, or P; $X^{16}$ is selected from F, S, D, T, or A; $X^{17}$ is selected from S, R, G, or D; $X^{18}$ is selected from G, D, or S; $X^{19}$ is selected from S, R, T, N, Y, A, D, or P; $X^{20}$ is selected from T, A, G, or Y; $X^{21}$ is selected from Y, H, A, S, or T; $X^{22}$ is selected from Y or N; $X^{23}$ is selected from A, P, Y, or S; $X^{24}$ is selected from S, T, N, D, Y, A, or P; $X^{25}$ is selected from W, S, A, or D; $X^{26}$ is selected from A, V, T, W, F, or S; $X^{27}$ is selected from K, W, A, Q, or V; $X^{28}$ is selected from G, A, or K; $X^{29}$ is present or absent, if present, is selected from K or G; and $X^{30}$ is present or absent, if present, is G; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}X^{47}X^{48}X^{49}$; wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{48}$ is present or absent, if present, is selected from D or L; and $X^{49}$ is present or absent, if present, is L. In some embodiments, the VH region comprises CDR1 sequence GFSLX$^5$X$^6$X$^7$X$^8$MX$^{10}$, wherein $X^5$ is selected from S or N; $X^6$ is selected from S, N, T, or D; $X^7$ is selected from Y or H; $X^8$ is selected from G, A, or Y; and $X^{10}$ is selected from S, G, or N. In some embodiments, the VH region comprises CDR2 sequence GX$^{13}$IX$^{15}$X$^{16}$X$^{17}$X$^{18}$X$^{19}$X$^{20}$YYAX$^{24}$WAKG, wherein $X^{13}$ is selected from W, I, or Y; $X^{15}$ is selected from S or G; $X^{16}$ is selected from F, S, D, or T; $X^{17}$ is selected from S or R; $X^{18}$ is selected from G or D; $X^{19}$ is selected from S, R, T, or N; $X^{20}$ is selected from T or A; and $X^{24}$ is selected from S, T, or N. In some embodiments, the VH region comprises CDR3 sequence $X^{31}$RX$^{33}$X$^{34}$X$^{35}$X$^{36}$X$^{37}$X$^{38}$X$^{39}$X$^{40}$X$^{41}$X$^{42}$X$^{43}$X$^{44}$X$^{45}$X$^{46}$X$^{47}$X$^{48}$X$^{49}$, wherein $X^{31}$ is selected from A or V; $X^{33}$ is selected from G or D; $X^{34}$ is selected from G, P, W, or D; $X^{35}$ is selected from D, Y, S, or L; $X^{36}$ is selected from Y, D, V, or L; $X^{37}$ is selected from G, S, or D; $X^{38}$ is selected from G, Y, F, or S; $X^{39}$ is selected from S, D, G, or T; $X^{40}$ is selected from T, A, D, S, or Y; $X^{41}$ is selected from Y, A, G, or I; $X^{42}$ is selected from I, Y, or R; $X^{43}$ is selected from L, R, Y, or G; $X^{44}$ is selected from N, L, Y, or S; $X^{45}$ is present or absent, if present, is selected from L, Y, or F; $X^{46}$ is present or absent, if present, is D; $X^{47}$ is present or absent, if present, is selected from M or P; $X^{48}$ is present or absent, if present, is D; and $X^{49}$ is present or absent, if present, is L. In some embodiments, the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}X^{47}X^{48}X^{49}$, wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X_{48}$ is present or absent, if present, is selected from D or L; and $X^{49}$ is present or absent, if present, is L. In some embodiments, the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252. In some embodiments, the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240. In some embodiments, the VH region comprises CDR1 sequence selected from SEQ ID NOs: 241, 247 and 250; CDR2 sequence selected from SEQ ID NOs: 242, 244, 246, 248, and 251; and CDR3 sequence selected from SEQ ID NOs: 243, 245, 249, and 252. In some embodiments, the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284. In some embodiments, the second targeting moiety comprises a VH sequence selected from SEQ ID NOs: 289-309 and a VL sequence selected from SEQ ID NOs: 311-326 and 155. In some embodiments, the anti-ICAM1 antibody is a multi-specific antibody comprising an additional targeting moiety. In some embodiments, the additional targeting moiety specifically binds to CD38. In some embodiments, the additional targeting moiety comprises a variable heavy chain (VH) region and a variable light chain (VL) region, wherein the VH region comprises: CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from P, S, or D; $X_4$ is selected from F, L, or A; $X_5$ is selected from D, G, S, N, or T; $X_6$ is selected from V, A, T, R, S, I, or N; $X_7$ is selected from Y, I, N, R, A, G, or D; $X_8$ is selected from A, Y, D, G, W, C, or T; $X_9$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence $X_{13}X_{14}X_{15}X_{16}X_{17}X_{18}X_{19}X_{20}X_{21}X_{22}X_{23}X_{24}$ $X_{25}X_{26}X_{27}X_{28}X_{29}X_{30}X_{31}$; wherein $X_{13}$ is selected from A, G, or S; $X_{14}$ is selected from I, F, Y, V, S, or C; $X_{15}$ is selected from S, I, L, T, or M; $X_{16}$ is selected from G, Y, S, T, L, or V; $X_{17}$ is selected from S, I, K, Y, T, G, or A; $X_{18}$ is selected from G, S, T, P, V, or Y; $X_{19}$ is selected from G, A, D, S, or T; $X_{20}$ is selected from S, T, I, N, or G; $X_{21}$ is selected from T, I, D, N, S, or A; $X_{22}$ is selected from F, Y, N, T, I, or S; $X_{23}$ is selected from Y, D, K, or I; $X_{24}$ is selected from A or Y; $X_{25}$ is selected from D, T, S, N, R, A, or Y; $X_{26}$ is selected from S, W, T, A, or N; $X_{27}$ is selected from V, A, W, N, or S; $X_{28}$ is selected from K, R, Q, A, or W; $X_{29}$ is selected from G, K, or A; $X_{30}$ is present or absent, if present, is selected from G or K; $X_{31}$ is present or absent, if present, is G; and CDR3 sequence $X_{32}X_{33}X_{34}X_{35}X_{36}X_{37}X_{38}X_{39}X_{40}X_{41}X_{42}X_{43}X_{44}X_{45}X_{46}$ $X_{47}X_{48}X_{49}$; and wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L. In some embodiments, the VH region comprises CDR1 sequence $GFPFX_5X_6YAMS$, wherein $X_5$ is selected from D or G; and $X_6$ is selected from V, A, or T. In some embodiments, the VH region comprises CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from S or D; $X_4$ is selected from L, F, or A; $X_5$ is selected from S, N, or T; $X_6$ is selected from R, S, N, I, or T; $X_7$ is selected from Y, I, N, R, A, D, or G; $X_8$ is selected from Y, D, G, A, W, T, or C; $X_9$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C. In some embodiments, the VH region comprises CDR1 sequence $GFSLX_5X_6X_7X_8X_9X_{10}X_{11}$; wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; and $X_{11}$ is present or absent, if present, is C. In some embodiments, the VH region comprises CDR1 sequence $GFSX_4X_5X_6X_7X_8X_9X_{10}X_{11}X_{12}$; wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; and $X_{12}$ is present or absent, if present, is C. In some embodiments, the VH region comprises CDR2 sequence $AISGSGGSTX_{22}YADSVKG$, wherein $X_{22}$ is selected from F or Y. In some embodiments, the VH region comprises CDR2 sequence $X_{13}X_{14}X_{15}X_{16}X_{17}X_{18}X_{19}X_{20}X_{21}X_{22}X_{23}X_{24}X_{25}X_{26}X_{27}X_{28}$ $X_{29}X_{30}X_{31}$; wherein $X_{13}$ is selected from A, G, or S; $X_{14}$ is selected from I, F, Y, V, S, or C; $X_{15}$ is selected from I, L, M, or T; $X_{16}$ is selected from G, Y, S, T, L, or V; $X_{17}$ is selected from S, I, K, Y, T, G, or A; $X_{18}$ is selected from G, S, T, P, or V; $X_{19}$ is selected from G, A, D, S, or T; $X_{20}$ is selected from S, T, I, N, or G; $X_{21}$ is selected from T, I, D, N, S, or A; $X_{22}$ is selected from Y, N, T, I, or S; $X_{23}$ is selected from Y, D, K, or I; $X_{24}$ is selected from A or Y; $X_{25}$ is selected from T, S, N, R, A, or Y; $X_{26}$ is selected from S, W, T, A, or N; $X_{27}$ is selected from A, W, N, or S; $X_{28}$ is selected from K, R, Q, A, or W; $X_{29}$ is selected from G, K, or A; $X_{30}$ is present or absent, if present, is selected from G or K; and $X_{31}$ is present or absent, if present, is G. In some embodiments, the VH region comprises CDR2 sequence $X_{13}X_{14}IX_{16}X_{17}X_{18}X_{19}X_{20}X_{21}X_{22}X_{23}X_{24}X_{25}X_{26}X_{27}X_{28}$ $X_{29}X_{30}$; wherein $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; and $X_{30}$ is present or absent, if present, is G. In some embodiments, the VH region comprises CDR2 sequence $X_{13}CX_{15}X_{16}X_{17}X_{18}X_{19}X_{20}X_{21}X_{22}X_{23}YX_{25}X_{26}X_{27}X_{28}X_{29}$ $X_{30}X_{31}$; wherein $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; and $X_{31}$ is present or absent, if present, is G. In some embodiments, the VH region comprises CDR3 sequence $AKRGTYX_{38}YSX_{41}PTGFDY$, wherein $X_{38}$ is selected from A or G; and $X_{41}$ is selected from F or Y. In some embodiments, the VH region comprises CDR3 sequence $X_{32}X_{33}X_{34}X_{35}X_{36}X_{37}X_{38}X_{39}X_{40}X_{41}X_{42}X_{43}X_{44}X_{45}X_{46}$ $X_{47}X_{48}X_{49}$; wherein $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, or F; $X_{45}$ is present or absent, if present, is selected from L, F, E, S, or N; $X_{46}$ is present or absent, if present, is selected from S, L, or R; $X_{47}$ is present or absent, if present, is L; $X_{48}$ is present or absent, if present, is D; and $X_{49}$ is present or absent, if present, is L. In some embodiments, the VH region comprises CDR3 sequence $X_{32}X_{33}X_{34}X_{35}X_{36}X_{37}X_{38}X_{39}X_{40}X_{41}X_{42}X_{43}X_{44}X_{45}$; wherein $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F. In some embodiments, the VH region comprises CDR3 sequence $AX_{33}X_{34}X_{35}X_{36}X_{37}X_{38}X_{39}X_{40}X_{41}X_{42}X_{43}X_{44}X_{45}X_{46}$; wherein $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L. In some embodiments, the VH region comprises CDR1 sequence $GFPFX_{5}X_{6}YAMS$, CDR2 sequence $AISGSGGSTX_{22}YADSVKG$, and CDR3 sequence $AKRGTYX_{38}YSX_{41}PTGFDY$; wherein $X_{5}$ is selected from D or G; $X_{6}$ is selected from V, A, or T; $X_{22}$ is selected from F or Y; $X_{38}$ is selected from A or G; and $X_{41}$ is selected from F or Y. In some embodiments, the VH region comprises CDR1 sequence $GFSLX_{5}X_{6}X_{7}X_{8}X_{9}X_{10}X_{11}$, CDR2 sequence $X_{13}X_{14}IX_{16}X_{17}X_{18}X_{19}X_{20}X_{21}X_{22}$ $X_{23}X_{24}X_{25}X_{26}X_{27}X_{28}X_{29}X_{30}$, and CDR3 sequence $X_{32}X_{33}X_{34}X_{35}X_{36}X_{37}X_{38}X_{39}X_{40}X_{41}X_{42}X_{43}X_{44}X_{45}$; wherein $X_{5}$ is selected from S or N; $X_{6}$ is selected from R, S, or N; $X_{7}$ is selected from Y, I, or N; $X_{8}$ is selected from Y, D, G, or A; $X_{9}$ is selected from V, M, or I; $X_{10}$ is selected from T, S, or M; $X_{11}$ is present or absent, if present, is C; $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; $X_{30}$ is present or absent, if present, is G; $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F. In some embodiments, the VH region comprises CDR1 sequence $GFSX_{4}X_{5}X_{6}X_{7}X_{8}X_{9}X_{10}X_{11}X_{12}$, CDR2 sequence $X_{13}CX_{15}X_{16}X_{17}X_{18}X_{19}X_{20}X_{21}X_{22}X_{23}YX_{25}X_{26}X_{27}X_{28}X_{29}$ $X_{30}X_{31}$, and CDR3 sequence $AX_{33}X_{34}X_{35}X_{36}X_{37}X_{38}X_{39}X_{40}X_{41}X_{42}X_{43}X_{44}X_{45}X_{46}$; wherein $X_{4}$ is selected from F or A; $X_{5}$ is selected from S, T, or N; $X_{6}$ is selected from S, T, or N; $X_{7}$ is selected from Y, R, A, or G; $X_{8}$ is selected from W, Y, or C; $X_{9}$ is selected from I, W, Y, or D; $X_{10}$ is selected from C, I, Y, or M; $X_{11}$ is present or absent, if present, is selected from C or M; $X_{12}$ is present or absent, if present, is C; $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; $X_{31}$ is present or absent, if present, is G; $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L. In some embodiments, the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}$ $X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L. In some embodiments, the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58. In some embodiments, the VH region comprises CDR1 sequence selected from SEQ ID NOs: 1, 4, 6, 8, and 9; CDR2 sequence selected from SEQ ID NOs: 2 and 5; and CDR3 sequence selected from SEQ ID NOs: 3, 7, and 10. In some embodiments, the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58. In some embodiments, the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52. In some embodiments, the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence selected from SEQ ID NOs: 19, 25, 31, 46, and 58. In some embodiments, the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103. In some embodiments, the VL region comprises CDR1 sequence selected from SEQ ID NOs: 65, 68, 80, 86, 89, 92, and 98; CDR2 sequence selected from SEQ ID NOs: 66, 69, 81, 78, 90, and 99; and CDR3 sequence selected from SEQ ID NOs: 67, 70, 82, 87, 88, 91, 93, and 100. In some embodiments, the VL region comprises CDR1 sequence selected from SEQ ID NOs: 71, 77, 83, 94, and 102; CDR2 sequence selected from SEQ ID NOs: 72, 78, and 84; and CDR3 sequence selected from SEQ ID NOs: 73, 79, 85, 95, and 103. In some embodiments, the anti-CD38 antibody comprises a VH sequence selected from SEQ ID NOs: 104-128 and a VL sequence selected from SEQ ID NOs: 130-154. In some embodiments, the anti-ICAM1 antibody comprises a humanized antibody or binding fragment thereof or a chimeric antibody or binding fragment thereof. In some embodiments, the anti-ICAM1 antibody comprises a bispecific antibody or binding fragment thereof. In some embodiments, the bispecific antibody or binding fragment thereof comprises a IgG-scFv, nanobody, BiTE, diabody, DART, TandAb, scDiabody, scDiabody-CH3, triple body, mini-antibody, minibody, TriBi minibody, scFv-CH3 KIH, Fab-scFv-Fc KIH, Fab-scFv, scFv-CH-CL-scFv, F(ab')2, F(ab')2-scFv2. scFv-KIH, Fab-scFv-Fc, tetravalent HCAb, scDiabody-Fc, diabody-Fc, tandem scFv-Fc, or intrabody. In some embodiments, the anti-ICAM1 antibody comprises an IgG1 framework sequence. In some embodiments, the anti-ICAM1 antibody comprises an IgG2 framework sequence. In some embodiments, the anti-ICAM1 antibody comprises an IgG4 framework sequence. In some embodiments, the anti-ICAM1 antibody comprises a HC sequence selected from SEQ ID NOs: 329-349 and a LC sequence selected from SEQ ID NOs: 351-366 and 182. In some embodiments, the anti-ICAM1 antibody further comprises a payload. In some embodiments, the payload comprises a small molecule, a peptide, or a protein.

Disclosed herein, in certain embodiments, is a nucleic acid polymer encoding a bispecific antibody described herein, an anti-CD38 antibody described herein, or an anti-ICAM1 antibody described herein.

Disclosed herein, in certain embodiments, is a vector comprising a nucleic acid polymer which encodes a bispecific antibody described herein, an anti-CD38 antibody described herein, or an anti-ICAM1 antibody described herein.

Disclosed herein, in certain embodiments, is a pharmaceutical composition comprising: a bispecific antibody described herein, an anti-CD38 antibody described herein, or an anti-ICAM1 antibody described herein; and a pharmaceutically acceptable excipient. In some embodiments, the pharmaceutical composition is formulated for systemic administration. In some embodiments, the pharmaceutical composition is formulated for parenteral administration.

Disclosed herein, in certain embodiments, is a method of treating a cancer in a subject in need thereof, comprising: administering to the subject a bispecific antibody described herein, an anti-CD38 antibody described herein, an anti-ICAM1 antibody described herein, or a pharmaceutical composition described herein, thereby treating the cancer in the subject. In some embodiments, the subject has a solid tumor. In some embodiments, the solid tumor is bladder cancer, bone cancer, brain cancer, breast cancer, colorectal cancer, eye cancer, head and neck cancer, kidney cancer, liver cancer, lung cancer, ovarian cancer, pancreatic cancer, prostate cancer, skin cancer, stomach cancer, thyroid cancer, or uterine cancer. In some embodiments, the cancer is a hematologic malignancy. In some embodiments, the hematologic malignancy is a B cell lymphoma or T cell lymphoma. In some embodiments, the hematologic malignancy is a Hodgkin's lymphoma or a non-Hodgkin's lymphoma. In some embodiments, the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the cancer is a metastatic cancer. In some embodiments, the cancer is a relapsed or refractory cancer. In some embodiments, the method further comprises administering an additional therapeutic agent. In some embodiments, the additional therapeutic agent comprises chemotherapeutic agent, immunotherapeutic agent, targeted therapeutic agent, hormone-based therapeutic agent, stem-cell based therapeutic agent, or radiation. In some embodiments, the additional therapeutic agent comprises a first-line therapeutic agent. In some embodiments, the additional therapeutic agent and the antibody are administered simultaneously. In some embodiments, the additional therapeutic agent and the antibody are administered sequentially. In some embodiments, the additional therapeutic agent is administered prior to the antibody. In some embodiments, the additional therapeutic agent is administered after administration of the antibody. In some embodiments, the additional therapeutic agent and the antibody are administered as a separate dosage. In some embodiments, the subject has undergone surgery. In some embodiments, the subject is a human.

Disclosed herein, in certain embodiments, is a kit comprising a bispecific antibody described herein, an anti-CD38 antibody described herein, an anti-ICAM1 antibody described herein, or a pharmaceutical composition described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A and FIG. 1B are adapted from FIG. 2 of Brinkmann and Kontermann, "The making of bispecific antibodies," MABS 9(2): 182-212 (2017).

FIG. 2 illustrates exemplary bispecific formats described herein.

FIG. 19A-FIG. 19B show increased ADCC-mediated lysis of Raji (FIG. 19A) and KMS26 (FIG. 19B) cells with a CD38/ICAM1 KIH bispecific antibody having an Fc mutation (ADCC-high) that.

DETAILED DESCRIPTION OF THE DISCLOSURE

Figure 1A:
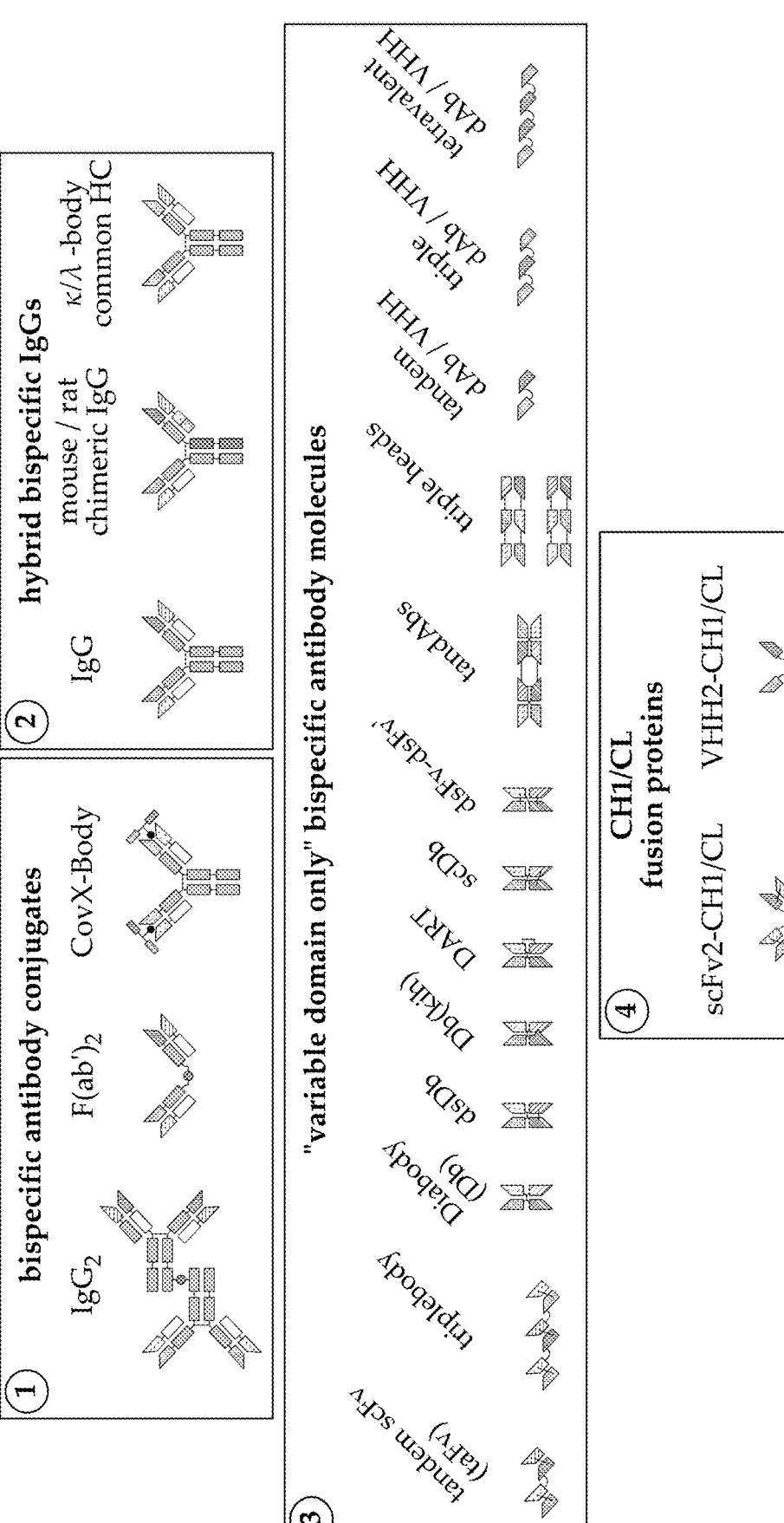
FIG. 1A-FIG. 1B illustrate exemplary bispecific antibody formats contemplated herein.

Antibody-based therapeutics has emerged as effective cancer treatment options, due to the specificity and affinity of the antibody to target binding and ease of chemical and molecular modifications. For example, approved antibody-based therapy includes monoclonal antibodies such as rituximab, tositumomab, and trastuzumab; and bispecific T-cell engager such as Blinatumomab.

In some instances, low receptor copy numbers on a target cell, or low affinity toward an antigen has hindered the therapeutic effect of an antibody-based therapy. In some cases, non-specificity of an antibody toward a target antigen, or the presence of a target in both cancer and non-cancer cells have further limited the use of an antibody-based therapy.

CD38, also known as cyclic ADP ribose hydrolase, is a type II transmembrane glycoprotein with a long C-terminal extracellular domain and a short N-terminal cytoplasmic domain. CD38 mediates cytokine secretion and activation and proliferation of lymphocytes (Funaro et al, J Immunology 145:2390-6, 1990; Guse et al, Nature 398:70-3, 1999), and via its NAD glycohydrolase activity regulates extracellular NAD+ levels which have been implicated in modulating the regulatory T-cell compartment (Adriouch et al., 14: 1284-92, 2012; Chiarugi et al., Nature Reviews 12:741-52, 2012). In some instances, CD38 is upregulated in different types of cancer, in particular, in hematologic malignancies such as multiple myeloma.

ICAM1, also known as CD54, is an Ig-like cell adhesion molecule. ICAM1 is an endothelial- and leukocyte-associated transmembrane protein and is involved in stabilizing cell-cell interactions and facilitating leukocyte endothelial transmigration. ICAM1 is expressed in various cell types, including endothelial cells and leukocytes and can be expressed and/or overexpressed in different cancer cells such as myeloma, pancreatic cancer, glioma, lung cancer, melanoma, colorectal cancer, and lymphoma.

In some embodiments, disclosed herein are anti-CD38 antibodies, anti-ICAM1 antibodies, and multi-specific antibodies which comprise a targeting moiety to CD38, a targeting moiety to ICAM1, or a combination thereof. In some embodiments, also described herein are bispecific antibodies which comprise a first targeting moiety to CD38 and a second targeting moiety to ICAM1. In additional embodiments, further described herein are methods of treating a cancer with use of an anti-CD38 antibody, an anti-ICAM1 antibody, or a multi-specific antibody (e.g., a bispecific CD38/ICAM1 antibody).

Multispecific Proteins

In certain embodiments disclosed herein are multispecific proteins comprising a first component that binds CD38 and a second component that binds ICAM1. The first component, in some instances, is a CD38 binding protein, such as an anti-CD38 antibody or an anti-CD38 antibody mimetic. The second component, in some instances, is an ICAM1 binding protein, such as an anti-ICAM1 antibody or an anti-ICAM1 antibody mimetic. See, e.g., Yu et al., Annu Rev Anal Chem (Palo Alto Calif). 2017 Jun. 12; 10(1): 293-320.

In some instances, the multispecific protein is bispecific, tri-specific, or tetra-specific. In some instances, the multispecific protein is bivalent, trivalent, tetravalent or more than tetravalent. In some instances, the multispecific protein has more than one binding site that binds to CD38. In some instances, the multispecific protein has more than one binding site that binds to ICAM1. In some instances, the multispecific protein has more than one binding sites for each of 1, 2, 3, or 4 different target proteins. In some instances, the multispecific protein binds to more than one epitope on CD38 and/or ICAM1. In some instances, the multispecific protein is bivalent for CD38 and monovalent for ICAM1. In some instances, the multispecific protein is bivalent for ICAM1 and monovalent for CD38.

In some embodiments, the first component comprises an antibody mimetic comprising a binding site specific for CD38 and is an affibody, an adnectin (also referred to as a monobody), an affimer, an affitin (also referred to as a nanofitin), an anticalin, an atrimer, an avimer, a fyonmer, an antibody mimetic comprising armadillo repeat domains, a kuntiz domain, a knottin, a DARpin, or any combinations thereof. In some embodiments, the second component comprises an antibody mimetic comprising a binding site specific for ICAM1 and is an affibody, an adnectin (also referred to as a monobody), an affimer, an affitin (also referred to as a nanofitin), an anticalin, an atrimer, an avimer, a fyonmer, an antibody mimetic comprising armadillo repeat domains, a kuntiz domain, a knottin, a DARpin, or any combinations thereof.

In some embodiments, the first component comprises an anti-CD38 antibody or an antigen binding fragment thereof. Non-limiting examples of the anti-CD38 antibody includes: an anti-CD38 IgG antibody comprising two polypeptides, each comprising a heavy chain (HC) and a light chain (LC), single domain antibody (sdAb), a VHH domain (or a camelized) antibody), a variable heavy domain (VH), a variable light domain (VL), an Fab, an F(ab')$_2$, a single chain variable fragment (scFv), an scFv comprising an Fc region (scFv Fc), a monovalent IgG, a V-NAR, an IgGNAR, a camelid heavy chain IgG (hcIgG), an scFv fused to a CH3 domain (scFv-CH3).

In some embodiments, the second component comprises an anti-ICAM1 antibody or an antigen binding fragment thereof. Non-limiting examples of the anti-ICAM1 antibody includes: an anti-ICAM1 IgG antibody comprising two polypeptides, each comprising a heavy chain (HC) and a light chain (LC), single domain antibody (sdAb), a VHH domain (or a camelized) antibody), a variable heavy domain (VH), a variable light domain (VL), an Fab, an F(ab')$_2$, a single chain variable fragment (scFv), an scFv comprising an Fc region (scFv Fc), a monovalent IgG, a V-NAR, an IgGNAR, a camelid heavy chain IgG (hcIgG), an scFv fused to a CH3 domain (scFv-CH3).

In some embodiments, the multispecific protein comprising a CD38-binding first component and an ICAM1-binding second component have different affinities ($K_D$) for their respective target antigens as measured by surface plasmon resonance. In some cases, the first component binds to human CD38 with a $K_D$ of from about 0.1 nM to about 100 nM, from about 0.15 nM to about 95 nM, from about 0.2 nM to about 90 nM, from 0.25 nM to about 85 nM, from about 0.3 nM to about 80 nM, from about 0.35 nM to about 75 nM, from about 0.4 nM to about 70 nM, from about 0.5 nM to about 70 nM, from about 0.6 nM to about 60 nM, from about 0.7 nM to about 50 nM, from about 0.8 nM to about 40 nM, from about 0.9 nM to about 30 nM, from about 1 nM to about 20 nM, from about 1.5 nM to about 10 nM, from about 0.01 nM to about 25 nM, from about 0.01 nM to about 20 nM, from about 0.01 nM to about 10 nM, from about 0.01 nM to about 5 nM, from about 0.02 nM to about 20 nM, from about 0.04 nM to about 20 nM, from about 0.06 nM to about 20 nM, from about 0.08 nM to about 20 nM, or from about 0.1 nM to about 20 nM.

In some cases, the second component binds to human ICAM1 with a $K_D$ of about 0.1 nM to about 100 nM, from about 0.15 nM to about 95 nM, from about 0.2 nM to about 90 nM, from 0.25 nM to about 85 nM, from about 0.3 nM to about 80 nM, from about 0.35 nM to about 75 nM, from about 0.4 nM to about 70 nM, from about 0.5 nM to about 70 nM, from about 0.6 nM to about 60 nM, from about 0.7 nM to about 50 nM, from about 0.8 nM to about 40 nM, from about 0.9 nM to about 30 nM, from about 1 nM to about 20 nM, from about 1.5 nM to about 10 nM, from about 0.15 nM to about 30 nM, from about 0.16 nM to about 25 nM, from about 0.17 nM to about 20 nM, from 0.18 nM to about 15 nM, from about 0.19 nM to about 10 nM, from about 0.1 nM to about 6 nM, from about 0.2 nM to about 6 nM, from about 0.2 nM to about 4 nM, from about 0.2 nM to about 2 nM, from about 0.2 nM to about 1.5 nM, from about 0.2 nM to about 1 nM, from about 0.2 nM to about 0.8 nM, from about 0.2 nM to about 0.6 nM, or from about 0.2 nM to about 0.4 nM.

In some embodiments, a multispecific protein provided herein binds to a target cell that expresses a higher level of ICAM1 than CD38, on its surface. For instance, the ratio of ICAM1 to CD38 protein expression on the target cell surface, is from about 1, 1.5, 2.0, 2.5, 5, 10, 15, 20, 50, 100, or 200 as measured by flow cytometry. For instance, the ratio of ICAM1 to CD38 protein expression on the target cell surface, is from about 1.1 to 700, such as about 2.5, 14.2, 29.1, 64.5, 34.0, 50.3, 357.1, 666.7, based on quantification of surface expression of the proteins.

In some instances, the target cell expresses at least 500, 1000, 2000, 3000, 5000, 10000, 150000, 20000, 30000, 50000, 100000, 150000, 200000, 250000, 300000, 400000, or 500000 ICAM1 proteins on its surface as measured by flow cytometry.

In some cases, the target cell expresses at least 100, 200, 300, 400, 500, 1000, 2000, 3000, 4000, or 5000 CD38 proteins on its surface as measured by flow cytometry. In some instances, the target cell expresses less than 350,000, 300,000, 250,000, 200,000, 150,000, 100,000, 50,000, 25,000 CD38 proteins on its surface as measured by flow cytometry. In some instances the number of CD38 proteins on the surface of a target cell is 100 to 350,000, 100 to 300,000, 100 to 250,000, 100 to 200,000, 100 to 150,000, 100 to 100,000, 100 to 80,000, 100 to 60,000, 100 to 50,000, 100 to 40,000, 100 to 30,000, 100 to 20,000, 100 to 10,000, 300 to 350,000, 300 to 300,000, 300 to 250,000, 300 to 200,000, 300 to 150,000, 300 to 100,000, 300 to 80,000, 300 to 60,000, 300 to 50,000, 300 to 40,000, 300 to 30,000, 300 to 20,000, or 300 to 10,000.

In some instances, the target cell has fewer CD38 proteins on its surface than a Daudi cell, a Raji cell, a KMS-26 cell, a HuNS1 cell, a HCC44 cell, an NCI-H2444 cell, or a DU145 cell. In some instances, the target cell has at least 200 CD38 proteins on its surface but fewer CD38 proteins on its surface than a Daudi cell, a Raji cell, a KMS-26 cell, a HuNS1 cell, a HCC44 cell, an NCI-H2444 cell, or a DU145 cell.

In some embodiments, the target cell is a transformed cell, wherein the ratio of ICAM1 to CD38 proteins is at least 1, 2, 5, 10, 15, 20, 35, 40, 50, or 200. In some cases, the transformed cell expresses at least 100, 200, 300, 400, 500, 750, 1000, 1250, 1500, 2000, 3000 CD38 cells on its surface. In some cases, the target cell is a myeloma cell, a lymphoma cell, a pancreatic cancer cell, a lung adenocarcinoma cell, or a prostate carcinoma cell wherein, the ratio of ICAM1 to CD38 protein is at least 0.15, 0.20, 0.3, 0.4, 0.5, 1.0, 2.5, or 5.0. In other cases, the target cell is derived from a lung adenocarcinoma, wherein the ratio of ICAM1 to CD38 proteins is at least 1, 2, 5, 10, 15, 20, 35, 40, 50, or 200. In some cases, the myeloma cell, a lymphoma cell, a pancreatic cancer cell, a lung adenocarcinoma cell, or a prostate carcinoma cell expresses at least 100, 200, 300, 400, 500, 750, 1000, 1250, 1500, 2000, 3000 CD38 cells on its surface.

In some embodiments, a multispecific protein with a CD38-binding domain and an ICAM1-binding domain has enhanced affinity for a cell that expresses CD38 and ICAM1 compared to a monospecific protein with a CD38-binding domain and/or a monospecific protein with an ICAM1-binding domain. In some instances, the multispecific protein has 1.5, 2, 3, 4, 5, or 10-fold higher affinity for the CD38-expressing cell than a monospecific protein that binds to CD38 or a monospecific protein that binds to ICAM1. In some embodiments, a multispecific protein with a CD38-binding domain and an ICAM1-binding domain has enhanced affinity for a cell that expresses higher levels of CD38 than ICAM1 compared to a monospecific protein with a CD38-binding domain. In some instances, the multispecific protein has 1.5, 2, 3, 4, 5, or 10-fold higher affinity for the cell with higher ICAM1 expression than CD38 expression compared to a monospecific protein that binds to CD38.

In some embodiments, larger amounts of a multispecific protein with a CD38-binding domain and an ICAM1-binding domain bind to the surface of cell that expresses CD38 and ICAM compared to a monospecific protein with a CD38-binding domain and/or a monospecific protein with an ICAM1-binding domain. In some instances, 1.5, 2, 3, 4, 5, or 10-fold more of the multispecific protein binds to the CD38-expressing cell than a monospecific protein that binds to CD38 or a monospecific protein that binds to ICAM1. In some embodiments, larger amounts of a multispecific protein with a CD38-binding domain and an ICAM1-binding domain bind to the surface of cell with higher ICAM1 expression than CD38 expression compared to a monospecific protein with a CD38-binding domain. In some instances, 1.5, 2, 3, 4, 5, or 10-fold more of the multispecific protein binds to the cell expressing more ICAM1 than CD38 compared to a monospecific protein that binds to CD38.

In some embodiments, a multispecific protein with a CD38-binding domain and an ICAM1-binding domain has a higher immunologic activity against a CD38-expressing cell compared to a monospecific protein with a CD38-binding domain and/or a monospecific protein with an ICAM1-binding domain. In some instances, the multispecific protein has a 1.5, 2, 3, 4, 5, or 10-fold higher immunological activity than a monospecific protein with a CD38-binding domain and/or a monospecific protein with an ICAM1-binding domain. Various immunological activities of a multispecific protein can be measured in in vitro assays such as an ADCC assay and a CDC assay. In some instances, the multispecific protein has a 1.5, 2, 3, 4, 5, or 10-fold higher ADCC activity than a monospecific protein with a CD38-binding domain and/or a monospecific protein with an ICAM1-binding domain. In some instances, the multispecific protein has a 1.5, 2, 3, 4, 5, or 10-fold higher CDC activity than a monospecific protein with a CD38-binding domain and/or a monospecific protein with an ICAM1-binding domain.

Immunological activity can also be measured in a cell-line derived xenograft assay, wherein transformed cells are injected into mice and form a tumor. In some instances, a multispecific protein with a CD38-binding domain and an ICAM1-binding domain inhibits the growth of a tumor comprising CD38-expressing cells to a greater extent than a monospecific protein with a CD38-binding domain and/or a monospecific protein with an ICAM1-binding domain. In some instances, the multispecific protein exhibits 1.5, 2, 3, 4, 5, or 10-fold higher inhibition of xenograft tumor growth compared to a monospecific protein with a CD38-binding domain and/or a monospecific protein with an ICAM1-binding domain.

As used herein, "Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, the target cell is a human cell, such as a tumor cell (e.g., a myeloma cell). While not wishing to be bound by any particular mechanism of action, the cytotoxic cells that mediate ADCC generally express Fc receptors (FcRs). Cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu. Rev. Immunol., 9:457-92 (1991).

To assess ADCC activity of a multispecific protein as described herein, an in vitro ADCC assay, such as a cytotoxic assay using a cancer cell lines, is carried out, in some embodiments. Useful effector cells for such assays include, but are not limited to, peripheral blood mononuclear cells (PBMC) and Natural Killer (NK) cells. Alternatively, or additionally, ADCC activity of the multispecific proteins of interest is assessed, in some embodiments, in vivo, e.g., in an animal.

"Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), is performed, in some embodiments.

In some embodiments, a multispecific protein as described herein, that binds CD38 and ICAM1 mediates complement dependent lysis of at least 50% of the cells in an exponentially growing population of Raji cells, at a concentration of about 2 nM. In some embodiments, a multispecific protein as described herein that binds CD38 and ICAM1 mediates ADCC by PBMC cells of 40% of the cells in an exponentially growing population of NCI-H2444 cells, at a concentration of about 1 nM. In certain embodiments, a multispecific, multivalent (such as bivalent, trivalent, tetravalent) protein as described herein, that binds CD38 and ICAM1, does not induce apoptosis without crosslinking.

Anti-CD38 Antibodies

In certain embodiments, disclosed herein is an anti-CD38 antibody. In some instances, the anti-CD38 antibody comprises a variable heavy chain (VH) region and a variable light chain (VL) region, in which the VH region comprises CDR1 sequence $X_1GX_2X_3X_4X_5X_6X_7X_8X_9X_{10}X_{11}X_{12}$; wherein $X_1$ is present or absent, if present, is S; $X_2$ is selected from F or I; $X_3$ is selected from P, S, or D; $X_4$ is selected from F, L, or A; $X_5$ is selected from D, G, S, N, or T; $X_6$ is selected from V, A, T, R, S, I, or N; $X_7$ is selected from Y, I, N, R, A, G, or D; $X_8$ is selected from A, Y, D, G, W, C, or T; $X_9$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence $X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}$; wherein $X_{13}$ is selected from A, G, or S; $X_{14}$ is selected from I, F, Y, V, S, or C; $X_{15}$ is selected from S, I, L, T, or M; $X_{16}$ is selected from G, Y, S, T, L, or V; $X_{17}$ is selected from S, I, K, Y, T, G, or A; $X_{18}$ is selected from G, S, T, P, V, or Y; $X_{19}$ is selected from G, A, D, S, or T; $X_{20}$ is selected from S, T, I, N, or G; $X_{21}$ is selected from T, I, D, N, S, or A; $X_{22}$ is selected from F, Y, N, T, I, or S; $X_{23}$ is selected from Y, D, K, or I; $X_{24}$ is selected from A or Y; $X_{25}$ is selected from D, T, S, N, R, A, or Y; $X_{26}$ is selected from S, W, T, A, or N; $X_{27}$ is selected from V, A, W, N, or S; $X_{28}$ is selected from K, R, Q, A, or W; $X_{29}$ is selected from G, K, or A; $X_{30}$ is present or absent, if present, is selected from G or K; $X_{31}$ is present or absent, if present, is G; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L In some instances, the VH region of the anti-CD38 antibody comprises CDR1 sequence GFPFX_5X_6YAMS (SEQ ID No. 423), in which $X_5$ is selected from D or G; and $X_6$ is selected from V, A, or T.

In some instances, the VH region of the anti-CD38 antibody comprises CDR1 sequence $X_1GX_2X_3X_4X_5X_6X_7X_8X_9X_{10}X_{11}X_{12}$; in which $X_1$ is present or absent, if present, is S; $X_2$ is selected from F or I; $X_3$ is selected from S or D; $X_4$ is selected from L, F, or A; $X_5$ is selected from S, N, or T; $X_6$ is selected from R, S, N, I, or T; $X_7$ is selected from Y, I, N, R, A, D, or G; $X_8$ is selected from Y, D, G, A, W, T, or C; $X_9$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C.

In some instances, the VH region of the anti-CD38 antibody comprises CDR1 sequence GFSLX_5X_6X_7X_8X_9X_{10}X_{11} (SEQ ID No. 426); in which $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; and $X_{11}$ is present or absent, if present, is C.

In some instances, the VH region of the anti-CD38 antibody comprises CDR1 sequence GFSX$_4$X$_5$X$_6$X$_7$X$_8$X$_9$X$_{10}$X$_{11}$X$_{12}$ (SEQ ID No. 419); in which $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; and $X_{12}$ is present or absent, if present, is C.

In some cases, the VH region of the anti-CD38 antibody comprises CDR2 sequence AISGSGGSTX$_{22}$YADSVKG (SEQ ID No. 418), in which $X_{22}$ is selected from F or Y.

In some cases, the VH region of the anti-CD38 antibody comprises CDR2 sequence X$_{13}$X$_{14}$X$_{15}$X$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$X$_{30}$X$_{31}$; in which $X_{13}$ is selected from A, G, or S; $X_{14}$ is selected from I, F, Y, V, S, or C; $X_{15}$ is selected from I, L, M, or T; $X_{16}$ is selected from G, Y, S, T, L, or V; $X_{17}$ is selected from S, I, K, Y, T, G, or A; $X_{18}$ is selected from G, S, T, P, or V; $X_{19}$ is selected from G, A, D, S, or T; $X_{20}$ is selected from S, T, I, N, or G; $X_{21}$ is selected from T, I, D, N, S, or A; $X_{22}$ is selected from Y, N, T, I, or S; $X_{23}$ is selected from Y, D, K, or I; $X_{24}$ is selected from A or Y; $X_{25}$ is selected from T, S, N, R, A, or Y; $X_{26}$ is selected from S, W, T, A, or N; $X_{27}$ is selected from A, W, N, or S; $X_{28}$ is selected from K, R, Q, A, or W; $X_{29}$ is selected from G, K, or A; $X_{30}$ is present or absent, if present, is selected from G or K; and $X_{31}$ is present or absent, if present, is G.

In some cases, the VH region of the anti-CD38 antibody comprises CDR2 sequence X$_{13}$X$_{14}$IX$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$X$_{30}$; in which $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; and $X_{30}$ is present or absent, if present, is G.

In some cases, the VH region of the anti-CD38 antibody comprises CDR2 sequence X$_{13}$CX$_{15}$X$_{16}$X$_{17}$X$_{18}$X$_{19}$X$_{20}$X$_{21}$X$_{22}$X$_{23}$YX$_{25}$X$_{26}$X$_{27}$X$_{28}$X$_{29}$X$_{30}$X$_{31}$; in which $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; and $X_{31}$ is present or absent, if present, is G.

In some cases, the VH region of the anti-CD38 antibody comprises CDR3 sequence AKRGTYX$_{38}$YSX$_{41}$PTGFDY (SEQ ID No. 421), in which $X_3$s is selected from A or G; and $X_{41}$ is selected from F or Y.

In some cases, the VH region of the anti-CD38 antibody comprises CDR3 sequence X$_{32}$X$_{33}$X$_{34}$X$_{35}$X$_{36}$X$_{37}$X$_{38}$X$_{39}$X$_{40}$X$_{41}$X$_{42}$X$_{43}$X$_{44}$X$_{45}$X$_{46}$X$_{47}$X$_{48}$X$_{49}$; in which $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, F; $X_{45}$ is present or absent, if present, is selected from L, F, E, S, or N; $X_{46}$ is present or absent, if present, is selected from S, L, or R; $X_{47}$ is present or absent, if present, is L; $X_{48}$ is present or absent, if present, is D; and $X_{49}$ is present or absent, if present, is L.

In some cases, the VH region of the anti-CD38 antibody comprises CDR3 sequence X$_{32}$X$_{33}$X$_{34}$X$_{35}$X$_{36}$X$_{37}$X$_{38}$X$_{39}$X$_{40}$X$_{41}$X$_{42}$X$_{43}$X$_{44}$X$_{45}$; in which $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{3}$s is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F.

In some cases, the VH region of the anti-CD38 antibody comprises CDR3 sequence AX$_{33}$X$_{34}$X$_{35}$X$_{36}$X$_{37}$X$_{38}$X$_{39}$X$_{40}$X$_{41}$X$_{42}$X$_{43}$X$_{44}$X$_{45}$X$_{46}$ (SEQ ID NO: 422); in which $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L.

In some instances, the VH region of the anti-CD38 antibody comprises CDR1 sequence GFPFX$_5$X$_6$YAMS (SEQ ID NO: 423), CDR2 sequence AISGSGGSTX$_{22}$YADSVKG (SEQ ID NO: 418), and CDR3 sequence AKRGTYX$_{38}$YSX$_{41}$PTGFDY (SEQ ID NO: 421); in which $X_5$ is selected from D or G; $X_6$ is selected from V, A, or T; $X_{22}$ is selected from F or Y; $X_{38}$ is selected from A or G; and $X_{41}$ is selected from F or Y.

In some instances, the VH region of the anti-CD38 antibody comprises CDR1 sequence GFSLX$_5$X$_6$X$_7$X$_8$X$_9$X$_{10}$X$_{11}$ (SEQ ID NO: 426), CDR2 sequence X$_{13}$X$_{14}$IX$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$X$_{30}$, and CDR3 sequence X$_{32}$X$_{33}$X$_{34}$X$_{35}$X$_{36}$X$_{37}$X$_{38}$X$_{39}$X$_{40}$X$_{41}$X$_{42}$X$_{43}$X$_{44}$X$_{45}$; in which $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; $X_{11}$ is present or absent, if present, is C; $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; $X_{30}$ is present or absent, if present, is G; $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F.

In some instances, the VH region of the anti-CD38 antibody comprises CDR1 sequence GFSX$_4$X$_5$X$_6$X$_7$X$_8$X$_9$X$_{10}$X$_{11}$X$_{12}$ (SEQ ID NO: 419), CDR2 sequence X$_{13}$CX$_{15}$X$_{16}$X$_{17}$X$_{18}$X$_{19}$X$_{20}$X$_{21}$X$_{22}$X$_{23}$YX$_{25}$X$_{26}$X$_{27}$X$_{28}$X$_{29}$X$_{30}$X$_{31}$, and CDR3 sequence AX$_{33}$X$_{34}$X$_{35}$X$_{36}$X$_{37}$X$_{38}$X$_{39}$X$_{40}$X$_{41}$X$_{42}$X$_{43}$X$_{44}$X$_{45}$X$_{46}$ (SEQ ID NO: 422); in which $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; $X_{12}$ is present or absent, if present, is C; $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; $X_{31}$ is present or absent, if present, is G; $X_{33}$ is selected from R or G; $X_{34}$ is selected from E, D, or 5; $X_{35}$ is selected from G, L, P, 5, or A; $X_{36}$ is selected from D, 5, or R; $X_{37}$ is selected from Y, T, N, or G; $X_{38}$ is selected from G, 5, F, or L; $X_{39}$ is selected from A, G, 5, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L.

In some embodiments, the VH region of the anti-CD38 antibody comprises CDR1, CDR2, and CDR3 sequences selected from Table 1.

TABLE1

| Heavy chain complementarity determining regions of exemplary anti-CD38 antibodies | | | | | | |
|---|---|---|---|---|---|---|
| CD38 VH | CDR1 | SEQ ID NO: | CDR2 | SEQ ID NO: | CDR3 | SEQ ID NO: |
| 4618_1 | GFPFDVYA MS | 1 | AISGSGGSTFY ADSVKG | 2 | AKRGTYAYSFPT GFDY | 3 |
| 4618_5 | GFPFDAYA MS | 4 | AISGSGGSTYY ADSVKG | 5 | AKRGTYAYSFPT GFDY | 3 |
| 4618_12 | GFPFGVYA MS | 6 | AISGSGGSTFY ADSVKG | 2 | AKRGTYAYSYP TGFDY | 7 |
| 4618_1_12 | GFPFDVYA MS | 1 | AISGSGGSTFY ADSVKG | 2 | AKRGTYAYSYP TGFDY | 7 |
| 4618_5_12 | GFPFDAYA MS | 4 | AISGSGGSTYY ADSVKG | 5 | AKRGTYAYSYP TGFDY | 7 |
| 4618_5F_12 | GFPFDAYA MS | 4 | AISGSGGSTFY ADSVKG | 2 | AKRGTYAYSYP TGFDY | 7 |
| 32218_1 | GFPFGVYA MS | 6 | AISGSGGSTFY ADSVKG | 2 | AKRGTYAYSFPT GFDY | 3 |
| 32218_2 | GFPFDTYA MS | 8 | AISGSGGSTYY ADSVKG | 5 | AKRGTYAYSFPT GFDY | 3 |
| 32018_7 | GFPFGTYA MS | 9 | AISGSGGSTFY ADSVKG | 2 | AKRGTYGYSFPT GFDY | 10 |
| 17E9 | GFSLSRYY VT | 11 | GIIYISGTTYYA TWAKG | 12 | AAAWPVGTYVL PL | 13 |
| 17F7 | GFSLSSYY MS | 14 | GFISKTAITYYA SWARG | 15 | ARVDAYSAGDL | 16 |
| 18E4 | GFSFNNY WIC | 17 | ACIYSPSGDIKY YANWAKG | 18 | ARELSGSSYEGY FES | 19 |
| 1E2 | GIDLNSYA MG | 20 | GIMTSGGNIYY ANWAKG | 21 | AREREFYGGGTS GSRLDL | 22 |
| 20B5 | GFSFSSRY WIC | 23 | ACIVAGTTNTY YASWAKG | 24 | AGDPRTGSNVG YFNL | 25 |
| 21G2 | GFSLSNYG VS | 26 | GYILTSGGTYY ANWAQG | 27 | GRPKDSDSSAFV SL | 28 |

TABLE1-continued

Heavy chain complementarity determining regions of exemplary anti-CD38 antibodies

| CD38 VH | CDR1 | SEQ ID NO: | CDR2 | SEQ ID NO: | CDR3 | SEQ ID NO: |
|---|---|---|---|---|---|---|
| 21H9 | GFSATTYY YYMC | 29 | ACTYTGDGAT YYATWAKG | 30 | ARSADNSIYYGY FNL | 31 |
| 22H6 | GFSLSNNA IS | 32 | GSIYGSGNTYY ATWAKG | 33 | AREGAGSSWGF NL | 34 |
| 23A2 | GFSLNNN AIS | 35 | GSIYGTGNTYY ATWAKG | 36 | ATEGAGSIWGFN L | 37 |
| 23B3 | GFSLSNYD MT | 38 | GVISSGDNTNY ARWAKG | 39 | ARILYNKGRYYF TF | 40 |
| 23D1 | GFSLSNIY VMC | 41 | ACIGTGSGDTD YATWAKG | 42 | ARDPGAGTWNL | 43 |
| 25C3 | GFSFSSAY DMC | 44 | ACLYTVSSDSI YYASWAKG | 45 | ARDGDYFAL | 46 |
| 25E4 | GIDLSIYT MA | 47 | GIISGYGTTYY ATWAKG | 48 | VRTTVQSTDL | 49 |
| 25F12 | GFSLSSYD MS | 50 | GYITYGGNIYY ATWAKG | 51 | ARTLYTGGRYY FSL | 52 |
| 26D4 | SGFSFSND AIC | 53 | ACIYAGSGNTY YASWAKG | 54 | ASADTIDYFNL | 55 |
| 27F6 | GFSFSSGC DMC | 56 | SCIYTGSGSTY YANWAKG | 57 | AGDSDYLGL | 58 |
| G1F4_VH | GFTFSTYA MS | 59 | AISGSGGSTYY ADSVKG | 60 | AKRGTYGYSFPT GFDY | 61 |

In some embodiments, the VH region of the anti-CD38 antibody comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L.

In some embodiments, the VH region of the anti-CD38 antibody comprises CDR1 sequence selected from SEQ ID NOs: 1, 4, 6, 8, and 9; CDR2 sequence selected from SEQ ID NOs: 2 and 5; and CDR3 sequence AKRGTYX$_{38}$YSX$_{41}$PTGFDY (SEQ ID NO: 421), in which $X_{38}$ is selected from A or G and $X_{41}$ is selected from F or Y.

In some embodiments, the VH region of the anti-CD38 antibody comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$, in which $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, or F; $X_{45}$ is present or absent, if present, is selected from L, F, E, S, or N; $X_{46}$ is present or absent, if present, is selected from S, L, or R; $X_{47}$ is present or absent, if present, is L; $X_{48}$ is present or absent, if present, is D; and $X_{49}$ is present or absent, if present, is L.

In some embodiments, the VH region of the anti-CD38 antibody comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence $X_{32}X_{33}X_{34}X_{35}X_{36}X_{37}X_{38}X_{39}X_{40}X_{41}X_{42}X_{43}X_{44}X_{45}$, in which $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F.

In some embodiments, the VH region of the anti-CD38 antibody comprises CDR1 sequence selected from SEQ ID NOs: 17, 23, 29, 44, and 56; CDR2 sequence selected from SEQ ID NOs: 18, 24, 30, 45, and 57; and CDR3 sequence $AX_{33}X_{34}X_{35}X_{36}X_{37}X_{38}X_{39}X_{40}X_{41}X_{42}X_{43}X_{44}X_{45}X_{46}$ (SEQ ID NO: 422), in which $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L.

In some embodiments, the VH region of the anti-CD38 antibody comprises CDR1 sequence $X_1GX_2X_3X_4X_5X_6X_7X_8X_9X_{10}X_{11}X_{12}$, wherein $X_1$ is present or absent, if present, is S; $X_2$ is selected from F or I; $X_3$ is selected from P, S, or D; $X_4$ is selected from F, L, or A; $X_5$ is selected from D, G, S, N, or T; $X_6$ is selected from V, A, T, R, S, I, or N; $X_7$ is selected from Y, I, N, R, A, G, or D; $X_8$ is selected from A, Y, D, G, W, C, or T; $X_9$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58.

In some embodiments, the VH region of the anti-CD38 antibody comprises CDR1 sequence $GFPFX_5X_6YAMS$ (SEQ ID NO: 423), in which $X_5$ is selected from D or G and $X_6$ is selected from V, A, or T; CDR2 sequence selected from SEQ ID NOs: 2 and 5; and CDR3 sequence selected from SEQ ID NOs: 3, 7, and 10.

In some embodiments, the VH region of the anti-CD38 antibody comprises CDR1 sequence $X_1GX_2X_3X_4X_5X_6X_7X_8X_9X_{10}X_{11}X_{12}$, wherein $X_1$ is present or absent, if present, is S; $X_2$ is selected from F or I; $X_3$ is selected from S or D; $X_4$ is selected from L, F, or A; $X_5$ is selected from S, N, or T; $X_6$ is selected from R, S, N, I, or T; $X_7$ is selected from Y, I, N, R, A, D, or G; $X_8$ is selected from Y, D, G, A, W, T, or C; $X_9$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58.

In some embodiments, the VH region of the anti-CD38 antibody comprises CDR1 sequence $GFSLX_5X_6X_7X_8X_9X_{10}X_{11}$ (SEQ ID No. 426), wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; and $X_{11}$ is present or absent, if present, is C; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52.

In some embodiments, the VH region of the anti-CD38 antibody comprises CDR1 sequence $GFSX_4X_5X_6X_7X_8X_9X_{10}X_{11}X_{12}$ (SEQ ID No. 419), wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; and $X_{12}$ is present or absent, if present, is C; CDR2 sequence selected from SEQ ID NOs: 18, 24, 30, 45, and 57; and CDR3 sequence selected from SEQ ID NOs: 19, 25, 31, 46, and 58.

In some embodiments, the VH region of the anti-CD38 antibody comprises CDR1 sequence selected from SEQ ID NOs: 1, 4, 6, 8, 9, 11, 14, 17, 20, 23, 26, 29, 32, 35, 38, 41, 44, 47, 50, 53, 56, and 59; CDR2 sequence $X_{13}X_{14}X_{15}X_{16}X_{17}X_{18}X_{19}X_{20}X_{21}X_{22}X_{23}X_{24}X_{25}X_{26}X_{27}X_{28}$ $X_{29}X_{30}X_{31}$, wherein $X_{13}$ is selected from A, G, or S; $X_{14}$ is selected from I, F, Y, V, S, or C; $X_{15}$ is selected from S, I, L, T, or M; $X_{16}$ is selected from G, Y, S, T, L, or V; $X_{17}$ is selected from S, I, K, Y, T, G, or A; $X_{18}$ is selected from G, S, T, P, V, or Y; $X_{19}$ is selected from G, A, D, S, or T; $X_{20}$ is selected from S, T, I, N, or G; $X_{21}$ is selected from T, I, D, N, S, or A; $X_{22}$ is selected from F, Y, N, T, I, or S; $X_{23}$ is selected from Y, D, K, or I; $X_{24}$ is selected from A or Y; $X_{25}$ is selected from D, T, S, N, R, A, or Y; $X_{26}$ is selected from S, W, T, A, or N; $X_{27}$ is selected from V, A, W, N, or S; $X_{28}$ is selected from K, R, Q, A, or W; $X_{29}$ is selected from G, K, or A; $X_{30}$ is present or absent, if present, is selected from G or K; $X_{31}$ is present or absent, if present, is G; and CDR3 sequence selected from SEQ ID NOs: 3, 7, 10, 13, 16, 19, 22, 25, 28, 31, 34, 37, 40, 43, 46, 49, 52, 55, and 58.

In some embodiments, the VH region of the anti-CD38 antibody comprises CDR1 sequence selected from SEQ ID NOs: 1, 4, 6, 8, and 9; CDR2 sequence $AISGSGGSTX_{22}YADSVKG$ (SEQ ID No. 418) in which $X_{22}$ is selected from F or Y; and CDR3 sequence selected from SEQ ID NOs: 3, 7, and 10.

In some embodiments, the VH region of the anti-CD38 antibody comprises CDR1 sequence selected from SEQ ID NOs: 11, 14, 17, 20, 23, 26, 29, 32, 35, 38, 41, 44, 47, 50, 53, and 56; CDR2 sequence $X_{13}X_{14}X_{15}X_{16}X_{17}X_{18}X_{19}X_{20}X_{21}X_{22}X_{23}X_{24}X_{25}X_{26}X_{27}X_{28}$ $X_{29}X_{30}X_{31}$, wherein $X_{13}$ is selected from A, G, or S; $X_{14}$ is selected from I, F, Y, V, S, or C; $X_{15}$ is selected from I, L, M, or T; $X_{16}$ is selected from G, Y, S, T, L, or V; $X_{17}$ is selected from S, I, K, Y, T, G, or A; $X_{18}$ is selected from G, S, T, P, or V; $X_{19}$ is selected from G, A, D, S, or T; $X_{20}$ is selected from S, T, I, N, or G; $X_{21}$ is selected from T, I, D, N, S, or A; $X_{22}$ is selected from Y, N, T, I, or S; $X_{23}$ is selected from Y, D, K, or I; $X_{24}$ is selected from A or Y; $X_{25}$ is selected from T, S, N, R, A, or Y; $X_{26}$ is selected from S, W, T, A, or N; $X_{27}$ is selected from A, W, N, or S; $X_{28}$ is selected from K, R, Q, A, or W; $X_{29}$ is selected from G, K, or A; $X_{30}$ is present or absent, if present, is selected from G or K; and $X_{31}$ is present or absent, if present, is G; and CDR3 sequence selected from SEQ ID NOs: 13, 16, 19, 22, 25, 28, 31, 34, 37, 40, 43, 46, 49, 52, 55, and 58.

In some embodiments, the VH region of the anti-CD38 antibody comprises CDR1 sequence selected from SEQ ID NOs: 11, 14, 26, 32, 35, 38, 41, and 50; CDR2 sequence $X_{13}X_{14}IX_{16}X_{17}X_{18}X_{19}X_{20}X_{21}X_{22}X_{23}X_{24}X_{25}X_{26}X_{27}X_{28}$ $X_{29}X_{30}$, wherein $X_{13}$ is selected from A or G; $X_{14}$ is selected from I, F, Y, V, S, or C; $X_{16}$ is selected from G, Y, S, T, or L; $X_{17}$ is selected from S, I, K, Y, T, or G; $X_{18}$ is selected from G, S, or T; $X_{19}$ is selected from G, A, D, or S; $X_{20}$ is selected from T, I, N, or G; $X_{21}$ is selected from T, I, or D; $X_{22}$ is selected from Y, N, or T; $X_{23}$ is selected from Y or D; $X_{24}$ is selected from A or Y; $X_{25}$ is selected from T, S, N, R, or A; $X_{26}$ is selected from W or T; $X_{27}$ is selected from A or W; $X_{28}$ is selected from K, R, Q, or A; $X_{29}$ is selected from G or K; and $X_{30}$ is present or absent, if present, is G; and CDR3 sequence selected from SEQ ID NOs: 13, 16, 28, 34, 37, 40, 43, and 52.

In some embodiments, the VH region of the anti-CD38 antibody comprises CDR1 sequence selected from SEQ ID NOs: 17, 23, 29, 44, and 56; CDR2 sequence $X_{13}CX_{15}X_{16}X_{17}X_{18}X_{19}X_{20}X_{21}X_{22}X_{23}YX_{25}X_{26}X_{27}X_{28}X_{29}$ $X_{30}X_{31}$, wherein $X_{13}$ is selected from A, or S; $X_{15}$ is selected from I, L, or T; $X_{16}$ is selected from Y or V; $X_{17}$ is selected from S, T, or A; $X_{18}$ is selected from G, P, or V; $X_{19}$ is selected from D, S, or T; $X_{20}$ is selected from S, T, or G; $X_{21}$ is selected from D, N, S, or A; $X_{22}$ is selected from T, I, or S; $X_{23}$ is selected from Y, K, or I; $X_{25}$ is selected from A or Y; $X_{26}$ is selected from S, T, A, or N; $X_{27}$ is selected from W, N, or S; $X_{28}$ is selected from A or W; $X_{29}$ is selected from K or A; $X_{30}$ is present or absent, if present, is selected from G or K; and $X_{31}$ is present or absent, if present, is G; and CDR3 sequence selected from SEQ ID NOs: 19, 25, 31, 46, and 58.

In some instances, the VH region of the anti-CD38 antibody comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58.

In some instances, the VH region of the anti-CD38 antibody comprises CDR1 sequence selected from SEQ ID NOs: 1, 4, 6, 8, and 9; CDR2 sequence selected from SEQ ID NOs: 2 and 5; and CDR3 sequence selected from SEQ ID NOs: 3, 7, and 10.

In some instances, the VH region of the anti-CD38 antibody comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58.

In some instances, the VH region of the anti-CD38 antibody comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52.

In some instances, the VH region of the anti-CD38 antibody comprises CDR1 sequence selected from SEQ ID NOs: 17, 23, 29, 44, and 56; CDR2 sequence selected from SEQ ID NOs: 18, 24, 30, 45, and 57; and CDR3 sequence selected from SEQ ID NOs: 19, 25, 31, 46, and 58.

In some embodiments, the VL region of the anti-CD38 antibody comprises CDR 1, CDR2, and CDR3 sequences selected from Table 2.

TABLE 2

| Light chain complementarity determining regions of exemplary anti-CD38 antibodies | | | | | | |
|---|---|---|---|---|---|---|
| CD38 VL | CDR1 | SEQ ID NO: | CDR2 | SEQ ID NO: | CDR3 | SEQ ID NO: |
| 4618_1[1] | RASQDVNTAVA | 62 | SASFLYS | 63 | QQHYTTPPT | 64 |
| 17E9 | QSSQSVVNANNLS | 65 | LASTLAS | 66 | LGVYDDDGDNA | 67 |
| 17F7 | QASQSVYSDNRLS | 68 | STSSLAS | 69 | QGEFICTSADCFV | 70 |
| 18E4 | QCSQSVYGHNWLA | 71 | RASNLAS | 72 | QGYYNGGSYA | 73 |
| 1E2 | QASQSIYNFLN | 74 | YASTLAF | 75 | QQGWNSGILDNS | 76 |
| 20B5 | QASQSVYNNNYLA | 77 | SASTLAS | 78 | QAYYSGGIYA | 79 |
| 21G2 | QASESIYSNLA | 80 | KASTLAS | 81 | QANHMIVIYGNG | 82 |
| 21H9 | QASENIYSSLA | 83 | RASTLAS | 84 | QTYYGSTSTGFT | 85 |
| 22H6 | QSSESVYKNNYLS | 86 | SASTLAS | 78 | AGGYSGNING | 87 |
| 23A2 | QSSESVYKNNYLS | 86 | SASTLAS | 78 | AGGYTGNING | 88 |
| 23B3 | QSSQSIANSDELA | 89 | DASTLAP | 90 | QGTVYDSGWYA A | 91 |
| 23D1 | QASQTIGSRLA | 92 | SASTLAS | 78 | QSYYYTSTSYPN A | 93 |
| 25C3 | QASQNIGGYLS | 94 | RASTLAS | 84 | QTYYYSGSSRYW A | 95 |
| 25E4 | QASQNIYSNLA | 96 | KASTLAS | 81 | QSYYGATSSSFG YG | 97 |
| 25F12 | QSSQSIANSNEVA | 98 | DASTLAS | 99 | QGTVYDNVWYA A | 100 |

TABLE2-continued

Light chain complementarity determining regions of exemplary anti-CD38 antibodies

| CD38 VL | CDR1 | SEQ ID NO: | CDR2 | SEQ ID NO: | CDR3 | SEQ ID NO: |
|---|---|---|---|---|---|---|
| 26D4 | QASQSVYNNNYLA | 77 | RASNLAS | 72 | QAYYRDPTTA | 101 |
| 27F6 | QASQNIGNYLA | 102 | RASTLAS | 84 | QSYYYTTDDNYR SWA | 103 |

[1]4618_1 shares the same VL CDR1, CDR2, and CDR3 sequence with 4618_5, 4618_12, 4618_1_12, 4618_5_12, 4618_5F_12, 32218_1, 32218_2, 32018_7, G1F4_VL, c05G01, c06F06, c05G07, 81618_3, and 62218_13.

In some embodiments, the VL region of the anti-CD38 antibody comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103. In some instances, the VL region comprises CDR1 sequence selected from SEQ ID NOs: 65, 68, 80, 86, 89, 92, and 98; CDR2 sequence selected from SEQ ID NOs: 66, 69, 81, 78, 90, and 99; and CDR3 sequence selected from SEQ ID NOs: 67, 70, 82, 87, 88, 91, 93, and 100. In some instances, the VL region comprises CDR1 sequence selected from SEQ ID NOs: 71, 77, 83, 94, and 102; CDR2 sequence selected from SEQ ID NOs: 72, 78, and 84; and CDR3 sequence selected from SEQ ID NOs: 73, 79, 85, 95, and 103.

In some embodiments, the anti-CD38 antibody comprises a VH region and a VL region, wherein the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L; and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some embodiments, the anti-CD38 antibody comprises a VH region and a VL region, wherein the VH region comprises CDR1 sequence selected from SEQ ID NOs: 1, 4, 6, 8, and 9; CDR2 sequence selected from SEQ ID NOs: 2 and 5; and CDR3 sequence AKRGTYX$_{38}$YSX$_{41}$PTGFDY (SEQ ID No. 421), in which X$_{38}$ is selected from A or G and X$_{41}$ is selected from F or Y; and wherein the VL region comprises CDR1 sequence consisting of SEQ ID NO: 62, CDR2 sequence consisting of SEQ ID NO: 63, and CDR3 sequence consisting of SEQ ID NO: 64.

In some embodiments, the anti-CD38 antibody comprises a VH region and a VL region, wherein the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}X_{48}X_{49}$, in which $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, or F; $X_{45}$ is present or absent, if present, is selected from L, F, E, S, or N; $X_{46}$ is present or absent, if present, is selected from S, L, or R; $X_{47}$ is present or absent, if present, is L; $X_{48}$ is present or absent, if present, is D; and $X_{49}$ is present or absent, if present, is L; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some embodiments, the anti-CD38 antibody comprises a VH region and a VL region, wherein the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence $X_{32}X_{33}X_{34}X_{35}X_{36}X_{37}X_{38}X_{39}X_{40}X_{41}X_{42}X_{43}X_{44}X_{45}$, in which $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and X$_{45}$ is present or absent, if present, is selected from L or F, and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some embodiments, the anti-CD38 antibody comprises a VH region and a VL region, wherein the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence $AX_{33}X_{34}X_{35}X_{36}X_{37}X_{38}X_{39}X_{40}X_{41}X_{42}X_{43}X_{44}X_{45}X_{46}$ (SEQ ID No. 422), in which $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L, and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some embodiments, the anti-CD38 antibody comprises a VH region and a VL region, wherein the VH region comprises CDR1 sequence $X_1GX_2X_3X_4X_5X_6X_7X_8X_9X_{10}X_{11}X_{12}$, wherein $X_1$ is present or absent, if present, is S; $X_2$ is selected from F or I; $X_3$ is selected from P, S, or D; $X_4$ is selected from F, L, or A; $X_5$ is selected from D, G, S, N, or T; $X_6$ is selected from V, A, T, R, S, I, or N; $X_7$ is selected from Y, I, N, R, A, G, or D; $X_8$ is selected from A, Y, D, G, W, C, or T; $X_9$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58, and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some embodiments, the anti-CD38 antibody comprises a VH region and a VL region, wherein the VH region comprises CDR1 sequence $GFPFX_5X_6YAMS$ (SEQ ID No. 423), in which $X_5$ is selected from D or G and $X_6$ is selected from V, A, or T; CDR2 sequence selected from SEQ ID NOs: 2 and 5; and CDR3 sequence selected from SEQ ID NOs: 3, 7, and 10; and wherein the VL region comprises CDR1 sequence consisting of SEQ ID NO: 62, CDR2 sequence consisting of SEQ ID NO: 63, and CDR3 sequence consisting of SEQ ID NO: 64.

In some embodiments, the anti-CD38 antibody comprises a VH region and a VL region, wherein the VH region comprises CDR1 sequence $X_1GX_2X_3X_4X_5X_6X_7X_8X_9X_{10}X_{11}X_{12}$, wherein $X_1$ is present or absent, if present, is S; $X_2$ is selected from F or I; $X_3$ is selected from S or D; $X_4$ is selected from L, F, or A; $X_5$ is selected from S, N, or T; $X_6$ is selected from R, S, N, I, or T; $X_7$ is selected from Y, I, N, R, A, D, or G; $X_8$ is selected from Y, D, G, A, W, T, or C; $X_9$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some embodiments, the anti-CD38 antibody comprises a VH region and a VL region, wherein the VH region comprises CDR1 sequence $GFSLX_5X_6X_7X_8X_9X_{10}X_{11}$ (SEQ ID NO: 426), wherein $X_5$ is selected from S or N; $X_6$ is selected from R, S, or N; $X_7$ is selected from Y, I, or N; $X_8$ is selected from Y, D, G, or A; $X_9$ is selected from V, M, or I; $X_{10}$ is selected from T, S, or M; and $X_{11}$ is present or absent, if present, is C; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52; and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some embodiments, the anti-CD38 antibody comprises a VH region and a VL region, wherein the VH region comprises CDR1 sequence $GFSX_4X_5X_6X_7X_8X_9X_{10}X_{11}X_{12}$ (SEQ ID NO: 419), wherein $X_4$ is selected from F or A; $X_5$ is selected from S, T, or N; $X_6$ is selected from S, T, or N; $X_7$ is selected from Y, R, A, or G; $X_8$ is selected from W, Y, or C; $X_9$ is selected from I, W, Y, or D; $X_{10}$ is selected from C, I, Y, or M; $X_{11}$ is present or absent, if present, is selected from C or M; and $X_{12}$ is present or absent, if present, is C; CDR2 sequence selected from SEQ ID NOs: 18, 24, 30, 45, and 57; and CDR3 sequence selected from SEQ ID NOs: 19, 25, 31, 46, and 58; and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some embodiments, the anti-CD38 antibody comprises a VH region and a VL region, wherein the VH region comprises CDR1 sequence selected from SEQ ID NOs: 1, 4, 6, 8, 9, 11, 14, 17, 20, 23, 26, 29, 32, 35, 38, 41, 44, 47, 50, 53, 56, and 59; CDR2 sequence $X_{13}X_{14}X_{15}X_{16}X_{17}X_{18}X_{19}X_{20}X_{21}X_{22}X_{23}X_{24}X_{25}X_{26}X_{27}X_{28}X_{29}X_{30}X_{31}$, wherein $X_{13}$ is selected from A, G, or S; $X_{14}$ is selected from I, F, Y, V, S, or C; $X_{15}$ is selected from S, I, L, T, or M; $X_{16}$ is selected from G, Y, S, T, L, or V; $X_{17}$ is selected from S, I, K, Y, T, G, or A; $X_{18}$ is selected from G, S, T, P, V, or Y; $X_{19}$ is selected from G, A, D, S, or T; $X_{20}$ is selected from S, T, I, N, or G; $X_{21}$ is selected from T, I, D, N, S, or A; $X_{22}$ is selected from F, Y, N, T, I, or S; $X_{23}$ is selected from Y, D, K, or I; $X_{24}$ is selected from A or Y; $X_{25}$ is selected from D, T, S, N, R, A, or Y; $X_{26}$ is selected from S, W, T, A, or N; $X_{27}$ is selected from V, A, W, N, or S; $X_{28}$ is selected from K, R, Q, A, or W; $X_{29}$ is selected from G, K, or A; $X_{30}$ is present or absent, if present, is selected from G or K; $X_{31}$ is present or absent, if present, is G; and CDR3 sequence selected from SEQ ID NOs: 3, 7, 10, 13, 16, 19, 22, 25, 28, 31, 34, 37, 40, 43, 46, 49, 52, 55, and 58; and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some embodiments, the anti-CD38 antibody comprises a VH region and a VL region, wherein the VH region comprises CDR1 sequence selected from SEQ ID NOs: 1, 4, 6, 8, and 9; CDR2 sequence AISGSGGSTX$_{22}$YADSVKG (SEQ ID No. 418) in which X$_{22}$ is selected from F or Y; and CDR3 sequence selected from SEQ ID NOs: 3, 7, and 10; and wherein the VL region comprises CDR1 sequence consisting of SEQ ID NO: 62, CDR2 sequence consisting of SEQ ID NO: 63, and CDR3 sequence consisting of SEQ ID NO: 64.

In some embodiments, the anti-CD38 antibody comprises a VH region and a VL region, wherein the VH region comprises CDR1 sequence selected from SEQ ID NOs: 11, 14, 17, 20, 23, 26, 29, 32, 35, 38, 41, 44, 47, 50, 53, and 56; CDR2 sequence X$_{13}$X$_{14}$X$_{15}$X$_{16}$X$_{17}$X$_{18}$X$_{19}$X$_{20}$X$_{21}$X$_{22}$X$_{23}$X$_{24}$ X$_{25}$X$_{26}$X$_{27}$X$_{28}$X$_{29}$X$_{30}$X$_{31}$, wherein X$_{13}$ is selected from A, G, or S; X$_{14}$ is selected from I, F, Y, V, S, or C; X$_{15}$ is selected from I, L, M, or T; X$_{16}$ is selected from G, Y, S, T, L, or V; X$_{17}$ is selected from S, I, K, Y, T, G, or A; X$_{18}$ is selected from G, S, T, P, or V; X$_{19}$ is selected from G, A, D, S, or T; X$_{20}$ is selected from S, T, I, N, or G; X$_{21}$ is selected from T, I, D, N, S, or A; X$_{22}$ is selected from Y, N, T, I, or S; X$_{23}$ is selected from Y, D, K, or I; X$_{24}$ is selected from A or Y; X$_{25}$ is selected from T, S, N, R, A, or Y; X$_{26}$ is selected from S, W, T, A, or N; X$_{27}$ is selected from A, W, N, or S; X$_{28}$ is selected from K, R, Q, A, or W; X$_{29}$ is selected from G, K, or A; X$_{30}$ is present or absent, if present, is selected from G or K; and X$_{31}$ is present or absent, if present, is G; and CDR3 sequence selected from SEQ ID NOs: 13, 16, 19, 22, 25, 28, 31, 34, 37, 40, 43, 46, 49, 52, 55, and 58; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some embodiments, the anti-CD38 antibody comprises a VH region and a VL region, wherein the VH region comprises CDR1 sequence selected from SEQ ID NOs: 11, 14, 26, 32, 35, 38, 41, and 50; CDR2 sequence X$_{13}$X$_{14}$IX$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$ X$_{29}$X$_{30}$, wherein X$_{13}$ is selected from A or G; X$_{14}$ is selected from I, F, Y, V, S, or C; X$_{16}$ is selected from G, Y, S, T, or L; X$_{17}$ is selected from S, I, K, Y, T, or G; X$_{18}$ is selected from G, S, or T; X$_{19}$ is selected from G, A, D, or S; X$_{20}$ is selected from T, I, N, or G; X$_{21}$ is selected from T, I, or D; X$_{22}$ is selected from Y, N, or T; X$_{23}$ is selected from Y or D; X$_{24}$ is selected from A or Y; X$_{25}$ is selected from T, S, N, R, or A; X$_{26}$ is selected from W or T; X$_{27}$ is selected from A or W; X$_{28}$ is selected from K, R, Q, or A; X$_{29}$ is selected from G or K; and X$_{30}$ is present or absent, if present, is G; and CDR3 sequence selected from SEQ ID NOs: 13, 16, 28, 34, 37, 40, 43, and 52; and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some embodiments, the anti-CD38 antibody comprises a VH region and a VL region, wherein the VH region comprises CDR1 sequence selected from SEQ ID NOs: 17, 23, 29, 44, and 56; CDR2 sequence X$_{13}$CX$_{15}$X$_{16}$X$_{17}$X$_{18}$X$_{19}$X$_{20}$X$_{21}$X$_{22}$X$_{23}$YX$_{25}$X$_{26}$X$_{27}$X$_{28}$X$_{29}$ X$_{30}$X$_{31}$, wherein X$_{13}$ is selected from A, or S; X$_{15}$ is selected from I, L, or T; X$_{16}$ is selected from Y or V; X$_{17}$ is selected from S, T, or A; X$_{18}$ is selected from G, P, or V; X$_{19}$ is selected from D, S, or T; X$_{20}$ is selected from S, T, or G; X$_{21}$ is selected from D, N, S, or A; X$_{22}$ is selected from T, I, or S; X$_{23}$ is selected from Y, K, or I; X$_{25}$ is selected from A or Y; X$_{26}$ is selected from S, T, A, or N; X$_{27}$ is selected from W, N, or S; X$_{28}$ is selected from A or W; X$_{29}$ is selected from K or A; X$_{30}$ is present or absent, if present, is selected from G or K; and X$_{31}$ is present or absent, if present, is G; and CDR3 sequence selected from SEQ ID NOs: 19, 25, 31, 46, and 58; and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some instances, the anti-CD38 antibody comprises a VH region and a VL region, wherein the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58; and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some instances, the anti-CD38 antibody comprises a VH region and a VL region, wherein the VH region comprises CDR1 sequence selected from SEQ ID NOs: 1, 4, 6, 8, and 9; CDR2 sequence selected from SEQ ID NOs: 2 and 5; and CDR3 sequence selected from SEQ ID NOs: 3, 7, and 10; and wherein the VL region comprises CDR1 sequence consisting of SEQ ID NO: 62, CDR2 sequence consisting of SEQ ID NO: 63, and CDR3 sequence consisting of SEQ ID NO: 64.

In some instances, the anti-CD38 antibody comprises a VH region and a VL region, wherein the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some instances, the anti-CD38 antibody comprises a VH region and a VL region, wherein the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52; and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some instances, the anti-CD38 antibody comprises a VH region and a VL region, wherein the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence selected from SEQ ID NOs: 19, 25, 31, 46, and 58; and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some embodiments, the anti-CD38 antibody comprises a VH region and a VL region in which the sequence of the VH region comprises about 80%, 85%, 90%, 95%, 96%

97%, 98%, 99%, or 100% sequence identity to SEQ ID NOs: 104-128 and the sequence of the VL region comprises about 80%, 85%, 90%, 95%, 96% 97%, 98%, 99%, or 100% sequence identity to SEQ ID NOs: 130-154.

In some embodiments, the VH region comprises a sequence selected from Table 3 and the VL region comprises a sequence selected from Table 4.

TABLE3

Heavy chain variable domains of exemplary anti-CD38 antibodies. The underlined regions denote the respective CDR1, CDR2, or CDR3 sequences.

| NAME | VH SEQUENCE | SEQ ID NO: |
|---|---|---|
| 4618_1 | EVQLLESGGGLVQPGGSLRLSCAASGFPFDVYAMSWVRQAPGKGLEW VSAISGSGGSTFYADSVKGRFTISRDNSKNTLYLQMNSLRAEDTAVYYC AKRGTYAYSFPTGFDYWGQGTLVTVSS | 104 |
| 4618_5 | EVQLLESGGGLVQPGGSLRLSCAASGFPFDAYAMSWVRQAPGKGLEW VSAISGSGGSTYYADSVKGRFTISRDNSKNTLYLQMNSLRAEDTAVYYC AKRGTYAYSFPTGFDYWGQGTLVTVSS | 105 |
| 4618_12 | EVQLLESGGGLVQPGGSLRLSCAASGFPFGVYAMSWVRQAPGKGLEW VSAISGSGGSTFYADSVKGRFTISRDNSKNTLYLQMNSLRAEDTAVYYC AKRGTYAYSYPTGFDYWGQGTLVTVSS | 106 |
| 4618_1_12 | EVQLLESGGGLVQPGGSLRLSCAASGFPFDVYAMSWVRQAPGKGLEW VSAISGSGGSTFYADSVKGRFTISRDNSKNTLYLQMNSLRAEDTAVYYC AKRGTYAYSYPTGFDYWGQGTLVTVSS | 107 |
| 4618_5_12 | EVQLLESGGGLVQPGGSLRLSCAASGFPFDAYAMSWVRQAPGKGLEW VSAISGSGGSTYYADSVKGRFTISRDNSKNTLYLQMNSLRAEDTAVYYC AKRGTYAYSYPTGFDYWGQGTLVTVSS | 108 |
| 4618_5F_12 | EVQLLESGGGLVQPGGSLRLSCAASGFPFDAYAMSWVRQAPGKGLEW VSAISGSGGSTFYADSVKGRFTISRDNSKNTLYLQMNSLRAEDTAVYYC AKRGTYAYSYPTGFDYWGQGTLVTVSS | 109 |
| 32218_1 | EVQLLESGGGLVQPGGSLRLSCAASGFPFGVYAMSWVRQAPGKGLEW VSAISGSGGSTFYADSVKGRFTISRDNSKNTLYLQMNSLRAEDTAVYYC AKRGTYAYSFPTGFDYWGQGTLVTVSS | 110 |
| 322182 | EVQLLESGGGLVQPGGSLRLSCAASGFPFDTYAMSWVRQAPGKGLEW VSAISGSGGSTYYADSVKGRFTISRDNSKNTLYLQMNSLRAEDTAVYYC AKRGTYAYSFPTGFDYWGQGTLVTVSS | 111 |
| 32018_7 | EVQLLESGGGLVQPGGSLRLSCAASGFPFGTYAMSWVRQAPGKGLEW VSAISGSGGSTFYADSVKGRFTISRDNSKNTLYLQMNSLRAEDTAVYYC AKRGTYGYSFPTGFDYWGQGTLVTVSS | 112 |
| 17E9 | QSVEESGGRLVTPGTPLTLTCTASGFSLSRYYVTWVRQAPGKGLEWIGII YISGTTYYATWAKGRFTISKSATTVDLRIASPTTEDTATYFCAAAWPVG TYVLPLWGPGTLVTVSS | 113 |
| 17F7 | QSVEESGGRLVTPGTPLTLTCTASGFSLSSYYMSWVRQAPGKGLEWIGF ISKTAITYYASWARGRFTISKTSTAVDLKITSPTTEDTATYFCARVDAYS AGDLWGPGTLVTVSS | 114 |
| 18E4 | QSLEESGGDLVKPGASLTLTCTASGFSFNNYWICWIRQAPGKGLEWVA CIYSPSGDIKYYANWAKGRFTVSKTSSTTVTLQMTSLTGADTATYFCAR ELSGSSYEGYFESWGPGTLVTVSS | 115 |
| 1E2 | QSVEESGGRLVTPGTPLTLTCTVSGIDLNSYAMGWVRQAPGKGLKYIGI MTSGGNIYYANWAKGRFTISKTSTTVDLRITSPTTEDTATYFCAREREFY GGGTSGSRLDLWGQGTLVTVSS | 116 |
| 20B5 | QSLEESGGDLVKPGASLTLTCTASGFSFSSRYWICWVRQAPGKGLEWIA CIVAGTTNTYYASWAKGRFTISKTSSTTVTLQMTSLTAADTATYFCAGD PRTGSNVGYFNLWGPGTLVTVSS | 117 |
| 21G2 | QSVEESGGRLVTPGTPLTLTCTVSGFSLSNYGVSWVRQAPGKGLEWIGY ILTSGGTYYANWAQGRFTISKTSTTVDLKITSPTTEDTATYFCGRPKDSD SSAFVSLWGPGTLVTVSS | 118 |
| 21H9 | QSLEESGGDLVKPGASLTLTCTASGFSATTYYYYMCWVRQAPGKGLE WIACTYTGDGATYYATWAKGRFTISKTSSTTVTLQMTSLTAADTATYF CARSADNSIYYGYFNLWGPGTLVTVSS | 119 |

TABLE3-continued

Heavy chain variable domains of exemplary anti-CD38 antibodies. The underlined
regions denote the respective CDR1, CDR2, or CDR3 sequences.

| NAME | VH SEQUENCE | SEQ ID NO: |
|------|-------------|------------|
| 22H6 | QSVEESGGRLVTPGTPLTLTCTVSGFSLSNNAISWVRQAPGKGLQWIGSI YGSGNTYYATWAKGRFTVSKTSTTVDLKINSPTTEDTATYFCAREGAG SSWGFNLWGPGTLVTVSS | 120 |
| 23A2 | QSVEESGGRLVTPGTPLTLTCTVSGFSLNNNAISWVRQAPGKGLQWIGS IYGTGNTYYATWAKGRFSVSKTSTTVDLKINSPTTEDTATYFCATEGAG SIWGFNLWGPGTLVTVSS | 121 |
| 23B3 | QSVEESGGRLVTPGTPLTLTCTVSGFSLSNYDMTWVRQAPGRGLEWIG VISSGDNTNYARWAKGRFTISKTSSTTVDLKITSPTTEDTATYFCARILY NKGRYYFTFWGPGTLVTVSS | 122 |
| 23D1 | QELVESGGGLFQPGGSLALTCKASGFSLSNIYVMCWVRQAPGKGLEWI ACIGTGSGDTDYATWAKGRFTISKTSSTTVTLQMTSLTAADTATYFCAR DPGAGTWNLWGPGTLVTVSS | 123 |
| 25C3 | QEQLEESGGDLVKPGASLTLTCKASGFSFSSAYDMCWVRQAPGKGLE WVACLYTVSSDSIYYASWAKGRFTISRTSSTTVTLQMTSLTAADTATYF CARDGDYFALWGPGTLVTVSS | 124 |
| 25E4 | QSLEESGGRLVTPGTPLTLTCTVSGIDLSIYTMAWVRQAPGKGLEYIGIIS GYGTTYYATWAKGRFIVSKTSTTVDLKITSPTTEDTATYFCVRTTVQST DLWGPGTLVTVSS | 125 |
| 25F12 | RSLEESGGRLVTPGTPLTLTCTTSGFSLSSYDMSWVRQAPGKGLEWIGY ITYGGNIYYATWAKGRFTTSKTSTTVDLKITSPTTEDTATYFCARTLYTG GRYYFSLWGPGTLVTVSS | 126 |
| 26D4 | QEQLEESGGDLVKPEGSLTLTCTASGFSFSNDAICWVRQAPGKGLEWIA CIYAGSGNTYYASWAKGRFSISKTSSTTVTLQMTSLTVADTATYFCASA DTIDYFNLWGPGTLVTVSS | 127 |
| 27F6 | QSLEESGGGLVKPGASLTLTCKASGFSFSSGCDMCWVRQAPGKGLEWI SCIYTGSGSTYYANWAKGRFTISRTSSTTVTLQMTSLTAADTATYFCAG DSDYLGLWGPGTLVTVSS | 128 |
| G1F4_VH | EVQLLESGGGLVQPGGSLRLSCAASGFTFSTYAMSWVRQAPGKGLEW VSAISGSGGSTYYADSVKGRFTISRDNSKNTLYLQMNSLRAEDTAVYYC AKRGTYGYSFPTGFDYWGQGTLVTVSS | 129 |

TABLE4

Light chain variable domains of exemplary anti-CD38 antibodies. The underlined
regions denote the respective CDR1, CDR2, or CDR3 sequences.

| NAME | VL SEQUENCE | SEQ ID NO: |
|------|-------------|------------|
| 4618_1 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 130 |
| 4618_5 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 131 |
| 4618_12 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 132 |
| 4618_1_12 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 133 |
| 4618_5_12 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 134 |
| 4618_5F_12 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 135 |

TABLE4-continued

Light chain variable domains of exemplary anti-CD38 antibodies. The underlined
regions denote the respective CDR1, CDR2, or CDR3 sequences.

| NAME | VL SEQUENCE | SEQ ID NO: |
|---|---|---|
| 32218_1 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 136 |
| 32218_2 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 137 |
| 32018_7 | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 138 |
| 17E9 | AAVLTQTPSPVSAAVGGTVTIKCQSSQSVVNANNLSWYQQKPGQPPKL LIYLASTLASGVPSRFSGSGSGTQFTLTISSVQSDDAATYYCLGVYDDDG DNAFGGGTEVVVK | 139 |
| 17F7 | AQVLTQTPSSVSAAVGGTVTINCQASQSVYSDNRLSWFQQKSGQPPKL LIYSTSSLASGVPSRFSGSGSGTQFTLTISGVQSDDAASYYCQGEFICTSA DCFVFGGGTEVVVK | 140 |
| 18E4 | AQVLTQTPSSVSAAVGGTVTINCQCSQSVYGHNWLAWYQHKPGQPPK LLMYRASNLASGVPSRFKGSGSGSQFTLTIGEVQSDDAATYYCQGYYN GGSYAFGGGTEVVVR | 141 |
| 1E2 | AYDMTQTPASVEAAVGGTVTIKCQASQSIYNFLNWYQQKPGQPPKLLI YYASTLAFGVPSRFKGSGSGTEYTLTISGVESADAATYYCQQGWNSGIL DNSFGGGTEVVVK | 142 |
| 20B5 | AQVLTQTPSPVSAAVGGTVTINCQASQSVYNNNYLAWFQQKPGQPPKL LIYSASTLASGVPSRFKGSGSGTQFTLTISEVQSDDAATYYCQAYYSGGI YAFGGGTEVVVK | 143 |
| 21G2 | ADVVMTQTPASVSEPVGGTVTINCQASESIYSNLAWYQQKPGQPPKLLI YKASTLASGVSSRFKGSGSGTEFTLTISDLESADAATYYCQANHMIVIY GNGFGGGTEVVVK | 144 |
| 21H9 | AFELTQTPFSVSEPVGGTVTINCQASENIYSSLAWYQQKPGQPPKLLIYR ASTLASGVPSRFSGSGSGTEFTLTISGVQSDDAATYYCQTYYGSTSTGFT FGGGTEVVVK | 145 |
| 22H6 | AQVLTQTASSVSAAVGGTVTISCQSSESVYKNNYLSWYQQKPGQPLKC LIYSASTLASGVPSRFKGSGSGTQFTLTISDLESDDAATYYCAGGYSGNI NGFGGGTEVVVK | 146 |
| 23A2 | AQVLTQTASSVSAAVGGTVTISCQSSESVYKNNYLSWYQQKPGQPPKG LIYSASTLASGVPSRFKGSGSGTQFTLTISDLESDDAATYYCAGGYTGNI NGFGGGTEVVVK | 147 |
| 23B3 | AQVLTQTPSSVSAAVGGTVTINCQSSQSIANSDELAWYQQKPGQPPKLL IYDASTLAPGVPSRFSGSGSGTQFTLTISGVQSDDAATYYCQGTVYDSG WYAAFGGGTEVVVK | 148 |
| 23D1 | ADIVMTQTPSSVEAAVGGTVTIKCQASQTIGSRLAWYQQKPGQPPKLLI YSASTLASGVSSRFKGSGSGTQFTLTISDLDSADAATYYCQSYYYTSTS YPNAFGGGTEVVVK | 149 |
| 25C3 | ADIVMTHTPASVEAAVGGTVTIKCQASQNIGGYLSWYQQKPGQRPKLL IYRASTLASGVPSRFKGSGSGTQFTLTISDLESADAATYYCQTYYYSGSS RYWAFGGGTEVVVK | 150 |
| 25E4 | ADIVMTQTPASVEAAVGGTVTINCQASQNIYSNLAWYQQKPGQRPKLL IYKASTLASGVSSRFKGSGSGTEFTLTISDLASADAATYYCQSYYGATSS SFGYGFGGGTEVVVK | 151 |
| 25F12 | AQVLTQTPSSVSAVVGGTVTINCQSSQSIANSNEVAWYQQKLGQPPKLL IYDASTLASGVPSRFSGSGSGTQFTLIISGVQSDDAATYYCQGTVYDNV WYAAFGGGTEVVVK | 152 |
| 26D4 | AQVLTQTPSPVSAAVGGTVTINCQASQSVYNNNYLAWYQQKPGQPPKL LIYRASNLASGVPSRFSASGSGTQFTLTISEVQSDDAATYYCQAYYRDPT TAFGGGTEVVVK | 153 |

TABLE4-continued

Light chain variable domains of exemplary anti-CD38 antibodies. The underlined
regions denote the respective CDR1, CDR2, or CDR3 sequences.

| NAME | VL SEQUENCE | SEQ ID NO: |
|------|-------------|------------|
| 27F6 | ADIVMTQTPSSVEAAVGGTVTIKCQASQNIGNYLAWYQQKPGQPPKVL TYRASTLASGVPSRFKGSGSGTHFTLTISDLESADAATYYCQSYYYTTDD NYRSWAFGGGTEVVVK | 154 |
| G1F4_VL | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPPTFG QGTKVEIK | 155 |

In some embodiments, an anti-CD38 antibody described supra is a frill-length antibody. In other embodiments, the anti-CD38 antibody is a binding fragment. In some instances, the anti-CD38 antibody comprises an antibody or binding fragment thereof, a chimeric antibody or binding fragment thereof, a monoclonal antibody or binding fragment thereof, or a bispecific antibody or binding fragment thereof. In some cases, the anti-CD38 antibody comprises a monovalent Fab, a divalent Fab'2, a single-chain variable fragment (scFv), a diabody, a minibody, a nanobody, a single-domain antibody (sdAb), or a camelid antibody or binding fragment thereof.

In some embodiments, the anti-CD38 antibody comprises a bispecific antibody or binding fragment thereof. In some instances, the bispecific antibody or binding fragment thereof is a bispecific antibody conjugate, a hybrid bispecific IgG, a variable domain only bispecific antibody, a CH1/CL fusion protein, a Fab fusion protein, a non-immunoglobulin fusion protein, a Fc-modified IgG, an appended & Fc-modified IgG, a modified Fc and CH3 fusion protein, an appended IgG-HC fusion, a Fc fusion, a CH3 fusion, an IgE/IgM CH2 fusion, or a F(ab')2 fusion.

In some embodiments, a bispecific antibody or binding fragment includes a Knobs-into-Holes (KIH), Asymmetric Re-engineering Technology-immunoglobulin (ART-Ig), Triomab quadroma, bispecific monoclonal antibody (BiMAb, BsmAb, BsAb, bsMab, BS-Mab, or Bi-MAb), FcAAdp, XmAb, Azymetric, Bispecific Engagement by Antibodies based on the T-cell receptor (BEAT), Bispecific T-cell Engager (BiTE), Biclonics, Fab-scFv-Fc, Two-in-one/Dual Action Fab (DAF), FinomAb, scFv-Fc-(Fab)-fusion, Dock-aNd-Lock (DNL), Adaptir (previously SCORPION), Tandem diAbody (TandAb), Dual-affinity-ReTargeting (DART), or nanobody.

In some embodiments, a variable domain only bispecific antibody comprises a tandem scFv (taFv), triplebody, diabody (Db), dsDb, Db(KIH), scDb, dsFv-dsFv', tandAbs, triple heads, tandem dAb/VHH, triple dAb/VHH, or tetravalent dAb/VHH.

In some embodiments, a CH1/CL fusion protein comprises a scFv2-CH1/CL or VHH2-CH1/CL.

In some instances, Fab fusion protein comprises a Fab-scFv (bibody), Fab-scFv2 (tribody), Fab-Fv, Fab-dsFv, Fab-VHH, or orthogonal Fab-Fab.

In some instances, a non-immunoglobulin fusion protein comprises a scFv2-albumin, scDb-albumin, taFv-albumin, taFv-toxin, miniantibody, DNL-Fab2, DNL-Fab2-scFv, DNL-Fab2-IgG-cytokine2, or ImmTAC (TCR-scFv).

In some instances, a Fc-modified IgG comprises a IgG (KIH), IgG (KIH) common LC, ZW1 IgG common LC, Biclonics common LC, CrossMAb, scFab-IgG (KIH), Fab-scFab-IgG (KIH), orthogonal Fab IgG (KIH), DuetMab, CH3 charge pair+CH1/CL charge pair, hinge/CH3 charge pair, DuoBody, four-in-one-CrossMab (KIH), LUZ-Y common LC, LUZ-Y scFab-IgG, or FcFc.

In some instances, an appended & Fc-modified IgG comprises an IgG(KIH)-Fv, IgG(HA-TF-FV), IgG(KIH)-scFab, scFab-Fc(KIH)-scFv2, scFab-Fc(KIH)-scFv, half DVD-Ig, Dual Variable Domain-immunoglobulin (DVD-Ig), or CrossMab-Fab.

In some cases, a modified Fc and CH3 fusion protein comprises a scFv-Fc (KIH), scFv-Fc (CH3 charge pair), scFv-FC (EW-RVT), scFv-Fc (HA-TF), scFv-Fc (SEED-body), taFv-Fc(KIH), scFv-Fc(KIH)-Fv, Fab-Fc(KIH)-scFv, Fab-scFv-Fc(KIH), Fab-scFv-Fc(BEAT), DART-Fc, scFv-CH3(KIH), or TriFabs.

In some cases, an appended IgG-HC fusion antibody comprises IgG-HC-scFv, IgG-dAb, IgG-taFv, IgG-Cross-Fab, IgG-orthogonal Fab, IgG-(CaCp) Fab, scFv-HC-IgG, tandem Fab-IgG, Fab-IgG(CaCpFab), Fab-IgG(CR3), or Fab-hinge-IgG(CR3).

In some cases, an appended IgG-LC fusion antibody comprises IgG-scFv(LC), scFv(LC)-IgG, or dAb-IgG.

In some cases, an appended IgG-HC & LC fusion antibody comprises DVD-Ig, TVD-Ig, CODV-Ig, scFv4-IgG, or Zybody.

In some instances, a Fc fusion antibody comprises Di-diabody, scDb-Fc, taFv-Fc, scFv-Fc-scFv, HCAb-VHH, Fab-scFv-Fc, scFv4-Ig, or scFv2-Fcab.

In some instances, a CH3 fusion antibody comprises Di-diabody or scDb-CH3.

In some instances, an IgE/IgM CH2 fusion antibody comprises scFv-EHD2-scFv or scFv-MHD2-scFv.

In some instances, F(ab')2 fusion antibody comprises F(ab')$_2$-scFv$_2$.

In some instances, a CH1/CL fusion protein comprises scFv2-CH1-hinge/CL.

In some instances, a modified IgG comprises DAF (two-in-one-IgG), DutaMab, or mAb$^2$.

In some cases, a non-immunoglobulin fusion antibody comprises DNL-Fab4-IgG.

Figure 1B:
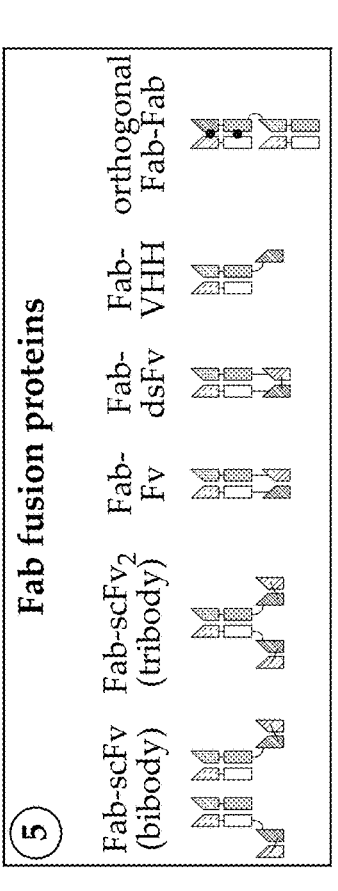
Figure 1B:
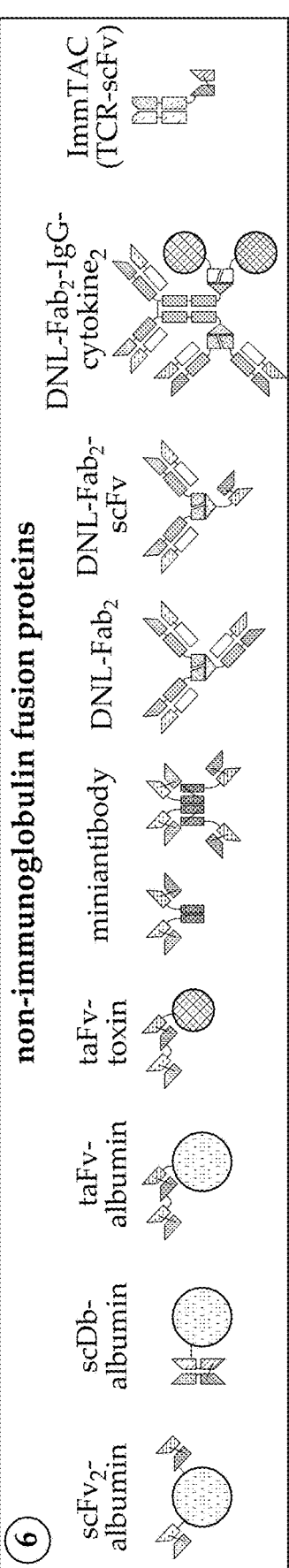
Figure 1C:
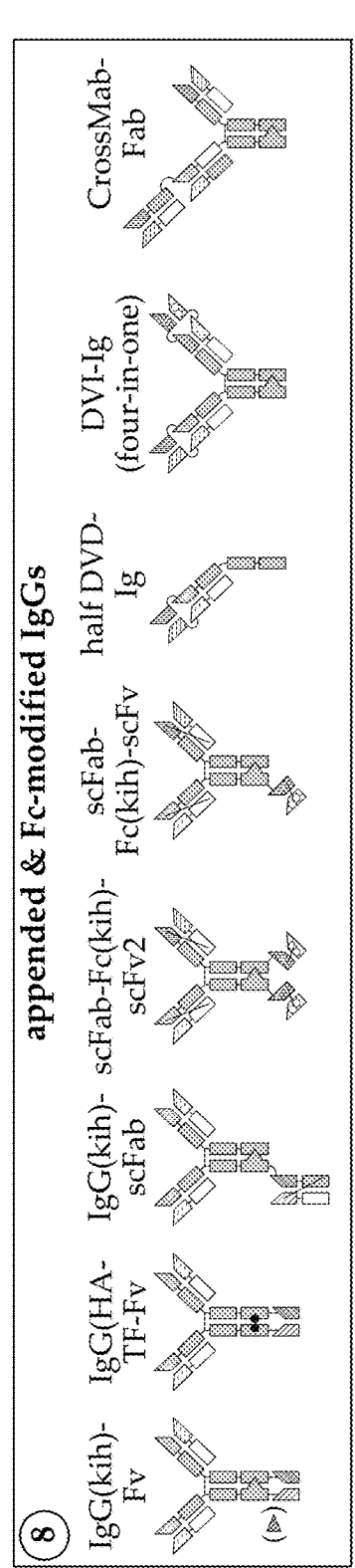
Figure 1D:
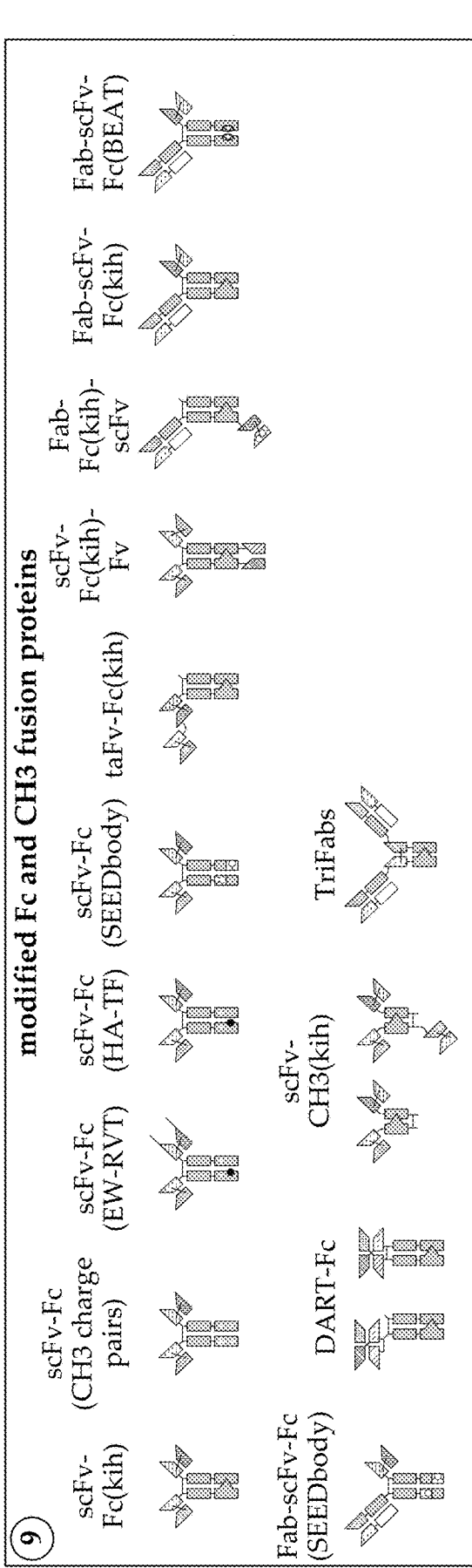
Figure 1E:
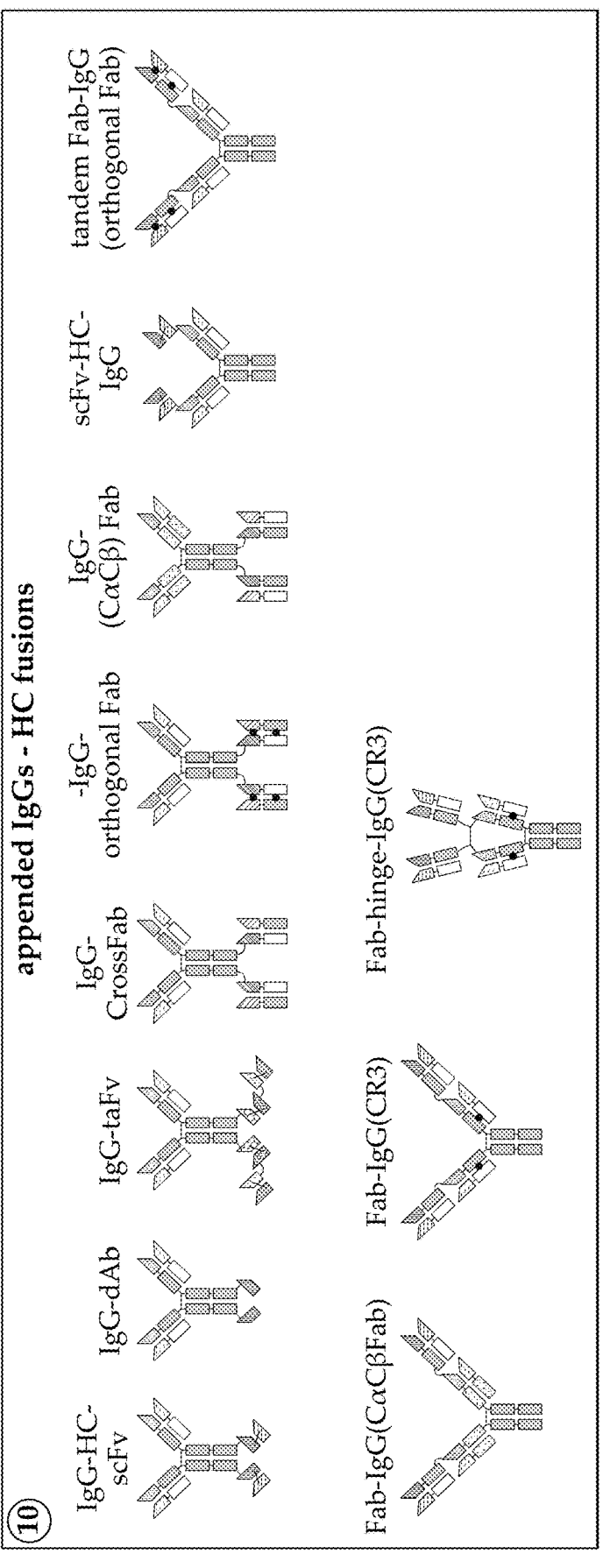
Figure 1F:
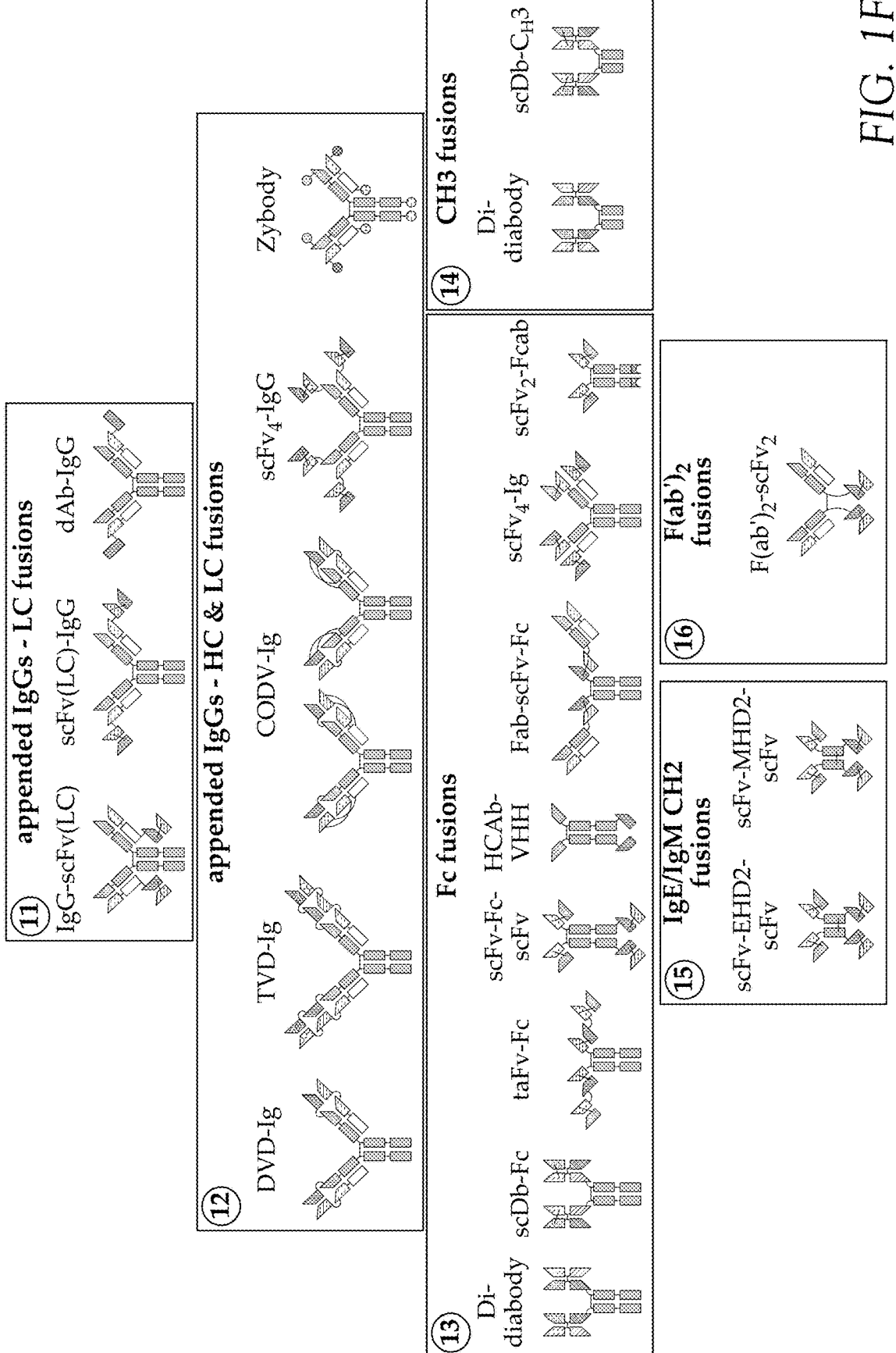
Figure 1G:
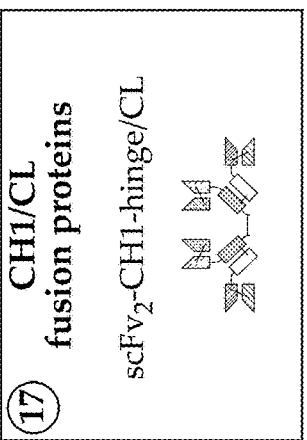
Figure 1G:
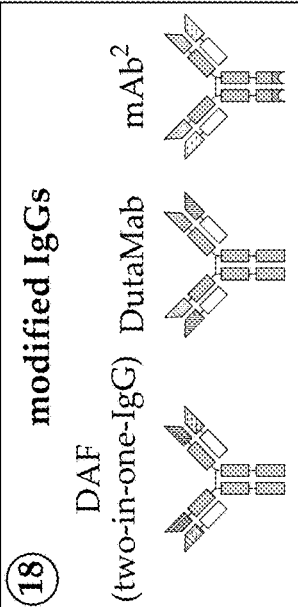
Figure 1G:
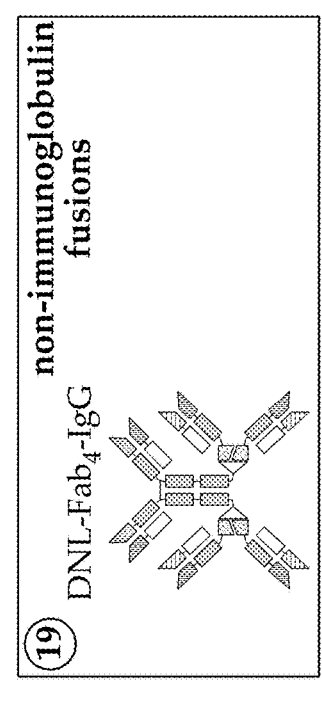

In some instances, the anti-CD38 antibody comprises a bispecific antibody or binding fragment thereof as illustrated in FIG. 1A or FIG. 1B.

In some embodiments, an anti-CD38 antibody described herein comprises an IgG framework, an IgA framework, an IgE framework, or an IgM framework. In some instances, the anti-CD38 antibody comprises an IgG framework (e.g., IgG1, IgG2, IgG3, or IgG4). In such instances, the anti-CD38 antibody comprises an IgG1, IgG2, IgG3, or an IgG4 framework.

In some cases, the anti-CD38 antibody further comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to increase ADCC or complement-dependent cytotoxicity (CDC). In other instances, the one or more mutations are to reduce or eliminate Fc effector functions such as FcγR-binding, ADCC or CDC. In additional instances, the one or more mutations are to modulate glycosylation.

In some cases, the anti-CD38 antibody comprises an IgG1 framework. In some embodiments, the constant region of the anti-CD38 antibody is modified at one or more amino acid positions to alter Fc receptor interaction. Exemplary residues that modulate or alter Fc receptor interaction include, but are not limited to, G236, S239, T250, M252, S254, T256, K326, A330, I332, E333A, M428, H433, or N434 (Kabat numbering; EU index of Kabat et al 1991 Sequences of Proteins of Immunological Interest). In some instances, the mutation comprises G236A, S239D, T250Q, M252Y, S254T, T256E, K326W, A330L, I332E, E333A, E333S, M428L, H433K, or N434F.

In some embodiments, the modification at one or more amino acid positions in the IgG1 constant region to alter Fc receptor interaction leads to increased half-life. In some instances, the modification at one or more amino acid positions comprise T250, M252, S254, T256, M428, H433, N434, or a combination thereof, e.g., comprising T250Q/M428L or M252Y/S254T/T256E and H433K/N434F.

In some embodiments, the modification at one or more amino acid positions in the IgG1 constant region to alter Fc receptor interaction leads to increased ADCC and/or CDC. In some instances, the modification at one or more amino acid positions comprises S239, K326, A330, I332, E333, or a combination thereof. In some instances, the modification at one or more amino acid positions for increased ADCC and/or CDC comprises, e.g., E333A, S239D/A330L/I332E, or K326W/E333S. In some cases, the modification at one or more amino acid positions for increased ADCC comprises S239D/A330L/I332E. In some cases, the modification at one or more amino acid positions for increased CDC comprises K326W/E333S.

In some embodiments, the modification at one or more amino acid positions in the IgG1 constant region to alter Fc receptor interaction leads to increased macrophage phagocytosis. In some instances, the modification at one or more amino acid positions comprises G236, S239, I332, or a combination thereof. In some cases, the modification at one or more amino acid positions for increased macrophage phagocytosis comprises the combination S239D/I332I/G236A.

In some embodiments, the IgG1 constant region is modified at amino acid N297 (Kabat numbering), for example to N297C.

In some embodiments, the anti-CD38 antibody comprises an IgG2 framework. In some instance, one or more amino acid positions in the IgG2 framework are modified to alter Fc receptor interaction, e.g., to increase ADCC and/or CDC. In some cases, one or more amino acid positions in the IgG2 framework are modified to stabilize the antibody and/or to increase half-life. In some instances, one or more amino acid positions in the IgG2 framework are modified to modulate glycosylation. In some cases, the IgG2 constant region is afucosylated.

In some embodiments, the anti-CD38 antibody comprises an IgG3 framework. In some instance, one or more amino acid positions in the IgG3 framework are modified to alter Fc receptor interaction, e.g., to increase ADCC and/or CDC. In some cases, one or more amino acid positions in the IgG3 framework are modified to stabilize the antibody and/or to increase half-life. In some instances, one or more amino acid positions in the IgG3 framework are modified to modulate glycosylation. In some cases, the constant region of the antibody is modified at amino acid R435 to extend the half-life, e.g., R435H (Kabat numbering). In some instances, the constant region is afucosylated.

In some embodiments, the anti-CD38 antibody comprises an IgG4 framework. In some instance, one or more amino acid positions in the IgG4 framework are modified to alter Fc receptor interaction, e.g., to increase ADCC and/or CDC. For example, mutations to increase ADCC comprises, in some embodiments, S239D, I332E, and A330L (amino acid numbering is according to the EU index in Kabat et al), such as described in U.S. Pat. No. 8,093,359. In some cases, one or more amino acid positions in the IgG4 framework are modified to stabilize the antibody and/or to increase half-life. In some instances, one or more amino acid positions in the IgG4 framework are modified to modulate glycosylation. In some cases, the constant region is modified at a hinge region to prevent or reduce strand exchange. In some instances, the amino acid that is modified is S228 (e.g., S228P).

In some embodiments, the human IgG constant region is modified to ADCC and/or CDC, e.g., with an amino acid modification described in Natsume et al., 2008 *Cancer Res,* 68(10): 3863-72; Idusogie et al., 2001 *J Immunol,* 166(4): 2571-5; Moore et al., 2010 *mAbs,* 2(2): 181-189; Lazar et al., 2006 *PNAS,* 103(11): 4005-4010, Shields et al., 2001 *JBC,* 276(9): 6591-6604; Stavenhagen et al., 2007 *Cancer Res,* 67(18): 8882-8890; Stavenhagen et al., 2008 *Advan. Enzyme Regul.,* 48: 152-164; Alegre et al, 1992 *J Immunol,* 148: 3461-3468; Reviewed in Kaneko and Niwa, 2011 Biodrugs, 25(1): 1-11.

In some embodiments, the human IgG constant region is modified to induce heterodimerization. For example, having an amino acid modification within the CH3 domain at Thr366, which when replaced with a more bulky amino acid, e.g., Trp (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). In some cases, heterodimerization via CH3 modifications is further stabilized by the introduction of a disulfide bond, for example by changing Ser354 to Cys (S354C) and Y349 to Cys (Y349C) on opposite CH3 domains (Reviewed in Carter, 2001 *Journal of Immunological Methods,* 248: 7-15).

In some instances, an anti-CD38 antibody described herein has reduced or lacks glycosylation but is not modified at amino acid Asn297 (Kabat numbering). In these instances, the glycosylation is, for example, eliminated by production of the antibody in a host cell that lacks a post-translational glycosylation capacity, for example a bacterial or yeast derived system or a modified mammalian cell expression system. In certain aspects, such a system is a cell-free expression system.

In some embodiments, an anti-CD38 antibody described herein is a full-length antibody, comprising a heavy chain (HC) and a light chain (LC). In some cases, the heavy chain (HC) comprises a sequence selected from Table 5. In some cases, the light chain (LC) comprises a sequence selected from Table 6.

TABLE 5

Heavy chains of exemplary anti-CD38 antibodies

| NAME | HC SEQUENCE | SEQ ID NO: |
|---|---|---|
| G1F4_VH | EVQLLESGGGLVQPGGSLRLSCAASGFTFSTYAMSWVRQAPGKGLEWV SAISGSGGSTYYADSVKGRFTISRDNSKNTLYLQMNSLRAEDTAVYYCA KRGTYGYSFPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 156 |
| 4618_1 | EVQLLESGGGLVQPGGSLRLSCAASGFPFDVYAMSWVRQAPGKGLEWV SAISGSGGSTFYADSVKGRFTISRDNSKNTLYLQMNSLRAEDTAVYYCA KRGTYAYSFPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 157 |
| 4618_5 | EVQLLESGGGLVQPGGSLRLSCAASGFPFDAYAMSWVRQAPGKGLEWV SAISGSGGSTYYADSVKGRFTISRDNSKNTLYLQMNSLRAEDTAVYYCA KRGTYAYSFPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 158 |
| 4618_1_2 | EVQLLESGGGLVQPGGSLRLSCAASGFPFGVYAMSWVRQAPGKGLEWV SAISGSGGSTFYADSVKGRFTISRDNSKNTLYLQMNSLRAEDTAVYYCA KRGTYAYSYPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 159 |
| 4618_1_12 | EVQLLESGGGLVQPGGSLRLSCAASGFPFDVYAMSWVRQAPGKGLEWV SAISGSGGSTFYADSVKGRFTISRDNSKNTLYLQMNSLRAEDTAVYYCA KRGTYAYSYPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 160 |
| 4618_5_12 | EVQLLESGGGLVQPGGSLRLSCAASGFPFDAYAMSWVRQAPGKGLEWV SAISGSGGSTYYADSVKGRFTISRDNSKNTLYLQMNSLRAEDTAVYYCA KRGTYAYSYPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 161 |
| 4618_F_12 | EVQLLESGGGLVQPGGSLRLSCAASGFPFDAYAMSWVRQAPGKGLEWV SAISGSGGSTFYADSVKGRFTISRDNSKNTLYLQMNSLRAEDTAVYYCA KRGTYAYSYPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT | 162 |

TABLE 5-continued

Heavy chains of exemplary anti-CD38 antibodies

| NAME | HC SEQUENCE | SEQ ID NO: |
|---|---|---|
| | KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | |
| 32218_1 | EVQLLESGGGLVQPGGSLRLSCAASGFPFGVYAMSWVRQAPGKGLEWV SAISGSGGSTFYADSVKGRFTISRDNSKNTLYLQMNSLRAEDTAVYYCA KRGTYAYSFPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 163 |
| 32218_2 | EVQLLESGGGLVQPGGSLRLSCAASGFPFDTYAMSWVRQAPGKGLEWV SAISGSGGSTYYADSVKGRFTISRDNSKNTLYLQMNSLRAEDTAVYYCA KRGTYAYSFPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 164 |
| 32018_7 | EVQLLESGGGLVQPGGSLRLSCAASGFPFGTYAMSWVRQAPGKGLEWV SAISGSGGSTFYADSVKGRFTISRDNSKNTLYLQMNSLRAEDTAVYYCA KRGTYGYSFPTGFDYWGQGTLVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK | 165 |
| 17E9 | QSVEESGGRLVTPGTPLTLTCTASGFSLSRYYVTWVRQAPGKGLEWIGII YISGTTYYATWAKGRFTISKSATTVDLRIASPTTEDTATYFCAAAWPVGT YVLPLWGPGTLVTVSSASTKGPSVFPLAPSSKSTSGGTAALGCLVKDYFP EPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNST YRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG K | 166 |
| 17F7 | QSVEESGGRLVTPGTPLTLTCTASGFSLSSYYMSWVRQAPGKGLEWIGFI SKTAITYYASWARGRFTISKTSTAVDLKITSPTTEDTATYFCARVDAYSA GDLWGPGTLVTVSSASTKGPSVFPLAPSSKSTSGGTAALGCLVKDYFPEP VTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK | 167 |
| 18E4 | QSLEESGGDLVKPGASLTLTCTASGFSFNNYWICWIRQAPGKGLEWVAC IYSPSGDIKYYANWAKGRFTVSKTSSTTVTLQMTSLTGADTATYFCARE LSGSSYEGYFESWGPGTLVTVSSASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQ KSLSLSPGK | 168 |
| 1E2 | QSVEESGGRLVTPGTPLTLTCTVSGIDLNSYAMGWVRQAPGKGLKYIGI MTSGGNIYYANWAKGRFTISKTSTTVDLRITSPTTEDTATYFCAREREFY GGGTSGSRLDLWGQGTLVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFPP | 169 |

TABLE 5-continued

Heavy chains of exemplary anti-CD38 antibodies

| NAME | HC SEQUENCE | SEQ ID NO: |
|---|---|---|
| | KPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQ KSLSLSPGK | |
| 20B5 | QSLEESGGDLVKPGASLTLTCTASGFSFSSRYWICWVRQAPGKGLEWIA CIVAGTTNTYYASWAKGRFTISKTSSTTVTLQMTSLTAADTATYFCAGD PRTGSNVGYFNLWGPGTLVTVSSASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQ KSLSLSPGK | 170 |
| 21G2 | QSVEESGGRLVTPGTPLTLTCTVSGFSLSNYGVSWVRQAPGKGLEWIGYI LTSGGTYYANWAQGRFTISKTSTTVDLKITSPTTEDTATYFCGRPKDSDS SAFVSLWGPGTLVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG K | 171 |
| 21H9 | QSLEESGGDLVKPGASLTLTCTASGFSATTYYYYMCWVRQAPGKGLEW IACTYTGDGATYYATWAKGRFTISKTSSTTVTLQMTSLTAADTATYFCA RSADNSIYYGYFNLWGPGTLVTVSSASTKGPSVFPLAPSSKSTSGGTAAL GCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHY TQKSLSLSPGK | 172 |
| 22H6 | QSVEESGGRLVTPGTPLTLTCTVSGFSLSNNAISWVRQAPGKGLQWIGSI YGSGNTYYATWAKGRFTVSKTSTTVDLKINSPTTEDTATYFCAREGAGS SWGFNLWGPGTLVTVSSASTKGPSVFPLAPSSKSTSGGTAALGCLVKDY FPEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG K | 173 |
| 23A2 | QSVEESGGRLVTPGTPLTLTCTVSGFSLNNNAISWVRQAPGKGLQWIGSI YGTGNTYYATWAKGRFSVSKTSTTVDLKINSPTTEDTATYFCATEGAGSI WGFNLWGPGTLVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG K | 174 |
| 23B3 | QSVEESGGRLVTPGTPLTLTCTVSGFSLSNYDMTWVRQAPGRGLEWIGV ISSGDNTNYARWAKGRFTISKTSSTTVDLKITSPTTEDTATYFCARILYNK GRYYFTFWGPGTLVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYN STYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSP GK | 175 |
| 23D1 | QELVESGGGLFQPGGSLALTCKASGFSLSNIYVMCWVRQAPGKGLEWIA CIGTGSGDTDYATWAKGRFTISKTSSTTVTLQMTSLTAADTATYFCARD PGAGTWNLWGPGTLVTVSSASTKGPSVFPLAPSSKSTSGGTAALGCLVK | 176 |

TABLE 5-continued

Heavy chains of exemplary anti-CD38 antibodies

| NAME | HC SEQUENCE | SEQ ID NO: |
|---|---|---|
| | DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLS LSPGK | |
| 25C3 | QEQLEESGGDLVKPGASLTLTCKASGFSFSSAYDMCWVRQAPGKGLEW VACLYTVSSDSIYYASWAKGRFTISRTSSTTVTLQMTSLTAADTATYFCA RDGDYFALWGPGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLS LSPGK | 177 |
| 25E4 | QSLEESGGRLVTPGTPLTLTCTVSGIDLSIYTMAWVRQAPGKGLEYIGIIS GYGTTYYATWAKGRFIVSKTSTTVDLKITSPTTEDTATYFCVRTTVQSTD LWGPGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDG SFFLYSKLTVDKSRWQQGNVFSCSVMHEALHNHYTQKSLSLSPGK | 178 |
| 25F12 | RSLEESGGRLVTPGTPLTLTCTTSGFSLSSYDMSWVRQAPGKGLEWIGYI TYGGNIYYATWAKGRFTTSKTSTTVDLKITSPTTEDTATYFCARTLYTGG RYYFSLWGPGTLVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG K | 179 |
| 26D4 | QEQLEESGGDLVKPEGSLTLTCTASGFSFSNDAICWVRQAPGKGLEWIA CIYAGSGNTYYASWAKGRFSISKTSSTTVTLQMTSLTVADTATYFCASA DTIDYFNLWGPGTLVTVSSASTKGPSVFPLAPSSKSTSGGTAALGCLVKD YFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYN STYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSP GK | 180 |
| 27F6 | QSLEESGGGLVKPGASLTLTCKASGFSFSSGCDMCWVRQAPGKGLEWIS CIYTGSGSTYYANWAKGRFTISRTSSTTVTLQMTSLTAADTATYFCAGDS DYLGLWGPGTLVTVSSASTKGPSVFPLAPSSKSTSGGTAALGCLVKDYFP EPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNST YRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG K | 181 |

TABLE 6

Light chains of exemplary anti-CD38 antibodies

| NAME | LC SEQUENCE | SEQ ID NO: |
|---|---|---|
| G1F4_VL | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV | 182 |

TABLE 6-continued

Light chains of exemplary anti-CD38 antibodies

| NAME | LC SEQUENCE | SEQ ID NO: |
|---|---|---|
| | DNALQSGNSQESVTEQDSKDSTYSLSSTLTLSKADYEKHKVYACEVTHQ GLSSPVTKSFNRGEC | |
| 4618_1 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 183 |
| 4618_5 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 184 |
| 4618_12 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 185 |
| 4618_1_12 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 186 |
| 4618_5_12 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 187 |
| 4618_5F_12 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 188 |
| 32218_1 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 189 |
| 32218_2 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 190 |
| 32018_7 | DIQMTQSPSSLSASVGDRVTITCRASQDVNTAVAWYQQKPGKAPKLLIY SASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQ GLSSPVTKSFNRGEC | 191 |
| 17E9 | AAVLTQTPSPVSAAVGGTVTIKCQSSQSVVNANNLSWYQQKPGQPPKLL IYLASTLASGVPSRFSGSGSGTQFTLTISSVQSDDAATYYCLGVYDDDGD NAFGGGTEVVVKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | 192 |
| 17F7 | AQVLTQTPSSVSAAVGGTVTINCQASQSVYSDNRLSWFQQKSGQPPKLLI YSTSSLASGVPSRFSGSGSGTQFTLTISGVQSDDAASYYCQGEFICTSADC FVFGGGTEVVVKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | 193 |
| 18E4 | AQVLTQTPSSVSAAVGGTVTINCQCSQSVYGHNWLAWYQHKPGQPPKL LMYRASNLASGVPSRFKGSGSGSQFTLTIGEVQSDDAATYYCQGYYNGG SYAFGGGTEVVVRRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC | 194 |

TABLE 6-continued

| NAME | LC SEQUENCE | SEQ ID NO: |
|---|---|---|
| 1E2 | AYDMTQTPASVEAAVGGTVTIKCQASQSIYNFLNWYQQKPGQPPKLLIY YASTLAFGVPSRFKGSGSGTEYTLTISGVESADAATYYCQQGWNSGILD NSFGGGTEVVVKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | 195 |
| 20B5 | AQVLTQTPSPVSAAVGGTVTINCQASQSVYNNNYLAWFQQKPGQPPKL LIYSASTLASGVPSRFKGSGSGTQFTLTISEVQSDDAATYYCQAYYSGGIY AFGGGTEVVVKRTVAAPSVFIFPPSDEQLKSGTASVVCLLNNFYPREAKV QWKVDNALQSGNSQESVTEQDSKDSTYSLSSTLTLSKADYEKHKVYAC EVTHQGLSSPVTKSFNRGEC | 196 |
| 21G2 | ADVVMTQTPASVSEPVGGTVTINCQASESIYSNLAWYQQKPGQPPKLLI YKASTLASGVSSRFKGSGSGTEFTLTISDLESADAATYYCQANHMIVIYG NGFGGGTEVVVKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | 197 |
| 21H9 | AFELTQTPFSVSEPVGGTVTINCQASENIYSSLAWYQQKPGQPPKLLIYRA STLASGVPSRFSGSGSGTEFTLTISGVQSDDAATYYCQTYYGSTSTGFTFG GGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVT HQGLSSPVTKSFNRGEC | 198 |
| 22H6 | AQVLTQTASSVSAAVGGTVTISCQSSESVYKNNYLSWYQQKPGQPLKCL IYSASTLASGVPSRFKGSGSGTQFTLTISDLESDDAATYYCAGGYSGNING FGGGTEVVVKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC | 199 |
| 23A2 | AQVLTQTASSVSAAVGGTVTISCQSSESVYKNNYLSWYQQKPGQPPKGL IYSASTLASGVPSRFKGSGSGTQFTLTISDLESDDAATYYCAGGYTGNIN GFGGGTEVVVKRTVAAPSVFIFPPSDEQLKSGTASVVCLLNNFYPREAKV QWKVDNALQSGNSQESVTEQDSKDSTYSLSSTLTLSKADYEKHKVYAC EVTHQGLSSPVTKSFNRGEC | 200 |
| 23B3 | AQVLTQTPSSVSAAVGGTVTINCQSSQSIANSDELAWYQQKPGQPPKLLI YDASTLAPGVPSRFSGSGSGTQFTLTISGVQSDDAATYYCQGTVYDSGW YAAFGGGTEVVVKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC | 201 |
| 23D1 | ADIVMTQTPSSVEAAVGGTVTIKCQASQTIGSRLAWYQQKPGQPPKLLIY SASTLASGVSSRFKGSGSGTQFTLTISDLDSADAATYYCQSYYYTSTSYP NAFGGGTEVVVKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | 202 |
| 25C3 | ADIVMTHTPASVEAAVGGTVTIKCQASQNIGGYLSWYQQKPGQRPKLLI YRASTLASGVPSRFKGSGSGTQFTLTISDLESADAATYYCQTYYYSGSSR YWAFGGGTEVVVKRTVAAPSVFIFPPSDEQLKSGTASVVCLLNNFYPRE AKVQWKVDNALQSGNSQESVTEQDSKDSTYSLSSTLTLSKADYEKHKV YACEVTHQGLSSPVTKSFNRGEC | 203 |
| 25E4 | ADIVMTQTPASVEAAVGGTVTINCQASQNIYSNLAWYQQKPGQRPKLLI YKASTLASGVSSRFKGSGSGTEFTLTISDLASADAATYYCQSYYGATSSS FGYGFGGGTEVVVKRTVAAPSVFIFPPSDEQLKSGTASVVCLLNNFYPRE AKVQWKVDNALQSGNSQESVTEQDSKDSTYSLSSTLTLSKADYEKHKV YACEVTHQGLSSPVTKSFNRGEC | 204 |
| 25F12 | AQVLTQTPSSVSAVVGGTVTINCQSSQSIANSNEVAWYQQKLGQPPKLLI YDASTLASGVPSRFSGSGSGTQFTLIISGVQSDDAATYYCQGTVYDNVW YAAFGGGTEVVVKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC | 205 |
| 26D4 | AQVLTQTPSPVSAAVGGTVTINCQASQSVYNNNYLAWYQQKPGQPPKL LIYRASNLASGVPSRFSASGSGTQFTLTISEVQSDDAATYYCQAYYRDPT TAFGGGTEVVVKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC | 206 |
| 27F6 | ADIVMTQTPSSVEAAVGGTVTIKCQASQNIGNYLAWYQQKPGQPPKVLI YRASTLASGVPSRFKGSGSGTHFTLTISDLESADAATYYCQSYYYTTDDN YRSWAFGGGTEVVVKRTVAAPSVFIFPPSDEQLKSGTASVVCLLNNFYP | 207 |

TABLE 6-continued

Light chains of exemplary anti-CD38 antibodies

| NAME | LC SEQUENCE | SEQ ID NO: |
|------|-------------|------------|
| | REAKVQWKVDNALQSGNSQESVTEQDSKDSTYSLSSTLTLSKADYEKH KVYACEVTHQGLSSPVTKSFNRGEC | |

In some embodiments, an anti-CD38 antibody described herein has an enhanced ADCC and/or CDC compared to daratumumab as a reference antibody. In some cases, the enhanced ADCC and/or CDC is an increase of at least 10%, 20%, 30%, 40%, 50%, 60%, 70%, 80%, 90%, 100%, 150%, 200%, 300%, 400%, or more compared to daratumumab. In some cases, the enhanced ADCC and/or CDC is an increase of about 10%, 20%, 30%, 40%, 50%, 60%, 70%, 80%, 90%, 100%, 150%, 200%, 300%, 400%, or more compared to daratumumab.

In some cases, the enhanced ADCC and/or CDC is an increase of at least 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, or more compared to reference antibody daratumumab. In some cases, the enhanced ADCC and/or CDC is an increase of about 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, or more compared to reference antibody daratumumab.

In some embodiments, an anti-CD38 antibody described herein has an $EC_{50}$ of from about $1\times10^{-6}$ nM to about 2 nM, such as about $4\times10^{-6}$ nM, about 0.000014 nM, 0.00007 nM, 0.00006 nM, about 0.00010 nM, about 0.0002 nM, about 0.0003 nM, 0.1 nM, about 0.2 nM, about 0.3 nM, about 0.4 nM, about 0.5 nM, about 0.6 nM, about 0.7 nM, about 0.8 nM, about 0.9 nM, about 1.0 nM, or from about 0.00001 to about 0.00003 nM in an in vitro cytotoxicity assay to determine ADCC activity, for instance, using PBMC effector cells and targeting cancer cells such as B-lymphoblast cells from a lymphoma, for example, Daudi cells.

In some embodiments, an anti-CD38 antibody described herein has an improved cell kill effect compared to reference antibody daratumumab. In some cases, the improved cell kill effect is an increase of at least 10%, 20%, 30%, 40%, 50%, 60%, 70%, 80%, 90%, 100%, 150%, 200%, 300%, 400%, or more compared to reference antibody daratumumab. In some cases, the improved cell kill effect is an increase of about 10%, 20%, 30%, 40%, 50%, 60%, 70%, 80%, 90%, 100%, 150%, 200%, 300%, 400%, or more compared to reference antibody daratumumab.

In some instances, the improved cell kill effect is an increase of at least 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, or more compared to reference antibody daratumumab. In some cases, the improved cell kill effect is an increase of about 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, or more compared to reference antibody daratumumab.

In some embodiments, an anti-CD38 antibody described herein has an improved serum half-life compared to reference antibody daratumumab. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference antibody daratumumab.

In some cases, the serum half-life of an anti-CD38 antibody described herein is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer. In some cases, the serum half-life of an anti-CD38 antibody described herein is about 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer.

Anti-ICAM1 Antibodies

In certain embodiments, disclosed herein is anti-ICAM1 antibody. In some instances, the anti-ICAM1 antibody comprises a variable heavy chain (VH) region and a variable light chain (VL) region, in which the VH region comprises CDR1 sequence $X^1X^2X^3X^4X^5X^6X^7X^8X^9X^{10}X^{11}$; wherein $X^1$ is selected from G or E; $X^2$ is selected from F or Y; $X^3$ is selected from S or T; $X^4$ is selected from L, F, or S; $X^5$ is selected from S or N; $X^6$ is selected from S, N, T, or D; $X^7$ is selected from Y, H, or G; $X^8$ is selected from G, A, Y, W, or F; $X^9$ is selected from M, W, Y, or I; $X^{10}$ is selected from S, G, N, M, or I; and $X^{11}$ is present or absent, if present, is C; CDR2 sequence $X^{12}X^{13}X^{14}X^{15}X^{16}X^{17}X^{18}X^{19}X^{20}X^{21}X^{22}X^{23}X^{24}X^{25}X^{26}X^{27}X^{28}X^{29}X^{30}$; wherein $X^{12}$ is selected from G, T, A, I, or Y; $X^{13}$ is selected from W, I, Y, or C; $X^{14}$ is selected from I, S or Y; $X^{15}$ is selected from S, G, T, D, or P; $X^{16}$ is selected from F, S, D, T, or A; $X^{17}$ is selected from S, R, G, or D; $X^{18}$ is selected from G, D, or S; $X^{19}$ is selected from S, R, T, N, Y, A, D, or P; $X^{20}$ is selected from T, A, G, or Y; $X^{21}$ is selected from Y, H, A, S, or T; $X^{22}$ is selected from Y or N; $X^{23}$ is selected from A, P, Y, or S; $X^{24}$ is selected from S, T, N, D, Y, A, or P; $X^{25}$ is selected from W, S, A, or D; $X^{26}$ is selected from A, V, T, W, F, or S; $X^{27}$ is selected from K, W, A, Q, or V; $X^{28}$ is selected from G, A, or K; $X^{29}$ is present or absent, if present, is selected from K or G; and $X^{30}$ is present or absent, if present, is G; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}X^{47}X^{48}X^{49}$; wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{41}$ is present or absent, if present, is selected from D or L; and $X^{49}$ is present or absent, if present, is L.

In some instances, the VH region of the anti-ICAM1 antibody comprises CDR1 sequence GFSLX$^5$X$^6$X$^7$X$^8$MX$^{10}$ (SEQ ID NO: 425), wherein X$^5$ is selected from S or N; X$^6$ is selected from S, N, T, or D; X$^7$ is selected from Y or H; X$^8$ is selected from G, A, or Y; and X$^{10}$ is selected from S, G, or N.

In some instances, the VH region of the anti-ICAM1 antibody comprises CDR2 sequence GX$^{13}$IX$^{15}$X$^{16}$X$^{17}$X$^{18}$X$^{19}$X$^{20}$YYAX$^{24}$WAKG (SEQ ID NO: 420), wherein X$^{13}$ is selected from W, I, or Y; X$^{15}$ is selected from S or G; X$^{16}$ is selected from F, S, D, or T; X$^{17}$ is selected from S or R; X$^{18}$ is selected from G or D; X$^{19}$ is selected from S, R, T, or N; X$^{20}$ is selected from T or A; and X$^{24}$ is selected from S, T, or N.

In some instances, the VH region of the anti-ICAM1 antibody comprises CDR3 sequence X$^{31}$RX$^{33}$X$^{34}$X$^{35}$X$^{36}$X$^{37}$X$^{38}$X$^{39}$X$^{40}$X$^{41}$X$^{42}$X$^{43}$X$^{44}$X$^{45}$X$^{46}$ X$^{47}$X$^{48}$X$^{49}$ (SEQ ID NO: 424), wherein X$^{31}$ is selected from A or V; X$^{33}$ is selected from G or D; X$^{34}$ is selected from G, P, W, or D; X$^{35}$ is selected from D, Y, S, or L; X$^{36}$ is selected from Y, D, V, or L; X$^{37}$ is selected from G, S, or D; X$^{38}$ is selected from G, Y, F, or S; X$^{39}$ is selected from S, D, G, or T; X$^{40}$ is selected from T, A, D, S, or Y; X$^{41}$ is selected from Y, A, G, or I; X$^{42}$ is selected from I, Y, or R; X$^{43}$ is selected from L, R, Y, or G; X$^{44}$ is selected from N, L, Y, or S; X$^{45}$ is present or absent, if present, is selected from L, Y, or F; X$^{46}$ is present or absent, if present, is D; X$^{47}$ is present or absent, if present, is selected from M or P; X$^{48}$ is present or absent, if present, is D; and X$^{49}$ is present or absent, if present, is L.

In some instances, the VH region of the anti-ICAM1 antibody comprises CDR1 sequence GFSLX$^5$X$^6$X$^7$X$^8$MX$^{10}$ (SEQ ID NO: 425), CDR2 sequence GX$^{13}$IX$^{15}$X$^{16}$X$^{17}$X$^{18}$X$^{19}$X$^{20}$YYAX$^{24}$WAKG (SEQ ID NO: 420), and CDR3 sequence X$^{31}$RX$^{33}$X$^{34}$X$^{35}$X$^{36}$X$^{37}$X$^{38}$X$^{39}$X$^{40}$X$^{41}$X$^{42}$X$^{43}$X$^{44}$X$^{45}$X$^{46}$ X$^{47}$X$^{48}$X$^{49}$ (SEQ ID NO: 424), wherein X$^5$ is selected from S or N; X$^6$ is selected from S, N, T, or D; X$^7$ is selected from Y or H; X$^8$ is selected from G, A, or Y; X$^{10}$ is selected from S, G, or N; X$^{13}$ is selected from W, I, or Y; X$^{15}$ is selected from S or G; X$^{16}$ is selected from F, S, D, or T; X$^{17}$ is selected from S or R; X$^{18}$ is selected from G or D; X$^{19}$ is selected from S, R, T, or N; X$^{20}$ is selected from T or A; X$^{24}$ is selected from S, T, or N; X$^{31}$ is selected from A or V; X$^{33}$ is selected from G or D; X$^{34}$ is selected from G, P, W, or D; X$^{35}$ is selected from D, Y, S, or L; X$^{36}$ is selected from Y, D, V, or L; X$^{37}$ is selected from G, S, or D; X$^{38}$ is selected from G, Y, F, or S; X$^{39}$ is selected from S, D, G, or T; X$^{40}$ is selected from T, A, D, S, or Y; X$^{41}$ is selected from Y, A, G, or I; X$^{42}$ is selected from I, Y, or R; X$^{43}$ is selected from L, R, Y, or G; X$^{44}$ is selected from N, L, Y, or S; X$^{45}$ is present or absent, if present, is selected from L, Y, or F; X$^{46}$ is present or absent, if present, is D; X$^{47}$ is present or absent, if present, is selected from M or P; X$^{48}$ is present or absent, if present, is D; and X$^{49}$ is present or absent, if present, is L.

In some embodiments, the VH region of the anti-ICAM1 antibody comprises CDR1, CDR2, and CDR3 sequences selected from Table 7.

TABLE 7

Heavy chain complementarity determining regions of exemplary anti-ICAM1 antibodies

| ICAM1 VH | CDR1 | SEQ ID NO: | CDR2 | SEQ ID NO: | CDR3 | SEQ ID NO: |
|---|---|---|---|---|---|---|
| 6B10 | GFSLSSYGMS | 208 | GWISFSGSTY YASWAKG | 209 | ARGGDYGGST YILNL | 210 |
| 3D8 | GFSFSSSYWMC | 211 | ACIDGGSAGY NYYATWAKG | 212 | ARGPGSSYNL | 213 |
| 6G8 | GFSLSSYAMG | 214 | GIIGSSGSTYY ATWAKG | 215 | VRDPYDSYDAA YRL | 216 |
| 15D10 | GFSLNNYYMS | 217 | GIISDSDNTYY ASWAKG | 218 | ARDWSLDSSSG YYYYDMDL | 219 |
| 2E3 | GFSLSSYAMG | 214 | GIIGSSGSTYY ASWAKG | 220 | VRDPYDSFGDG YRL | 221 |
| 8H1 | GFSLSNYYMS | 222 | GIISDSGSTYY ASWAKG | 223 | ARDWSYDSSSG YYYYDMDL | 224 |
| 11G7 | GFSLSDYYMS | 225 | GIISDSGSTYY ASWAKG | 223 | ARDWSYDSSSG YYYYDMDL | 224 |
| 14H1 | GFSLSNYYMS | 222 | GIISDSGSTYY ASWAKG | 223 | ARDWSYDSTSG YYYYDMDL | 226 |
| 4H5 | GFSLSNYYMS | 222 | GIISDSGTTYY ASWAKG | 227 | ARDWSYDSSSG YYYYDMDL | 224 |
| 11F2 | GFSLSSHAMG | 228 | GIIGSSDRTYY ASWAKG | 229 | VRDPYDSYDDG YRL | 230 |
| 16E4 | GFSLSSHAMG | 228 | GIIGSSGSTYY ASWAKG | 220 | VRDPYDSFGDA YRL | 231 |
| 8B12 | GFSLSTHAMG | 232 | GIIGSSDRTYY ASWAKG | 229 | VRDPYDSFDDG YRL | 233 |
| 5B12 | GFSLSSYGMS | 208 | GWISFSGSAY YANWAKG | 234 | ARGGDYGGST YILNL | 210 |

TABLE 7-continued

Heavy chain complementarity determining regions of exemplary anti-ICAM1 antibodies

| ICAM1 VH | CDR1 | SEQ ID NO: | CDR2 | SEQ ID NO: | CDR3 | SEQ ID NO: |
|---|---|---|---|---|---|---|
| 10B8 | GFSLSSYGMS | 208 | GWISFSGSAY YANWAKG | 234 | ARGGDYGGST YILNL | 210 |
| 14B3 | GFSSSSGYYIC | 235 | ACIGAGSGAA YYASWAKG | 236 | ARGGFVVGGG YGGYCFNL | 237 |
| 8E5 | GFSLSNYAMN | 238 | GYISTRGSAY YASWAKG | 239 | ARGDLVGGGYI RGSFDP | 240 |
| c05G01 | GFTFSNYGMS | 241 | TISTGGGYTH YPDSVKG | 242 | ARPDYYGSSYG PAWFAY | 243 |
| c06F06 | GFTFSNYGMS | 241 | TISTGGGYTY YPDSVKG | 244 | ARPDYYGSSYG PAWLAY | 245 |
| c05G07 | GFTFSNYGMS | 241 | TISTGGSYTYY PDSVKG | 246 | ARPDYYGSSYG PAWLAY | 245 |
| 81618_3 | EFTFSDYFMS | 247 | YISSGRSPYTN YADSVKG | 248 | ARVRGPGDVFD I | 249 |
| 62218_13 | GYSFSSHWIS | 250 | IIYPGDSDTSY SPSFQG | 251 | AIANWGEGAFD V | 252 |
| G12 | GFTFSSYAMS | 404 | AISGSGGSTYY ADSVKG | 405 | ANSAYTGGWY DY | 406 |

In some embodiments, the VH region of the anti-ICAM1 antibody comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}$ $X^{47}X^{48}X^{49}$, wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{48}$ is present or absent, if present, is selected from D or L; and $X^{49}$ is present or absent, if present, is L.

In some embodiments, the VH region of the anti-ICAM1 antibody comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence $X^{31}RX^{33}X^{34}X^{35}X^{36}X^{37}X^{38}X^{39}X^{40}X^{41}X^{42}X^{43}X^{44}X^{45}X^{46}$ $X^{47}X^{48}X^{49}$ (SEQ ID NO: 424), wherein $X^{31}$ is selected from A or V; $X^{33}$ is selected from G or D; $X^{34}$ is selected from G, P, W, or D; $X^{35}$ is selected from D, Y, S, or L; $X^{36}$ is selected from Y, D, V, or L; $X^{37}$ is selected from G, S, or D; $X^{38}$ is selected from G, Y, F, or S; $X^{39}$ is selected from S, D, G, or T; $X^{40}$ is selected from T, A, D, S, or Y; $X^{41}$ is selected from Y, A, G, or I; $X^{42}$ is selected from I, Y, or R; $X^{43}$ is selected from L, R, Y, or G; $X^{44}$ is selected from N, L, Y, or S; $X^{45}$ is present or absent, if present, is selected from L, Y, or F; $X^{46}$ is present or absent, if present, is D; $X^{47}$ is present or absent, if present, is selected from M or P; $X^{48}$ is present or absent, if present, is D; and $X^{49}$ is present or absent, if present, is L.

In some embodiments, the VH region of the anti-ICAM1 antibody comprises CDR1 sequence $X^{1}X^{2}X^{3}X^{4}X^{5}X^{6}X^{7}X^{8}X^{9}X^{10}X^{11}$, wherein $X^{1}$ is selected from G or E; $X^{2}$ is selected from F or Y; $X^{3}$ is selected from S or T; $X^{4}$ is selected from L, F, or S; $X^{5}$ is selected from S or N; $X^{6}$ is selected from S, N, T, or D; $X^{7}$ is selected from Y, H, or G; $X^{8}$ is selected from G, A, Y, W, or F; $X^{9}$ is selected from M, W, Y, or I; $X^{10}$ is selected from S, G, N, M, or I; and $X^{11}$ is present or absent, if present, is C; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252.

In some embodiments, the VH region of the anti-ICAM1 antibody comprises CDR1 sequence GFSLX$^{5}$X$^{6}$X$^{7}$X$^{8}$MX$^{10}$ (SEQ ID NO: 425), wherein X$^{5}$ is selected from S or N; X$^{6}$ is selected from S, N, T, or D; X$^{7}$ is selected from Y or H; X$^{8}$ is selected from G, A, or Y; and X$^{10}$ is selected from S, G, or N; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240.

In some embodiments, the VH region of the anti-ICAM1 antibody comprises CDR1 sequence selected from SEQ ID NOs: 208, 211, 214, 217, 222, 225, 228, 232, 235, 238, 241, 247, and 250; CDR2 sequence $X^{12}X^{13}X^{14}X^{15}X^{16}X^{17}X^{18}X^{19}X^{20}X^{21}X^{22}X^{23}X^{24}X^{25}X^{26}X^{27}$ $X^{28}X^{29}X^{30}$, $X^{12}$ is selected from G, T, A, I, or Y; $X^{13}$ is selected from W, I, Y, or C; $X^{14}$ is selected from I, S or Y; $X^{15}$ is selected from S, G, T, D, or P; $X^{16}$ is selected from F, S, D, T, or A; $X^{17}$ is selected from S, R, G, or D; $X^{18}$ is selected from G, D, or S; $X^{19}$ is selected from S, R, T, N, Y, A, D, or P; $X^{20}$ is selected from T, A, G, or Y; $X^{21}$ is selected from Y, H, A, S, or T; $X^{22}$ is selected from Y or N; $X^{23}$ is selected from A, P, Y, or S; $X^{24}$ is selected from S, T, N, D, Y, A, or P; $X^{25}$ is selected from W, S, A, or D; $X^{26}$ is selected from A, V, T, W, F, or S; $X^{27}$ is selected from K, W, A, Q, or V; $X^{28}$ is selected from G, A, or K; $X^{29}$ is present or absent, if present, is selected from K or G; and $X^{30}$ is present or absent, if present, is G; and CDR3 sequence selected from SEQ ID NOs: 210, 213, 216, 219, 221, 224, 226, 230, 231, 233, 237, 240, 243, 245, 249, and 252.

In some embodiments, the VH region of the anti-ICAM1 antibody comprises CDR1 sequence selected from SEQ ID NOs: 208, 211, 214, 217, 222, 225, 228, 232, 235, and 238; CDR2 sequence $GX^{13}IX^{15}X^{16}X^{17}X^{18}X^{19}X^{20}YYAX^{24}WAKG$ (SEQ ID NO: 420), wherein $X^{13}$ is selected from W, I, or Y; $X^{15}$ is selected ID NOs: 210, 213, 216, 219, 221, 224, 226, 230, 231, 233, 237, 240, 243, 245, 249, and 252.

In some embodiments, the VH region of the anti-ICAM1 antibody comprises CDR1 sequence selected from SEQ ID NOs: 208, 211, 214, 217, 222, 225, 228, 232, 235, 238, and 412; CDR2 sequence selected from SEQ ID NOs: 209, 212, 218, 220, 223, 227, 229, 234, 236, 239, and 413; and CDR3 sequence selected from SEQ ID NOs: 210, 213, 216, 219, 221, 224, 226, 230, 231, 233, 237, 240, and 414.

In some embodiments, the VH region of the anti-ICAM1 antibody comprises CDR1 sequence selected from SEQ ID NOs: 241, 247, and 250; CDR2 sequence selected from SEQ ID NOs: 242, 244, 246, 248, and 251; and CDR3 sequence selected from SEQ ID NOs: 243, 245, 249, and 252.

In some embodiments, the VL region of the anti-ICAM1 antibody comprises CDR1, CDR2, and CDR3 sequences selected from Table 8.

TABLE 8

Light chain complementarity determining regions of exemplary anti-ICAM1 antibodies

| ICAM1 VL | CDR1 | SEQ ID NO: | CDR2 | SEQ ID NO: | CDR3 | SEQ ID NO: |
|---|---|---|---|---|---|---|
| 6B10 | QASESVYNNKWLS | 253 | LASTLAS | 254 | AGYKNRGTDGLA | 255 |
| 3D8 | QASQSISSYLS | 256 | RASTLAS | 257 | QSYVFGSSRSYDNA | 258 |
| 6G8 | QASQSIYSYLS | 259 | DASKLAS | 260 | QQAYSSSNVDNV | 261 |
| 15D10 | QASQNIHSWLA | 262 | KASTLAS | 263 | QQGYSRSDGEHV | 264 |
| 2E3 | QASENIYRYLL | 265 | DASKLAS | 260 | QQAYSSSNVDNA | 266 |
| 8H1 | QASQSINSWLA | 267 | KASTLAS | 263 | QQGYSRSDGEHV | 264 |
| 11G7 | QASQSINSWLS | 268 | KASTLAS | 263 | QQGYSRSDGEHV | 264 |
| 14H1 | QASQSINSWLS | 268 | KASTLAS | 263 | QQGYSRSDGEHV | 264 |
| 4H5 | QASQSINSWLV | 269 | KASTLAS | 263 | QQGYSRSDGEHV | 264 |
| 11F2 | QASQSIYRYLS | 270 | DASKLAS | 260 | QQAYSSGSIDNA | 271 |
| 16E4 | QASQSIYSYCS | 272 | DASKLAS | 260 | QQAYSSSNVDNA | 266 |
| 8B12 | QASQSIYSYLS | 259 | DASKVAS | 273 | QQAYSSSNVDNA | 266 |
| 5B12 | QASESIDSYLS | 274 | AASTLAS | 275 | QSYSGTITTSGGA | 276 |
| 10B8 | QASESINSYLS | 277 | AASTLAS | 275 | QSYSGTISTSGGA | 278 |
| 14B3 | QSSESVDVNNLA | 279 | SASTLAS | 280 | AGGYSGNIFA | 281 |
| 8E5 | QSSQSVVSDKLLS | 282 | GASTLAS | 283 | AGAYSTDSDIRA | 284 |
| 4618_1 | RASQDVNTAVA | 62 | SASFLYS | 63 | QQHYTTPPT | 64 |
| G12 | QGDSLRTYYAS | 407 | GENSRPS | 408 | NSRDSSGNHLRV | 409 | from S or G; $X^{16}$ is selected from F, S, D, or T; $X^{17}$ is selected from S or R; $X^{18}$ is selected from G or D; $X^{19}$ is selected from S, R, T, or N; $X^{20}$ is selected from T or A; and $X^{24}$ is selected from S, T, or N; and CDR3 sequence selected from SEQ ID NOs: 210, 213, 216, 219, 221, 224, 226, 230, 231, 233, 237, and 240.

In some embodiments, the VH region of the anti-ICAM1 antibody comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence selected from SEQ In some embodiments, the VL region of the anti-ICAM1 antibody comprises CDR1 sequence selected from SEQ ID NOs: 253, 256, 259, 262, 265, 267, 268, 269, 270, 272, 274, 277, 279, 282, and 415; CDR2 sequence selected from SEQ ID NOs: 254, 257, 260, 263, 273, 275, 280, 283, and 416; and CDR3 sequence selected from SEQ ID NOs: 255, 258, 261, 264, 266, 271, 276, 278, 281, 284, and 417.

In some embodiments, the VL region of the anti-ICAM1 antibody comprises CDR1, CDR2, and CDR3 sequences SEQ ID NOs: 62-64, respectively.

In some embodiments, the anti-ICAM1 antibody comprises a VH region and a VL region, wherein the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}X^{47}X^{48}X^{49}$, wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{48}$ is present or absent, if present, is selected from D or L; and $X^{49}$ is present or absent, if present, is L; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the anti-ICAM1 antibody comprises a VH region and a VL region, wherein the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence $X^{31}RX^{33}X^{34}X^{35}X^{36}X^{37}X^{38}X^{39}X^{40}X^{41}X^{42}X^{43}X^{44}X^{45}X^{46}X^{47}X^{48}X^{49}$ (SEQ ID NO: 424), wherein $X^{31}$ is selected from A or V; $X^{33}$ is selected from G or D; $X^{34}$ is selected from G, P, W, or D; $X^{35}$ is selected from D, Y, S, or L; $X^{36}$ is selected from Y, D, V, or L; $X^{37}$ is selected from G, S, or D; $X^{38}$ is selected from G, Y, F, or S; $X^{39}$ is selected from S, D, G, or T; $X^{40}$ is selected from T, A, D, S, or Y; $X^{41}$ is selected from Y, A, G, or I; $X^{42}$ is selected from I, Y, or R; $X^{43}$ is selected from L, R, Y, or G; $X^{44}$ is selected from N, L, Y, or S; $X^{45}$ is present or absent, if present, is selected from L, Y, or F; $X^{46}$ is present or absent, if present, is D; $X^{47}$ is present or absent, if present, is selected from M or P; $X^{48}$ is present or absent, if present, is D; and $X^{49}$ is present or absent, if present, is L; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the anti-ICAM1 antibody comprises a VH region and a VL region, wherein the VH region comprises CDR1 sequence $X^{1}X^{2}X^{3}X^{4}X^{5}X^{6}X^{7}X^{8}X^{9}X^{10}X^{11}$, wherein $X^{1}$ is selected from G or E; $X^{2}$ is selected from F or Y; $X^{3}$ is selected from S or T; $X^{4}$ is selected from L, F, or S; $X^{5}$ is selected from S or N; $X^{6}$ is selected from S, N, T, or D; $X^{7}$ is selected from Y, H, or G; $X^{8}$ is selected from G, A, Y, W, or F; $X^{9}$ is selected from M, W, Y, or I; $X^{10}$ is selected from S, G, N, M, or I; and $X^{11}$ is present or absent, if present, is C; CDR2 sequence selected from SEQ ID NOs: 209, 212, 218, 220, 223, 227, 229, 234, 236, 239, 242, 244, 246, 248, and 251;

and CDR3 sequence selected from SEQ ID NOs: 210, 213, 216, 219, 221, 224, 226, 230, 231, 233, 237, 240, 243, 245, 249, and 252; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the anti-ICAM1 antibody comprises a VH region and a VL region, wherein the VH region comprises CDR1 sequence $GFSLX^{5}X^{6}X^{7}X^{8}MX^{10}$ (SEQ ID NO: 425), wherein $X^{5}$ is selected from S or N; $X^{6}$ is selected from S, N, T, or D; $X^{7}$ is selected from Y or H; $X^{8}$ is selected from G, A, or Y; and $X^{10}$ is selected from S, G, or N; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the anti-ICAM1 antibody comprises a VH region and a VL region, wherein the VH region comprises CDR1 sequence selected from SEQ ID NOs: 208, 211, 214, 217, 222, 225, 228, 232, 235, 238, 241, 247, and 250; CDR2 sequence $X^{12}X^{13}X^{14}X^{15}X^{16}X^{17}X^{18}X^{19}X^{20}X^{21}X^{22}X^{23}X^{24}X^{25}X^{26}X^{27}X^{28}X^{29}X^{30}$, in which $X^{12}$ is selected from G, T, A, I, or Y; $X^{13}$ is selected from W, I, Y, or C; $X^{14}$ is selected from I, S or Y; $X^{15}$ is selected from S, G, T, D, or P; $X^{16}$ is selected from F, S, D, T, or A; $X^{17}$ is selected from S, R, G, or D; $X^{18}$ is selected from G, D, or S; $X^{19}$ is selected from S, R, T, N, Y, A, D, or P; $X^{20}$ is selected from T, A, G, or Y; $X^{21}$ is selected from Y, H, A, S, or T; $X^{22}$ is selected from Y or N; $X^{23}$ is selected from A, P, Y, or S; $X^{24}$ is selected from S, T, N, D, Y, A, or P; $X^{25}$ is selected from W, S, A, or D; $X^{26}$ is selected from A, V, T, W, F, or S; $X^{27}$ is selected from K, W, A, Q, or V; $X^{28}$ is selected from G, A, or K; $X^{29}$ is present or absent, if present, is selected from K or G; and $X^{30}$ is present or absent, if present, is G; and CDR3 sequence selected from SEQ ID NOs: 210, 213, 216, 219, 221, 224, 226, 230, 231, 233, 237, 240, 243, 245, 249, and 252; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the anti-ICAM1 antibody comprises a VH region and a VL region, wherein the VH region comprises CDR1 sequence selected from SEQ ID NOs: 208, 211, 214, 217, 222, 225, 228, 232, 235, and 238; CDR2 sequence $GX^{13}IX^{15}X^{16}X^{17}X^{18}X^{19}X^{20}YYAX^{24}WAKG$ (SEQ ID No. 420), wherein $X^{13}$ is selected from W, I, or Y; $X^{15}$ is selected from S or G; $X^{16}$ is selected from F, S, D, or T; $X^{17}$ is selected from S or R; $X^{18}$ is selected from G or D; $X^{19}$ is selected from S, R, T, or N; $X^{20}$ is selected from T or A; and $X^{24}$ is selected from S, T, or N; and CDR3 sequence selected from SEQ ID NOs: 210, 213, 216, 219, 221, 224, 226, 230, 231, 233, 237, and 240; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the anti-ICAM1 antibody comprises a VH region and a VL region, wherein the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the anti-ICAM1 antibody comprises a VH region and a VL region, wherein the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the anti-ICAM1 antibody comprises a VH region and a VL region, wherein the VH region comprises CDR1 sequence selected from SEQ ID NOs: 241, 247, and 250; CDR2 sequence selected from SEQ ID NOs: 242, 244, 246, 248, and 251; and CDR3 sequence selected from SEQ ID NOs: 243, 245, 249, and 252; and wherein the VL region comprises CDR1, CDR2, and CDR3 sequences SEQ ID NOs: 62-64, respectively.

In some embodiments, the anti-ICAM1 antibody comprises a VH region and a VL region in which the sequence of the VH region comprises about 80%, 85%, 90%, 95%, 96% 97%, 98%, 99%, or 100% sequence identity to SEQ ID NOs: 289-309 and the sequence of the VL region comprises about 80%, 85%, 90%, 95%, 96% 97%, 98%, 99%, or 100% sequence identity to SEQ ID NOs: 311-326 and 155.

In some embodiments, the VH region comprises a sequence selected from Table 9 and the VL region comprises a sequence selected from Table 10.

TABLE 9

Heavy chain variable domains of exemplary anti-ICAM1 antibodies. The underlined regions denote the respective CDR1, CDR2, or CDR3 sequences.

| NAME | VH SEQUENCE | SEQ ID NO: |
|---|---|---|
| G12 | QVQLQESGGGLVQPGGSLRLSCAASGFTFSSYAM SWVRQAPGKGLEWVSAISGSGGSTYYADSVKGRF TISRDNSKNTLYLQMSSLRAEDTAFYYCANSAYT GGWYDYWGHGTLVTVSS | 288 |
| 6B10 | QSLEESGGRLVTPGGSLTLTCTVSGFSLSSYGMS WVRQAPGKGLEYIGWISFSGSTYYASWAKGRFTI SKTSTTVDLKITSPTTEDTATYFCARGGDYGGST YILNLWGPGTLVTVSS | 289 |

TABLE 9-continued

Heavy chain variable domains of exemplary anti-ICAM1 antibodies. The underlined regions denote the respective CDR1, CDR2, or CDR3 sequences.

| NAME | VH SEQUENCE | SEQ ID NO: |
|---|---|---|
| 3D8 | QSLEESGGDLVKPGASLTLTCTASGFSFSSSYWM CWVRQAPGKGLEWIACIDGGSAGYNYYATWAKGR FTISKTSSTTVTLQMTSLTAADRATYFCARGPGS SYNLWGPGTLVTVSS | 290 |
| 6G8 | QSVEESGGGLVKPGGTLTLTCTVSGFSLSSYAMG WVRQAPGKGLEYIGIIGSSGSTYYATWAKGRFTI SKTSTTVDLKITSPTTEDTATYFCVRDPYDSYDA AYRLWGPGTLVTVSS | 291 |
| 15D10 | QSVEESGGRLVTPGTPLTLTCTASGFSLNNYYMS WVRQAPGKGLEWIGIISDSDNTYYASWAKGRFTI SKTSTTVDLKITSPTTEDTATYFCARDWSLDSSS GYYYYDMDLWGPGTLVTVSA | 292 |
| 2E3 | QSVEESGGGLVKPGGTLTLTCTVSGFSLSSYAMG WVRQAPGKGLEYIGIIGSSGSTYYASWAKGRFTI SKTSTTVDLKITSPTTEDTATYFCVRDPYDSFGD GYRLWGPGTLVTVSS | 293 |
| 8H1 | QSVEESGGRLVTPGTPLTLTCTASGFSLSNYYMS WVRQAPGKGLEWIGIISDSGSTYYASWAKGRFTI SKTSTTVDLKITSPTTEDTATYFCARDWSYDSSS GYYYYDMDLWGPGTLVTVSA | 294 |
| 11G7 | QSVEESGGRLVTPGTPLTLTCTVSGFSLSDYYMS WVRQAPGKGLEWIGIISDSGSTYYASWAKGRFTI SKTSSTTVDLKITSPTTEDTATYFCARDWSYDSS SGYYYYDMDLWGPGTLVTVSA | 295 |
| 14H1 | QSVEESGGRLVTPGTPLTLTCTVSGFSLSNYYMS WVRQAPGKGLEWIGIISDSGSTYYASWAKGRFTI SKTSTTVDLSITSPTTEDTATYFCARDWSYDSTS GYYYYDMDLWGPGTLVTVSA | 296 |
| 4H5 | QSVEESGGRLVTPGTPLTLTCTASGFSLSNYYMS WVRQAPGKGLEWIGIISDSGTTYYASWAKGRFTI SKTSTTVDLKITSPTTEDTATYFCARDWSYDSSS GYYYYDMDLWGPGTLVTVSA | 297 |
| 11F2 | QSVEESGGGLVKPGGTLTLTCTVSGFSLSSHAMG WVRQAPGKGLEYIGIIGSSDRTYYASWAKGRFTI SKTSTTVDLKITSPTTEDTATYFCVRDPYDSYDD GYRLWGPGTLVTVSS | 298 |
| 16E4 | QSVEESGGRLVTPGTPLTLTCTVSGFSLSSHAMG WVRQAPGKGLQYIGIIGSSGSTYYASWAKGRFTI SKTSTTVDLRLTSPTTEDTATYFCVRDPYDSFGD AYRLWGPGTLVTVSS | 299 |
| 8B12 | QSVEESGGGLVKPGGTLTLTCTVSGFSLSTHAMG WVRQAPGKGLEYIGIIGSSDRTYYASWAKGRFTI SKTSTTVDLKITSPTTEDTATYFCVRDPYDSFDD GYRLWGPGTLVTVSS | 300 |
| 5B12 | QSLEESGGRLVTPGTPLTLTCTVSGFSLSSYGMS WVRQAPGKGLEYIGWISFSGSAYYANWAKGRFTI SKTSTTVDLKITSPTTEDTATYFCARGGDYGGST YILNLWGPGTLVTVSS | 301 |
| 10B8 | QSLEESGGRLVTPGGSLTLTCTVSGFSLSSYGMS WVRQAPGKGLEYIGWISFSGSAYYANWAKGRFTI SKTSTTVDLKITSPTTEDTATYFCARGGDYGGST YILNLWGPGTLVTVSS | 302 |
| 14B3 | QSLEESGGDLVKPGASLTLTCTASGFSSSGYYI CWVRQAPGKGLEWIACIGAGSGAAYYASWAKGRF TMSKTSSTTVTLQMTSLTAADTATYFCARGGFVV GGGYGGYCFNLWGPGTLVTVSS | 303 |

TABLE 9-continued

Heavy chain variable domains of
exemplary anti-ICAM1 antibodies. The underlined
regions denote the respective CDR1, CDR2,
or CDR3 sequences.

| NAME | VH SEQUENCE | SEQ ID NO: |
|---|---|---|
| 8E5 | QSLEESGGRLVTPGTPLTLTCTVSGFSLSNYAMN WVRQAPGKGLEWIGYISTRGSAYYASWAKGRFTI SKTSTTVDLKMTSPTTEDTATYFCARGDLVGGGY IRGSFDPWGPGTLVTVSS | 304 |
| c05G01 | EVKLMESGGDLVKPGGSLKLSCAASGFTFSNYGM SWVRQTPDKRLEWVATISTGGGYTHYPDSVKGRF TISRDNAKNTLYLQMSSLKSEDTAMYYCARPDYY GSSYGPAWFAYWGQGTLVTVSA | 305 |
| c06F06 | EVQLMESGGDLVKPGGSLKLSCAASGFTFSNYGM SWVRQTPDKRLEWVATISTGGGYTYYPDSVKGRF TISRDNAKNTLYLQMSSLKSEDTAMYYCARPDYY GSSYGPAWLAYWGQGTLVTVSA | 306 |
| c05G07 | EVQLVESGGDLVKPGGSLKLSCAASGFTFSNYGM SWVRQTPDKRLEQVATISTGGSYTYYPDSVKGRF TISRDNAKNTLYLQMSSLKSEDTAMYYCARPDYY GSSYGPAWLAYWGQGTLVTVSA | 307 |
| 81618_3 | EVQLVESGGGLVKPGGSLRLSCAASEFTFSDYFM SWIRQAPGKGLEWVSYISSGRSPYTNYADSVKGR FTISRDNAKNSLYLQMNSLRVEDTAVYFCARVRG PGDVFDIWGQGTLVTVSS | 308 |
| 62218_13 | EVQLVQSGAEVKKPGESLKISCKGSGYSFSSHWI SWVRQMPGKGLEWMGIIYPGDSDTSYSPSFQGQV TISADKSISTAYLQWSSLKASDTAMYYCAIANWG EGAFDVWGQGTLVTVSS | 309 |

TABLE 10

Light chain variable domains of
exemplary anti-ICAM1 antibodies.
The underlined regions denote the respective
CDR1, CDR2, or CDR3 sequences.

| NAME | VL SEQUENCE | SEQ ID NO: |
|---|---|---|
| G12 | ASELTQDPAVSVALGQTVKITCQGDSLRTYYA SWYQQRPGQAPVLVIYGENSRPSGIPDRFSGS SSGNTASLTITGAQAEDEADYYCNSRDSSGNH LRVFGGGTKLTVL | 310 |
| 6B10 | AIVMTQTPSSKSVPVGDTVTINCQASESVYNN KWLSWYQQKPGQPPKLLIYLASTLASGVPSRF KGSGSGTQFTLTISDVVSDDAATYYCAGYKNR GTDGLAFGGGTEVVVE | 311 |
| 3D8 | ADIVMTQTPASVEAAVGGTVTIKCQASQSISS YLSWYQQKPGQPPKLLIYRASTLASGVPSRFK GSGSGTEFTLTISDLESADAATYYCQSYVFGS SRSYDNAFGGGTEVVVK | 312 |
| 6G8 | AYDMSQTPASVEVAVGGTVTIKCQASQSIYSY LSWYQQKPGQRPKLLIYDASKLASGVPSRFTG SGSGTEFTLTISGVQSDDAATYYCQQAYSSSN VDNVFGGGTEVVVK | 313 |
| 15D10 | AYDMTQTPASMEVAVGGTVTIKCQASQNIHSW LAWFQQKPGQPPKRLIYKASTLASGVPSRFKG SGSGTQFTLTISGVQSDDAATYYCQQGYSRSD GEHVFGGGTEVVVK | 314 |
| 2E3 | AYDMTQTPASVEVAVGGTVTIKCQASENIYRY LLWYQQKLGQRPSLLIYDASKLASGVPSRFKG SGSGTEFTLTISGVQSDDAATYYCQQAYSSSN VDNAFGGGTEVVVK | 315 |

TABLE 10-continued

Light chain variable domains of
exemplary anti-ICAM1 antibodies.
The underlined regions denote the respective
CDR1, CDR2, or CDR3 sequences.

| NAME | VL SEQUENCE | SEQ ID NO: |
|---|---|---|
| 8H1 | GYDMTQTPASVEVAVGGTVTIKCQASQSINSW LAWFQHKPGQPPKRLIYKASTLASGVSSRFKG SGSGTQFTLTISGVESADAATYYCQQGYSRSD GEHVFGGGTEVVVK | 316 |
| 11G7 | AYDMTQTPASVEVAVGGTVTIKCQASQSINSW LSWFHQKPGQPPKRLIYKASTLASGVSSRFKG SGSGTQFTLTISGVESADAATYYCQQGYSRSD GEHVFGGGTEVVVK | 317 |
| 14H1 | AYDMTQTPASVEVAVGGTVTIKCQASQSINSW LSWFHQKPGQPPKRLIYKASTLASGVSSRFKG SGSGTQFTLTISGVESADAATYYCQQGYSRSD GEHVFGGGTEVVVK | 318 |
| 4H5 | GYDMTQTPASVEVAVGGTVTIKCQASQSINSW LVWFQHKPGQPPKRLIYKASTLASGVSSRFKG SGSGTHFTLTISGVESADAATYYCQQGYSRSD GEHVFGGGTEVVVK | 319 |
| 11F2 | AYDMTQTPASVEVAVGGTVTIKCQASQSIYRY LSWYQKKPGQRPKFLIYDASKLASGVPSRFEG SGSGTEFTLTISGAQSDDAATYYCQQAYSSGS IDNAFGGGTEVVVK | 320 |
| 16E4 | AYDMTQTPASVEVAVGGTVTIKCQASQSIYSY CSWYQQKPGQRPKFLIYDASKLASGVPSRFKG SGSGTEFTLTISGMQSDDAATYYCQQAYSSSN VDNAFGGGTEVVVK | 321 |
| 8B12 | AYDMTQTPASVEVAVGGTVTIKCQASQSIYSY LSWYQQKPGQRPKFLIYDASKVASGVPSRFKG SGSGTEFTLTISAVQSDDAATYYCQQAYSSSN VDNAFGGGTEVMVK | 322 |
| 5B12 | AFELTQTPSSVEAAVGGTVTIKCQASESIDSY LSWYQQKPGQPPKLLIYAASTLASGVSSRFKG SGSGTEFTLTISDLESADAATYYCQSYSGTIT TSGGAFGGGTEVVVK | 323 |
| 10B8 | AFELTQTPSSVEAAVGGTVTIKCQASESINSY LSWYQQKPGQPPKLLIYAASTLASGVSSRFKG SGSGTEFTLTISDLESADAATYYCQSYSGTIS TSGGAFGGGTEVVVK | 324 |
| 14B3 | AQVLTQTASSVSATVGGTVTISCQSSESVDVN NLAWYQQKPGQPPKLLIYSASTLASGVPSRFK GSGSGTQFTLTVSDLESADAATYYCAGGYSGN IFAFGGGTAVVVK | 325 |
| 8E5 | AQVLTQTPSPVSAAVGGTVTINCQSSQSVVSD KLLSWFQQKPGQPPKLLIYGASTLASGVPSRF KGSGSGTQFTLTISDVQSDDAATYYCAGAYST DSDIRAFGGGTEVVVK | 326 |
| G1F4_VL | DIQMTQSPSSLSASVGDRVTITCRASQDVNTA VAWYQQKPGKAPKLLIYSASFLYSGVPSRFSG SRSGTDFTLTISSLQPEDFATYYCQQHYTTPP TFGQGTKVEIK | 155 |

In some embodiments, an anti-ICAM1 antibody described supra is a full-length antibody. In other embodiments, the anti-ICAM1 antibody is a binding fragment. In some instances, the anti-ICAM1 antibody comprises an antibody or binding fragment thereof, a chimeric antibody or binding fragment thereof, a monoclonal antibody or binding fragment thereof, or a bispecific antibody or binding fragment thereof. In some cases, the anti-CD38 antibody comprises a monovalent Fab, a divalent Fab'2, a single-chain variable fragment (scFv), a diabody, a minibody, a nanobody, a single-domain antibody (sdAb), or a camelid antibody or binding fragment thereof.

In some embodiments, the anti-ICAM1 antibody comprises a bispecific antibody or binding fragment thereof. In some instances, the bispecific antibody or binding fragment thereof is a bispecific antibody conjugate, a hybrid bispecific IgG, a variable domain only bispecific antibody, a CH1/CL fusion protein, a Fab fusion protein, a non-immunoglobulin fusion protein, a Fc-modified IgG, an appended & Fc-modified IgG, a modified Fc and CH3 fusion protein, an appended IgG-HC fusion, a Fc fusion, a CH3 fusion, an IgE/IgM CH2 fusion, or a F(ab')2 fusion.

In some embodiments, a bispecific antibody or binding fragment includes a Knobs-into-Holes (KIH), Asymmetric Re-engineering Technology-immunoglobulin (ART-Ig), Tri-omab quadroma, bispecific monoclonal antibody (BiMAb, BsmAb, BsAb, bsMab, BS-Mab, or Bi-MAb), FcAAdp, XmAb, Azymetric, Bispecific Engagement by Antibodies based on the T-cell receptor (BEAT), Bispecific T-cell Engager (BiTE), Biclonics, Fab-scFv-Fc, Two-in-one/Dual Action Fab (DAF), FinomAb, scFv-Fc-(Fab)-fusion, Dock-aNd-Lock (DNL), Adaptir (previously SCORPION), Tandem diAbody (TandAb), Dual-affinity-ReTargeting (DART), or nanobody.

In some embodiments, a variable domain only bispecific antibody comprises a tandem scFv (taFv), triplebody, diabody (Db), dsDb, Db(KIH), scDb, dsFv-dsFv', tandAbs, triple heads, tandem dAb/VHH, triple dAb/VHH, or tetravalent dAb/VHH.

In some embodiments, a CH1/CL fusion protein comprises a scFv2-CH1/CL or VHH2-CH1/CL.

In some instances, Fab fusion protein comprises a Fab-scFv (bibody), Fab-scFv2 (tribody), Fab-Fv, Fab-dsFv, Fab-VHH, or orthogonal Fab-Fab.

In some instances, a non-immunoglobulin fusion protein comprises a scFv2-albumin, scDb-albumin, taFv-albumin, taFv-toxin, miniantibody, DNL-Fab2, DNL-Fab2-scFv, DNL-Fab2-IgG-cytokine2, or ImmTAC (TCR-scFv).

In some instances, a Fc-modified IgG comprises a IgG (KIH), IgG (KIH) common LC, ZW1 IgG common LC, Biclonics common LC, CrossMAb, scFab-IgG (KIH), Fab-scFab-IgG (KIH), orthogonal Fab IgG (KIH), DuetMab, CH3 charge pair+CH1/CL charge pair, hinge/CH3 charge pair, DuoBody, four-in-one-CrossMab (KIH), LUZ-Y common LC, LUZ-Y scFab-IgG, or FcFc*.

In some instances, an appended & Fc-modified IgG comprises an IgG(KIH)-Fv, IgG(HA-TF-FV), IgG(KIH)-scFab, scFab-Fc(KIH)-scFv2, scFab-Fc(KIH)-scFv, half DVD-Ig, Dual Variable Domain-immunoglobulin (DVD-Ig), or CrossMab-Fab.

In some cases, a modified Fc and CH3 fusion protein comprises a scFv-Fc (KIH), scFv-Fc (CH3 charge pair), scFv-FC (EW-RVT), scFv-Fc (HA-TF), scFv-Fc (SEED-body), taFv-Fc(KIH), scFv-Fc(KIH)-Fv, Fab-Fc(KIH)-scFv, Fab-scFv-Fc(KIH), Fab-scFv-Fc(BEAT), DART-Fc, scFv-CH3(KIH), or TriFabs.

In some cases, an appended IgG-HC fusion antibody comprises IgG-HC-scFv, IgG-dAb, IgG-taFv, IgG-Cross-Fab, IgG-orthogonal Fab, IgG-(CaCp) Fab, scFv-HC-IgG, tandem Fab-IgG, Fab-IgG(CaCpFab), Fab-IgG(CR3), or Fab-hinge-IgG(CR3).

In some cases, an appended IgG-LC fusion antibody comprises IgG-scFv(LC), scFv(LC)-IgG, or dAb-IgG.

In some cases, an appended IgG-HC & LC fusion antibody comprises DVD-Ig, TVD-Ig, CODV-Ig, scFv4-IgG, or Zybody.

In some instances, a Fc fusion antibody comprises Di-diabody, scDb-Fc, taFv-Fc, scFv-Fc-scFv, HCAb-VHH, Fab-scFv-Fc, scFv4-Ig, or scFv2-Fcab.

In some instances, a CH3 fusion antibody comprises Di-diabody or scDb-CH3.

In some instances, an IgE/IgM CH2 fusion antibody comprises scFv-EHD2-scFv or scFv-MHD2-scFv.

In some instances, F(ab')2 fusion antibody comprises $F(ab')_2$-$scFv_2$.

In some instances, a CH1/CL fusion protein comprises scFv2-CH1-hinge/CL.

In some instances, a modified IgG comprises DAF (two-in-one-IgG), DutaMab, or $mAb^2$.

In some cases, a non-immunoglobulin fusion antibody comprises DNL-Fab4-IgG.

In some instances, the anti-ICAM1 antibody comprises a bispecific antibody or binding fragment thereof as illustrated in FIG. 1A or FIG. 1B.

In some embodiments, an anti-ICAM1 antibody described herein comprises an IgG framework, an IgA framework, an IgE framework, or an IgM framework. In some instances, the anti-CD38 antibody comprises an IgG framework (e.g., IgG1, IgG2, IgG3, or IgG4). In such instances, the anti-CD38 antibody comprises an IgG1, IgG2, IgG3, or an IgG4 framework.

In some cases, the anti-ICAM1 antibody further comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to increase ADCC or CDC. In other instances, the one or more mutations are to reduce or eliminate Fc effector functions such as FcγR, ADCC or CDC. In additional instances, the one or more mutations are to modulate glycosylation.

In some cases, the anti-ICAM1 antibody comprises an IgG1 framework. In some embodiments, the constant region of the anti-ICAM1 antibody is modified at one or more amino acid positions to alter Fc receptor interaction. Exemplary residues that modulate or alter Fc receptor interaction include, but are not limited to, G236, S239, T250, M252, S254, T256, K326, A330, I332, E333A, M428, H433, or N434 (Kabat numbering; EU index of Kabat et al 1991 Sequences of Proteins of Immunological Interest). In some instances, the mutation comprises G236A, S239D, T250Q, M252Y, S254T, T256E, K326W, A330L, I332E, E333A, E333S, M428L, H433K, or N434F.

In some embodiments, the modification at one or more amino acid positions in the IgG1 constant region to alter Fc receptor interaction leads to increased half-life. In some instances, the modification at one or more amino acid positions comprise T250, M252, S254, T256, M428, H433, N434, or a combination thereof, e.g., comprising T250Q/M428L or M252Y/S254T/T256E and H433K/N434F.

In some embodiments, the modification at one or more amino acid positions in the IgG1 constant region to alter Fc receptor interaction leads to increased ADCC and/or CDC. In some instances, the modification at one or more amino acid positions comprises S239, K326, A330, I332, E333, or a combination thereof. In some instances, the modification at one or more amino acid positions for increased ADCC and/or CDC comprises, e.g., E333A, S239D/A330L/I332E, or K326W/E333S. In some cases, the modification at one or more amino acid positions for increased ADCC comprises S239D/A330L/I332E. In some cases, the modification at one or more amino acid positions for increased CDC comprises K326W/E333S.

In some embodiments, the modification at one or more amino acid positions in the IgG1 constant region to alter Fc receptor interaction leads to increased macrophage phagocytosis. In some instances, the modification at one or more amino acid positions comprises G236, S239, I332, or a combination thereof. In some cases, the modification at one or more amino acid positions for increased macrophage phagocytosis comprises the combination S239D/I332I/G236A.

In some embodiments, the IgG1 constant region is modified at amino acid N297 (Kabat numbering) in which residue N297 is afucosylated, wherein the oligosaccharides do not contain fucose sugar units.

In some embodiments, the anti-ICAM1 antibody comprises an IgG2 framework. In some instance, one or more amino acid positions in the IgG2 framework are modified to alter Fc receptor interaction, e.g., to increase ADCC and/or CDC. In some cases, one or more amino acid positions in the IgG2 framework are modified to stabilize the antibody and/or to increase half-life. In some instances, one or more amino acid positions in the IgG2 framework are modified to modulate glycosylation. In some cases, the IgG2 constant region is afucosylated at residue N297.

In some embodiments, the anti-ICAM1 antibody comprises an IgG3 framework. In some instance, one or more amino acid positions in the IgG3 framework are modified to alter Fc receptor interaction, e.g., to increase ADCC and/or CDC. In some cases, one or more amino acid positions in the IgG3 framework are modified to stabilize the antibody and/or to increase half-life. In some instances, one or more amino acid positions in the IgG3 framework are modified to modulate glycosylation. In some cases, the constant region of the antibody is modified at amino acid R435 to extend the half-life, e.g., R435H (Kabat numbering). In some instances, the constant region is afucosylated at residue N297.

In some embodiments, the anti-ICAM1 antibody comprises an IgG4 framework. In some instance, one or more amino acid positions in the IgG4 framework are modified to alter Fc receptor interaction, e.g., to increase ADCC and/or CDC. In some cases, one or more amino acid positions in the IgG4 framework are modified to stabilize the antibody and/or to increase half-life. In some instances, one or more amino acid positions in the IgG4 framework are modified to modulate glycosylation. In some cases, the constant region is modified at a hinge region to prevent or reduce strand exchange. In some instances, the amino acid that is modified is S228 (e.g., S228P).

In some embodiments, the human IgG constant region is modified to alter ADCC and/or CDC, e.g., with an amino acid modification described in Natsume et al., 2008 *Cancer Res*, 68(10): 3863-72; Idusogie et al., 2001 *J Immunol*, 166(4): 2571-5; Moore et al., 2010 *mAbs*, 2(2): 181-189; Lazar et al., 2006 *PNAS*, 103(11): 4005-4010, Shields et al., 2001 *JBC*, 276(9): 6591-6604; Stavenhagen et al., 2007 *Cancer Res*, 67(18): 8882-8890; Stavenhagen et al., 2008 *Advan. Enzyme Regul.*, 48: 152-164; Alegre et al, 1992 *J Immunol*, 148: 3461-3468; Reviewed in Kaneko and Niwa, 2011 Biodrugs, 25(1): 1-11.

In some embodiments, the human IgG constant region is modified to induce heterodimerization. For example, having an amino acid modification within the CH3 domain at Thr366, which when replaced with a more bulky amino acid, e.g., Trp (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). In some cases, heterodimerization via CH3 modifications is further stabilized by the introduction of a disulfide bond, for example by changing Ser354 to Cys (S354C) and Y349 to Cys (Y349C) on opposite CH3 domains (Reviewed in Carter, 2001 *Journal of Immunological Methods*, 248: 7-15).

In some instances, an anti-ICAM1 antibody described herein has reduced or lacks glycosylation but is not modified at amino acid Asn297 (Kabat numbering). In these instances, the glycosylation is, for example, eliminated by production of the antibody in a host cell that lacks a post-translational glycosylation capacity, for example a bacterial or yeast derived system or a modified mammalian cell expression system. In certain aspects, such a system is a cell-free expression system.

In some embodiments, an anti-ICAM1 antibody described herein is a full-length antibody, comprising a heavy chain (HC) and a light chain (LC). In some cases, the heavy chain (HC) comprises a sequence selected from Table 11. In some cases, the light chain (LC) comprises a sequence selected from Table 12.

TABLE 11

Heavy chains of exemplary anti-ICAM1 antibodies

| NAME | HC SEQUENCE | SEQ ID NO: |
|---|---|---|
| G12 | QVQLQESGGGLVQPGGSLRLSCAASGFTFSSYAMSWVRQAPGKGLEW VSAISGSGGSTYYADSVKGRFTISRDNSKNTLYLQMSSLRAEDTAFYYC ANSAYTGGWYDYWGHGTLVTVSSASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKRVEPKSCDKTHTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPGK | 328 |
| 6B10 | QSLEESGGRLVTPGGSLTLTCTVSGFSLSSYGMSWVRQAPGKGLEYIG WISFSGSTYYASWAKGRFTISKTSTTVDLKITSPTTEDTATYFCARGGDY GGSTYILNLWGPGTLVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK | 329 |

TABLE 11-continued

| Heavy chains of exemplary anti-ICAM1 antibodies | | |
|---|---|---|
| NAME | HC SEQUENCE | SEQ ID NO: |
| | GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYT QKSLSLSPGK | |
| 3D8 | QSLEESGGDLVKPGASLTLTCTASGFSFSSSYWMCWVRQAPGKGLEWI ACIDGGSAGYNYYATWAKGRFTISKTSSTTVTLQMTSLTAADRATYFC ARGPGSSYNLWGPGTLVTVSSASTKGPSVFPLAPSSKSTSGGTAALGCL VKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNH YTQKSLSLSPGK | 330 |
| 6G8 | QSVEESGGGLVKPGGTLTLTCTVSGFSLSSYAMGWVRQAPGKGLEYIGI IGSSGSTYYATWAKGRFTISKTSTTVDLKITSPTTEDTATYFCVRDPYDS YDAAYRLWGPGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYT QKSLSLSPGK | 331 |
| 15D10 | QSVEESGGRLVTPGTPLTLTCTASGFSLNNYYMSWVRQAPGKGLEWIGI ISDSDNTYYASWAKGRFTISKTSTTVDLKITSPTTEDTATYFCARDWSLD SSSGYYYYDMDLWGPGTLVTVSAASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | 332 |
| 2E3 | QSVEESGGGLVKPGGTLTLTCTVSGFSLSSYAMGWVRQAPGKGLEYIGI IGSSGSTYYASWAKGRFTISKTSTTVDLKITSPTTEDTATYFCVRDPYDS FGDGYRLWGPGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPGK | 333 |
| 8H1 | QSVEESGGRLVTPGTPLTLTCTASGFSLSNYYMSWVRQAPGKGLEWIGI ISDSGSTYYASWAKGRFTISKTSTTVDLKITSPTTEDTATYFCARDWSYD SSSGYYYYDMDLWGPGTLVTVSAASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | 334 |
| 11G7 | QSVEESGGRLVTPGTPLTLTCTVSGFSLSDYMSWVRQAPGKGLEWIGI ISDSGSTYYASWAKGRFTISKTSSTTVDLKITSPTTEDTATYFCARDWSY DSSSGYYYYDMDLWGPGTLVTVSAASTKGPSVFPLAPSSKSTSGGTAA LGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPGK | 335 |
| 14H1 | QSVEESGGRLVTPGTPLTLTCTVSGFSLSNYYMSWVRQAPGKGLEWIGI ISDSGSTYYASWAKGRFTISKTSTTVDLSITSPTTEDTATYFCARDWSYD STSGYYYYDMDLWGPGTLVTVSAASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV | 336 |

TABLE 11-continued

| | Heavy chains of exemplary anti-ICAM1 antibodies | |
|---|---|---|
| NAME | HC SEQUENCE | SEQ ID NO: |
| | FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | |
| 4H5 | QSVEESGGRLVTPGTPLTLTCTASGFSLSNYYMSWVRQAPGKGLEWIGI ISDSGTTYYASWAKGRFTISKTSTTVDLKITSPTTEDTATYFCARDWSYD SSSGYYYYDMDLWGPGTLVTVSAASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | 337 |
| 11F2 | QSVEESGGGLVKPGGTLTLTCTVSGFSLSSHAMGWVRQAPGKGLEYIGI IGSSDRTYYASWAKGRFTISKTSTTVDLKITSPTTEDTATYFCVRDPYDS YDDGYRLWGPGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYT QKSLSLSPGK | 338 |
| 16E4 | QSVEESGGRLVTPGTPLTLTCTVSGFSLSSHAMGWVRQAPGKGLQYIGII GSSGSTYYASWAKGRFTISKTSTTVDLRLTSPTTEDTATYFCVRDPYDSF GDAYRLWGPGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPGK | 339 |
| 8B12 | QSVEESGGGLVKPGGTLTLTCTVSGFSLSTHAMGWVRQAPGKGLEYIGI IGSSDRTYYASWAKGRFTISKTSTTVDLKITSPTTEDTATYFCVRDPYDS FDDGYRLWGPGTLVTVSSASTKGPSVFPLAPSSKSTSGGTAALGCLVKD YFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPGK | 340 |
| 5B12 | QSLEESGGRLVTPGTPLTLTCTVSGFSLSSYGMSWVRQAPGKGLEYIGW ISFSGSAYYANWAKGRFTISKTSTTVDLKITSPTTEDTATYFCARGGDYG GSTYILNLWGPGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYT QKSLSLSPGK | 341 |
| 10B8 | QSLEESGGRLVTPGGSLTLTCTVSGFSLSSYGMSWVRQAPGKGLEYIG WISFSGSAYYANWAKGRFTISKTSTTVDLKITSPTTEDTATYFCARGGD YGGSTYILNLWGPGTLVTVSSASTKGPSVFPLAPSSKSTSGGTAALGCL VKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNH YTQKSLSLSPGK | 342 |
| 14B3 | QSLEESGGDLVKPGASLTLTCTASGFSSSSGYYICWVRQAPGKGLEWIA CIGAGSGAAYYASWAKGRFTMSKTSSTTVTLQMTSLTAADTATYFCAR GGFVVGGGYGGYCFNLWGPGTLVTVSSASTKGPSVFPLAPSSKSTSGG | 343 |

TABLE 11-continued

| Heavy chains of exemplary anti-ICAM1 antibodies | | |
|---|---|---|
| NAME | HC SEQUENCE | SEQ ID NO: |
|  | TAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMH EALHNHYTQKSLSLSPGK |  |
| 8E5 | QSLEESGGRLVTPGTPLTLTCTVSGFSLSNYAMNWVRQAPGKGLEWIG YISTRGSAYYASWAKGRFTISKTSTTVDLKMTSPTTEDTATYFCARGDL VGGGYIRGSFDPWGPGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | 344 |
| c05G01 | EVKLMESGGDLVKPGGSLKLSCAASGFTFSNYGMSWVRQTPDKRLEW VATISTGGGYTHYPDSVKGRFTISRDNAKNTLYLQMSSLKSEDTAMYY CARPDYYGSSYGPAWFAYWGQGTLVTVSAASTKGPSVFPLAPSSKSTS GGTAALGCLVKDYFPEPVTVSWNSGALTSGVHTFPAVLQSSGLYSLSS VVTVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCS VMHEALHNHYTQKSLSLSPGK | 345 |
| c06F06 | EVQLMESGGDLVKPGGSLKLSCAASGFTFSNYGMSWVRQTPDKRLEW VATISTGGGYTYYPDSVKGRFTISRDNAKNTLYLQMSSLKSEDTAMYY CARPDYYGSSYGPAWLAYWGQGTLVTVSAASTKGPSVFPLAPSSKSTS GGTAALGCLVKDYFPEPVTVSWNSGALTSGVHTFPAVLQSSGLYSLSS VVTVPSSSLGTQTYICNVNHKPSNTKVDKKVEPKSCDKTHTCPPCPAPE LLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCS VMHEALHNHYTQKSLSLSPGK | 346 |
| c05G07 | EVQLVESGGDLVKPGGSLKLSCAASGFTFSNYGMSWVRQTPDKRLEQV ATISTGGSYTYYPDSVKGRFTISRDNAKNTLYLQMSSLKSEDTAMYYC ARPDYYGSSYGPAWLAYWGQGTLVTVSAASTKGPSVFPLAPSSKSTSG GTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEL LGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPGK | 347 |
| 81618_3 | EVQLVESGGGLVKPGGSLRLSCAASEFTFSDYFMSWIRQAPGKGLEWV SYISSGRSPYTNYADSVKGRFTISRDNAKNSLYLQMNSLRVEDTAVYFC ARVRGPGDVFDIWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | 348 |
| 62218_13 | EVQLVQSGAEVKKPGESLKISCKGSGYSFSSHWISWVRQMPGKGLEW MGIIYPGDSDTSYSPSFQGQVTISADKSISTAYLQWSSLKASDTAMYYC AIANWGEGAFDVWGQGTLVTVSSASTKGPSVFPLAPSSKSTSGGTAAL GCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK | 349 |

TABLE 12

| Light chains of exemplary anti-ICAM1 antibodies | | |
|---|---|---|
| NAME | LC SEQUENCE | SEQ ID NO: |
| G12 | ASELTQDPAVSVALGQTVKITCQGDSLRTYYASWYQQRPGQAPVLVIYGE NSRPSGIPDRFSGSSSGNTASLTITGAQAEDEADYYCNSRDSSGNHLRVFGG GTKLTVLGQPKAAPSVTLFPPSSEELQANKATLVCLISDFYPGAVTVAWKA DSSPVKAGVETTTPSKQSNNKYAASSYLSLTPEQWKSHRSYSCQVTHEGST VEKTVAPTECS | 350 |
| 6B10 | AIVMTQTPSSKSVPVGDTVTINCQASESVYNNKWLSWYQQKPGQPPKLLIY LASTLASGVPSRFKGSGSGTQFTLTISDVVSDDAATYYCAGYKNRGTDGLA FGGGTEVVVERTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 351 |
| 3D8 | ADIVMTQTPASVEAAVGGTVTIKCQASQSISSYLSWYQQKPGQPPKLLIYR ASTLASGVPSRFKGSGSGTEFTLTISDLESADAATYYCQSYVFGSSRSYDNA FGGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 352 |
| 6G8 | AYDMSQTPASVEVAVGGTVTIKCQASQSIYSYLSWYQQKPGQRPKLLIYD ASKLASGVPSRFTGSGSGTEFTLTIGVQSDDAATYYCQQAYSSSNVDNVF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 353 |
| 15D10 | AYDMTQTPASMEVAVGGTVTIKCQASQNIHSWLAWFQQKPGQPPKRLIYK ASTLASGVPSRFKGSGSGTQFTLTISGVQSDDAATYYCQQGYSRSDGEHVF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 354 |
| 2E3 | AYDMTQTPASVEVAVGGTVTIKCQASENIYRYLLWYQQKLGQRPSLLIYD ASKLASGVPSRFKGSGSGTEFTLTISGVQSDDAATYYCQQAYSSSNVDNAF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 355 |
| 8H1 | GYDMTQTPASVEVAVGGTVTIKCQASQSINSWLAWFQHKPGQPPKRLIYK ASTLASGVSSRFKGSGSGTQFTLTISGVESADAATYYCQQGYSRSDGEHVF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 356 |
| 11G7 | AYDMTQTPASVEVAVGGTVTIKCQASQSINSWLSWFHQKPGQPPKRLIYK ASTLASGVSSRFKGSGSGTQFTLTISGVESADAATYYCQQGYSRSDGEHVF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 357 |
| 14H1 | AYDMTQTPASVEVAVGGTVTIKCQASQSINSWLSWFHQKPGQPPKRLIYK ASTLASGVSSRFKGSGSGTQFTLTISGVESADAATYYCQQGYSRSDGEHVF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 358 |
| 4H5 | GYDMTQTPASVEVAVGGTVTIKCQASQSINSWLVWFQHKPGQPPKRLIYK ASTLASGVSSRFKGSGSGTHFTLTISGVESADAATYYCQQGYSRSDGEHVF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 359 |
| 11F2 | AYDMTQTPASVEVAVGGTVTIKCQASQSIYRYLSWYQKPGQRPKFLIYD ASKLASGVPSRFEGSGSGTEFTLTISGAQSDDAATYYCQQAYSSGSIDNAFG GGTEVVVKRTVAAPSVFIFPPSDEQLKSGTASVVCLLNNFYPREAKVQWK VDNALQSGNSQESVTEQDSKDSTYSLSSTLTLSKADYEKHKVYACEVTHQ GLSSPVTKSFNRGEC | 360 |
| 16E4 | AYDMTQTPASVEVAVGGTVTIKCQASQSIYSYCSWYQQKPGQRPKFLIYD ASKLASGVPSRFKGSGSGTEFTLTISGMQSDDAATYYCQQAYSSSNVDNAF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 361 |
| 8B12 | AYDMTQTPASVEVAVGGTVTIKCQASQSIYSYLSWYQQKPGQRPKFLIYD ASKVASGVPSRFKGSGSGTEFTLTISAVQSDDAATYYCQQAYSSSNVDNAF GGGTEVMVKRTVAAPSVFIFPPSDEQLKSGTASVVCLLNNFYPREAKVQW | 362 |

TABLE 12-continued

Light chains of exemplary anti-ICAM1 antibodies

| NAME | LC SEQUENCE | SEQ ID NO: |
|---|---|---|
| | KVDNALQSGNSQESVTEQDSKDSTYSLSSTLTLSKADYEKHKVYACEVTH QGLSSPVTKSFNRGEC | |
| 5B12 | AFELTQTPSSVEAAVGGTVTIKCQASESIDSYLSWYQQKPGQPPKLLIYAAS TLASGVSSRFKGSGSGTEFTLTISDLESADAATYYCQSYSGTITTSGGAFGG GTEVVVKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 363 |
| 10B8 | AFELTQTPSSVEAAVGGTVTIKCQASESINSYLSWYQQKPGQPPKLLIYAAS TLASGVSSRFKGSGSGTEFTLTISDLESADAATYYCQSYSGTISTSGGAFGG GTEVVVKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 364 |
| 14B3 | AQVLTQTASSVSATVGGTVTISCQSSESVDVNNLAWYQQKPGQPPKLLIYS ASTLASGVPSRFKGSGSGTQFTLTVSDLESADAATYYCAGGYSGNIFAFGG GTAVVVKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 365 |
| 8E5 | AQVLTQTPSPVSAAVGGTVTINCQSSQSVVSDKLLSWFQQKPGQPPKLLIY GASTLASGVPSRFKGSGSGTQFTLTISDVQSDDAATYYCAGAYSTDSDIRAF GGGTEVVVKRTVAAPSVFIFPPSDEQLKSGTASVVCLLNNFYPREAKVQW KVDNALQSGNSQESVTEQDSKDSTYSLSSTLTLSKADYEKHKVYACEVTH QGLSSPVTKSFNRGEC | 366 |
| G1F4_VL | DIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGTKV EIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVT KSFNRGEC | 182 |

In some embodiments, an anti-ICAM1 antibody described herein has an $EC_{50}$ of from about 0.001 nM to about 2.5 nM, such as about 0.02 nM, 0.03 nM, about 0.04 nM, about 0.05 nM, about 0.06 nM, about 0.09 nM, about 0.1 nM, about 1.2 nM, about 1.7 nM, about 2.0 nM, about 2.5 nM, in an in vitro cytotoxicity assay to determine ADCC activity, for instance, using cancer cells such as human prostate cancer cells.

In some cases, the serum half-life of an anti-ICAM1 antibody described herein is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer. In some cases, the serum half-life of an anti-ICAM1 antibody described herein is about 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer.

Multi-Specific Anti-CD38 and Anti-ICAM1 Antibodies

In certain embodiments, described herein is a multi-specific anti-CD38 antibody or a multi-specific anti-ICAM1 antibody. In some instances, the multi-specific anti-CD38 antibody or multi-specific anti-ICAM1 antibody comprises target binding moieties that recognize two or more antigens. In some cases, the multi-specific anti-CD38 antibody comprises target binding moieties that specifically binds to two or more antigens, e.g., three or more, four or more, or five or more antigens. In some cases, the multi-specific anti-ICAM1 antibody comprises target binding moieties that specifically binds to two or more antigens, e.g., three or more, four or more, or five or more antigens.

In some embodiments, described herein is a bispecific anti-CD38 antibody. In some instances, the bispecific anti-CD38 antibody comprises a first targeting moiety that specifically binds to CD38 and a second targeting moiety that specifically binds to a non-CD38 target. In some cases, the second target includes, but is not limited to, ICAM1, ephrin type-A receptor 2 (EphA2), ephrin type-A receptor 3 (EphA3), ephrin type-A receptor 4 (EphA4), activated leukocyte cell adhesion molecule (ALCAM), BCMA (B-cell maturation antigen or TNFRSF17), PDL1, CD30, CD33, PSMA, mesothelin, CD44, CD73, Mucin 1 cell surface associated (MUC1), Mucin 2 oligomeric mucus gel-forming (MUC2), Mucin 16 cell surface associated (MUC16), carcinoembryonic antigen (CEA), cathepsin G, preferentially expressed antigen of melanoma (PRAME), CD52, EpCAM, tumor associated glycoprotein 72 (TAG-72), carbonic anhydrase IX, PSMA, folate binding protein, gangliosides, Lewis-Y, immature laminin receptor, BING-4, calcium-activated chloride channel 2 (CaCC), gp100, synovial sarcoma X breakpoint 2 (SSX-2), or SAP-1.

In some embodiments, described herein is a bispecific anti-ICAM1 antibody. In some instances, the bispecific anti-ICAM1 antibody comprises a targeting moiety that specifically binds to ICAM1 and a targeting moiety that specifically binds to a non-ICAM1 target. In some cases, the non-ICAM1 target includes, but is not limited to, CD38, CD47, receptor tyrosine kinase like orphan receptor 1 (ROR1), receptor tyrosine kinase like orphan receptor 2 (ROR2), Erb3, IGFRIR, EGFR, PDL1, PDL2, PD1, CTLA4, or Tim3.

In some embodiments, described herein is a bispecific antibody which comprises a first targeting moiety that specifically binds to CD38 or ICAM1.

In some embodiments, a bispecific antibody of the present disclosure that comprises a first component that binds CD38 and a second component that binds ICAM1, binds to a cell that expresses on its surface target antigens of the bispecific protein, with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% or more higher affinity (e.g., preferentially binds) compared to the binding affinity of an antibody that is monospecific to only one of CD38 or ICAM1, to the cell.

In some instances, the bispecific antibody further comprises an enhanced complement dependent cytotoxicity (CDC) effect compared to a CDC effect by reference antibody daratumumab. In some instances, the bispecific antibody further comprises an enhanced ADCC effect compared to an ADCC effect by reference antibody daratumumab. In some instances, the bispecific antibody further comprises a reduced immune cell kill effect compared to an immune cell kill effect of reference antibody daratumumab. In some cases, the enhanced CDC is at least 2-fold, 3-fold, 4-fold, or higher than the CDC effect of reference antibody daratumumab. In some cases, the enhanced CDC is at least 30%, 40%, 50%, 60%, 70%, 80%, 90%, or higher than the CDC effect of reference antibody daratumumab. In some cases, the enhanced ADCC is at least 2-fold, 3-fold, 4-fold, 5-fold, or higher than the ADCC effect of reference antibody daratumumab. In some cases, the enhanced ADCC is at least 30%, 40%, 50%, 60%, 70%, 80%, 90%, or higher than the ADCC effect of reference antibody daratumumab. In some cases, the immune cell is a Natural Killer cell. In some cases, the immune cell viability is improved by about 10%, 20%, 30%, 40%, 50%, 60%, 70%, 80%, 90%, or higher compared to the immune cell viability in the presence of reference antibody daratumumab.

In some embodiments, described herein is a bispecific antibody which comprises a first targeting moiety that specifically binds to CD38 and a second targeting moiety that specifically binds to ICAM1. In some instances, the bispecific antibody further comprises an enhanced CDC effect compared to a CDC effect by reference antibody daratumumab. In some instances, the bispecific antibody further comprises an enhanced ADCC effect compared to an ADCC effect by reference antibody daratumumab. In some cases, the enhanced CDC is at least 2-fold, 3-fold, 4-fold, or higher than the CDC effect of reference antibody daratumumab. In some cases, the enhanced CDC is at least 30%, 40%, 50%, 60%, 70%, 80%, 90%, or higher than the CDC effect of reference antibody daratumumab. In some cases, the enhanced ADCC is at least 2-fold, 3-fold, 4-fold, 5-fold, or higher than the ADCC effect of reference antibody daratumumab. In some cases, the enhanced ADCC is at least 30%, 40%, 50%, 60%, 70%, 80%, 90%, or higher than the ADCC effect of reference antibody daratumumab.

In some embodiments, described herein is bispecific antibody comprising a first component that binds specifically to CD38 and a second component that binds specifically to ICAM1, wherein the bispecific antibody mediates ADCC more efficiently than a monospecific antibody that comprises either the first component or the second component, wherein the ADCC activity is determined using an in vitro cytotoxicity assay. In some embodiments, the bispecific antibody mediates at least about 5%, at least about 10%, at least about 20%, at least about 30%, at least about 40%, at least about 50%, at least about 75%, at least about 100% higher maximum cytotoxicity in an in vitro ADCC assay than the monospecific antibody that comprises either the first component or the second component. In some embodiments, the bispecific antibody mediates at least 2 fold, at least 3 fold, at least 4 fold, at least 5 fold or at least 10 fold higher maximum cytotoxicity in an in vitro ADCC assay than the monospecific antibody that comprises either the first component or the second component.

In some embodiments, described herein is bispecific antibody comprising a first component that binds specifically to CD38 and a second component that binds specifically to ICAM1, wherein the bispecific antibody mediates complement-dependent cytotoxicity (CDC) more efficiently than a monospecific antibody that comprises either the first component or the second component, wherein the ADCC activity is determined using an in vitro cytotoxicity assay, wherein the CDC activity is determined using an in vitro cytotoxicity assay. In some embodiments, the bispecific antibody mediates at least about 5%, at least about 10%, at least about 20%, at least about 30%, at least about 40%, at least about 50%, at least about 75%, at least about 100% higher maximum cytotoxicity in an in vitro CDC assay than the monospecific antibody that comprises either the first component or the second component.

In some instances, the bispecific antibody further comprises a reduced immune cell kill effect compared to an immune cell kill effect of reference antibody daratumumab. In some cases, the immune cell viability is improved by about 10%, 20%, 30%, 40%, 50%, 60%, 70%, 80%, 90%, or higher compared to the immune cell viability in the presence of reference antibody daratumumab. In some cases, the immune cell is a Natural Killer cell.

In some embodiments, the bispecific antibody comprising a CD38 targeting moiety and an ICAM1 targeting moiety comprises a bispecific antibody conjugate, a hybrid bispecific IgG, a variable domain only bispecific antibody, a CH1/CL fusion protein, a Fab fusion protein, a non-immunoglobulin fusion protein, a Fc-modified IgG, an appended & Fc-modified IgG, a modified Fc and CH3 fusion protein, an appended IgG-HC fusion, a Fc fusion, a CH3 fusion, an IgE/IgM CH2 fusion, or a F(ab')2 fusion.

In some embodiments, the bispecific antibody comprising a CD38 targeting moiety and an ICAM1 targeting moiety comprises a Knobs-into-Holes (KIH), Asymmetric Re-engineering Technology-immunoglobulin (ART-Ig), Triomab quadroma, bispecific monoclonal antibody (BiMAb, BsmAb, BsAb, bsMab, BS-Mab, or Bi-MAb), FcAAdp, XmAb, Azymetric, Bispecific Engagement by Antibodies based on the T-cell receptor (BEAT), Bispecific T-cell Engager (BiTE), Biclonics, Fab-scFv-Fc, Two-in-one/Dual Action Fab (DAF), FinomAb, scFv-Fc-(Fab)-fusion, Dock-aNd-Lock (DNL), Adaptir (previously SCORPION), Tandem diAbody (TandAb), Dual-affinity-ReTargeting (DART), or nanobody.

In some embodiments, a variable domain only bispecific antibody comprises a tandem scFv (taFv), triplebody, diabody (Db), dsDb, Db(KIH), scDb, dsFv-dsFv', tandAbs, triple heads, tandem dAb/VHH, triple dAb/VHH, or tetravalent dAb/VHH.

In some embodiments, a CH1/CL fusion protein comprises a scFv2-CH1/CL or VHH2-CH1/CL.

In some instances, Fab fusion protein comprises a Fab-scFv (bibody), Fab-scFv2 (tribody), Fab-Fv, Fab-dsFv, Fab-VHH, or orthogonal Fab-Fab.

In some instances, a non-immunoglobulin fusion protein comprises a scFv2-albumin, scDb-albumin, taFv-albumin, taFv-toxin, miniantibody, DNL-Fab2, DNL-Fab2-scFv, DNL-Fab2-IgG-cytokine2, or ImmTAC (TCR-scFv).

In some instances, a Fc-modified IgG comprises a IgG (KIH), IgG (KIH) common LC, ZW1 IgG common LC, Biclonics common LC, CrossMAb, scFab-IgG (KIH), Fab-scFab-IgG (KIH), orthogonal Fab IgG (KIH), DuetMab, CH3 charge pair+CH1/CL charge pair, hinge/CH3 charge pair, DuoBody, four-in-one-CrossMab (KIH), LUZ-Y common LC, LUZ-Y scFab-IgG, or FcFc*.

In some instances, an appended & Fc-modified IgG comprises an IgG(KIH)-Fv, IgG(HA-TF-FV), IgG(KIH)-scFab, scFab-Fe(KIH)-scFv2, scFab-Fe(KIH)-scFv, half DVD-Ig, Dual Variable Domain-immunoglobulin (DVD-Ig), or CrossMab-Fab.

In some cases, a modified Fe and CH3 fusion protein comprises a scFv-Fc (KIH), scFv-Fc (CH3 charge pair), scFv-FC (EW-RVT), scFv-Fc (HA-TF), scFv-Fc (SEED-body), taFv-Fe(KIH), scFv-Fe(KIH)-Fv, Fab-Fe(KIH)-scFv, Fab-scFv-Fe(KIH), Fab-scFv-Fe(BEAT), DART-Fe, scFv-CH3(KIH), or TriFabs.

In some cases, an appended IgG-HC fusion antibody comprises IgG-HC-scFv, IgG-dAb, IgG-taFv, IgG-Cross-Fab, IgG-orthogonal Fab, IgG-(CaCp) Fab, scFv-HC-IgG, tandem Fab-IgG, Fab-IgG(CaCpFab), Fab-IgG(CR3), or Fab-hinge-IgG(CR3).

In some cases, an appended IgG-LC fusion antibody comprises IgG-scFv(LC), scFv(LC)-IgG, or dAb-IgG.

In some cases, an appended IgG-HC & LC fusion antibody comprises DVD-Ig, TVD-Ig, CODV-Ig, scFv4-IgG, or Zybody.

In some instances, a Fe fusion antibody comprises Di-diabody, scDb-Fe, taFv-Fe, scFv-Fe-scFv, HCAb-VHH, Fab-scFv-Fe, scFv4-Ig, or scFv2-Fcab.

In some instances, a CH3 fusion antibody comprises Di-diabody or scDb-CH3.

In some instances, an IgE/IgM CH2 fusion antibody comprises scFv-EHD2-scFv or scFv-MHD2-scFv.

In some instances, F(ab')2 fusion antibody comprises $F(ab')_2$-scFv$_2$.

In some instances, a CH1/CL fusion protein comprises scFv2-CH1-hinge/CL.

In some instances, a modified IgG comprises DAF (two-in-one-IgG), DutaMab, or $mAb^2$.

In some cases, a non-immunoglobulin fusion antibody comprises DNL-Fab4-IgG.

In some instances, the bispecific antibody comprising a CD38 targeting moiety and an ICAM1 targeting moiety comprises an antibody format as illustrated in FIG. 1A or FIG. 1B.

Figures 2A, 2B, 2C, 2D:
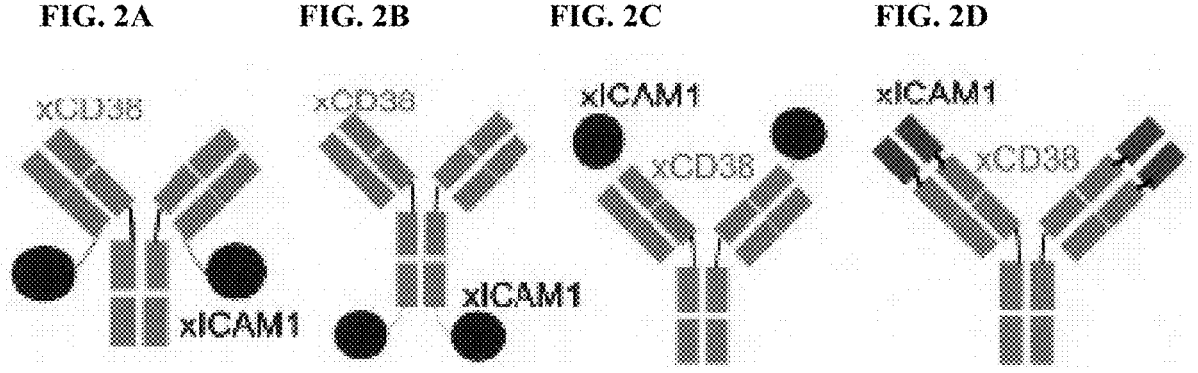
FIG. 2A: Light chain C-terminal fusion.
FIG. 2B: Heavy chain C-terminal fusion.
FIG. 2C: Heavy chain N-terminal fusion.
FIG. 2D: DVD format.

In some instances, the bispecific antibody comprising a CD38 targeting moiety and an ICAM1 targeting moiety is a bivalent antibody or binding fragments thereof. In some instances, the bivalent antibody or binding fragments thereof comprises an IgG-scFv(LC)C-terminal fusion format (FIG. 2A), an IgG-HC-scFv C-terminal fusion format (FIG. 2B), a scFv-HC-IgG N-terminal fusion format (FIG. 2C), or a DVD-Ig format (FIG. 2D).

Figures 2E, 2F:
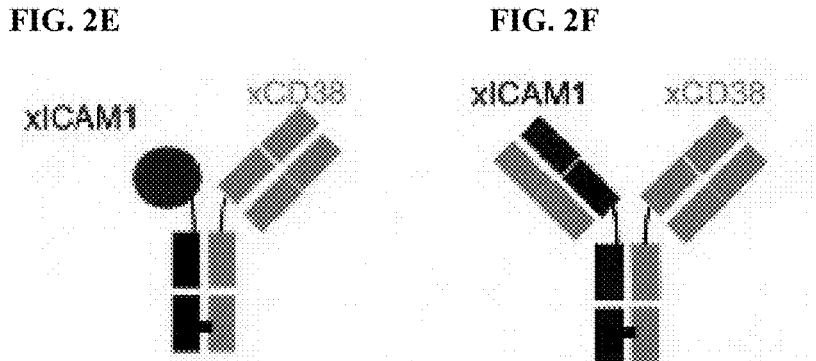
FIG. 2E: Three chain knobs-into-holes (KIH)
FIG. 2F: Common light chain bispecific.

In some instances, the bispecific antibody comprising a CD38 targeting moiety and an ICAM1 targeting moiety is a monovalent antibody or binding fragments thereof. In some cases, the monovalent antibody or binding fragments thereof comprises a Fab-scFv-Fe(KIH) format (also referred to herein as three chain knobs-into-holes) (FIG. 2E) or a Biclonics common LC format (also referred to herein as a common light chain bispecific) (FIG. 2F).

In some embodiments, the bispecific antibody comprising a CD38 targeting moiety and an ICAM1 targeting moiety comprises a $K_D$ to CD38 from about 1 nM to about 100 nM. In some instances, the $K_D$ is at least 1 nM, 2 nM, 3 nM, 3.15 nM, 3.2 nM, 3.39 nM, 3.5 nM, 4 nM, 4.5 nM, 5 nM, 5.32 nM, 5.5 nM, 6 nM, 6.5 nM, 7 nM, 7.5 nM, 8 nM, 8.5 nM, 9 nM, 9.5 nM, 10 nM, 15 nM, 18 nM, 20 nM, 25 nM, 30 nM, 35 nM, 40 nM, 45 nM, 50 nM, 60 nM, 70 nM, 80 nM, 90 nM, or 100 nM.

In some embodiments, the bispecific antibody comprising a CD38 targeting moiety and an ICAM1 targeting moiety comprises a $K_D$ to ICAM1 from about 0.1 nM to about 20 nM. In some instances, the $K_D$ is about 0.15 nM, 0.2 nM, 0.24 nM, 0.25 nM, 0.29 nM, 0.3 nM, 0.4 nM, 0.5 nM, 0.6 nM, 0.7 nM, 0.8 nM, 0.9 nM, 1 nM, 1.5 nM, 1.72 nM, 2 nM, 2.28 nM, 2.5 nM, 3 nM, 3.5 nM, 4 nM, 4.5 nM, 5 nM, 6 nM, 7 nM, 8 nM, 9 nM, 10 nM, 1 nM, 12 nM, 13 nM, 14 nM, 15 nM, 16 nM, 17 nM, 18 nM, 19 nM, or 20 nM.

In some embodiments, the first targeting moiety that specifically binds to CD38 comprises a VH region and a VL region, wherein the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}$ $X_{45}X_{46}X_{47}X_{48}X_{49}$; wherein $X_{32}$ is selected from A, G, or V; $X_{33}$ is selected from K, A, R, T, G, or S; $X_{34}$ is selected from R, A, V, T, P, I, E, D, or S; $X_{35}$ is selected from G, W, D, L, K, P, S, A, T, or R; $X_{36}$ is selected from T, P, A, Y, D, G, S, R, V, or E; $X_{37}$ is selected from Y, V, T, S, N, A, G, Q, F, or I; $X_{38}$ is selected from G, A, S, D, K, F, L, or Y; $X_{39}$ is selected from Y, T, A, G, S, or I; $X_{40}$ is selected from S, Y, G, R, W, N, L, D, or F; $X_{41}$ is present or absent, if present, is selected from F, Y, V, D, A, N, G, E, or L; $X_{42}$ is present or absent, if present, is selected from P, L, Y, F, G, or T; $X_{43}$ is present or absent, if present, is selected from T, P, F, V, N, Y, or S; $X_{44}$ is present or absent, if present, is selected from G, L, S, T, or F; $X_{45}$ is present or absent, if present, is selected from F, L, E, N, or S; $X_{46}$ is present or absent, if present, is selected from D, S, L, or R; $X_{47}$ is present or absent, if present, is selected from Y or L; $X_{48}$ is present or absent, if present, is D; and $X_{49}$ is present or absent, if present, is L; and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some embodiments, the first targeting moiety that specifically binds to CD38 comprises a VH region and a VL region, wherein the VH region comprises CDR1 sequence selected from SEQ ID NOs: 1, 4, 6, 8, and 9; CDR2 sequence selected from SEQ ID NOs: 2 and 5; and CDR3 sequence $AKRGTYX_{38}YSX_{41}PTGFDY$ (SEQ ID No. 421), in which $X_{38}$ is selected from A or G and $X_{41}$ is selected from F or Y; and wherein the VL region comprises CDR1 sequence consisting of SEQ ID NO: 62, CDR2 sequence consisting of SEQ ID NO: 63, and CDR3 sequence consisting of SEQ ID NO: 64.

In some embodiments, the first targeting moiety that specifically binds to CD38 comprises a VH region and a VL region, wherein the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence $X_{32}X_{33}X_{34}X_{35}X_{36}X_{37}X_{38}X_{39}X_{40}X_{41}X_{42}X_{43}X_{44}X_{45}X_{46}X_{47}$ $X_{48}X_{49}$, in which $X_{32}$ is selected from A, G, or V; $X_{33}$ is selected from A, R, T, S, or G; $X_{34}$ is selected from A, V, T, P, I, E, D, or S; $X_{35}$ is selected from G, W, D, L, K, P, S, R, or A; $X_{36}$ is selected from P, A, Y, D, G, S, R, V, E, or T; $X_{37}$ is selected from Y, V, T, S, N, A, G, Q, F, or I; $X_{38}$ is selected from G, S, D, K, F, L, or Y; $X_{39}$ is selected from T, A, G, S, I, or Y; $X_{40}$ is selected from S, Y, G, R, W, N, L, D, or F; $X_{41}$ is present or absent, if present, is selected from V, D, Y, A, N, G, L, or E; $X_{42}$ is present or absent, if present, is selected from L, Y, F, T, or G; $X_{43}$ is present or absent, if present, is selected from P, F, V, N, S, or Y; $X_{44}$ is present or absent, if present, is selected from L, S, T, G, or F; $X_{45}$ is present or absent, if present, is selected from L, F, E, S, or N; $X_{46}$ is present or absent, if present, is selected from S, L, or R; $X_{47}$ is present or absent, if present, is L; $X_{48}$ is present or absent, if present, is D; and $X_{49}$ is present or absent, if present, is L; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some embodiments, the first targeting moiety that specifically binds to CD38 comprises a VH region and a VL region, wherein the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence $X_{32}X_{33}X_{34}X_{35}X_{36}X_{37}X_{38}X_{39}X_{40}X_{41}X_{42}X_{43}X_{44}X_{45}$, in which $X_{32}$ is selected from A or G; $X_{33}$ is selected from A, R, or T; $X_{34}$ is selected from A, V, T, P, I, E, or D; $X_{35}$ is selected from G, W, D, L, K, or P; $X_{36}$ is selected from P, A, Y, D, or G; $X_{37}$ is selected from Y, V, T, S, N, A, or G; $X_{38}$ is selected from G, S, D, or K; $X_{39}$ is selected from T, A, G, S, or I; $X_{40}$ is selected from S, Y, G, R, or W; $X_{41}$ is selected from V, D, Y, A, N, or G; $X_{42}$ is selected from L, Y, or F; $X_{43}$ is present or absent, if present, is selected from P, F, V, or N; $X_{44}$ is present or absent, if present, is selected from L, S, or T; and $X_{45}$ is present or absent, if present, is selected from L or F, and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some embodiments, the first targeting moiety that specifically binds to CD38 comprises a VH region and a VL region, wherein the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence $AX_{33}X_{34}X_{35}X_{36}X_{37}X_{38}X_{39}X_{40}X_{41}X_{42}X_{43}X_{44}X_{45}X_{46}$ (SEQ ID No. 422), in which $X_{33}$ is selected from R or G; $X_{34}$ is selected from E, D, or S; $X_{35}$ is selected from G, L, P, S, or A; $X_{36}$ is selected from D, S, or R; $X_{37}$ is selected from Y, T, N, or G; $X_{38}$ is selected from G, S, F, or L; $X_{39}$ is selected from A, G, S, or I; $X_{40}$ is selected from Y, N, or L; $X_{41}$ is present or absent, if present, is selected from V, Y, or E; $X_{42}$ is present or absent, if present, is G; $X_{43}$ is present or absent, if present, is Y; $X_{44}$ is present or absent, if present, is F; $X_{45}$ is present or absent, if present, is selected from E or N; and $X_{46}$ is present or absent, if present, is selected from S or L, and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some embodiments, the first targeting moiety that specifically binds to CD38 comprises a VH region and a VL region, wherein the VH region comprises CDR1 sequence $X_{1}GX_{2}X_{3}X_{4}X_{5}X_{6}X_{7}X_{8}X_{9}X_{10}X_{11}X_{12}$, wherein $X_{1}$ is present or absent, if present, is S; $X_{2}$ is selected from F or I; $X_{3}$ is selected from P, S, or D; $X_{4}$ is selected from F, L, or A; $X_{5}$ is selected from D, G, S, N, or T; $X_{6}$ is selected from V, A, T, R, S, I, or N; $X_{7}$ is selected from Y, I, N, R, A, G, or D; $X_{8}$ is selected from A, Y, D, G, W, C, or T; $X_{9}$ is selected from M, V, I, W, D, or Y; $X_{10}$ is selected from S, T, M, C, I, Y, A, or G; $X_{11}$ is present or absent, if present, is selected from C or M; and $X_{12}$ is present or absent, if present, is C; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58, and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some embodiments, the first targeting moiety that specifically binds to CD38 comprises a VH region and a VL region, wherein the VH region comprises CDR1 sequence GFPFX$_{5}$X$_{6}$YAMS (SEQ ID NO: 423), in which $X_{5}$ is selected from D or G and $X_{6}$ is selected from V, A, or T; CDR2 sequence selected from SEQ ID NOs: 2 and 5; and CDR3 sequence selected from SEQ ID NOs: 3, 7, and 10; and wherein the VL region comprises CDR1 sequence consisting of SEQ ID NO: 62, CDR2 sequence consisting of SEQ ID NO: 63, and CDR3 sequence consisting of SEQ ID NO: 64.

In some embodiments, the first targeting moiety that specifically binds to CD38 comprises a VH region and a VL region, wherein the VH region comprises CDR1 sequence $X_{1}GX_{2}X_{3}X_{4}X_{5}X_{6}X_{7}X_{8}X_{9}X_{10}X_{11}X_{12}$, wherein $X_{1}$ is present or absent, if present, is S; $X_{2}$ is selected from F or I; $X_{3}$ is selected from S or D; $X_{4}$ is selected from L, F, or A; $X_{5}$ is selected from S, N, or T; $X_{6}$ is selected from R, S, N, I, or T; $X_{7}$ is selected from Y, I, N, R, A, D, or G; $X_{8}$ is selected from Y, D, G, A, W, T, or C; $X_{9}$ is selected from V, M, I, W, Y, or D; $X_{10}$ is selected from T, S, M, C, I, Y, A, or G; $X_{11}$ is present or absent, if present, is selected from C or M; and $X_{12}$ is present or absent, if present, is C; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some embodiments, the first targeting moiety that specifically binds to CD38 comprises a VH region and a VL region, wherein the VH region comprises CDR1 sequence GFSLX$_{5}$X$_{6}$X$_{7}$X$_{8}$X$_{9}$X$_{10}$X$_{11}$ (SEQ ID NO: 426), wherein $X_{5}$ is selected from S or N; $X_{6}$ is selected from R, S, or N; $X_{7}$ is selected from Y, I, or N; $X_{8}$ is selected from Y, D, G, or A; $X_{9}$ is selected from V, M, or I; $X_{10}$ is selected from T, S, or M; and $X_{11}$ is present or absent, if present, is C; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52; and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some embodiments, the first targeting moiety that specifically binds to CD38 comprises a VH region and a VL region, wherein the VH region comprises CDR1 sequence GFSX$_4$X$_5$X$_6$X$_7$X$_8$X$_9$X$_{10}$X$_{11}$X$_{12}$ (SEQ ID NO: 419), wherein X$_4$ is selected from F or A; X$_5$ is selected from S, T, or N; X$_6$ is selected from S, T, or N; X$_7$ is selected from Y, R, A, or G; X$_8$ is selected from W, Y, or C; X$_9$ is selected from I, W, Y, or D; X$_{10}$ is selected from C, I, Y, or M; X$_{11}$ is present or absent, if present, is selected from C or M; and X$_{12}$ is present or absent, if present, is C; CDR2 sequence selected from SEQ ID NOs: 18, 24, 30, 45, and 57; and CDR3 sequence selected from SEQ ID NOs: 19, 25, 31, 46, and 58; and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some embodiments, the first targeting moiety that specifically binds to CD38 comprises a VH region and a VL region, wherein the VH region comprises CDR1 sequence selected from SEQ ID NOs: 1, 4, 6, 8, 9, 11, 14, 17, 20, 23, 26, 29, 32, 35, 38, 41, 44, 47, 50, 53, 56, and 59; CDR2 sequence X$_{13}$X$_{14}$X$_{15}$X$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$X$_{30}$X$_{31}$, wherein X$_{13}$ is selected from A, G, or S; X$_{14}$ is selected from I, F, Y, V, S, or C; X$_{15}$ is selected from S, I, L, T, or M; X$_{16}$ is selected from G, Y, S, T, L, or V; X$_{17}$ is selected from S, I, K, Y, T, G, or A; X$_{18}$ is selected from G, S, T, P, V, or Y; X$_{19}$ is selected from G, A, D, S, or T; X$_{20}$ is selected from S, T, I, N, or G; X$_{21}$ is selected from T, I, D, N, S, or A; X$_{22}$ is selected from F, Y, N, T, I, or S; X$_{23}$ is selected from Y, D, K, or I; X$_{24}$ is selected from A or Y; X$_{25}$ is selected from D, T, S, N, R, A, or Y; X$_{26}$ is selected from S, W, T, A, or N; X$_{27}$ is selected from V, A, W, N, or S; X$_{28}$ is selected from K, R, Q, A, or W; X$_{29}$ is selected from G, K, or A; X$_{30}$ is present or absent, if present, is selected from G or K; X$_{31}$ is present or absent, if present, is G; and CDR3 sequence selected from SEQ ID NOs: 3, 7, 10, 13, 16, 19, 22, 25, 28, 31, 34, 37, 40, 43, 46, 49, 52, 55, and 58; and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some embodiments, the first targeting moiety that specifically binds to CD38 comprises a VH region and a VL region, wherein the VH region comprises CDR1 sequence selected from SEQ ID NOs: 1, 4, 6, 8, and 9; CDR2 sequence AISGSGGSTX$_{22}$YADSVKG (SEQ ID NO: 418) in which X$_{22}$ is selected from F or Y; and CDR3 sequence selected from SEQ ID NOs: 3, 7, and 10; and wherein the VL region comprises CDR1 sequence consisting of SEQ ID NO: 62, CDR2 sequence consisting of SEQ ID NO: 63, and CDR3 sequence consisting of SEQ ID NO: 64.

In some embodiments, the first targeting moiety that specifically binds to CD38 comprises a VH region and a VL region, wherein the VH region comprises CDR1 sequence selected from SEQ ID NOs: 11, 14, 17, 20, 23, 26, 29, 32, 35, 38, 41, 44, 47, 50, 53, and 56; CDR2 sequence X$_{13}$X$_{14}$X$_{15}$X$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$X$_{30}$X$_{31}$, wherein X$_{13}$ is selected from A, G, or S; X$_{14}$ is selected from I, F, Y, V, S, or C; X$_{15}$ is selected from I, L, M, or T; X$_{16}$ is selected from G, Y, S, T, L, or V; X$_{17}$ is selected from S, I, K, Y, T, G, or A; X$_{18}$ is selected from G, S, T, P, or V; X$_{19}$ is selected from G, A, D, S, or T; X$_{20}$ is selected from S, T, I, N, or G; X$_{21}$ is selected from T, I, D, N, S, or A; X$_{22}$ is selected from Y, N, T, I, or S; X$_{23}$ is selected from Y, D, K, or I; X$_{24}$ is selected from A or Y; X$_{25}$ is selected from T, S, N, R, A, or Y; X$_{26}$ is selected from S, W, T, A, or N; X$_{27}$ is selected from A, W, N, or S; X$_{28}$ is selected from K, R, Q, A, or W; X$_{29}$ is selected from G, K, or A; X$_{30}$ is present or absent, if present, is selected from G or K; and X$_{31}$ is present or absent, if present, is G; and CDR3 sequence selected from SEQ ID NOs: 13, 16, 19, 22, 25, 28, 31, 34, 37, 40, 43, 46, 49, 52, 55, and 58; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some embodiments, the first targeting moiety that specifically binds to CD38 comprises a VH region and a VL region, wherein the VH region comprises CDR1 sequence selected from SEQ ID NOs: 11, 14, 26, 32, 35, 38, 41, and 50; CDR2 sequence X$_{13}$X$_{14}$IX$_{16}$X$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$X$_{30}$, wherein X$_{13}$ is selected from A or G; X$_{14}$ is selected from I, F, Y, V, S, or C; X$_{16}$ is selected from G, Y, S, T, or L; X$_{17}$ is selected from S, I, K, Y, T, or G; X$_{18}$ is selected from G, S, or T; X$_{19}$ is selected from G, A, D, or S; X$_{20}$ is selected from T, I, N, or G; X$_{21}$ is selected from T, I, or D; X$_{22}$ is selected from Y, N, or T; X$_{23}$ is selected from Y or D; X$_{24}$ is selected from A or Y; X$_{25}$ is selected from T, S, N, R, or A; X$_{26}$ is selected from W or T; X$_{27}$ is selected from A or W; X$_{28}$ is selected from K, R, Q, or A; X$_{29}$ is selected from G or K; and X$_{30}$ is present or absent, if present, is G; and CDR3 sequence selected from SEQ ID NOs: 13, 16, 28, 34, 37, 40, 43, and 52; and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some embodiments, the first targeting moiety that specifically binds to CD38 comprises a VH region and a VL region, wherein the VH region comprises CDR1 sequence selected from SEQ ID NOs: 17, 23, 29, 44, and 56; CDR2 sequence X$_{13}$CX$_{15}$X$_{16}$X$_{17}$X$_{18}$X$_{19}$X$_{20}$X$_{21}$X$_{22}$X$_{23}$YX$_{25}$X$_{26}$X$_{27}$X$_{28}$X$_{29}$X$_{30}$X$_{31}$, wherein X$_{13}$ is selected from A, or S; X$_{15}$ is selected from I, L, or T; X$_{16}$ is selected from Y or V; X$_{17}$ is selected from S, T, or A; X$_{18}$ is selected from G, P, or V; X$_{19}$ is selected from D, S, or T; X$_{20}$ is selected from S, T, or G; X$_{21}$ is selected from D, N, S, or A; X$_{22}$ is selected from T, I, or S; X$_{23}$ is selected from Y, K, or I; X$_{25}$ is selected from A or Y; X$_{26}$ is selected from S, T, A, or N; X$_{27}$ is selected from W, N, or S; X$_{28}$ is selected from A or W; X$_{29}$ is selected from K or A; X$_{30}$ is present or absent, if present, is selected from G or K; and X$_{31}$ is present or absent, if present, is G; and CDR3 sequence selected from SEQ ID NOs: 19, 25, 31, 46, and 58; and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some instances, the first targeting moiety that specifically binds to CD38 comprises a VH region and a VL region, wherein the VH region comprises CDR1 sequence selected from SEQ ID NOs: 1, 4, 6, 8, 9, 11, 14, 17, 20, 23, 26, 29, 32, 35, 38, 41, 44, 47, 50, 53, and 56; CDR2 sequence selected from SEQ ID NOs: 2, 5, 12, 15, 18, 21, 24, 27, 30, 33, 36, 39, 42, 45, 48, 51, 54, and 57; and CDR3 sequence selected from SEQ ID NOs: 3, 7, 10, 13, 16, 19, 22, 25, 28, 31, 34, 37, 40, 43, 46, 49, 52, 55, and 58; and wherein the VL region comprises CDR1 sequence selected from SEQ ID NOs: 62, 65, 68, 71, 74, 77, 80, 83, 86, 89, 92, 94, 96, 98, and 102; CDR2 sequence selected from SEQ ID NOs: 63, 66, 69, 72, 75, 78, 81, 84, 90, and 99; and CDR3 sequence selected from SEQ ID NOs: 64, 67, 70, 73, 76, 79, 82, 85, 87, 88, 91, 93, 95, 97, 100, 101, and 103.

In some instances, the first targeting moiety that specifically binds to CD38 comprises a VH region and a VL region, wherein the VH region comprises CDR1 sequence selected from SEQ ID NOs: 1, 4, 6, 8, and 9; CDR2 sequence selected from SEQ ID NOs: 2 and 5; and CDR3 sequence selected from SEQ ID NOs: 3, 7, and 10; and wherein the VL region comprises CDR1 sequence consisting of SEQ ID NO: 62, CDR2 sequence consisting of SEQ ID NO: 63, and CDR3 sequence consisting of SEQ ID NO: 64.

In some instances, the first targeting moiety that specifically binds to CD38 comprises a VH region and a VL region, wherein the VH region comprises CDR1 sequence selected from SEQ ID NOs: 11, 14, 17, 20, 23, 26, 29, 32, 35, 38, 41, 44, 47, 50, 53, and 56; CDR2 sequence selected from SEQ ID NOs: 12, 15, 18, 21, 24, 27, 30, 33, 36, 39, 42, 45, 48, 51, 54, and 57; and CDR3 sequence selected from SEQ ID NOs: 13, 16, 19, 22, 25, 28, 31, 34, 37, 40, 43, 46, 49, 52, 55, and 58; and wherein the VL region comprises CDR1 sequence selected from SEQ ID NOs: 65, 68, 71, 74, 77, 80, 83, 86, 89, 92, 94, 96, 98, and 102; CDR2 sequence selected from SEQ ID NOs: 66, 69, 72, 75, 78, 81, 84, 90, and 99; and CDR3 sequence selected from SEQ ID NOs: 67, 70, 73, 76, 79, 82, 85, 87, 88, 91, 93, 95, 97, 100, 101, and 103.

In some instances, the first targeting moiety that specifically binds to CD38 comprises a VH region and a VL region, wherein the VH region comprises CDR1 sequence selected from SEQ ID NOs: 11, 14, 26, 32, 35, 38, 41, and 50; CDR2 sequence selected from SEQ ID NOs: 12, 15, 27, 33, 36, 39, 42, and 51; and CDR3 sequence selected from SEQ ID NOs: 13, 16, 28, 34, 37, 40, 43, and 52; and wherein the VL region comprises CDR1 sequence selected from SEQ ID NOs: 65, 68, 80, 86, 89, 92, and 98; CDR2 sequence selected from SEQ ID NOs: 66, 69, 78, 81, 90, and 99; and CDR3 sequence selected from SEQ ID NOs: 67, 70, 82, 87, 88, 91, 93, and 100.

In some instances, the first targeting moiety that specifically binds to CD38 comprises a VH region and a VL region, wherein the VH region comprises CDR1 sequence selected from SEQ ID NOs: 17, 23, 29, 44, and 56; CDR2 sequence selected from SEQ ID NOs: 18, 24, 30, 45, and 57; and CDR3 sequence selected from SEQ ID NOs: 19, 25, 31, 46, and 58; and wherein the VL region comprises CDR1 sequence selected from SEQ ID NOs: 71, 77, 83, 94, and 102; CDR2 sequence selected from SEQ ID NOs: 72, 78, and 84; and CDR3 sequence selected from 73, 79, 85, 95, and 103.

In some embodiments, the second targeting moiety that specifically binds to ICAM1 comprises a VH region and a VL region, wherein the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence $X^{31}X^{32}X^{33}X^{34}X^{35}X^{36}X^{37}X^{38}X^{39}X^{40}X^{41}X^{42}X^{43}X^{44}X^{45}X^{46}X^{47}X^{48}X^{49}$, wherein $X^{31}$ is selected from A or V; $X^{32}$ is selected from R or I; $X^{33}$ is selected from G, D, P, A, or V; $X^{34}$ is selected from G, P, W, D, N, or R; $X^{35}$ is selected from D, Y, S, L, G, F, or W; $X^{36}$ is selected from Y, D, V, L, S, G, or P; $X^{37}$ is selected from G, S, D, V, or E; $X^{38}$ is selected from G, Y, F, S, or D; $X^{39}$ is selected from S, D, G, T, N, A, or V; $X^{40}$ is selected from T, A, D, S, Y, L, or F; $X^{41}$ is present or absent, if present, is selected from Y, A, G, I, or D; $X^{42}$ is present or absent, if present, is selected from I, Y, R, P, V, or G; $X^{43}$ is present or absent, if present, is selected from L, R, Y, G, or A; $X^{44}$ is present or absent, if present, is selected from N, L, Y, S, or W; $X^{45}$ is present or absent, if present, is selected from L, Y, F, or C; $X^{46}$ is present or absent, if present, is selected from D, A, or F; $X^{47}$ is present or absent, if present, is selected from M, P, Y, or N; $X^{48}$ is present or absent, if present, is selected from D or L; and $X^{49}$ is present or absent, if present, is L; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the second targeting moiety that specifically binds to ICAM1 comprises a VH region and a VL region, wherein the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence $X^{31}RX^{33}X^{34}X^{35}X^{36}X^{37}X^{38}X^{39}X^{40}X^{41}X^{42}X^{43}X^{44}X^{45}X^{46}X^{47}X^{48}X^{49}$ (SEQ ID NO: 424), wherein $X^{31}$ is selected from A or V; $X^{33}$ is selected from G or D; $X^{34}$ is selected from G, P, W, or D; $X^{35}$ is selected from D, Y, S, or L; $X^{36}$ is selected from Y, D, V, or L; $X^{37}$ is selected from G, S, or D; $X^{38}$ is selected from G, Y, F, or S; $X^{39}$ is selected from S, D, G, or T; $X^{40}$ is selected from T, A, D, S, or Y; $X^{41}$ is selected from Y, A, G, or I; $X^{42}$ is selected from I, Y, or R; $X^{43}$ is selected from L, R, Y, or G; $X^{44}$ is selected from N, L, Y, or S; $X^{45}$ is present or absent, if present, is selected from L, Y, or F; $X^{46}$ is present or absent, if present, is D; $X^{47}$ is present or absent, if present, is selected from M or P; $X^{48}$ is present or absent, if present, is D; and $X^{49}$ is present or absent, if present, is L; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the second targeting moiety that specifically binds to ICAM1 comprises a VH region and a VL region, wherein the VH region comprises CDR1 sequence $X^{1}X^{2}X^{3}X^{4}X^{5}X^{6}X^{7}X^{8}X^{9}X^{10}X^{11}$, wherein $X^{1}$ is selected from G or E; $X^{2}$ is selected from F or Y; $X^{3}$ is selected from S or T; $X^{4}$ is selected from L, F, or S; $X^{5}$ is selected from S or N; $X^{6}$ is selected from S, N, T, or D; $X^{7}$ is selected from Y, H, or G; $X^{8}$ is selected from G, A, Y, W, or F; $X^{9}$ is selected from M, W, Y, or I; $X^{10}$ is selected from S, G, N, M, or I; and $X^{11}$ is present or absent, if present, is C; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the second targeting moiety that specifically binds to ICAM1 comprises a VH region and a VL region, wherein the VH region comprises CDR1 sequence GFSLX$^5$X$^6$X$^7$X$^8$MX$^{10}$ (SEQ ID NO: 425), wherein X$^5$ is selected from S or N; X$^6$ is selected from S, N, T, or D; X$^7$ is selected from Y or H; X$^8$ is selected from G, A, or Y; and X$^{10}$ is selected from S, G, or N; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the second targeting moiety that specifically binds to ICAM1 comprises a VH region and a VL region, wherein the VH region comprises CDR1 sequence selected from SEQ ID NOs: 208, 211, 214, 217, 222, 225, 228, 232, 235, 238, 241, 247, and 250; CDR2 sequence X$^{12}$X$^{13}$X$^{14}$X$^{15}$X$^{16}$X$^{17}$X$^{18}$X$^{19}$X$^{20}$X$^{21}$X$^{22}$X$^{23}$X$^{24}$X$^{25}$X$^{26}$X$^{27}$X$^{28}$X$^{29}$X$^{30}$, in which X$^{12}$ is selected from G, T, A, I, or Y; X$^{13}$ is selected from W, I, Y, or C; X$^{14}$ is selected from I, S or Y; X$^{15}$ is selected from S, G, T, D, or P; X$^{16}$ is selected from F, S, D, T, or A; X$^{17}$ is selected from S, R, G, or D; X$^{18}$ is selected from G, D, or S; X$^{19}$ is selected from S, R, T, N, Y, A, D, or P; X$^{20}$ is selected from T, A, G, or Y; X$^{21}$ is selected from Y, H, A, S, or T; X$^{22}$ is selected from Y or N; X$^{23}$ is selected from A, P, Y, or S; X$^{24}$ is selected from S, T, N, D, Y, A, or P; X$^{25}$ is selected from W, S, A, or D; X$^{26}$ is selected from A, V, T, W, F, or S; X$^{27}$ is selected from K, W, A, Q, or V; X$^{28}$ is selected from G, A, or K; X$^{29}$ is present or absent, if present, is selected from K or G; and X$^{30}$ is present or absent, if present, is G; and CDR3 sequence selected from SEQ ID NOs: 210, 213, 216, 219, 221, 224, 226, 230, 231, 233, 237, 240, 243, 245, 249, and 252; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the second targeting moiety that specifically binds to ICAM1 comprises a VH region and a VL region, wherein the VH region comprises CDR1 sequence selected from SEQ ID NOs: 208, 211, 214, 217, 222, 225, 228, 232, 235, and 238; CDR2 sequence GX$^{13}$IX$^{15}$X$^{16}$X$^{17}$X$^{18}$X$^{19}$X$^{20}$YYAX$^{24}$WAKG (SEQ ID NO: 420), wherein X$^{13}$ is selected from W, I, or Y; X$^{15}$ is selected from S or G; X$^{16}$ is selected from F, S, D, or T; X$^{17}$ is selected from S or R; X$^{18}$ is selected from G or D; X$^{19}$ is selected from S, R, T, or N; X$^{20}$ is selected from T or A; and X$^{24}$ is selected from S, T, or N; and CDR3 sequence selected from SEQ ID NOs: 210, 213, 216, 219, 221, 224, 226, 230, 231, 233, 237, and 240; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the second targeting moiety that specifically binds to ICAM1 comprises a VH region and a VL region, wherein the VH region comprises CDR1 sequence selected from SEQ ID NOs: 208, 211, 214, 217, 222, 225, 228, 232, 235, 238, 241, 247, and 250; CDR2 sequence selected from SEQ ID NOs: 209, 212, 218, 220, 223, 227, 229, 234, 236, 239, 242, 244, 246, 248, and 251; and CDR3 sequence selected from SEQ ID NOs: 210, 213, 216, 219, 221, 224, 226, 230, 231, 233, 237, 240, 243, 245, 249, and 252; and wherein the VL region comprises CDR1 sequence selected from SEQ ID NOs: 253, 256, 259, 262, 265, 267, 268, 269, 270, 272, 274, 277, 279, 282, and 62; CDR2 sequence selected from SEQ ID NOs: 254, 257, 260, 263, 273, 275, 280, 283, and 63; and CDR3 sequence selected from SEQ ID NOs: 255, 258, 261, 264, 266, 271, 276, 278, 281, 284, and 64.

In some embodiments, the second targeting moiety that specifically binds to ICAM1 comprises a VH region and a VL region, wherein the VH region comprises CDR1 sequence selected from SEQ ID NOs: 208, 211, 214, 217, 222, 225, 228, 232, 235, and 238; CDR2 sequence selected from SEQ ID NOs: 209, 212, 218, 220, 223, 227, 229, 234, 236, and 239; and CDR3 sequence selected from SEQ ID NOs: 210, 213, 216, 219, 221, 224, 226, 230, 231, 233, 237, and 240; and wherein the VL region comprises CDR1 sequence selected from SEQ ID NOs: 253, 256, 259, 262, 265, 267, 268, 269, 270, 272, 274, 277, 279, and 282; CDR2 sequence selected from SEQ ID NOs: 254, 257, 260, 263, 273, 275, 280, and 283; and CDR3 sequence selected from SEQ ID NOs: 255, 258, 261, 264, 266, 271, 276, 278, 281, and 284.

In some embodiments, the second targeting moiety that specifically binds to ICAM1 comprises a VH region and a VL region, wherein the VH region comprises CDR1 sequence selected from SEQ ID NOs: 241, 247, and 250; CDR2 sequence selected from SEQ ID NOs: 242, 244, 246, 248, and 251; and CDR3 sequence selected from SEQ ID NOs: 243, 245, 249, and 252; and wherein the VL region comprises CDR1, CDR2, and CDR3 sequences SEQ ID NOs: 62-64, respectively.

In some embodiments, the constant region of a bispecific antibody comprising a CD38 targeting moiety and an ICAM1 targeting moiety is from IgG (e.g., IgG1, IgG2, IgG3, or IgG4), IgA, IgE, or IgM. In some instances and based on the bispecific antibody format, the constant region further comprises one or more mutations in, e.g., the CH1 domain, CH2, domain, CH3 domain, hinge region, or a combination thereof. In some cases, the one or more mutations enhance stability, increase half-life, decrease glycosylation, and/or modulate Fc receptor interactions, e.g., to increase or decrease ADCC and/or CDC.

Exemplary mutations that modulate Fc receptor interaction include, but are not limited to, E333A, S239D/A330L/I332E, K326W/E333S, or S239D/I332I/G236A, the residue numbering are in Kabat numbering in reference to IgG1.

Exemplary mutations that increases half-life include, but are not limited to, T250Q/M428L or M252Y/S254T/T256E and H433K/N434F (Kabat numbering) in reference to IgG1; and R435H (Kabat numbering) in reference to IgG3.

Exemplary mutations that prevent or reduce strand exchange comprise S228P (Kabat numbering) in reference to IgG4.

Exemplary mutation that modulate glycosylation include N297 (Kabat numbering) in reference to IgG1, in which the residue is afucosylated to increase ADCC.

In some embodiments, a bispecific antibody described above comprises a knobs-into-holes (KIH) format. In some cases, the KIH is located in the Fc region, in which the residues within the CH3 domain are optionally modified based on the disclosure of WO96/027011; Ridgway, et. al., *Protein Eng.* 9 (1996) 617-621; or Merchant, et. al., *Nat. Biotechnol.* 16 (1998) 677-681. In some cases, one of the CH3 domain pair is the "knob" chain while the other is the "hole" chain and additional disulfide bridges are optionally introduced to further stabilize the antibody and/or to increase yield.

In some instances, the CH3 domain of the "knob" chain comprises a T366W mutation and the CH3 domain of the "hole" chain comprises mutations T366S, L368A, and Y407V. In some cases, the CH3 domain of the "knob" chain further comprises a Y349C mutation which forms an interchain disulfide bridge with either E356C or S354C in the CH3 domain of the "hole" chain.

In some instances, the CH3 domain of the "knob" chain comprises R409D and K370E mutations and the CH3 domain of the "hole" chain comprises D399K and E357K. In some cases, the CH3 domain of the "knob" chain further comprises a T366W mutation and the CH3 domain of the "hole" chain further comprises mutations T366S, L368A, and Y407V.

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Clinical Pharmacy 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFast-Bac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway®pDEST™ 14 vector, Gateway®pDEST™ 15 vector, Gateway®pDEST™ 17 vector, Gateway®pDEST™ 24 vector, Gateway®pYES-DEST52 vector, pBAD-DEST49 Gateway® destination vector, pAO815 *Pichia* vector, pFLD1 *Pichia pastoris* vector, pGAPZA,B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors.

Mammalian transient expression vectors may include pRK5, p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cell include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, *Deinococcus-Thermus*, Fibrobacteres-Chlorobi/Bacteroidetes (FCB group), Fusobacteria, Gemmatimonadetes, Nitrospirae, Planctomycetes-Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or *Coli* bacilli.

Exemplary prokaryotic host cells include, but are not limited to, BL21, Mach1™, DH10B™ TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium,* or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica,* Trichosporonpullulans, *Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii,* or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Payloads

In some embodiments, an anti-CD38 antibody described herein, an anti-ICAM1 antibody described herein, or a multi-specific antibody described herein is further conjugated to one or more payloads. In some instances, the one or more payloads comprise a small molecule, a protein or peptide, or a nucleic acid polymer. In some cases, the one or more payloads are conjugated directed to the anti-CD38 antibody, the anti-ICAM1 antibody, or the multi-specific antibody. In other cases, the one or more payloads are conjugated to the anti-CD38 antibody, the anti-ICAM1 antibody, or the multi-specific antibody indirectly via a linker.

In some instances, the antibody is an anti-CD38 antibody and the number of payloads conjugated to the antibody (e.g., the drug-to-antibody ratio or DAR) is about 1:1, one payload to one anti-CD38 antibody. In some instances, the ratio of the payload to the anti-CD38 antibody is about 2:1, 3:1, 4:1, 5:1, 6:1, 7:1, 8:1, 9:1, 10:1, 11:1, or 12:1. In some cases, the ratio of the payload to the anti-CD38 antibody is about 2:1. In some cases, the ratio of the payload to the anti-CD38 antibody is about 4:1. In some cases, the ratio of the payload to the anti-CD38 antibody is about 8:1. In some cases, the ratio of the payload to the anti-CD38 antibody is about 12:1.

In some instances, the antibody is an anti-ICAM1 antibody and the number of payloads conjugated to the antibody (e.g., the drug-to-antibody ratio or DAR) is about 1:1, one payload to one anti-ICAM1 antibody. In some instances, the ratio of the payload to the anti-ICAM1 antibody is about 2:1, 3:1, 4:1, 5:1, 6:1, 7:1, 8:1, 9:1, 10:1, 11:1, or 12:1. In some cases, the ratio of the payload to the anti-ICAM1 antibody is about 2:1. In some cases, the ratio of the payload to the anti-ICAM1 antibody is about 4:1. In some cases, the ratio of the payload to the anti-ICAM1 antibody is about 8:1. In some cases, the ratio of the payload to the anti-ICAM1 antibody is about 12:1.

In some instances, the antibody is a multi-specific antibody comprising a targeting moiety to either CD38 or ICAM1 and the number of payloads conjugated to the multi-specific antibody (e.g., the drug-to-antibody ratio or DAR) is about 1:1. In some instances, the ratio of the payload to the multi-specific antibody is about 2:1, 3:1, 4:1, 5:1, 6:1, 7:1, 8:1, 9:1, 10:1, 11:1, or 12:1. In some cases, the ratio of the payload to the multi-specific antibody is about 2:1. In some cases, the ratio of the payload to the multi-specific antibody is about 4:1. In some cases, the ratio of the payload to the multi-specific antibody is about 8:1. In some cases, the ratio of the payload to the multi-specific antibody is about 12:1.

In some instances, the antibody is a bispecific antibody comprising a first targeting moiety to CD38 and a second targeting moiety to ICAM1 and the number of payloads conjugated to the bispecific antibody (e.g., the drug-to-antibody ratio or DAR) is about 1:1. In some instances, the ratio of the payload to the bispecific antibody is about 2:1, 3:1, 4:1, 5:1, 6:1, 7:1, 8:1, 9:1, 10:1, 11:1, or 12:1. In some cases, the ratio of the payload to the bispecific antibody is about 2:1. In some cases, the ratio of the payload to the bispecific antibody is about 4:1. In some cases, the ratio of the payload to the bispecific antibody is about 8:1. In some cases, the ratio of the payload to the bispecific antibody is about 12:1.

In some embodiment, the payload is a small molecule. In some instances, the small molecule is a cytotoxic payload. Exemplary cytotoxic payloads include, but are not limited to, microtubule disrupting agents, DNA modifying agents, or Akt inhibitors.

In some embodiments, the payload comprises a microtubule disrupting agent. Exemplary microtubule disrupting agents include, but are not limited to, 2-methoxyestradiol, auristatin, chalcones, colchicine, combretastatin, cryptophycin, dictyostatin, discodermolide, dolastain, eleutherobin, epothilone, halichondrin, laulimalide, maytansine, noscapinoid, paclitaxel, peloruside, phomopsin, podophyllotoxin, rhizoxin, spongistatin, taxane, tubulysin, vinca alkaloid, vinorelbine, or derivatives or analogs thereof.

In some embodiments, the tubulysin is a tubulysin analog or derivative such as described in U.S. Pat. Nos. 8,580,820 and 8,980,833 and in U.S. Publication Nos. 20130217638, 20130224228, and 201400363454.

In some embodiments, the maytansine is a maytansinoid. In some embodiments, the maytansinoid is DM1, DM4, or ansamitocin. In some embodiments, the maytansinoid is DM1. In some embodiments, the maytansinoid is DM4. In some embodiments, the maytansinoid is ansamitocin. In some embodiments, the maytansinoid is a maytansionid derivative or analog such as described in U.S. Pat. Nos. 5,208,020, 5,416,064, 7,276,497, and 6,716,821 or U.S. Publication Nos. 2013029900 and US20130323268.

In some embodiments, the payload is a dolastatin, or a derivative or analog thereof. In some embodiments, the dolastatin is dolastatin 10 or dolastatin 15, or derivatives or analogs thereof. In some embodiments, the dolastatin 10 analog is auristatin, soblidotin, symplostatin 1, or symplostatin 3. In some embodiments, the dolastatin 15 analog is cemadotin or tasidotin.

In some embodiments, the dolastatin 10 analog is auristatin or an auristatin derivative. In some embodiments, the auristatin or auristatin derivative is auristatin E (AE), auristatin F (AF), auristatin E5-benzoylvaleric acid ester (AEVB), monomethyl auristatin E (MMAE), monomethyl auristatin F (MMAF), or monomethyl auristatin D (MMAD), auristatin PE, or auristatin PYE. In some embodiments, the auristatin derivative is monomethyl auristatin E (MMAE). In some embodiments, the auristatin derivative is monomethyl auristatin F (MMAF). In some embodiments, the auristatin is an auristatin derivative or analog such as described in U.S. Pat. Nos. 6,884,869, 7,659,241, 7,498,298, 7,964,566, 7,750,116, 8,288,352, 8,703,714 and 8,871,720.

In some embodiments, the payload comprises a DNA modifying agent. In some embodiments, the DNA modifying agent comprises DNA cleavers, DNA intercalators, DNA transcription inhibitors, or DNA cross-linkers. In some instances, the DNA cleaver comprises bleomycine A2, calicheamicin, or derivatives or analogs thereof. In some instances, the DNA intercalator comprises doxorubicin, epirubicin, PNU-159682, duocarmycin, pyrrolobenzodiazepine, oligomycin C, daunorubicin, valrubicin, topotecan, or derivatives or analogs thereof. In some instances, the DNA transcription inhibitor comprises dactinomycin. In some instances, the DNA cross-linker comprises mitomycin C.

In some embodiments, the DNA modifying agent comprises amsacrine, anthracycline, camptothecin, doxorubicin, duocarmycin, enediyne, etoposide, indolinobenzodiazepine, netropsin, teniposide, or derivatives or analogs thereof.

In some embodiments, the anthracycline is doxorubicin, daunorubicin, epirubicin, idarubicin, mitomycin-C, dactinomycin, mithramycin, nemorubicin, pixantrone, sabarubicin, or valrubicin.

In some embodiments, the analog of camptothecin is topotecan, irinotecan, silatecan, cositecan, exatecan, lurtotecan, gimatecan, belotecan, rubitecan, or SN-38.

In some embodiments, the duocarmycin is duocarmycin A, duocarmycin Bi, duocarmycin B2, duocarmycin C1, duocarmycin C2, duocarmycin D, duocarmycin SA, or CC-1065. In some embodiments, the enediyne is a calicheamicin, esperamicin, or dynemicin A.

In some embodiments, the pyrrolobenzodiazepine is anthramycin, abbeymycin, chicamycin, DC-81, mazethramycin, neothramycins A, neothramycin B, porothramycin, prothracarcin, sibanomicin (DC-102), sibiromycin, or tomaymycin. In some embodiments, the pyrrolobenzodiazepine is a tomaymycin derivative, such as described in U.S. Pat. Nos. 8,404,678 and 8,163,736. In some embodiments, the pyrrolobenzodiazepine is such as described in U.S. Pat. Nos. 8,426,402, 8,802,667, 8,809,320, 6,562,806, 6,608,192, 7,704,924, 7,067,511, 7,612,062, 7,244,724, 7,528,126, 7,049,311, 8,633,185, 8,501,934, and 8,697,688 and U.S. Publication No. US20140294868.

In some embodiments, the pyrrolobenzodiazepine is a pyrrolobenzodiazepine dimer. In some embodiments, the PBD dimer is a symmetric dimer. Examples of symmetric PBD dimers include, but are not limited to, SJG-136 (SG-2000), ZC-423 (SG2285), SJG-720, SJG-738, ZC-207 (SG2202), and DSB-120. In some embodiments, the PBD dimer is an unsymmetrical dimer. Examples of unsymmetrical PBD dimers include, but are not limited to, SJG-136 derivatives such as described in U.S. Pat. Nos. 8,697,688 and 9,242,013 and U.S. Publication No. 20140286970.

In some embodiments, the payload comprises an Akt inhibitor. In some cases, the Akt inhibitor comprises ipatasertib (GDC-0068) or derivatives thereof.

In some embodiments, the payload comprises a polymerase inhibitor, including, but not limited to polymerase II inhibitors such as a-amanitin, and poly(ADP-ribose) polymerase (PARP) inhibitors. Exemplary PARP inhibitors include but are not limited to Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, or 3-aminobenzamide.

In some embodiments, the payload is an imaging agent. In some instances, the payload comprises a "radio-opaque" label, e.g. a label visualized using x-rays. Radio-opaque materials are well known to those of skill in the art. Exemplary radio-opaque materials include iodide, bromide or barium salts. Additional radiopaque materials include, but are not limited to, organic bismuth derivatives {see, e.g., U.S. Pat. No. 5,939,045), radio-opaque polyurethanes (see, e.g., U.S. Pat. No. 5,346,981), organobismuth composites (see, e.g., U.S. Pat. No. 5,256,334), radio-opaque barium polymer complexes (see, e.g., U.S. Pat. No. 4,866,132), and the like.

In some instances, the payload comprises a detectable label, for example, for use in immunoconjugates include any composition detectable by spectroscopic, photochemical, biochemical, immunochemical, electrical, optical or chemical means. Useful labels in the include magnetic beads (e.g., DYNABEADS™), fluorescent dyes (e.g., fluorescein isothiocyanate, texas red, rhodamine, green fluorescent protein, and the like), radiolabels (e.g., $^3$H, $^{125}$I, $^{35}$S $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In some embodiments, suitable radiolabels include, but are not limited to, $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{115}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

In some instances, the payload comprises a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

In some instances, the payload comprises an alpha emitter, i.e. a radioactive isotope that emits alpha particles. Alpha-emitters have recently been shown to be effective in the treatment of cancer (see, e.g., McDevitt et al. (2001) Science 294: 1537-1540; Ballangrud et al. (2001) Cancer Res. 61: 2008-2014; Borchardt et al. (2003) Cancer Res. 63: 5084-50). Suitable alpha emitters include, but are not limited to $^{213}$Bi, $^{211}$At, and the like.

In some instances, the payload comprises an immunomodulatory agent. Useful immunomodulatory agents include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Illustrative immunosuppressive agents include but are not limited to 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, streptokinase, or rapamycin.

In some embodiments, the payload comprises a protein or peptide toxin or fragment thereof. Exemplary enzymatically active toxins and fragments thereof include, but are not limited to, diphtheria toxin A fragment, nonbinding active fragments of diphtheria toxin, exotoxin A (from *Pseudomonas aeruginosa*), ricin A chain, abrin A chain, modeccin A chain, a-sacrin, certain A leurites fordii proteins, certain Dianthin proteins, *Phytolacca americana* proteins (PAP, PAPII and PAP-S), Morodica charantia inhibitor, curcin, crotin, *Saponaria officinalis* inhibitor, gelonin, mitogillin, restrictocin, phenomycin, enomycin, and tricothecenes.

In some instances, the payload is an immune modulator. Exemplary immune modulators include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, xanthines, stem cell growth factors, lymphotoxins, hematopoietic factors, tumor necro-sis factor (TNF) (e.g., TNFα), interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-alpha, interferon-beta, interferon-gamma), the stem cell growth factor designated "S1 factor," erythropoietin and thrombopoietin, or a combination thereof.

In some instances, the payload comprises a cytokine. In some embodiments, the cytokine comprises IL-2, IL-2, IL-3, IL-6, IL-10, IL-12, IL-18, IL-21, interferon (e.g., IFNα, IFNβ), or TNFα.

In some embodiments, the payload is a nucleic acid polymer. In some instances, the nucleic acid polymers include those for use in gene therapy, such as in RNA interference (RNAi) or gene silencing (or antisense oligonucleotide) techniques. Exemplary nucleic acid polymers that participate in the RNA interference process include short interfering nucleic acid (siNA), short interfering RNA (siRNA), double-stranded RNA (dsRNA), micro-RNA (miRNA), or short hairpin RNA (shRNA).

Antisense oligonucleotides include nucleotide sequence that is substantially complementary to a target nucleotide sequence in e.g., a pre-mRNA molecule, hrRNA (heterogeneous nuclear RNA), or mRNA molecule. The degree of complementarity (or substantial complementarity) of the antisense sequence is preferably such that a molecule comprising the antisense sequence form a stable hybrid with the target nucleotide sequence in the RNA molecule under physiological condition.

In some embodiments, the nucleic acid polymer is an mRNA. In some cases, the mRNA encodes a cytotoxic protein or peptide. Exemplary cytotoxic proteins or peptides include a bacterial cytotoxin such as an alpha-pore forming toxin (e.g., cytolysin A from *E. coli*), a beta-pore-forming toxin (e.g., α-Hemolysin, PVL—panton Valentine leukocidin, aerolysin, clostridial Epsilon-toxin, *Clostridium perfringens* enterotoxin), binary toxins (anthrax toxin, edema toxin, *C. botulinum* C2 toxin, C spirofome toxin, *C. perfringens* iota toxin, *C. difficile* cyto-lethal toxins (A and B)), prion, parasporin, a cholesterol-dependent cytolysins (e.g., pneumolysin), a small pore-forming toxin (e.g., Gramicidin A), a cyanotoxin (e.g., microcystins, nodularins), a hemotoxin, a neurotoxin (e.g., botulinum neurotoxin), a cytotoxin, cholera toxin, diphtheria toxin, *Pseudomonas* exotoxin A, tetanus toxin, or an immunotoxin (idarubicin, ricin A, CRM9, Pokeweed antiviral protein, DT).

In some instances, the mRNA encodes a cytotoxic peptide or peptide related to the immune system such as a cytotoxic T cell or B cell epitope to stimulate a specific immune response via presentation of such epitope with an MHC I complex, an membrane attack complex protein (MAC) of the complement system, perforin, a granzyme and a granulysin.

In some cases, the mRNA encodes an apoptotic triggering protein or peptide such as an apoptotic protease activating factor-1 (Apaf-1), cytochrome-c, caspase initiator proteins (CASP2, CASP8, CASP9, CASP10), apoptosis inducing factor (AIF), p53, p73, p63, Bcl-2, Bax, granzyme B, poly-ADP ribose polymerase (PARP), and P 21-activated kinase 2 (PAK2).

In some embodiments, the nucleic acid polymer is a nucleic acid decoy. In some instances, the nucleic acid decoy is a mimic of protein-binding nucleic acids such as RNA-based protein-binding mimics. Exemplary nucleic acid decoys include transactivating region (TAR) decoy and Rev response element (RRE) decoy.

In some instances, the payload is an aptamer. Aptamers are small oligonucleotide or peptide molecules that bind to specific target molecules. Exemplary nucleic acid aptamers include DNA aptamers, RNA aptamers, or XNA aptamers which are RNA and/or DNA aptamers comprising one or more unnatural nucleotides. Exemplary nucleic acid aptamers include ARC19499 (Archemix Corp.), REG1 (Regado Biosciences), and ARC1905 (Ophthotech).

Nucleic acids in accordance with the embodiments described herein optionally include naturally occurring nucleic acids, or one or more nucleotide analogs or have a structure that otherwise differs from that of a naturally occurring nucleic acid. For example, 2'-modifications include halo, alkoxy, and allyloxy groups. In some embodiments, the 2'-OH group is replaced by a group selected from H, OR, R, halo, SH, SR, $NH_2$, NHR, $NR_2$ or CN, wherein R is $C_1$-$C_6$ alkyl, alkenyl, or alkynyl, and halo is F, Cl, Br, or I. Examples of modified linkages include phosphorothioate and 5'-N-phosphoramidite linkages.

Nucleic acids having a variety of different nucleotide analogs, modified backbones, or non-naturally occurring internucleoside linkages are utilized in accordance with the embodiments described herein. In some cases, nucleic acids include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, 0(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Different nucleotide modifications and/or backbone structures may exist at various positions in the nucleic acid. Such modification include morpholinos, peptide nucleic acids (PNAs), methylphosphonate nucleotides, thiolphosphonate nucleotides, 2'-fluoro N3-P5'-phosphoramidites, 1',5'-anhydrohexitol nucleic acids (HNAs), or a combination thereof.

Conjugation Chemistry

In some instances, the payload is conjugated to an anti-CD38 antibody, an anti-ICAM1 antibody, or a multi-specific antibody (e.g., a bispecific anti-CD38/ICAM1 antibody) described herein by a native ligation. In some instances, the conjugation is as described in: Dawson, et al. "Synthesis of proteins by native chemical ligation," Science 1994, 266, 776-779; Dawson, et al. "Modulation of Reactivity in Native Chemical Ligation through the Use of Thiol Additives," J. Am. Chem. Soc. 1997, 119, 4325-4329; Hackeng, et al. "Protein synthesis by native chemical ligation: Expanded scope by using straightforward methodology," Proc. Natl. Acad. Sci. USA 1999, 96, 10068-10073; or Wu, et al. "Building complex glycopeptides: Development of a cysteine-free native chemical ligation protocol," Angew. Chem. Int. Ed. 2006, 45, 4116-4125. In some instances, the conjugation is as described in U.S. Pat. No. 8,936,910.

In some instances, the payload is conjugated to an anti-CD38 antibody, an anti-ICAM1 antibody, or a multi-specific antibody (e.g., a bispecific anti-CD38/ICAM1 antibody) described herein by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," JACS 134(13): 5887-5892 (2012))

In some instances, the payload is conjugated to an anti-CD38 antibody, an anti-ICAM1 antibody, or a multi-specific antibody (e.g., a bispecific anti-CD38/ICAM1 antibody) described herein by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," PNAS 109(40): 16101-16106 (2012)).

In some instances, the payload is conjugated to an anti-CD38 antibody, an anti-ICAM1 antibody, or a multi-specific antibody (e.g., a bispecific anti-CD38/ICAM1 antibody) described herein by a site-directed method utilizing an enzyme-catalyzed process. In some instances, the site-directed method utilizes SMARTag™ technology (Redwood). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," PNAS 106(9): 3000-3005 (2009); Agarwal, et al., "A Pictet-Spengler ligation for protein chemical modification," PNAS 110(1): 46-51 (2013)).

In some instances, the enzyme-catalyzed process comprises microbial transglutaminase (mTG). In some cases, the payload is conjugated to the anti-CD38 antibody, the anti-ICAM1 antibody, or the multi-specific antibody (e.g., the bispecific anti-CD38/ICAM1 antibody) utilizing a microbial transglutaminze catalyzed process. In some instances, mTG catalyzes the formation of a covalent bond between the amide side chain of a glutamine within the recognition sequence and a primary amine of a functionalized polynucleic acid molecule. In some instances, mTG is produced from Streptomyces mobarensis. (see Strop et al., "Location matters: site of conjugation modulates stability and pharmacokinetics of antibody drug conjugates," *Chemistry and Biology* 20(2) 161-167 (2013)).

In some instances, the payload is conjugated to an anti-CD38 antibody, an anti-ICAM1 antibody, or a multi-specific antibody (e.g., a bispecific anti-CD38/ICAM1 antibody) described herein by a method as described in PCT Publication No. WO2014/140317, which utilizes a sequence-specific transpeptidase.

In some instances, the payload is conjugated to an anti-CD38 antibody, an anti-ICAM1 antibody, or a multi-specific antibody (e.g., a bispecific anti-CD38/ICAM1 antibody) described herein by a method as described in U.S. Patent Publication Nos. 2015/0105539 and 2015/0105540.

Linkers

In some embodiments, the payload is conjugated to an anti-CD38 antibody, an anti-ICAM1 antibody, or a multi-specific antibody (e.g., a bispecific anti-CD38/ICAM1 antibody) described herein indirectly via a linker. In some instances, the linker comprises a natural or synthetic polymer, consisting of long chains of branched or unbranched monomers, and/or cross-linked network of monomers in two or three dimensions. In some instances, the linker includes a polysaccharide, lignin, rubber, or polyalkylene oxide (e.g., polyethylene glycol).

In some instances, the linker includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalate (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is built up from monomers of another polymer. In some instances, the linker comprises polyalkylene oxide. In some instances, the linker comprises PEG. In some instances, the linker comprises polyethylene imide (PEI) or hydroxy ethyl starch (HES).

In some cases, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, the linker is poly- or monodispersed polyalkylene oxide (e.g., PEG) and the indicated molecular weight represents an average of the molecular weight of the polyalkylene oxide, e.g., PEG, molecules.

In some embodiments, the linker comprises a polyalkylene oxide (e.g., PEG) and the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, the polyalkylene oxide (e.g., PEG) is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units.

In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some instances, the linker is a discrete PEG, optionally comprising from 2 to 60, from 2 to 50, or from 2 to 48 repeating ethylene oxide units. In some cases, the linker comprises a dPEG comprising about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some cases, the linker is a dPEG from Quanta Biodesign, LMD.

In some embodiments, the linker is a polypeptide linker. In some instances, the polypeptide linker comprises at least 2, 3, 4, 5, 6, 7, 8, 10, 15, 20, 25, 30, 35, 40, 45, 50, 60, 70, 80, 90, 100, or more amino acid residues. In some instances, the polypeptide linker comprises at least 2, 3, 4, 5, 6, 7, 8, or more amino acid residues. In some instances, the polypeptide linker comprises at most 2, 3, 4, 5, 6, 7, 8, or less amino acid residues. In some cases, the polypeptide linker is a cleavable polypeptide linker (e.g., either enzymatically or chemically). In some cases, the polypeptide linker is a non-cleavable polypeptide linker. In some instances, the polypeptide linker comprises Val-Cit (valine-citrulline), Gly-Gly-Phe-Gly (SEQ ID NO: 429), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 428), or Gly-Phe-Leu-Gly (SEQ ID NO: 427). In some instances, the polypeptide linker comprises a peptide such as: Val-Cit (valine-citrulline), Gly-Gly-Phe-Gly (SEQ ID NO: 429), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 428), or Gly-Phe-Leu-Gly (SEQ ID NO: 427). In some cases, the polypeptide linker comprises L-amino acids, D-amino acids, or a mixture of both L- and D-amino acids.

In some instances, the linker comprises a homobifuctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[D-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio)

propionate (sPDP), long-chain N-succinimidyl 3-(2-pyridyl-dithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldi-thio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-car-boxylate (sMCC), sulfosuccinimidyl-4-(N-maleimidom-ethyl)cyclohexane-1-carboxylate (sulfo-sMCC), m-male-imidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexano-ate (sIAX), succinimidyl 6-[6-(((iodoacetyl)amino) hexanoyl)amino]hexanoate (sIAXX), succinimidyl 4-(((io-doacetyl)amino)methyl)cyclohexane-1-carboxylate (sIAC), succinimidyl 6-((((4-iodoacetyl)amino)methyl)cyclo-hexane-1-carbonyl)amino) hexanoate (sIACX), p-nitrophe-nyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M$_2$C$_2$H), 3-(2-pyridyldithio)propionyl hydrazide (PDPH), amine-reactive and photoreactive cross-linkers such as N-hydroxysuccin-imidyl-4-azidosalicylic acid (NHs-AsA), N-hydroxysulfos-uccinimidyl-4-azidosalicylic acid (sulfo-NHs-AsA), sulfos-uccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexano-ate (sulfo-sANPAH), N-5-azido-2-nitrobenzoyloxysuccin-imide (ANB-NOs), sulfosuccinimidyl-2-(m-azido-o-ni-trobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithio-propionate (sulfo-sADP), sulfosuccinimidyl 4-(p-azidophe-nyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-ac-etate (sulfo-sAMCA), ρ-nitrophenyl diazopyruvate (pNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido) butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido) butylamine (AsBA), and arginine-reactive and photoreactive cross-linkers such as ρ-azidophenyl glyoxal (APG).

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In addi-tional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker comprises PAMAM dendrimers.

In some embodiments, the linker is a traceless linker or a linker in which after cleavage does not leave behind a linker moiety (e.g., an atom or a linker group) to the antibody or payload. Exemplary traceless linkers include, but are not limited to, germanium linkers, silicium linkers, sulfur link-ers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a trace-less linker described in Blaney, et al., "Traceless solid-phase organic synthesis," *Chem. Rev.* 102: 2607-2024 (2002). In some instances, a linker is a traceless linker as described in U.S. Pat. No. 6,821,783.

Methods of Use

In certain embodiments, described herein is a method of treating a cancer with use of an anti-CD38 antibody, an anti-ICAM1 antibody, or a multi-specific antibody (e.g., a bispecific CD38/ICAM1 antibody) described above. In some instances, the cancer is a solid tumor. In other instances, the cancer is a hematologic malignancy. In addi-tional instances, the cancer is a metastatic, relapsed, or refractory cancer.

In some cases, an anti-CD38 antibody, an anti-ICAM1 antibody, or a multi-specific antibody (e.g., a bispecific CD38/ICAM1 antibody) described above is used for the treatment of a solid tumor. In some cases, the solid tumor is bladder cancer, bone cancer, brain cancer, breast cancer, colorectal cancer, eye cancer, head and neck cancer, kidney cancer, liver cancer, lung cancer, ovarian cancer, pancreatic cancer, prostate cancer, skin cancer, stomach cancer, thyroid cancer, or uterine cancer. In some cases, the anti-CD38 antibody, the anti-ICAM1 antibody, or the multi-specific antibody (e.g., the bispecific CD38/ICAM1 antibody) described above is used for the treatment of bladder cancer, bone cancer, brain cancer, breast cancer, colorectal cancer, eye cancer, head and neck cancer, kidney cancer, liver cancer, lung cancer, ovarian cancer, pancreatic cancer, pros-tate cancer, skin cancer, stomach cancer, thyroid cancer, or uterine cancer. In some cases, the solid tumor is a metastatic, relapsed, or refractory solid tumor.

In some cases, an anti-CD38 antibody, an anti-ICAM1 antibody, or a multi-specific antibody (e.g., a bispecific CD38/ICAM1 antibody) described above is used for the treatment of a hematologic malignancy. In some cases, the hematologic malignancy is a B cell lymphoma or a T cell lymphoma. In some cases, the hematologic malignancy is a Hodgkin's lymphoma or a non-Hodgkin's lymphoma. In some cases, the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the anti-CD38 antibody, the anti-ICAM1 antibody, or the multi-specific antibody (e.g., the bispecific CD38/ICAM1 antibody) described above is used for the treatment of chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the hematologic malignancy is a metastatic, relapsed, or refractory hematologic malignancy.

In some embodiments, the anti-CD38 antibody, the anti-ICAM1 antibody, or the multi-specific antibody (e.g., the bispecific CD38/ICAM1 antibody) is further administered with an additional therapeutic agent. In some instances, the additional therapeutic agent is a chemotherapeutic agent, an immunotherapeutic agent, a targeted therapeutic agent, a hormone-based therapeutic agent, a stem-cell based therapeutic agent, or radiation. In some instances, the additional therapeutic agent is a first-line therapeutic agent.

In some instances, the additional therapeutic agent comprises a chemotherapeutic agent. Exemplary chemotherapeutic agents include, but are not limited to, alkylating agents such as cyclophosphamide, mechlorethamine, chlorambucil, melphalan, dacarbazine, or nitrosoureas; anthracyclines such as daunorubicin, doxorubicin, epirubicin, idarubicin, mitoxantrone, or valrubicin; cytoskeletal disruptors such as paclitaxel, docetaxel, abraxane, or taxotere; epothilones; histone deacetylase inhibitors such as vorinostat or romidepsin; topoisomerase I inhibitors such as irinotecan or topotecan; topoisomerase II inhibitors such as etoposide, teniposide, or tafluposide; kinase inhibitors such as bortezomib, erlotinib, gefitinib, imatinib, vemurafenib, or vismodegib; nucleotide analogs and precursor analogs such as azacitidine, azathioprine, capecitabine, cytarabine, doxifluridine, fluorouracil, gemcitabine, hydrozyurea, mercaptopurine, methotrexate, or tioguanine; platinum-based agents such as carboplatin, cisplatin, or oxaliplatin; retinoids such as tretinoin, alitretinoin, or bexarotene; thalidomide and its analogs such as thalidomide, lenalidomide, or pomalidomide; or proteasome inhibitors such as bortezomib, carfilzomib, or ixazomib; or corticosteroids such as hydrocortisone, hydrocortisone acetate, cortisone acetate, tixocortol pivalate, prednisolone, methylprednisolone, prednisone, beclometasone, betamethasone, dexamethasone, fluocortolone, halometasone, or mometasone; or vinca alkaloids and derivatives such as vinblastine, vincristine, vindesine, or vinorelbine.

In some instances, the additional therapeutic agent comprises an immunotherapeutic agent. In some instances, the immunotherapy is an adoptive cell therapy. Exemplary adoptive cell therapies include AFP TCR, MAGE-A10 TCR, or NY-ESO-TCR from Adaptimmune; ACTR087/rituximab from Unum Therapeutics; anti-BCMA CAR-T cell therapy, anti-CD19 "armored" CAR-T cell therapy, JCAR014, JCAR018, JCAR020, JCAR023, JCAR024, or JTCR016 from Juno Therapeutics; JCAR017 from Celgene/Juno Therapeutics; anti-CD19 CAR-T cell therapy from Intrexon; anti-CD19 CAR-T cell therapy, axicabtagene ciloleucel, KITE-718, KITE-439, or NY-ESO-1 T-cell receptor therapy from Kite Pharma; anti-CEA CAR-T therapy from Sorrento Therapeutics; anti-PSMA CAR-T cell therapy from TNK Therapeutics/Sorrento Therapeutics; ATA520 from Atara Biotherapeutics; AU101 and AU105 from Aurora BioPharma; baltaleucel-T (CMD-003) from Cell Medica; bb2121 from bluebird bio; BPX-501, BPX-601, or BPX-701 from Bellicum Pharmaceuticals; BSKO1 from Kiromic; IMCgp100 from Immunocore; JTX-2011 from Jounce Therapeutics; LN-144 or LN-145 from Lion Biotechnologies; MB-101 or MB-102 from Mustang Bio; NKR-2 from Celyad; PNK-007 from Celgene; tisagenlecleucel-T from Novartis Pharmaceuticals; or TT12 from Tessa Therapeutics.

In some instances, the immunotherapy is a dendritic cell-based therapy.

In some instances, the immunotherapy comprises a cytokine-based therapy, comprising e.g., an interleukin (IL) such as IL-2, IL-15, or IL-21, interferon (IFN)-$\alpha$, or granulocyte macrophage colony-stimulating factor (GM-CSF).

In some instances, the immunotherapy comprises an immune checkpoint modulator. Exemplary immune checkpoint modulators include PD-1 modulators such as nivolumab (Opdivo) from Bristol-Myers Squibb, pembrolizumab (Keytruda) from Merck, AGEN 2034 from Agenus, BGB-A317 from BeiGene, Bl-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, MGA 012 from MacroGenics, PDR001 from Novartis Pharmaceuticals, PF-06801591 from Pfizer, REGN2810 (SAR439684) from Regeneron Pharmaceuticals/Sanofi, or TSR-042 from TESARO; CTLA-4 modulators such as ipilimumab (Yervoy), or AGEN 1884 from Agenus; PD-L1 modulators such as durvalumab (Imfinzi) from AstraZeneca, atezolizumab (MPDL3280A) from Genentech, avelumab from EMD Serono/Pfizer, CX-072 from CytomX Therapeutics, FAZ053 from Novartis Pharmaceuticals, KN035 from 3D Medicine/Alphamab, LY3300054 from Eli Lilly, or M7824 (anti-PD-L1/TGFbeta trap) from EMD Serono; LAG3 modulators such as BMS-986016 from Bristol-Myers Squibb, IMP701 from Novartis Pharmaceuticals, LAG525 from Novartis Pharmaceuticals, or REGN3767 from Regeneron Pharmaceuticals; OX40 modulators such as BMS-986178 from Bristol-Myers Squibb, GSK3174998 from GlaxoSmithKline, INCAGN1949 from Agenus/Incyte, MEDI0562 from MedImmune, PF-04518600 from Pfizer, or RG7888 from Genentechp; GITR modulators such as GWN323 from Novartis Pharmaceuticals, INCAGN1876 from Agenus/Incyte, MEDI1873 from MedImmune, MK-4166 from Merck, or TRX518 from Leap Therapeutics; KIR modulators such as lirilumab from Bristol-Myers Squibb; or TIM modulators such as MBG453 from Novartis Pharmaceuticals or TSR-022 from Tesaro.

In some instances, the additional therapeutic agent comprises a hormone-based therapeutic agent. Exemplary hormone-based therapeutic agents include, but are not limited to, aromatase inhibitors such as letrozole, anastrozole, exemestane, or aminoglutethimide; gonadotropin-releasing hormone (GnRH) analogues such as leuprorelin or goserelin; selective estrogen receptor modulators (SERMs) such as tamoxifen, raloxifene, toremifene, or fulvestrant; antiandrogens such as flutamide or bicalutamide; progestogens such as megestrol acetate or medroxyprogesterone acetate; androgens such as fluoxymesterone; estrogens such as estrogen diethylstilbestrol (DES), Estrace, or polyestradiol phosphate; or somatostatin analogs such as octreotide.

In some instances, the additional therapeutic agent and the antibody (e.g., the anti-CD38 antibody, anti-ICAM1 antibody, or the multi-specific antibody such as the bispecific CD38/ICAM1 antibody) are administered simultaneously.

In other instances, the additional therapeutic agent and the antibody (e.g., the anti-CD38 antibody, anti-ICAM1 antibody, or the multi-specific antibody such as the bispecific CD38/ICAM1 antibody) are administered sequentially. In some cases, the additional therapeutic agent is administered to a subject prior to administering the antibody (e.g., the anti-CD38 antibody, anti-ICAM1 antibody, or the multi-specific antibody such as the bispecific CD38/ICAM1 antibody). In other cases, the additional therapeutic agent is administered to a subject after the antibody (e.g., the anti-CD38 antibody, anti-ICAM1 antibody, or the multi-specific antibody such as the bispecific CD38/ICAM1 antibody) is administered.

In additional instances, the additional therapeutic agent and the antibody (e.g., the anti-CD38 antibody, anti-ICAM1 antibody, or the multi-specific antibody such as the bispecific CD38/ICAM1 antibody) are administered as a separate dosage.

In some cases, the subject has undergone surgery. In some cases, the antibody (e.g., the anti-CD38 antibody, anti-ICAM1 antibody, or the multi-specific antibody such as the bispecific CD38/ICAM1 antibody) and optionally the additional therapeutic agent are administered to the subject after surgery. In additional cases, the antibody (e.g., the anti-CD38 antibody, anti-ICAM1 antibody, or the multi-specific antibody such as the bispecific CD38/ICAM1 antibody) and optionally the additional therapeutic agent is administered to the subject prior to surgery.

In some cases, the antibody is administered intravenously to a subject with multiple myeloma. In some cases, the subject has undergone chemotherapeutic treatment for multiple myeloma. In some cases, the subject is administered a proteasome inhibitor or an immunomodulatory agent. In some cases, the antibody (e.g., the anti-CD38 antibody, anti-ICAM1 antibody, or the multi-specific antibody such as the bispecific CD38/ICAM1 antibody) is administered together with a chemotherapeutic agent, a proteasome inhibitor and/or an immunomodulatory agent. In some cases, the antibody (e.g., the anti-CD38 antibody, anti-ICAM1 antibody, or the multi-specific antibody such as the bispecific CD38/ICAM1 antibody) is administered after the subject has undergone more than three treatments of a chemotherapeutic agent, a proteasome inhibitor and/or an immunomodulatory agent. In some cases, the antibody (e.g., the anti-CD38 antibody, anti-ICAM1 antibody, or the multispecific antibody such as the bispecific CD38/ICAM1 antibody) is administered after the subject is double refractory to the proteasome inhibitor and/or immunomodulatory agent.

In some cases, the subject is a human.

Pharmaceutical Formulations

In some embodiments, the pharmaceutical formulations described herein are administered to a subject by multiple administration routes, including but not limited to, parenteral (e.g., intravenous, intra-arterial, subcutaneous, intramuscular, intraocular, intraperitoneal, intrathecal, intravesical, or intravitreal), oral, intranasal, buccal, rectal, or transdermal administration routes. In some instances, the pharmaceutical composition describe herein is formulated for parenteral (e.g., intravenous, intra-arterial, subcutaneous, intramuscular, intraocular, intraperitoneal, intrathecal, intravesical, or intravitreal) administration. In other instances, the pharmaceutical composition describe herein is formulated for oral administration. In still other instances, the pharmaceutical composition describe herein is formulated for intranasal administration.

In some instances, the pharmaceutical formulations further include pH-adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide, and the like.

Stabilizers include compounds such as any antioxidation agents, buffers, acids, preservatives and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, are optionally reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Articles of Manufacture

Disclosed herein, in certain embodiments, are kits and articles of manufacture for use with one or more anti-CD38 antibodies, anti-ICAM1 antibodies, or multi-specific antibodies (e.g., bispecific CD38/ICAM1 antibodies) described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include anti-CD38 antibodies, anti-ICAM1 antibodies, or multi-specific antibodies (e.g., bispecific CD38/ICAM1 antibodies) described herein and reagents for use with the antibodies as disclosed herein. Such kits optionally include an identifying description or label or instructions relating to its use in the methods described herein.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

"Antibodies" and "immunoglobulins" (Igs) are glycoproteins having the same structural characteristics. The terms are used synonymously. In some instances, the antigen specificity of the immunoglobulin is known.

The term "antibody" is used in the broadest sense and covers fully assembled antibodies, antibody fragments that can bind antigen (e.g., Fab, $F(ab')_2$, Fv, single chain antibodies, diabodies, antibody chimeras, hybrid antibodies, bispecific antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages vanes among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (x) and lambda (Q), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, IgM, and IgY, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

In some instances, the CDRs of an antibody is determined according to (i) the Kabat numbering system (Kabat et al. (197) Ann. NY Acad. Sci. 190:382-391 and, Kabat et al. (1991) Sequences of Proteins of Immunological Interest Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, *J Mol. Biol.*, 196:901-917; Al-Lazikani et al., 1997, *J Mol. Biol.*, 273:927-948; Chothia et al., 1992, *J Mol. Biol.*, 227:799-817; Tramontano A et al., 1990, *J Mol. Biol.* 215(1): 175-82; and U.S. Pat. No. 7,709,226); or (iii) the ImMunoGeneTics (IMGT) numbering system, for example, as described in Lefranc, M.-P., 1999, *The Immunologist*, 7: 132-136 and Lefranc, M.-P. et al, 1999, *Nucleic Acids Res.*, 27:209-212 ("IMGT CDRs"); or (iv) MacCallum et al, 1996, *J Mol. Biol.*, 262:732-745. See also, e.g., Martin, A., "Protein Sequence and Structure Analysis of Antibody Variable Domains," in Antibody Engineering, Kontermann and Dübel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35 A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The term "chimeric" antibody refers to an antibody in which a portion of the heavy and/or light chain is derived from a particular source or species, while the remainder of the heavy and/or light chain is derived from a different source or species.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). In some instances, human antibodies are also produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al, Proc. Natl. Acad. Sci. USA 90 (1993) 2551-2555; Jakobovits, A., et al, Nature 362 (1993) 255-258; Brugge-mann, M., et al, Year Immunol. 7 (1993) 33-40). In additional instances, human antibodies are also produced in phage display libraries (Hoogenboom, H. R., and Winter, G., J. Mol. Biol. 227 (1992) 381-388; Marks, J. D., et al, J. Mol. Biol. 222 (1991) 581-597). The techniques of Cole et al. and Boerner et al. are also available for the preparation of human monoclonal antibodies (Cole, et al., Monoclonal Antibodies and Cancer Therapy, Alan R. Liss, p. 77 (1985); and Boerner, P., et al, J. Immunol. 147 (1991) 86-95).

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. In some cases, the recombinant human antibodies have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "anti-CD38 BMK" antibody refers to reference antibody daratumumab.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

EXAMPLES

These examples are provided for illustrative purposes only and not to limit the scope of the claims provided herein.

Example 1: Generation and Characterization of Bispecific Anti-CD38/Anti-ICAM1 Antibodies Six different bispecific antibody formats were tested (FIG. 2). Four of the bispecific antibody formats were tetravalent, with two CD38 binding sites and two ICAM1 binding sites. The tetravalent formats had a core structure with a complete anti-CD38 antibody and had ICAM1-binding sequences fused to the N-terminus or C-terminus of the heavy or light chains of the anti-CD38 antibody. The ICAM1 binding site could be formed from a single polypeptide chain or two polypeptide chains. The other two bispecific antibody formats were bivalent, with one CD38 binding site and one ICAM1 binding site. The bivalent bispecific antibodies incorporated knob-in-hole mutations in their Fc domains to form an asymmetric structure. In one bivalent bispecific antibody format, the ICAM1 binding site was a single chain variable domain. In the other format, the same light chain was used for the CD38 binding site and the ICAM1 binding site.

For proof of concept studies, bispecific antibodies were constructed from anti-CD38 BMK and anti-ICAM1 G12 sequences. The anti-CD38 BMK benchmark antibody has an amino acid sequence based on Daratumumab. The G12 anti-ICAM1 clone was identified through naïve phage selection against human ICAM1. The sequences of the heavy and light chains of these proof of concept antibodies are identified in Table 13.

TABLE 13

| | | Proof of concept bispecific antibodies | |
| | | SEQ ID Nos. | |
| Format | HC1 (heavy chain 1) | LC1 (light chain 1) | HC2 (heavy chain 2) |
|---|---|---|---|
| LC C-fusion | 376 | 380 | |
| HC C-fusion | 377 | 381 | |
| DVD format | 378 | 382 | |
| HC N-fusion | 379 | 381 | |
| Three Chain KIH | 376 | 381 | 383 |

The corresponding heavy chain (HC) and light chain (LC) DNAs were synthesized and cloned into the pRK5 mammalian expression vector (ATCC). Each HC and LC pair was then co-transfected in CHO cells. The conditioned medium was harvested by centrifugation (4° C., 4000 rpm for 40 min), then filtered to remove cell debris. The clarified medium was loaded onto MabSelect SuRe column (GE, 17-5438) which was pre-equilibrated with Buffer A (25 mM Tris, 150 mM NaCl, pH 8.0). The column was washed sequentially with 5 column volumes of Buffer A, then 30 column volumes of Buffer B (Buffer A+0.1% Triton X100+0.1% Triton X114), then 15 column volumes of Buffer A. The antibodies were eluted with Buffer C (100 mM sodium citrate, 150 mM NaCl, pH 3.0) and neutralized immediately with Buffer D (200 mM Arginine, 137 mM Succinic acid, pH 5.0). The final product was dialyzed against the buffer PBS, pH 7.4, concentrated and filtrated through MILLEX-MP 0.22 um (MILLIPORE).

The binding kinetics of the bispecific anti-CD38/anti-ICAM1 antibodies were evaluated using Biacore T200 (GE Healthcare). The recombinant CD38 or ICAM1 were immobilized at low density on Biacore Series S CM5 sensor chips using the amine coupling kit (GE Healthcare). Serial 3-fold dilutions of each antibody were injected at a flow rate of 30 ul/min. Each sample was analyzed with 3m association and 15 min dissociation at room temperature (25° C.). After each injection, the chip was regenerated using 10 mM Glycine pH1.5. A 1:1 Langmuir model of simultaneous fitting of $k_{on}$ and $k_{off}$ was used for kinetics analysis. Tables 14 and 15 summarizes the binding kinetics for each antibody.

TABLE 14

Summary of Biacore ™ kinetic analysis of benchmark and proof of concept bispecific antibody binding to recombinant human ICAM1.

| Ag | Sample | ka (1/Ms) | kd (1/s) | $K_D$ (nM) |
|---|---|---|---|---|
| ICAM-1 | Anti-ICAM1 G12 | 2.42E+05 | 7.63E−04 | 3.2 |
| | LC C-fusion | 7.56E+04 | 1.36E−03 | 18.0 |
| | HC C-fusion | 1.45E+05 | 1.47E−03 | 10.1 |
| | HC N-fusion | 1.95E+05 | 6.16E−04 | 3.15 |
| | DVD format | 1.71E+05 | 5.78E−04 | 3.39 |
| | Three chain KIH | 4.85E+05 | 2.58E−03 | 5.32 |

TABLE 15

Summary of Biacore ™ kinetic analysis of benchmark and proof of concept bispecific antibody binding to recombinant human CD38.

| Ag | Sample | ka (1/Ms) | kd (1/s) | $K_D$ (nM) |
|---|---|---|---|---|
| CD38 | Anti-CD38 BMK | 5.09E+05 | 1.20E−04 | 0.24 |
| | LC C-fusion | 3.65E+05 | 7.30E−05 | 0.2 |
| | HC C-fusion | 3.51E+05 | 5.30E−05 | 0.15 |
| | DVD format | 1.03E+05 | 1.78E−04 | 1.72 |
| | HC N-fusion | 2.33E+05 | 6.68E−05 | 0.29 |
| | Three chain KIH | 2.04E+05 | 4.65E−04 | 2.28 |

Example 2: Functional Assays on Bispecific Anti-CD38/Anti-ICAM1 Antibodies

Cell Lines
Antibody functions were tested on the cell lines described in Table 16.

TABLE 16

| | | Origin of cell lines | |
| Cell Line | Source | Vendor | Catalog number |
|---|---|---|---|
| Daudi | Burkitt lymphoma | ATCC | CCL-213 |
| Raji | Burkitt lymphoma | ATCC | CCL-86 |
| KMS-26 | Plasma cell myeloma | JCRB | JCRB1187 |
| HuNS1 | Plasma cell myeloma | ATCC | CRL-8644 |
| HCC44 | Lung adenocarcinoma | KCLB | 70044 |
| NCI-H2291 | Lung adenocarcinoma | ATCC | CRL-5939 |
| NCI-H2342 | Lung adenocarcinoma | ATCC | CRL-5941 |
| NCI-H2444 | Non-small cell lung carcinoma | ATCC | CRL-5945 |
| DU145 | Prostate carcinoma | ATCC | HTB-81 |

Figures 3A, 3B:
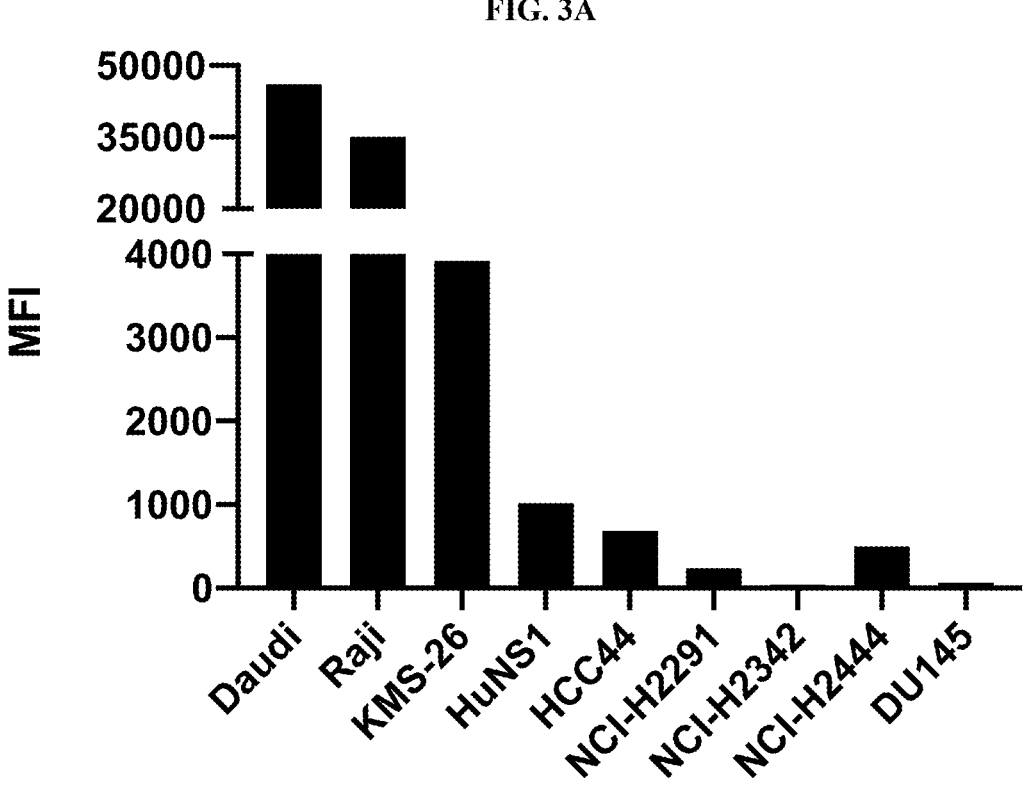
FIGS. 3A-3B show levels of CD38 (FIG. 3A) and ICAM1 (FIG. 3B) on the surface of various cell lines as measured by flow cytometry with PE-labeled anti-hCD38 (Biolegend) or AlexaFluor488-labeled anti-hCD54 (Biolegend).

Surface expression of CD38 and ICAM1 was quantified by flow cytometry using fluorescently-labeled antibodies. Results are summarized in Table 17 and FIG. 3.

TABLE 17

Summary of the surface expression of CD38 or ICAM1 on different cell types as measured by flow cytometry. MFI = mean fluorescence index.

| Cell Line | CD38 (MFI) | ICAM1 (MFI) |
|---|---|---|
| Daudi | 46116 | 1158 |
| Raji | 35114 | 5489 |

TABLE 17-continued

Summary of the surface expression of CD38 or
ICAM1 on different cell types as measured by
flow cytometry. MFI = mean fluorescence index.

| Cell Line | CD38 (MFI) | ICAM1 (MFI) |
|---|---|---|
| KMS-26 | 3920 | 3433 |
| HuNS1 | 1016 | 1817 |
| HCC44 | 689 | 2734 |
| NCI-H2291 | 239 | 500 |
| NCI-H2342 | 41 | 912 |
| NCI-H2444 | 501 | 1547 |
| DU145 | 60 | 2539 |

Complement-Dependent Cytotoxicity

To assay for complement-dependent cytotoxicity, the complement, antibodies or target cells were diluted in cell culture medium without FBS. Target cells were harvested in logarithmic growth phase and washed twice with cell culture medium without FBS. Cell density was adjusted to $4 \times 10^5$/ml and 50 μL of cell suspension were added to each well of the assay plate. Antibodies were prepared at $4 \times$ of final concentrations. 25 μL of serially diluted antibodies were then added to each well of the assay plate and incubated at 37° C. for 30 mins. 25 μL of diluted human serum was then added to each well of the assay plate. The working concentration of complement was 10%. All the media used for complement, antibody and target cells dilution was serum free. The assay plates were incubated at 37° C. for 4 hrs. Then 50 μL CellTiter-Glo Luminescent buffer was added to each well, mixed extensively on an orbital shaker for 2 minutes to induce cell lysis. The plate was then incubated at room temperature for 10 minutes to stabilize luminescent signal. Luminescence was measured by SpectraMax M5. Data was analyzed by GraphPad prism 5 using nonlinear regression fit.

Figure 4A:
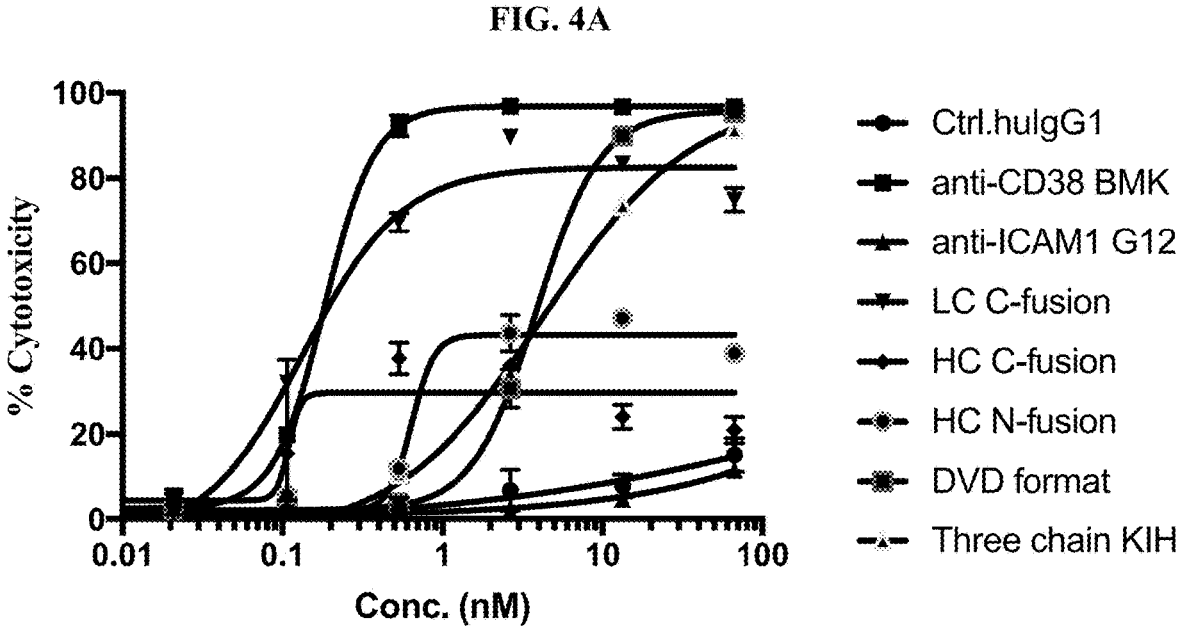
FIG. 4A-FIG. 4B show complement-dependent cytotoxicity (CDC) mediated lysis of Daudi cells (FIG. 4A) and Raji cells (FIG. 4B) by selected monoclonal and bispecific antibodies.
Figure 4B:
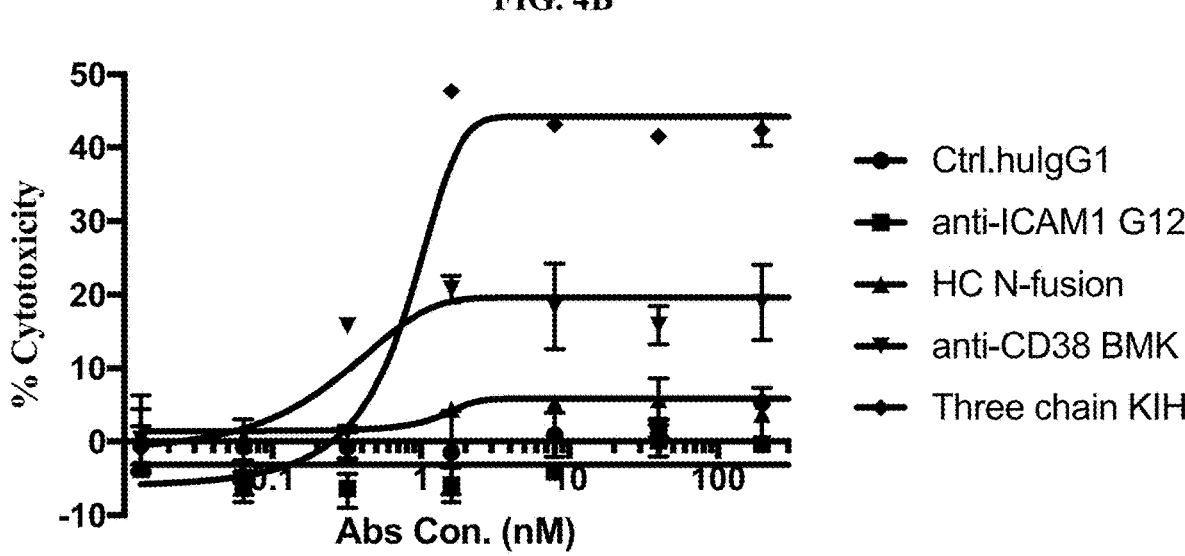

The CDC activity of bispecific anti-CD38/ICAM1 antibodies with various formats was determined in Daudi cells (FIG. 4A) and Raji cells (FIG. 4B) and was compared to the CDC activity of monospecific anti-CD38 and anti-ICAM1 antibodies with the same binding sequences. Bispecific antibodies of all formats had CDC activity in Daudi cells, but the monospecific anti-CD38 antibody had higher activity. In Raji cells, which have lower CD38 expression and higher ICAM1 expression, the three chain KIH bispecific antibody had about two-fold higher CDC activity than the monospecific anti-CD38 antibody.

Antibody-Dependent Cellular Cytotoxicity

To assay for antibody-dependent cellular cytotoxicity (ADCC), target cells were washed once with balanced salt solution or culture medium and cell numbers were adjusted to $1 \times 10^6$ cells/ml. 2 μL of BATDA fluorescence enhancing ligand (Perkin Elmer, Cat #C136-100) was then added to each mL of cells and incubated for 20 min at 37° C. in a cell incubator. After incubation, cells were centrifuged, culture medium was aspirated. The labeled cells were washed 4 times with PBS. After the final wash, cells were resuspended in culture medium and adjusted to $5 \times 10^4$ cell/ml. 200 μL cell suspension was then added to each well of the 96-well plate to make the cell number per well to $1 \times 10^4$. Background release was determined by withdrawing an aliquot of the labeled target cells, centrifuge and supernatant was transferred into an empty well. The reading was background release. $1 \times 10^4$ labeled target cells were transferred to sterile 96-well assay plate. Antibodies were serially diluted with RPMI-1640 containing 10% FBS. 50 μL of serially-diluted antibodies were added to assay plate containing target cell and incubated at 37° C., 5% CO2 for 5-10 min. Effector cells NK92/CD16a176V or freshly isolated PBMC were harvested and suspended in RPMI-1640 containing 10% FBS. 50 ul/well effector cells were added to each well of assay plate at different ET ratio. Set up controls: target spontaneous (target cell+100 μL medium); target maximum (target cell+100 μL medium+10 μL lysis buffer); background (100 μL the labeled target cell supernatant and 100 μL dilution medium). The plates were incubated in a humidified 5% $CO_2$ atmosphere at 37° C. for 2 hours. At the end of incubation, 10 μL of Lysis Buffer (Perkin Elmer, Cat #4005-0010) was added to the maximum release well. The plates were centrifuged for 5 min at 500 g. 20 μL of the supernatant from each well was transferred to a flat-bottom detection plate. 200 μL of Europium Solution (Perkin Elmer, Cat #C135-100) was then added to each well of the detection plate. The plate was shaken at 250 rpm for 15 min at room temperature and the fluorescence was then measured in a time-resolved fluorometer within 5 hrs.

Figure 5A:
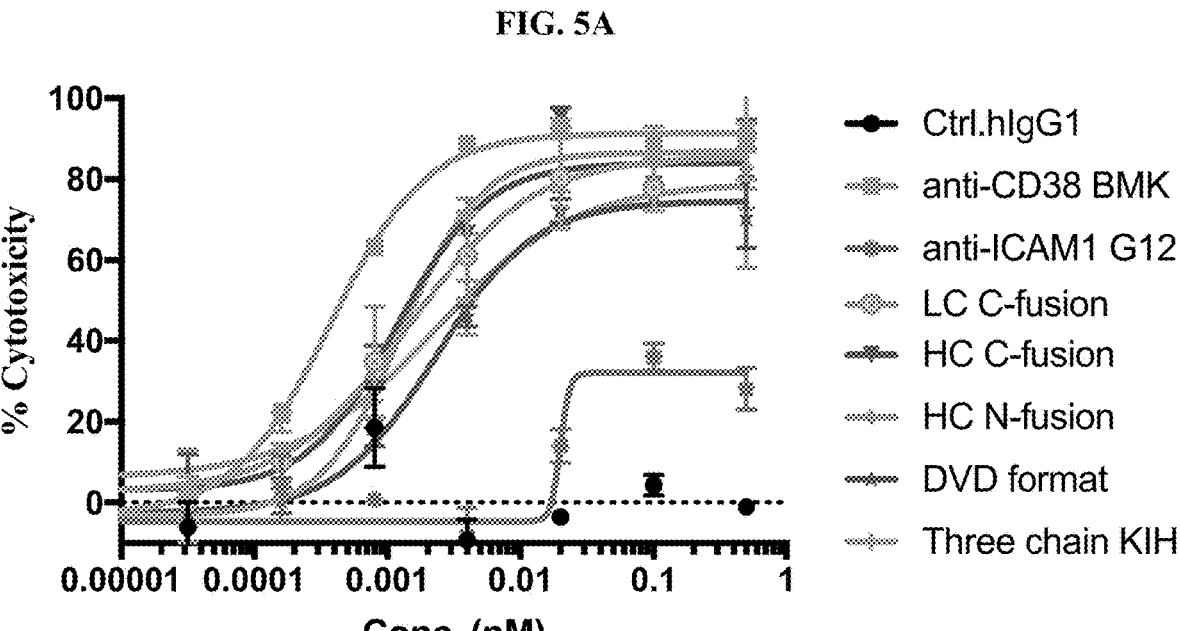
FIG. 5A-FIG. 5F illustrate antibody-dependent cellular cytotoxicity (ADCC)-mediated lysis of Daudi cells (FIG. 5A), DU145 cells (FIG. 5B), NCI-H2444 cells (FIG. 5C), HCC44 cells (FIG. 5D), NCI-H2291 cells (FIG. 5E) and NCI-H2342 (FIG. 5F) cells using NK92/CD16A as effector cells.

The ADCC activity of bispecific anti-CD38/ICAM1 antibodies with various formats was determined in Daudi cells using NK92/CD16A effector cells (FIG. 5A). Monospecific anti-CD38 had higher activity than monospecific anti-ICAM, consistent with the high CD38 and low ICAM1 surface expression levels. The bispecific antibodies all had ADCC activity in Daudi cells, but they had less activity than the monospecific anti-CD38 antibody.

Figure 5B:
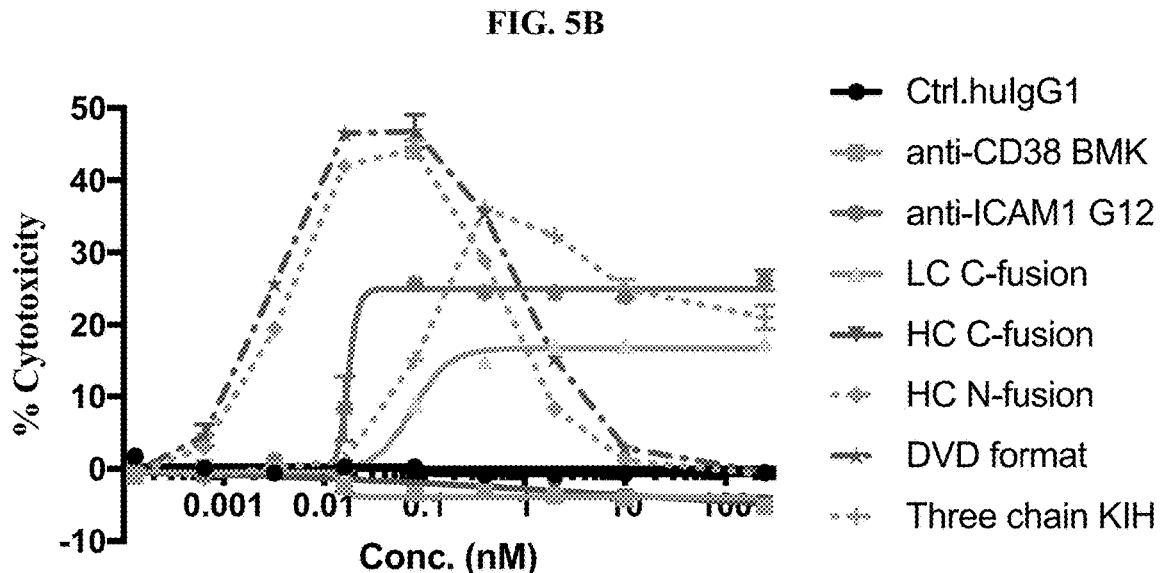
Figure 5C:
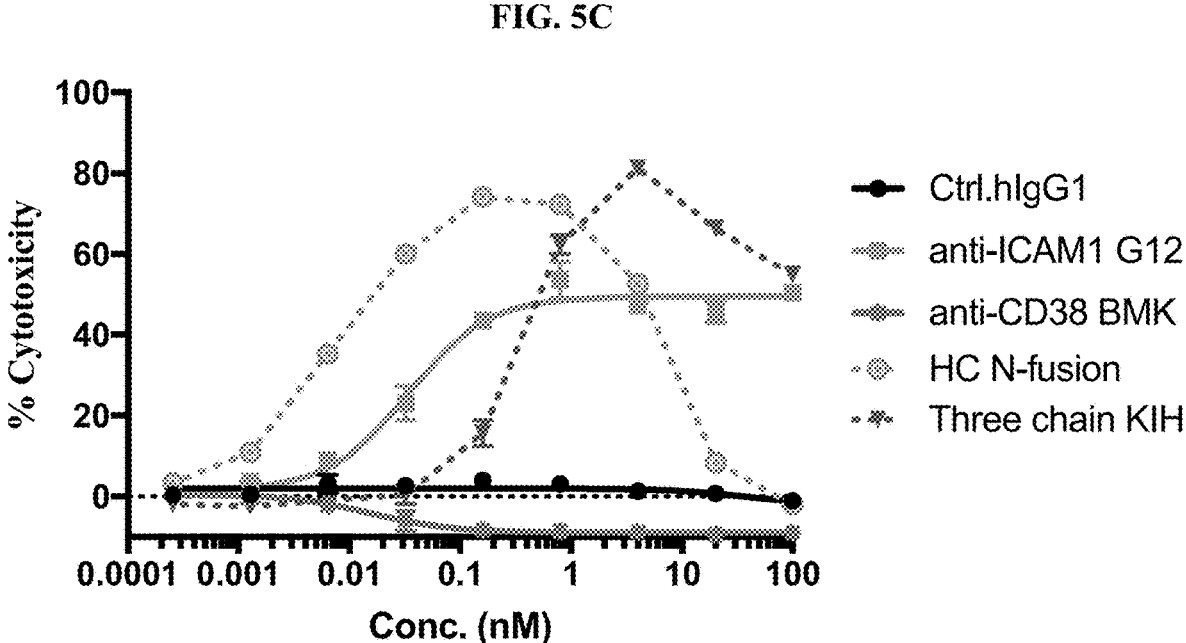
Figure 5D:
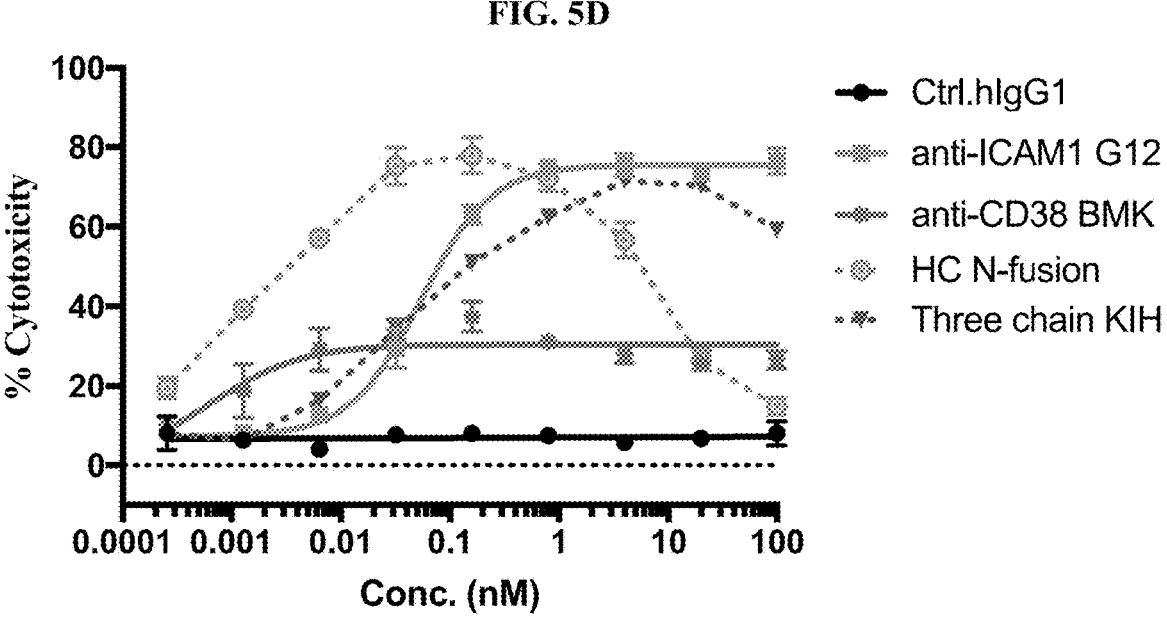
Figure 5E:
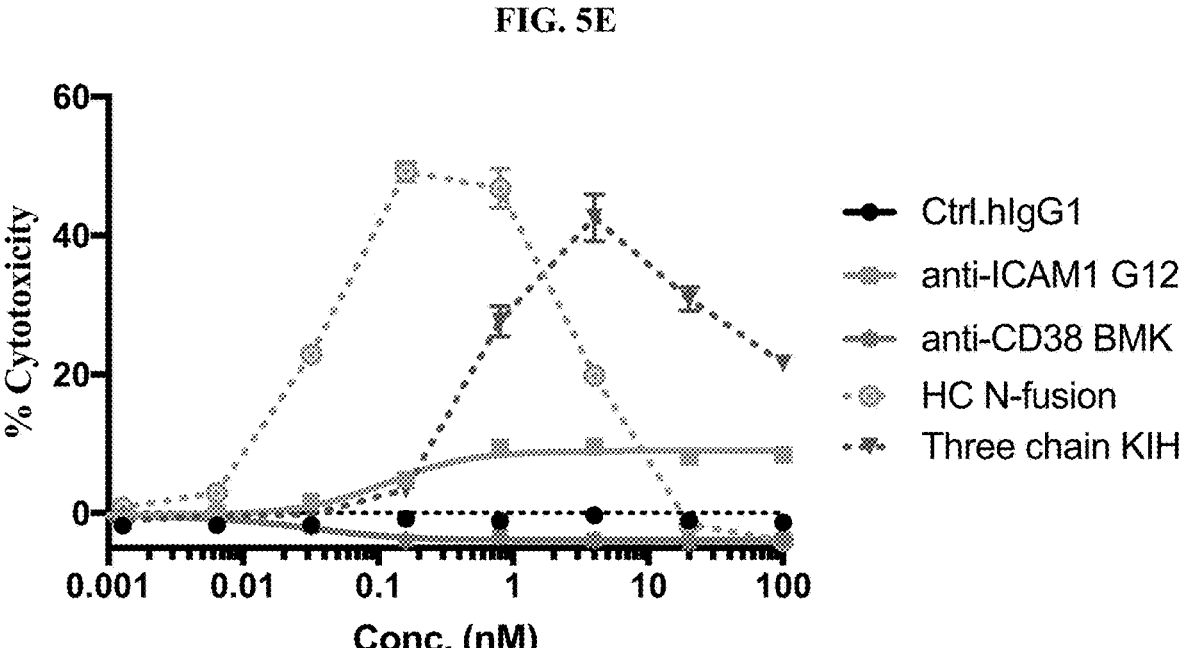
Figure 5F:
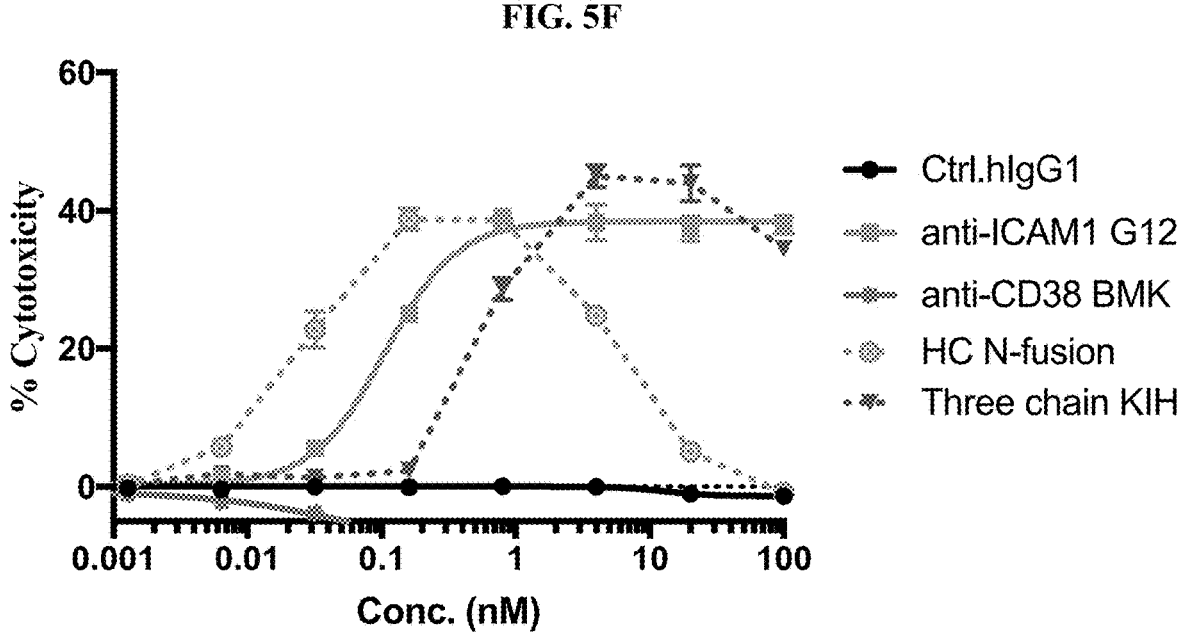

In contrast to the results in Daudi cells, the monospecific anti-CD38 antibody had little or no ADCC activity in cell lines with lower CD38 surface expression, including DU145 cells, NCI-H2444 cells, HCC44 cells, NCI-H2291 cells and NCI-H2342 cells (FIGS. 5B-5F). However, one or more of the bispecific antibody formats had robust ADCC activity in these cells. In DU145 cells, the DVD and HC N-fusion bispecific antibodies had highest activity, and the LC C-fusion and three chain KIH bispecific antibodies also had higher activity than the monospecific anti-CD38 antibody (FIG. 5B). In NCI-H2444 cells, HCC44 cells, NCI-H2291 cells and NCI-H2342 cells, the HC N-fusion and three chain KIH bispecific antibodies had higher ADCC activity than the monospecific anti-CD38 antibody (FIG. 5C-FIG. 5F).

Figure 6A:
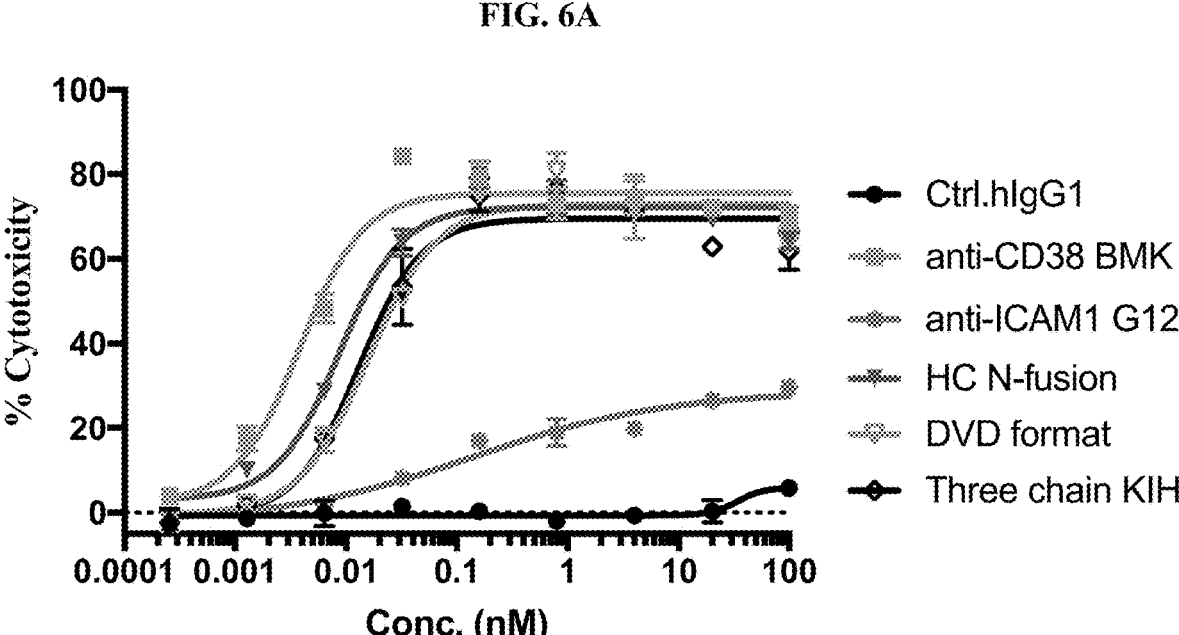
FIG. 6A-FIG. 6D show ADCC-mediated lysis of Daudi cells (FIG. 6A), DU145 cells (FIG. 6B), HCC44 cells (FIG. 6C) and NCI-H2444 cells (FIG. 6D) using fresh PBMCs as effector cells.
Figure 6B:
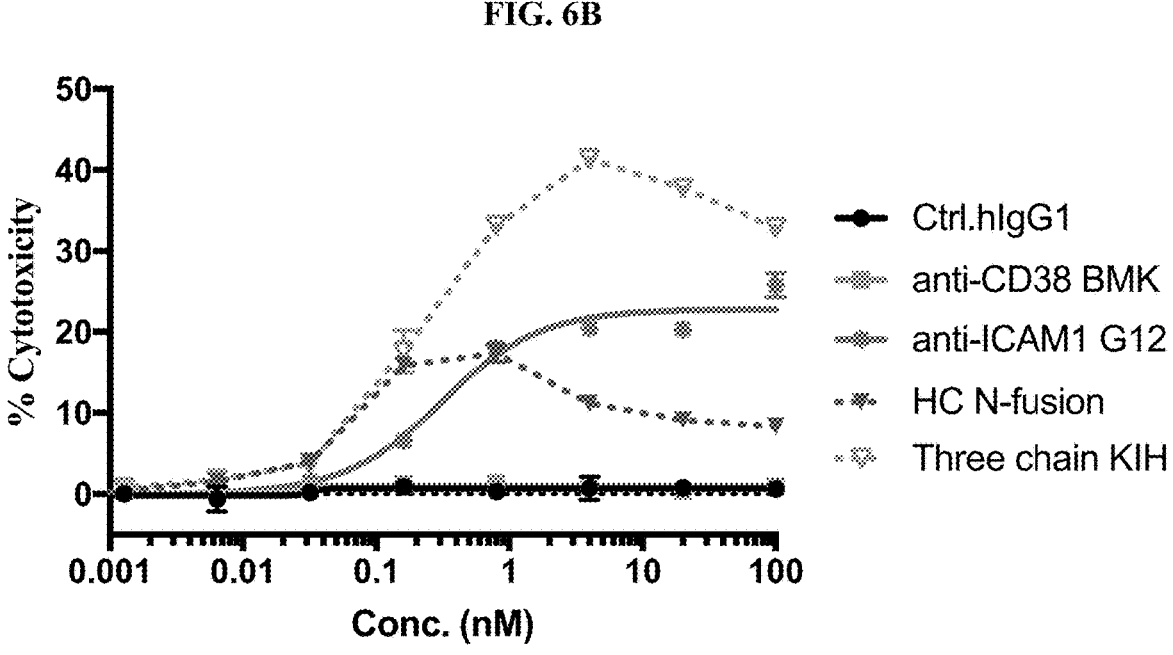
Figure 6C:
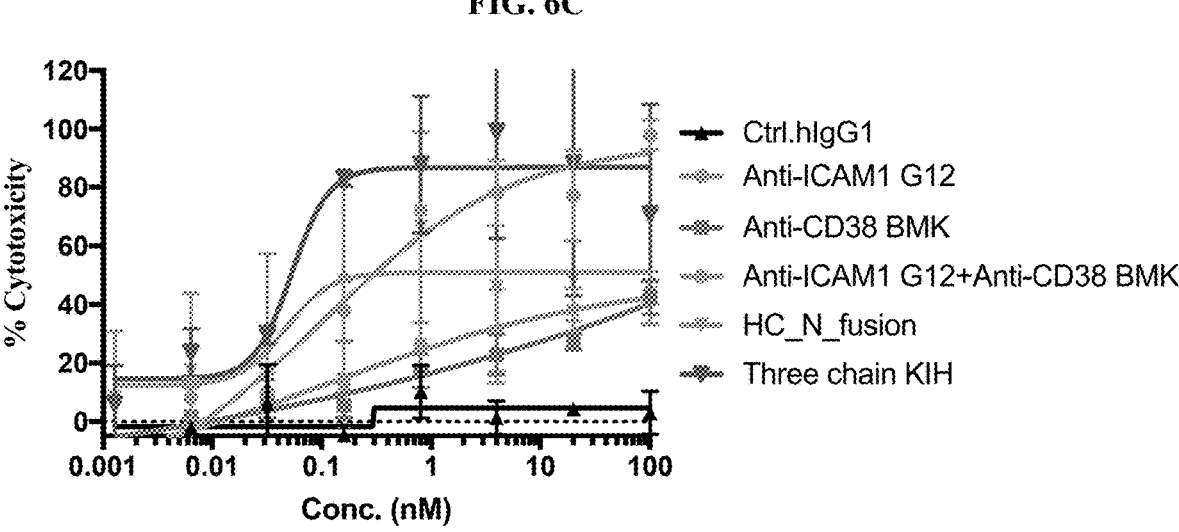
Figure 6D:
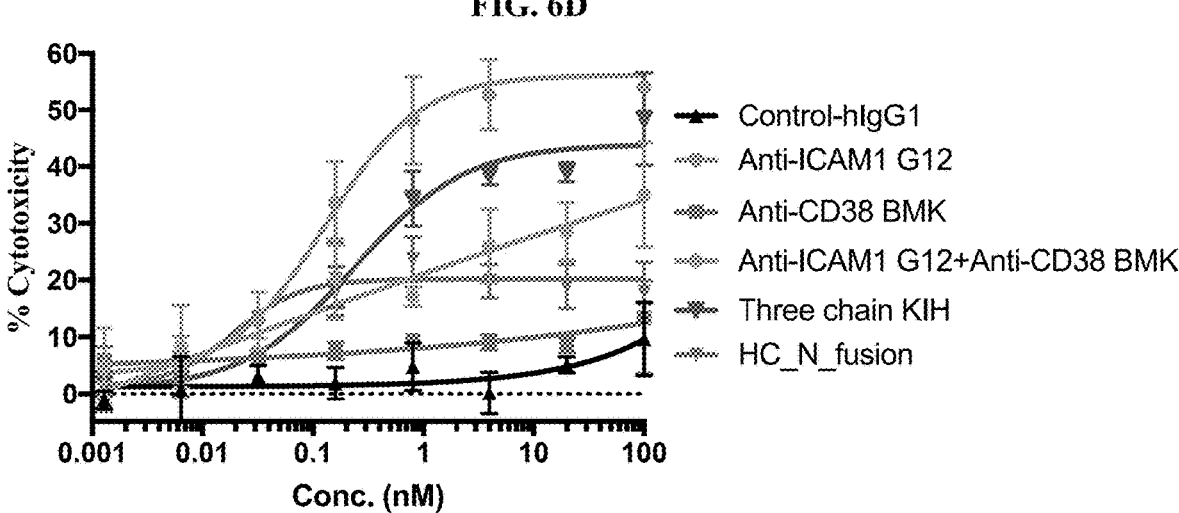

ADCC assays were also conducted using peripheral blood mononuclear cells (PBMCs) as effector cells. Bispecific antibodies with the NC N-fusion, DVD, and three chain KIH formats all had robust activity in Daudi cells with PBMC effector cells (FIG. 6A). In DU145 cells, bispecific antibodies with the HC N-fusion and three-chain KIH formats had higher ADCC activity than monospecific anti CD38 antibodies (FIG. 6B). In HCC44 cells, the three chain KIH bispecific antibody had more potent ADCC cytotoxicity than monospecific anti-CD38 antibodies, monospecific anti-ICAM1 antibodies, or a mixture of both monospecific antibodies (FIG. 6C). In NCI-H2444 cells, the three chain KIH and HC N-fusion bispecific antibodies both had higher activity than a monospecific anti-CD38 antibody (FIG. 6D).

Apoptosis

To assay for Apoptosis, Daudi cells were seeded at $1 \times 10^5$ cells per well in 24-well plates (0.5 ml culture medium per well) and incubated with 0 (No Ab control) and 0.1 μg/ml antibody for 30 min. Then 5 μg/ml goat anti-human IgG F(ab)'2 fragments was added to the cross-linking group cells. Cells were incubated for 24 hours, harvested and washed once with ice-cold PBS. 1× annexinV binding buffer and 100 g/ml working solution of PI were prepared. The cells were resuspended in 1× annexinV binding buffer. The cell density was determined and the cells were diluted in 1× annexin-binding buffer to ~$1 \times 10^6$ cells/ml. About 5 μL of Alexa Fluor® 488 annexin V and 5 µL of 100 µg/mL PI working solution were added to each 100 µL of cell suspension. The cells were incubated at room temperature for 15 minutes. Then about 400 µL of 1× annexinV binding buffer was added, then mixed gently, and kept on ice. The stained cells were analyzed immediately by flow cytometry, and the fluorescence emissions at 530 nm and 575 nm were measured using 488 nm excitation.

Figure 7:
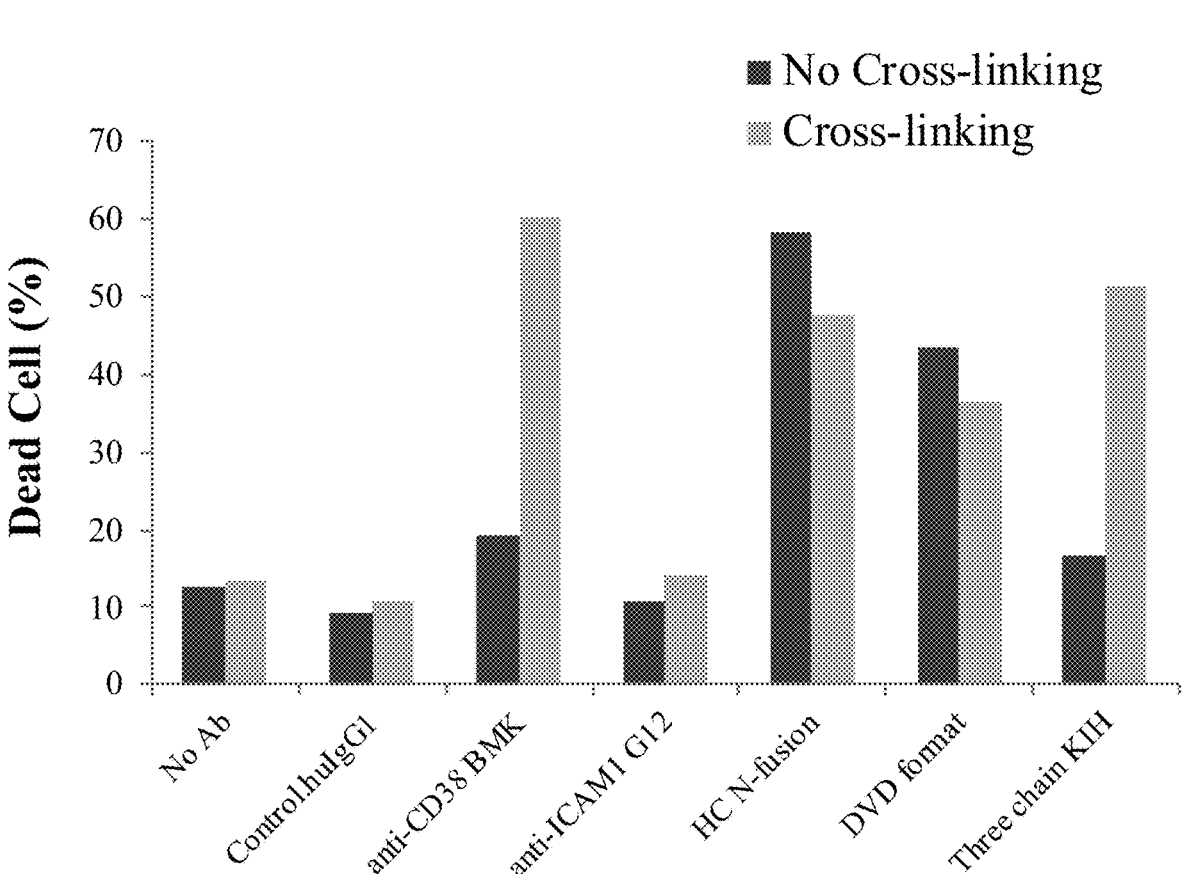
FIG. 7 illustrates induction of cell death and apoptosis in the presence (gray bar) or absence (black bar) of crosslinker by selected monoclonal and bispecific antibodies in Daudi cells.

Apoptosis by the monospecific anti-CD38 BMK antibody was only observed upon cross-linking. The tetravalent HC N-fusion and DVD format bispecific antibodies had cross-linking independent apoptosis, whereas the three chain KIH bispecific antibody, which has one binding site for each target antigen, had cross-linking dependent apoptosis activity, like the monospecific anti-CD38 antibody (FIG. 7).

Natural Killer Fratricide

Natural killer (NK) fratricide activity was assayed on fresh human whole blood from an individual donor. The blood was diluted by the same volume of sterile PBS and mix sufficiently by gentle shake. 15 mL Ficoll-Paque medium was transferred into a new 50 ml centrifuge tube and then the diluted blood sample was added onto the surface of the Ficoll medium. The tube was centrifuged at 400 g for 30 min at 20° C. Then the layer of mononuclear cells was transferred into another new sterile centrifuge tube. The PBMC cells or NK92/CD16a cells were resuspended to $4 \times 10^6$ cells/ml in blocking buffer. Serial diluted antibodies were prepared in blocking buffer. 50 µL cells were dispensed into the plate and 50 µl antibody solution was added to each well. The plates were incubated at 4° C. for 130 min. The plates were washed twice with 200 µL buffer per well. The cells were resuspended with 100 µl/well detection antibody solution and the plates were incubated at 4° C. for 1 hr. The plates were washed with 200 µL buffer/well twice. The cells were resuspended in 200 µL buffer and analyzed on a BD FACSVerse™

Figure 8A:
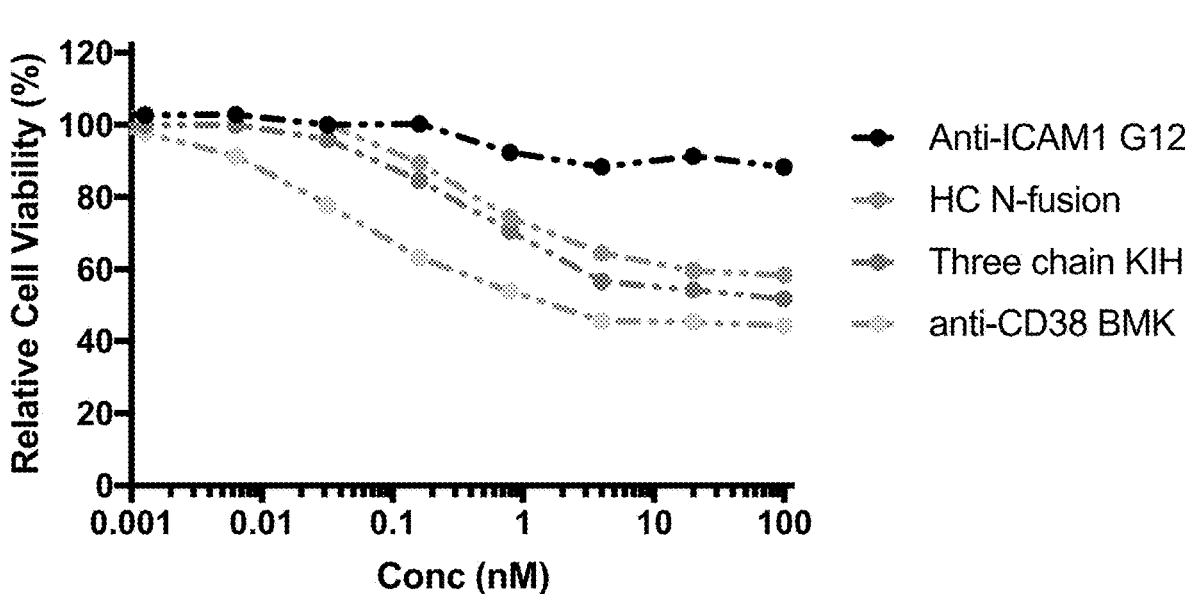
FIG. 8A-FIG. 8B show antibody induced cell death of NK92/CD16a cells (FIG. 8A) and the NK cells in fresh PBMCs (FIG. 8B). The HC N-fusion and three chain KIH antibodies showed reduced NK killing compared to the anti-CD38 BMK clone (or reference antibody daratumumab).
Figure 8B:
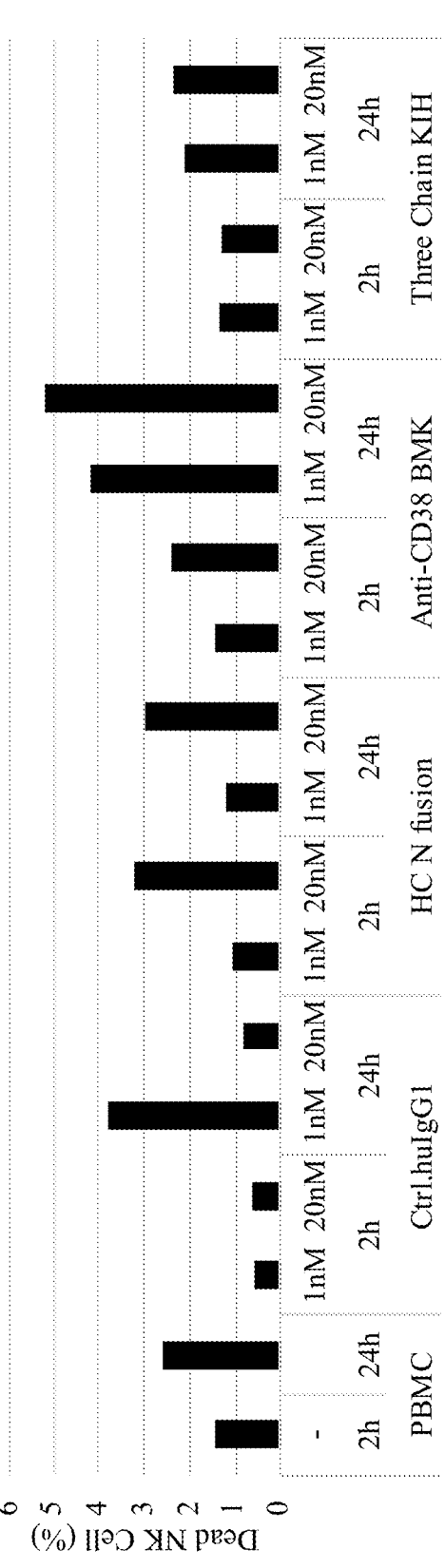

When NK fratricide was assayed with NK92 target cells, the anti-ICAM1 G12 had minimal effects, whereas the CD38 BMK antibody showed potent killing within 2 hours (FIG. 8A). The HC N-fusion and three chain KIH bispecific anti-CD38/ICAM1 antibodies killed fewer NK92 cells than the monospecific anti-CD38 BMK (FIG. 8A). Similarly, the three chain KIH bispecific antibody killed fewer NK cells during a 24-hour treatment of fresh PBMCs than the monospecific anti-CD38 antibody (FIG. 8B).

Example 3: Antibody Discovery

Recombinant Expression and Purification of CD38 and ICAM1 Antigens

The DNA sequences of human CD38 ECD (SEQ ID NO: 367), human ICAM1 ECD (SEQ ID NO: 370), human ICAM1 D2D5 (SEQ ID NO: 371), human ICAM1 D4D5 (SEQ ID NO: 372), and rhesus ICAM1 D2D5 (SEQ ID NO: 375) were cloned into the pFuse_hIgG1_Fc2 vector (InvivoGen cat #pfuse-hglfc2) to generate Fc fusion constructs and transfected in HEK293 cells. The culture was centrifuged at 2000 rpm, 4° C. for 10 min, and the supernatant were collected. Protein A resin was pre-equilibrated with equilibration buffer (25 mM Tris, 300 mM NaCl, 5% glycerol, 1 mM TCEP, pH 8.2), then incubated with the supernatant pre-equilibrated at 4° C. for 2.0 hrs on a rotator. Then the resin was filled to a column and washed with equilibration buffer until no signal was observed by G-250. The target protein was eluted by 0.1M glycine, pH 3.5 for 5 column volumes (CV). The eluate was neutralized with 1M Tris, pH 8.0. The eluate was dialyzed against equilibration buffer, then concentrated for Superdex™ 200 column (10/300GL 1CV=24 ml, GE company). The Superdex™ 200 column was pre-equilibrated with equilibration buffer, a small aliquot of the samples was loaded onto the Superdex™ 200 column for aggregation analysis. The rest protein in equilibration buffer was dialyzed against the storage buffer (137 mM NaCl, 2.7 mM KCl, 10 mM $Na_2HPO_4$, 1.76 mM $KH_2PO_4$, 6% Sucrose, pH 7.4), and was concentrated by ultra-filtration tube at the molecular cutoff 30 KDa, then snap frozen with liquid $N_2$ and stored at −80° C.

The human CD38 ECD (SEQ ID NO: 368) and cynomolgus CD38 ECD (SEQ ID NO: 369) and human ICAM1 ECD (SEQ ID NO: 373) and rhesus ICAM1 ECD (SEQ ID NO: 374) were cloned into pCDNA3.1 vector and transfected in Expi293 cells. Each construct contained an AviTag for direct biotinylation. The cultures were centrifuged at 2000 rpm, 4° C. for 10 min, and the supernatants were collected for loading onto Ni-NTA column. The Ni-NTA resin was pre-equilibrated with equilibration buffer (137 mM NaCl, 2.7 mM KCl, 10 mM $Na_2HPO_4$, 2 mM $KH_2PO_4$, pH 7.4), then incubated with the supernatant at 4° C. for 2 hrs on a rotator; the resin was filled to a column and washed with washing buffer (137 mM NaCl, 2.7 mM KCl, 10 mM $Na_2HPO_4$, 2 mM $KH_2PO_4$, pH 7.4, 20 mM imidazole) until no signal was observed by G-250. The target protein was eluted by elution buffer (137 mM NaCl, 2.7 mM KCl, 10 mM $Na_2HPO_4$, 2 mM $KH_2PO_4$, pH 7.4, 250 mM imidazole) for 5CV. The eluate was dialyzed against equilibration buffer, then cleaved by TEV protease at the ratio of TEV:protein=1:10 at 4° C. overnight. The following reagents (35 µL ATP (100 mM stock); 100 µL Biotin (5 mM stock); 50 µL His-BirA enzyme (stock at ~2.3 mg/ml) were then added for every 1 mg protein of interest, and $MgCl_2$ to 7.5 mM) to the target protein solution for biotinylation at 18° C. for 4 hrs. The sample was loaded onto a $2^{nd}$ Ni-NTA column which was pre-equilibrated with equilibration buffer, and eluted with equilibration buffer, washing buffer and elution buffer orderly until no signal was observed by G-250. The target protein was eluted in equilibration buffer, the eluate was dialyzed against equilibration buffer (to remove biotin, ATP, MgCl2), then concentrated, aliquoted a small sample for Superdex™ 200 column (10/300GL 1CV=24 mL, GE company) for aggregation analysis. The remaining protein was concentrated by ultra-filtration tube at the molecular cutoff 30 KDa, then aliquoted and snap frozen with liquid $N_2$ and stored at −80° C. Biotinylation analysis was performed by mixing 10 µg (1 µl) avidin and 4 µg biotinylated protein, bring total volume to 20 µL with PBS Buffer, and incubated for 10 minutes at room temperature. A 5 µL non-reducing 5×SDS-PAGE loading buffer was added without heating or boiling the sample. 25 µL of the sample were loaded on 12% tris-glycine SDS-PAGE gel for analysis.

TABLE 18 illustrates the sequences of the antigens generated in this example.
The underlined regions denote linker sequences.

| ANTIGEN NAME | SEQUENCE | SEQ ID NO: |
|---|---|---|
| Fc-human CD38 ECD | DKTHTCPPCPAPELLGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDG SFFLYSKLTVDKSRWQQGNVFSCSVMHEALHNHYTQKSLSLSPGA RTGGGGSGGGGSVPRWRQQWSGPGTTKRFPETVLARCVKYTEIHP EMRHVDCQSVWDAFKGAFISKHPCNITEEDYQPLMKLGTQTVPCN KILLWSRIKDLAHQFTQVQRDMFTLEDTLLGYLADDLTWCGEFNT SKINYQSCPDWRKDCSNNPVSVFWKTVSRRFAEAACDVVHVMLN GSRSKIFDKNSTFGSVEVHNLQPEKVQTLEAWVIHGGREDSRDLC QDPTIKELESIISKRNIQFSCKNIYRPDKFLQCVKNPEDSSCTSEI | 367 |
| Avi-human CD38 ECD | SGLNDIFEAQKIEWHEVPRWRQQWSGPGTTKRFPETVLARCVKYT EIHPEMRHVDCQSVWDAFKGAFISKHPCNITEEDYQPLMKLGTQT VPCNKILLWSRIKDLAHQFTQVQRDMFTLEDTLLGYLADDLTWCG EFNTSKINYQSCPDWRKDCSNNPVSVFWKTVSRRFAEAACDVVH VMLNGSRSKIFDKNSTFGSVEVHNLQPEKVQTLEAWVIHGGREDS RDLCQDPTIKELESIISKRNIQFSCKNIYRPDKFLQCVKNPEDSSCTS EI | 368 |
| Avi-Cyno CD38 ECD | SGLNDIFEAQKIEWHELPRWRQQWSGSGTTSRFPETVLARCVKYT EVHPEMRHVDCQSVWDAFKGAFISKYPCNITEEDYQPLVKLGTQT VPCNKTLLWSRIKDLAHQFTQVQRDMFTLEDMLLGYLADDLTWC GEFNTFEINYQSCPDWRKDCSNNPVSVFWKTVSRRFAETACGVVH VMLNGSRSKIFDKNSTFGSVEVHNLQPEKVQALEAWVIHGGREDS RDLCQDPTIKELESIISKRNIRFFCKNIYRPDKFLQCVKNPEDSSCLS GI | 369 |
| Human ICAM-1 Full Length ECD-Fc | QTSVSPSKVILPRGGSVLVTCSTSCDQPKLLGIETPLPKKELLLPGN NRKVYELSNVQEDSQPMCYSNCPDGQSTAKTFLTVYWTPERVEL APLPSWQPVGKNLTLRCQVEGGAPRANLTVVLLRGEKELKREPAV GEPAEVTITVLVRRDHHGANFSCRTELDLRPQGLELFENTSAPYQL QTFVLPATPPQLVSPRVLEVDTQGTVVCSLDGLFPVSEAQVHLALG DQRLNPTVTYGNDSFSAKASVSVTAEDEGTQRLTCAVILGNQSQE TLQTVTIYSFPAPNVILTKPEVSEGTEVTVKCEAHPRAKVTLNGVP AQPLGPRAQLLLKATPEDNGRSFSCSATLEVAGQLIHKNQTRELRV LYGPRLDERDCPGNWTWPENSQQTPMCQAWGNPLPELKCLKDGT FPLPIGESVTVTRDLEGTYLCRARSTQGEVTRKVTVNVLSPRYEGG GGGSGGGGSDKTHTCPPCPAPELLGGPSVFLFPPKPKDTLMISRTPE VTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSREEMTKNQVSLTCLVKGFYPSDIAVEWESNGQPENNY KTTPPVLDSDGSFFLYSKLTVDKSRWQQGNVFSCSVMHEALHNHY TQKSLSLSPGK | 370 |
| Human ICAM1 D2D5-Fc | YWTPERVELAPLPSWQPVGKNLTLRCQVEGGAPRANLTVVLLRG EKELKREPAVGEPAEVTTTVLVRRDHHGANFSCRTELDLRPQGLE LFENTSAPYQLQTFVLPATPPQLVSPRVLEVDTQGTVVCSLDGLFP VSEAQVHLALGDQRLNPTVTYGNDSFSAKASVSVTAEDEGTQRLT CAVILGNQSQETLQTVTIYSFPAPNVILTKPEVSEGTEVTVKCEAHP RAKVTLNGVPAQPLGPRAQLLLKATPEDNGRSFSCSATLEVAGQLI HKNQTRELRVLYGPRLDERDCPGNWTWPENSQQTPMCQAWGNP LPELKCLKDGTFPLPIGESVTVTRDLEGTYLCRARSTQGEVTRKVT VNVLSPRYEGGGGGSGGGGSDKTHTCPPCPAPELLGGPSVFLFPPK PKDTLMISRTPEVTCVVVDVSHEDPEVKFNWYVDGVEVHNAKTK PREEQYNSTYRVVSVLTVLHQDWLNGKEYKCKVSNKALPAPIEKT ISKAKGQPREPQVYTLPPSREEMTKNQVSLTCLVKGFYPSDIAVEW ESNGQPENNYKTTPPVLDSDGSFFLYSKLTVDKSRWQQGNVFSCS VMHEALHNHYTQKSLSLSPGK | 371 |
| Human ICAM1 D4D5-Fc | FPAPNVILTKPEVSEGTEVTVKCEAHPRAKVTLNGVPAQPLGPRAQ LLLKATPEDNGRSFSCSATLEVAGQLIHKNQTRELRVLYGPRLDER DCPGNWTWPENSQQTPMCQAWGNPLPELKCLKDGTFPLPIGESVT VTRDLEGTYLCRARSTQGEVTRKVTVNVLSPRYEGGGGGSGGGG SDKTHTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPSRE EMTKNQVSLTCLVKGFYPSDIAVEWESNGQPENNYKTTPPVLDSD GSFFLYSKLTVDKSRWQQGNVFSCSVMHEALHNHYTQKSLSLSPG K | 372 |
| Human ICAM1 full length ECD-avi | QTSVSPSKVILPRGGSVLVTCSTSCDQPKLLGIETPLPKKELLLPGN NRKVYELSNVQEDSQPMCYSNCPDGQSTAKTFLTVYWTPERVEL APLPSWQPVGKNLTLRCQVEGGAPRANLTVVLLRGEKELKREPAV | 373 |

TABLE 18-continued illustrates the sequences of the antigens generated in this example.
The underlined regions denote linker sequences.

| ANTIGEN NAME | SEQUENCE | SEQ ID NO: |
|---|---|---|
| | GEPAEVTTTVLVRRDHHGANFSCRTELDLRPQGLELFENTSAPYQL QTFVLPATPPQLVSPRVLEVDTQGTVVCSLDGLFPVSEAQVHLALG DQRLNPTVTYGNDSFSAKASVSVTAEDEGTQRLTCAVILGNQSQE TLQTVTIYSFPAPNVILTKPEVSEGTEVTVKCEAHPRAKVTLNGVP AQPLGPRAQLLLKATPEDNGRSFSCSATLEVAGQLIHKNQTRELRV LYGPRLDERDCPGNWTWPENSQQTPMCQAWGNPLPELKCLKDGT FPLPIGESVTVTRDLEGTYLCRARSTQGEVTRKVTVNVLSPRYEGG SGGSGLNDIFEAQKIEWHEENLYFQ | |
| Rhesus ICAM1 full length ECD-avi | QTSVFPPEVILPRGGSVKVNCSASCDQPISLGMETPLPKKEILPGGN NWKMYELSNVQEDSQPMCYSNCPDGQSSAKTLLTVYWTPERVEL APLPPWQPVGKNLTLRCQVEGGAPRANLTVMLLRGEKELSRQSA VGEPAEVTTTVPVGRDDHGANFSCRTELDLRPYVLKLFENTSAPH QLQTFDLPATPPQLVSPQVLEVDTQGTVVCSLDGLFPVSEAQVSLA LGDQKLNPTITYGNNSLSAKASVKVTAEEEGTQQLLCGVMLGNQT QETRQTVTIYSFPAPNVNLTKPEVSEGTEVIVECEAHPRAKVMLNG VPAQPPGPRAQFLLKATPEDNGRSFSCSATLEVAGQLVHKNQTRE LRVLYGPRLDEKDCPGNWTWPENSQQTPMCQAWGNPLPQLKCLK DGTFPLPIGQSVTVTRDLEGTYLCQARSTRGEVTREVTVNVLSPRY EGGSGGSGLNDIFEAQKIEWHEENLYFQ | 374 |
| Rhesus ICAM1 (D2D5)-Fc | YWTPERVELAPLPPWQPVGKNLTLRCQVEGGAPRANLTVMLLRG EKELSRQSAVGEPAEVTTTVPVGRDDHGANFSCRTELDLRPYVLK LFENTSAPHQLQTFDLPATPPQLVSPQVLEVDTQGTVVCSLDGLFP VSEAQVSLALGDQKLNPTITYGNNSLSAKASVKVTAEEEGTQQLL CGVMLGNQTQETRQTVTIYSFPAPNVNLTKPEVSEGTEVIVECEAH PRAKVMLNGVPAQPPGPRAQFLLKATPEDNGRSFSCSATLEVAGQ LVHKNQTRELRVLYGPRLDEKDCPGNWTWPENSQQTPMCQAWG NPLPQLKCLKDGTFPLPIGQSVTVTRDLEGTYLCQARSTRGEVTRE VTVNVLSPRYEGGGGGSGGGGSDKTHTCPPCPAPELLGGPSVFLFP PKPKDTLMISRTPEVTCVVVDVSHEDPEVKFNWYVDGVEVHNAK TKPREEQYNSTYRVVSVLTVLHQDWLNGKEYKCKVSNKALPAPIE KTISKAKGQPREPQVYTLPPSREEMTKNQVSLTCLVKGFYPSDIAV EWESNGQPENNYKTTPPVLDSDGSFFLYSKLTVDKSRWQQGNVFS CSVMHEALHNHYTQKSLSLSPGK | 375 |

Antibody Discovery from Phage and Yeast Libraries

Phage or yeast libraries with a fixed light chain from an antd-HER2 antibody (SEQ ID NO: 130) were used for screening. For the phage antibody display library, the heavy chain was constructed from a pool of naïve human VH repertoire. For the yeast antibody display library, both synthetic and pooled naïve VH repertoires were used, resulting in synthetic and naïve libraries, respectively, that bear the common anti-HER2 light chain. For selection of phage libraries, biotin-tagged soluble recombinant antigens (human CD38 ECD and ICAM1 ECD) were incubated with phage in 1 mL PBS containing 1% bovine serum albumin at room temperature for one hour, followed by affinity capture by streptavidin-coated beads, washed, eluted, neutralized and used to infect log phase TG1 for propagation. Polyclonal phage from the first round of selection were prepared and incubated with recombinant biotin-tagged cynomolgus/rhesus antigens with bound phage enriched following affinity capture by streptavidin beads. Polyclonal phage from the second round of selection were harvested from bacterial culture supernatant and purified, and scFv gene fragments were amplified by PCR and used to make a transfer library in yeast using the gap repair method. The phage to yeast transfer library was further selected by FACS. For selection of the yeast display libraries (synthetic VH, naïve VH, and phage to yeast transfer libraries), the libraries were first sorted against Fc fusion antigens (human CD38 ECD Fc and human ICAM1 ECD Fc), followed by biotinylated human antigens and biotinylated cynomolgus/rhesus antigens. Antigen concentrations were reduced with increasing rounds to increase selection stringency. Positive binders were screened by flow cytometry, sequenced and re-transformed into yeast for secondary verification. Verified binders were converted into recombinant human IgG1 for affinity measurement against human and cynomolgus/rhesus antigens by surface plasmon resonance or bio-layer interferometry. For affinity maturation, two types of mutagenesis libraries were constructed in yeast by error-prone PCR and CDR randomization. Starting at low nM and decreasing through rounds to 50-100 pM, recombinant antigens were used for selection by FACS to identify affinity improved scFvs that bind to both human and cynomolgus/rhesus antigens.

Antibody Discovery by Rabbit Immunization

Rabbits were immunized four times with 108 CHO-G10 cells (a stable clone expressing ICAM1) or Daudi cells. Serum titers were monitored by ELISA using recombinant human and cynomolgus ICAM1 and CD38 proteins. Target recognition was further monitored using flow cytometry. For each target, a rabbit with a high ELISA titer and a strong flow cytometry signal was boosted via IV using 400 µg of recombinant human ICAM1 or CD38, 4 days ahead of splenectomy. Fresh splenocytes were isolated from spleen. For each target, 1.2E8 splenocytes were cultured overnight in customized B cell medium before sorting. Splenocytes were processed using the SMab™ platform to enrich antigen-recognizing B cells. FACS-sorted B cells were cultured at 1 cell/well in a 96-well plate for 10-14 days.

Clones positive for antigen recognition were identified using a direct antigen ELISA. Cynomolgus homologs of ICAM1 and CD38 were used to identify positive clones able to bind both human and non-human primate homologs. To identify monoclonal antibodies suitable for FACS analysis, initial positive clones from the ICAM1 and CD38 projects were screened against CHO-G10 (ICAM1) and a CD38 stable cell line (CHO-F10) respectively. Untransfected CHO Tables 1-12 present the SEQ ID NOs of the chimeric anti-CD38 and anti-ICAM1 monoclonal antibodies discovered by these methods, including their heavy and light chains, variable domains, and complementarity determining regions (CDRs). Table 19 presents an alignment of the CDR sequences of various anti-ICAMG rabbit antibodies.

TABLE 19

Alignment of CDRs from exemplary anti-ICAM1 clones.
A vertical line denotes a conserved residue at the specified position.

| ICAM1 Clones | CDR-H1 | SEQ ID NO: | CDR-H2 | SEQ ID NO: | CDR-H3 | SEQ ID NO: |
|---|---|---|---|---|---|---|
| Consensus HC CDR | GFSLSZZAMG | 412 | GIIGSSZZTYYAZWAKG | 413 | VRDPYDSZZZZYRL | 414 |
| 8B12 | GFSLSTHAMG | 232 | GIIGSSDRTYYASWAKG | 229 | VRDPYDSFDDGYRL | 233 |
| 16E4 | \|\|\|\|\|S\|\|\|\| | 228 | \|\|\|\|\|\|GS\|\|\|\|\|\|\|\|\| | 220 | \|\|\|\|\|\|\|\|G\|A\|\|\| | 231 |
| 11F2 | \|\|\|\|\|S\|\|\|\| | 228 | \|\|\|\|\|\|\|\|\|\|\|\|\|\|\|\|\| | 229 | \|\|\|\|\|\|\|Y\|\|\|\|\|\| | 230 |
| 2E3 | \|\|\|\|\|SY\|\|\| | 214 | \|\|\|\|\|\|GS\|\|\|\|\|\|\|\|\| | 220 | \|\|\|\|\|\|\|\|G\|\|\|\| | 221 |
| 6G8 | \|\|\|\|\|SY\|\|\| | 214 | \|\|\|\|\|\|GS\|\|\|\|T\|\|\|\| | 215 | \|\|\|\|\|\|\|Y\|AA\|\|\| | 216 |

| ICAM1 Clones | CDR-L1 | SEQ ID NO: | CDR-L2 | SEQ ID NO: | CDR-L3 | SEQ ID NO: |
|---|---|---|---|---|---|---|
| Consensus LC CDR | QASZZIYZYZZ | 415 | DASKZAS | 416 | QQAYSSZZZDNZ | 417 |
| 8B12 | QASQSIYSYLS | 259 | DASKVAS | 273 | QQAYSSSNVDNA | 266 |
| 16E4 | \|\|\|\|\|\|\|\|\|C\| | 272 | \|\|\|\|L\|\| | 260 | \|\|\|\|\|\|\|\|\|\|\|\| | 266 |
| 11F2 | \|\|\|\|\|\|\|R\|\|\| | 270 | \|\|\|\|L\|\| | 260 | \|\|\|\|\|\|GSI\|\|\| | 430 |
| 2E3 | \|\|\|EN\|\|R\|\|L | 265 | \|\|\|\|L\|\| | 260 | \|\|\|\|\|\|\|\|\|\|\|\| | 266 |
| 6G8 | \|\|\|\|\|\|\|\|\|\|\| | 259 | \|\|\|\|L\|\| | 260 | \|\|\|\|\|\|\|\|\|\|\|V | 261 | cells were used as a negative control. FACS-positive mAb clones were further confirmed using linear expression module (LEM) supernatants from HEK293F cell transiently expressing recombinant IgG genes recovered from the initial positive clones. Additional flow cytometry analysis was performed against HEK293T cells transiently expressing cynomolgus CD38 to validate cross-reactivity of the human CD38 positive clones to its cynomolgus homolog.

Stable cell lines were maintained using their designated selection medium with selection antibiotics to stimulate the expression of target transgenes. CHO-G10 cells were grown in F12 medium supplemented with 1000 FBS and 5 ug/ml puromycin. CHO-F10 cells were grown in F12 medium supplemented with 1000 FBS and 5 ug/ml puromycin and 2 mg/ml neomycin.

Chimeric antibodies with rabbit variable domains and human constant domains were generated by fusing the VH domain of the anti-CD38 and anti-ICAM1 monoclonal antibodies to a human IgG1 constant region and the VL domain of the anti-CD38 and anti-ICAM1 monoclonal antibodies to a human Kappa constant region. Because the human Kappa constant region does not have a cysteine corresponding to the cysteine in the rabbit Kappa constant region that forms an interdomain disulfide bond with the rabbit VL (Cys80-Cys171), Cys80 in the VL region was replaced with Ser to eliminate the free cysteine.

Example 4: Binding and Functional Evaluation of the Anti-CD38 and Anti-ICAM1 Antibodies Discovered in this Study ELISA Binding Assay The plate was coated overnight at 4° C. with 1 μg/ml recombinant CD38 or ICAM1. After washing 3 times, the plate was blocked with 300 μl 1% BSA in PBST at 37° C. for 1 hour. Serially diluted antibodies were added and incubated at 37° C. for 1 hour. The plate was then washed 4 times with PBST and incubated with 1:5000 diluted $2_{nd}$ antibody (Sigma, Cat #A0293) at 37° C. for 1 hour. The plate was washed again 4 times with PBST, incubated with TMB substrate for 15 min at room temperature, terminated with 1N HCl, and then read at 450 nM.

Figure 9A:
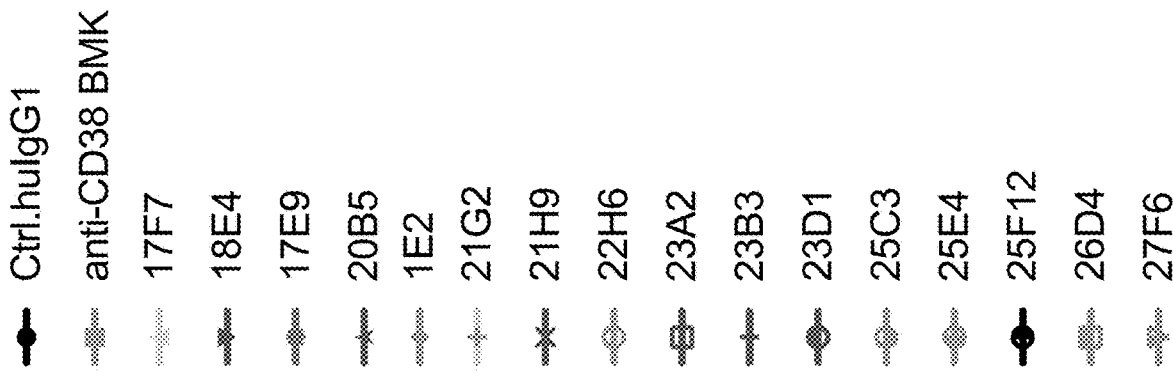
FIG. 9A-FIG. 9B show ELISA binding of exemplary anti-CD38 rabbit human chimeric clones to recombinant human CD38 ECD (FIG. 9A) and cynomolgus CD38 ECD (FIG. 9B).
Figure 9A:
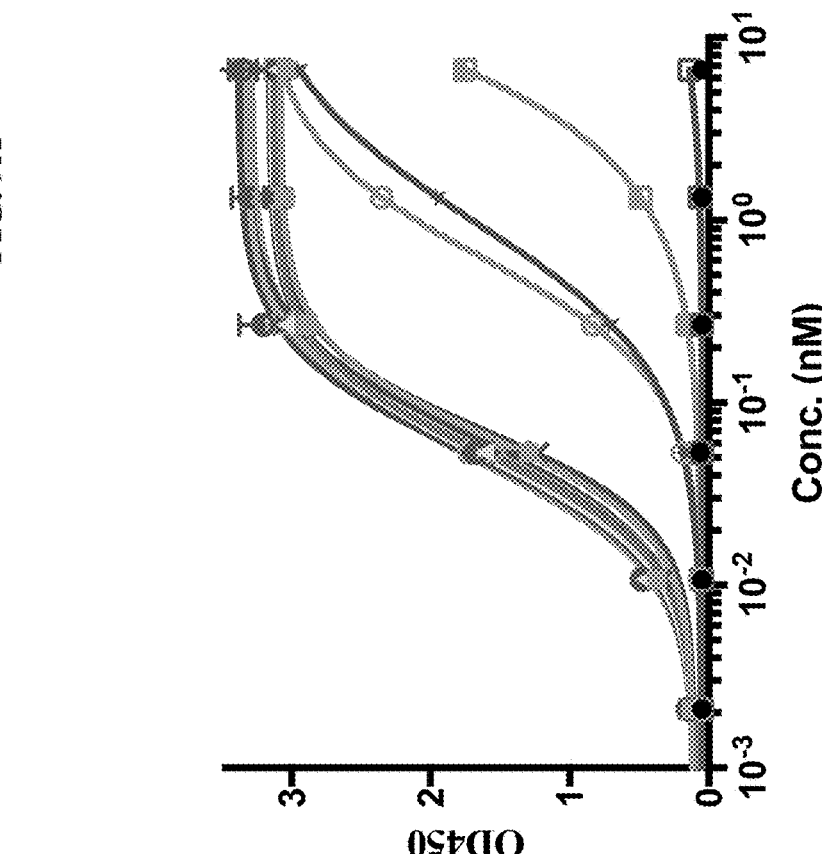
Figure 9B:
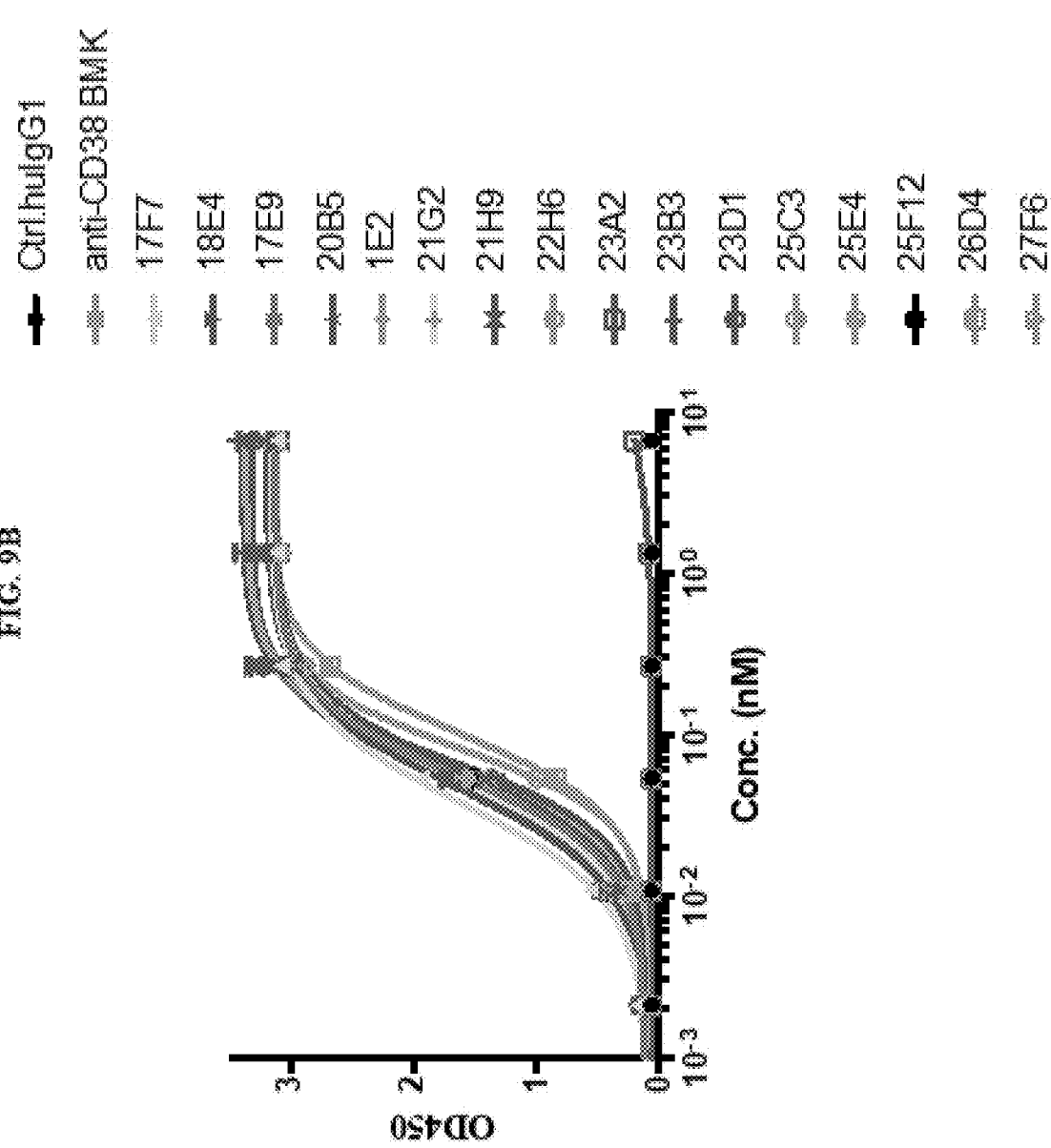
Figure 10A:
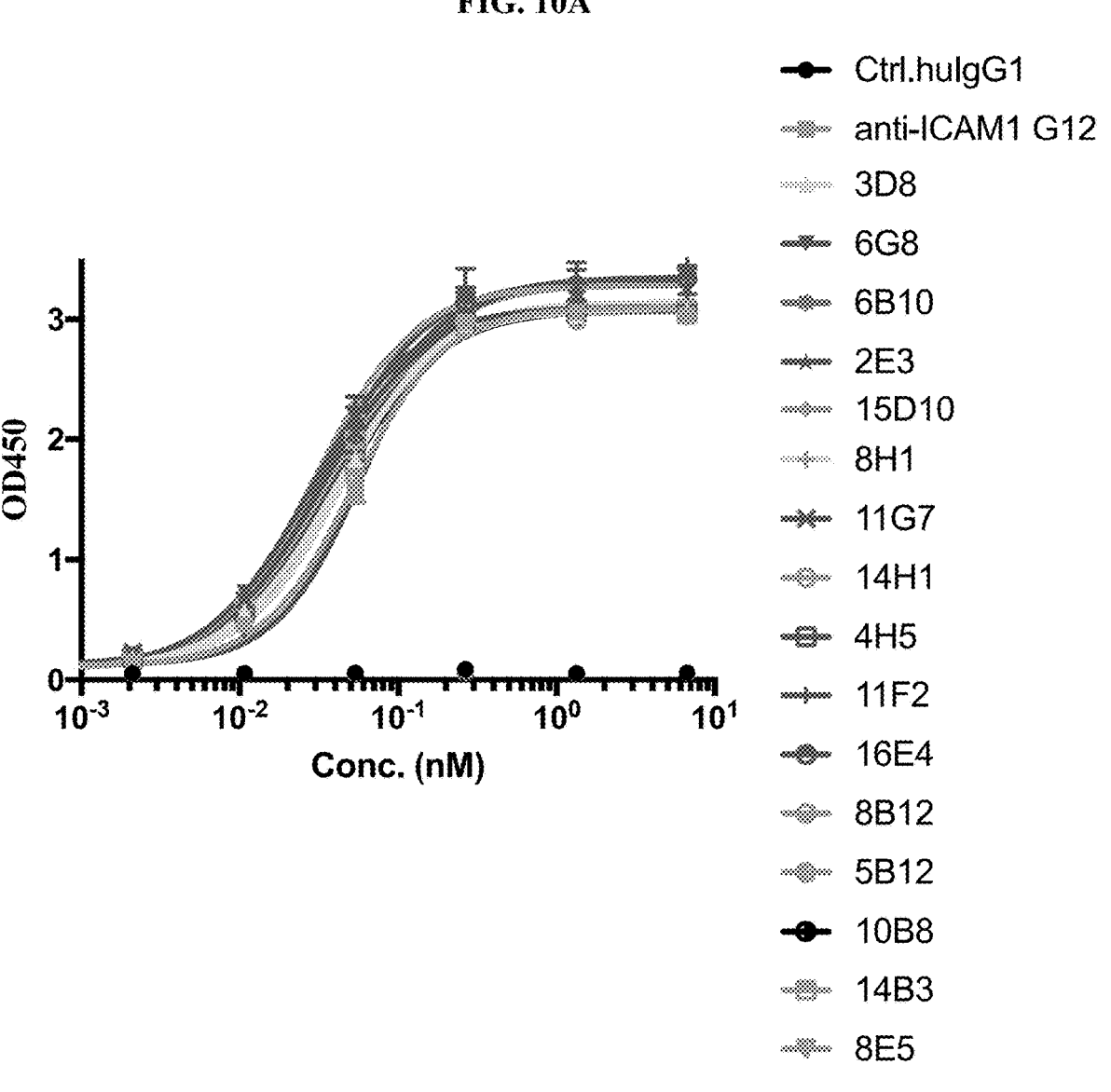
FIG. 10A-FIG. 10B show ELISA binding of exemplary anti-ICAM1 rabbit human chimeric clones to the recombinant human ICAM1 ECD (FIG. 10A) and rhesus ICAM1 ECD (FIG. 10B).
Figure 10B:
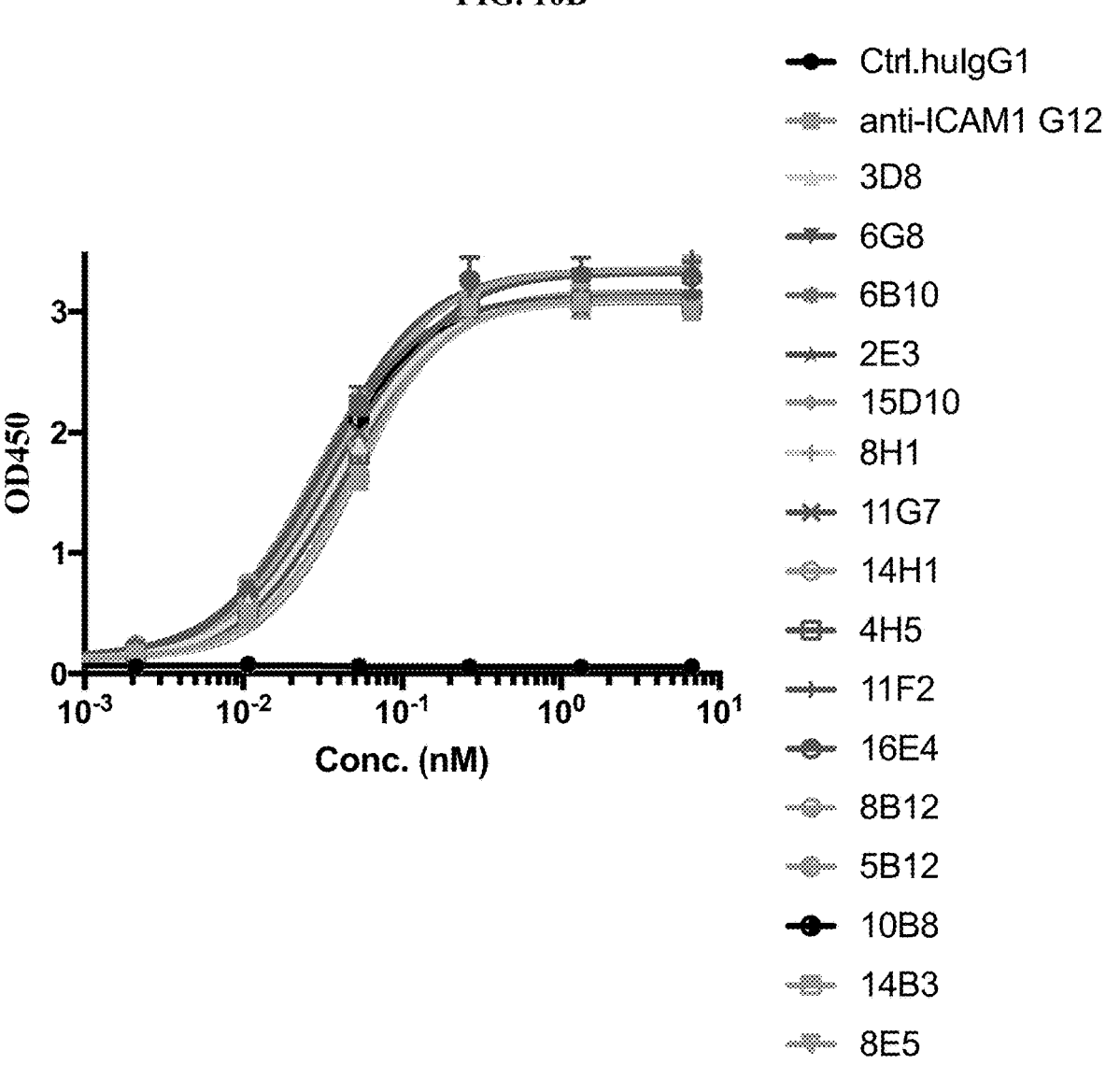

FIG. 9A and FIG. 9B show ELISA binding results for anti-CD38 rabbit human chimeric clones. FIG. 10A and FIG. 10B show ELISA binding results for anti-ICAM1 rabbit human chimeric clones.

Flow Cytometry Binding Assay

Harvested cells were centrifuged at 2000 rpm for 5 min and resuspended with 10-15 ml ice-cold culture medium. Cells were counted and then $3\times10^6$ cells were resuspended per mL of blocking buffer (PBS plus 2% FBS). 100 μl of the cell suspension was dispensed into each well of a 96-well plate and incubated at room temperature for 10-20 min. For Fc receptor expressing cells, 5 ul human Fc block (BD, Cat

: 564220) was added and incubated for 15 minutes. While incubating, purified antibodies were diluted to the desired dilution with blocking buffer. After a 10-20 minutes incubation, cells were centrifuged for 5 min at 2000 rmp in a refrigerated centrifuge. Blocking buffer was aspirated, and cells were resuspended in 100 µl/well diluted antibodies and incubated for 1 hour at 4° C. The cells were then washed 3 times with PBS plus 2% FBS. After the final wash, the cells were resuspended in 100 µl 1:500 diluted secondary antibody (Invitrogen, Cat #: A10631) and incubated for 1 hour at 4° C. in the dark. The cells were then washed 3 times with 200 µl PBS by centrifuging at 2000 rpm for 5 min. After the last wash, the cells were resuspended in 300 µl cold PBS and analyzed on a FACSVerse™ (BD Biosciences) flow cytometer.

Figure 11:
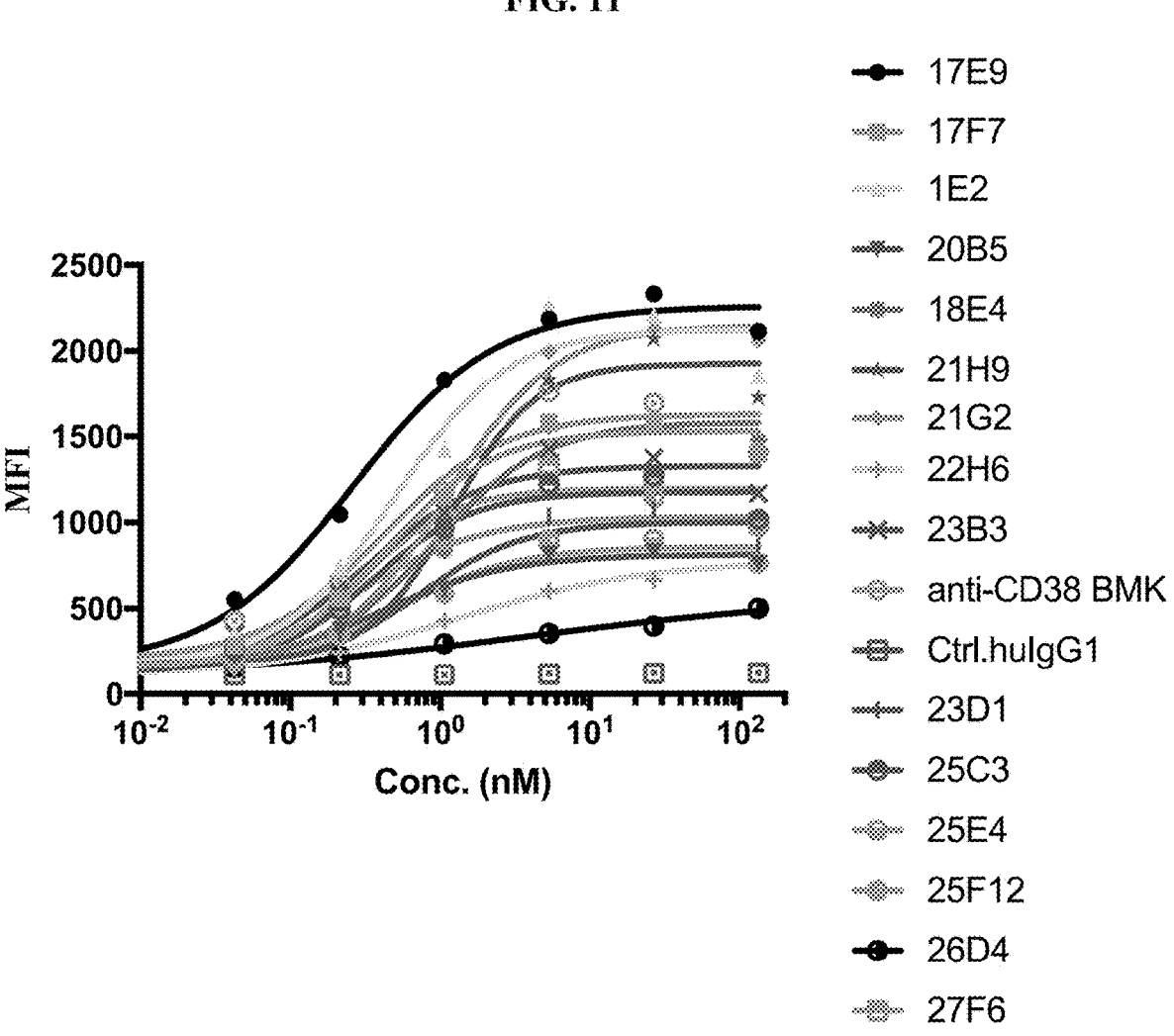
FIG. 11 shows binding of exemplary anti-CD38 rabbit human chimeric clones to Daudi cells as determined by flow cytometry.

Binding of the anti-CD38 antibodies discovered in this study to Daudi cells is shown in FIG. 11. The results are quantified in Table 20.

TABLE 20

Summary of flow cytometry binding of exemplary anti-CD38 rabbit-human chimeric antibodies to Daudi cells.

| Clone name | Max Binding MFI | EC50 (nM) |
|---|---|---|
| 17E9 | 2262 | 0.2631 |
| 17F7 | 1533 | 0.432 |
| 18E4 | 1585 | 0.9 |
| 1E2 | 2126 | 0.4973 |
| 20B5 | 815.5 | 0.3728 |
| 21G2 | 2147 | 1.131 |
| 21H9 | 1927 | 1.196 |
| 22H6 | 782 | 1.324 |
| 23B3 | 1330 | 0.3248 |
| anti-CD38 BMK | 1631 | 0.3997 |
| Ctrl.huIgG1 | N.D.* | N.D. |
| 23D1 | 1003 | 0.7043 |
| 25C3 | 1178 | 0.347 |
| 25E4 | 859 | 0.5034 |
| 25F12 | 1034 | 0.2631 |
| 26D4 | 576.6 | 4.06 |
| 27F6 | 1197 | 0.298 |

*N.D.: Not determined - binding too weak to quantify.

Figure 12:
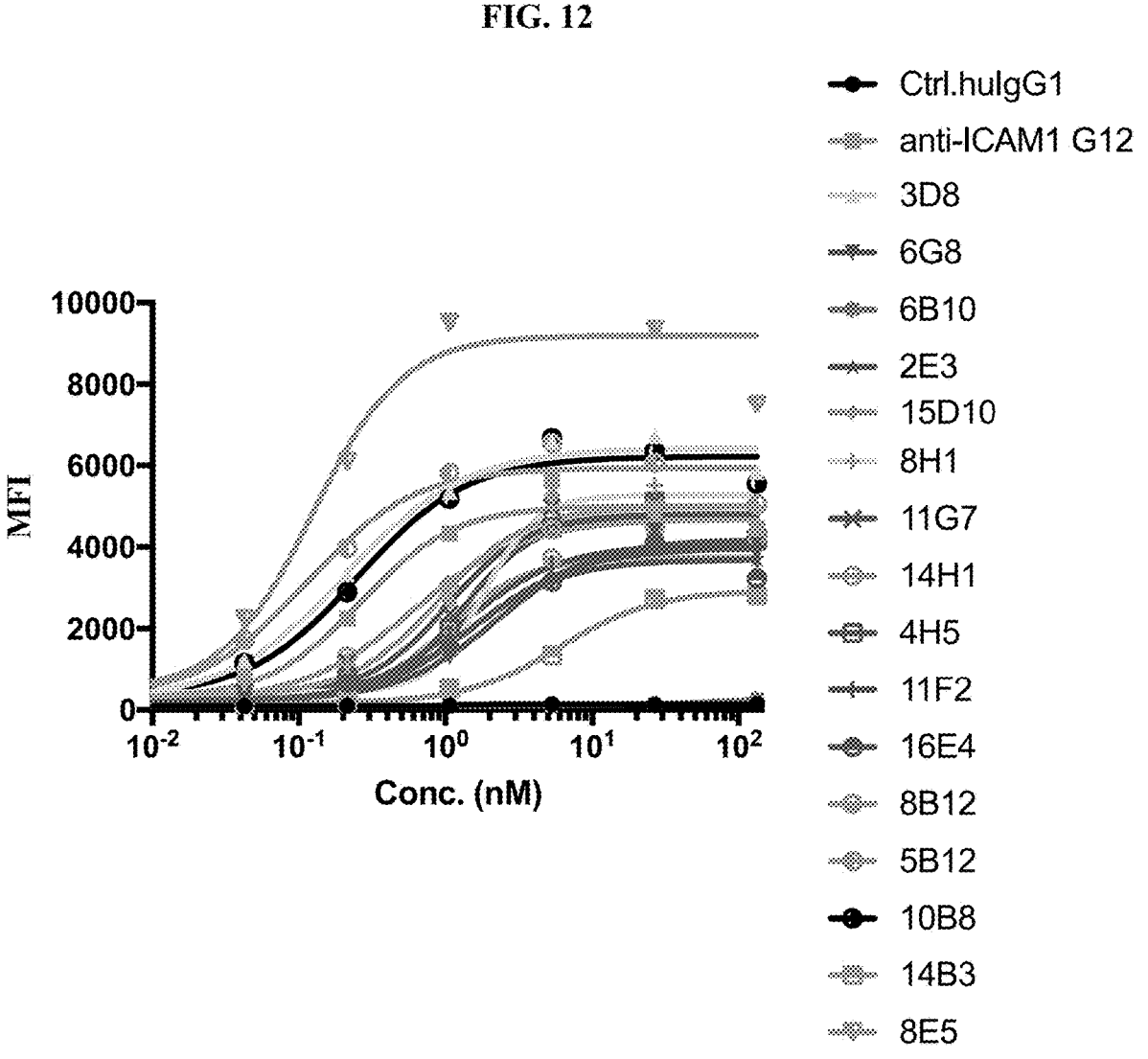
FIG. 12 shows binding of anti-ICAM1 rabbit human chimeric clones to DU145 cells as determined by flow cytometry.

Binding of the anti-ICAM1 antibodies discovered in this study to DU145 cells is shown in FIG. 12. The results are quantified in Table 21.

TABLE 21

Summary of flow cytometry binding of exemplary anti-ICAM1 rabbit-human chimeric antibodies to DU145 cells.

| Clone name | Max Binding MFI | EC 50 (nM) |
|---|---|---|
| Ctrl.huIgG1 | N.D. | N.D. |
| anti-ICAM1 G12 | 5011 | 0.26 |
| 6B10 | N.D. | N.D. |
| 3D8 | 6427 | 0.2085 |
| 6G8 | 4188 | 2.227 |
| 15D10 | 5000 | 0.879 |
| 2E3 | 3978 | 1.592 |
| 8H1 | 5270 | 1.818 |
| 11G7 | 4819 | 1.036 |
| 14H1 | 4692 | 0.5909 |
| 4H5 | 4716 | 1.309 |
| 11F2 | 4058 | 1.306 |
| 16E4 | 3695 | 1.448 |
| 8B12 | 3747 | 1.025 |
| 5B12 | 5942 | 0.1125 |
| 10B8 | 6220 | 0.2511 |
| 14B3 | 2943 | 6.006 |
| 8E5 | 9193 | 0.1244 |

Surface Plasmon Resonance Binding Assay

The binding kinetics of the anti-CD38 and anti-ICAM1 antibodies were evaluated on a Biacore 8K instrument (GE Healthcare). Biacore Series S CM5 sensor chips were immobilized with monoclonal mouse anti-human IgG (Fc) antibody (human antibody capture kit from GE Healthcare). Antibodies were captured on each flow cell. Serial 3-fold dilutions of each antigen were injected at a flow rate of 30 µl/min. Each sample was analyzed with 1 min association and 10 min dissociation at room temperature (25° C.). After each injection, the chip was regenerated using 3M $MgCl_2$. A 1:1 Langmuir model of simultaneous fitting of $k_{on}$ and $k_{off}$ was used for kinetics analysis. Tables 22-24 shows the binding kinetics for each antibody.

TABLE 22

Binding kinetics of anti-CD38 antibodies (including anti-CD38 antibodies discovered by screening of yeast and phase libraries) as determined by surface plasmon resonance, including reference antibodies, and an exemplary bispecific antibody

| | Human-CD38 | | | Cyno-CD38 | | |
|---|---|---|---|---|---|---|
| Antibody | ka (1/Ms) | kd (1/s) | $K_D$ (nM) | ka (1/Ms) | kd (1/s) | $K_D$ (nM) |
| Anti-CD38 BMK | 2.81E+05 | 4.83E−04 | 1.72 | NA | NA | NA |
| Anti-CD38 G1F4 | 5.15E+05 | 1.83E−02 | 35.53 | 2.07E+06 | 5.49E−02 | 26.52 |
| G1F4_G12scFv_KIH | 5.28E+05 | 3.38E−02 | 64.02 | 1.01E+07 | 1.42E−01 | 14.06 |
| 4618_1 | 4.94E+05 | 1.88E−03 | 3.81 | 1.71E+06 | 2.88E−03 | 1.68 |
| 4618_5 | 5.42E+05 | 1.21E−03 | 2.23 | 2.17E+06 | 3.21E−03 | 1.48 |
| 4618_12 | 4.30E+05 | 7.70E−04 | 1.79 | 1.53E+06 | 2.53E−03 | 1.65 |
| 4618_1_12 | 6.57E+05 | 2.73E−04 | 0.42 | 2.53E+06 | 1.57E−03 | 0.62 |
| 4618_5_12 | 3.54E+05 | 5.96E−04 | 1.68 | 1.26E+06 | 1.68E−03 | 1.33 |
| 4618_5F_12 | 4.49E+05 | 2.95E−04 | 0.66 | 1.74E+06 | 1.44E−03 | 0.83 |
| 32218_1 | 4.93E+05 | 1.78E−03 | 3.61 | 1.21E+06 | 4.96E−03 | 4.10 |
| 32218_2 | 6.75E+05 | 8.87E−03 | 13.14 | 2.10E+06 | 1.56E−02 | 7.43 |
| 32018_7 | 3.04E+05 | 1.16E−02 | 38.16 | 1.25E+06 | 1.55E−02 | 12.40 |

TABLE 23

Binding kinetics of chimeric anti-CD38 antibodies as determined by surface plasmon resonance, including a reference antibody

| Antibody | Human-CD38 | | | Cyno-CD38 | | |
|---|---|---|---|---|---|---|
| | ka (1/Ms) | kd (1/s) | $K_D$ (nM) | ka (1/Ms) | kd (1/s) | $K_D$ (nM) |
| Anti-CD38 BMK | 2.00E+05 | 2.73E−04 | 1.37 | NA | NA | NA |
| 17E9 | 9.23E+05 | 1.42E−04 | 0.15 | 2.64E+06 | 1.66E−04 | 0.06 |
| 17F7 | 5.00E+05 | 3.78E−03 | 7.56 | 1.65E+06 | 3.82E−03 | 2.32 |
| 18E4 | 3.03E+05 | 8.13E−05 | 0.27 | 5.63E+05 | 2.36E−04 | 0.42 |
| 1E2 | 2.40E+05 | 3.88E−04 | 1.62 | 1.82E+05 | 1.24E−02 | 68.13 |
| 20B5 | 3.46E+05 | 3.41E−02 | 98.55 | 5.88E+05 | 3.22E−02 | 54.76 |
| 21G2 | 1.67E+05 | 3.10E−05 | 0.19 | 2.53E+05 | 4.32E−04 | 1.71 |
| 21H9 | 1.66E+05 | 5.99E−07 | 0.004 | 1.84E+05 | 1.40E−04 | 0.76 |
| 22H6 | 3.21E+05 | 2.10E−02 | 65.42 | 5.64E+05 | 3.52E−02 | 62.41 |
| 23B3 | 9.70E+05 | 2.77E−08 | 2.9E−5 | 2.43E+06 | 9.46E−05 | 0.04 |
| 23D1 | 1.87E+05 | 1.25E−04 | 0.67 | 5.36E+05 | 2.94E−04 | 0.55 |
| 25C3 | 1.15E+06 | 3.48E−05 | 0.03 | 1.23E+06 | 1.87E−04 | 0.15 |
| 25E4 | 3.80E+05 | 2.59E−05 | 0.07 | 1.23E+06 | 1.75E−04 | 0.14 |
| 25F12 | 1.84E+06 | 2.24E−05 | 0.01 | 1.04E+06 | 1.85E−04 | 0.18 |
| 26D4 | 2.00E+05 | 1.02E−01 | 510.00 | 7.15E+05 | 3.13E−02 | 43.78 |
| 27F6 | 3.76E+05 | 1.17E−04 | 0.31 | 1.02E+06 | 2.90E−04 | 0.28 |

TABLE 24

Binding kinetics of chimeric anti-ICAM1 antibodies as determined by surface plasmon resonance, including a reference antibody

| Antibody | Human-ICAM1 | | | Rhesus-ICAM1 | | |
|---|---|---|---|---|---|---|
| | ka (1/Ms) | kd (1/s) | $K_D$ (nM) | ka (1/Ms) | kd (1/s) | $K_D$ (nM) |
| Anti-ICAM1 G12 | 2.72E+05 | 3.31E−03 | 12.2 | 1.27E+06 | 2.24E−02 | 17.70 |
| 3D8 | 5.40E+05 | 9.09E−03 | 16.80 | 2.01E+06 | 3.48E−02 | 17.30 |
| 6G8 | 3.14E+05 | 5.33E−04 | 1.70 | 1.47E+06 | 1.26E−03 | 0.85 |
| 15D10 | 8.55E+04 | 1.81E−04 | 2.12 | 2.36E+05 | 4.21E−04 | 1.79 |
| 2E3 | 2.27E+05 | 1.49E−04 | 0.65 | 3.30E+05 | 3.87E−04 | 1.17 |
| 8H1 | 1.11E+05 | 3.45E−04 | 3.10 | 4.27E+05 | 1.25E−03 | 2.92 |
| 11G7 | 1.03E+05 | 2.71E−04 | 2.65 | 1.46E+06 | 6.24E−04 | 4.28 |
| 14H1 | 1.46E+05 | 2.37E−04 | 1.62 | 1.93E+05 | 4.34E−04 | 2.25 |
| 4H5 | 7.56E+04 | 2.56E−04 | 3.39 | 1.38E+05 | 5.68E−04 | 4.11 |
| 11F2 | 4.56E+05 | 1.31E−04 | 0.29 | 9.14E+05 | 2.24E−04 | 0.25 |
| 16E4 | 2.37E+05 | 1.34E−04 | 0.57 | 5.17E+05 | 2.77E−04 | 0.54 |
| 8B12 | 4.42E+05 | 1.15E−04 | 0.26 | 7.46E+05 | 6.58E−04 | 0.88 |
| 5B12 | 2.13E+05 | 5.84E−04 | 2.74 | 2.66E+05 | 2.18E−03 | 8.20 |
| 10B8 | 2.06E+05 | 6.82E−04 | 3.32 | 2.96E+05 | 2.45E−03 | 8.27 |
| 14B3 | 9.48E+04 | 2.70E−04 | 2.85 | 1.86E+05 | 5.96E−04 | 3.20 |
| 8E5 | 1.48E+05 | 3.61E−03 | 24.40 | 2.68E+05 | 1.89E−03 | 7.06 |

Functional Activities

Figure 13:
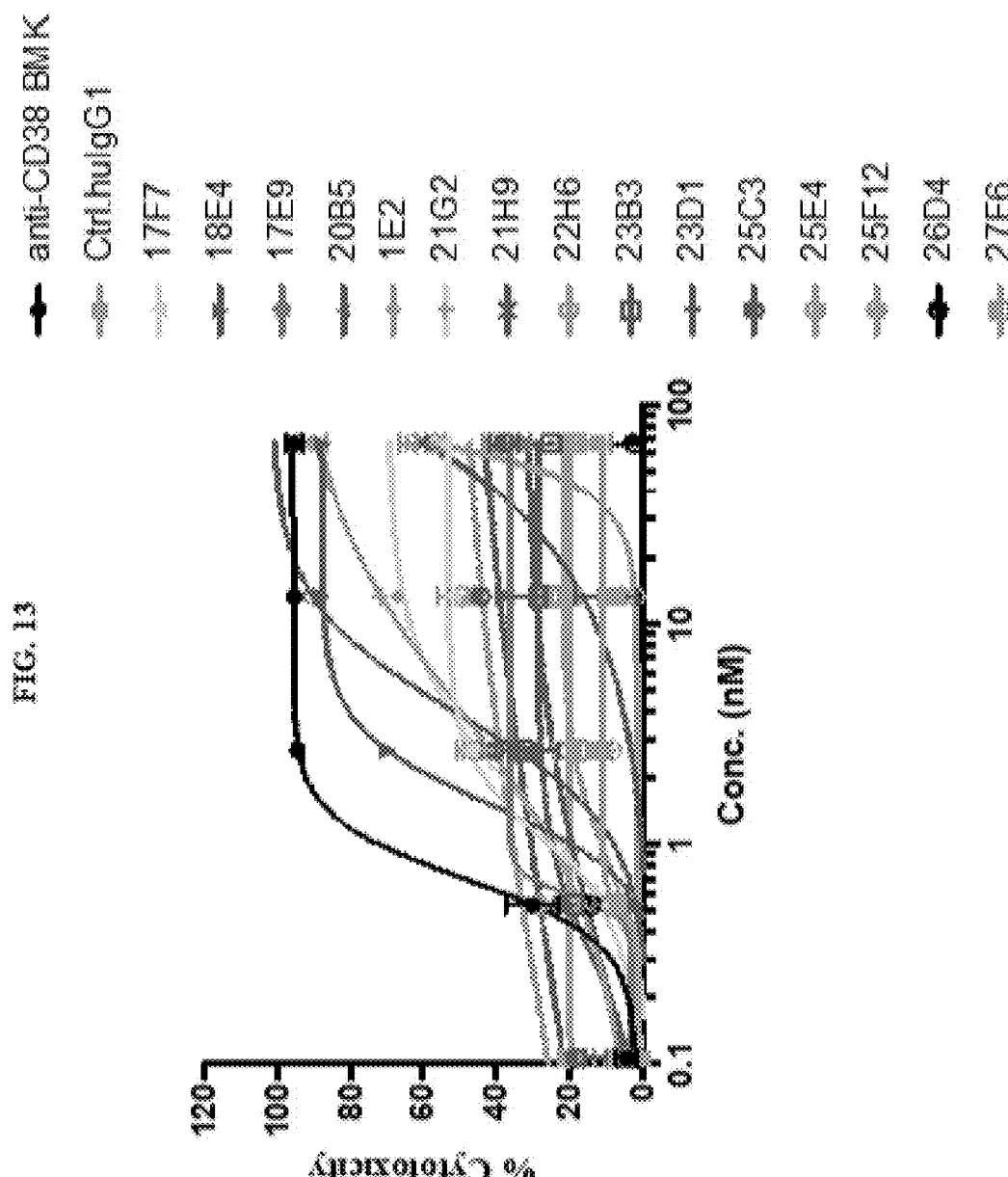
FIG. 13 shows CDC-mediated lysis of Daudi cells by benchmark and exemplary rabbit human chimeric anti-CD38 antibodies.

The CDC and ADCC activities of the library-derived and chimeric anti-CD38 and anti-ICAM1 monoclonal antibodies were determined by the same methods used for the exemplary bispecific antibodies. Multiple anti-CD38 antibodies had potent CDC activity on Daudi cells (FIG. 13). These results are quantified in Table 25.

TABLE 25

CDC activity of chimeric anti-CD38 antibodies on Daudi cells

| Clone name | Max Killing | EC 50 (nM) |
|---|---|---|
| anti-CD38 BMK | 95.6 | 0.7006 |
| Ctrl.huIgG1 | N.D. | N.D. |
| 17E9 | 36.78 | 0.6 |
| 17F7 | 53.41 | 1.019 |
| 18E4 | 87.81 | 1.511 |
| 1E2 | 96.7 | 4.018 |

TABLE 25-continued

CDC activity of chimeric anti-CD38 antibodies on Daudi cells

| Clone name | Max Killing | EC 50 (nM) |
|---|---|---|
| 20B5 | 101.5 | 3.857 |
| 21G2 | 69.89 | 1.664 |
| 21H9 | N.D. | N.D. |
| 22H6 | N.D. | N.D. |
| 23B3 | 28.9 | 0.3146 |
| 23D1 | 32.54 | 0.349 |
| 25C3 | 50.58 | 0.2393 |
| 25E4 | 19.93 | 0.002331 |
| 25F12 | 52.63 | 0.1694 |
| 26D4 | N.D. | N.D. |
| 27F6 | 21.86 | 0.9699 |

Many of the anti-CD38 antibodies discovered in this study had potent ADCC activity. The ADCC activity of anti-CD38 antibodies derived from yeast or phage libraries

US 12,583,932 B2

Figure 14A:
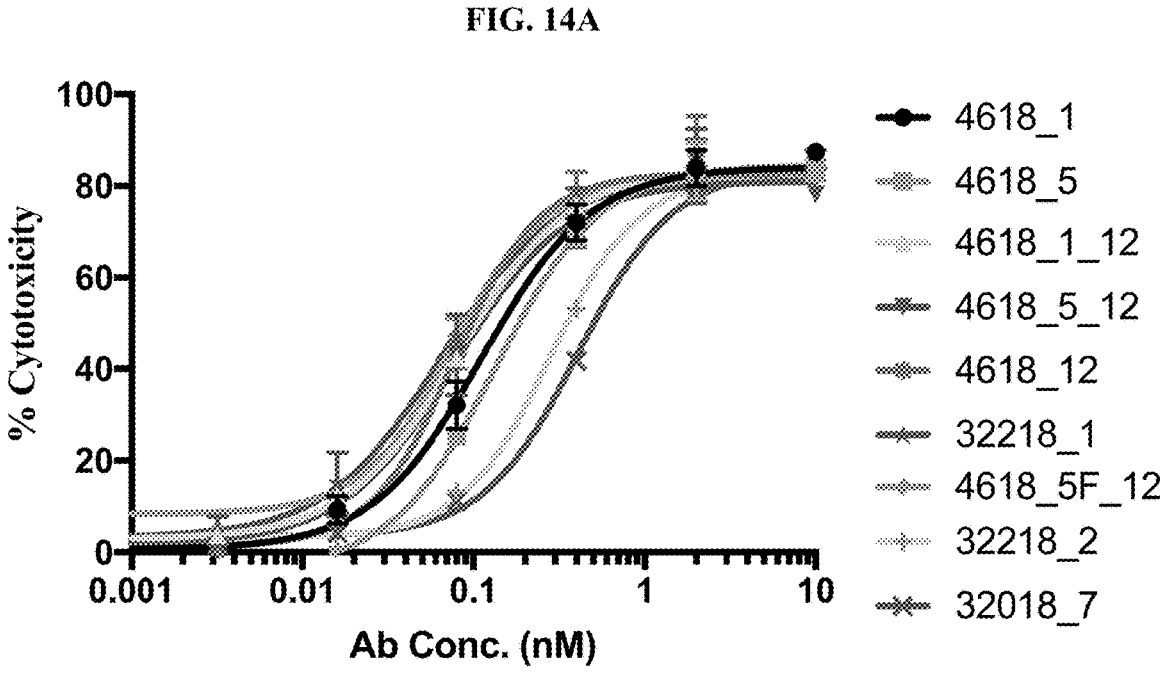
FIG. 14A-FIG. 14B show ADCC-mediated lysis of Daudi cells (FIG. 14A) and HuNS1 cells (FIG. 14B) by anti-CD38 antibodies using NK92/CD16A as effector cells.
Figure 14B:
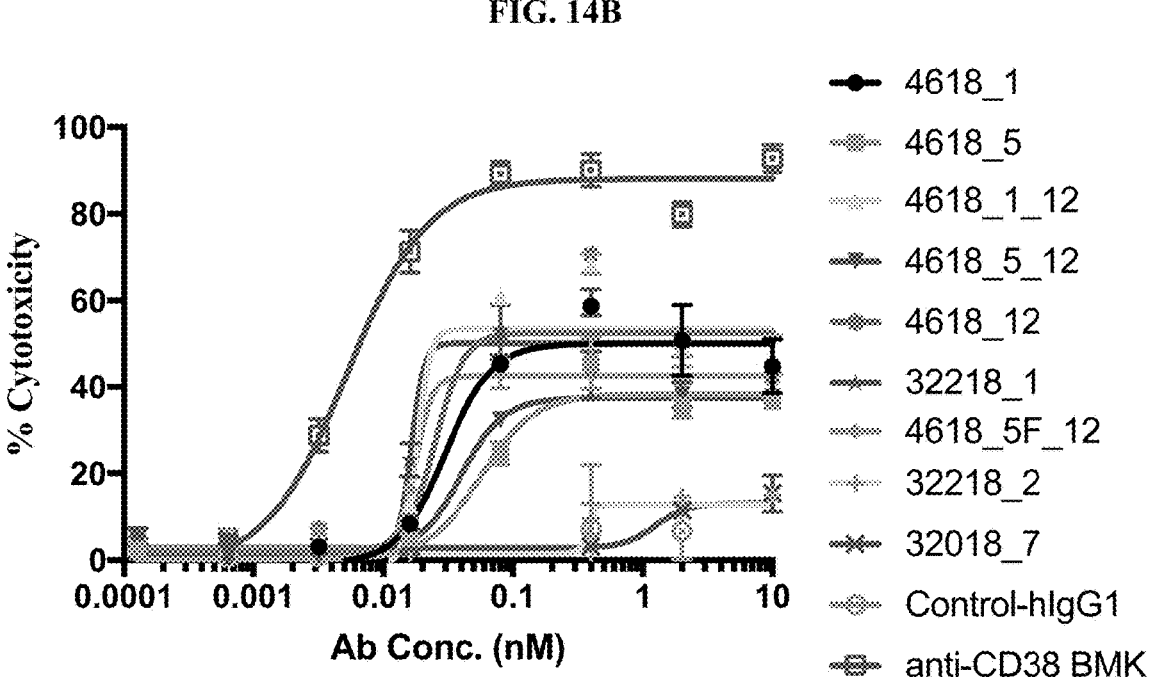
Figure 15A:
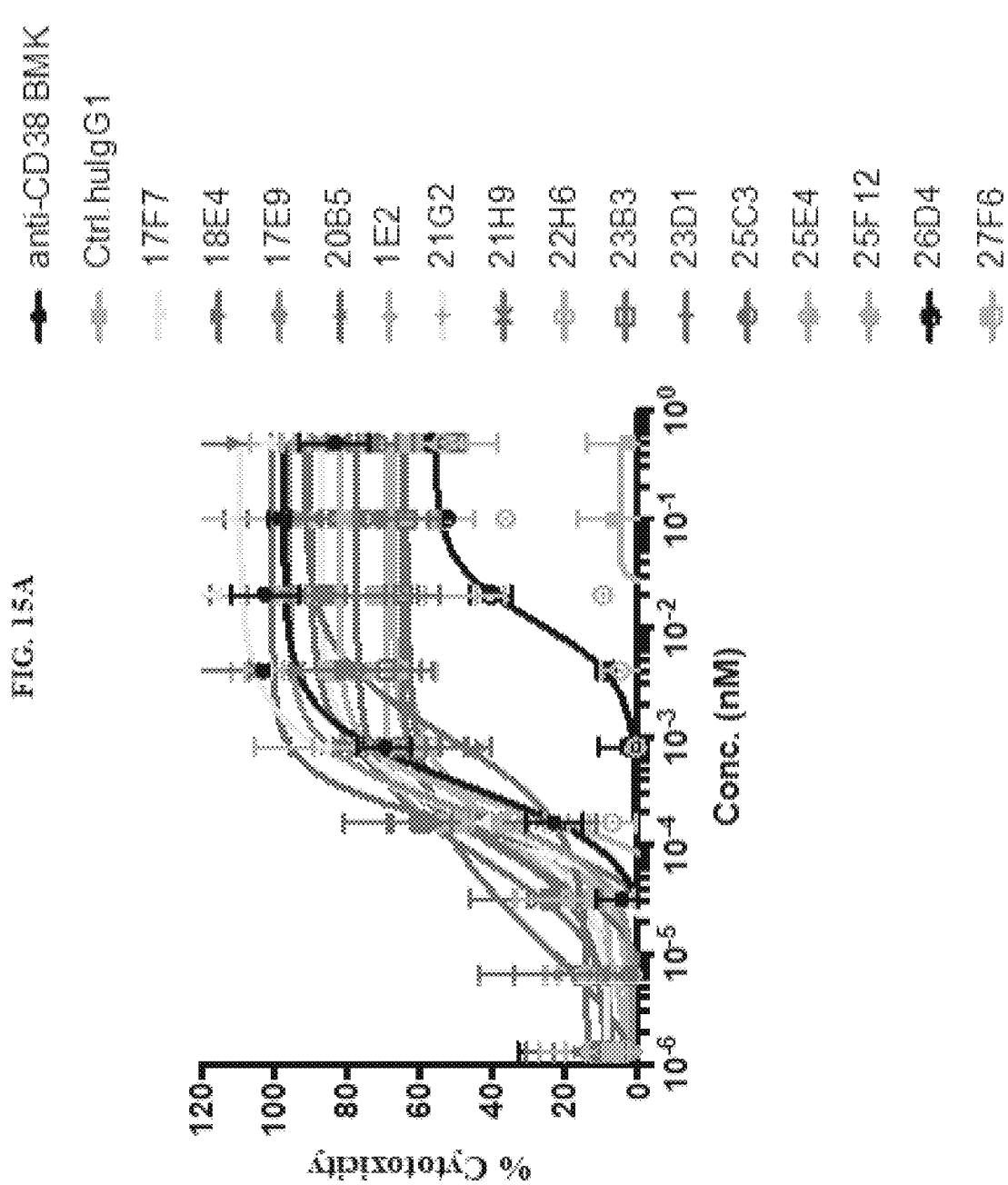
FIG. 15A-FIG. 15B show ADCC-mediated lysis of Daudi cells (FIG. 15A) and HuNS1 cells (FIG. 15B) by benchmark and exemplary rabbit human chimeric anti-CD38 antibodies using NK92/CD16A as effector cells.
Figure 15B:
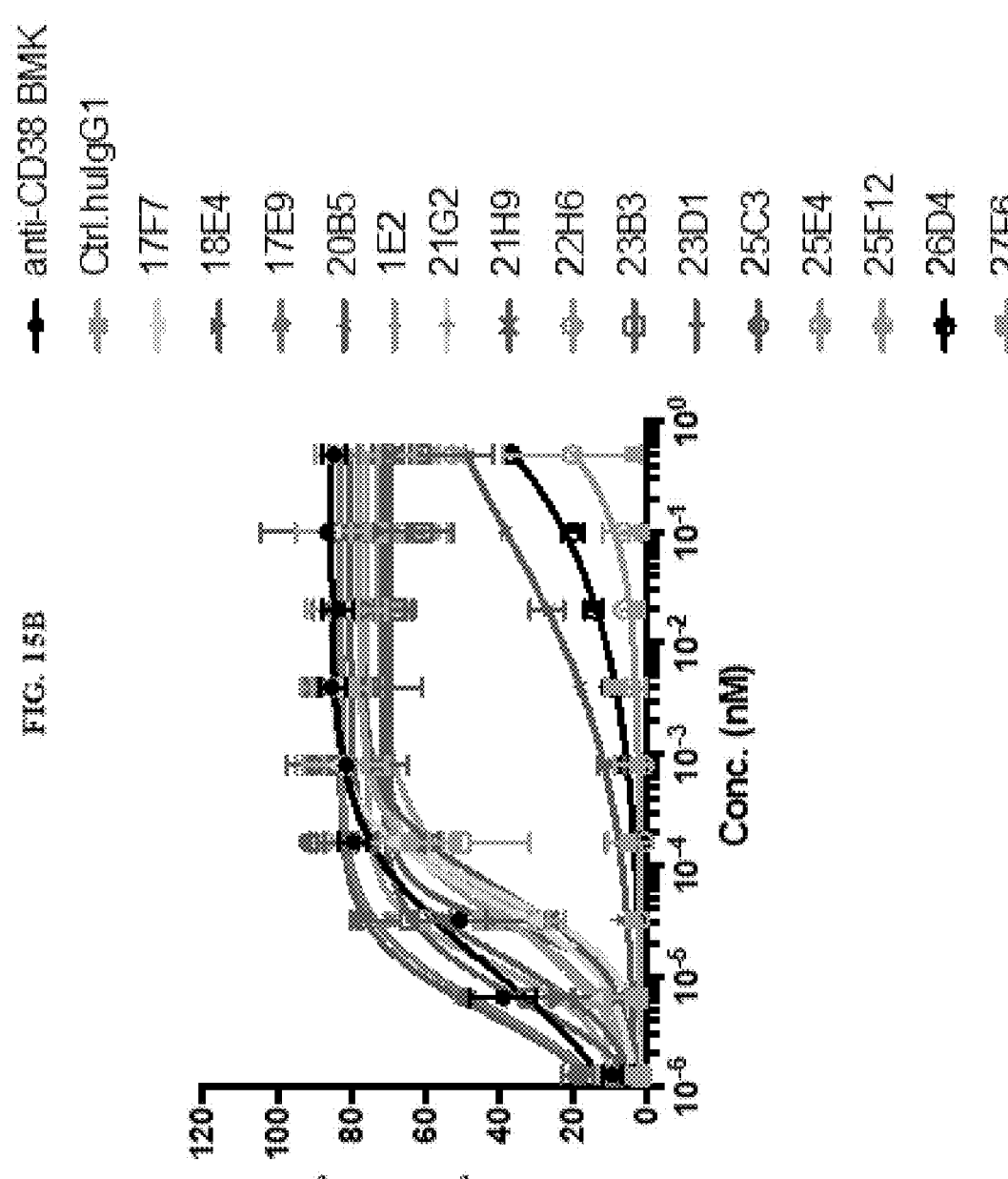

163 was determined in Daudi (FIG. 14A) and HuNS1 cells (FIG. 14B). The ADCC activity of the chimeric anti-CD38 antibodies derived from rabbit immunization was also determined in Daudi (FIG. 15A) and HuNS1 (FIG. 15B) cells. These results are quantified in Tables 26-27.

TABLE 26

| ADCC activity of anti-CD38 antibodies on Daudi cells | | |
|---|---|---|
| Clone name | Max Killing | EC 50 (nM) |
| 4618_1 | 84.11 | 0.1116 |
| 4618_5 | 84.56 | 0.135 |
| 4618_12 | 82.79 | 0.07774 |
| 4618_1_12 | 84.03 | 0.08129 |
| 4618_5_12 | 81.08 | 0.07836 |
| 4618_5F_12 | 81.49 | 0.07542 |
| 32218_1 | 82.39 | 0.06558 |
| 32218_2 | 82.29 | 0.2817 |
| 32018_7 | 83.67 | 0.4094 |
| anti-CD38 BMK | 97.47 | 0.0003484 |
| Ctrl.huIgG1 | N.D. | N.D. |
| 17E9 | 96.06 | 0.0002126 |
| 17F7 | 109.9 | 0.0002006 |
| 18E4 | 100.6 | 0.0001459 |
| 1E2 | 82.13 | 0.0002055 |
| 20B5 | 91.95 | 0.001001 |
| 21G2 | 87.46 | 0.0001929 |
| 21H9 | 90.27 | 0.0001652 |
| 22H6 | N.D. | N.D. |
| 23B3 | 63.95 | 0.00001399 |
| 23D1 | 64.97 | 0.00006639 |
| 25C3 | 77.6 | 0.00007088 |
| 25E4 | 69.18 | 0.0001042 |
| 25F12 | 64.48 | 0.0001007 |
| 26D4 | 56.05 | 0.0113 |
| 27F6 | 67.15 | 0.00015 |

TABLE 27

| ADCC activity of anti-CD38 antibodies on HuNS1 cells (N.D. = not determined) | | |
|---|---|---|
| Clone name | Max Killing | EC 50 (nM) |
| 4618_1 | 50.12 | 0.03001 |
| 4618_5 | 38.31 | 0.05668 |
| 4618_12 | 52.62 | 0.02505 |
| 4618_1_12 | 53.41 | ~0.01810 |
| 4618_5_12 | 37.4 | 0.03982 |
| 4618_5F_12 | 42.63 | ~0.01760 |
| 32218_1 | 50.24 | ~0.01650 |
| 32218_2 | 12.89 | ~0.3767 |
| 32018_7 | 13.12 | 1.251 |
| anti-CD38 BMK | 85.53 | 0.00001175 |
| 17E9 | 82.72 | 4.847E–06 |
| 17F7 | 85.45 | 0.00005212 |
| 18E4 | 80.18 | 0.00001557 |
| 1E2 | 77.71 | 0.00003238 |
| 20B5 | 73.41 | 0.09986 |
| 21G2 | 77.36 | 0.00005421 |
| 21H9 | 77.21 | 0.00006157 |
| 22H6 | N.D. | N.D. |
| 23B3 | 71.58 | 5.832E–06 |
| 23D1 | 69.78 | 0.00002696 |
| 25C3 | 83.01 | 4.414E–06 |
| 25E4 | 69.75 | 0.00005096 |
| 25F12 | 75.62 | 0.00001295 |
| 26D4 | N.D. | N.D. |
| 27F6 | 72.83 | 0.00002874 |

164

Figure 16A:
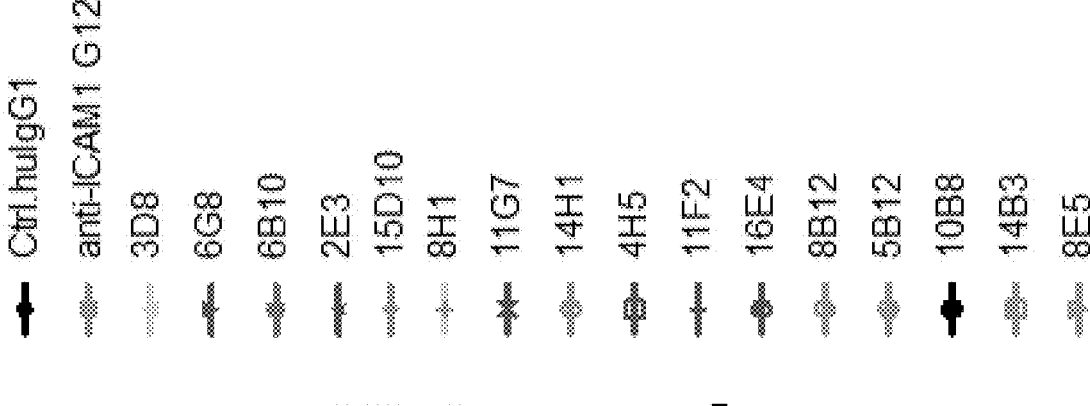
FIG. 16A-FIG. 16C show ADCC-mediated lysis of DU145 (FIG. 16A), Daudi cells (FIG. 16B) and HuNS1 cells (FIG. 16C) by the anti-ICAM1 clone G12 and exemplary rabbit human chimeric anti-ICAM1 antibodies using NK92/CD16A as effector cells.
Figure 16A:
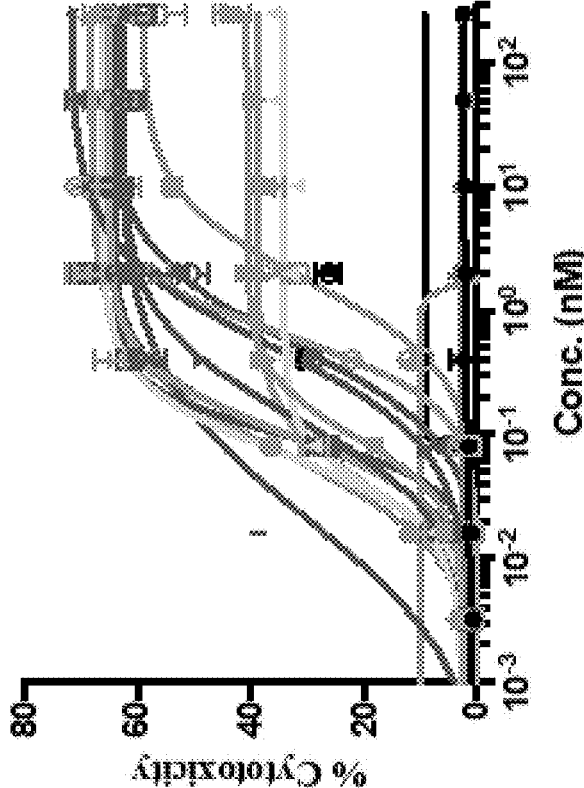

Many of the chimeric anti-ICAM11 antibodies discovered in this study had potent ADCC activity in DU145 cells, which have high ICAM1 expression (FIG. 16A). These results were quantified (Table 28).

TABLE 28

| Summary of ADCC activity for exemplary anti-ICAM1 clones on DU145 cells | | |
|---|---|---|
| Clone name | Max Killing | EC 50 (nM) |
| Ctrl.huIgG1 | 3.014 | 0.03443 |
| anti-ICAM1 G12 | 40.8 | 0.09562 |
| 6B10 | N.D. | N.D. |
| 3D8 | 34.2 | 0.03507 |
| 6G8 | 62.78 | 0.1335 |
| 15D10 | 65.19 | 0.1009 |
| 2E3 | 71.74 | 0.5194 |
| 8H1 | 66.24 | 0.06957 |
| 11G7 | 64.55 | 0.09704 |
| 14H1 | 68.3 | 0.6368 |
| 4H5 | 63.76 | 0.09592 |
| 11F2 | 63.39 | 0.02138 |
| 16E4 | 65.25 | 0.5263 |
| 8B12 | 68.18 | 0.06837 |
| 5B12 | N.D. | N.D. |
| 10B8 | N.D. | N.D. |
| 14B3 | 59.3 | 1.702 |
| 8E5 | 38.83 | 0.0401 |

Figures 16B, 16C:
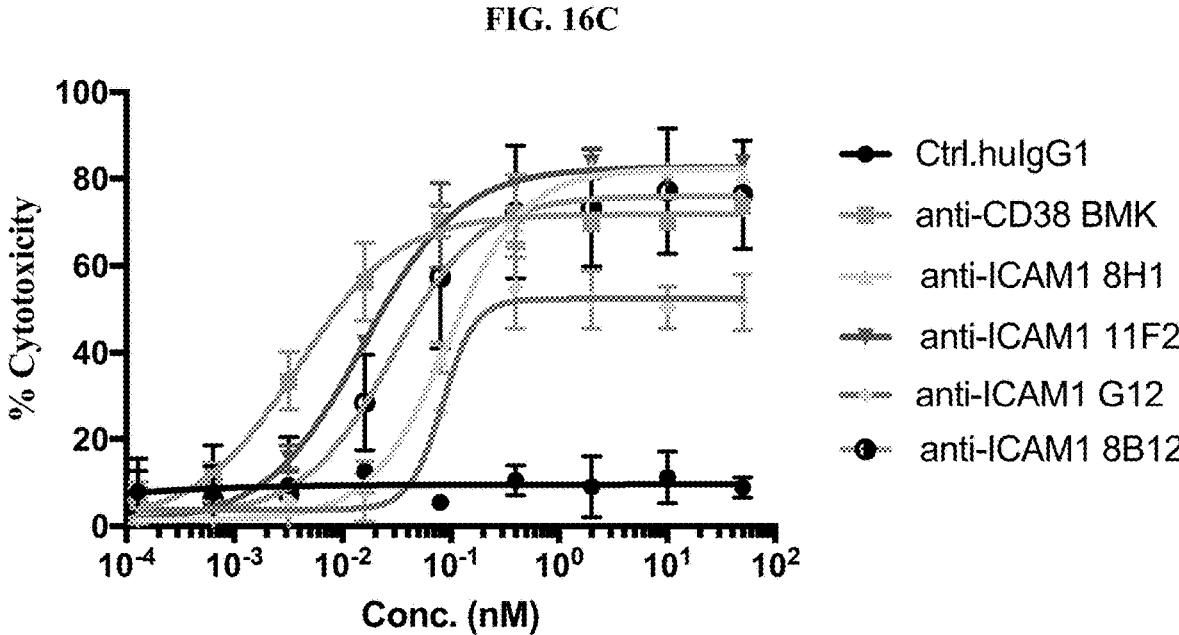

In Daudi cells, which have lower ICAM1 expression and very high CD38 expression, a monospecific anti-CD38 antibody had higher ADCC activity than the ICAM1 antibodies (FIG. 16B). The 8B12 anti-ICAM antibody had higher ADCC activity than other anti-ICAM1 antibodies discovered in this study. In HuNS1 which express intermediate levels of ICAM1 and CD38, the 8B12 and 11F2 antibodies had the highest activity among the monospecific anti-ICAM1 antibodies (FIG. 16C).

Example 5: ADCC Activity of Bispecific Antibodies Constructed from the CD38 and ICAM1 Binding Domains Discovered in this Study The human and chimeric anti-CD38 and anti-ICAM1 antibodies discovered in this study were used to construct additional bispecific antibodies in the formats described in FIG. 2 using the methods described in Example 1. The component polypeptide chains of exemplary bispecific antibodies are presented in Table 29. All of these bispecific antibodies had ADCC activity in Daudi, Raji and/or DU145 cells.

TABLE 29

| | | | SEQ ID Nos. | | | |
| | anti-CD38 | anti-ICAM1 | Heavy | Light | Heavy | Light |
| Format | domain | domain | Chain 1 | Chain 1 | Chain 2 | Chain 2 |
| --- | --- | --- | --- | --- | --- | --- |
| LC C-fusion (High) | 4618_1_12 | G12 | 160 | 397 | | |
| HC C-fusion (High) | 4618_1_12 | G12 | 389 | 186 | | |
| 3 chain KIH (High) | 4618_1_12 | G12 | 391 | 186 | 383 | |
| LC C-fusion (Med) | 32218_1 | G12 | 163 | 395 | | |
| HC N-fusion (Med) | 32218_1 | G12 | 387 | 189 | | |
| 3 chain KIH (Med) | 32218_1 | G12 | 390 | 189 | 383 | |
| LC C-fusion (Low) | 32218_2 | G12 | 164 | 396 | | |
| HC N-fusion (Low) | 32218_2 | G12 | 388 | 190 | | |
| 3 chain KIH (Low) | 32218_2 | G12 | 392 | 190 | 383 | |
| LC C-fusion | G1F4 | G12 | 156 | 393 | | |
| HC C-fusion | G1F4 | G12 | 384 | 182 | | |
| HC N-fusion | G1F4 | G12 | 385 | 182 | | |
| DVD | G1F4 | G12 | 386 | 394 | | |
| 3 chain KIH | G1F4 | G12 | 156 | 182 | 383 | |
| Common LC | 32218_1 | 81618_3 | 390 | 189 | 348 | 189 |
| Common LC | 32218_1 | 62218_13 | 390 | 189 | 349 | 189 |
| Common LC | 4618_1_12 | 81618_3 | 391 | 186 | 348 | 186 |
| Common LC | 4618_1_12 | 62218_13 | 391 | 186 | 349 | 186 |

Figure 17A:
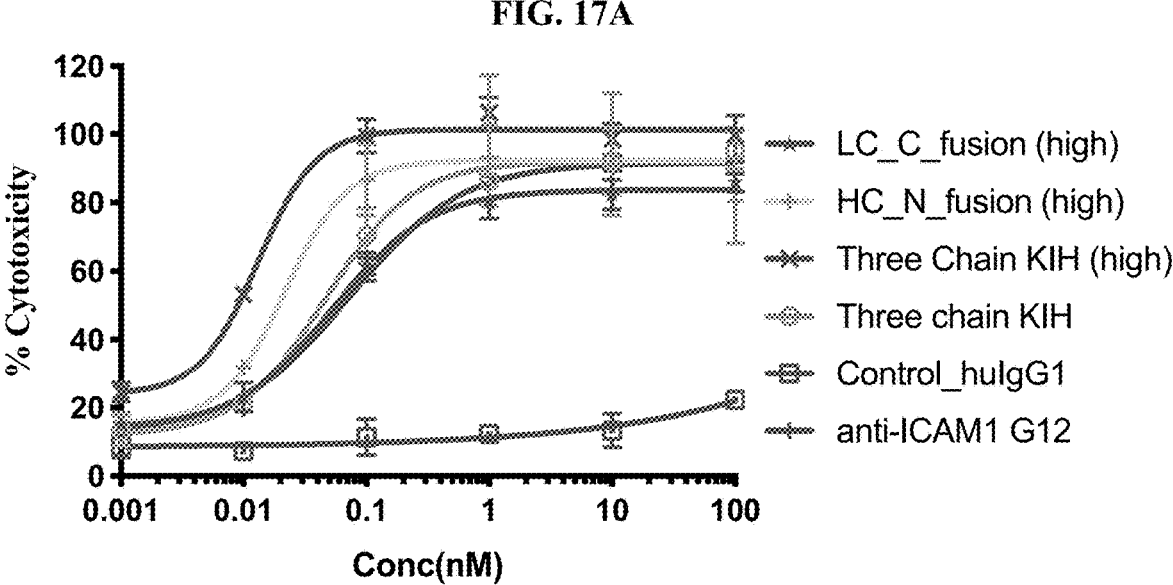
FIG. 17A-FIG. 17C show ADCC-mediated lysis of DU145 cells by exemplary high affinity anti-CD38 4618_1_12 bispecific antibodies (FIG. 17A), exemplary mid affinity anti-CD38 32218_1 bispecific antibodies (FIG. 17B) and exemplary low affinity anti-CD38 33218_2 bispecific antibodies (FIG. 17C) using fresh PBMC as effector cells.
Figure 17B:
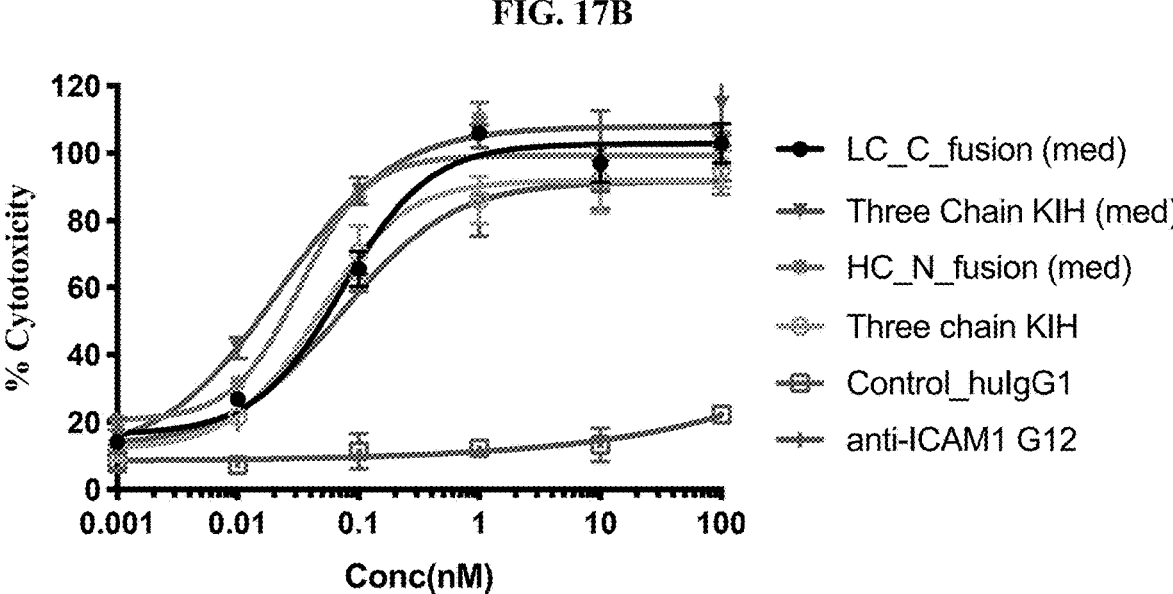
Figure 17C:
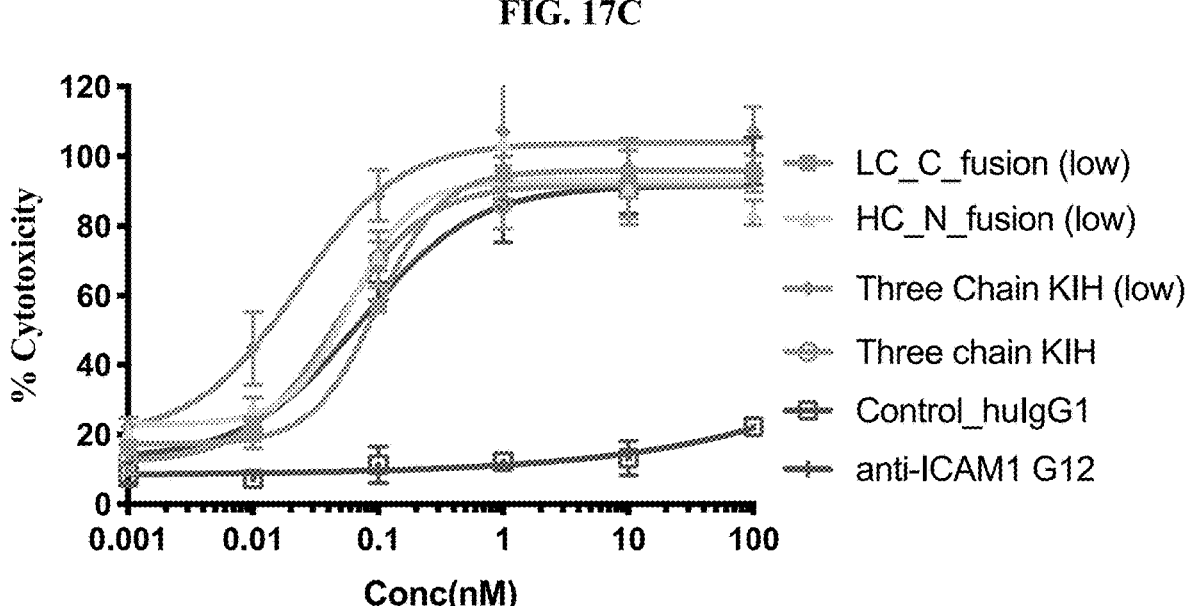

The effect of the CD38 affinity of a CD38/ICAM1 bispecific antibody on ADCC activity with fresh PBMC effector cells was tested in DU145 cells, which have low CD38 expression and high ICAM1 expression. Bispecific antibodies were assembled from anti-CD38 antibodies with high (X), medium (Y) and low (Z) affinity for CD38 in combination with a constant ICAM1 binding domain (G12). The CD38 binding affinities are ranging from sub-nanomolar to double digit nanomolar in Tables 20 and 21. All of these bispecific antibodies had comparable ADCC activity to a reference three chain KIH bispecific antibody, regardless of whether they had a three chain KIH format, and HC N-fusion format, or an LC C-fusion format (FIG. 17A-FIG. 17C). The monovalent bispecific format, three chain KIH, showed the best ADCC activities, whereas the CD38 binding affinities have minimal impact on the bispecific antibody ADCC activities (FIG. 17A-FIG. 17C).

Figure 18A:
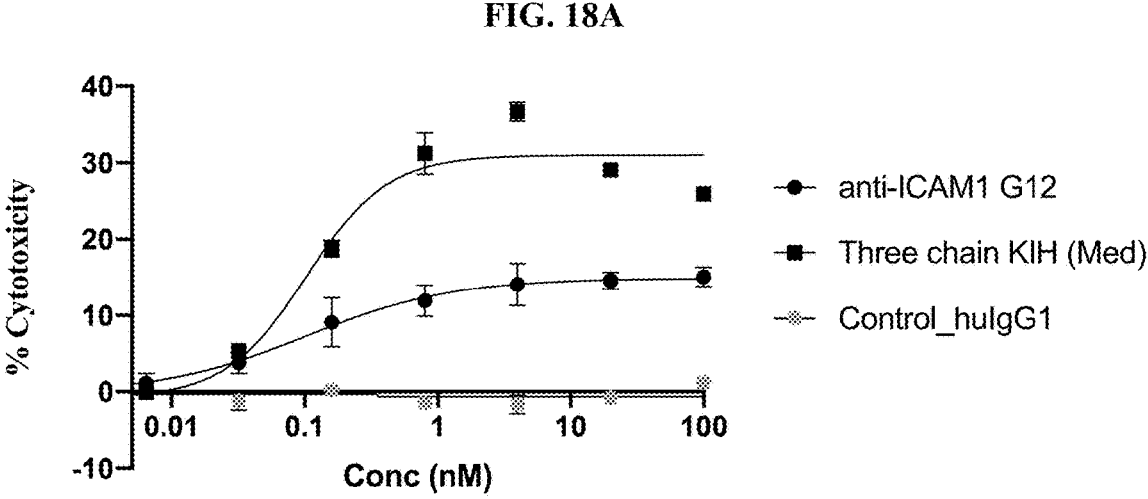
FIG. 18A-FIG. 18C show ADCC-mediated lysis of Raji (FIG. 18A), DU145 (FIG. 18B), and HCC44 (FIG. 18C) using exemplary monovalent anti-CD38 (medium affinity, 322181), monovalent anti-ICAM1, and anti-CD38/ICAM1 bispecific antibodies
Figure 18B:
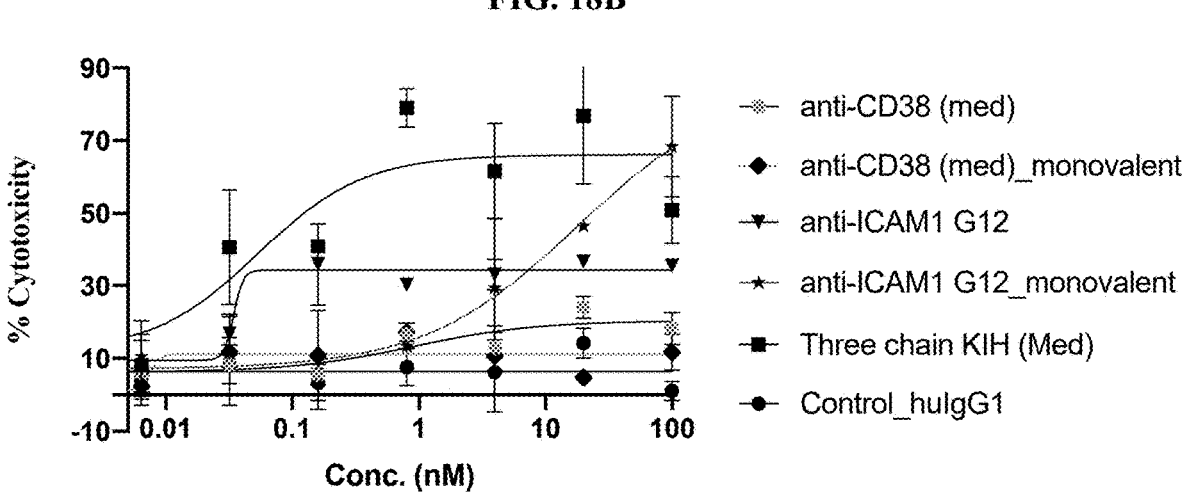
Figure 18C:
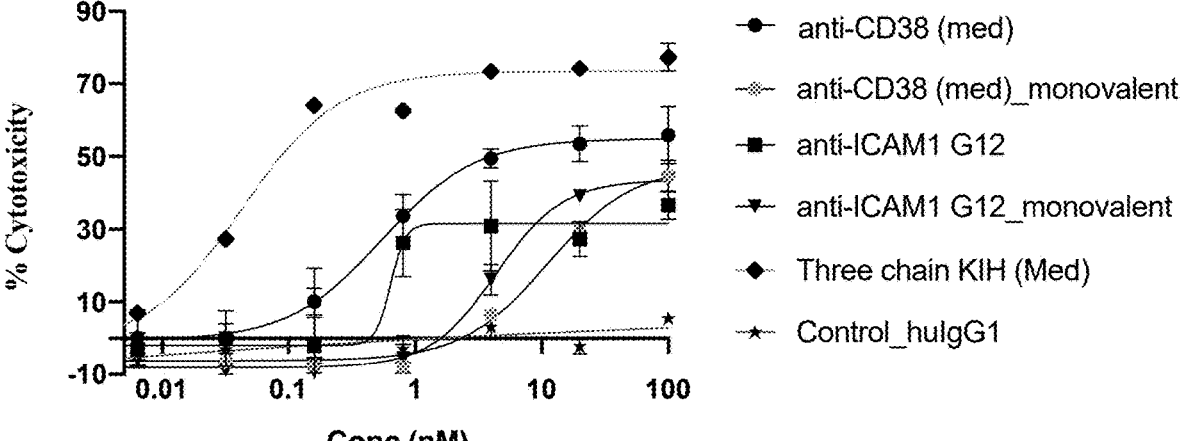

The three chain KIH antibody with medium CD38 affinity also had ADCC activity in Raji cells (FIG. 18A), DU145 cells (FIG. 18B), and HCC44 cells (FIG. 18C). In DU145 and HCC44 cells, the bispecific antibody had higher ADCC activity than monospecific CD38 or ICAM1 antibodies, regardless of whether they were bivalent (2 HC+2 LC) or maintained in a monovalent (1 HC+1 LC) state with a knob mutation.

Example 6: Fc Engineering/Modification Further Improved ADCC Activities of the CD38/ICAM1 Bispecific Antibodies To determine whether Fc engineering or modification improves ADCC activities of the CD38/ICAM1 bispecific antibodies on ICAM$^{high}$/CD38$^{low}$ cells, mutations were introduced (S239D/I332E/A330L) on both knob and hole chains of the Fc in a bispecific antibody with a CD38 binding domain with CDR sequences from 18E4 and an ICAM1 binding domain with CDR sequences from 11F2.

Figures 19A, 19B:
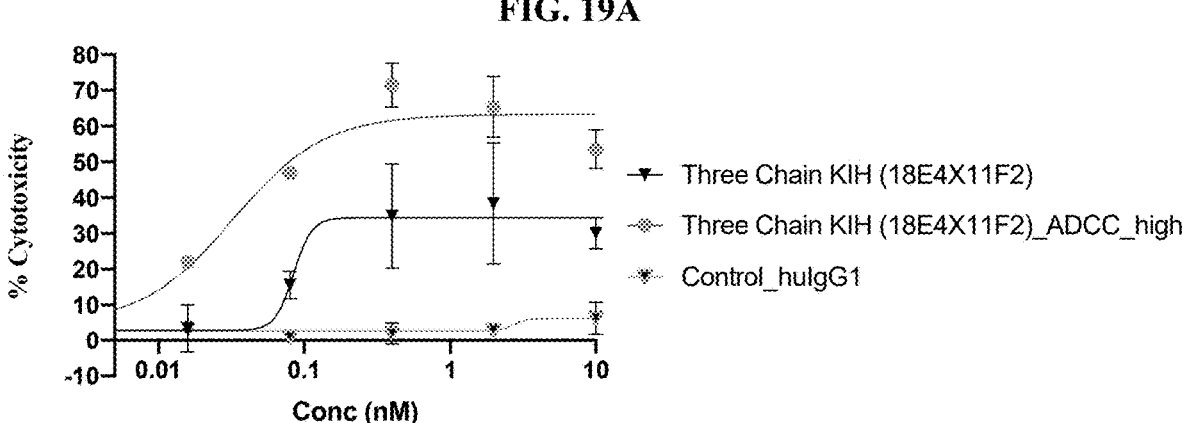
Figure 20A:
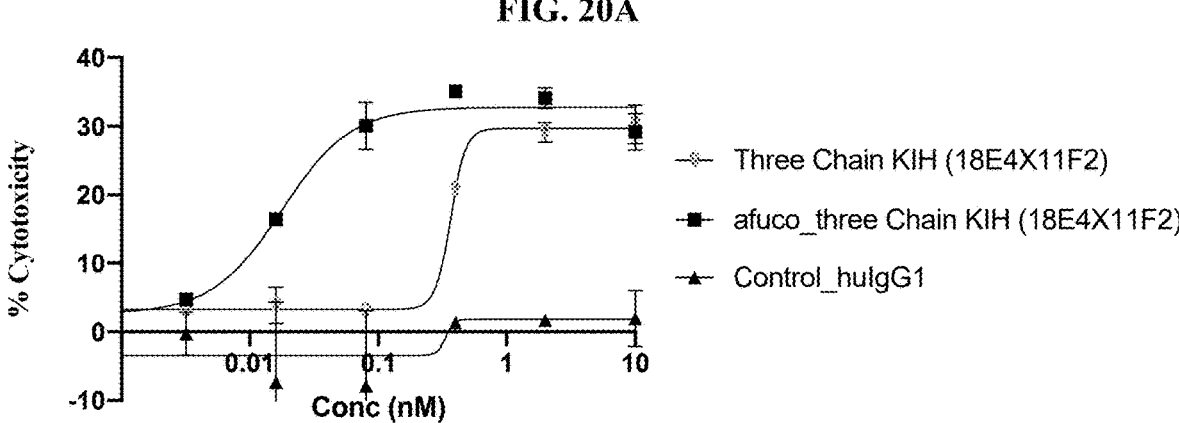
FIG. 20A-FIG. 20B show increased ADCC-mediated lysis of Raji (FIG. 20A) and KMS26 (FIG. 20B) cells with an afucosylated CD38/ICAM1 KIH bispecific antibody.
Figure 20B:
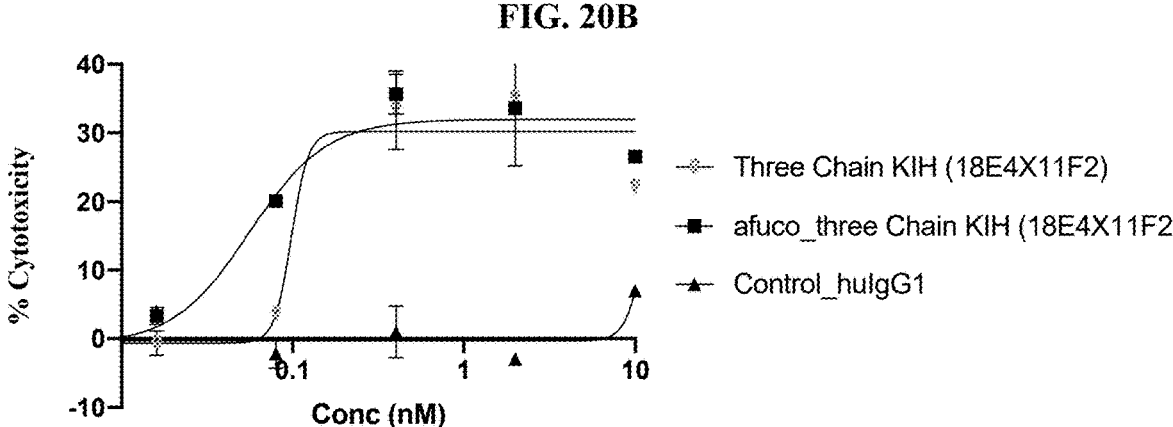

Significant ADCC improvement was observed on both Raji (lymphoma) and KMS26 (myeloma) cell lines (FIG. 19A-FIG. 19B). Independently, the same bispecific antibodies were produced in a CHO cell line which lacked FUT8 (fucosyltransferase 8) expression, yielding bispecific antibodies with little to no fucose in the Fc region. The absence of fucosylation enhanced ADCC activity on both Raji (lymphoma) and KMS26 (myeloma) cells (FIG. 20A-FIG. 20B).

Example 8: In Vivo Xenograft Studies

Cell-line derived xenograft (CDX) models were used to compare the in vivo anti-tumor activity of bispecific CD38/ICAM1 antibodies with monospecific anti-CD38 and anti-ICAM1 antibodies in using Raji lymphoma cells, HuNS1 myeloma cells, and HCC44 lung adenocarcinoma cells Raji Cell (Lymphoma) CDX Model Raji cells were maintained in vitro as a suspension culture in 90% RPMI-1640 supplemented with 10% heat-inactivated fetal bovine serum, 100 U/ml penicillin and 100 μg/ml streptomycin at 37° C. in an atmosphere of 5% $CO_2$ in air. Raji cells were routinely sub-cultured trypsin-EDTA treatment at a ratio of 1:2-1:3 every 2-3 days and were maintained by the addition or replacement of fresh medium. An optimal density of between $4 \times 10^5$ and $3 \times 10^6$ cells/mL was maintained. Cells growing in exponential growth were harvested and counted for tumor inoculation. At harvest time, the concentration was $2.5 \times 10^7$ cells/mL with over 97% cell viability before inoculation.

Female CB.17 SCID mice were subcutaneously inoculated with $10^7$ Raji cells in 0.2 mL of PBS supplemented with BD Matrigel (1:1) for tumor development. Treatments were started when the average tumor size reached approximately 127 mm$^3$. The animals were assigned into groups using an Excel-based randomization software performing stratified randomization based upon their tumor volumes. Each group consisted of 5 tumor-bearing mice. The testing antibodies were administrated to the mice intravenously at a dose of 10 mg/kg, twice per week, in three successive weeks. Tumor volume was monitored, and animals were sacrificed if tumors reached 2000 mm$^3$ in size or became necrotic. Test antibodies were well tolerated at all doses tested.

Figures 21, 22:
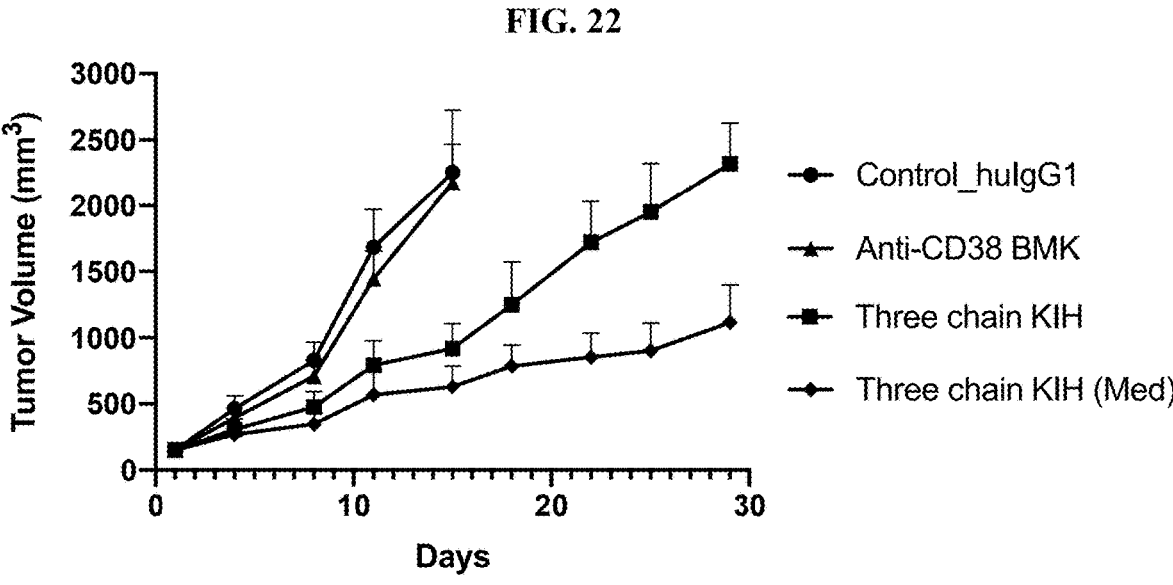
FIG. 21 shows the mean volume of Raji cell-derived xenograft tumors treated with monospecific CD38 or ICAM1 antibodies or a three chain KIH CD38/ICAM1 bispecific antibody.
FIG. 22 shows the mean volume of Raji cell-derived xenograft tumors treated with a monospecific CD38 antibody, a three chain KIH CD38/ICAM1 bispecific antibody with the anti-CD38-binding domain from anti-CD38 BMK, or a three chain KIH CD38/ICAM1 bispecific antibody with the CD38-binding domain from 32218_1 (Three chain KIH (Med)).

At Day 16, the mean tumor size in the human IgG1 isotype control group reached 2183.49 mm$^3$. In mice treated with anti-CD38 BMK, anti-ICAM1 G12 and three chain KIH bispecific, the mean tumor sizes were 1228.54 mm$^3$, 946.11 mm$^3$ and 655.17 mm$^3$, respectively. The T/C (%) value of tumor volume was 56.49%, 43.68% and 30.38% of the isotype control group. The anti-ICAM1 G12 and the three chain KIH showed significant inhibition of tumor growth compared to the human IgG1 Isotype control group against the Raji subcutaneous xenografts. The bispecific three chain KIH antibody had substantially more inhibition than the monospecific anti-CD38 antibody (FIG. 21).

The in vivo anti-tumor activity of the three chain KIH (med) bispecific was analyzed in a separate Raji CDX model experiment. At Day 15, the mean tumor size in the isotype control group reached 2252.75 mm$^3$. Treatment with the three chain KIH, the anti-CD38 BMK, or the three chain KIH (med) antibodies resulted in mean tumor sizes of 918.63 mm$^3$, 2177.89 mm$^3$ and 628.89 mm$^3$, respectively, with T/C (%) values of tumor volume of 40.82%, 96.59% and 27.89% compared to the control group. The three chain KIH (med) showed significant inhibition of tumor growth compared to the human IgG1 Isotype control group (FIG. 22).

HuNS1 Cell (Multiple Myeloma) CDX Model

HuNS1 cells were maintained in vitro as a suspension culture in 85% RPMI-1640 medium supplemented with 15% fetal bovine serum, 2 mM L-glutamine, 4.5 g/L glucose, 10 mM HEPES, 1 mM sodium pyruvate, 1.5 g/L sodium bicarbonate, and 0.02 mM 2-amino-6-methylmercaptopurine. Media was typically refreshed two to three time per week by removing the old medium, splitting the cells, and then adding fresh medium. The calculated cell concentration at the time of harvest was 5×10$^7$ cells/mL with over 97% cell viability before inoculation.

Female CB.17 SCID mice were inoculated subcutaneously with 5×10$^6$ HuNS1 cells supplemented with BD Matrigel (1:1) for tumor development. Treatments were started when the average tumor size reached approximately 115 mm$^3$. The animals were assigned to groups using an Excel-based randomization software performing stratified randomization based upon their tumor volumes. Each group consisted of 5 tumor-bearing mice. The testing antibodies were administrated to the mice intravenously at a dose of 10 mg/kg, twice per week, for three successive weeks. Tumor volume was monitored, and animals were sacrificed if tumors reached 2000 mm$^3$ in size or became necrotic. Test antibodies were well tolerated at all doses tested.

Figure 23:
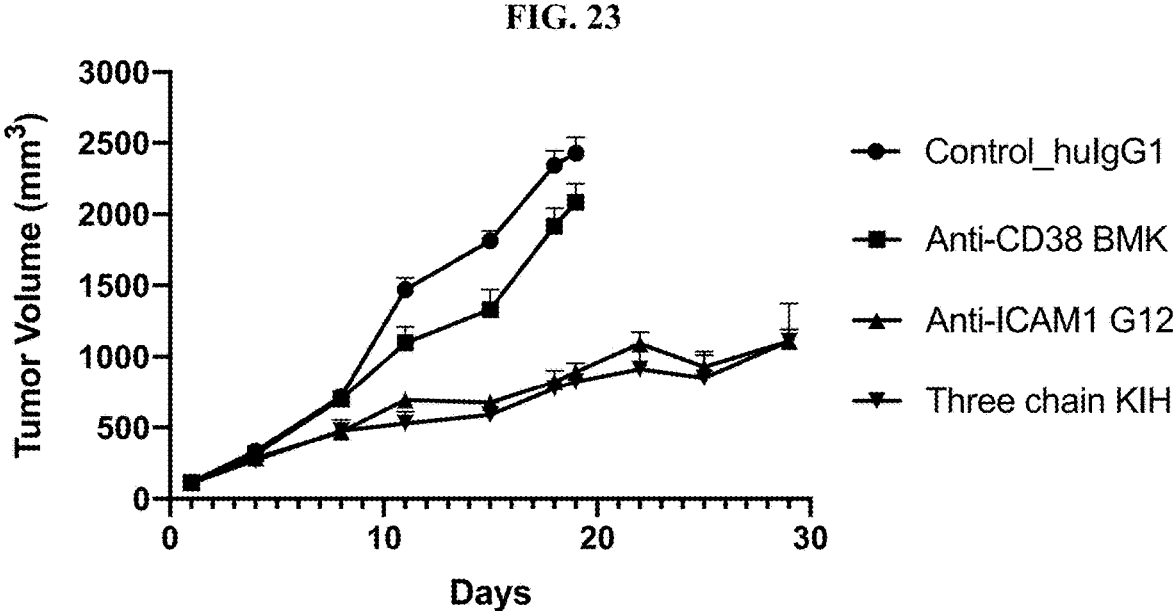
FIG. 23 shows the mean volume of HuNS1 cell-derived xenograft tumors treated with monospecific CD38 or ICAM1 antibodies or a three chain KIH CD38/ICAM1 bispecific antibody.

At day 19, the mean tumor sizes for the isotype control, anti-CD38 BMK, anti-ICAM1 G12 and three chain KIH were 2429.35 mm$^3$, 2084.94 mm$^3$, 893.69 mm$^3$, and 822.59 mm$^3$, respectively. The T/C (%) value of tumor volume for anti-CD38 BMK, anti-ICAM1 G12 and three chain KIH was 86.52%, 37.48% and 34.81% of the control group, respectively. The three chain KIH bispecific antibody and the monospecific anti-ICAM1 G12 antibody showed significant inhibition of tumor growth compared to the isotype control group (FIG. 23).

HCC44 Cell (Non-Small Cell Lung Carcinoma) CDX Model

HCC44 cells were maintained in vitro as a monolayer culture in RPMI 1640 culture medium supplemented with 10% heat inactivated fetal bovine serum, 300 mg/L L-glutamine, 100 U/mL penicillin and 100 µg/mL streptomycin, at 37° C. in an atmosphere of 5% $CO_2$ in air. The HCC44 cells were routinely sub-cultured twice weekly by trypsin-EDTA treatment. Cells growing in an exponential growth phase were harvested and counted in preparation for tumor inoculation.

Female Balb/c nude mice were inoculated subcutaneously with 5×10$^6$ cells supplemented with BD Matrigel (1:1) for tumor development. Treatments were started when the average tumor size reached approximately 124 mm$^3$. The animals were assigned into groups using an Excel-based randomization software performing stratified randomization based upon their tumor volumes. Each group consisted of 5 tumor-bearing mice. The testing antibodies were administrated to the mice intravenously at a dose of 10 mg/kg, twice per week. Tumor volume was monitored, and animals were sacrificed if tumors reached 3000 mm$^3$ in size or became necrotic. Test antibodies were well tolerated at all doses tested.

Figure 24:
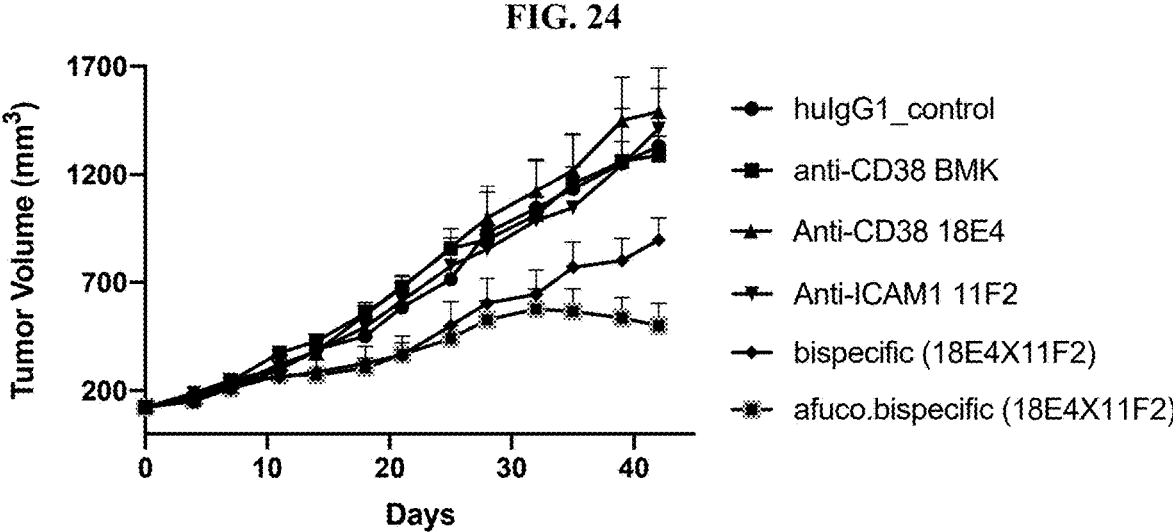
FIG. 24 shows the mean volume of HCC44 cell-derived xenograft tumors treated with fucosylated and afucosylated forms of a bispecific antibody with a CD38 binding domain derived from 18E4 and an ICAM1 binding domain derived from 11F2, monospecific antibodies having the same binding domains, and a monospecific anti-CD38 reference antibody (anti-CD38 BMK).

At Day 39, the mean tumor sizes for the isotype control, anti-CD38 BMK, anti-CD38 (18E4), andti-ICAM1 (11F2), bispecific (18E4X11F2) and afucosylated bispecific (18E4X11F2) were 1243 mm$^3$, 1262 mm$^3$, 1450 mm$^3$, 1246 mm$^3$, 801 mm$^3$, and 536 mm$^3$ respectively. The bispecific (18E4X11F2) and afucosylated bispecific (18E4X11F2) showed significant inhibition of tumor growth compared to the isotype control group against the HCC44 subcutaneous xenografts, with the afucosylated bispecific showing substantially more inhibition than the fucosylated bispecific (FIG. 24).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Sequence Tables:

TABLE 30

| Heavy chain sequences of proof-of-concept bispecific antibodies | | |
| --- | --- | --- |
| SEQ ID | Name | Sequence |
| 376 | Dara | EVQLLESGGGLVQPGGSLRLSCAVSGFTFNSFAMSWVRQAP GKGLEWVSAISGSGGGTYYADSVKGRFTISRDNSKNTLYLQ MNSLRAEDTAVYFCAKDKILWFGEPVFDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKRVEPKSCDKTHTCPPCPAPELLGGPSVFLF PPKPKDTLMISRTPEVTCVVVDVSHEDPEVKFNWYVDGVEV HNAKTKPREEQYNSTYRVVSVLTVLHQDWLNGKEYKCKVS |

TABLE 30-continued

| Heavy chain sequences of proof-of-concept bispecific antibodies | | |
|---|---|---|
| SEQ ID | Name | Sequence |
| | | NKALPAPIEKTISKAKGQPREPQVYTLPPSREEMTKNQVSLT<br>CLVKGFYPSDIAVEWESNGQPENNYKTTPPVLDSDGSFFLYS<br>KLTVDKSRWQQGNVFSCSVMHEALHNHYTQKSLSLSPGK |
| 377 | Dara/G12(scFv) | EVQLLESGGGLVQPGGSLRLSCAVSGFTFNSFAMSWVRQAP<br>GKGLEWVSAISGSGGGTYYADSVKGRFTISRDNSKNTLYLQ<br>MNSLRAEDTAVYFCAKDKILWFGEPVFDYWGQGTLVTVSS<br>ASTKGPSVFPLAPSSKSTSGGTAALGCLVKDYFPEPVTVSWN<br>SGALTSGVHTFPAVLQSSGLYSLSSVVTVPSSSLGTQTYICN<br>VNHKPSNTKVDKRVEPKSCDKTHTCPPCPAPELLGGPSVFLF<br>PPKPKDTLMISRTPEVTCVVVDVSHEDPEVKFNWYVDGVEV<br>HNAKTKPREEQYNSTYRVVSVLTVLHQDWLNGKEYKCKVS<br>NKALPAPIEKTISKAKGQPREPQVYTLPPSREEMTKNQVSLT<br>CLVKGFYPSDIAVEWESNGQPENNYKTTPPVLDSDGSFFLYS<br>KLTVDKSRWQQGNVFSCSVMHEALHNHYTQKSLSLSPGGG<br>GGSGGGGSGGGGSASQVQLVESGGGLVQPGGSLRLSCAAS<br>GFTFSSYAMSWVRQAPGKGLEWVSAISGSGGSTYYADSVK<br>GRFTISRDNSKNTLYLQMSSLRAEDTAFYYCANSAYTGGW<br>YDYWGHGTLVTVSSGGGGSGGGGSGGGGSSELTQDPAVSV<br>ALGQTVKITCQGDSLRTYYASWYQQRPGQAPVLVIYGENSR<br>PSGIPDRFSGSSSGNTASLTITGAQAEDEADYYCNSRDSSGN<br>HLRVFGGGTKVTVL* |
| 378 | Dara/G12(VH) | QVQLQESGGGLVQLGGSLRLSCAASGFTFSSYAMSWVRQA<br>PGKGLEWVSAISGSGGSTYYADSVKGRFTISRDNSKNTLYL<br>QMSSLRAEDTAFYYCANSAYTGGWYDYWGHGTLVTVSSA<br>STKGPSVFPLAPEVQLLESGGGLVQPGGSLRLSCAVSGFTFN<br>SFAMSWVRQAPGKGLEWVSAISGSGGGTYYADSVKGRFTIS<br>RDNSKNTLYLQMNSLRAEDTAVYFCAKDKILWFGEPVFDY<br>WGQGTLVTVSSASTKGPSVFPLAPSSKSTSGGTAALGCLVK<br>DYFPEPVTVSWNSGALTSGVHTFPAVLQSSGLYSLSSVVTVP<br>SSSLGTQTYICNVNHKPSNTKVDKKVEPKSCDKTHTCPPCPA<br>PELLGGPSVFLFPPKPKDTLMISRTPEVTCVVVDVSHEDPEV<br>KFNWYVDGVEVHNAKTKPREEQYNSTYRVVSVLTVLHQD<br>WLNGKEYKCKVSNKALPAPIEKTISKAKGQPREPQVYTLPPS<br>RDELTKNQVSLTCLVKGFYPSDIAVEWESNGQPENNYKTTP<br>PVLDSDGSFFLYSKLTVDKSRWQQGNVFSCSVMHEALHNH<br>YTQKSLSLSPGK |
| 379 | G12scFv/Dara | QVQLQESGGGLVQLGGSLRLSCAASGFTFSSYAMSWVRQA<br>PGKGLEWVSAISGSGGSTYYADSVKGRFTISRDNSKNTLYL<br>QMSSLRAEDTAFYYCANSAYTGGWYDYWGHGTLVTVSSA<br>STKGPRGSTSGGGSGGGSGGGGSSSSELTQDPAVSVALGQT<br>VKITCQGDSLRTYYASWYQQRPGQAPVLVIYGENSRPSGIPD<br>RFSGSSSGNTASLTITGAQAEDEADYYCNSRDSSGNHLRVFG<br>GGTKLTVLGGGSGGGSGGGSEVQLLESGGGLVQPGGSLRLS<br>CAVSGFTFNSFAMSWVRQAPGKGLEWVSAISGSGGGTYYA<br>DSVKGRFTISRDNSKNTLYLQMNSLRAEDTAVYFCAKDKIL<br>WFGEPVFDYWGQGTLVTVSSASTKGPSVFPLAPSSKSTSGG<br>TAALGCLVKDYFPEPVTVSWNSGALTSGVHTFPAVLQSSGL<br>YSLSSVVTVPSSSLGTQTYICNVNHKPSNTKVDKRVEPKSCD<br>KTHTCPPCPAPELLGGPSVFLFPPKPKDTLMISRTPEVTCVVV<br>DVSHEDPEVKFNWYVDGVEVHNAKTKPREEQYNSTYRVVS<br>VLTVLHQDWLNGKEYKCKVSNKALPAPIEKTISKAKGQPRE<br>PQVYTLPPSREEMTKNQVSLTCLVKGFYPSDIAVEWESNGQ<br>PENNYKTTPPVLDSDGSFFLYSKLTVDKSRWQQGNVFSCSV<br>MHEALHNHYTQKSLSLSPGK |

TABLE 31

| Light chain sequences of proof-of-concept bispecific antibodies | | |
|---|---|---|
| SEQ ID | Name | Sequence |
| 380 | Dara/G12(scFv) | MGWSCIILFLVATATGVHSEIVLTQSPATLSLSPGE<br>RATLSCRASQSVSSYLAWYQQKPGQAPRLLIYDASN<br>RATGIPARFSGSGSGTDFTLTISSLEPEDFAVYYCQ<br>QRSNWPPTFGQGTKVEIKRTVAAPSVFIFPPSDEQL<br>KSGTASVVCLLNNFYPREAKVQWKVDNALQSGNSQE<br>SVTEQDSKDSTYSLSSTLTLSKADYEKHKVYACEVT |

TABLE 31-continued

| Light chain sequences of proof-of-concept bispecific antibodies | | |
|---|---|---|
| SEQ ID | Name | Sequence |
| | | HQGLSSPVTKSFNRGECGGGGSGGGGSGGGGSRSQV<br>QLVESGGGLVQPGGSLRLSCAASGFTFSSYAMSWVR<br>QAPGKGLEWVSAISGSGGSTHCADSVKGRFTISRDN<br>SKNTLYLQMSSLRAEDTAFYYCANSAYTGGWYDYWG<br>HGTLVTVSSGGGGSGGGGSGGGGSSELTQDPAVSVA<br>LGQTVKITCQGDSLRTYYASWYQQRPGQAPVLVIYG |

TABLE 31-continued

Light chain sequences of
proof-of-concept bispecific antibodies

| SEQ ID | Name | Sequence |
|---|---|---|
| | | ENSRPSGIPDRFSGSSSGNTASLTITGAQAEDEADY YCNSRDSSGNHLRVFGGGTKLTVLG |
| 381 | Dara | EIVLTQSPATLSLSPGERATLSCRASQSVSSYLAWY QQKPGQAPRLLIYDASNRATGIPARFSGSGSGTDFT LTISSLEPEDFAVYYCQQRSNWPPTFGQGTKVEIKR TVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |

TABLE 31-continued

Light chain sequences of
proof-of-concept bispecific antibodies

| SEQ ID | Name | Sequence |
|---|---|---|
| 382 | Dara/G12 (VL) | SSELTQDPAVSVALGQTVKITCQGDSLRTYYASWYQ QRPGQAPVLVIYGENSRPSGIPDRFSGSSSGNTASL TITGAQAEDEADYYCNSRDSSGNHLRVFGGGTKLTV LRTVAAPSVFIFPEIVLTQSPATLSLSPGERATLSC RASQSVSSYLAWYQQKPGQAPRLLIYDASNRATGIP ARFSGSGSGTDFTLTISSLEPEDFAVYYCQQRSNWP PTFGQGTKVEIKRTVAAPSVFIFPPSDEQLKSGTAS VVCLLNNFYPREAKVQWKVDNALQSGNSQESVTEQD SKDSTYSLSSTLTLSKADYEKHKVYACEVTHQGLSS PVTKSFNRGEC |

TABLE 32

Heavy chain sequences of bispecific
antibodies constructed from antibodies
discovered in this study

| SEQ ID | Name | Sequence |
|---|---|---|
| 383 | G12(CH + scFv)-H | QVQLQESGGGLVQLGGSLRLSCAASGFTFSSYAMSWVRQA PGKGLEWVSAISGSGGSTYYADSVKGRFTISRDNSKNTLYL QMSSLRAEDTAFYYCANSAYTGGWYDYWGHGTLVTVSSA STKGPRGSTSGGGSGGGSGGGGSSSSELTQDPAVSVALGQT VKITCQGDSLRTYYASWYQQRPGQAPVLVIYGENSRPSGIP DRFSGSSSGNTASLTITGAQAEDEADYYCNSRDSSGNHLRV FGGGTKLTVLGGSGGSGGASKTHTCPPCPAPELLGGPSVFLF PPKPKDTLMISRTPEVTCVVVDVSHEDPEVKFNWYVDGVE VHNAKTKPREEQYNSTYRVVSVLTVLHQDWLNGKEYKCK VSNKALPAPIEKTISKAKGQPREPQVYTLPPSRDELTKNQVS LSCAVKGFYPSDIAVEWESNGQPENNYKTTPPVLDSDGSFFL VSKLTVDKSRWQQGNVFSCSVMHEALHNHYTQKSLSLSPG K |
| 384 | G1F4/G12 (scFv) | EVQLLESGGGLVQPGGSLRLSCAASGFTFSTYAMSWVRQAP GKGLEWVSAISGSGGSTYYADSVKGRFTISRDNSKNTLYLQ MNSLRAEDTAVYYCAKRGTYGYSFPTGFDYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GKGGGGSGGGGSGGGGSRSQVQLVESGGGLVQPGGSLRLS CAASGFTFSSYAMSWVRQAPGKGLEWVSAISGSGGSTHCA DSVKGRFTISRDNSKNTLYLQMSSLRAEDTAFYYCANSAYT GGWYDYWGHGTLVTVSSGGGGSGGGGSGGGGSSELTQDP AVSVALGQTVKITCQGDSLRTYYASWYQQRPGQAPVLVIY GENSRPSGIPDRFSGSSSGNTASLTITGAQAEDEADYYCNSR DSSGNHLRVFGGGTKLTVLG |
| 385 | G12(scFv)/G1F4 | QVQLQESGGGLVQLGGSLRLSCAASGFTFSSYAMSWVRQA PGKGLEWVSAISGSGGSTYYADSVKGRFTISRDNSKNTLYL QMSSLRAEDTAFYYCANSAYTGGWYDYWGHGTLVTVSSA STKGPRGSTSGGGSGGGSGGGGSSSSELTQDPAVSVALGQT VKITCQGDSLRTYYASWYQQRPGQAPVLVIYGENSRPSGIP DRFSGSSSGNTASLTITGAQAEDEADYYCNSRDSSGNHLRV FGGGTKLTVLGGGSGGGSGGGSEVQLLESGGGLVQPGGSL RLSCAASGFTFSTYAMSWVRQAPGKGLEWVSAISGSGGSTY YADSVKGRFTISRDNSKNTLYLQMNSLRAEDTAVYYCAKR GTYGYSFPTGFDYWGQGTLVTVSSASTKGPSVFPLAPSSKST SGGTAALGCLVKDYFPEPVTVSWNSGALTSGVHTFPAVLQS SGLYSLSSVVTVPSSSLGTQTYICNVNHKPSNTKVDKKVEPK SCDKTHTCPPCPAPELLGGPSVFLFPPKPKDTLMISRTPEVTC VVVDVSHEDPEVKFNWYVDGVEVHNAKTKPREEQYNSTY RVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFS CSVMHEALHNHYTQKSLSLSPGK |

TABLE 32-continued

Heavy chain sequences of bispecific
antibodies constructed from antibodies
discovered in this study

| SEQ ID | Name | Sequence |
|---|---|---|
| 386 | G1F4/G12(VH) | QVQLQESGGGLVQLGGSLRLSCAASGFTFSSYAMSWVRQA PGKGLEWVSAISGSGGSTYYADSVKGRFTISRDNSKNTLYL QMSSLRAEDTAFYYCANSAYTGGWYDYWGHGTLVTVSSA STKGPSVFPLAPEVQLLESGGGLVQPGGSLRLSCAASGFTFS TYAMSWVRQAPGKGLEWVSAISGSGGSTYYADSVKGRFTI SRDNSKNTLYLQMNSLRAEDTAVYYCAKRGTYGYSFPTGF DYWGQGTLVTVSSASTKGPSVFPLAPSSKSTSGGTAALGCL VKDYFPEPVTVSWNSGALTSGVHTFPAVLQSSGLYSLSSVV TVPSSSLGTQTYICNVNHKPSNTKVDKKVEPKSCDKTHTCPP CPAPELLGGPSVFLFPPKPKDTLMISRTPEVTCVVVDVSHED PEVKFNWYVDGVEVHNAKTKPREEQYNSTYRVVSVLTVLH QDWLNGKEYKCKVSNKALPAPIEKTISKAKGQPREPQVYTL PPSRDELTKNQVSLTCLVKGFYPSDIAVEWESNGQPENNYK TTPPVLDSDGSFFLYSKLTVDKSRWQQGNVFSCSVMHEALH NHYTQKSLSLSPGK |
| 387 | G12(ScFv)/32218_1 | QVQLQESGGGLVQLGGSLRLSCAASGFTFSSYAMSWVRQA PGKGLEWVSAISGSGGSTYYADSVKGRFTISRDNSKNTLYL QMSSLRAEDTAFYYCANSAYTGGWYDYWGHGTLVTVSSA STKGPRGSTSGGGSGGGSGGGGSSSSELTQDPAVSVALGQT VKITCQGDSLRTYYASWYQQRPGQAPVLVIYGENSRPSGIP DRFSGSSSGNTASLTITGAQAEDEADYYCNSRDSSGNHLRV FGGGTKLTVLGGGSGGGSGGGSEVQLLESGGGLVQPGGSL RLSCAASGFPFGVYAMSWVRQAPGKGLEWVSAISGSGGSTF YADSVKGRFTISRDNSKNTLYLQMNSLRAEDTAVYYCAKR GTYAYSFPTGFDYWGQGTLVTVSSASTKGPSVFPLAPSSKST SGGTAALGCLVKDYFPEPVTVSWNSGALTSGVHTFPAVLQS SGLYSLSSVVTVPSSSLGTQTYICNVNHKPSNTKVDKKVEPK SCDKTHTCPPCPAPELLGGPSVFLFPPKPKDTLMISRTPEVTC VVVDVSHEDPEVKFNWYVDGVEVHNAKTKPREEQYNSTY RVVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVFS CSVMHEALHNHYTQKSLSLSPGK |
| 388 | G12(ScFv)/32218_2 | QVQLQESGGGLVQLGGSLRLSCAASGFTFSSYAMSWVRQA PGKGLEWVSAISGSGGSTYYADSVKGRFTISRDNSKNTLYL QMSSLRAEDTAFYYCANSAYTGGWYDYWGHGTLVTVSSA STKGPRGSTSGGGSGGGSGGGGSSSSELTQDPAVSVALGQT VKITCQGDSLRTYYASWYQQRPGQAPVLVIYGENSRPSGIP DRFSGSSSGNTASLTITGAQAEDEADYYCNSRDSSGNHLRV FGGGTKLTVLGGGSGGGSGGGSEVQLLESGGGLVQPGGSL RLSCAASGFPFDTYAMSWVRQAPGKGLEWVSAISGSGGST YYADSVKGRFTISRDNSKNTLYLQMNSLRAEDTAVYYCAK RGTYAYSFPTGFDYWGQGTLVTVSSASTKGPSVFPLAPSSKS TSGGTAALGCLVKDYFPEPVTVSWNSGALTSGVHTFPAVLQ SSGLYSLSSVVTVPSSSLGTQTYICNVNHKPSNTKVDKKVEP KSCDKTHTCPPCPAPELLGGPSVFLFPPKPKDTLMISRTPEVT CVVVDVSHEDPEVKFNWYVDGVEVHNAKTKPREEQYNST YRVVSVLTVLHQDWLNGKEYKCKVSNKALPAPIEKTISKAK GQPREPQVYTLPPSRDELTKNQVSLTCLVKGFYPSDIAVEW ESNGQPENNYKTTPPVLDSDGSFFLYSKLTVDKSRWQQGNV FSCSVMHEALHNHYTQKSLSLSPGK |
| 389 | G12(scFv)/4618_1_12 | QVQLQESGGGLVQLGGSLRLSCAASGFTFSSYAMSWVRQA PGKGLEWVSAISGSGGSTYYADSVKGRFTISRDNSKNTLYL QMSSLRAEDTAFYYCANSAYTGGWYDYWGHGTLVTVSSA STKGPRGSTSGGGSGGGSGGGGSSSSELTQDPAVSVALGQT VKITCQGDSLRTYYASWYQQRPGQAPVLVIYGENSRPSGIP DRFSGSSSGNTASLTITGAQAEDEADYYCNSRDSSGNHLRV FGGGTKLTVLGGGSGGGSGGGSEVQLLESGGGLVQPGGSL RLSCAASGFPFDVYAMSWVRQAPGKGLEWVSAISGSGGSTF YADSVKGRFTISRDNSKNTLYLQMNSLRAEDTAVYYCAKR GTYAYSYPTGFDYWGQGTLVTVSSASTKGPSVFPLAPSSKS TSGGTAALGCLVKDYFPEPVTVSWNSGALTSGVHTFPAVLQ SSGLYSLSSVVTVPSSSLGTQTYICNVNHKPSNTKVDKKVEP KSCDKTHTCPPCPAPELLGGPSVFLFPPKPKDTLMISRTPEVT CVVVDVSHEDPEVKFNWYVDGVEVHNAKTKPREEQYNST YRVVSVLTVLHQDWLNGKEYKCKVSNKALPAPIEKTISKAK GQPREPQVYTLPPSRDELTKNQVSLTCLVKGFYPSDIAVEW ESNGQPENNYKTTPPVLDSDGSFFLYSKLTVDKSRWQQGNV FSCSVMHEALHNHYTQKSLSLSPGK |

US 12,583,932 B2

175                     176

TABLE 32-continued

---

Heavy chain sequences of bispecific
antibodies constructed from antibodies
discovered in this study

---

| SEQ ID | Name | Sequence |
|---|---|---|
| 390 | 32218_1-K | EVQLLESGGGLVQPGGSLRLSCAASGFPFGVYAMSWVRQA PGKGLEWVSAISGSGGSTFYADSVKGRFTISRDNSKNTLYLQ MNSLRAEDTAVYYCAKRGTYAYSFPTGFDYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSRDELTKNQV SLWCLVKGFYPSDIAVEWESNGQPENNYKTTPPVLDSDGSF FLYSKLTVDKSRWQQGNVFSCSVMHEALHNHYTQKSLSLS PGK |
| 391 | 4618_1_12-K | EVQLLESGGGLVQPGGSLRLSCAASGFPFDVYAMSWVRQA PGKGLEWVSAISGSGGSTFYADSVKGRFTISRDNSKNTLYLQ MNSLRAEDTAVYYCAKRGTYAYSYPTGFDYWGQGTLVTV SSASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYK CKVSNKALPAPIEKTISKAKGQPREPQVYTLPPSRDELTKNQ VSLWCLVKGFYPSDIAVEWESNGQPENNYKTTPPVLDSDGS FFLYSKLTVDKSRWQQGNVFSCSVMHEALHNHYTQKSLSL SPGK |
| 392 | 32218_2-K | EVQLLESGGGLVQPGGSLRLSCAASGFPFDTYAMSWVRQA PGKGLEWVSAISGSGGSTYYADSVKGRFTISRDNSKNTLYL QMNSLRAEDTAVYYCAKRGTYAYSFPTGFDYWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCDKTHTCPPCPAPELLGGPS VPLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSRDELTKN QVSLWCLVKGFYPSDIAVEWESNGQPENNYKTTPPVLDSDG SFFLYSKLTVDKSRWQQGNVFSCSVMHEALHNHYTQKSLS LSPGK |

---

TABLE 33

---

Light chain sequences of bispecific
antibodies discovered in this study

---

| SEQ ID | Name | Sequence |
|---|---|---|
| 393 | G1F4/G12(scFv) | DIQMTQSPSSLSASVGDRVTITCRASQDVNTAVAWYQQKPG KAPKLLIYSASFLYSGVPSRFSGSRSGTDFTLTISSLQPEDFAT YYCQQHYTTPPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSGGGGSGGGGSRSQVQLVESGGGLVQPGGSL RLSCAASGFTFSSYAMSWVRQAPGKGLEWVSAISGSGGSTH CADSVKGRFTISRDNSKNTLYLQMSSLRAEDTAFYYCANSA YTGGWYDYWGHGTLVTVSSGGGGSGGGGSGGGGSSELTQ DPAVSVALGQTVKITCQGDSLRTYYASWYQQRPGQAPVLVI YGENSRPSGIPDRFSGSSSGNTASLTITGAQAEDEADYYCNS RDSSGNHLRVFGGGTKLTVLG |
| 394 | G1F4/G12(VL) | SSELTQDPAVSVALGQTVKITCQGDSLRTYYASWYQQRPGQ APVLVIYGENSRPSGIPDRFSGSSSGNTASLTITGAQAEDEAD YYCNSRDSSGNHLRVFGGGTKLTVLRTVAAPSVFIFPDIQMT QSPSSLSASVGDRVTITCRASQDVNTAVAWYQQKPGKAPKL |

TABLE 33-continued

| Light chain sequences of bispecific antibodies discovered in this study | | |
|---|---|---|
| SEQ ID | Name | Sequence |
| | | LIYSASFLYSGVPSRFSGSRSGTDFTLTISSLQPEDFATYYCQ QHYTTPPTFGQGTKVEIKRTVAAPSVFIFPPSDEQLKSGTASV VCLLNNFYPREAKVQWKVDNALQSGNSQESVTEQDSKDST YSLSSTLTLSKADYEKHKVYACEVTHQGLSSPVTKSFNRGE C |
| 395 | 32218_1/G12 | DIQMTQSPSSLSASVGDRVTITCRASQDVNTAVAWYQQKPG KAPKLLIYSASFLYSGVPSRFSGSRSGTDFTLTISSLQPEDFAT YYCQQHYTTPPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSGGGGSGGGGSRSQVQLVESGGGLVQPGGSL RLSCAASGFTFSSYAMSWVRQAPGKGLEWVSAISGSGGSTH CADSVKGRFTISRDNSKNTLYLQMSSLRAEDTAFYYCANSA YTGGWYDYWGHGTLVTVSSGGGGSGGGGSGGGGSELTQ DPAVSVALGQTVKITCQGDSLRTYYASWYQQRPGQAPVLVI YGENSRPSGIPDRFSGSSSGNTASLTITGAQAEDEADYYCNS RDSSGNHLRVFGGGTKLTVLG |
| 396 | 32218_2/G12 | DIQMTQSPSSLSASVGDRVTITCRASQDVNTAVAWYQQKPG KAPKLLIYSASFLYSGVPSRFSGSRSGTDFTLTISSLQPEDFAT YYCQQHYTTPPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSGGGGSGGGGSRSQVQLVESGGGLVQPGGSL RLSCAASGFTFSSYAMSWVRQAPGKGLEWVSAISGSGGSTH CADSVKGRFTISRDNSKNTLYLQMSSLRAEDTAFYYCANSA YTGGWYDYWGHGTLVTVSSGGGGSGGGGSGGGGSELTQ DPAVSVALGQTVKITCQGDSLRTYYASWYQQRPGQAPVLVI YGENSRPSGIPDRFSGSSSGNTASLTITGAQAEDEADYYCNS RDSSGNHLRVFGGGTKLTVLG |
| 397 | 4618_1_12/G12 (scFv) | DIQMTQSPSSLSASVGDRVTITCRASQDVNTAVAWYQQKPG KAPKLLIYSASFLYSGVPSRFSGSRSGTDFTLTISSLQPEDFAT YYCQQHYTTPPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGGGGSGGGGSGGGGSRSQVQLVESGGGLVQPGGSL RLSCAASGFTFSSYAMSWVRQAPGKGLEWVSAISGSGGSTH CADSVKGRFTISRDNSKNTLYLQMSSLRAEDTAFYYCANSA YTGGWYDYWGHGTLVTVSSGGGGSGGGGSGGGGSELTQ DPAVSVALGQTVKITCQGDSLRTYYASWYQQRPGQAPVLVI YGENSRPSGIPDRFSGSSSGNTASLTITGAQAEDEADYYCNS RDSSGNHLRVFGGGTKLTVLG |

TABLE 34

| Daratumumab CDR Sequences | | | | | |
|---|---|---|---|---|---|
| SEQ ID | CDR-H1 | SEQ ID | CDR-H2 | SEQ ID | CDR-H3 |
| 398 | GFTFNSFAMS | 399 | ISGSGGGT YYADSVK | 400 | AKDKILWFG EPVFDY |
| SEQ ID | CDR1-L1 | SEQ ID | CDR-L2 | SEQ ID | CDR-L3 |
| 401 | RASQSVSSYLA | 402 | DASNRAT | 403 | QQRSNWPPT |

TABLE 35

| G12 CDR Sequences | | | | | |
|---|---|---|---|---|---|
| SEQ ID | CDR-H1 | SEQ ID | CDR-H2 | SEQ ID | CDR-H3 |
| 404 | GFTFSSYA MS | 405 | AISGSGGST YYADSVKG | 406 | ANSAYTGG WYDY |

TABLE 35-continued

| G12 CDR Sequences | | | | | |
|---|---|---|---|---|---|
| VL | CDR1-L1 | SEQ ID | CDR-L2 | SEQ ID | CDR-L3 |
| 407 | QGDSLRTY YAS | 408 | GENSRPS | 409 | NSRDSSGN HLRV |

TABLE 36

| Anti-ICAM1 Consensus Sequences | | |
|---|---|---|
| SEQ ID | Name | |
| 410 | Heavy Chain | QSVEESGG$U_1$LV$U_2$PG$U_3$$U_4$LTLTCTVSGFSLS$Z_1$$Z_2$AM GWVRQAPGKGLU$_5$YIGIIGSS$Z_3$$Z_4$TYY$AZ_5$WAKGRFT ISKTSTTVDLU$_6$$U_7$TSPTTEDTATYFCVRDPYDS$Z_6$$Z_7$ $Z_8$$Z_9$YRLWGPGTLVTVSSASTKGPSVFPLAPSSKSTSG GTAALGCLVKDYFPEPVTVSWNSGALTSGVHTFPAVL QSSGLYSLSSVVTVPSSSLGTQTYICNVNHKPSNTKV |

TABLE 36-continued

Anti-ICAM1 Consensus Sequences

| SEQ ID | Name | |
|---|---|---|
| | | DKKVEPKSCDKTHTCPPCPAPELLGGPSVFLFPPKPK DTLMISRTPEVTCVVVDVSHEDPEVKFNWYVDGVEVH NAKTKPREEQYNSTYRVVSVLTVLHQDWLNGKEYKCK VSNKALPAPIEKTISKAKGQPREPQVYTLPPSRDELT KNQVSLTCLVKGFYPSDIAVEWESNGQPENNYKTTPP VLDSDGSFFLYSKLTVDKSRWQQGNVFSCSVMHEALH NHYTQKSLSLSPGK |
| 411 | Light Chain | AYDMU$_8$QTPASVEVAVGGTVTIKCQASZ$_{10}$Z$_{11}$IYZ$_{12}$Y Z$_{13}$Z$_{14}$WYQU$_9$KU$_{10}$GQRPU$_{11}$U$_{12}$LIYDASKZ$_{15}$ASGVPSR FU$_{13}$GSGSGTEFTLTISU$_{14}$U$_{15}$QSDDAATYYCQQAYSS Z$_{16}$Z$_{17}$Z$_{18}$DNZ$_{19}$FGGGTEVU$_{16}$VKRTVAAPSVFIFPPSD EQLKSGTASVVCLLNNFYPREAKVQWKVDNALQSGNS QESVTEQDSKDSTYSLSSTLTLSKADYEKHKVYACEV THQGLSSPVTKSFNRGEC |

TABLE 37

Anti-ICAM1 CDR Sequences

| SEQ ID | CDR-H1 | SEQ ID | CDR-H2 | SEQ ID | CDR-H3 |
|---|---|---|---|---|---|
| 412 | GFSLSZ$_1$Z$_2$A MG | 413 | GIIGSSZ$_3$Z$_4$TY YAZ$_5$WAKG | 414 | VRDPYDSZ$_6$ Z$_7$Z$_8$Z$_9$YRL |

| VL | CDR1-L1 | SEQ ID | CDR-L2 | SEQ ID | CDR-L3 |
|---|---|---|---|---|---|
| 415 | QASZ$_{10}$Z$_{11}$IY Z$_{12}$YZ$_{13}$Z$_{14}$ | 416 | DASKZ$_{15}$AS | 417 | QQAYSSZ$_{16}$ Z$_{17}$Z$_{18}$DNZ$_{19}$ |

*Wherein U1 is glycine or arginine; U2 is lysine or threonine; U3 is glycine or threonine; U4 is threonine or proline; U5 is glutamine or glutamic acid; U6 is lysine or arginine; U7 is isoleucine or leucine; U8 is threonine or serine; U9 is lysine or glutamine; U10 is leucine or proline; U11 is lysine or serine; U12 is leucine or phenylalanine; U13 is lysine or glutamic acid or threonine; U14 is alanine or glycine; U15 is valine, methionine, or alanine; and U16 is valine or methionine.

What is claimed is:

1. A multispecific protein comprising (i) a first component comprising an antibody or an antigen binding fragment thereof that specifically binds to CD38 and (ii) a second component comprising an antibody or an antigen binding fragment thereof that specifically binds to ICAM1, wherein:

(a) the first component that specifically binds to CD38 comprises:

(i) a heavy chain variable domain (VH) comprising complementarity determining regions HCDR1, HCDR2, and HCDR3 comprising the sequences of SEQ ID NO: 1, 2, and 7, respectively, and (ii) a light chain variable domain (VL) comprising complementarity determining regions LCDR1, LCDR2, and LCDR3 comprising the sequences of SEQ ID NO: 62, 63, and 64, respectively; and (b) the second component that specifically binds to ICAM1 comprises:

(i) a heavy chain variable domain (VH) comprising complementarity determining regions HCDR1, HCDR2, and HCDR3 comprising the sequences of 228, 229, and 230, respectively, and (ii) a light chain variable domain (VL) comprising complementarity determining regions LCDR1, LCDR2, and LCDR3 comprising the sequences of SEQ ID NO: 270, 260, and 271, respectively.

2. The multispecific protein of claim 1, wherein the multispecific protein comprises an Fc region that is a heterodimeric Fc region.

3. The multispecific protein of claim 2, wherein the Fc region is afucosylated.

4. The multispecific protein of claim 2, wherein the Fc region comprises one or more mutations that increases ADCC or CDC activity.

5. The multispecific protein of claim 4, wherein the Fc region comprises the one or more mutations that increase ADCC activity, wherein the mutations that increase ADCC activity are at positions corresponding to positions 239, 332, and 330 of human IgG1, wherein the mutations are S239D, 1332E, and A330L, and wherein the amino acid numbering is according to the EU index.

6. The multispecific protein of claim 2, comprising the heterodimeric Fc region, wherein the heterodimeric Fc region comprises a knob chain and a hole chain, forming a knob-in-hole (KIH) structure.

7. The multispecific protein of claim 1, wherein the second component that specifically binds to ICAM1 comprises a Fab and the first component that specifically binds to CD38 comprises a single-chain variable fragment (scFv).

8. The multispecific protein of claim 1, wherein the first component that specifically binds to CD38 comprises a heavy chain variable (VH) domain comprising SEQ ID NO: 107.

9. The multispecific protein of claim 1, wherein the first component that specifically binds to CD38 comprises a light chain variable (VL) domain comprising SEQ ID NO: 133.

10. The multispecific protein of claim 1, wherein the second component that specifically binds to ICAM1 comprises a VH domain comprising SEQ ID NO: 298.

11. The multispecific protein of claim 1, wherein the second component that specifically binds to ICAM1 comprises a VL domain comprising SEQ ID NO: 320.

12. The multispecific protein of claim 1, wherein the second component that specifically binds to ICAM1 comprises a full-length antibody comprising a light chain (LC) and a heavy chain (HC), wherein the HC comprises SEQ ID NO: 338.

13. The multispecific protein of claim 1, wherein the multispecific protein induces an enhanced ADCC effect on a target cell compared to an ADCC effect induced on the target cell by a control monospecific protein that comprises only the first component that specifically binds to CD38 or only the second component that specifically binds to ICAM1, wherein the target cell is a cancer cell expressing CD38 and ICAM1.

14. The multispecific protein of claim 1, wherein multispecific protein induces an enhanced CDC effect on a target cell compared to a CDC effect induced on the target cell by a control monospecific protein that comprises only the first component that specifically binds to CD38 or only the second component that specifically binds to ICAM1, wherein the target cell is a cancer cell expressing CD38 and ICAM1.

15. The multispecific protein of claim 1, wherein the second component that specifically binds to ICAM1 comprises a full-length antibody comprising a LC and a HC, wherein the LC comprises SEQ ID NO: 360.

16. The multispecific protein of claim 1, wherein the first component that specifically binds to CD38 comprises a full-length antibody comprising a LC and a HC, wherein the HC comprises SEQ ID NO: 160.

17. The multispecific protein of claim 1, wherein the first component that specifically binds to CD38 comprises a full-length antibody comprising a LC and a HC, wherein the LC comprises SEQ ID NO: 186.

18. The multispecific protein of claim 1, wherein the multispecific protein comprises one of the following structures:

(a) the first component comprises a full-length anti-CD38 immunoglobulin (IgG) molecule, and the second component comprises an anti-ICAM1 scFv;

(b) the first component comprises a Fab fragment of an anti-CD38 IgG, and the second component comprises an anti-ICAM1 scFv; and (c) the first component comprises a VH domain and a VL domain of an anti-CD38 IgG, and the second component comprises a VH wherein the multispecific protein is of a common light chain bispecific format.

19. The multispecific protein of claim 18, wherein the full-length anti-CD38 IgG comprises two LCs and each LC is fused to a single anti-ICAM1 scFv.

20. The multispecific protein of claim 19, wherein the C-terminus of each LC of the full-length anti-CD38 IgG is fused to a single anti-ICAM1 scFv.

21. The multispecific protein of claim 19, wherein the N-terminus of each HC of the full-length anti-CD38 IgG is fused to a single anti-ICAM1 scFv.

22. The multispecific protein of claim 1, wherein the full-length anti-CD38 IgG comprises two HCs and the C-terminus of each HC is conjugated to a single anti-ICAM1 scFv.

23. The multispecific protein of claim 1, wherein the first component comprises a full-length anti-CD38 IgG comprising two HCs and two LCs and the second component comprises two anti-ICAM1 VH domains and two anti-ICAM-1 VL domains, and wherein the N-terminus of each HC of the full-length anti-CD38 IgG is fused to one of the anti-ICAM1 VH domains and the N-terminus of each LC of the full-length anti-CD38 IgG is fused to one of the anti-ICAM1 VL domains.

\* \* \* \* \*